US011414704B2

(12) United States Patent
Dogan et al.

(10) Patent No.: US 11,414,704 B2
(45) Date of Patent: Aug. 16, 2022

(54) COMPOSITIONS AND METHODS FOR DETECTING PREDISPOSITION TO CARDIOVASCULAR DISEASE

(71) Applicant: University of Iowa Research Foundation, Iowa City, IA (US)

(72) Inventors: Meeshanthini Dogan, Iowa City, IA (US); Robert Philibert, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 280 days.

(21) Appl. No.: 16/308,238

(22) PCT Filed: Jun. 8, 2017

(86) PCT No.: PCT/US2017/036555
§ 371 (c)(1),
(2) Date: Dec. 7, 2018

(87) PCT Pub. No.: WO2017/214397
PCT Pub. Date: Dec. 14, 2017

(65) Prior Publication Data

US 2019/0264286 A1 Aug. 29, 2019

Related U.S. Application Data

(60) Provisional application No. 62/455,468, filed on Feb. 6, 2017, provisional application No. 62/347,479, filed on Jun. 8, 2016.

(51) Int. Cl.
*C12Q 1/6883* (2018.01)

(52) U.S. Cl.
CPC ..... *C12Q 1/6883* (2013.01); *C12Q 2600/154* (2013.01); *C12Q 2600/156* (2013.01)

(58) Field of Classification Search
CPC ............ C12Q 1/6883; C12Q 2600/154; C12Q 2600/156
See application file for complete search history.

(56) References Cited

U.S. PATENT DOCUMENTS

| | | | | |
|---|---|---|---|---|
| 4,683,195 | A | 7/1987 | Mullis et al. | |
| 4,683,202 | A | 7/1987 | Mullis | |
| 4,800,159 | A | 1/1989 | Mullis et al. | |
| 4,965,188 | A | 10/1990 | Mullis et al. | |
| 7,972,779 | B2 | 7/2011 | Caspi et al. | |
| 2004/0142334 | A1 | 7/2004 | Schacht | |
| 2004/0241651 | A1 | 12/2004 | Olek et al. | |
| 2006/0099610 | A1* | 5/2006 | Salonen ............... | C12Q 1/6883 435/6.11 |
| 2007/0054295 | A1* | 3/2007 | Spivack ................ | C12Q 1/686 435/6.12 |
| 2010/0234242 | A1 | 9/2010 | Petronis et al. | |
| 2011/0196614 | A1 | 8/2011 | Kariyasu et al. | |
| 2012/0108444 | A1 | 5/2012 | Philibert et al. | |

FOREIGN PATENT DOCUMENTS

| | | |
|---|---|---|
| CA | 2974097 | 7/2016 |
| WO | WO 2001/077384 | 10/2001 |
| WO | WO 2002/046454 | 6/2002 |
| WO | WO 2005/087953 | 9/2005 |
| WO | WO 2006/099365 | 9/2006 |
| WO | WO 2012/012709 | 1/2012 |
| WO | WO 2013/001504 | 1/2013 |
| WO | WO 2013/135830 | 9/2013 |
| WO | WO 2016/057485 | 4/2016 |
| WO | WO 2017/214397 | 12/2017 |

OTHER PUBLICATIONS

Altintas, Zeynep et al. Cardiovascular disease detection using bio-sensing techniques (2014), Talanta, 128:177-186 (Year: 2014).*
Andiappan et al. BMC Genetics. 2010. 11:36. (Year: 2010).*
Byun et al. Human Molecular Genetics. 2009. 18(24):4808-4817. (Year: 2009).*
Tan et al. Carcinogenesis. 2002. 23(2):231-236. (Year: 2002).*
Rask-Andersen et al. Human Molecular Genetics. 2016. 25(21):4739-4748. (Year: 2016).*
Sotos et al. Statistics Education Research Journal. 2009. 8(2):33-55. (Year: 2009).*
Zaina et al. Circulation: Cardiovascular Genetics. 2014. 7(5):692-700 and Supplemental Material. (Year: 2014).*
Samani et al. The New England Journal of Medicine. 2007. 357(5):443-453 and Supplementary Appendix. (Year: 2007).*
Andersen et al, "Current and Future Prospects for Epigenetic Biomarkers of Substance Use Disorders," Genes 6, 2015, 991-1022.
Armour et al, "Annual Smoking-Attributable Mortality, Years of Potential Life Lost, and Productivity Losses—United States, 1997-2001," MMWR, Jul. 1, 2005, 54(25):625-628.
Auer et al, "Association of major and minor ECG abnormalities with coronary heart disease events," JAMA, 307:1497-1505.
Beach et al, "Child maltreatment moderates the association of MAOA with symptoms of depression and antisocial personality disorder," J. Fam. Psychol., Feb. 2010, 24:12-20.
Beck & Shultz,. The use of relative operating characteristic (ROC) curves in test performance evaluation. Arch. Pathol. Lab. Med., 1986 110:13-20.
Breitling et al, "Smoking F2RL3 methylation, and prognosis in stable coronary heart disease," European Hearth Journal, Apr. 17, 2012, 33:22:2841-2848.
Brückmann et al, "Validation of differential GDAP1 DNA methylation in alcohol dependence and its potential function as a biomarker for disease severity and therapy outcome," Epigenetics, 11:6:456-463.
Buckley et al, "M. C-reactive protein as a risk factor for coronary heart disease: a systematic review and meta-analyses for the US Preventive Services Task Force," Ann. Intern. Med. 151:483-495.
Caraballo et al, "Associated with discrepancies between self-reports on cigarette smoking and measured serum cotinine levels among persons aged 17 years or older," Third National Health and Nutrition Examination Survey, 1988-1994, Am. J. Epidemiol., 2001, 153:807-814.

(Continued)

*Primary Examiner* — Joseph G. Dauner
(74) *Attorney, Agent, or Firm* — Fish & Richardson P.C.

(57) ABSTRACT

Methods and compositions are provided for detecting a predisposition for cardiovascular disease in an individual.

4 Claims, 123 Drawing Sheets

(56) References Cited

OTHER PUBLICATIONS

Caraballo et al, "Self-reported cigarette smoking vs. serum cotinine among U.S. adolescents," Nicotine & Tobacco Research, Feb. 2004, 6:19-25.
Caspi et al, "Influence of life stress on depression: moderation by a polymorphism in the 5-HTT gene," Science, 2003, 301:386-389.
Caspi et al, "Role of genotype in the cycle of violence in maltreated children," Science, Aug. 2, 2002, 297:851-854.
Dawber et al, "An approach to longitudinal studies in a community: the Framingham Study," Ann. N. Y. Acad. Sci., May 22, 1963, 107:539-556.
Dogan et al, "Ethnicity and Smoking-Associated DNA Methylation Changes at HIV Co-Receptor GPR15," Frontiers in Psychiatry, Sep. 2015, 11 pages.
Du et al, "lumi: a pipeline for processing Illumina microarray," Bioinformatics, 2008, 24:1547-1548.
Frey et al, "Mutations in Adenosine Deaminase-like (ADAL) Protein Confer Resistance to the Antiproliferative Agents N^6. Cyclopropyl-PMEDAP and GS-9219," Anticancer Research, 2013, 33:1899-1912.
Garret et al, "Control & Prevention. Cigarette smoking—United States, 1965-2008," MMWR Surveill. Summ., 2011, 60:109-113.
Gluckman et al, "Epigenetic mechanisms that underpin metabolic and cardiovascular diseases," Nat. Rev. Endocrinol., 2009, 5:401-408.
Guida et al, "Dynamics of Smoking Induced Genome-Wide Methylation Changes with Time Since Smoking Cessation," Hum. Mol. Genet., 2015, 24:8:2349-2359.
Klengel et al, "The role of DNA methylation in stress-related psychiatric disorders," Neuropharmacology, 2014, 18 pages.
Kolassa et al, "Association study of trauma load and SLC6A4 promoter polymorphism in posttraumatic stress disorder: evidence from survivors of the Rwandan genocide," J Clinical Psychiatry, 2010, 71:543-547.
Lin et al, "Methylome-wide association study of atrial fibrillation in Framingham heart study," Scientific Reports, Jan. 9, 2017, 9 pages.
Mahmood et al, "The Framingham Heart Study and the epidemiology of cardiovascular disease: a historical perspective," The Lancet, Mar. 15, 2014, 383:999-1008.
McEwen, "Physiology and Neurobiology of Stress and Adaptation: Central Role of the Brain," Physiol. Rev., 2007, 87:873-904.
McKinney et al, "Machine learning for detecting gene-gene interactions: a review," Appl. Bioinformatics, 2006, 5:(2):77-88.
Mega et al, "Genetic risk, coronary heart disease events, and the clinical benefit of statin therapy: an analysis of primaiy and secondaiy prevention trials," The Lancet, Mar. 4, 2015, 385:2264-2271.
Monick et al, "Coordinated changes in AHRR methylation in lymphoblasts and pulmonary macrophages from smokers," Am. J. Med Genet., 2012, 159B(2):141-151.
Mozzafarian et al, "Executive Summary: Heart Disease and Stroke Statistics—2016 Update: A Report From the American Heart Association," Circulation, Jan. 26, 2016, 133:447-454.
Paynter et al, Are Genetic Tests for Atherosclerosis Ready for Routine Clinical Use? Circ. Res. 118, 607-619 (2016).
PCT International Preliminary Report on Patentability in International Appln. No. PCT/US2017/0365555, dated Dec. 11, 2018, 12 pages.
PCT International Search Report and Written Opinion in International Appln. No. PCT/US2017/0365555, dated Nov. 7, 2017, 22 pages.
Philibert et al, "A pilot examination of the genome-wide DNA methylation signatures of subjects entering and exiting short-term alcohol dependence treatment programs," Epigenetics, Sep. 2014, 9:9:1212-1219.
Philibert et al, "A Quantitative Epigenetic Approach for the Assessment of Cigarette Consumption," Front. Psychol., 2015, 8 pages.
Philibert et al, "MAOA methylation is associated with nicotine and alcohol dependence in women," Am. J. Med. Genet., Jul. 2008, 565-570.
Philibert et al, "The effect of smoking on MAOA promoter methylation in DNA prepared from lymphoblasts and whole blood," Am. J. Med. Genet., Mar. 2010, 619-628.
Philibert et al, "The search for peripheral biomarkers for major depression: Benefiting from successes in the biology of smoking," American Journal of Medical Genetics Part B: Neuropsychiatric Genetics, Jan. 2014, 165:230-234.
Pidsley et al, "A data-driven approach to preprocessing Illumina 450K methylation array data," BMC Genomics, 2013, 14:1-10.
Purcell et al, "PLINK: a tool set for whole-genome association and population-based linkage analyses," The American Journal of Human Genetics, 2007, 81:559-575.
Qiu et al, "Variable DNA Methylation Is Associated with Chronic Obstructive Pulmonary Disease and Lung Function," Am. J. Respir. Crit. Care Med., 2012, 185:373-381.
Shabalin, "Matrix eQTL: ultra-fast eQTL analysis via large matrix operations," Bioinformatics, 2012, 28:1353-1358.
Sharma et al, "Detection of altered global DNA methylation in coronary artery disease patients," DNA Cell Biol., 2008, 27:357-365.
Shipton et al, "Reliability of self-reported smoking status by pregnant women for estimating smoking prevalence: a retrospective, cross sectional study," BMJ, 2009, 8 pages.
Shumay et al, "Evidence that the methylation state of the monoamine oxidase A (MAOA) gene predicts brain activity of MAOA enzyme in healthy men," Epigenetics, 2012, 7:10:1151-1160.
Toperoff et al, "Genome-wide survey reveals predisposing diabetes type 2-related DNA methylation variations in human peripheral blood," Hum. Mol. Genet., 2012, 21:371-383.
Tsaprouni et al, "Cigarette smoking reduces DNA methylation levels at multiple genomic loci but the effect is partially reversible upon cessation," Epigenetics, Oct. 2014, 9:10:1382-1396.
Webb et al, "The discrepancy between self-reported smoking status and urine cotinine levels among women enrolled in prenatal care at four publicly funded clinical sites," J. Public Health Manag. Pract., 2003, 9:322-325.
Wolke et al, "Selective drop-out in longitudinal studies and non-biased prediction of behaviour disorders," The British Journal of Psychiatiy, 2009, 195:249-256.
Yang & Khoury, "Evolving methods in genetic epidemiology. III. Gene-environment interaction in epidemiologic research," Epidemiol. Rev., Feb. 1997, 19:33-43 (1997).
Zeilinger et al, "Tobacco smoking leads to extensive genome-wide changes in DNA methylation," PLoS One, May 2013, 14 pages.
Zhang et al, "F2RL3 methylation in blood DNA is a strong predictor of mortality. Int. J. Epidemiol," 2014, 1215-1225.
Zhang et al, "Smoking-Associated DNA Methylation Biomarkers and Their Predictive Value for All-Cause and Cardiovascular Mortality," Environ. Health Perspect., 2015, 124:68-74.
Drong et al., "The Presence of Methylation Quantitative Trait Loci Indicates a Direct Genetic Influence on the Level of DNA Methylation in Adipose Tissue," PLOS ONE, Feb. 2013, 8(2): e55923 (12 pages).
Heyn et al., "Linkage of DNA Methylation Quantitative Trait Loci to Human Cancer Risk," Cell Reports, Apr. 24, 2014, 7:331-338.
JP Office Action in Japanese Appln. No. 2018-564383, dated Jun. 21, 2021, 12 pages (with English translation).
Rushton et al., "Methylation quantitative trait locus analysis of osteoarthritis links epigenetics with genetic risk," Human Molecular Genetics, Oct. 2015, 24(25):7432-7444.
Altschul et al., "Basic Local Alignment Search Tool," J. Mol. Biol., May 1990, 215:403-410.
Andersen et al., "An Examination of Risk Factors for Tobacco and Cannabis Smoke Exposure in Adolescents Using an Epigenetic Biomarker," Front. Psychiatiy, 2021, 12:1-13.
Borges et al., "Promoter Polymorphisms and Methylation of E-Cadherin (CDH1) and KIT in Gastric Cancer Patients from Northern Brazil," Anticancer Research, 2010, 30:2225-2234.
Corpet et al., "Multiple sequence alignment with hierarchical clustering," Nucl. Acids Res., 1988, 16:10881-10890.

(56) References Cited

OTHER PUBLICATIONS

Dogan et al., "Blood-Based Biomarkers for Predicting the Risk for Five-Year incident Coronary Heart Disease in the Framingham Heart Study via Machine Learning," Genes, Dec. 2018, 9(641):1-15.
Dogan et al., "External validation of integrated genetic-epigenetic biomakers for predicting incident coronary heart disease," Epigenomics, 2021, 13(14):1095-1112.
Dogan et al., "Integrated genetic and epigenetic prediction of coronary heart disease in the Framingham Heart Study," PLoS One, Jan. 2018, 13(1):1-18.
Higgins et al., "Fast and sensitive multiple sequence alignments on a microcomputer," CABIOS Comm., 1989, 5(2):151-153.
Huang et al., "Parallelization of a local similarity algorithm," CABIOS, 1992, 8(2):155-165.
International Search Report and Written Opinion in International Appln. No. PCT/US2021/049100, dated Jan. 21, 2022, 22 pages.
Karlin et al., "Applications and statistics for multiple high-scoring segments in molecular sequences," Proc. Natl. Acad. Sci. USA, Jun. 1993, 90:5873-5877.
Karlin et al., "Methods for assessing the statistical significance of molecular sequence features by using general scoring schemes," Proc. Natl. Acad. Sci. USA, Mar. 1990, 87:2264-2268.
Needleman et al., "A General Method Applicable to the Search for Similarities in the Amino Acid Sequence of Two Proteins," J. Mol. Bio., 1970 48:443-453.
Nielsen et al., "Sequence-Selective Recognition of DNA by Strand Displacement with a Thymine-Substituted Polyamide," Science, 1991, 254:1497-1500.
Nikpay et al., "A comprehensive 1000 Genomes-based genome-wide association meta-analysis of coronary artery disease," Nat. Genet., Sep. 2015, 47(10):1121-1130.
Ogutu et al., "A comparison of random forests, boosting and support vector machines for genomic selection," BMC Proceedings, 2011, 5(Suppl 3):1-5.
Pearson et al., "Improved tools for biological sequence comparison," Proc. Natl. Acad. Sci. USA, Apr. 1988, 85:2444-2448.
Philibert et al., "AHRR methylation predicts smoking status and smoking intensity in both saliva and blood DNA," Am. J. Med. Genet. B Neuropsychiatr. Genet., 2019:1-10.
Philibert et al., "Reversion of DNA methylation at cardiac risk predictor loci demonstrates the potential of epigenetics to guide CHD prevention therapy using DNA from blood or saliva," Poster, Presented at American College of Cardiology World Congress ACC 2021, Atlanta, GA, May 15-17, 2021; JACC, May 3, 2021, 77(18), 1 page.
Seman et al., "Genetic, epigenetic and protein analyses of intercellular adhesion molecule 1 in Malaysian subjects with type 2 diabetes and diabetic nephropathy," J. Diabetes Complicat., 2015, 29(8):1234-1239.
Smith et al., "Comparison of Biosequences," Adv. Appl. Math., 1981, 2:482-489.

* cited by examiner

| A2BP1 | ACAD9 | ACVR2A | ADPRHL2 | AK1 | ALS2CR8 | ANKRD40 |
|---|---|---|---|---|---|---|
| A2LD1 | ACADM | ADAL | ADRA1B | AK2 | ALX3 | ANKRD42 |
| A4GALT | ACAP2 | ADAM10 | ADRA2A | AK3 | ALX4 | ANKRD44 |
| AACS | ACAP3 | ADAM11 | ADRA2C | AK3L1 | AMDHD2 | ANKRD53 |
| AACSL | ACAT2 | ADAM12 | ADRB2 | AK7 | AMICA1 | ANKRD54 |
| AADAT | ACBD3 | ADAM15 | ADSL | AKAP1 | AMIGO1 | ANKRD6 |
| AAK1 | ACBD4 | ADAM19 | AEBP1 | AKAP10 | AMIGO2 | ANKRD9 |
| AANAT | ACBD5 | ADAM22 | AEBP2 | AKAP11 | AMIGO3 | ANKS1A |
| AARS2 | ACBD6 | ADAM23 | AEN | AKAP13 | AMMECR1L | ANKS1B |
| AARSD1 | ACBD7 | ADAM33 | AFAP1 | AKAP8 | AMN1 | ANKS3 |
| AASDH | ACCN1 | ADAM6 | AFARP1 | AKAP8L | AMOTL2 | ANKS4B |
| AASDHPPT | ACCN4 | ADAM8 | AFF1 | AKAP9 | AMPD2 | ANKS6 |
| AATF | ACCN5 | ADAM9 | AFF3 | AKD1 | AMPD3 | ANLN |
| AATK | ACCS | ADAMTS12 | AFG3L1 | AKIRIN1 | AMPH | ANO1 |
| ABCA1 | ACCSL | ADAMTS14 | AFG3L2 | AKR1A1 | AMZ2 | ANO10 |
| ABCA2 | ACD | ADAMTS15 | AGAP1 | AKR1B1 | ANAPC1 | ANO2 |
| ABCB9 | ACE | ADAMTS16 | AGAP11 | AKR1B15 | ANAPC11 | ANO5 |
| ABCC1 | ACIN1 | ADAMTS17 | AGAP3 | AKR1C2 | ANAPC7 | ANO6 |
| ABCC5 | ACLY | ADAMTS2 | AGBL3 | AKR1E2 | ANG | ANO7 |
| ABCC6P2 | ACN9 | ADAMTS20 | AGBL4 | AKR7A3 | ANGEL1 | ANO8 |
| ABCD3 | ACO2 | ADAMTS5 | AGER | AKT1 | ANGEL2 | ANO9 |
| ABCD4 | ACOT11 | ADAMTS7 | AGFG1 | AKT2 | ANGPT4 | ANP32A |
| ABCE1 | ACOT13 | ADAMTSL2 | AGK | AKT3 | ANK1 | ANP32B |
| ABCF3 | ACOT2 | ADAMTSL4 | AGMAT | ALAS1 | ANKDD1A | ANP32E |
| ABCG1 | ACOT4 | ADAP1 | AGPAT3 | ALCAM | ANKFY1 | ANTXR1 |
| ABCG2 | ACOT7 | ADAR | AGPAT4 | ALDH16A1 | ANKH | ANTXR2 |
| ABHD10 | ACOX1 | ADARB1 | AGPAT5 | ALDH3A2 | ANKHD1 | ANUBL1 |
| ABHD14A | ACOX3 | ADARB2 | AGPAT6 | ALDH5A1 | ANKLE1 | ANXA13 |
| ABHD2 | ACOXL | ADAT1 | AGPAT9 | ALDH7A1 | ANKLE2 | ANXA3 |
| ABHD5 | ACP1 | ADC | AGRN | ALDH9A1 | ANKRD10 | ANXA4 |
| ABHD6 | ACP6 | ADCK2 | AGTR1 | ALDOA | ANKRD11 | ANXA5 |
| ABI2 | ACSF3 | ADCK5 | AHCTF1 | ALG10B | ANKRD12 | ANXA6 |
| ABI3BP | ACSL1 | ADCY10 | AHCY | ALG14 | ANKRD16 | ANXA7 |
| ABL1 | ACSL3 | ADCY2 | AHCYL1 | ALG2 | ANKRD17 | ANXA9 |
| ABL2 | ACTB | ADCY3 | AHDC1 | ALG5 | ANKRD18A | AP1AR |
| ABLIM1 | ACTG1 | ADCY5 | AHI1 | ALG9 | ANKRD24 | AP1B1 |
| ABLIM2 | ACTL6A | ADCY9 | AHNAK | ALKBH2 | ANKRD26 | AP1M2 |
| ABO | ACTN1 | ADCYAP1 | AHNAK2 | ALKBH3 | ANKRD27 | AP2A2 |
| ABR | ACTN2 | ADD1 | AHR | ALKBH4 | ANKRD28 | AP2M1 |
| ABT1 | ACTN4 | ADD2 | AHRR | ALKBH5 | ANKRD30A | AP2S1 |
| ABTB1 | ACTR10 | ADD3 | AHSG | ALKBH7 | ANKRD30B | AP3B1 |
| ABTB2 | ACTR1A | ADH1C | AIG1 | ALMS1 | ANKRD32 | AP3B2 |
| ACAA1 | ACTR5 | ADH5 | AIM1 | ALOX12B | ANKRD33 | AP3D1 |
| ACAA2 | ACTR8 | ADM | AIMP2 | ALOX15 | ANKRD33B | AP3M1 |
| ACACA | ACVR1 | ADNP | AIP | ALOX5 | ANKRD34A | AP3M2 |
| ACACB | ACVR1B | ADPGK | AIRE | ALS2 | ANKRD36 | AP3S2 |
| ACAD10 | ACVR1C | ADPRHL1 | AJAP1 | ALS2CR4 | ANKRD39 | AP4E1 |
| AP4S1 | ARHGAP12 | ARMC6 | ATAD3A | ATP6V0C | B4GALT7 | BCL2 |
| APAF1 | ARHGAP15 | ARMC8 | ATAD3B | ATP6V0D1 | B9D1 | BCL2L11 |
| APBB2 | ARHGAP17 | ARMS2 | ATAD3C | ATP6V1B1 | BAALC | BCL6 |
| APBB3 | ARHGAP19 | ARNT2 | ATE1 | ATP6V1C2 | BACE2 | BCL7B |
| APC | ARHGAP20 | ARPC1B | ATF1 | ATP6V1E1 | BACH2 | BCLAF1 |
| APCDD1L | ARHGAP21 | ARPC2 | ATF2 | ATP6V1F | BAD | BCO2 |
| APH1A | ARHGAP22 | ARPC3 | ATF3 | ATP6V1G1 | BAG2 | BCR |
| APH1B | ARHGAP25 | ARPC4 | ATF4 | ATP6V1H | BAG5 | BDH2 |

Figure 15-1

| API5 | ARHGAP29 | ARPC5 | ATF6B | ATP8A1 | BAHCC1 | BDP1 |
|---|---|---|---|---|---|---|
| APITD1 | ARHGAP5 | ARPP19 | ATF7 | ATP8B2 | BAI1 | BEAN |
| APLF | ARHGAP9 | ARRB1 | ATF7IP | ATP8B3 | BAI3 | BECN1 |
| APLP1 | ARHGEF1 | ARRB2 | ATG12 | ATP9A | BAIAP2 | BEGAIN |
| APOA1BP | ARHGEF10 | ARRDC2 | ATG16L1 | ATPBD4 | BAIAP2L1 | BEND3 |
| APOA4 | ARHGEF11 | ARSA | ATG16L2 | ATPIF1 | BAIAP2L2 | BEND7 |
| APOB | ARHGEF12 | ARSB | ATG2B | ATR | BAK1 | BET1 |
| APOBEC3A | ARHGEF15 | ARSG | ATG5 | ATRN | BAMBI | BET1L |
| APOBEC3F | ARHGEF16 | ARSI | ATG7 | ATRNL1 | BANP | BFAR |
| APOBEC3G | ARHGEF17 | ARSK | ATHL1 | ATXN1 | BARHL2 | BHLHE23 |
| APOC1 | ARHGEF18 | ART3 | ATIC | ATXN1L | BARX2 | BHLHE40 |
| APOL1 | ARHGEF19 | ARVCF | ATL2 | ATXN2 | BAT1 | BICD1 |
| APOL6 | ARHGEF2 | ASAH1 | ATL3 | ATXN2L | BAT2 | BICD2 |
| APOLD1 | ARHGEF3 | ASAH2B | ATM | ATXN3 | BAT2L1 | BIK |
| APOM | ARHGEF4 | ASAP1 | ATOH8 | ATXN7 | BAT2L2 | BIN3 |
| APP | ARHGEF7 | ASAP1IT1 | ATP11A | ATXN7L1 | BAT3 | BIRC2 |
| APPL1 | ARID1A | ASAP2 | ATP11B | ATXN7L3 | BAT4 | BIRC5 |
| APPL2 | ARID1B | ASAP3 | ATP13A1 | AUH | BAT5 | BIRC6 |
| APRT | ARID3A | ASB1 | ATP13A2 | AURKA | BATF3 | BIVM |
| APTX | ARID4A | ASB13 | ATP1A1 | AURKAIP1 | BAX | BLCAP |
| AQP10 | ARID5A | ASB18 | ATP1A2 | AUTS2 | BAZ1A | BLM |
| AQR | ARID5B | ASB6 | ATP1B1 | AVEN | BAZ2A | BLMH |
| ARAP1 | ARIH2 | ASB7 | ATP1B2 | AVL9 | BBC3 | BLOC1S2 |
| ARAP2 | ARL1 | ASF1B | ATP1B3 | AVPR1B | BBS10 | BLVRA |
| ARAP3 | ARL10 | ASGR1 | ATP2A2 | AXIN1 | BBS2 | BLZF1 |
| ARC | ARL11 | ASH2L | ATP2B2 | AXIN2 | BBS5 | BMF |
| ARCN1 | ARL15 | ASL | ATP2B4 | AXL | BBS9 | BMP2 |
| ARF1 | ARL2 | ASNS | ATP5B | AZI1 | BBX | BMP2K |
| ARF3 | ARL2BP | ASNSD1 | ATP5C1 | B2M | BCAP29 | BMP4 |
| ARF4 | ARL3 | ASPDH | ATP5D | B3GALNT2 | BCAR1 | BMP6 |
| ARF5 | ARL6 | ASPM | ATP5EP2 | B3GALT4 | BCAR3 | BMP7 |
| ARFGAP2 | ARL6IP1 | ASPSCR1 | ATP5G1 | B3GALTL | BCAS2 | BMP8A |
| ARFGAP3 | ARL6IP4 | ASRGL1 | ATP5G2 | B3GAT2 | BCAS3 | BMPER |
| ARFGEF1 | ARL6IP5 | ASS1 | ATP5H | B3GAT3 | BCAT1 | BMPR1A |
| ARFIP1 | ARL6IP6 | ASTN1 | ATP5J | B3GNT1 | BCAT2 | BMPR2 |
| ARGFX | ARL8A | ASXL1 | ATP5L | B3GNT7 | BCCIP | BMS1 |
| ARGLU1 | ARL8B | ASXL2 | ATP5SL | B3GNTL1 | BCDIN3D | BNC2 |
| ARHGAP1 | ARMC10 | ATAD1 | ATP6V0A2 | B4GALNT1 | BCL10 | BNIP1 |
| ARHGAP10 | ARMC5 | ATAD2 | ATP6V0B | B4GALNT3 | BCL11A | BNIP2 |
| BNIP3 | BTRC | C11orf83 | C14orf28 | C17orf80 | C1orf151 | C20orf199 |
| BOC | BUB1 | C11orf9 | C14orf38 | C17orf82 | C1orf152 | C20orf20 |
| BOD1L | BUB1B | C11orf91 | C14orf39 | C17orf85 | C1orf156 | C20orf26 |
| BOLA1 | BUB3 | C11orf92 | C14orf43 | C17orf89 | C1orf159 | C20orf27 |
| BOLA3 | BUD13 | C12orf11 | C14orf45 | C17orf90 | C1orf173 | C20orf29 |
| BOP1 | BUD31 | C12orf23 | C14orf68 | C17orf93 | C1orf183 | C20orf3 |
| BPHL | BZRAP1 | C12orf26 | C14orf72 | C17orf95 | C1orf187 | C20orf30 |
| BPNT1 | BZW1 | C12orf34 | C14orf93 | C17orf96 | C1orf190 | C20orf43 |
| BPTF | BZW2 | C12orf35 | C15orf37 | C17orf98 | C1orf198 | C20orf46 |
| BRCA1 | C10orf114 | C12orf41 | C15orf42 | C18orf10 | C1orf200 | C20orf7 |
| BRCA2 | C10orf119 | C12orf42 | C15orf51 | C18orf18 | C1orf201 | C20orf94 |
| BRD1 | C10orf129 | C12orf45 | C15orf59 | C18orf19 | C1orf203 | C21orf129 |
| BRD2 | C10orf131 | C12orf49 | C15orf60 | C18orf20 | C1orf212 | C21orf15 |
| BRD3 | C10orf137 | C12orf5 | C16orf35 | C18orf21 | C1orf213 | C21orf33 |
| BRD8 | C10orf140 | C12orf50 | C16orf42 | C18orf22 | C1orf216 | C21orf59 |
| BRF1 | C10orf18 | C12orf53 | C16orf46 | C18orf34 | C1orf220 | C21orf63 |

Figure 15-2

| | | | | | | |
|---|---|---|---|---|---|---|
| BRI3 | C10orf2 | C12orf56 | C16orf53 | C18orf54 | C1orf229 | C21orf66 |
| BRI3BP | C10orf32 | C12orf57 | C16orf55 | C18orf55 | C1orf25 | C21orf70 |
| BRIX1 | C10orf4 | C12orf59 | C16orf57 | C19orf10 | C1orf35 | C21orf91 |
| BRMS1 | C10orf41 | C12orf61 | C16orf58 | C19orf12 | C1orf53 | C22orf13 |
| BRMS1L | C10orf46 | C12orf65 | C16orf62 | C19orf20 | C1orf55 | C22orf23 |
| BRP44 | C10orf58 | C12orf66 | C16orf65 | C19orf22 | C1orf56 | C22orf24 |
| BRP44L | C10orf67 | C12orf68 | C16orf67 | C19orf25 | C1orf57 | C22orf26 |
| BRPF1 | C10orf75 | C12orf73 | C16orf68 | C19orf28 | C1orf58 | C22orf28 |
| BRPF3 | C10orf76 | C13orf1 | C16orf7 | C19orf29 | C1orf59 | C22orf32 |
| BRSK2 | C10orf78 | C13orf18 | C16orf70 | C19orf36 | C1orf66 | C22orf36 |
| BRUNOL4 | C10orf79 | C13orf23 | C16orf71 | C19orf39 | C1orf70 | C22orf40 |
| BRUNOL5 | C10orf93 | C13orf27 | C16orf72 | C19orf40 | C1orf74 | C22orf46 |
| BRUNOL6 | C11orf10 | C13orf31 | C16orf75 | C19orf41 | C1orf83 | C22orf9 |
| BRWD1 | C11orf17 | C13orf35 | C16orf80 | C19orf48 | C1orf85 | C2CD4A |
| BSCL2 | C11orf2 | C13orf37 | C16orf87 | C19orf51 | C1orf86 | C2CD4D |
| BSX | C11orf20 | C14orf101 | C16orf90 | C19orf52 | C1orf89 | C2orf14 |
| BTBD1 | C11orf21 | C14orf102 | C16orf92 | C19orf55 | C1orf9 | C2orf15 |
| BTBD10 | C11orf30 | C14orf104 | C17orf100 | C19orf57 | C1orf92 | C2orf27A |
| BTBD12 | C11orf34 | C14orf106 | C17orf101 | C19orf6 | C1orf93 | C2orf27B |
| BTBD2 | C11orf48 | C14orf126 | C17orf104 | C19orf66 | C1orf95 | C2orf28 |
| BTBD7 | C11orf49 | C14orf133 | C17orf106 | C19orf69 | C1QA | C2orf29 |
| BTBD9 | C11orf51 | C14orf135 | C17orf42 | C1GALT1 | C1QL1 | C2orf42 |
| BTC | C11orf54 | C14orf138 | C17orf48 | C1orf101 | C1QL2 | C2orf43 |
| BTD | C11orf57 | C14orf142 | C17orf51 | C1orf103 | C1QL3 | C2orf52 |
| BTF3 | C11orf58 | C14orf145 | C17orf53 | C1orf107 | C1QL4 | C2orf53 |
| BTG1 | C11orf67 | C14orf147 | C17orf56 | C1orf109 | C20orf111 | C2orf58 |
| BTG3 | C11orf68 | C14orf149 | C17orf57 | C1orf110 | C20orf117 | C2orf60 |
| BTN2A1 | C11orf71 | C14orf162 | C17orf62 | C1orf113 | C20orf12 | C2orf61 |
| BTN2A2 | C11orf75 | C14orf174 | C17orf66 | C1orf115 | C20orf151 | C2orf62 |
| BTN3A2 | C11orf80 | C14orf182 | C17orf70 | C1orf124 | C20orf152 | C2orf64 |
| BTNL2 | C11orf82 | C14orf21 | C17orf77 | C1orf125 | C20orf196 | C2orf68 |
| C2orf69 | C5orf37 | C7orf20 | C9orf69 | CAMK2N1 | CBLL1 | CCDC46 |
| C2orf70 | C5orf39 | C7orf23 | C9orf82 | CAMK4 | CBLN1 | CCDC47 |
| C2orf71 | C5orf43 | C7orf25 | C9orf85 | CAMKK2 | CBLN3 | CCDC49 |
| C2orf73 | C5orf44 | C7orf26 | C9orf86 | CAMSAP1 | CBR4 | CCDC51 |
| C2orf74 | C5orf45 | C7orf27 | C9orf89 | CAMSAP1L1 | CBS | CCDC55 |
| C2orf77 | C5orf51 | C7orf36 | C9orf93 | CAMTA1 | CBX1 | CCDC57 |
| C2orf81 | C5orf52 | C7orf38 | C9orf98 | CAMTA2 | CBX2 | CCDC59 |
| C2orf82 | C5orf62 | C7orf40 | CA12 | CAND1 | CBX3 | CCDC6 |
| C2orf88 | C6orf1 | C7orf41 | CA13 | CAND2 | CBX4 | CCDC60 |
| C2orf89 | C6orf10 | C7orf44 | CA4 | CANT1 | CBX6 | CCDC61 |
| C3orf1 | C6orf103 | C7orf46 | CA5A | CANX | CBX8 | CCDC62 |
| C3orf17 | C6orf108 | C7orf49 | CAB39L | CAP1 | CC2D1A | CCDC64 |
| C3orf18 | C6orf118 | C7orf50 | CABC1 | CAPN1 | CC2D1B | CCDC64B |
| C3orf19 | C6orf122 | C7orf51 | CABIN1 | CAPN10 | CCAR1 | CCDC66 |
| C3orf24 | C6orf125 | C7orf52 | CABLES1 | CAPNS1 | CCBE1 | CCDC7 |
| C3orf54 | C6orf126 | C7orf57 | CABLES2 | CAPRIN1 | CCDC105 | CCDC72 |
| C3orf57 | C6orf129 | C7orf59 | CABP7 | CAPS2 | CCDC106 | CCDC77 |
| C3orf58 | C6orf130 | C7orf60 | CABYR | CAPZA1 | CCDC107 | CCDC79 |
| C3orf63 | C6orf134 | C7orf61 | CACHD1 | CARD10 | CCDC109B | CCDC83 |
| C3orf71 | C6orf136 | C7orf64 | CACNA1A | CARD11 | CCDC111 | CCDC84 |
| C3orf72 | C6orf145 | C7orf70 | CACNA1C | CARD6 | CCDC12 | CCDC85A |
| C3orf75 | C6orf147 | C7orf71 | CACNA1D | CARHSP1 | CCDC121 | CCDC85B |
| C3orf77 | C6orf150 | C8G | CACNA1G | CARM1 | CCDC122 | CCDC86 |
| C4orf10 | C6orf163 | C8orf12 | CACNA2D2 | CARS | CCDC123 | CCDC88A |

Figure 15-3

| | | | | | | |
|---|---|---|---|---|---|---|
| C4orf14 | C6orf167 | C8orf33 | CACNB2 | CARS2 | CCDC126 | CCDC88B |
| C4orf21 | C6orf168 | C8orf37 | CACNG2 | CASC1 | CCDC129 | CCDC88C |
| C4orf22 | C6orf192 | C8orf38 | CACNG4 | CASC5 | CCDC13 | CCDC90B |
| C4orf23 | C6orf195 | C8orf40 | CACNG8 | CASD1 | CCDC134 | CCDC92 |
| C4orf29 | C6orf203 | C8orf42 | CACYBP | CASKIN1 | CCDC135 | CCDC93 |
| C4orf3 | C6orf204 | C8orf55 | CAD | CASKIN2 | CCDC136 | CCDC96 |
| C4orf32 | C6orf217 | C8orf59 | CADPS2 | CASP1 | CCDC137 | CCHCR1 |
| C4orf33 | C6orf218 | C8orf76 | CAGE1 | CASP10 | CCDC144B | CCKAR |
| C4orf34 | C6orf221 | C9 | CALB1 | CASP2 | CCDC146 | CCKBR |
| C4orf36 | C6orf226 | C9orf102 | CALCA | CASP4 | CCDC148 | CCL18 |
| C4orf41 | C6orf25 | C9orf106 | CALCB | CASP7 | CCDC15 | CCL23 |
| C4orf42 | C6orf27 | C9orf116 | CALCOCO2 | CASP8AP2 | CCDC151 | CCL3 |
| C4orf48 | C6orf41 | C9orf122 | CALHM2 | CASP9 | CCDC157 | CCL5 |
| C4orf51 | C6orf47 | C9orf130 | CALM1 | CAST | CCDC163P | CCNA2 |
| C4orf52 | C6orf48 | C9orf140 | CALM3 | CASZ1 | CCDC21 | CCND1 |
| C4orf6 | C6orf52 | C9orf163 | CALN1 | CATSPER2 | CCDC25 | CCND2 |
| C5orf13 | C6orf64 | C9orf171 | CALR | CATSPER4 | CCDC28A | CCND3 |
| C5orf24 | C6orf70 | C9orf21 | CALU | CATSPERG | CCDC34 | CCNDBP1 |
| C5orf27 | C6orf72 | C9orf25 | CAMK1 | CAV1 | CCDC37 | CCNE2 |
| C5orf28 | C6orf81 | C9orf3 | CAMK1D | CBFA2T3 | CCDC40 | CCNF |
| C5orf33 | C6orf94 | C9orf4 | CAMK2B | CBFB | CCDC42 | CCNJL |
| C5orf34 | C7orf10 | C9orf41 | CAMK2D | CBLB | CCDC42B | CCNL1 |
| C5orf36 | C7orf13 | C9orf64 | CAMK2G | CBLC | CCDC45 | CCNL2 |
| CCNO | CDC25A | CDKN1C | CEP55 | CHRNA1 | CLK2P | CNTNAP2 |
| CCNT1 | CDC25B | CDKN2AIP | CEP57 | CHRNB1 | CLK3 | CNTNAP4 |
| CCNY | CDC25C | CDKN2BAS | CEP63 | CHRNB2 | CLK4 | COASY |
| CCNYL1 | CDC26 | CDKN2C | CEP68 | CHST1 | CLN3 | COBL |
| CCR1 | CDC27 | CDKN3 | CEP72 | CHST10 | CLN8 | COBRA1 |
| CCR6 | CDC42BPA | CDNF | CEP76 | CHST11 | CLOCK | COG1 |
| CCRN4L | CDC42BPB | CDO1 | CEP97 | CHST12 | CLP1 | COG2 |
| CCT3 | CDC42BPG | CDRT15P | CES3 | CHST15 | CLPB | COG3 |
| CCT5 | CDC42EP2 | CDV3 | CETN3 | CHST2 | CLPP | COG4 |
| CCT6A | CDC42EP3 | CDX2 | CFDP1 | CHST6 | CLPTM1 | COG5 |
| CCT6B | CDC42EP4 | CDYL | CFL1 | CHSY1 | CLPX | COG6 |
| CCT6P1 | CDC42EP5 | CEACAM16 | CFL2 | CHTF8 | CLSPN | COG7 |
| CCT7 | CDC42SE1 | CEACAM21 | CFLAR | CHUK | CLTA | COIL |
| CCT8 | CDC42SE2 | CEACAM5 | CGB2 | CHURC1 | CLTC | COL11A2 |
| CD163L1 | CDC7 | CEBPB | CGGBP1 | CIB1 | CLUAP1 | COL12A1 |
| CD164 | CDC73 | CEBPG | CGRRF1 | CIDEA | CLUL1 | COL18A1 |
| CD226 | CDCA2 | CEBPZ | CH25H | CIITA | CLVS2 | COL1A1 |
| CD248 | CDCA4 | CECR4 | CHAC1 | CINP | CLYBL | COL1A2 |
| CD276 | CDCA7 | CECR6 | CHAF1A | CIRBP | CMBL | COL22A1 |
| CD2BP2 | CDCA8 | CECR7 | CHCHD1 | CISD1 | CMC1 | COL25A1 |
| CD300LB | CDCP1 | CELA2A | CHCHD2 | CISH | CMIP | COL29A1 |
| CD320 | CDH11 | CELA3A | CHCHD3 | CIT | CMPK1 | COL2A1 |
| CD34 | CDH13 | CELA3B | CHCHD5 | CITED2 | CMPK2 | COL5A1 |
| CD38 | CDH15 | CELSR1 | CHCHD6 | CKAP2 | CMTM7 | COL5A3 |
| CD3E | CDH23 | CELSR3 | CHCHD8 | CKAP2L | CN5H6.4 | COL6A2 |
| CD3EAP | CDH24 | CENPA | CHD3 | CKAP5 | CNBD1 | COL9A3 |
| CD4 | CDH26 | CENPB | CHD5 | CKB | CNBP | COLEC12 |
| CD44 | CDH5 | CENPBD1 | CHD6 | CKLF | CNDP2 | COMMD1 |
| CD46 | CDK11A | CENPC1 | CHD7 | CKS1B | CNFN | COMMD10 |
| CD48 | CDK11B | CENPE | CHEK1 | CKS2 | CNKSR3 | COMMD4 |
| CD55 | CDK12 | CENPF | CHERP | CLASP1 | CNN2 | COMMD5 |
| CD58 | CDK13 | CENPH | CHFR | CLCA4 | CNNM2 | COPB2 |

Figure 15-4

| | | | | | | |
|---|---|---|---|---|---|---|
| CD59 | CDK14 | CENPK | CHIC2 | CLCN2 | CNNM3 | COPE |
| CD81 | CDK17 | CENPL | CHID1 | CLCN6 | CNO | COPG |
| CD83 | CDK19 | CENPN | CHKA | CLCNKB | CNOT10 | COPS6 |
| CD8A | CDK2AP2 | CENPO | CHKB | CLDN19 | CNOT2 | COPS7B |
| CD9 | CDK4 | CENPQ | CHKB-CPT1B | CLDN3 | CNOT3 | COQ10A |
| CD96 | CDK5 | CENPT | CHL1 | CLDND2 | CNOT6 | COQ10B |
| CD97 | CDK5R1 | CENPV | CHMP2A | CLEC12B | CNOT8 | COQ3 |
| CDADC1 | CDK5RAP1 | CEP120 | CHMP2B | CLEC16A | CNP | COQ4 |
| CDAN1 | CDK6 | CEP135 | CHMP7 | CLEC17A | CNPY2 | COQ6 |
| CDC14A | CDK7 | CEP152 | CHN2 | CLIC1 | CNPY3 | COQ7 |
| CDC14B | CDK8 | CEP164 | CHP | CLIC4 | CNR2 | CORO1A |
| CDC14C | CDKAL1 | CEP170 | CHPF2 | CLIC6 | CNRIP1 | CORO1B |
| CDC20 | CDKL2 | CEP192 | CHPT1 | CLIP2 | CNST | CORO6 |
| CDC20B | CDKN1A | CEP250 | CHRAC1 | CLIP4 | CNTN4 | CORO7 |
| CDC23 | CDKN1B | CEP350 | CHRM5 | CLK1 | CNTN5 | COX10 |
| COX11 | CROCCL2 | CTNNA1 | CYBASC3 | DAXX | DDX1 | DGCR9 |
| COX15 | CRTAC1 | CTNNA2 | CYCS | DAZAP1 | DDX10 | DGKD |
| COX16 | CRTAP | CTNNA3 | CYCSP52 | DAZAP2 | DDX11 | DGKE |
| COX18 | CRTC1 | CTNNAL1 | CYFIP1 | DBF4B | DDX12 | DGKH |
| COX5B | CRTC2 | CTNNB1 | CYFIP2 | DBH | DDX17 | DGKI |
| COX6A1 | CRX | CTNNBIP1 | CYLD | DBI | DDX19A | DGKZ |
| COX6B1 | CRY2 | CTNND2 | CYP11A1 | DBNDD1 | DDX20 | DHCR24 |
| COX7A2L | CRYGC | CTNS | CYP17A1 | DBNDD2 | DDX21 | DHODH |
| COX7B2 | CRYGN | CTPS | CYP1A1 | DBNL | DDX24 | DHPS |
| COX8A | CRYL1 | CTR9 | CYP1B1 | DBP | DDX27 | DHRS12 |
| CPAMD8 | CRYM | CTRC | CYP20A1 | DBX1 | DDX28 | DHRS13 |
| CPEB3 | CSAD | CTSA | CYP26A1 | DCAF10 | DDX31 | DHRS2 |
| CPEB4 | CSDAP1 | CTSB | CYP26B1 | DCAF12 | DDX39 | DHRS3 |
| CPLX1 | CSDE1 | CTSC | CYP27A1 | DCAF13 | DDX41 | DHRS7B |
| CPN2 | CSE1L | CTSO | CYP2A6 | DCAF4 | DDX42 | DHRS7C |
| CPNE1 | CSF1 | CTSZ | CYP2A7 | DCAF4L1 | DDX49 | DHRS9 |
| CPNE7 | CSF1R | CTTN | CYP2C9 | DCAF5 | DDX50 | DHX16 |
| CPOX | CSF2RB | CTTNBP2NL | CYP2F1 | DCAF6 | DDX51 | DHX29 |
| CPSF1 | CSGALNACT2 | CTU1 | CYP2R1 | DCAF7 | DDX54 | DHX33 |
| CPSF3 | CSHL1 | CTXN1 | CYP3A4 | DCAF8 | DDX59 | DHX34 |
| CPSF3L | CSK | CUBN | CYP3A43 | DCAKD | DDX60 | DHX35 |
| CPSF6 | CSMD1 | CUEDC2 | CYP3A5 | DCBLD1 | DECR2 | DHX36 |
| CPT1A | CSMD2 | CUGBP1 | CYP4F12 | DCHS1 | DEF8 | DHX37 |
| CPT2 | CSMD3 | CUL2 | CYP4F2 | DCHS2 | DEFB125 | DHX38 |
| CPZ | CSNK1D | CUL3 | CYP4F3 | DCK | DEFB132 | DHX58 |
| CR1 | CSNK1E | CUL4A | CYP4V2 | DCLK1 | DEK | DHX8 |
| CR1L | CSNK2A1 | CUL5 | CYP4Z2P | DCLRE1B | DENND1A | DHX9 |
| CRABP2 | CSPG4 | CUL7 | CYP51A1 | DCLRE1C | DENND2A | DIABLO |
| CRAMP1L | CSPG5 | CUL9 | CYTH1 | DCP1A | DENND2C | DICER1 |
| CRB2 | CSPP1 | CUTA | CYTH2 | DCP1B | DENND3 | DIDO1 |
| CRBN | CSRNP2 | CUX1 | CYTH3 | DCP2 | DENND4B | DIMT1L |
| CRCP | CSRP1 | CUX2 | CYTSA | DCTD | DENND4C | DIP2B |
| CREB3L2 | CSRP2 | CXCL3 | CYTSB | DCTN5 | DEPDC1B | DIP2C |
| CREB5 | CST2 | CXCR1 | D2HGDH | DCTN6 | DEPDC5 | DIRC2 |
| CREBBP | CST3 | CXCR2 | DAAM1 | DCTPP1 | DEPDC7 | DIS3 |
| CREBL2 | CST4 | CXCR4 | DAB1 | DCUN1D1 | DERL1 | DISC1 |
| CREG1 | CST6 | CXCR7 | DAB2IP | DCUN1D3 | DERL2 | DKFZP434H168 |
| CRELD1 | CSTF1 | CXXC1 | DACH1 | DCUN1D4 | DERL3 | DKFZp686A1627 |
| CREM | CSTF3 | CXXC4 | DACT3 | DDA1 | DET1 | DKFZp686O24166 |
| CRHR1 | CTAGE5 | CXXC5 | DAD1 | DDAH1 | DEXI | DKKL1 |

Figure 15-5

| CRIP2 | CTBP1 | CYB561 | DAGLB | DDB2 | DGAT1 | DLAT |
|---|---|---|---|---|---|---|
| CRISPLD2 | CTBP2 | CYB5B | DAK | DDC | DGAT2 | DLC1 |
| CRKL | CTBS | CYB5D2 | DALRD3 | DDHD2 | DGCR14 | DLD |
| CRLS1 | CTDSPL | CYB5R1 | DAND5 | DDN | DGCR2 | DLEU1 |
| CRMP1 | CTDSPL2 | CYB5R3 | DAP | DDO | DGCR5 | DLG2 |
| CRNKL1 | CTF1 | CYB5R4 | DAP3 | DDOST | DGCR6L | DLG4 |
| CROCC | CTH | CYBA | DARS | DDR1 | DGCR8 | DLGAP1 |
| DLGAP2 | DNM1P35 | DST | EBF1 | EGFL8 | ELF3 | EPC1 |
| DLGAP3 | DNM2 | DSTN | EBF3 | EGLN2 | ELFN2 | EPCAM |
| DLGAP4 | DNM3 | DTD1 | EBPL | EGR1 | ELK3 | EPDR1 |
| DLGAP5 | DNMT1 | DTNB | ECD | EHBP1 | ELL | EPHA1 |
| DLK1 | DNMT3A | DTNBP1 | ECE1 | EHBP1L1 | ELL2 | EPHA2 |
| DLK2 | DNPEP | DTWD1 | ECEL1 | EHD1 | ELL3 | EPHA3 |
| DLL1 | DNTTIP2 | DTWD2 | ECEL1P2 | EHD3 | ELMO1 | EPHA6 |
| DLL3 | DOC2A | DTX3 | ECHDC3 | EHD4 | ELMO2 | EPHA7 |
| DLL4 | DOC2B | DTX4 | ECHS1 | EHMT1 | ELMOD3 | EPHA8 |
| DLX3 | DOCK1 | DTYMK | EDC4 | EHMT2 | ELOF1 | EPHB1 |
| DLX5 | DOCK2 | DUOX1 | EDEM1 | EID2 | ELOVL1 | EPHB3 |
| DLX6AS | DOCK5 | DUS2L | EDEM2 | EID2B | ELOVL2 | EPHB4 |
| DMBT1 | DOCK6 | DUS3L | EDEM3 | EIF1AD | ELOVL5 | EPHB6 |
| DMKN | DOCK7 | DUSP1 | EDF1 | EIF1B | ELOVL6 | EPHX1 |
| DMP1 | DOK5 | DUSP11 | EDIL3 | EIF2AK2 | ELOVL7 | EPHX3 |
| DMPK | DOLK | DUSP14 | EDN1 | EIF2AK3 | ELP2 | EPHX4 |
| DMRTA2 | DOLPP1 | DUSP18 | EDNRB | EIF2AK4 | ELP2P | EPM2AIP1 |
| DMTF1 | DOM3Z | DUSP28 | EEA1 | EIF2B1 | ELP3 | EPN2 |
| DMXL1 | DPAGT1 | DUSP4 | EED | EIF2B4 | ELP4 | EPO |
| DMXL2 | DPEP2 | DUSP5 | EEF1A1 | EIF2C1 | EME1 | EPPK1 |
| DNA2 | DPEP3 | DUSP5P | EEF1A2 | EIF2C2 | EMID1 | EPS8 |
| DNAH1 | DPF1 | DUSP6 | EEF1B2 | EIF2C3 | EMID2 | EPS8L2 |
| DNAH12 | DPF3 | DUSP7 | EEF1D | EIF2S1 | EMILIN2 | ERAL1 |
| DNAI1 | DPH1 | DUT | EEF1DP3 | EIF2S2 | EMILIN3 | ERBB2IP |
| DNAJA2 | DPH2 | DVL2 | EEF1E1 | EIF3A | EML3 | ERBB3 |
| DNAJB1 | DPH3 | DVL3 | EEF1G | EIF3D | EMX1 | ERBB4 |
| DNAJB13 | DPH3B | DYDC2 | EEF2 | EIF3F | EMX2 | ERC2 |
| DNAJB14 | DPM2 | DYM | EEFSEC | EIF3J | ENAH | ERCC3 |
| DNAJB2 | DPM3 | DYNC1H1 | EEPD1 | EIF3K | ENC1 | ERCC5 |
| DNAJB6 | DPP3 | DYNC1I1 | EFCAB1 | EIF3M | ENDOD1 | ERCC6 |
| DNAJC1 | DPP6 | DYNC1I2 | EFCAB4A | EIF4A1 | ENDOG | ERF |
| DNAJC10 | DPP9 | DYNC1LI1 | EFCAB5 | EIF4A2 | ENGASE | ERGIC2 |
| DNAJC13 | DPPA2 | DYNLL1 | EFCAB6 | EIF4B | ENO3 | ERGIC3 |
| DNAJC21 | DPY19L1 | DYNLL2 | EFCAB7 | EIF4E | ENOPH1 | ERI1 |
| DNAJC27 | DPY19L2P2 | DYNLT1 | EFCAB9 | EIF4E3 | ENPP1 | ERI3 |
| DNAJC28 | DPY19L2P4 | DYRK1B | EFEMP2 | EIF4EBP2 | ENPP7 | ERLIN1 |
| DNAJC4 | DPY19L4 | DYRK2 | EFHA1 | EIF4ENIF1 | ENSA | ERLIN2 |
| DNAJC5 | DPYD | DYRK3 | EFHA2 | EIF4G3 | ENTPD4 | ERN1 |
| DNAJC7 | DPYSL2 | DZIP1 | EFHD1 | EIF4H | ENTPD6 | ERO1LB |
| DNAJC8 | DPYSL4 | DZIP1L | EFNA1 | EIF5 | ENY2 | ERP29 |
| DNAL4 | DPYSL5 | E2F1 | EFNA2 | EIF5A | EP400 | ERP44 |
| DNASE2 | DR1 | E2F3 | EFNA3 | EIF5B | EP400NL | ESAM |
| DND1 | DRAM1 | E2F6 | EFNA5 | EIF6 | EPAS1 | ESF1 |
| DNER | DSCR3 | E2F8 | EFNB2 | ELAC2 | EPB41 | ESPL1 |
| DNLZ | DSE | E4F1 | EFR3B | ELANE | EPB41L1 | ESPN |
| DNM1 | DSN1 | EARS2 | EFTUD1 | ELAVL1 | EPB41L2 | ESR1 |
| DNM1L | DSP | EBAG9 | EFTUD2 | ELF2 | EPB49 | ESR2 |
| ESRRA | FADS1 | FAM157A | FAM46C | FASTK | FDFT1 | FLJ22536 |

Figure 15-6

| ESRRB | FADS6 | FAM158A | FAM47E | FASTKD2 | FDPS | FLJ25363 |
|---|---|---|---|---|---|---|
| ESYT2 | FAF1 | FAM159A | FAM48A | FASTKD5 | FDXR | FLJ31306 |
| ESYT3 | FAF2 | FAM159B | FAM49B | FAT1 | FECH | FLJ33630 |
| ETAA1 | FAH | FAM160A2 | FAM53A | FAT2 | FEM1A | FLJ35220 |
| ETFDH | FAHD1 | FAM161B | FAM53B | FAU | FEM1B | FLJ36777 |
| ETHE1 | FAHD2A | FAM162A | FAM53C | FBLIM1 | FER1L4 | FLJ39582 |
| ETNK1 | FAHD2B | FAM162B | FAM54B | FBLN1 | FERMT2 | FLJ41856 |
| ETS1 | FAIM | FAM163A | FAM55C | FBLN2 | FERMT3 | FLJ42709 |
| ETS2 | FAM100A | FAM168B | FAM55D | FBLN7 | FEZF1 | FLJ43390 |
| ETV1 | FAM100B | FAM169A | FAM57A | FBRSL1 | FGD3 | FLJ43663 |
| ETV2 | FAM101A | FAM171A2 | FAM59A | FBXL12 | FGD5 | FLJ44606 |
| ETV6 | FAM101B | FAM175A | FAM60A | FBXL13 | FGD6 | FLJ45079 |
| EVC2 | FAM103A1 | FAM175B | FAM64A | FBXL14 | FGF11 | FLJ45244 |
| EVPL | FAM104A | FAM176A | FAM65A | FBXL16 | FGF12 | FLJ45983 |
| EVX1 | FAM105A | FAM180A | FAM65B | FBXL17 | FGF14 | FLJ90757 |
| EVX2 | FAM107B | FAM181B | FAM66B | FBXL18 | FGF18 | FLOT1 |
| EWSR1 | FAM108A1 | FAM183A | FAM69A | FBXL6 | FGF20 | FLOT2 |
| EXD3 | FAM108B1 | FAM183B | FAM72B | FBXL7 | FGF22 | FLT1 |
| EXO1 | FAM108C1 | FAM184A | FAM72D | FBXL8 | FGF3 | FLT3 |
| EXOC2 | FAM109A | FAM185A | FAM73B | FBXO11 | FGF8 | FLYWCH1 |
| EXOC4 | FAM10A4 | FAM186B | FAM76A | FBXO15 | FGF9 | FLYWCH2 |
| EXOC6 | FAM110A | FAM187B | FAM78A | FBXO18 | FGFBP2 | FMN1 |
| EXOC7 | FAM110B | FAM188A | FAM78B | FBXO22 | FGFR1 | FMNL1 |
| EXOC8 | FAM111A | FAM189A1 | FAM7A2 | FBXO22OS | FGFR1OP2 | FMO5 |
| EXOSC10 | FAM111B | FAM189B | FAM82A2 | FBXO24 | FGFR2 | FN3KRP |
| EXOSC4 | FAM113A | FAM18B | FAM82B | FBXO25 | FGFR4 | FNBP4 |
| EXOSC5 | FAM114A2 | FAM190A | FAM83H | FBXO28 | FGFRL1 | FNDC3A |
| EXOSC6 | FAM115A | FAM195B | FAM86A | FBXO30 | FGGY | FNDC3B |
| EXOSC9 | FAM115C | FAM198B | FAM86B1 | FBXO31 | FHIT | FNIP1 |
| EXPH5 | FAM116A | FAM19A5 | FAM86B2 | FBXO32 | FIBCD1 | FNIP2 |
| EXT1 | FAM117B | FAM20B | FAM89A | FBXO33 | FILIP1 | FNTA |
| EXTL3 | FAM118A | FAM20C | FAM89B | FBXO36 | FIS1 | FNTB |
| EYA3 | FAM119A | FAM21A | FAM91A1 | FBXO38 | FIZ1 | FOSB |
| EZH2 | FAM119B | FAM21C | FAM96A | FBXO46 | FKBP10 | FOSL1 |
| EZR | FAM120AOS | FAM32A | FAM96B | FBXO5 | FKBP14 | FOSL2 |
| F10 | FAM120B | FAM36A | FAM98A | FBXO6 | FKBP1A | FOXA1 |
| F12 | FAM122A | FAM38A | FANCA | FBXO7 | FKBP1B | FOXA2 |
| F13A1 | FAM125A | FAM38B | FANCC | FBXO8 | FKBP2 | FOXB1 |
| F13B | FAM125B | FAM3C | FANCE | FBXW4 | FKBP3 | FOXC1 |
| F2R | FAM128A | FAM3D | FANCF | FBXW9 | FKBP4 | FOXF1 |
| F2RL3 | FAM129A | FAM40A | FANK1 | FCAR | FKBPL | FOXJ3 |
| F3 | FAM131B | FAM40B | FAR1 | FCF1 | FLCN | FOXK1 |
| F7 | FAM13B | FAM41C | FARP1 | FCGRT | FLG | FOXK2 |
| FABP5 | FAM13C | FAM43A | FARSA | FCHO2 | FLII | FOXN3 |
| FABP6 | FAM149A | FAM43B | FAS | FCHSD2 | FLJ10038 | FOXN4 |
| FADD | FAM150A | FAM46A | FASN | FCRLA | FLJ11235 | FOXO1 |
| FOXO3 | FYTTD1 | GART | GGA3 | GLYCTK | GOLGA4 | GPSM2 |
| FOXP1 | FZD10 | GAS2 | GGCT | GM2A | GOLGA7 | GPSM3 |
| FOXP4 | FZD4 | GAS5 | GGH | GMCL1 | GOLGA7B | GPT |
| FOXR1 | FZD5 | GAS7 | GGPS1 | GMCL1L | GOLIM4 | GPX1 |
| FOXRED2 | FZD7 | GAS8 | GGT1 | GMDS | GOLPH3 | GPX6 |
| FPR1 | FZR1 | GATA2 | GGT5 | GMEB2 | GON4L | GRAMD1C |
| FPR2 | G2E3 | GATA3 | GGTLC1 | GMFB | GOPC | GRASP |
| FRAS1 | G3BP1 | GATA5 | GH1 | GMIP | GORASP1 | GRB2 |
| FRAT1 | G3BP2 | GATA6 | GH2 | GML | GORASP2 | GREB1 |

Figure 15-7

| FRAT2 | G6PC | GATAD2A | GHDC | GMPPA | GOSR2 | GREM1 |
|---|---|---|---|---|---|---|
| FREQ | GAA | GATAD2B | GHITM | GMPPB | GOT1 | GRHL2 |
| FRG1 | GAB2 | GATS | GHR | GMPR | GOT2 | GRHPR |
| FRG2B | GAB4 | GATSL3 | GIGYF1 | GMPR2 | GPATCH1 | GRIA1 |
| FRG2C | GABARAP | GBAP1 | GIMAP1 | GMPS | GPATCH3 | GRID1 |
| FRK | GABARAPL1 | GBAS | GIMAP4 | GNA11 | GPBAR1 | GRID2 |
| FRMD4A | GABARAPL2 | GBP3 | GIMAP7 | GNA13 | GPBP1 | GRID2IP |
| FRMD5 | GABARAPL3 | GBP4 | GIN1 | GNA14 | GPBP1L1 | GRIK4 |
| FRMD6 | GABBR1 | GBP5 | GINS1 | GNAI2 | GPC1 | GRIN1 |
| FRMD8 | GABPB1 | GBX1 | GINS3 | GNAI3 | GPC6 | GRIN2A |
| FRS3 | GABPB2 | GCAT | GIPC2 | GNAL | GPHN | GRIN2C |
| FRY | GABRA4 | GCDH | GIPR | GNAO1 | GPIHBP1 | GRIN2D |
| FRYL | GABRA5 | GCH1 | GIT2 | GNAQ | GPN1 | GRINA |
| FSCN1 | GABRB1 | GCLM | GJA3 | GNAS | GPN2 | GRINL1A |
| FSCN2 | GABRD | GCNT4 | GJA4 | GNASAS | GPN3 | GRIP2 |
| FSD1 | GABRG3 | GCNT7 | GJB2 | GNB1 | GPR108 | GRK4 |
| FSD1L | GAD2 | GCSH | GJB4 | GNB1L | GPR12 | GRK5 |
| FSTL3 | GADD45B | GDAP1 | GLB1 | GNB2 | GPR123 | GRK6 |
| FTHL3 | GAK | GDAP2 | GLB1L2 | GNB2L1 | GPR124 | GRM4 |
| FTL | GALC | GDE1 | GLB1L3 | GNB5 | GPR125 | GRM7 |
| FTO | GALE | GDF1 | GLCCI1 | GNE | GPR133 | GRM8 |
| FTSJD1 | GALK1 | GDF11 | GLI2 | GNG10 | GPR137 | GRN |
| FUBP1 | GALK2 | GDF6 | GLIS2 | GNG12 | GPR152 | GRPEL1 |
| FUCA1 | GALNT10 | GDF7 | GLIS3 | GNG2 | GPR153 | GRSF1 |
| FUCA2 | GALNT2 | GDI2 | GLO1 | GNG4 | GPR160 | GSK3A |
| FUK | GALNT3 | GDNF | GLOD4 | GNG7 | GPR177 | GSR |
| FUS | GALNT6 | GDPD1 | GLP1R | GNGT1 | GPR19 | GSTA1 |
| FUT10 | GALNT7 | GDPD5 | GLRA3 | GNL1 | GPR26 | GSTCD |
| FUT11 | GALNT8 | GEM | GLRX2 | GNL2 | GPR4 | GSTM4 |
| FUT2 | GALNTL4 | GEMIN6 | GLRX5 | GNMT | GPR45 | GSTO1 |
| FUT4 | GALNTL5 | GEN1 | GLS | GNPAT | GPR63 | GSTO2 |
| FUT6 | GALNTL6 | GFI1 | GLT1D1 | GNPNAT1 | GPR68 | GSTP1 |
| FUT8 | GAN | GFM1 | GLT25D2 | GNPTG | GPR89B | GSTZ1 |
| FUZ | GANC | GFM2 | GLTPD1 | GNRHR2 | GPRC5B | GSX2 |
| FXR1 | GAPDH | GFOD1 | GLTSCR2 | GNS | GPRC5C | GTDC1 |
| FXR2 | GAPDHS | GFPT2 | GLUD1 | GOLGA2 | GPRC5D | GTF2A1 |
| FXYD3 | GAPVD1 | GFRA2 | GLUL | GOLGA2L1 | GPS1 | GTF2B |
| FXYD5 | GARS | GGA2 | GLYATL1 | GOLGA3 | GPS2 | GTF2E2 |
| GTF2F2 | HAND1 | HELZ | HIST1H3C | HMGXB4 | HPGD | HVCN1 |
| GTF2H2C | HAND2 | HEMK1 | HIST1H3E | HMHA1 | HPS1 | HYAL1 |
| GTF2H4 | HARS | HERC1 | HIST1H3G | HMMR | HPS3 | HYAL3 |
| GTF2I | HAS1 | HERC2 | HIST1H3I | HMSD | HPS5 | HYAL4 |
| GTF3C1 | HAT1 | HERC3 | HIST1H3J | HMX3 | HPSE | HYI |
| GTF3C5 | HAUS3 | HERC5 | HIST1H4A | HN1L | HPSE2 | HYLS1 |
| GTF3C6 | HAUS6 | HERPUD2 | HIST1H4C | HNF1B | HPX | IAH1 |
| GTPBP1 | HAX1 | HES1 | HIST1H4E | HNRNPA0 | HRH4 | IBTK |
| GTPBP3 | HBP1 | HES4 | HIST1H4G | HNRNPA1L2 | HRK | ICA1 |
| GTPBP4 | HBXIP | HES6 | HIST1H4H | HNRNPA2B1 | HRNBP3 | ICA1L |
| GTPBP5 | HCCA2 | HEXA | HIST1H4J | HNRNPA3 | HS2ST1 | ICAM1 |
| GTPBP8 | HCFC1R1 | HEXB | HIST1H4K | HNRNPA3P1 | HS3ST1 | ICAM5 |
| GTSE1 | HCFC2 | HEXIM2 | HIST1H4L | HNRNPAB | HS3ST5 | ICK |
| GUCY1A2 | HCG18 | HEY2 | HIST2H2AB | HNRNPC | HS3ST6 | ID1 |
| GUCY2D | HCG22 | HFM1 | HIST2H2BE | HNRNPCL1 | HS6ST3 | ID2 |
| GUCY2E | HCG26 | HGD | HIST2H2BF | HNRNPD | HSD17B12 | ID2B |
| GUCY2G | HCG27 | HGFAC | HIST3H2A | HNRNPF | HSD17B4 | IDE |

Figure 15-8

| GUF1 | HCG4 | HGS | HIST3H3 | HNRNPH1 | HSD3B2 | IDH1 |
|---|---|---|---|---|---|---|
| GUK1 | HCG9 | HGSNAT | HIST4H4 | HNRNPH3 | HSDL1 | IDI1 |
| GULP1 | HCN1 | HHAT | HIVEP1 | HNRNPK | HSDL2 | IDUA |
| GUSB | HCN2 | HHEX | HIVEP3 | HNRNPL | HSF1 | IER2 |
| GUSBL2 | HCN4 | HHIPL1 | HK1 | HNRNPM | HSF2 | IER3 |
| GXYLT2 | HCP5 | HHLA3 | HK2 | HNRNPR | HSF2BP | IER3IP1 |
| GYG1 | HDAC1 | HIAT1 | HLA-A | HNRNPU | HSF4 | IER5 |
| GYPB | HDAC10 | HIBCH | HLA-B | HNRNPUL1 | HSP90AB1 | IFFO1 |
| GYPC | HDAC11 | HIC1 | HLA-C | HNRPDL | HSPA12B | IFI27L1 |
| GYS1 | HDAC2 | HIF1A | HLA-DMB | HOMER3 | HSPA13 | IFI27L2 |
| GZMM | HDAC4 | HIGD2B | HLA-DOA | HOOK1 | HSPA14 | IFI35 |
| H19 | HDAC5 | HILS1 | HLA-DPB1 | HOOK2 | HSPA1A | IFIT5 |
| H1F0 | HDAC7 | HINFP | HLA-DPB2 | HOXA1 | HSPA1B | IFITM2 |
| H1FX | HDDC2 | HIP1R | HLA-DQA1 | HOXA10 | HSPA1L | IFITM3 |
| H2AFJ | HDDC3 | HIPK1 | HLA-E | HOXA11AS | HSPA2 | IFNAR1 |
| H2AFV | HDGF | HIPK3 | HLA-F | HOXB13 | HSPA6 | IFNAR2 |
| H2AFX | HDGF2 | HIPK4 | HLA-G | HOXB2 | HSPA8 | IFNGR2 |
| H2AFY2 | HDGFRP3 | HIRIP3 | HLA-H | HOXB3 | HSPB1 | IFRD2 |
| H3F3A | HDHD2 | HIST1H1D | HLA-J | HOXB4 | HSPB6 | IFT122 |
| H3F3C | HEATR1 | HIST1H1E | HLA-L | HOXB7 | HSPBAP1 | IFT140 |
| H6PD | HEATR2 | HIST1H2AG | HMBS | HOXB8 | HSPD1 | IFT57 |
| HAAO | HEATR4 | HIST1H2AL | HMCN1 | HOXB9 | HSPE1 | IFT80 |
| HABP2 | HEATR6 | HIST1H2BA | HMG20A | HOXC11 | HSPG2 | IFT88 |
| HACE1 | HEATR7A | HIST1H2BD | HMGA2 | HOXD1 | HSPH1 | IGDCC4 |
| HACL1 | HEBP2 | HIST1H2BE | HMGB1 | HOXD11 | HTR6 | IGF1R |
| HADH | HECW1 | HIST1H2BF | HMGB1L1 | HOXD9 | HTR7 | IGF2BP1 |
| HADHB | HECW2 | HIST1H2BI | HMGB2 | HP1BP3 | HTRA3 | IGF2BP2 |
| HAGH | HELB | HIST1H2BJ | HMGCR | HPCA | HTT | IGF2BP3 |
| HAGHL | HELLS | HIST1H2BN | HMGN1 | HPCAL1 | HUNK | IGF2R |
| HAMP | HELQ | HIST1H3A | HMGN3 | HPCAL4 | HUS1 | IGFBP2 |
| IGFBP3 | INHA | IRF9 | JMJD1C | KCNK1 | KIAA0355 | KIAA1826 |
| IGFBP4 | INHBB | IRGM | JMJD5 | KCNK10 | KIAA0415 | KIAA1841 |
| IGFBP7 | INO80 | IRS1 | JMJD6 | KCNK12 | KIAA0427 | KIAA1875 |
| IGFL2 | INO80B | IRS2 | JMJD7-PLA2G4B | KCNK15 | KIAA0494 | KIAA1908 |
| IGFL3 | INO80D | IRX2 | JMY | KCNK4 | KIAA0528 | KIAA1949 |
| IGFL4 | INPP1 | IRX3 | JOSD1 | KCNK9 | KIAA0556 | KIAA1967 |
| IGFN1 | INPP4B | IRX4 | JPH1 | KCNMB2 | KIAA0649 | KIAA1984 |
| IGHMBP2 | INPP5A | ISCA1 | JPH3 | KCNMB4 | KIAA0652 | KIDINS220 |
| IGSF11 | INPP5B | ISCU | JRK | KCNN1 | KIAA0664 | KIF11 |
| IGSF3 | INPP5D | ISL1 | JTB | KCNQ1 | KIAA0754 | KIF13A |
| IGSF8 | INPP5F | ISLR | JUB | KCNQ3 | KIAA0892 | KIF13B |
| IGSF9B | INPPL1 | ISLR2 | JUN | KCNQ4 | KIAA0895 | KIF15 |
| IK | INSC | ISM1 | JUND | KCNQ5 | KIAA0895L | KIF16B |
| IKBIP | INS-IGF2 | ISOC1 | KANK2 | KCNT2 | KIAA0907 | KIF17 |
| IKBKB | INSM1 | ISPD | KANK4 | KCNU1 | KIAA0913 | KIF18A |
| IKZF1 | INSR | ITCH | KARS | KCTD13 | KIAA1009 | KIF18B |
| IKZF5 | INTS1 | ITGA1 | KAT2A | KCTD18 | KIAA1012 | KIF20B |
| IL12A | INTS12 | ITGA11 | KAT2B | KCTD2 | KIAA1026 | KIF21A |
| IL15 | INTS2 | ITGA2 | KATNAL1 | KCTD21 | KIAA1033 | KIF21B |
| IL15RA | INTS6 | ITGA9 | KATNAL2 | KCTD6 | KIAA1045 | KIF22 |
| IL17RA | INTS7 | ITGAD | KATNB1 | KCTD7 | KIAA1143 | KIF23 |
| IL17RC | INTS8 | ITGAE | KAZALD1 | KDELC1 | KIAA1191 | KIF26B |
| IL17RD | INTS9 | ITGAM | KBTBD11 | KDELC2 | KIAA1199 | KIF3B |
| IL1RAP | INVS | ITGAV | KBTBD3 | KDM2A | KIAA1211 | KIF3C |
| IL21R | IP6K1 | ITGB1BP1 | KBTBD4 | KDM2B | KIAA1244 | KIF5C |

Figure 15-9

| | | | | | | |
|---|---|---|---|---|---|---|
| IL26 | IP6K2 | ITGB2 | KBTBD6 | KDM3A | KIAA1279 | KIF6 |
| IL27RA | IPMK | ITGB3BP | KBTBD7 | KDM3B | KIAA1310 | KIF9 |
| IL28RA | IPO4 | ITGB4 | KBTBD8 | KDM4A | KIAA1324L | KIFC1 |
| IL6ST | IPO7 | ITGB5 | KCNA3 | KDM4B | KIAA1328 | KIFC3 |
| IL7 | IQCB1 | ITGB7 | KCNAB2 | KDM4C | KIAA1370 | KIN |
| ILDR1 | IQCD | ITIH5 | KCNE3 | KDM5A | KIAA1407 | KIR3DL1 |
| ILF3 | IQCE | ITM2B | KCNF1 | KDM5B | KIAA1409 | KIR3DL2 |
| ILK | IQCF1 | ITPK1 | KCNG3 | KDM6B | KIAA1429 | KISS1R |
| IMMT | IQCG | ITPKB | KCNH2 | KDR | KIAA1430 | KIT |
| IMP3 | IQCK | ITPR1 | KCNH3 | KHDRBS1 | KIAA1462 | KLC1 |
| IMP4 | IQGAP2 | ITPR2 | KCNH6 | KHNYN | KIAA1522 | KLC2 |
| IMPA1 | IQGAP3 | ITPR3 | KCNH8 | KIAA0020 | KIAA1524 | KLC4 |
| IMPA2 | IQSEC1 | IVD | KCNIP2 | KIAA0100 | KIAA1530 | KLF10 |
| IMPDH1 | IRAK1BP1 | IVNS1ABP | KCNIP3 | KIAA0141 | KIAA1543 | KLF12 |
| IMPDH2 | IRAK3 | IWS1 | KCNJ10 | KIAA0146 | KIAA1586 | KLF13 |
| INCA1 | IRAK4 | JAG2 | KCNJ11 | KIAA0174 | KIAA1609 | KLF14 |
| INCENP | IREB2 | JAGN1 | KCNJ12 | KIAA0182 | KIAA1688 | KLF15 |
| INF2 | IRF2 | JAK2 | KCNJ14 | KIAA0226 | KIAA1712 | KLF17 |
| ING1 | IRF2BP1 | JAM2 | KCNJ4 | KIAA0232 | KIAA1731 | KLF2 |
| ING2 | IRF2BP2 | JARID2 | KCNJ5 | KIAA0247 | KIAA1737 | KLF3 |
| ING3 | IRF3 | JAZF1 | KCNJ6 | KIAA0284 | KIAA1751 | KLF5 |
| ING5 | IRF4 | JDP2 | KCNJ9 | KIAA0319 | KIAA1755 | KLF7 |
| KLF9 | KRTAP4-11 | LDHD | LMAN2 | LOC100240735 | LOC348926 | LOC643719 |
| KLHDC1 | KRTAP4-3 | LDLRAD1 | LMAN2L | LOC100272217 | LOC349114 | LOC643763 |
| KLHDC3 | KRTAP4-8 | LDLRAD3 | LMBR1 | LOC100286844 | LOC360030 | LOC643923 |
| KLHDC4 | KRTAP5-7 | LDLRAP1 | LMBRD2 | LOC100287718 | LOC374443 | LOC644172 |
| KLHDC8B | KRTAP6-1 | LDOC1L | LMCD1 | LOC100287834 | LOC387763 | LOC644936 |
| KLHL11 | KTELC1 | LEKR1 | LMF1 | LOC100302652 | LOC388588 | LOC645166 |
| KLHL14 | KYNU | LEMD2 | LMF2 | LOC100329108 | LOC388692 | LOC646498 |
| KLHL17 | L1TD1 | LEMD3 | LMLN | LOC100329109 | LOC388789 | LOC646762 |
| KLHL18 | L2HGDH | LENG1 | LMNA | LOC121952 | LOC388796 | LOC646851 |
| KLHL2 | L3MBTL3 | LEO1 | LMNB1 | LOC126536 | LOC388946 | LOC647121 |
| KLHL21 | LACE1 | LEPREL1 | LMNB2 | LOC145783 | LOC389033 | LOC647288 |
| KLHL22 | LACTB2 | LEPREL2 | LMO1 | LOC145814 | LOC389332 | LOC650368 |
| KLHL23 | LAMA3 | LEPROTL1 | LMO2 | LOC145845 | LOC389493 | LOC651250 |
| KLHL25 | LAMA5 | LETM1 | LMO3 | LOC148709 | LOC391322 | LOC652276 |
| KLHL26 | LAMB1 | LETM2 | LMO4 | LOC150776 | LOC399744 | LOC723972 |
| KLHL28 | LAMB2L | LETMD1 | LMOD1 | LOC151174 | LOC399815 | LOC728190 |
| KLHL31 | LAMB3 | LFNG | LMTK3 | LOC151534 | LOC400027 | LOC728392 |
| KLHL33 | LAMC3 | LGALS12 | LMX1B | LOC152217 | LOC400043 | LOC728407 |
| KLHL7 | LAMP1 | LGALS14 | LNP1 | LOC153684 | LOC400752 | LOC728411 |
| KLK10 | LAP3 | LGALS3 | LNPEP | LOC154761 | LOC400794 | LOC728643 |
| KLK2 | LARP1 | LGALS7 | LOC100009676 | LOC202181 | LOC400891 | LOC728723 |
| KLRC3 | LARP4 | LGALS9 | LOC100101938 | LOC219347 | LOC400927 | LOC728743 |
| KLRD1 | LARS2 | LGR4 | LOC100128239 | LOC220115 | LOC401010 | LOC728855 |
| KLRG2 | LASP1 | LGR5 | LOC100128292 | LOC220429 | LOC401052 | LOC728875 |
| KNDC1 | LASS2 | LGR6 | LOC100128822 | LOC222699 | LOC401097 | LOC728927 |
| KNTC1 | LASS4 | LHB | LOC100129716 | LOC253724 | LOC401431 | LOC729080 |
| KPNA1 | LASS6 | LHFPL2 | LOC100129726 | LOC254559 | LOC404266 | LOC729082 |
| KPNA2 | LAT | LHFPL3 | LOC100129935 | LOC255025 | LOC440335 | LOC729121 |
| KPNA3 | LATS2 | LHX3 | LOC100130015 | LOC255167 | LOC440356 | LOC729156 |
| KPNA4 | LBH | LHX4 | LOC100130017 | LOC282997 | LOC440461 | LOC729234 |
| KPNA6 | LBR | LHX9 | LOC100130093 | LOC283999 | LOC440563 | LOC729338 |
| KPNA7 | LBXCOR1 | LIAS | LOC100130331 | LOC284023 | LOC440839 | LOC729603 |
| KPRP | LCE1A | LIFR | LOC100130581 | LOC284379 | LOC440905 | LOC729668 |

Figure 15-10

| KRAS | LCE1E | LIG1 | LOC100130691 | LOC284551 | LOC441046 | LOC729678 |
|---|---|---|---|---|---|---|
| KRBA1 | LCE1F | LIG4 | LOC100130987 | LOC284749 | LOC441089 | LOC730101 |
| KREMEN2 | LCE2B | LILRA6 | LOC100133091 | LOC285074 | LOC441208 | LOC731779 |
| KRIT1 | LCE3D | LILRB2 | LOC100133315 | LOC285548 | LOC441455 | LOC731789 |
| KRT1 | LCLAT1 | LIMK1 | LOC100133612 | LOC285550 | LOC442245 | LOC81691 |
| KRT14 | LCMT1 | LIN52 | LOC100133985 | LOC285830 | LOC552889 | LOC84989 |
| KRT18 | LCN15 | LIN54 | LOC100133991 | LOC286016 | LOC595101 | LOC91316 |
| KRT19 | LCOR | LINGO3 | LOC100134229 | LOC338758 | LOC619207 | LOC92659 |
| KRT35 | LCORL | LINS1 | LOC100134713 | LOC338799 | LOC641367 | LOXL1 |
| KRT72 | LDB1 | LIPG | LOC100134868 | LOC339535 | LOC641746 | LOXL2 |
| KRT76 | LDB3 | LIPT1 | LOC100190938 | LOC340357 | LOC642006 | LOXL3 |
| KRT86 | LDHA | LIX1L | LOC100192426 | LOC342346 | LOC642587 | LPAR1 |
| KRTAP10-11 | LDHAL6A | LLGL1 | LOC100216001 | LOC344967 | LOC643387 | LPAR2 |
| KRTAP19-3 | LDHB | LLGL2 | LOC100216545 | LOC348840 | LOC643406 | LPAR3 |
| LPAR6 | LRTOMT | MAEA | MAPK8IP1 | MCL1 | MEIS1 | MGC16142 |
| LPCAT1 | LRWD1 | MAEL | MAPK8IP2 | MCM10 | MEIS2 | MGC16275 |
| LPCAT4 | LSG1 | MAF | MAPK8IP3 | MCM2 | MELK | MGC23284 |
| LPHN1 | LSM1 | MAF1 | MAPK9 | MCM3 | MEN1 | MGC26597 |
| LPHN3 | LSM10 | MAFB | MAPKAPK2 | MCM3APAS | MEP1A | MGC2889 |
| LPIN1 | LSM14B | MAFF | MAPKAPK5 | MCM6 | MEPCE | MGC34034 |
| LPP | LSM2 | MAFG | MAPKBP1 | MCM7 | MERTK | MGC72080 |
| LRCH3 | LSM4 | MAFK | MAPKSP1 | MCM8 | MESDC1 | MGLL |
| LRCH4 | LSM5 | MAGI1 | MAPRE2 | MCOLN1 | MESP1 | MGMT |
| LRFN1 | LSM6 | MAGI3 | MAPRE3 | MCOLN2 | MET | MGRN1 |
| LRFN2 | LST1 | Magmas | MAPT | MCOLN3 | METAP2 | MIA3 |
| LRGUK | LTA | MAGOH | MARK2 | MCPH1 | METRN | MIAT |
| LRIG1 | LTB | MAGOHB | MARK3 | MDC1 | METRNL | MICA |
| LRIG2 | LTBP1 | MAL2 | MARS | MDFI | METT10D | MICAL3 |
| LRIT1 | LTBP2 | MALAT1 | MARS2 | MDFIC | METT11D1 | MICALCL |
| LRP1 | LTBP3 | MAML1 | MARVELD1 | MDGA1 | METTL1 | MICALL2 |
| LRP10 | LTBP4 | MAML3 | MAS1L | MDH1 | METTL10 | MICB |
| LRP5 | LTBR | MAN1A1 | MAST1 | MDK | METTL13 | MIER1 |
| LRP5L | LTV1 | MAN1B1 | MAST3 | MDM1 | METTL2A | MIIP |
| LRP6 | LUC7L2 | MAN2A1 | MAST4 | MDM2 | METTL2B | MIOS |
| LRPAP1 | LUC7L3 | MAN2B2 | MAT2A | MDN1 | METTL3 | MIPOL1 |
| LRPPRC | LUZP1 | MAN2C1 | MAT2B | MEA1 | METTL4 | MIR1180 |
| LRRC20 | LY6D | MANBAL | MATK | MEAF6 | METTL5 | MIR124-3 |
| LRRC25 | LY6E | MANEAL | MATN1 | MECOM | METTL7B | MIR1283-1 |
| LRRC26 | LY6G5C | MANF | MATR3 | MECR | METTL9 | MIR1297 |
| LRRC27 | LY6H | MAP2K3 | MAVS | MED1 | MEX3B | MIR1307 |
| LRRC28 | LY75 | MAP2K5 | MAX | MED11 | MEX3C | MIR132 |
| LRRC32 | LYN | MAP2K6 | MAZ | MED12L | MEX3D | MIR1470 |
| LRRC33 | LYNX1 | MAP3K1 | MBD3 | MED13 | MFAP1 | MIR17HG |
| LRRC37B | LYPD3 | MAP3K11 | MBLAC1 | MED16 | MFAP2 | MIR1908 |
| LRRC37B2 | LYPD6B | MAP3K12 | MBLAC2 | MED17 | MFAP3 | MIR1910 |
| LRRC41 | LYRM1 | MAP3K14 | MBNL1 | MED18 | MFHAS1 | MIR196A1 |
| LRRC42 | LYRM2 | MAP3K3 | MBOAT2 | MED20 | MFI2 | MIR1973 |
| LRRC43 | LYRM4 | MAP3K7IP1 | MBOAT7 | MED24 | MFN2 | MIR212 |
| LRRC47 | LYRM5 | MAP3K8 | MBP | MED25 | MFNG | MIR24-2 |
| LRRC49 | LYSMD1 | MAP4 | MBTD1 | MED26 | MFSD1 | MIR330 |
| LRRC4B | LYSMD2 | MAP4K5 | MBTPS1 | MED27 | MFSD10 | MIR372 |
| LRRC4C | LYST | MAP6 | MC1R | MED30 | MFSD2A | MIR375 |
| LRRC56 | LZTFL1 | MAP7D1 | MCAM | MED4 | MFSD2B | MIR492 |
| LRRC8A | M6PR | MAP9 | MCART1 | MED7 | MFSD5 | MIR515-2 |
| LRRC8D | MACF1 | MAPK1 | MCART3P | MED8 | MFSD8 | MIR516A2 |

Figure 15-11

| | | | | | | |
|---|---|---|---|---|---|---|
| LRRFIP1 | MACROD1 | MAPK11 | MCC | MED9 | MGA | MIR516B1 |
| LRRFIP2 | MAD1L1 | MAPK14 | MCCD1 | MEF2D | MGAT1 | MIR517A |
| LRRK1 | MAD2L1 | MAPK15 | MCF2L | MEGF10 | MGAT4A | MIR517B |
| LRRK2 | MAD2L1BP | MAPK1IP1L | MCF2L2 | MEGF11 | MGAT4C | MIR517C |
| LRRN1 | MAD2L2 | MAPK4 | MCFD2 | MEGF8 | MGAT5B | MIR518A1 |
| LRSAM1 | MADD | MAPK6 | MCHR1 | MEGF9 | MGC13005 | MIR518A2 |
| MIR518F | MMP21 | MRPL19 | MT1G | MXI1 | MZF1 | NCBP2 |
| MIR519A1 | MMP25 | MRPL20 | MT1H | MXRA8 | N4BP2 | NCDN |
| MIR519A2 | MMP28 | MRPL21 | MT2A | MYADM | N4BP3 | NCEH1 |
| MIR519C | MMRN2 | MRPL22 | MT4 | MYADML2 | N6AMT2 | NCF1C |
| MIR520A | MNAT1 | MRPL23 | MTA1 | MYB | NAA20 | NCK2 |
| MIR520B | MNS1 | MRPL24 | MTA3 | MYBL1 | NAA25 | NCKAP5 |
| MIR524 | MNT | MRPL30 | MTBP | MYBPC3 | NAA30 | NCKIPSD |
| MIR526A2 | MNX1 | MRPL32 | MTCH1 | MYC | NAA35 | NCL |
| MIR526B | MOBKL1A | MRPL37 | MTDH | MYCBP | NAALADL2 | NCLN |
| MIR548H3 | MOBKL2B | MRPL44 | MTERFD1 | MYCBP2 | NACAP1 | NCOA2 |
| MIR548H4 | MOBP | MRPL45 | MTERFD2 | MYCN | NADK | NCOA4 |
| MIR548N | MOCS3 | MRPL46 | MTERFD3 | MYCNOS | NADSYN1 | NCOA5 |
| MIR611 | MOG | MRPS14 | MTF1 | MYEOV2 | NAGA | NCOR1 |
| MIR618 | MOGS | MRPS15 | MTF2 | MYF6 | NAGK | NCOR2 |
| MIR632 | MON1A | MRPS16 | MTFMT | MYH10 | NANOG | NCRNA00094 |
| MIR636 | MON2 | MRPS17 | MTHFD1 | MYH11 | NANOS1 | NCRNA00095 |
| MIR642 | MORG1 | MRPS18A | MTHFD1L | MYH3 | NANP | NCRNA00115 |
| MIR663 | MORN1 | MRPS18B | MTHFD2 | MYH9 | NAP1L4 | NCRNA00119 |
| MIR7-2 | MORN2 | MRPS2 | MTHFR | MYL10 | NAP1L5 | NCRNA00120 |
| MIR760 | MORN3 | MRPS22 | MTHFSD | MYL12A | NAPA | NCRNA00164 |
| MIR9-1 | MORN4 | MRPS24 | MTIF2 | MYL12B | NAPG | NCRNA00171 |
| MIS12 | MOSPD3 | MRPS28 | MTIF3 | MYL2 | NARF | NCRNA00173 |
| MIXL1 | MOV10 | MRPS31 | MTL5 | MYL6 | NARFL | NCRNA00174 |
| MKI67 | MOXD1 | MRPS35 | MTMR10 | MYL6B | NARG2 | NCRNA00188 |
| MKI67IP | MPDU1 | MRPS36 | MTMR14 | MYLIP | NARS | NCRNA00189 |
| MKL1 | MPHOSPH10 | MRPS5 | MTMR4 | MYLK2 | NARS2 | NCRNA00219 |
| MKL2 | MPHOSPH8 | MRPS7 | MTMR9 | MYLPF | NASP | NDC80 |
| MKLN1 | MPL | MRPS9 | MTNR1A | MYNN | NAT1 | NDE1 |
| MKNK2 | MPP7 | MRS2 | MTO1 | MYO10 | NAT14 | NDEL1 |
| MKRN1 | MPPE1 | MRTO4 | MTOR | MYO15A | NAT15 | NDFIP1 |
| MKX | MPPED1 | MS4A10 | MTPN | MYO18A | NAT2 | NDN |
| MLC1 | MPPED2 | MS4A6A | MTR | MYO19 | NAV1 | NDNL2 |
| MLF1IP | MPRIP | MSH5 | MTRF1L | MYO1C | NAV2 | NDRG1 |
| MLKL | MPV17L | MSH6 | MTRR | MYO1E | NBEAL1 | NDRG3 |
| MLL | MPV17L2 | MSI2 | MTSS1 | MYO1F | NBEAL2 | NDRG4 |
| MLL5 | MPZL1 | MSL1 | MTUS2 | MYO1G | NBL1 | NDUFA10 |
| MLLT1 | MRAP2 | MSL2 | MTX1 | MYO3B | NBPF1 | NDUFA12 |
| MLLT10 | MRAS | MSL3L2 | MUC1 | MYO5A | NBPF14 | NDUFA13 |
| MLLT3 | MRC2 | MSLN | MUC4 | MYO9B | NBPF3 | NDUFA2 |
| MLLT6 | MRE11A | MSLNL | MUC5B | MYOM2 | NBPF9 | NDUFA3 |
| MLX | MRFAP1 | MSRA | MUC6 | MYRIP | NBR1 | NDUFA4L2 |
| MLXIPL | MRFAP1L1 | MSRB3 | MUDENG | MYST1 | NCAM1 | NDUFA5 |
| MMAB | MRP63 | MST1P2 | MUS81 | MYST2 | NCAN | NDUFA6 |
| MMADHC | MRPL1 | MSTO1 | MUTYH | MYST3 | NCAPD2 | NDUFA7 |
| MMP15 | MRPL12 | MSTO2P | MVP | MYST4 | NCAPD3 | NDUFAB1 |
| MMP17 | MRPL16 | MSX1 | MX1 | MYT1 | NCAPG | NDUFAF1 |
| MMP19 | MRPL18 | MT1F | MXD3 | MYT1L | NCAPH2 | NDUFAF2 |
| NDUFAF3 | NFKB1 | NLRC3 | NR2C2AP | NUDCD1 | OCLN | OSBPL9 |
| NDUFB1 | NFKBIA | NLRC4 | NR2E1 | NUDT14 | OCM | OSGEP |

Figure 15-12

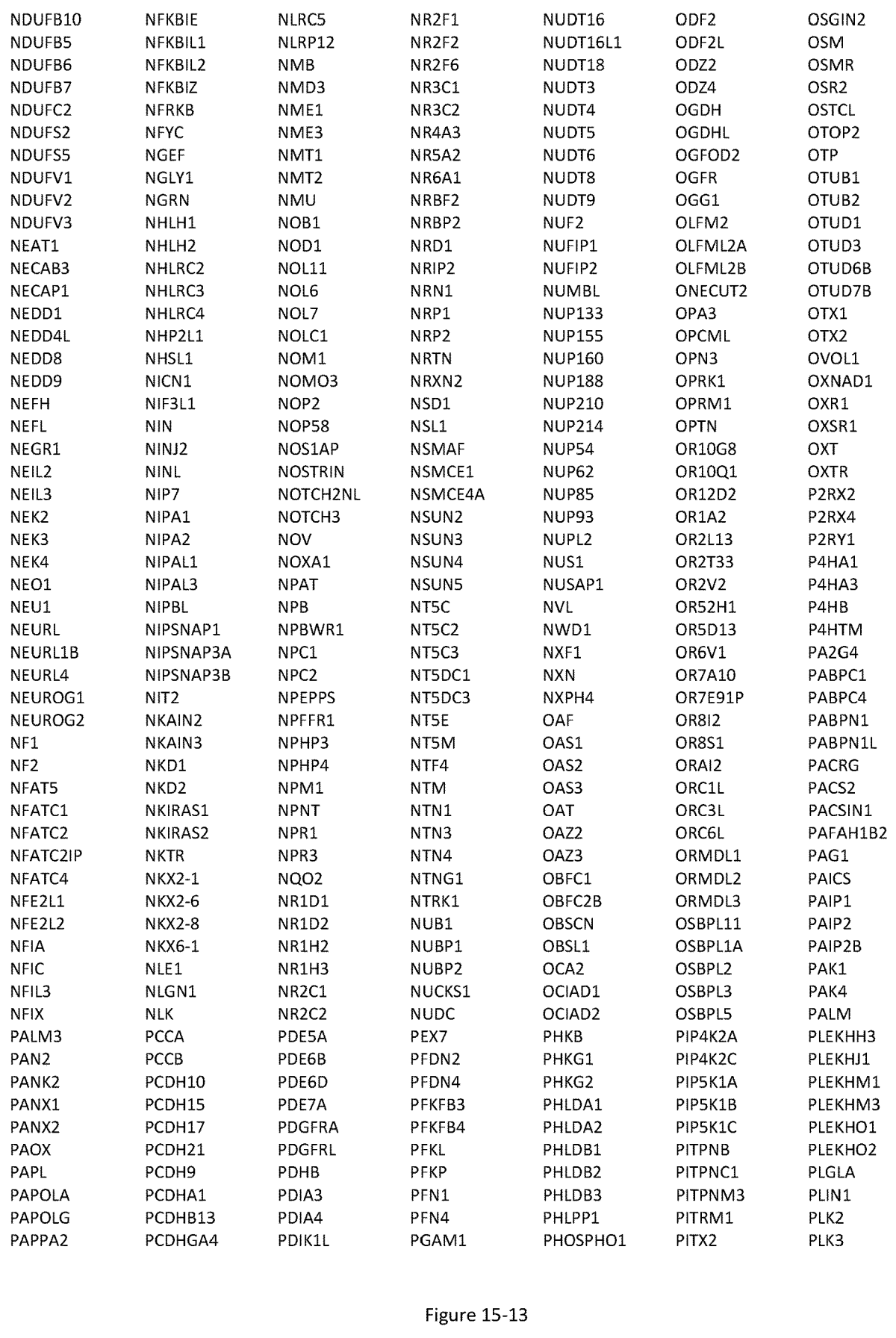

NDUFB10
NDUFB5
NDUFB6
NDUFB7
NDUFC2
NDUFS2
NDUFS5
NDUFV1
NDUFV2
NDUFV3
NEAT1
NECAB3
NECAP1
NEDD1
NEDD4L
NEDD8
NEDD9
NEFH
NEFL
NEGR1
NEIL2
NEIL3
NEK2
NEK3
NEK4
NEO1
NEU1
NEURL
NEURL1B
NEURL4
NEUROG1
NEUROG2
NF1
NF2
NFAT5
NFATC1
NFATC2
NFATC2IP
NFATC4
NFE2L1
NFE2L2
NFIA
NFIC
NFIL3
NFIX
NFKBIE
NFKBIL1
NFKBIL2
NFKBIZ
NFRKB
NFYC
NGEF
NGLY1
NGRN
NHLH1
NHLH2
NHLRC2
NHLRC3
NHLRC4
NHP2L1
NHSL1
NICN1
NIF3L1
NIN
NINJ2
NINL
NIP7
NIPA1
NIPA2
NIPAL1
NIPAL3
NIPBL
NIPSNAP1
NIPSNAP3A
NIPSNAP3B
NIT2
NKAIN2
NKAIN3
NKD1
NKD2
NKIRAS1
NKIRAS2
NKTR
NKX2-1
NKX2-6
NKX2-8
NKX6-1
NLE1
NLGN1
NLK
NLRC5
NLRP12
NMB
NMD3
NME1
NME3
NMT1
NMT2
NMU
NOB1
NOD1
NOL11
NOL6
NOL7
NOLC1
NOM1
NOMO3
NOP2
NOP58
NOS1AP
NOSTRIN
NOTCH2NL
NOTCH3
NOV
NOXA1
NPAT
NPB
NPBWR1
NPC1
NPC2
NPEPPS
NPFFR1
NPHP3
NPHP4
NPM1
NPNT
NPR1
NPR3
NQO2
NR1D1
NR1D2
NR1H2
NR1H3
NR2C1
NR2C2
NR2F1
NR2F2
NR2F6
NR3C1
NR3C2
NR4A3
NR5A2
NR6A1
NRBF2
NRBP2
NRD1
NRIP2
NRN1
NRP1
NRP2
NRTN
NRXN2
NSD1
NSL1
NSMAF
NSMCE1
NSMCE4A
NSUN2
NSUN3
NSUN4
NSUN5
NT5C
NT5C2
NT5C3
NT5DC1
NT5DC3
NT5E
NT5M
NTF4
NTM
NTN1
NTN3
NTN4
NTNG1
NTRK1
NUB1
NUBP1
NUBP2
NUCKS1
NUDC
NUDT16
NUDT16L1
NUDT18
NUDT3
NUDT4
NUDT5
NUDT6
NUDT8
NUDT9
NUF2
NUFIP1
NUFIP2
NUMBL
NUP133
NUP155
NUP160
NUP188
NUP210
NUP214
NUP54
NUP62
NUP85
NUP93
NUPL2
NUS1
NUSAP1
NVL
NWD1
NXF1
NXN
NXPH4
OAF
OAS1
OAS2
OAS3
OAT
OAZ2
OAZ3
OBFC1
OBFC2B
OBSCN
OBSL1
OCA2
OCIAD1
OCIAD2
ODF2
ODF2L
ODZ2
ODZ4
OGDH
OGDHL
OGFOD2
OGFR
OGG1
OLFM2
OLFML2A
OLFML2B
ONECUT2
OPA3
OPCML
OPN3
OPRK1
OPRM1
OPTN
OR10G8
OR10Q1
OR12D2
OR1A2
OR2L13
OR2T33
OR2V2
OR52H1
OR5D13
OR6V1
OR7A10
OR7E91P
OR8I2
OR8S1
ORAI2
ORC1L
ORC3L
ORC6L
ORMDL1
ORMDL2
ORMDL3
OSBPL11
OSBPL1A
OSBPL2
OSBPL3
OSBPL5
OSGIN2
OSM
OSMR
OSR2
OSTCL
OTOP2
OTP
OTUB1
OTUB2
OTUD1
OTUD3
OTUD6B
OTUD7B
OTX1
OTX2
OVOL1
OXNAD1
OXR1
OXSR1
OXT
OXTR
P2RX2
P2RX4
P2RY1
P4HA1
P4HA3
P4HB
P4HTM
PA2G4
PABPC1
PABPC4
PABPN1
PABPN1L
PACRG
PACS2
PACSIN1
PAFAH1B2
PAG1
PAICS
PAIP1
PAIP2
PAIP2B
PAK1
PAK4
PALM
PALM3
PAN2
PANK2
PANX1
PANX2
PAOX
PAPL
PAPOLA
PAPOLG
PAPPA2
PCCA
PCCB
PCDH10
PCDH15
PCDH17
PCDH21
PCDH9
PCDHA1
PCDHB13
PCDHGA4
PDE5A
PDE6B
PDE6D
PDE7A
PDGFRA
PDGFRL
PDHB
PDIA3
PDIA4
PDIK1L
PEX7
PFDN2
PFDN4
PFKFB3
PFKFB4
PFKL
PFKP
PFN1
PFN4
PGAM1
PHKB
PHKG1
PHKG2
PHLDA1
PHLDA2
PHLDB1
PHLDB2
PHLDB3
PHLPP1
PHOSPHO1
PIP4K2A
PIP4K2C
PIP5K1A
PIP5K1B
PIP5K1C
PITPNB
PITPNC1
PITPNM3
PITRM1
PITX2
PLEKHH3
PLEKHJ1
PLEKHM1
PLEKHM3
PLEKHO1
PLEKHO2
PLGLA
PLIN1
PLK2
PLK3

Figure 15-13

| | | | | | | |
|---|---|---|---|---|---|---|
| PAQR3 | PCF11 | PDK1 | PGAM5 | PHPT1 | PITX3 | PLK4 |
| PAQR4 | PCGF1 | PDLIM1 | PGAP1 | PHTF2 | PIWIL3 | PLLP |
| PARD3 | PCGF3 | PDLIM3 | PGAP2 | PHYHIPL | PJA2 | PLOD2 |
| PARD3B | PCGF6 | PDLIM5 | PGAP3 | PI4K2B | PKD1 | PLXDC2 |
| PARD6A | PCK2 | PDLIM7 | PGBD4 | PIAS1 | PKD1L3 | PLXNA1 |
| PARD6B | PCLO | PDPK1 | PGCP | PIAS2 | PKD2 | PLXNA2 |
| PARD6G | PCM1 | PDPR | PGD | PIAS3 | PKM2 | PLXNA4 |
| PARL | PCMT1 | PDS5A | PGGT1B | PIAS4 | PKN1 | PLXNB2 |
| PARP1 | PCMTD1 | PDS5B | PGLS | PIBF1 | PKN2 | PLXNC1 |
| PARP11 | PCNP | PDSS1 | PGLYRP2 | PICK1 | PKN3 | PLXND1 |
| PARP15 | PCNT | PDSS2 | PGM1 | PIF1 | PKNOX2 | PMAIP1 |
| PARP16 | PCNX | PDX1 | PGM2 | PIGB | PKP4 | PMEPA1 |
| PARP2 | PCNXL3 | PDXDC2 | PGM3 | PIGG | PLA2G15 | PMF1 |
| PARP8 | PCOLCE | PDXK | PGP | PIGM | PLA2G6 | PML |
| PARP9 | PCOTH | PDZD2 | PGPEP1 | PIGN | PLAC8 | PMM1 |
| PARS2 | PCSK2 | PDZD7 | PGS1 | PIGO | PLAG1 | PMM2 |
| PARVB | PCSK6 | PDZD8 | PHACTR1 | PIGP | PLAGL1 | PMPCB |
| PASK | PCSK7 | PEBP1 | PHACTR4 | PIGQ | PLAT | PMS1 |
| PATE2 | PCTP | PECI | PHAX | PIGT | PLAU | PMS2 |
| PATE4 | PCYT1A | PEF1 | PHB | PIGU | PLCD1 | PMS2L1 |
| PATL1 | PDAP1 | PEG3 | PHC1 | PIGV | PLCE1 | PMS2L2 |
| PATZ1 | PDCD11 | PELI1 | PHC2 | PIGX | PLCH2 | PMS2L3 |
| PAWR | PDCD2 | PELI2 | PHC3 | PIGY | PLCL2 | PMS2L4 |
| PAX2 | PDCD2L | PEMT | PHF1 | PIK3AP1 | PLD2 | PMS2L5 |
| PAX5 | PDCD5 | PER1 | PHF10 | PIK3C2G | PLD3 | PMVK |
| PAX6 | PDCD6 | PER2 | PHF11 | PIK3CA | PLD5 | PNKD |
| PAX7 | PDCD6IP | PER3 | PHF12 | PIK3CD | PLEC1 | PNLIP |
| PAXIP1 | PDCD7 | PERP | PHF13 | PIK3R2 | PLEKHA1 | PNMA2 |
| PBLD | PDE10A | PET117 | PHF15 | PIK3R3 | PLEKHA2 | PNMT |
| PBX3 | PDE11A | PEX10 | PHF17 | PIK3R5 | PLEKHA6 | PNN |
| PBX4 | PDE12 | PEX11B | PHF19 | PIKFYVE | PLEKHA7 | PNO1 |
| PC | PDE3A | PEX12 | PHF2 | PILRB | PLEKHB1 | PNPLA6 |
| PCBD2 | PDE3B | PEX13 | PHF21A | PIM1 | PLEKHF2 | PNPLA7 |
| PCBP1 | PDE4A | PEX19 | PHF21B | PIM3 | PLEKHG3 | PNPLA8 |
| PCBP2 | PDE4B | PEX26 | PHF5A | PIN1 | PLEKHG4 | PNRC2 |
| PCBP3 | PDE4D | PEX5 | PHGDH | PINK1 | PLEKHG5 | PODN |
| PCBP4 | PDE4DIP | PEX6 | PHIP | PION | PLEKHG6 | PODXL |
| PODXL2 | POU6F2 | PPP1R3E | PRDX5 | PRMT8 | PSMA6 | PTH1R |
| POFUT2 | PPA1 | PPP1R7 | PRDX6 | PRNP | PSMA7 | PTK2 |
| POGK | PPA2 | PPP1R8 | PRDXDD1P | PROCA1 | PSMB1 | PTK2B |
| POLD1 | PPAP2B | PPP1R9B | PREB | PROCR | PSMB10 | PTMA |
| POLD2 | PPAP2C | PPP2CA | PRELID1 | PRODH2 | PSMB5 | PTMS |
| POLD3 | PPAPDC1A | PPP2R1A | PRELID2 | PROKR1 | PSMB6 | PTP4A1 |
| POLDIP2 | PPARG | PPP2R1B | PRELP | PROKR2 | PSMB7 | PTPMT1 |
| POLE2 | PPARGC1A | PPP2R2B | PREP | PROSC | PSMB8 | PTPN1 |
| POLG | PPARGC1B | PPP2R3A | PREPL | PRPF19 | PSMB9 | PTPN12 |
| POLH | PPCDC | PPP2R3C | PREX1 | PRPF3 | PSMC2 | PTPN14 |
| POLI | PPCS | PPP2R5A | PREX2 | PRPF31 | PSMC3IP | PTPN18 |
| POLK | PPDPF | PPP2R5C | PRHOXNB | PRPF38B | PSMC4 | PTPN21 |
| POLN | PPFIA1 | PPP2R5D | PRIC285 | PRPF40B | PSMC5 | PTPN22 |
| POLQ | PPFIA3 | PPP3CA | PRICKLE1 | PRPF8 | PSMC6 | PTPN23 |
| POLR1B | PPFIBP2 | PPP3CB | PRIM1 | PRPSAP2 | PSMD1 | PTPN4 |
| POLR1C | PPHLN1 | PPP3CC | PRIMA1 | PRR11 | PSMD11 | PTPN6 |
| POLR2B | PPIA | PPP3R1 | PRKAA1 | PRR13 | PSMD12 | PTPN9 |
| POLR2D | PPIB | PPP4C | PRKAA2 | PRR14 | PSMD13 | PTPRCAP |

Figure 15-14

| POLR2E | PPID | PPP4R2 | PRKAB2 | PRR23C | PSMD2 | PTPRE |
|---|---|---|---|---|---|---|
| POLR2G | PPIE | PPP5C | PRKACA | PRR3 | PSMD3 | PTPRF |
| POLR2I | PPIH | PPPDE1 | PRKACG | PRR5 | PSMD4 | PTPRG |
| POLR2J2 | PPIL2 | PPPDE2 | PRKAG2 | PRR5L | PSMD6 | PTPRJ |
| POLR2J4 | PPIL3 | PPRC1 | PRKAR1A | PRR7 | PSMD7 | PTPRK |
| POLR3B | PPIL4 | PPT1 | PRKAR1B | PRRC1 | PSMD9 | PTPRM |
| POLR3C | PPIL5 | PPT2 | PRKAR2B | PRRG4 | PSME2 | PTPRN2 |
| POLR3D | PPM1A | PPY2 | PRKCA | PRRT1 | PSME3 | PTPRO |
| POLR3K | PPM1E | PQLC1 | PRKCB | PRRT2 | PSMG1 | PTPRS |
| POLRMT | PPM1F | PQLC3 | PRKCD | PRRT4 | PSMG2 | PTPRU |
| POLS | PPM1G | PRAGMIN | PRKCDBP | PRSS12 | PSMG3 | PTPRZ1 |
| POM121 | PPM1J | PRAMEF18 | PRKCE | PRSS23 | PSMG4 | PTRF |
| POM121L10P | PPM1K | PRAMEF20 | PRKCG | PRSS38 | PSPC1 | PTTG1 |
| POM121L2 | PPM1L | PRAMEF22 | PRKCI | PRSS48 | PSPN | PTTG1IP |
| POMC | PPM1M | PRB2 | PRKCSH | PRSS8 | PSRC1 | PUF60 |
| POMP | PPOX | PRB3 | PRKCZ | PRSSL1 | PTAFR | PUM1 |
| POMT2 | PPP1CA | PRC1 | PRKD1 | PRTG | PTBP2 | PURA |
| POMZP3 | PPP1CB | PRCC | PRKD2 | PRUNE2 | PTCD3 | PURG |
| PON2 | PPP1CC | PRDM11 | PRKDC | PSAT1 | PTCH1 | PUS1 |
| POP1 | PPP1R11 | PRDM12 | PRKG1 | PSD2 | PTCH2 | PUS10 |
| POP7 | PPP1R12B | PRDM14 | PRKRA | PSD3 | PTDSS2 | PUSL1 |
| POT1 | PPP1R12C | PRDM15 | PRKRIP1 | PSD4 | PTEN | PVR |
| POTEC | PPP1R14B | PRDM16 | PRKRIR | PSG3 | PTER | PVRL1 |
| POTED | PPP1R14C | PRDM2 | PRMT1 | PSIP1 | PTGER4 | PVRL2 |
| POTEF | PPP1R15A | PRDM5 | PRMT10 | psiTPTE22 | PTGES | PVRL3 |
| POU2F1 | PPP1R15B | PRDM6 | PRMT2 | PSMA1 | PTGES2 | PVT1 |
| POU3F1 | PPP1R2 | PRDM8 | PRMT3 | PSMA2 | PTGES3 | PWP1 |
| POU3F2 | PPP1R2P1 | PRDX1 | PRMT6 | PSMA3 | PTGFRN | PWP2 |
| POU6F1 | PPP1R3B | PRDX2 | PRMT7 | PSMA4 | PTGIS | PXMP2 |
| PXMP3 | RAB8A | RASAL2 | RBPJL | RG9MTD1 | RNASEH1 | RNMTL1 |
| PXMP4 | RABAC1 | RASD1 | RBPMS | RG9MTD2 | RNASEH2B | RNPC3 |
| PXN | RABEP2 | RASD2 | RBX1 | RG9MTD3 | RNASEH2C | RNPEP |
| PYCR1 | RABGEF1 | RASGEF1B | RC3H2 | RGL2 | RNASEK | RNU5D |
| PYCR2 | RABL4 | RASGEF1C | RCAN3 | RGMA | RNASEN | RNU5E |
| PYCRL | RAC2 | RASGRP2 | RCBTB1 | RGMB | RNF103 | ROBLD3 |
| PYGB | RACGAP1 | RASGRP3 | RCBTB2 | RGPD2 | RNF11 | ROBO1 |
| PYGL | RAD1 | RASIP1 | RCC2 | RGPD3 | RNF111 | ROCK1 |
| PYGM | RAD17 | RASL11A | RCCD1 | RGPD5 | RNF114 | ROD1 |
| PYGO1 | RAD21 | RASSF1 | RCE1 | RGS16 | RNF122 | ROGDI |
| PYGO2 | RAD51AP2 | RASSF2 | RCOR1 | RGS17 | RNF125 | ROMO1 |
| PYY | RAD51L1 | RASSF3 | RCOR2 | RGS19 | RNF126 | ROPN1L |
| QARS | RAD52 | RASSF4 | RCOR3 | RGS2 | RNF130 | RORA |
| QDPR | RAD9A | RASSF5 | RCSD1 | RGS20 | RNF138 | RP11-529I10.4 |
| QKI | RADIL | RASSF6 | RDBP | RGS7 | RNF139 | RP1L1 |
| QPCTL | RAE1 | RASSF8 | RDH10 | RGS8 | RNF14 | RP5-1022P6.2 |
| QRICH1 | RAET1G | RB1 | RDH13 | RHBDD1 | RNF141 | RP9P |
| QRSL1 | RAET1K | RB1CC1 | REC8 | RHBDD2 | RNF145 | RPA1 |
| QSER1 | RAGE | RBAK | RECQL | RHBDF1 | RNF152 | RPA2 |
| QTRT1 | RAI1 | RBBP4 | RECQL5 | RHBDF2 | RNF157 | RPA3 |
| R3HDM1 | RAI14 | RBBP6 | REEP1 | RHEB | RNF160 | RPAIN |
| RAB10 | RALB | RBBP8 | REEP3 | RHEBL1 | RNF165 | RPAP1 |
| RAB11A | RALGAPA2 | RBCK1 | REEP4 | RHOA | RNF168 | RPAP2 |
| RAB11B | RALGAPB | RBKS | REEP5 | RHOB | RNF182 | RPAP3 |
| RAB11FIP3 | RALGDS | RBL1 | REEP6 | RHOC | RNF187 | RPE |
| RAB11FIP5 | RALGPS1 | RBM12B | REG3G | RHOD | RNF19A | RPF1 |

Figure 15-15

| RAB12 | RALGPS2 | RBM14 | REL | RHOF | RNF20 | RPF2 |
|---|---|---|---|---|---|---|
| RAB14 | RALY | RBM15 | RELA | RHOG | RNF213 | RPGRIP1 |
| RAB15 | RALYL | RBM18 | RELL1 | RHOJ | RNF215 | RPGRIP1L |
| RAB18 | RAMP1 | RBM19 | RERE | RHOT2 | RNF216L | RPH3AL |
| RAB1B | RANBP1 | RBM24 | RET | RHPN1 | RNF220 | RPIA |
| RAB20 | RANBP2 | RBM27 | RETSAT | RHPN2 | RNF24 | RPL10A |
| RAB21 | RANBP9 | RBM33 | REV3L | RIC8A | RNF25 | RPL10L |
| RAB22A | RANGRF | RBM34 | REXO1 | RIC8B | RNF32 | RPL13AP20 |
| RAB27A | RAP1A | RBM38 | RFC1 | RICS | RNF34 | RPL13AP5 |
| RAB2A | RAP1B | RBM39 | RFC2 | RICTOR | RNF39 | RPL14 |
| RAB32 | RAP1GDS1 | RBM42 | RFC4 | RILPL2 | RNF4 | RPL18 |
| RAB39 | RAP2B | RBM44 | RFPL1S | RIMKLA | RNF40 | RPL18AP3 |
| RAB3D | RAPGEF6 | RBM45 | RFPL2 | RIMS2 | RNF41 | RPL19 |
| RAB3GAP1 | RAPH1 | RBM46 | RFT1 | RIN3 | RNF44 | RPL22 |
| RAB40B | RARA | RBM4B | RFTN1 | RING1 | RNF6 | RPL22L1 |
| RAB42 | RARB | RBM5 | RFWD2 | RINL | RNF7 | RPL23 |
| RAB43 | RARRES1 | RBM6 | RFX1 | RLF | RNF8 | RPL23AP53 |
| RAB4B | RASA1 | RBM9 | RFX2 | RLTPR | RNFT1 | RPL23AP7 |
| RAB6A | RASA2 | RBMXL1 | RFX4 | RMND1 | RNFT2 | RPL23AP82 |
| RAB6B | RASA3 | RBP1 | RFX8 | RMND5A | RNGTT | RPL24 |
| RAB7A | RASAL1 | RBPJ | RFXANK | RNASE3 | RNLS | RPL27 |
| RPL27A | RREB1 | S100A7A | SCARNA20 | SEC14L2 | SERPINE2 | SGTA |
| RPL28 | RRM1 | S100PBP | SCCPDH | SEC16A | SERPINH1 | SGTB |
| RPL29 | RRM2 | S1PR1 | SCD | SEC22B | SERTAD3 | SH2B1 |
| RPL30 | RRM2B | S1PR2 | SCD5 | SEC23A | SERTAD4 | SH2B3 |
| RPL31 | RRN3 | S1PR4 | SCFD1 | SEC23B | SESN3 | SH2D3A |
| RPL32 | RRN3P2 | S1PR5 | SCFD2 | SEC23IP | SETD1A | SH2D5 |
| RPL32P3 | RRN3P3 | SAA4 | SCGB1D4 | SEC24B | SETD1B | SH3BGR |
| RPL36 | RRP1 | SACM1L | SCGB3A1 | SEC24D | SETD2 | SH3BP1 |
| RPL37 | RRP15 | SACS | SCHIP1 | SEC31A | SETD3 | SH3BP2 |
| RPL37A | RRP7B | SAFB | SCIN | SEC61G | SETD4 | SH3BP4 |
| RPL5 | RRS1 | SALL1 | SCLT1 | SEC63 | SETD7 | SH3BP5 |
| RPL6 | RSBN1L | SALL3 | SCMH1 | SECISBP2 | SETD8 | SH3D20 |
| RPL7 | RSF1 | SALL4 | SCN1B | SECTM1 | SETMAR | SH3GL1 |
| RPL8 | RSL1D1 | SAMD10 | SCN4B | SEL1L | SEZ6 | SH3PXD2A |
| RPLP0 | RSPH1 | SAMD12 | SCN8A | SELI | SEZ6L2 | SH3PXD2B |
| RPLP2 | RSPH3 | SAMD13 | SCNM1 | SELK | SF3A1 | SH3RF3 |
| RPN1 | RSPH6A | SAMD4A | SCRIB | SELM | SF3A3 | SH3TC1 |
| RPP21 | RSPH9 | SAMM50 | SCRN2 | SELPLG | SF3B1 | SHANK1 |
| RPP25 | RSPO4 | SAP130 | SCRT1 | SELS | SF3B4 | SHANK2 |
| RPP30 | RSPRY1 | SAP30 | SCRT2 | SELT | SFI1 | SHANK3 |
| RPP40 | RSRC2 | SAPS1 | SCUBE1 | SEMA3A | SFMBT1 | SHBG |
| RPRD1A | RSU1 | SAPS2 | SCUBE2 | SEMA3B | SFMBT2 | SHC1 |
| RPRD1B | RTEL1 | SAPS3 | SCUBE3 | SEMA3F | SFRP5 | SHC4 |
| RPRD2 | RTKN | SARS | SCYL1 | SEMA3G | SFRS1 | SHD |
| RPS10P7 | RTN1 | SARS2 | SCYL2 | SEMA4B | SFRS11 | SHF |
| RPS11 | RTN2 | SART1 | SCYL3 | SEMA4C | SFRS12 | SHFM1 |
| RPS12 | RTN4 | SASH1 | SDC1 | SEMA5A | SFRS13A | SHH |
| RPS13 | RTN4IP1 | SATB1 | SDC2 | SEMA5B | SFRS14 | SHISA3 |
| RPS15 | RTN4R | SATB2 | SDC4 | SEMA6B | SFRS2 | SHISA5 |
| RPS15A | RTTN | SAV1 | SDCBP | SEMA7A | SFRS2IP | SHMT2 |
| RPS19BP1 | RUFY1 | SBDS | SDCBP2 | SENP1 | SFRS3 | SHPRH |
| RPS21 | RUFY2 | SBDSP | SDCCAG8 | SENP2 | SFRS4 | SHQ1 |
| RPS23 | RUNDC2A | SBF1 | SDF2L1 | SENP3 | SFRS6 | SIAH2 |
| RPS26 | RUNDC2C | SBF2 | SDF4 | SENP7 | SFRS7 | SIDT1 |

Figure 15-16

| RPS27 | RUNDC3A | SBK2 | SDHA | SEPHS1 | SFRS8 | SIGIRR |
|---|---|---|---|---|---|---|
| RPS3A | RUNDC3B | SBNO2 | SDHAF2 | SEPSECS | SFT2D2 | SIGLEC10 |
| RPS6KA2 | RUNX1 | SC5DL | SDHAP3 | SERAC1 | SFXN5 | SIGLEC11 |
| RPS7 | RUNX1T1 | SCAMP1 | SDHB | SERBP1 | SGCB | SIK1 |
| RPS9 | RUNX2 | SCAMP3 | SDHC | SERF2 | SGCE | SIK3 |
| RPSA | RUNX3 | SCAMP4 | SDK1 | SERINC2 | SGEF | SIM2 |
| RPTOR | RUSC1 | SCAND1 | SDK2 | SERINC4 | SGK1 | SIN3A |
| RPUSD1 | RUVBL2 | SCAND3 | SDR39U1 | SERP1 | SGK196 | SIP1 |
| RPUSD2 | RWDD1 | SCARB1 | SDR42E1 | SERPINB2 | SGK269 | SIPA1 |
| RPUSD4 | RWDD2A | SCARB2 | SEC1 | SERPINB6 | SGMS2 | SIPA1L1 |
| RQCD1 | RXRA | SCARF2 | SEC11A | SERPINB8 | SGSH | SIPA1L2 |
| RRAGA | RYR1 | SCARNA16 | SEC11C | SERPINB9 | SGSM1 | SIRPA |
| RRBP1 | S100A6 | SCARNA2 | SEC14L1 | SERPIND1 | SGSM3 | SIRT2 |
| SIRT3 | SLC22A17 | SLC30A6 | SLC4A1AP | SMARCA5 | SNORD104 | SNUPN |
| SIRT5 | SLC22A18 | SLC30A7 | SLC4A4 | SMARCAD1 | SNORD114-15 | SNX1 |
| SIRT7 | SLC22A18AS | SLC30A9 | SLC5A10 | SMARCC1 | SNORD114-29 | SNX11 |
| SIX2 | SLC22A23 | SLC31A2 | SLC5A5 | SMARCC2 | SNORD114-31 | SNX14 |
| SIX4 | SLC22A3 | SLC33A1 | SLC5A7 | SMARCD2 | SNORD115-1 | SNX16 |
| SIX5 | SLC22A4 | SLC34A2 | SLC6A17 | SMARCE1 | SNORD115-11 | SNX17 |
| SKA1 | SLC22A5 | SLC35A1 | SLC6A18 | SMC3 | SNORD115-13 | SNX19 |
| SKA3 | SLC23A2 | SLC35A3 | SLC6A19 | SMC4 | SNORD115-14 | SNX21 |
| SKAP1 | SLC24A2 | SLC35B1 | SLC6A2 | SMCR7 | SNORD115-15 | SNX22 |
| SKAP2 | SLC25A11 | SLC35D1 | SLC6A20 | SMCR8 | SNORD115-17 | SNX29 |
| SKI | SLC25A15 | SLC35E1 | SLC6A3 | SMG6 | SNORD115-3 | SNX3 |
| SKIL | SLC25A16 | SLC35E2 | SLC6A5 | SMG7 | SNORD115-35 | SNX32 |
| SKIV2L | SLC25A17 | SLC35E3 | SLC6A6 | SMOC2 | SNORD115-38 | SNX4 |
| SKP1 | SLC25A19 | SLC35E4 | SLC7A1 | SMOX | SNORD115-39 | SNX6 |
| SKP2 | SLC25A2 | SLC35F1 | SLC7A10 | SMPD1 | SNORD115-41 | SNX7 |
| SLAIN1 | SLC25A21 | SLC35F2 | SLC7A14 | SMPD3 | SNORD115-44 | SNX8 |
| SLC10A4 | SLC25A24 | SLC35F5 | SLC7A4 | SMPD4 | SNORD115-6 | SNX9 |
| SLC10A7 | SLC25A28 | SLC36A1 | SLC7A6 | SMPDL3B | SNORD115-7 | SOBP |
| SLC11A2 | SLC25A30 | SLC36A4 | SLC7A6OS | SMTN | SNORD115-8 | SOCS1 |
| SLC12A2 | SLC25A32 | SLC37A1 | SLC7A8 | SMUG1 | SNORD116-8 | SOCS5 |
| SLC12A4 | SLC25A33 | SLC37A3 | SLC8A1 | SMURF1 | SNORD1C | SOCS6 |
| SLC12A5 | SLC25A35 | SLC37A4 | SLC8A2 | SMURF2 | SNORD24 | SOD1 |
| SLC12A6 | SLC25A36 | SLC38A1 | SLC8A3 | SMYD3 | SNORD32B | SOLH |
| SLC12A7 | SLC25A38 | SLC38A10 | SLC9A3 | SMYD5 | SNORD38A | SON |
| SLC12A9 | SLC25A4 | SLC38A2 | SLC9A3R2 | SNAP23 | SNORD42B | SORBS1 |
| SLC13A5 | SLC25A40 | SLC38A3 | SLC9A5 | SNAP25 | SNORD43 | SORBS3 |
| SLC14A2 | SLC25A42 | SLC38A6 | SLCO1C1 | SNAPC1 | SNORD50B | SORCS2 |
| SLC16A1 | SLC25A44 | SLC38A7 | SLCO2A1 | SNAPC2 | SNORD58A | SORD |
| SLC16A10 | SLC25A45 | SLC38A9 | SLCO3A1 | SNAPC3 | SNORD83A | SORL1 |
| SLC16A12 | SLC25A46 | SLC39A10 | SLCO4A1 | SNAR-G1 | SNORD83B | SOX12 |
| SLC16A13 | SLC26A1 | SLC39A11 | SLCO5A1 | SNCAIP | SNORD88A | SOX18 |
| SLC16A14 | SLC26A10 | SLC39A14 | SLFN11 | SNCG | SNPH | SOX2 |
| SLC16A3 | SLC26A11 | SLC39A7 | SLFN12L | SND1 | SNRNP27 | SOX5 |
| SLC17A1 | SLC26A2 | SLC39A8 | SLFN5 | SNHG10 | SNRNP40 | SOX7 |
| SLC17A5 | SLC26A4 | SLC39A9 | SLIT1 | SNHG12 | SNRPA1 | SP1 |
| SLC17A7 | SLC27A1 | SLC41A1 | SLIT2 | SNHG3-RCC1 | SNRPB | SP100 |
| SLC19A1 | SLC29A1 | SLC41A3 | SLIT3 | SNHG4 | SNRPB2 | SP2 |
| SLC19A2 | SLC29A2 | SLC43A1 | SLK | SNHG5 | SNRPC | SP3 |
| SLC1A2 | SLC29A4 | SLC43A2 | SLMAP | SNHG6 | SNRPD1 | SP4 |
| SLC1A3 | SLC2A1 | SLC44A1 | SLTM | SNHG7 | SNRPD3 | SP7 |
| SLC1A4 | SLC2A11 | SLC44A2 | SLU7 | SNHG9 | SNRPE | SP8 |
| SLC1A5 | SLC2A13 | SLC44A3 | SMAD3 | SNIP1 | SNRPF | SPAG1 |

Figure 15-17

| SLC1A6 | SLC2A3 | SLC44A4 | SMAD4 | SNORA14B | SNRPG | SPAG11A |
|---|---|---|---|---|---|---|
| SLC1A7 | SLC2A4 | SLC45A4 | SMAD7 | SNORA20 | SNRPN | SPARC |
| SLC20A1 | SLC2A5 | SLC46A3 | SMAGP | SNORA52 | SNTA1 | SPATA13 |
| SLC22A15 | SLC2A6 | SLC48A1 | SMAP1 | SNORA76 | SNTB1 | SPATA2 |
| SLC22A16 | SLC30A5 | SLC4A11 | SMARCA4 | SNORA8 | SNTG2 | SPATA20 |
| SPATA5 | SRI | STAR | STT3A | SYN3 | TAS2R43 | TCP11L2 |
| SPATA5L1 | SRP14 | STARD13 | STX11 | SYNCRIP | TATDN1 | TCTA |
| SPC25 | SRP68 | STARD3 | STX18 | SYNGAP1 | TATDN2 | TCTE3 |
| SPCS2 | SRP72 | STARD3NL | STX1A | SYNGR3 | TATDN3 | TCTEX1D2 |
| SPCS3 | SRPK2 | STARD4 | STX3 | SYNPO | TAX1BP1 | TCTN1 |
| SPDYA | SRPRB | STARD5 | STX4 | SYNPO2L | TBC1D1 | TDH |
| SPDYE4 | SRRM1 | STARD7 | STX5 | SYNRG | TBC1D12 | TDP1 |
| SPDYE7P | SRRM2 | STARD9 | STX7 | SYPL1 | TBC1D14 | TDRD10 |
| SPEF1 | SRRT | STAT2 | STX8 | SYT1 | TBC1D15 | TDRD3 |
| SPEG | SS18 | STAT3 | STXBP2 | SYT17 | TBC1D16 | TDRKH |
| SPEN | SSB | STAT5A | STXBP4 | SYT3 | TBC1D2 | TEAD1 |
| SPG11 | SSBP1 | STAT5B | STXBP5 | SYT5 | TBC1D22A | TEAD3 |
| SPG21 | SSBP2 | STAU1 | STXBP6 | SYT7 | TBC1D24 | TECPR2 |
| SPG7 | SSBP3 | STAU2 | STYX | SYT9 | TBC1D26 | TECR |
| SPHK1 | SSBP4 | STBD1 | STYXL1 | SYTL1 | TBC1D2B | TEF |
| SPHK2 | SSFA2 | STC2 | SUCLG1 | SYTL2 | TBC1D3P2 | TEKT4 |
| SPINK2 | SSH2 | STEAP2 | SUCLG2 | SYTL3 | TBC1D7 | TELO2 |
| SPIRE2 | SSH3 | STEAP4 | SUDS3 | T | TBCA | TERF2 |
| SPN | SSPN | STIL | SUFU | TAAR6 | TBCC | TERF2IP |
| SPNS3 | SSR1 | STIM2 | SUGT1L1 | TACC1 | TBCD | TERT |
| SPOPL | SSTR1 | STIP1 | SUGT1P1 | TACC2 | TBCE | TES |
| SPPL2A | SSX2IP | STK10 | SULF1 | TACC3 | TBCEL | TESK2 |
| SPPL2B | ST13 | STK11 | SULF2 | TACR1 | TBL1XR1 | TET2 |
| SPR | ST14 | STK16 | SULT1A2 | TAF10 | TBL3 | TET3 |
| SPRED1 | ST20 | STK17B | SULT1A3 | TAF11 | TBRG1 | TEX10 |
| SPRED2 | ST3GAL1 | STK19 | SULT1C4 | TAF15 | TBRG4 | TEX2 |
| SPRR2B | ST3GAL2 | STK24 | SULT2B1 | TAF1C | TBX18 | TEX264 |
| SPRR2D | ST3GAL3 | STK25 | SULT4A1 | TAF1D | TBX5 | TFAM |
| SPRYD3 | ST3GAL4 | STK3 | SUMO1 | TAF4 | TBXAS1 | TFAMP1 |
| SPSB2 | ST3GAL5 | STK32B | SUMO2 | TAF4B | TCEA1 | TFAP2B |
| SPSB3 | ST5 | STK32C | SUPT16H | TAF6 | TCEA3 | TFAP2C |
| SPTB | ST6GAL1 | STK35 | SUPT5H | TAF6L | TCEB1 | TFAP2E |
| SPTBN1 | ST6GALNAC2 | STK36 | SUPT6H | TAF7 | TCEB3 | TFB2M |
| SPTBN2 | ST6GALNAC4 | STK38 | SUPT7L | TAF8 | TCEB3CL | TFCP2 |
| SPTBN4 | ST7 | STK39 | SUSD1 | TAGLN | TCERG1 | TFDP1 |
| SPTBN5 | ST7L | STK40 | SUSD4 | TAGLN2 | TCERG1L | TFEB |
| SPTY2D1 | ST7OT1 | STMN1 | SUV420H1 | TANC1 | TCF12 | TFG |
| SQLE | ST8SIA1 | STMN3 | SUV420H2 | TAOK2 | TCF20 | TFPI |
| SQRDL | ST8SIA3 | STOM | SUZ12 | TAOK3 | TCF25 | TFPT |
| SQSTM1 | ST8SIA4 | STOML2 | SUZ12P | TAP1 | TCF3 | TFR2 |
| SR140 | ST8SIA6 | STOX1 | SV2B | TAP2 | TCF4 | TFRC |
| SRCIN1 | STAC2 | STRADA | SV2C | TAPBP | TCF7L1 | TGDS |
| SRD5A3 | STAG1 | STRAP | SVIL | TAPBPL | TCHH | TGFA |
| SREBF2 | STAG3 | STRC | SVIP | TAPT1 | TCHP | TGFB2 |
| SRF | STAMBP | STRN | SYCE2 | TARSL2 | TCL1B | TGFB3 |
| SRFBP1 | STAP1 | STRN3 | SYDE1 | TAS1R1 | TCP10 | TGFBR1 |
| SRGAP1 | STAP2 | STRN4 | SYF2 | TAS2R31 | TCP11L1 | TGFBR2 |
| TGFBR3 | TINF2 | TMEM11 | TMEM233 | TNFRSF10B | TP53TG1 | TRIM26 |
| TGFBRAP1 | TIPIN | TMEM115 | TMEM30A | TNFRSF10D | TPBG | TRIM27 |
| TGIF1 | TIPRL | TMEM116 | TMEM33 | TNFRSF11A | TPCN1 | TRIM29 |

Figure 15-18

| TGIF2 | TJP2 | TMEM120B | TMEM38B | TNFRSF12A | TPCN2 | TRIM3 |
|---|---|---|---|---|---|---|
| TGM6 | TJP3 | TMEM121 | TMEM41A | TNFRSF13B | TPD52 | TRIM31 |
| TGOLN2 | TKT | TMEM123 | TMEM41B | TNFRSF19 | TPD52L1 | TRIM33 |
| THADA | TLE2 | TMEM126B | TMEM43 | TNFRSF1B | TPD52L2 | TRIM36 |
| THAP1 | TLE3 | TMEM128 | TMEM44 | TNFRSF25 | TPI1 | TRIM37 |
| THAP11 | TLE4 | TMEM131 | TMEM45A | TNIK | TPK1 | TRIM39 |
| THAP2 | TLE6 | TMEM132A | TMEM5 | TNIP2 | TPM2 | TRIM41 |
| THAP3 | TLK1 | TMEM132E | TMEM50B | TNK2 | TPM4 | TRIM43 |
| THAP4 | TLR5 | TMEM134 | TMEM55A | TNKS | TPMT | TRIM44 |
| THAP5 | TLX3 | TMEM141 | TMEM55B | TNKS2 | TPR | TRIM45 |
| THAP7 | TM2D2 | TMEM143 | TMEM56 | TNPO1 | TPRKB | TRIM47 |
| THAP9 | TM2D3 | TMEM144 | TMEM57 | TNPO3 | TPRX1 | TRIM50 |
| THBD | TM4SF4 | TMEM145 | TMEM59 | TNRC18 | TPRXL | TRIM54 |
| THBS1 | TM7SF2 | TMEM146 | TMEM61 | TNRC6A | TPST1 | TRIM58 |
| THBS2 | TM7SF3 | TMEM14B | TMEM65 | TNRC6B | TPST2 | TRIM59 |
| THBS3 | TM9SF3 | TMEM150A | TMEM66 | TNS1 | TPT1 | TRIM60 |
| THEM4 | TM9SF4 | TMEM151B | TMEM67 | TNS3 | TPX2 | TRIM62 |
| THG1L | TMBIM4 | TMEM160 | TMEM68 | TNXB | TRA2A | TRIM65 |
| THOC1 | TMBIM6 | TMEM161A | TMEM80 | TOB2 | TRADD | TRIM7 |
| THOC4 | TMC2 | TMEM161B | TMEM82 | TOLLIP | TRAF3IP1 | TRIM71 |
| THOC5 | TMC5 | TMEM163 | TMEM86A | TOM1L1 | TRAF4 | TRIM73 |
| THOC7 | TMC6 | TMEM167B | TMEM87B | TOMM22 | TRAF5 | TRIM8 |
| THOP1 | TMC8 | TMEM169 | TMEM90A | TOMM34 | TRAF6 | TRIO |
| THRA | TMCC1 | TMEM175 | TMEM91 | TOMM40 | TRAF7 | TRIOBP |
| THRAP3 | TMCC2 | TMEM179B | TMEM93 | TOMM5 | TRAFD1 | TRIP10 |
| THRB | TMCO1 | TMEM18 | TMEM99 | TOMM6 | TRAM1 | TRIP11 |
| THSD1P | TMED1 | TMEM181 | TMEM9B | TOMM7 | TRAM2 | TRIP4 |
| THSD4 | TMED10 | TMEM182 | TMIE | TOP1MT | TRANK1 | TRIT1 |
| THSD7B | TMED2 | TMEM184A | TMOD3 | TOP1P2 | TRAPPC1 | TRMT12 |
| THUMPD1 | TMED4 | TMEM184C | TMPPE | TOP2A | TRAPPC4 | TRMT2A |
| THY1 | TMED5 | TMEM199 | TMPRSS2 | TOP2B | TRAPPC6A | TRMT5 |
| TIA1 | TMED7 | TMEM2 | TMPRSS4 | TOP3A | TRAPPC6B | TRMT61B |
| TIAF1 | TMED7-TICAM2 | TMEM201 | TMSB10 | TOPBP1 | TRAPPC9 | TRNAU1AP |
| TIAM2 | TMED9 | TMEM209 | TMSL3 | TOR1A | TRERF1 | TRNT1 |
| TIFA | TMEFF1 | TMEM212 | TMTC2 | TOR2A | TRIAP1 | TROAP |
| TIGD3 | TMEM100 | TMEM214 | TMTC3 | TOR3A | TRIB1 | TROVE2 |
| TIMM10 | TMEM101 | TMEM216 | TMTC4 | TOX | TRIB2 | TRPC3 |
| TIMM13 | TMEM105 | TMEM217 | TMUB1 | TOX2 | TRIB3 | TRPC4AP |
| TIMM17A | TMEM106A | TMEM219 | TMUB2 | TP53 | TRIM11 | TRPM1 |
| TIMM22 | TMEM106B | TMEM22 | TMX1 | TP53BP1 | TRIM14 | TRPM2 |
| TIMM44 | TMEM106C | TMEM222 | TMX3 | TP53I13 | TRIM15 | TRPM4 |
| TIMM50 | TMEM107 | TMEM223 | TNFAIP3 | TP53I3 | TRIM16L | TRPM7 |
| TIMM8B | TMEM108 | TMEM229B | TNFAIP8L1 | TP53INP2 | TRIM2 | TRPS1 |
| TIMP2 | TMEM109 | TMEM231 | TNFRSF10A | TP53RK | TRIM23 | TRPV1 |
| TRUB1 | TTC4 | TXNDC11 | UBE4B | UNC84A | UTP3 | VPS8 |
| TSC22D1 | TTC7B | TXNDC12 | UBFD1 | UNC93B1 | UTRN | VRK2 |
| TSC22D4 | TTF2 | TXNDC15 | UBIAD1 | UNCX | UVRAG | VSIG10 |
| TSEN15 | TTK | TXNDC16 | UBL3 | UNG | VAC14 | VSNL1 |
| TSEN2 | TTLL1 | TXNDC17 | UBL5 | UNK | VAMP4 | VSTM2A |
| TSEN54 | TTLL10 | TXNDC5 | UBL7 | UNKL | VANGL2 | VSX2 |
| TSG101 | TTLL13 | TXNIP | UBLCP1 | UPF1 | VAPA | VTI1A |
| TSGA10 | TTLL2 | TXNL1 | UBN1 | UPF2 | VARS | VTI1B |
| TSGA13 | TTLL4 | TXNL4A | UBOX5 | UPK3B | VASH1 | VTRNA1-1 |
| TSGA14 | TTLL5 | TXNL4B | UBP1 | UQCC | VASH2 | VTRNA1-2 |
| TSKU | TTLL6 | TXNRD1 | UBQLN4 | UQCR | VASP | VWC2 |

Figure 15-19

| | | | | | | |
|---|---|---|---|---|---|---|
| TSNARE1 | TTLL8 | TXNRD2 | UBR2 | UQCRB | VAT1 | WAC |
| TSNAXIP1 | TTPA | TYK2 | UBTD2 | URB2 | VAV2 | WAPAL |
| TSPAN1 | TTPAL | TYMS | UBTF | USE1 | VAV3 | WARS2 |
| TSPAN16 | TTR | TYRO3 | UBXN1 | USO1 | VCP | WASF1 |
| TSPAN17 | TTYH1 | TYROBP | UBXN11 | USP1 | VCPIP1 | WASH2P |
| TSPAN3 | TTYH3 | TYSND1 | UBXN2B | USP15 | VDR | WASH3P |
| TSPAN31 | TUB | U2AF1 | UBXN6 | USP16 | VEGFB | WASH5P |
| TSPAN4 | TUBA1A | U2AF2 | UBXN7 | USP18 | VENTX | WASL |
| TSPAN5 | TUBA1B | UBA2 | UCHL3 | USP19 | VENTXP7 | WBP1 |
| TSPAN9 | TUBA1C | UBA5 | UCK1 | USP2 | VGLL2 | WBP11P1 |
| TSPYL3 | TUBA3C | UBA52 | UCKL1 | USP21 | VGLL4 | WBP2 |
| TSPYL4 | TUBA3D | UBA7 | UCRC | USP3 | VHL | WBP4 |
| TSR1 | TUBA8 | UBAC1 | UFC1 | USP32 | VIM | WBSCR16 |
| TSSC1 | TUBB | UBAC2 | UFD1L | USP33 | VIPR1 | WBSCR17 |
| TSSC4 | TUBB1 | UBAP2 | UFM1 | USP36 | VIPR2 | WBSCR22 |
| TSSK2 | TUBB2A | UBASH3B | UFSP1 | USP37 | VKORC1 | WDHD1 |
| TTBK1 | TUBB2B | UBB | UFSP2 | USP38 | VKORC1L1 | WDR18 |
| TTBK2 | TUBB4 | UBC | UGDH | USP39 | VOPP1 | WDR19 |
| TTC14 | TUBB6 | UBD | UGGT1 | USP4 | VPRBP | WDR20 |
| TTC15 | TUBB8 | UBE2C | UGP2 | USP42 | VPS11 | WDR24 |
| TTC17 | TUBBP5 | UBE2D1 | UGT1A10 | USP43 | VPS13B | WDR26 |
| TTC18 | TUBD1 | UBE2D2 | UGT8 | USP44 | VPS13C | WDR27 |
| TTC19 | TUBE1 | UBE2D3 | UHRF1 | USP45 | VPS18 | WDR3 |
| TTC21B | TUBGCP2 | UBE2E1 | UIMC1 | USP46 | VPS24 | WDR33 |
| TTC22 | TUBGCP3 | UBE2E2 | ULBP1 | USP47 | VPS26B | WDR34 |
| TTC25 | TUBGCP6 | UBE2G1 | ULBP2 | USP48 | VPS28 | WDR35 |
| TTC26 | TULP2 | UBE2H | ULBP3 | USP49 | VPS29 | WDR36 |
| TTC27 | TULP4 | UBE2I | ULK4 | USP5 | VPS37A | WDR37 |
| TTC28 | TUSC2 | UBE2J2 | UMPS | USP53 | VPS37C | WDR4 |
| TTC30A | TUSC3 | UBE2K | UNC119B | USP6NL | VPS37D | WDR45L |
| TTC31 | TUT1 | UBE2L3 | UNC13A | USP7 | VPS4A | WDR46 |
| TTC32 | TWF1 | UBE2N | UNC45A | USPL1 | VPS4B | WDR47 |
| TTC35 | TWISTNB | UBE2Q1 | UNC50 | UST | VPS52 | WDR48 |
| TTC39A | TWSG1 | UBE2W | UNC5A | UTF1 | VPS53 | WDR5 |
| TTC39B | TXLNA | UBE3A | UNC5B | UTP11L | VPS54 | WDR51A |
| TTC39C | TXN2 | UBE3B | UNC80 | UTP15 | VPS72 | WDR51B |
| WDR52 | WRNIP1 | YY1 | ZCCHC9 | ZMYM5 | ZNF253 | ZNF354A |
| WDR53 | WSB1 | YY1AP1 | ZDHHC1 | ZNF100 | ZNF254 | ZNF354B |
| WDR55 | WSCD2 | ZADH2 | ZDHHC11 | ZNF101 | ZNF256 | ZNF354C |
| WDR59 | WTAP | ZAP70 | ZDHHC14 | ZNF107 | ZNF257 | ZNF358 |
| WDR60 | WTIP | ZAR1 | ZDHHC16 | ZNF114 | ZNF259 | ZNF365 |
| WDR62 | WWC1 | ZAR1L | ZDHHC17 | ZNF117 | ZNF26 | ZNF366 |
| WDR65 | WWC2 | ZBED5 | ZDHHC18 | ZNF12 | ZNF260 | ZNF37A |
| WDR7 | WWOX | ZBP1 | ZDHHC20 | ZNF121 | ZNF263 | ZNF37B |
| WDR70 | XAB2 | ZBTB1 | ZDHHC22 | ZNF133 | ZNF264 | ZNF384 |
| WDR73 | XBP1 | ZBTB12 | ZDHHC23 | ZNF134 | ZNF266 | ZNF385A |
| WDR74 | XCL2 | ZBTB16 | ZDHHC24 | ZNF138 | ZNF271 | ZNF385B |
| WDR75 | XKR3 | ZBTB2 | ZDHHC3 | ZNF14 | ZNF276 | ZNF391 |
| WDR76 | XKR4 | ZBTB20 | ZDHHC5 | ZNF140 | ZNF28 | ZNF394 |
| WDR77 | XKR5 | ZBTB22 | ZDHHC7 | ZNF141 | ZNF280B | ZNF395 |
| WDR8 | XKR7 | ZBTB24 | ZDHHC8 | ZNF143 | ZNF280D | ZNF396 |
| WDR81 | XPC | ZBTB25 | ZDHHC8P | ZNF146 | ZNF281 | ZNF397 |
| WDR82 | XPNPEP1 | ZBTB26 | ZEB1 | ZNF148 | ZNF282 | ZNF398 |
| WDR86 | XPNPEP3 | ZBTB3 | ZFAND1 | ZNF155 | ZNF284 | ZNF410 |
| WDR87 | XRCC1 | ZBTB34 | ZFAND2A | ZNF16 | ZNF285A | ZNF414 |

Figure 15-20

| | | | | | | |
|---|---|---|---|---|---|---|
| WDR89 | XRCC2 | ZBTB4 | ZFAND2B | ZNF160 | ZNF346 | ZNF688 |
| WDR91 | XRCC3 | ZBTB40 | ZFAND3 | ZNF167 | ZNF419 | ZNF689 |
| WDR92 | XRCC4 | ZBTB42 | ZFAND6 | ZNF17 | ZNF420 | ZNF69 |
| WDR93 | XRCC6BP1 | ZBTB43 | ZFC3H1 | ZNF174 | ZNF426 | ZNF691 |
| WDTC1 | XRN1 | ZBTB45 | ZFHX3 | ZNF177 | ZNF429 | ZNF695 |
| WEE1 | XRN2 | ZBTB46 | ZFP1 | ZNF181 | ZNF43 | ZNF697 |
| WFDC3 | XYLT1 | ZBTB47 | ZFP161 | ZNF184 | ZNF431 | ZNF7 |
| WHAMM | XYLT2 | ZBTB48 | ZFP36L1 | ZNF187 | ZNF433 | ZNF70 |
| WHAMML1 | YAF2 | ZBTB5 | ZFP36L2 | ZNF195 | ZNF436 | ZNF701 |
| WHSC1 | YARS | ZBTB7A | ZFP41 | ZNF2 | ZNF438 | ZNF702P |
| WHSC1L1 | YBX1 | ZBTB7B | ZFP64 | ZNF20 | ZNF439 | ZNF703 |
| WHSC2 | YBX2 | ZBTB9 | ZFPM1 | ZNF207 | ZNF440 | ZNF705A |
| WIBG | YEATS2 | ZC3H10 | ZFPM2 | ZNF211 | ZNF441 | ZNF705D |
| WIPF2 | YIF1A | ZC3H11A | ZFR2 | ZNF212 | ZNF443 | ZNF706 |
| WIPI2 | YIF1B | ZC3H12A | ZFYVE1 | ZNF213 | ZNF444 | ZNF784 |
| WISP3 | YIPF2 | ZC3H12C | ZFYVE16 | ZNF214 | ZNF446 | ZNF786 |
| WNK2 | YIPF5 | ZC3H13 | ZFYVE19 | ZNF219 | ZNF451 | ZNF787 |
| WNK4 | YJEFN3 | ZC3H15 | ZFYVE26 | ZNF22 | ZNF461 | ZNF788 |
| WNT11 | YLPM1 | ZC3H3 | ZFYVE28 | ZNF224 | ZNF462 | ZNF789 |
| WNT2B | YME1L1 | ZC3H6 | ZHX2 | ZNF225 | ZNF467 | ZNF79 |
| WNT3 | YPEL1 | ZC3HAV1 | ZIC1 | ZNF226 | ZNF468 | ZNF790 |
| WNT3A | YPEL3 | ZCCHC11 | ZKSCAN1 | ZNF229 | ZNF480 | ZNF792 |
| WNT5A | YTHDC1 | ZCCHC14 | ZKSCAN2 | ZNF23 | ZNF484 | ZNF793 |
| WNT5B | YTHDF3 | ZCCHC17 | ZKSCAN5 | ZNF230 | ZNF486 | ZNF799 |
| WNT9B | YWHAE | ZCCHC2 | ZMAT3 | ZNF236 | ZNF487 | ZNF8 |
| WRAP53 | YWHAH | ZCCHC24 | ZMIZ1 | ZNF248 | ZNF490 | ZNF80 |
| WRB | YWHAQ | ZCCHC4 | ZMPSTE24 | ZNF250 | ZNF493 | ZNF805 |
| WRN | YWHAZ | ZCCHC8 | ZMYM4 | ZNF252 | ZNF496 | ZNF808 |
| ZNF498 | ZNF600 | ZNF707 | ZNF828 | ZNF286A | ZNF497 | ZNF813 |
| ZNF500 | ZNF605 | ZNF709 | ZNF829 | ZNF286B | ZNF560 | ZNF814 |
| ZNF506 | ZNF607 | ZNF71 | ZNF83 | ZNF292 | ZNF561 | ZNF815 |
| ZNF507 | ZNF608 | ZNF710 | ZNF830 | ZNF295 | ZNF562 | ZNF816A |
| ZNF511 | ZNF609 | ZNF716 | ZNF837 | ZNF296 | ZNF564 | ZNF823 |
| ZNF512 | ZNF610 | ZNF720 | ZNF839 | ZNF3 | ZNF565 | ZNF827 |
| ZNF512B | ZNF611 | ZNF721 | ZNF84 | ZNF302 | ZNF566 | ZSWIM6 |
| ZNF513 | ZNF614 | ZNF727 | ZNF845 | ZNF304 | ZNF567 | ZSWIM7 |
| ZNF514 | ZNF619 | ZNF735 | ZNF860 | ZNF311 | ZNF57 | ZW10 |
| ZNF516 | ZNF620 | ZNF737 | ZNF876P | ZNF317 | ZNF570 | ZWILCH |
| ZNF517 | ZNF622 | ZNF738 | ZNF880 | ZNF318 | ZNF574 | ZWINT |
| ZNF519 | ZNF626 | ZNF74 | ZNF90 | ZNF320 | ZNF578 | ZXDC |
| ZNF521 | ZNF627 | ZNF747 | ZNF92 | ZNF321 | ZNF581 | ZYG11A |
| ZNF527 | ZNF628 | ZNF749 | ZNF98 | ZNF322B | ZNF582 | ZYX |
| ZNF528 | ZNF629 | ZNF761 | ZNHIT1 | ZNF323 | ZNF583 | ZZZ3 |
| ZNF540 | ZNF638 | ZNF763 | ZNHIT2 | ZNF324 | ZNF584 | |
| ZNF541 | ZNF639 | ZNF764 | ZNHIT3 | ZNF324B | ZNF586 | |
| ZNF543 | ZNF641 | ZNF766 | ZNRD1 | ZNF326 | ZNF589 | |
| ZNF546 | ZNF643 | ZNF768 | ZNRF1 | ZNF330 | ZNF593 | |
| ZNF547 | ZNF644 | ZNF77 | ZNRF2 | ZNF331 | ZNF594 | |
| ZNF549 | ZNF649 | ZNF770 | ZRANB2 | ZNF335 | ZNF599 | |
| ZNF550 | ZNF652 | ZNF771 | ZSCAN12 | ZNF33A | ZNF672 | |
| ZNF551 | ZNF655 | ZNF773 | ZSCAN21 | ZNF33B | ZNF680 | |
| ZNF554 | ZNF662 | ZNF774 | ZSCAN29 | ZNF34 | ZNF681 | |
| ZNF555 | ZNF665 | ZNF777 | ZSCAN5A | ZNF341 | ZNF682 | |
| ZNF557 | ZNF667 | ZNF778 | ZSCAN5B | ZNF343 | ZNF684 | |
| ZNF559 | ZNF668 | ZNF780B | ZSWIM5 | ZNF345 | ZNF687 | |

Figure 15-21

| Illumina Probe | Chr | Mapinfo | Correlation | Gene |
|---|---|---|---|---|
| cg26910465 | 15 | 43622671 | -0.369416263 | ADAL |
| cg09238957 | 16 | 46723420 | -0.368456321 | ORC6L |
| cg04099813 | 11 | 2422520 | -0.365611798 | TSSC4 |
| cg13567813 | 19 | 50879636 | -0.365173256 | NR1H2 |
| cg20808462 | 4 | 2243252 | -0.36430563 | HAUS3 |
| cg24475210 | 4 | 6642433 | -0.36277689 | MRFAP1 |
| cg16968115 | 1 | 27560829 | -0.362667157 | WDTC1 |
| cg02357877 | 7 | 56032049 | -0.362235622 | GBAS |
| cg07546106 | 6 | 32806236 | -0.362071249 | TAP2 |
| cg03031660 | 17 | 73257791 | -0.361995457 | MRPS7 |
| cg22111723 | 13 | 21872664 | -0.361752464 | |
| cg06117184 | 2 | 113522207 | -0.361522945 | CKAP2L |
| cg07478100 | 17 | 5389857 | -0.36091616 | MIS12 |
| cg07734253 | 16 | 30194717 | -0.360701477 | CORO1A |
| cg12124516 | 2 | 136634144 | -0.35967703 | MCM6 |
| cg00544901 | 19 | 49999417 | -0.359472362 | RPS11 |
| cg04022019 | 8 | 104427717 | -0.359443861 | DCAF13 |
| cg15318396 | 21 | 38593284 | -0.359215395 | |
| cg11877270 | 2 | 65658583 | -0.358719667 | SPRED2 |
| cg22605179 | 22 | 29664171 | -0.358025806 | EWSR1 |
| cg21292152 | 19 | 37406949 | -0.357927947 | ZNF829 |
| cg06339248 | 11 | 57435803 | -0.357896597 | ZDHHC5 |
| cg20935862 | 9 | 77643594 | -0.357798005 | C9orf41 |
| cg25352856 | 1 | 180472145 | -0.357760161 | ACBD6 |
| cg24478630 | 2 | 74692696 | -0.357714953 | MOGS |
| cg01349853 | 3 | 36986697 | -0.357373489 | TRANK1 |
| cg01089095 | 10 | 75541668 | -0.357252974 | CHCHD1 |
| cg24208426 | 11 | 3819031 | -0.356927065 | PGAP2 |
| cg05389560 | 12 | 21654664 | -0.356743185 | RECQL |
| cg14036868 | 2 | 38604442 | -0.356545803 | ATL2 |
| cg05051152 | 8 | 124408913 | -0.356529845 | ATAD2 |
| cg09691861 | 4 | 77870047 | -0.356470204 | 11-Sep |
| cg22037798 | 1 | 231473786 | -0.356436551 | C1orf124 |
| cg17360140 | 4 | 128886135 | -0.356384274 | C4orf29 |
| cg11786005 | 6 | 170863399 | -0.356267908 | PSMB1 |
| cg18451256 | 2 | 128284158 | -0.356095802 | IWS1 |
| cg04836154 | 11 | 62439314 | -0.356083167 | C11orf83 |
| cg18116217 | 10 | 3215066 | -0.356080372 | PITRM1 |
| cg03699307 | 16 | 75600014 | -0.356059532 | GABARAPL2 |
| cg01559663 | 8 | 53852274 | -0.355914129 | NPBWR1 |

| Illumina Probe | Chr | Mapinfo | Correlation | Gene |
|---|---|---|---|---|
| cg14172283 | 9 | 37592468 | -0.355875087 | TOMM5 |
| cg07377675 | 1 | 62901875 | -0.355718933 | USP1 |
| cg08800530 | 5 | 175788722 | -0.3556852 | KIAA1191 |
| cg13436085 | 3 | 183904316 | -0.355620125 | ABCF3 |
| cg24106894 | 15 | 48623432 | -0.355615703 | DUT |
| cg04265971 | 4 | 2470698 | -0.355580707 | RNF4 |
| cg18036763 | 22 | 45404910 | -0.355575081 | PHF21B |
| cg15012981 | 1 | 11741009 | -0.355483562 | MAD2L2 |
| cg05112885 | 3 | 57541942 | -0.355372677 | PDE12 |
| cg00993799 | 7 | 104653126 | -0.355352224 | LOC10021654 |
| cg12043106 | 10 | 131909379 | -0.355340866 | |
| cg25261764 | 18 | 55288998 | -0.355205982 | NARS |
| cg24756528 | 16 | 4466888 | -0.355098809 | CORO7 |
| cg09387687 | 3 | 110791400 | -0.355091479 | PVRL3 |
| cg26649251 | 19 | 44598564 | -0.355066228 | ZNF224 |
| cg00657871 | 1 | 85156634 | -0.355028754 | SSX2IP |
| cg09127400 | 6 | 30712331 | -0.355007014 | IER3 |
| cg16448126 | 12 | 123921461 | -0.354679968 | RILPL2 |
| cg19767650 | 1 | 183605181 | -0.354614315 | ARPC5 |
| ch.7.44221780F | 7 | 44255255 | -0.354492711 | |
| cg24334809 | 2 | 178483498 | -0.354227715 | TTC30A |
| cg27597069 | 6 | 37321822 | -0.354033924 | RNF8 |
| cg05719877 | 11 | 114271629 | -0.353958328 | C11orf71 |
| cg21795699 | 17 | 15903687 | -0.353487486 | ZSWIM7 |
| cg24095088 | 6 | 160210874 | -0.35348061 | MRPL18 |
| cg01114951 | 1 | 117664707 | -0.353473797 | TRIM45 |
| cg13934093 | 19 | 4458039 | -0.353410594 | UBXN6 |
| cg25707994 | 7 | 157129685 | -0.35334422 | DNAJB6 |
| cg23213688 | 1 | 231473791 | -0.353293198 | C1orf124 |
| cg19340909 | 1 | 1821422 | -0.353260277 | GNB1 |
| cg10583683 | 15 | 23034700 | -0.353250105 | NIPA2 |
| cg07003055 | 20 | 3776921 | -0.353234852 | CDC25B |
| cg08554462 | 18 | 60986911 | -0.353193116 | BCL2 |
| cg10945667 | 13 | 91999862 | -0.353153014 | MIR17HG |
| cg08133824 | 7 | 99698538 | -0.35281738 | MCM7 |
| cg12375025 | 18 | 67873125 | -0.352752991 | RTTN |
| cg13455597 | 9 | 2844149 | -0.352751091 | KIAA0020 |
| cg10831504 | 12 | 69005104 | -0.352746691 | RAP1B |
| cg24410064 | 7 | 7222050 | -0.352721437 | C1GALT1 |
| cg08208917 | 15 | 42565872 | -0.3526641 | GANC |

Figure 16-1

| | | | | | | | | | |
|---|---|---|---|---|---|---|---|---|---|
| cg11338389 | 11 | 63742044 | -0.35253464 | COX8A | cg05533552 | 11 | 34074141 | -0.349881331 | CAPRIN1 |
| cg10185519 | 16 | 30621987 | -0.352505088 | ZNF689 | cg11728900 | 10 | 13203459 | -0.34985572 | MCM10 |
| cg11744351 | 13 | 30424153 | -0.352378107 | UBL3 | cg22704520 | 2 | 200820451 | -0.349795351 | C2orf60 |
| cg25632648 | 11 | 77899776 | -0.35231018 | KCTD21 | cg22223655 | 18 | 67872902 | -0.349780733 | RTTN |
| cg24692716 | 6 | 133119484 | -0.352277704 | C6orf192 | cg04887335 | 3 | 196044632 | -0.349757753 | TCTEX1D2 |
| cg05598205 | 16 | 46723426 | -0.352256355 | ORC6L | cg05907386 | 19 | 46195928 | -0.349587917 | QPCTL |
| cg26188571 | 5 | 179050811 | -0.352163814 | HNRNPH1 | cg07786668 | 16 | 73092391 | -0.349565761 | ZFHX3 |
| cg24275354 | 2 | 240964415 | -0.352075663 | NDUFA10 | cg19282742 | 16 | 31469983 | -0.349456878 | ARMC5 |
| cg19034708 | 8 | 17780168 | -0.352018329 | PCM1 | cg16203711 | 3 | 169491183 | -0.349452418 | MYNN |
| cg26442458 | 11 | 65728985 | -0.351971658 | SART1 | cg04912466 | 11 | 63742028 | -0.349437282 | COX8A |
| cg01532694 | 8 | 8243576 | -0.351842355 | | cg24591563 | 3 | 40498842 | -0.349425049 | RPL14 |
| cg25696485 | 21 | 38445943 | -0.351819435 | PIGP | cg25807061 | 7 | 74306919 | -0.349389402 | PMS2L5 |
| cg01245787 | 4 | 71859630 | -0.351805399 | DCK | cg05300158 | 4 | 140477727 | -0.349376124 | SETD7 |
| cg04533881 | 14 | 50583218 | -0.351610642 | C14orf138 | cg03754076 | 1 | 232766254 | -0.349370038 | |
| cg02342053 | 9 | 37592791 | -0.351470964 | TOMM5 | cg00636124 | 16 | 27215281 | -0.349364602 | JMJD5 |
| cg24341498 | 9 | 137217390 | -0.35144523 | RXRA | cg03584288 | 19 | 37407041 | -0.349320209 | ZNF829 |
| cg14229247 | 9 | 100745139 | -0.351420669 | ANP32B | cg19568834 | 20 | 34252926 | -0.349268405 | CPNE1 |
| cg01061025 | 1 | 212209225 | -0.351336548 | INTS7 | cg08570275 | 3 | 152553089 | -0.349215983 | P2RY1 |
| cg05982271 | 4 | 76555948 | -0.351325807 | CDKL2 | cg11508669 | 12 | 6643545 | -0.349120673 | GAPDH |
| cg06703062 | 1 | 31191648 | -0.351283493 | MATN1 | cg14369264 | 10 | 14996383 | -0.348977237 | DCLRE1C |
| cg00101895 | 6 | 108279135 | -0.351042033 | SEC63 | cg24044479 | 1 | 116518910 | -0.348959186 | SLC22A15 |
| cg11232610 | 5 | 140027381 | -0.351012033 | NDUFA2 | cg12426141 | 15 | 57210872 | -0.348852729 | TCF12 |
| cg19594024 | 19 | 58919948 | -0.351005384 | ZNF584 | cg07262328 | 11 | 35160709 | -0.34883205 | CD44 |
| cg04049556 | 2 | 71357511 | -0.350977473 | MPHOSPH10 | cg23333420 | 10 | 105677801 | -0.348822412 | OBFC1 |
| cg04956913 | 6 | 30712436 | -0.350940018 | IER3 | cg02759005 | 3 | 53925912 | -0.348819472 | SELK |
| cg10284592 | 11 | 57434942 | -0.350922588 | ZDHHC5 | cg17221980 | 6 | 117996486 | -0.348733124 | NUS1 |
| cg06939115 | 16 | 47007824 | -0.350891907 | DNAJA2 | cg16436509 | 12 | 120875898 | -0.34868729 | COX6A1 |
| cg07743799 | 20 | 2821434 | -0.350883356 | FAM113A | cg10101463 | 1 | 202780506 | -0.348583286 | |
| cg22702784 | 2 | 26100814 | -0.350733874 | ASXL2 | cg18062281 | 19 | 19030222 | -0.348576964 | DDX49 |
| cg11826116 | 22 | 39916314 | -0.350701027 | ATF4 | cg12460105 | 5 | 68665773 | -0.348558635 | RAD17 |
| cg15749322 | 11 | 82905199 | -0.350698438 | ANKRD42 | cg19233923 | 11 | 63753598 | -0.348512343 | OTUB1 |
| cg07519049 | 6 | 154830998 | -0.35064233 | CNKSR3 | cg14664575 | 19 | 40476624 | -0.348433102 | PSMC4 |
| cg04977109 | 17 | 46125622 | -0.350639743 | NFE2L1 | cg19859486 | 3 | 45730655 | -0.348268548 | SACM1L |
| cg21028463 | 17 | 74733682 | -0.350620143 | MIR636 | cg13717023 | 5 | 53606639 | -0.348268378 | ARL15 |
| cg00989323 | 10 | 49864621 | -0.350605578 | | cg26279152 | 13 | 20356101 | -0.348260688 | PSPC1 |
| cg20819397 | 9 | 123964132 | -0.350505001 | RAB14 | cg13390975 | 5 | 34915890 | -0.348254715 | BRIX1 |
| cg15072612 | 6 | 32862352 | -0.350502852 | | cg03989244 | 15 | 72523736 | -0.348226451 | PKM2 |
| cg03595861 | 6 | 26126282 | -0.350205476 | | cg01176150 | 16 | 31519952 | -0.348099043 | C16orf58 |
| cg01438737 | 20 | 42086396 | -0.350132682 | SFRS6 | cg12809842 | 3 | 196438875 | -0.34798469 | PIGX |
| cg15838288 | 1 | 228225687 | -0.35001719 | WNT3A | cg05144147 | 10 | 6018955 | -0.347911393 | IL15RA |
| cg18493069 | 6 | 108582623 | -0.349929704 | SNX3 | cg17696166 | 17 | 36981606 | -0.347896862 | CCDC49 |

Figure 16-2

| | | | | | | | | | |
|---|---|---|---|---|---|---|---|---|---|
| cg27110132 | 16 | 3661765 | -0.34789074 | BTBD12 | cg05731183 | 15 | 68132796 | -0.345780026 | |
| cg24356797 | 19 | 18682387 | -0.347849748 | UBA52 | cg06642177 | 6 | 134496341 | -0.345683812 | SGK1 |
| cg26858892 | 12 | 118573640 | -0.3477998 | PEBP1 | cg13193676 | 8 | 80942319 | -0.345665718 | MRPS28 |
| cg24654547 | 16 | 68057165 | -0.347750542 | DUS2L | cg16041611 | 6 | 43139680 | -0.345663235 | SRF |
| cg26376168 | 6 | 30712439 | -0.347656413 | IER3 | cg16362983 | 14 | 50335243 | -0.345602286 | |
| cg19954613 | 22 | 22020219 | -0.347627559 | PPIL2 | cg21028326 | 22 | 50683188 | -0.345583858 | TUBGCP6 |
| cg26910488 | 17 | 66243590 | -0.347560803 | AMZ2 | cg10932242 | 14 | 100659592 | -0.345556762 | |
| cg01457080 | 14 | 77278578 | -0.34755422 | ANGEL1 | cg20940459 | 1 | 173793922 | -0.345432063 | CENPL |
| cg27275634 | 20 | 37590967 | -0.3475078 | DHX35 | cg20349687 | 2 | 88927127 | -0.34541042 | EIF2AK3 |
| cg00080118 | 6 | 31126173 | -0.347473329 | CCHCR1 | cg27033716 | 13 | 24463018 | -0.345404389 | PCOTH |
| cg03951132 | 20 | 5931305 | -0.347463514 | MCM8 | cg02184643 | 11 | 10879647 | -0.345372598 | ZBED5 |
| cg08525207 | 2 | 3622752 | -0.347367499 | RPS7 | cg21352959 | 17 | 62340143 | -0.345371598 | TEX2 |
| cg20731804 | 6 | 42858765 | -0.347356586 | C6orf226 | cg03183872 | 20 | 3140552 | -0.345353027 | FASTKD5 |
| cg04488215 | 1 | 174968829 | -0.3473125 | CACYBP | cg11316940 | 10 | 69524027 | -0.345331326 | |
| cg00368987 | 19 | 57703364 | -0.347300739 | ZNF264 | cg13799898 | 9 | 136858673 | -0.345307107 | VAV2 |
| cg04553410 | 7 | 150864885 | -0.347252146 | GBX1 | cg04726800 | 3 | 128598191 | -0.345277515 | ACAD9 |
| cg14189758 | 20 | 36156486 | -0.347218357 | BLCAP | cg05489143 | 3 | 40498640 | -0.345275356 | RPL14 |
| cg10794915 | 17 | 33569985 | -0.347155264 | SLFN5 | cg13872356 | 11 | 62341519 | -0.345266442 | EEF1G |
| cg15147060 | 3 | 88108213 | -0.346991106 | CGGBP1 | cg02594498 | 15 | 22893147 | -0.34524021 | CYFIP1 |
| cg02815282 | 11 | 67141135 | -0.346921732 | LOC100130987 | cg02627531 | 19 | 52873085 | -0.34521987 | ZNF880 |
| cg21359254 | 2 | 128144817 | -0.346861046 | | cg20994084 | 17 | 79269488 | -0.345214296 | SLC38A10 |
| cg04145065 | 4 | 40057559 | -0.346845767 | N4BP2 | cg13360562 | 15 | 39872883 | -0.34520363 | THBS1 |
| cg26439238 | 13 | 45563672 | -0.346800727 | NUFIP1 | cg24315188 | 7 | 77428849 | -0.345162831 | PHTF2 |
| cg22493809 | 1 | 120838387 | -0.346777693 | FAM72B | cg05055720 | 3 | 49449599 | -0.345143613 | TCTA |
| cg06012509 | 6 | 43027269 | -0.346683899 | KLC4 | cg21605986 | 5 | 175788725 | -0.345121854 | KIAA1191 |
| cg16993440 | 5 | 80597283 | -0.346603526 | RNU5E | cg22020752 | 12 | 22697546 | -0.345107002 | KIAA0528 |
| cg03837627 | 17 | 28443756 | -0.346569719 | CCDC55 | cg00155504 | 1 | 11160113 | -0.345068005 | EXOSC10 |
| cg03133725 | 12 | 133563452 | -0.346328436 | ZNF26 | cg08602604 | 2 | 198364282 | -0.345041863 | HSPD1 |
| cg03149313 | 1 | 226595334 | -0.346305037 | PARP1 | cg11430659 | 2 | 201374471 | -0.345027605 | KCTD18 |
| cg04278597 | 1 | 63154320 | -0.346231031 | DOCK7 | cg06893225 | 1 | 24306863 | -0.345019478 | SFRS13A |
| cg16370446 | 4 | 15683284 | -0.346175403 | LOC285550 | cg04347293 | 6 | 32862350 | -0.344982957 | |
| cg25180252 | 10 | 51828127 | -0.346129807 | FAM21A | cg05164570 | 5 | 140071033 | -0.344861201 | HARS |
| cg00730780 | 10 | 30316187 | -0.346074915 | KIAA1462 | cg08125972 | 19 | 36705377 | -0.344833493 | ZNF565 |
| cg23077509 | 3 | 142166793 | -0.346066945 | XRN1 | cg16120422 | 12 | 113590924 | -0.344798006 | CCDC42B |
| cg20791839 | 3 | 53926047 | -0.346041914 | SELK | cg15967188 | 4 | 2470700 | -0.344763143 | RNF4 |
| cg02750935 | 5 | 145214981 | -0.345995489 | PRELID2 | cg23604584 | 13 | 50367114 | -0.344602629 | KPNA3 |
| cg19180542 | 10 | 43047893 | -0.345987363 | ZNF37B | ch.8.20603847F | 8 | 20559567 | -0.344536045 | |
| cg06752163 | 3 | 170588210 | -0.34598497 | RPL22L1 | cg03519303 | 4 | 139936796 | -0.344445444 | CCRN4L |
| cg00603498 | 17 | 5322775 | -0.345968144 | RPAIN | cg18471460 | 14 | 54863582 | -0.344350015 | CDKN3 |
| cg07222113 | 8 | 104427719 | -0.345951657 | DCAF13 | cg08809260 | 2 | 177054140 | -0.344270537 | HOXD1 |
| cg25365783 | 7 | 108166722 | -0.345788162 | PNPLA8 | cg19545621 | 2 | 208491029 | -0.344255359 | FAM119A |

Figure 16-3

| | | | | | | | | | |
|---|---|---|---|---|---|---|---|---|---|
| cg12646754 | 1 | 2574751 | -0.34424681 | | cg05467106 | 16 | 30621996 | -0.343059665 | ZNF689 |
| cg05525867 | 15 | 75661090 | -0.344245323 | MAN2C1 | cg21108767 | 7 | 99933721 | -0.343038938 | PILRB |
| cg08256065 | 5 | 77081163 | -0.344157358 | | cg05014952 | 14 | 35873130 | -0.343036506 | NFKBIA |
| cg10450899 | 17 | 685900 | -0.344141295 | RNMTL1 | cg05165580 | 16 | 75657337 | -0.343003926 | ADAT1 |
| cg17868994 | 9 | 107526283 | -0.344110253 | NIPSNAP3B | cg15970156 | 22 | 22863219 | -0.342934202 | ZNF280B |
| cg23556447 | 6 | 90529595 | -0.344109611 | MDN1 | cg05557255 | 11 | 2422385 | -0.342892148 | TSSC4 |
| cg06140118 | 16 | 68056778 | -0.344096404 | DDX28 | cg13549897 | 1 | 70820344 | -0.342862036 | HHLA3 |
| cg02083259 | 16 | 57220135 | -0.344089138 | RSPRY1 | cg11975206 | 10 | 135192160 | -0.342797511 | PAOX |
| cg14082963 | 4 | 89444434 | -0.344044173 | PIGY | cg02320003 | 5 | 60139293 | -0.34271244 | ELOVL7 |
| cg02776251 | 12 | 62654319 | -0.344017998 | USP15 | cg17168838 | 19 | 54663528 | -0.342708227 | LENG1 |
| cg14400631 | 11 | 14666512 | -0.344011614 | PDE3B | cg10536369 | 2 | 170335894 | -0.342699288 | BBS5 |
| cg03631596 | 13 | 73301985 | -0.344009358 | C13orf37 | cg19951638 | 7 | 66461658 | -0.342659456 | SBDS |
| cg00166327 | 13 | 73356072 | -0.343955799 | PIBF1 | cg24269276 | 17 | 56084441 | -0.342633553 | SFRS1 |
| cg16710791 | 1 | 193028559 | -0.343809007 | TROVE2 | cg20601096 | 14 | 93799719 | -0.342627677 | KIAA1409 |
| cg14037413 | 11 | 9482594 | -0.343769054 | ZNF143 | cg26236440 | 2 | 113341947 | -0.342625276 | CHCHD5 |
| cg18106800 | 5 | 94890715 | -0.343714226 | ARSK | cg26745551 | 6 | 97285260 | -0.342576277 | GPR63 |
| cg26260369 | 14 | 68141723 | -0.343674296 | VTI1B | cg10041390 | 10 | 89623018 | -0.34257548 | PTEN |
| cg17663101 | 3 | 49131524 | -0.343661059 | QRICH1 | cg18283779 | 2 | 85107426 | -0.342566426 | C2orf89 |
| cg25444615 | 19 | 24184550 | -0.34362926 | | cg02942644 | 3 | 119217190 | -0.342547763 | C3orf1 |
| cg10037053 | 6 | 30181425 | -0.343590062 | TRIM26 | cg09434803 | 4 | 26863372 | -0.342528142 | STIM2 |
| cg17607973 | 7 | 100027408 | -0.343575086 | MEPCE | cg16826947 | 7 | 44084618 | -0.342488561 | DBNL |
| cg07156296 | 4 | 108911347 | -0.343545924 | HADH | cg20725936 | 5 | 175875158 | -0.342479582 | FAF2 |
| cg21497607 | 2 | 74425593 | -0.343512873 | MTHFD2 | cg24647403 | 3 | 97483221 | -0.342423833 | ARL6 |
| cg21840888 | 18 | 33709847 | -0.343507536 | ELP2 | cg06069179 | 17 | 33288421 | -0.342384202 | CCT6B |
| cg08357601 | 4 | 71554472 | -0.343484954 | UTP3 | cg03392679 | 3 | 71773917 | -0.342270192 | EIF4E3 |
| cg04845077 | 9 | 34126958 | -0.343478878 | DCAF12 | cg13226139 | 14 | 45605129 | -0.342197272 | FKBP3 |
| cg17591343 | 1 | 93646016 | -0.343439092 | TMED5 | cg24131747 | 14 | 68141730 | -0.34214382 | VTI1B |
| cg06364629 | 2 | 27592939 | -0.34337586 | EIF2B4 | cg27024417 | 1 | 32645813 | -0.342141324 | TXLNA |
| cg22450146 | 17 | 74733660 | -0.343370831 | MIR636 | cg07187585 | 17 | 10600923 | -0.342113783 | C17orf48 |
| cg19695335 | 20 | 25604759 | -0.343357654 | NANP | cg15238008 | 12 | 9600875 | -0.342103104 | DDX12 |
| cg15268622 | 1 | 167189846 | -0.343305096 | POU2F1 | cg23627909 | 14 | 60337760 | -0.342050841 | RTN1 |
| cg13129662 | 17 | 48227708 | -0.343299397 | PPP1R9B | cg02146966 | 17 | 18967117 | -0.341935501 | |
| cg10386445 | 2 | 26205648 | -0.343295593 | KIF3C | cg09172817 | 18 | 9915098 | -0.341927048 | VAPA |
| cg21076271 | 14 | 32546633 | -0.343294027 | ARHGAP5 | cg26260386 | 4 | 140477698 | -0.341892239 | SETD7 |
| cg05165989 | 2 | 26101121 | -0.343269941 | ASXL2 | cg14278893 | 1 | 145610795 | -0.341871099 | POLR3C |
| cg18715511 | 12 | 1058965 | -0.343259378 | RAD52 | cg22198449 | 19 | 4458029 | -0.341806928 | UBXN6 |
| cg04210544 | 13 | 111806530 | -0.343215126 | ARHGEF7 | cg09507884 | 11 | 67084689 | -0.341778429 | LOC10013098 |
| cg03616195 | 17 | 29233260 | -0.343207091 | C17orf42 | cg23285750 | 10 | 46223127 | -0.341751954 | FAM21C |
| cg14804635 | 15 | 75747750 | -0.343193716 | SIN3A | cg22468803 | 18 | 9136381 | -0.341654961 | ANKRD12 |
| cg25187227 | 4 | 40058080 | -0.34313652 | N4BP2 | cg20879576 | 11 | 125034747 | -0.341634193 | PKNOX2 |
| cg17424056 | 11 | 46615413 | -0.343133568 | | cg21619228 | 19 | 38085153 | -0.341616764 | ZNF540 |

Figure 16-4

| | | | | | | | | | |
|---|---|---|---|---|---|---|---|---|---|
| cg19720917 | 19 | 36606221 | -0.341572082 | POLR2I | cg00582820 | 3 | 125314599 | -0.340279515 | OSBPL11 |
| cg26187219 | 5 | 52095812 | -0.341547987 | ITGA1 | cg20064106 | 2 | 178257871 | -0.340274617 | LOC10013069 |
| cg06880557 | 13 | 103425546 | -0.341516192 | C13orf27 | cg00533923 | 6 | 116892543 | -0.340247554 | RWDD1 |
| cg23508052 | 10 | 102106811 | -0.341503998 | SCD | cg01547051 | 7 | 150777654 | -0.340177433 | FASTK |
| cg04310649 | 10 | 35416472 | -0.341493565 | CREM | cg22183232 | 11 | 9406733 | -0.340165978 | IPO7 |
| cg07485181 | 2 | 131851172 | -0.341466368 | FAM168B | cg06027057 | 14 | 90849959 | -0.340153017 | |
| cg17154187 | 17 | 18163844 | -0.34141669 | SMCR7 | cg07532072 | 22 | 42016555 | -0.340147304 | PPPDE2 |
| cg12481283 | 20 | 19997705 | -0.341407558 | NAA20 | cg08209042 | 3 | 196295218 | -0.340011253 | WDR53 |
| cg12342027 | 7 | 44835729 | -0.341387876 | PPIA | cg21222634 | 20 | 57465926 | -0.339988699 | GNAS |
| cg24121211 | 4 | 128887195 | -0.341245085 | MFSD8 | cg04847817 | 22 | 28315981 | -0.339984914 | PITPNB |
| cg13196826 | 10 | 98945664 | -0.341208404 | SLIT1 | cg10977398 | 3 | 124606490 | -0.339926205 | ITGB5 |
| cg18500714 | 14 | 100706288 | -0.341145751 | YY1 | cg09947615 | 4 | 42659549 | -0.339898856 | ATP8A1 |
| cg04706880 | 19 | 40023151 | -0.34113833 | EID2B | cg20555477 | 9 | 86594889 | -0.339896109 | HNRNPK |
| cg04223366 | 3 | 66024364 | -0.34113271 | MAGI1 | cg03639675 | 16 | 46723204 | -0.339853359 | ORC6L |
| cg03956646 | 8 | 143750859 | -0.341036652 | JRK | cg14928532 | 9 | 133454630 | -0.339830098 | LOC10027221 |
| cg18610261 | 2 | 37899776 | -0.341024743 | CDC42EP3 | cg15062310 | 7 | 100450120 | -0.339814389 | SLC12A9 |
| cg21824902 | 1 | 27560832 | -0.341008302 | WDTC1 | cg25452632 | 12 | 56754141 | -0.339796555 | STAT2 |
| cg14369405 | 18 | 32556760 | -0.340930302 | MAPRE2 | cg03762505 | 1 | 171750926 | -0.339768415 | METTL13 |
| cg17865108 | 17 | 18086721 | -0.340881269 | ALKBH5 | cg03959891 | 7 | 99933717 | -0.339753847 | PILRB |
| cg12972275 | 4 | 122722461 | -0.340847607 | EXOSC9 | cg08938976 | 1 | 247095660 | -0.339510494 | AHCTF1 |
| cg10952801 | 17 | 43568353 | -0.340833001 | PLEKHM1 | cg16696730 | 21 | 43916444 | -0.339504756 | RSPH1 |
| cg05337192 | 1 | 108113367 | -0.340804487 | | cg12995410 | 6 | 151712734 | -0.339426493 | ZBTB2 |
| cg09771049 | 17 | 66031798 | -0.34077698 | KPNA2 | cg04410587 | 7 | 156743073 | -0.339404606 | NOM1 |
| cg11162385 | 20 | 25604740 | -0.340764818 | NANP | cg15115510 | 20 | 33872603 | -0.339402915 | EIF6 |
| cg11673391 | 1 | 10459052 | -0.340762424 | PGD | cg13654902 | 19 | 38853053 | -0.339266935 | CATSPERG |
| cg25764824 | 22 | 42085083 | -0.34073195 | NHP2L1 | cg00415582 | 6 | 43027202 | -0.339252662 | KLC4 |
| cg22167839 | 7 | 35840133 | -0.340717966 | 7-Sep | cg19080138 | 7 | 35734733 | -0.339233487 | HERPUD2 |
| cg13047843 | 7 | 101386679 | -0.340694773 | | cg23255280 | 9 | 131710198 | -0.339211261 | DOLK |
| cg25604067 | 11 | 126226068 | -0.340686906 | ST3GAL4 | cg15409468 | 5 | 31532111 | -0.33920929 | RNASEN |
| cg14871712 | 9 | 102861491 | -0.340649397 | INVS | cg21157115 | 9 | 33001303 | -0.339133006 | APTX |
| cg02550592 | 1 | 762915 | -0.340597342 | NCRNA00115 | cg14735242 | 2 | 64371651 | -0.339124372 | PELI1 |
| cg25597233 | 5 | 140027233 | -0.340581453 | NDUFA2 | cg08522087 | 5 | 14871910 | -0.339113582 | ANKH |
| cg04949346 | 2 | 169746998 | -0.340572877 | SPC25 | cg11826708 | 3 | 115502895 | -0.339095025 | |
| cg14237749 | 9 | 136344651 | -0.340539992 | SLC2A6 | cg25794819 | 19 | 55629097 | -0.339018136 | PPP1R12C |
| cg07093111 | 17 | 18585732 | -0.340503429 | ZNF286B | cg23709121 | 14 | 59951523 | -0.339011084 | C14orf149 |
| cg27619163 | 17 | 7982806 | -0.340502786 | ALOX12B | cg21806917 | 11 | 66384012 | -0.33900967 | RBM14 |
| cg06888550 | 17 | 43238612 | -0.340497253 | HEXIM2 | cg13537196 | 9 | 15553060 | -0.338954497 | C9orf93 |
| cg19738812 | 7 | 99102438 | -0.340461305 | ZKSCAN5 | cg10845251 | 19 | 19314334 | -0.338901169 | NR2C2AP |
| cg00102920 | 6 | 18156401 | -0.340421049 | TPMT | cg10545927 | 1 | 33117362 | -0.338896144 | RBBP4 |
| cg09276863 | 17 | 60501233 | -0.340329001 | METTL2A | cg18538332 | 22 | 24372958 | -0.338876485 | LOC391322 |
| cg13423282 | 19 | 19174731 | -0.340310262 | SLC25A42 | cg03437731 | 2 | 198570720 | -0.338864329 | MARS2 |

Figure 16-5

| | | | | | | | | | |
|---|---|---|---|---|---|---|---|---|---|
| cg04936382 | 20 | 36662003 | -0.338824445 | RPRD1B | cg03228804 | 16 | 86589205 | -0.337823033 | MTHFSD |
| cg13663190 | 2 | 73461428 | -0.338733202 | CCT7 | cg18212591 | 13 | 103425442 | -0.337813706 | C13orf27 |
| cg05380793 | 13 | 73301995 | -0.33869999 | C13orf37 | cg15806518 | 9 | 127177817 | -0.337783085 | PSMB7 |
| cg05947570 | 10 | 89623020 | -0.338696742 | PTEN | cg10076931 | 6 | 27100556 | -0.337689661 | HIST1H2AG |
| cg18451983 | 6 | 139695471 | -0.338677427 | CITED2 | cg07906495 | 14 | 31028426 | -0.337584149 | G2E3 |
| cg08142263 | 19 | 17420206 | -0.3386661 | DDA1 | cg11515196 | 15 | 44829065 | -0.337575868 | EIF3J |
| cg04226364 | 17 | 47865990 | -0.338660284 | MYST2 | cg27084994 | 5 | 175875161 | -0.337456092 | FAF2 |
| cg05376810 | 17 | 74511493 | -0.338656653 | | cg11821927 | 15 | 45694435 | -0.337434226 | SPATA5L1 |
| cg02985708 | 6 | 32940921 | -0.338623166 | BRD2 | cg09223439 | 15 | 65282374 | -0.337432597 | SPG21 |
| cg24251484 | 10 | 119133804 | -0.338612263 | PDZD8 | cg19752449 | 12 | 109915316 | -0.337347729 | UBE3B |
| cg04844543 | 3 | 47324470 | -0.338597541 | KIF9 | cg02286335 | 10 | 58121068 | -0.337242066 | ZWINT |
| cg08108993 | 17 | 38136923 | -0.338568569 | PSMD3 | cg18354764 | 22 | 31064165 | -0.337224388 | DUSP18 |
| cg10392378 | 6 | 90348606 | -0.338564001 | LYRM2 | cg07303308 | 7 | 128695042 | -0.337192042 | LOC286016 |
| cg17536750 | 4 | 6642118 | -0.33855133 | MRFAP1 | cg04875007 | 16 | 2014871 | -0.33713364 | SNHG9 |
| cg23358710 | 17 | 60704660 | -0.338546749 | MRC2 | cg04798796 | 10 | 88855483 | -0.337109935 | GLUD1 |
| cg19929624 | 18 | 11851551 | -0.338542298 | GNAL | cg25937832 | 3 | 23958525 | -0.33710947 | NKIRAS1 |
| cg23924007 | 4 | 140099401 | -0.338492183 | | cg11422045 | 11 | 43701985 | -0.337105913 | HSD17B12 |
| cg16340159 | 2 | 240322705 | -0.338477653 | HDAC4 | cg08108155 | 22 | 29999444 | -0.337097091 | NF2 |
| cg23472502 | 6 | 42420509 | -0.338457955 | TRERF1 | cg22675162 | 2 | 70520975 | -0.337088686 | SNRPG |
| cg13468174 | 19 | 58919984 | -0.338454129 | ZNF584 | cg12174498 | 8 | 80942140 | -0.337066105 | MRPS28 |
| cg08795962 | 11 | 93862716 | -0.338439787 | PANX1 | cg26597500 | 13 | 73356092 | -0.337065249 | PIBF1 |
| cg18751306 | 15 | 81294292 | -0.338412617 | MESDC1 | cg26149167 | 19 | 16187889 | -0.336937163 | TPM4 |
| cg01154537 | 10 | 95462167 | -0.338367211 | C10orf4 | cg14397361 | 9 | 140149997 | -0.33685328 | COBRA1 |
| cg18255595 | 13 | 20735871 | -0.338346231 | GJA3 | cg10122932 | 7 | 99698990 | -0.336815584 | MCM7 |
| cg21160472 | 1 | 212782112 | -0.338299524 | ATF3 | cg22033189 | 1 | 28908551 | -0.336801092 | SNHG12 |
| cg03780073 | 15 | 48624255 | -0.3382899 | DUT | cg04690289 | 3 | 45017999 | -0.336741375 | ZDHHC3 |
| cg01162436 | 10 | 15902292 | -0.338252874 | FAM188A | cg07987587 | 22 | 42486991 | -0.336685183 | NDUFA6 |
| cg14042131 | 11 | 48003169 | -0.338229781 | PTPRJ | cg14320593 | 18 | 47088343 | -0.336585646 | LIPG |
| cg05835456 | 15 | 43785425 | -0.338227429 | TP53BP1 | cg13023681 | 2 | 10444156 | -0.336536883 | HPCAL1 |
| cg02996684 | 17 | 73257924 | -0.338182454 | GGA3 | cg25976786 | 12 | 53662079 | -0.336502852 | ESPL1 |
| cg01040759 | 2 | 86116384 | -0.338179448 | ST3GAL5 | cg21869055 | 19 | 51522454 | -0.336482161 | KLK10 |
| cg00965391 | 11 | 92930777 | -0.33816811 | SLC36A4 | cg06172942 | 3 | 50378529 | -0.336440527 | RASSF1 |
| cg16026760 | 19 | 4791699 | -0.338110531 | FEM1A | cg01534423 | 17 | 18965556 | -0.336440304 | |
| cg26693760 | 6 | 33267069 | -0.338036566 | RGL2 | cg25423402 | 1 | 185286075 | -0.336437794 | IVNS1ABP |
| cg03272292 | 12 | 48577362 | -0.338014964 | C12orf68 | cg17019204 | 6 | 86303781 | -0.336395163 | SNX14 |
| cg18721605 | 18 | 44676421 | -0.338008133 | HDHD2 | cg16587974 | 5 | 76383162 | -0.336371888 | LOC728723 |
| cg27227786 | 17 | 54911265 | -0.337998411 | DGKE | cg09695652 | 3 | 139108473 | -0.336350018 | COPB2 |
| cg10742605 | 3 | 18485411 | -0.337975785 | | cg07031532 | 15 | 64995684 | -0.336327401 | OAZ2 |
| cg26674752 | 10 | 43634212 | -0.337965086 | CSGALNACT2 | cg15408407 | 19 | 1438438 | -0.33632339 | RPS15 |
| cg18881776 | 1 | 28052146 | -0.337951707 | FAM76A | cg01608030 | 19 | 1605680 | -0.33630646 | UQCR |
| cg23542858 | 8 | 125486752 | -0.337873291 | RNF139 | cg24899068 | 19 | 49999470 | -0.33629556 | RPS11 |

Figure 16-6

| | | | | | | | | | |
|---|---|---|---|---|---|---|---|---|---|
| cg15248577 | 10 | 7450456 | -0.336289824 | SFMBT2 | cg27417846 | 2 | 88927289 | -0.334841202 | EIF2AK3 |
| cg22974920 | 21 | 40686053 | -0.336239274 | BRWD1 | cg26097011 | 13 | 103046943 | -0.334809987 | FGF14 |
| cg19656070 | 17 | 3571978 | -0.33620493 | TMEM93 | cg00045190 | 6 | 33216612 | -0.334802668 | |
| cg02043083 | 6 | 150070997 | -0.336167693 | PCMT1 | cg21799605 | 6 | 42713881 | -0.334798892 | TBCC |
| cg17985418 | 17 | 66031785 | -0.336153694 | KPNA2 | cg09000178 | 16 | 67063319 | -0.334792867 | CBFB |
| cg08533424 | 17 | 37009973 | -0.336111477 | RPL23 | cg13883202 | 3 | 47422330 | -0.334784079 | PTPN23 |
| cg23623107 | 2 | 128284154 | -0.336034419 | IWS1 | cg02063919 | 20 | 50418044 | -0.334759579 | SALL4 |
| cg03537747 | 2 | 27886640 | -0.335985854 | SLC4A1AP | cg08293367 | 22 | 22089752 | -0.334757322 | YPEL1 |
| cg27376617 | 7 | 30518048 | -0.335976424 | NOD1 | cg01888767 | 5 | 131832552 | -0.334722039 | |
| cg11081185 | 11 | 208423 | -0.335925672 | RIC8A | cg01993413 | 14 | 21979151 | -0.334646308 | METTL3 |
| cg16162927 | 6 | 136610857 | -0.335914151 | BCLAF1 | cg06719391 | 11 | 2554330 | -0.334566917 | KCNQ1 |
| cg03719625 | 19 | 38806411 | -0.335905207 | YIF1B | cg19853927 | 3 | 153839743 | -0.334558308 | SGEF |
| cg02932736 | 1 | 67896194 | -0.335904392 | SERBP1 | cg12173535 | 19 | 54694174 | -0.334525555 | MBOAT7 |
| cg12023693 | 2 | 102091115 | -0.335883486 | RFX8 | cg06770993 | 3 | 49158462 | -0.334440256 | USP19 |
| cg07281688 | 12 | 57082442 | -0.33587995 | PTGES3 | cg09069257 | 12 | 94495988 | -0.334379901 | |
| cg04966789 | 14 | 35591779 | -0.335849953 | PPP2R3C | cg22813744 | 11 | 77899778 | -0.33435308 | KCTD21 |
| cg00124011 | 1 | 14075958 | -0.335816174 | PRDM2 | cg11781847 | 8 | 67837483 | -0.334340593 | SNHG6 |
| cg16632994 | 5 | 158690246 | -0.335777127 | UBLCP1 | cg04508286 | 7 | 35840410 | -0.334324966 | 7-Sep |
| cg00166750 | 8 | 102138594 | -0.335746557 | | cg10163945 | 5 | 115421152 | -0.334322447 | COMMD10 |
| cg12700464 | 11 | 78128424 | -0.335732831 | GAB2 | cg07623022 | 16 | 18801545 | -0.334315908 | RPS15A |
| ch.2.223778692R | 2 | 224070448 | -0.335658333 | | cg26900616 | 4 | 159593389 | -0.334314375 | ETFDH |
| cg01963240 | 14 | 54421117 | -0.335639893 | BMP4 | cg03156112 | 10 | 22630065 | -0.334306438 | |
| cg13189086 | 15 | 23034679 | -0.33558978 | NIPA2 | cg23616383 | 17 | 7487132 | -0.33418011 | MPDU1 |
| cg11718235 | 19 | 56915184 | -0.335579288 | ZNF583 | cg16458021 | 21 | 43430507 | -0.334176037 | ZNF295 |
| cg03486485 | 11 | 14927004 | -0.335529526 | | cg23542284 | 19 | 19314328 | -0.334093906 | NR2C2AP |
| cg19057882 | 20 | 37101373 | -0.335494105 | RALGAPB | cg05325390 | 16 | 23464715 | -0.334092741 | COG7 |
| cg22916109 | 15 | 78730334 | -0.335448305 | IREB2 | cg03373442 | 13 | 31736396 | -0.334091312 | HSPH1 |
| cg05529236 | 11 | 62341449 | -0.335439973 | EEF1G | cg11775492 | 12 | 51158663 | -0.334088908 | ATF1 |
| cg16971831 | 5 | 56110935 | -0.335391253 | MAP3K1 | cg02836531 | 1 | 78225436 | -0.334087771 | USP33 |
| cg10035432 | 14 | 39644345 | -0.335371447 | PNN | cg26460378 | 19 | 36545594 | -0.334084374 | WDR62 |
| cg24458288 | 18 | 12702185 | -0.335350301 | CEP76 | cg25776555 | 19 | 52531777 | -0.334015183 | ZNF614 |
| cg17488985 | 6 | 86159426 | -0.335309044 | NT5E | cg24429831 | 19 | 36120171 | -0.334009297 | RBM42 |
| cg24218077 | 11 | 125495856 | -0.335291751 | CHEK1 | cg18438837 | 1 | 42922100 | -0.334007624 | PPCS |
| cg25587211 | 3 | 43663662 | -0.335137657 | ANO10 | cg21656600 | 12 | 111181027 | -0.333981092 | PPP1CC |
| cg20009215 | 6 | 2765204 | -0.335084301 | WRNIP1 | cg18469778 | 11 | 18548623 | -0.333980159 | TSG101 |
| cg08167214 | 16 | 81040017 | -0.335066258 | CENPN | cg09099697 | 10 | 65281856 | -0.333966701 | REEP3 |
| cg20670292 | 2 | 131099506 | -0.334908121 | IMP4 | cg04291082 | 1 | 193028561 | -0.333948446 | TROVE2 |
| cg03092918 | 10 | 126107592 | -0.334894767 | OAT | cg23091255 | 6 | 64345855 | -0.333910281 | |
| cg14694896 | 8 | 104427370 | -0.334874376 | SLC25A32 | cg13519464 | 19 | 9938554 | -0.333892355 | UBL5 |
| cg02410754 | 1 | 32410520 | -0.334866327 | | cg02249648 | 12 | 1703181 | -0.333884751 | FBXL14 |
| cg22782929 | 10 | 21784432 | -0.334849606 | C10orf114 | cg12109968 | 20 | 50383676 | -0.333860522 | ATP9A |

Figure 16-7

| | | | | | | | | | |
|---|---|---|---|---|---|---|---|---|---|
| cg17417191 | 1 | 218458683 | -0.333843085 | RRP15 | cg11980791 | 9 | 131084797 | -0.333048165 | COQ4 |
| cg16465128 | 16 | 30389462 | -0.333818099 | 1-Sep | cg24441068 | 11 | 32605279 | -0.332965766 | EIF3M |
| cg00881254 | 18 | 657522 | -0.33380022 | TYMS | cg05871607 | 1 | 28241317 | -0.332942938 | RPA2 |
| cg04759220 | 5 | 78532560 | -0.33379053 | JMY | cg03054141 | 12 | 8234711 | -0.332925228 | NECAP1 |
| cg17227014 | 4 | 6642450 | -0.333789496 | MRFAP1 | cg13912060 | 14 | 68141881 | -0.332914146 | VTI1B |
| cg04273556 | 9 | 35096672 | -0.333788718 | PIGO | cg08703520 | 19 | 58978336 | -0.332806554 | ZNF324 |
| cg16687867 | 11 | 111896092 | -0.333765466 | DLAT | cg16114773 | 1 | 20209461 | -0.33274614 | OTUD3 |
| cg21442773 | 1 | 236029828 | -0.333760901 | LYST | cg08230118 | 6 | 30181847 | -0.332732541 | TRIM26 |
| cg02775028 | 4 | 184580387 | -0.333708668 | C4orf41 | cg06746074 | 3 | 87276268 | -0.332721405 | CHMP2B |
| cg17978996 | 6 | 107436496 | -0.333702545 | BEND3 | cg14797322 | 12 | 58165899 | -0.332706773 | FAM119B |
| cg18264306 | 3 | 97483471 | -0.333667009 | ARL6 | cg13676204 | 14 | 61447818 | -0.332696358 | SLC38A6 |
| cg14815005 | 22 | 22222162 | -0.333664785 | MAPK1 | cg02455615 | 11 | 33183110 | -0.332660661 | CSTF3 |
| cg13433446 | 9 | 128170534 | -0.333649537 | | cg14650559 | 14 | 77843620 | -0.332652103 | C14orf174 |
| cg22512377 | 22 | 42475683 | -0.333590254 | C22orf32 | cg18652923 | 2 | 109745344 | -0.332643816 | SH3RF3 |
| cg03883519 | 4 | 128886524 | -0.3335571 | MFSD8 | cg09007244 | 22 | 51221736 | -0.332619131 | RPL23AP82 |
| cg26681912 | 1 | 169455321 | -0.333538715 | SLC19A2 | cg01840575 | 2 | 38977957 | -0.332607879 | SFRS7 |
| cg03875450 | 9 | 98269581 | -0.333525673 | PTCH1 | cg17310611 | 1 | 113615709 | -0.332607374 | LRIG2 |
| cg14532069 | 18 | 59993399 | -0.333512013 | TNFRSF11A | cg21008684 | 2 | 157198370 | -0.332570497 | |
| cg21243939 | 14 | 55033137 | -0.333490511 | SAMD4A | cg06873684 | 19 | 4472059 | -0.332541702 | HDGF2 |
| cg08402439 | 4 | 180980552 | -0.333467778 | | cg13398135 | 17 | 80250214 | -0.332512383 | |
| cg25264554 | 3 | 142166789 | -0.33345286 | XRN1 | cg10130446 | 14 | 55658398 | -0.332488734 | DLGAP5 |
| cg14031414 | 20 | 13765665 | -0.333434352 | ESF1 | cg21851142 | 6 | 132129008 | -0.332480761 | ENPP1 |
| cg25296860 | 13 | 20702426 | -0.333422067 | | cg27209395 | 6 | 26172397 | -0.332468423 | |
| cg03456512 | 7 | 107531689 | -0.333416916 | DLD | cg27196102 | 16 | 23464713 | -0.332459641 | COG7 |
| cg13425677 | 5 | 56112090 | -0.333399843 | MAP3K1 | cg19049616 | 17 | 58042270 | -0.332388499 | RNFT1 |
| cg09690659 | 20 | 33680871 | -0.333380273 | TRPC4AP | cg18467110 | 3 | 140661601 | -0.332388305 | SLC25A36 |
| cg14838017 | 1 | 160232450 | -0.333342358 | DCAF8 | cg25346576 | 17 | 28443852 | -0.332386846 | CCDC55 |
| cg27090007 | 13 | 28519388 | -0.333335858 | ATP5EP2 | cg17691309 | 9 | 35690459 | -0.332372078 | TPM2 |
| cg22546696 | 15 | 41952645 | -0.333330686 | MGA | cg26541587 | 10 | 43950885 | -0.332361766 | ZNF487 |
| cg24663255 | 8 | 146228920 | -0.333316172 | ZNF252 | cg24085655 | 6 | 35436189 | -0.332342699 | RPL10A |
| cg11652947 | 17 | 80605508 | -0.333315291 | WDR45L | cg10867947 | 8 | 95835263 | -0.33232296 | INTS8 |
| cg00090767 | 14 | 65569376 | -0.333308366 | MAX | cg14242042 | 12 | 24715250 | -0.332312405 | SOX5 |
| cg26387966 | 8 | 144503421 | -0.333303594 | | cg17290332 | 10 | 14880008 | -0.332273357 | CDNF |
| cg22992588 | 18 | 74207551 | -0.333283222 | | cg03803211 | 2 | 70313772 | -0.332237304 | PCBP1 |
| cg08867499 | 19 | 33667906 | -0.333246525 | | cg23576473 | 17 | 47785586 | -0.332213148 | SLC35B1 |
| cg24079997 | 4 | 52709183 | -0.333214481 | DCUN1D4 | cg24395128 | 17 | 57184525 | -0.332158046 | TRIM37 |
| cg19014302 | 19 | 18303893 | -0.333200277 | MPV17L2 | cg06733736 | 16 | 3661771 | -0.332145324 | BTBD12 |
| cg11841349 | 3 | 9791615 | -0.333154093 | OGG1 | cg11075994 | 15 | 102192790 | -0.332097287 | TM2D3 |
| cg04175957 | 15 | 23207925 | -0.333117315 | WHAMML1 | cg13776499 | 2 | 12858298 | -0.332095052 | TRIB2 |
| cg02994863 | 1 | 64059297 | -0.333092579 | PGM1 | cg15433422 | 3 | 196670053 | -0.332087969 | LOC152217 |
| cg02246053 | 17 | 57184577 | -0.333089625 | TRIM37 | cg18588934 | 9 | 132083215 | -0.332072066 | C9orf106 |

Figure 16-8

| | | | | | | | | | |
|---|---|---|---|---|---|---|---|---|---|
| cg04855748 | 11 | 64067763 | -0.332055228 | C11orf20 | cg03876184 | 2 | 27886755 | -0.331155759 | SUPT7L |
| cg11969467 | 1 | 174992598 | -0.332046422 | MRPS14 | cg05228735 | 16 | 30621825 | -0.33113014 | ZNF689 |
| cg13112249 | 22 | 32870603 | -0.331957858 | FBXO7 | cg04165128 | 19 | 52693149 | -0.331126428 | PPP2R1A |
| cg03758774 | 6 | 32936478 | -0.331943135 | BRD2 | cg21454030 | 4 | 17812573 | -0.331117392 | NCAPG |
| cg05417615 | 4 | 147443478 | -0.331926153 | SLC10A7 | cg18913076 | 2 | 99771244 | -0.331105406 | TSGA10 |
| cg00656411 | 7 | 140773422 | -0.331922334 | | cg16788234 | 11 | 108093338 | -0.331044887 | NPAT |
| cg04364194 | 1 | 202114085 | -0.33191902 | ARL8A | cg13841901 | 1 | 45805975 | -0.331042314 | MUTYH |
| cg13741289 | 4 | 17578858 | -0.331910311 | LAP3 | cg04183933 | 2 | 198363868 | -0.331036343 | HSPD1 |
| cg08655589 | 3 | 14444175 | -0.33189884 | SLC6A6 | cg16722292 | 10 | 7830180 | -0.33100122 | KIN |
| cg16787025 | 15 | 51200723 | -0.331886894 | AP4E1 | cg01141237 | 2 | 198175400 | -0.330992643 | |
| cg06067302 | 22 | 40766481 | -0.331886115 | SGSM3 | cg01896926 | 17 | 685509 | -0.330935504 | GLOD4 |
| cg04024692 | 11 | 16760046 | -0.331876611 | C11orf58 | cg22825116 | 2 | 88991018 | -0.330934628 | RPIA |
| cg21914984 | 2 | 37899464 | -0.331855246 | CDC42EP3 | cg23528168 | 5 | 89770579 | -0.330912105 | MBLAC2 |
| cg05907686 | 6 | 7389956 | -0.331796661 | CAGE1 | cg03857186 | 2 | 27255618 | -0.330891687 | TMEM214 |
| cg24140832 | 11 | 236743 | -0.331795445 | PSMD13 | cg06776953 | 1 | 149859104 | -0.330889713 | HIST2H2AB |
| cg24608684 | 6 | 130686865 | -0.33179082 | | cg16697775 | 6 | 43543259 | -0.330855149 | POLH |
| cg09293699 | 16 | 81040972 | -0.331787171 | CENPN | cg04404789 | 16 | 46722505 | -0.330808488 | ORC6L |
| cg23792258 | 6 | 17988404 | -0.331775019 | KIF13A | cg02461956 | 11 | 134093940 | -0.330779359 | NCAPD3 |
| cg21777696 | 11 | 57283154 | -0.331765301 | SLC43A1 | ch.5.2925238F | 5 | 154966064 | -0.330778913 | |
| cg26526596 | 6 | 170190117 | -0.331751477 | C6orf122 | cg01456938 | 4 | 2470303 | -0.330772779 | RNF4 |
| cg02656441 | 13 | 111367915 | -0.331677653 | ING1 | cg10620501 | 8 | 37620046 | -0.330734318 | PROSC |
| cg05119514 | 19 | 58459218 | -0.331599642 | ZNF256 | cg20692684 | 10 | 32735158 | -0.330729196 | CCDC7 |
| cg10093594 | 1 | 206858754 | -0.331588177 | MAPKAPK2 | cg24705286 | 16 | 27215306 | -0.330717403 | JMJD5 |
| cg20288129 | 3 | 122745632 | -0.331587361 | SEMA5B | cg04084597 | 11 | 75479652 | -0.330714488 | DGAT2 |
| cg13601636 | 19 | 55385010 | -0.331584884 | FCAR | cg23060735 | 22 | 51066924 | -0.330695727 | ARSA |
| cg00911981 | 3 | 142297824 | -0.331561866 | ATR | cg00389713 | 6 | 43138877 | -0.330690404 | SRF |
| cg04696559 | 5 | 36152378 | -0.331496606 | SKP2 | cg26852602 | 15 | 83735291 | -0.330660947 | BTBD1 |
| cg08423350 | 4 | 57253668 | -0.331474314 | AASDH | cg06183820 | 6 | 2972097 | -0.330587105 | SERPINB6 |
| cg16221634 | 6 | 73332885 | -0.331472593 | KCNQ5 | cg20214067 | 12 | 133065776 | -0.330579629 | FBRSL1 |
| cg10025462 | 17 | 27046956 | -0.331415963 | SNORD42B | cg27211204 | 15 | 99791508 | -0.330421962 | LRRC28 |
| cg02228635 | 1 | 93298093 | -0.331368722 | RPL5 | cg00673674 | 19 | 19144826 | -0.330408764 | SFRS14 |
| cg03509024 | 3 | 10184013 | -0.331335827 | VHL | cg14092529 | 5 | 21459600 | -0.330396605 | LOC728411 |
| cg16706751 | 7 | 130792127 | -0.331314893 | FLJ43663 | cg03406394 | 15 | 60296138 | -0.330384228 | FOXB1 |
| cg19956166 | 2 | 85980874 | -0.331293005 | ATOH8 | cg10205287 | 4 | 100815590 | -0.330308839 | MAPKSP1 |
| cg09507928 | 5 | 140027484 | -0.331282327 | IK | cg10046127 | 14 | 57735694 | -0.330305427 | MUDENG |
| cg04219700 | 1 | 228594657 | -0.331244918 | TRIM11 | cg08515713 | 11 | 64037528 | -0.330302972 | BAD |
| cg08794928 | 6 | 144537264 | -0.331234417 | | ch.7.3356624R | 7 | 157205374 | -0.330248054 | DNAJB6 |
| cg24962978 | 11 | 118889279 | -0.331201305 | TRAPPC4 | cg11014794 | 10 | 93999688 | -0.330247179 | CPEB3 |
| cg21482837 | 2 | 85581528 | -0.331193559 | ELMOD3 | cg17218495 | 19 | 11071743 | -0.330236689 | SMARCA4 |
| cg12564650 | 5 | 179050814 | -0.331190047 | HNRNPH1 | cg14645526 | 11 | 91959086 | -0.330177668 | |
| cg07697850 | 16 | 29973177 | -0.331174192 | TMEM219 | cg02888906 | 11 | 107798972 | -0.330173159 | RAB39 |

Figure 16-9

| | | | | | | | | | |
|---|---|---|---|---|---|---|---|---|---|
| cg05544840 | 13 | 44716513 | -0.330172563 | | cg13022174 | 18 | 23671059 | -0.329296728 | SS18 |
| cg18396041 | 7 | 149571256 | -0.330142961 | LOC401431 | cg02750587 | 1 | 85156370 | -0.329283668 | SSX2IP |
| cg20296188 | 17 | 77397067 | -0.330124447 | HRNBP3 | cg14209549 | 10 | 3215073 | -0.329273083 | PITRM1 |
| cg09909775 | 12 | 45610071 | -0.330113482 | ANO6 | ch.12.1878964R | 12 | 95773961 | -0.329225409 | |
| cg16811230 | 3 | 39149235 | -0.330102471 | GORASP1 | cg13992236 | 6 | 86352429 | -0.329180395 | SYNCRIP |
| cg10289190 | 9 | 37422575 | -0.330090784 | GRHPR | cg24523585 | 13 | 49821926 | -0.329131905 | CDADC1 |
| cg03468945 | 10 | 126107610 | -0.330046689 | OAT | cg12482557 | 8 | 6693103 | -0.329111356 | XKR5 |
| cg01606576 | 14 | 50065185 | -0.330030329 | PPIL5 | cg24503272 | 6 | 160210831 | -0.32909182 | MRPL18 |
| cg06150468 | 1 | 212874085 | -0.329986237 | BATF3 | cg15605445 | 10 | 88470986 | -0.329087132 | LDB3 |
| cg19759549 | 3 | 128211096 | -0.329982456 | GATA2 | cg03332970 | 11 | 124632552 | -0.329078936 | ESAM |
| cg14150915 | 11 | 66056828 | -0.329925721 | YIF1A | cg23961842 | 6 | 85483800 | -0.329056959 | |
| cg18573544 | 6 | 38608108 | -0.329910686 | BTBD9 | cg22100476 | 1 | 43638037 | -0.329045984 | WDR65 |
| cg03327386 | 18 | 8609878 | -0.329888992 | RAB12 | cg11594927 | 6 | 29720600 | -0.329035996 | |
| cg00715047 | 17 | 73522054 | -0.329888061 | LLGL2 | cg10533351 | 20 | 19997722 | -0.329024014 | NAA20 |
| cg05223847 | 10 | 124913846 | -0.329873737 | BUB3 | cg25700848 | 6 | 7911417 | -0.329001846 | TXNDC5 |
| cg06015203 | 14 | 51297334 | -0.329860308 | NIN | cg25525163 | 3 | 38178867 | -0.328973986 | ACAA1 |
| cg21350283 | 14 | 69445743 | -0.3298468 | ACTN1 | cg15617768 | 10 | 101492447 | -0.328958999 | COX15 |
| cg15928538 | 7 | 140773578 | -0.329823422 | | cg01747792 | 20 | 61806628 | -0.328940871 | |
| cg00795915 | 5 | 70751728 | -0.329814781 | BDP1 | ch.21.43742285F | 21 | 44917857 | -0.328927234 | |
| cg26570218 | 2 | 25195142 | -0.329814307 | DNAJC27 | cg12100751 | 1 | 109203672 | -0.32889872 | C1orf59 |
| cg19789848 | 17 | 30454741 | -0.329802051 | | cg02127607 | 17 | 61920694 | -0.328880807 | SMARCD2 |
| cg13854983 | 2 | 136875315 | -0.329784901 | CXCR4 | cg13383235 | 7 | 7680321 | -0.328838527 | RPA3 |
| cg14810343 | 5 | 139028149 | -0.329784087 | CXXC5 | cg08527566 | 12 | 95611432 | -0.328828162 | FGD6 |
| cg05766425 | 17 | 48796751 | -0.329774497 | LUC7L3 | cg11072887 | 6 | 37322624 | -0.328795855 | RNF8 |
| cg04455180 | 1 | 227506639 | -0.32972059 | CDC42BPA | cg25136353 | 10 | 44185896 | -0.328760659 | |
| cg21899921 | 7 | 73669227 | -0.329717337 | RFC2 | cg06942064 | 1 | 208417143 | -0.328703622 | PLXNA2 |
| cg06689961 | 12 | 12870959 | -0.32970149 | CDKN1B | cg04453241 | 17 | 76374567 | -0.328685109 | PGS1 |
| cg06366345 | 14 | 101459591 | -0.329635447 | SNORD114-31 | cg21106899 | 1 | 11779803 | -0.328665514 | C1orf187 |
| cg15802848 | 6 | 33359461 | -0.329613772 | KIFC1 | cg04496899 | 1 | 70820341 | -0.328636972 | HHLA3 |
| cg21959594 | 19 | 1813058 | -0.329600725 | ATP8B3 | cg22301261 | 13 | 50655392 | -0.328630197 | DLEU1 |
| cg02036077 | 22 | 35653364 | -0.329597849 | HMGXB4 | cg07209631 | 4 | 89205728 | -0.328611241 | PPM1K |
| cg21487637 | 19 | 46195684 | -0.329549442 | QPCTL | cg14225021 | 2 | 161126482 | -0.328609562 | |
| cg24819738 | 19 | 19314415 | -0.329524338 | NR2C2AP | cg00345965 | 1 | 151226992 | -0.328602417 | PSMD4 |
| ch.13.1834088F | 13 | 112692382 | -0.329479887 | | cg26761504 | 19 | 49140601 | -0.328575675 | SEC1 |
| cg14119616 | 11 | 17099403 | -0.329449318 | RPS13 | cg14191109 | 10 | 70287438 | -0.328532882 | SLC25A16 |
| cg23000464 | 19 | 633785 | -0.329422167 | POLRMT | cg14229702 | 15 | 89164377 | -0.328511617 | AEN |
| cg08730330 | 17 | 61904790 | -0.329415823 | PSMC5 | cg13710842 | 5 | 72251735 | -0.328487963 | FCHO2 |
| cg18917495 | 2 | 74006961 | -0.329336715 | DUSP11 | cg22792272 | 6 | 43597128 | -0.328464093 | MAD2L1BP |
| cg11712217 | 17 | 80455631 | -0.329336375 | | cg12774432 | 7 | 141438008 | -0.328432793 | SSBP1 |
| cg23054379 | 1 | 176176226 | -0.329317899 | RFWD2 | cg02690350 | 17 | 27620209 | -0.328418474 | NUFIP2 |
| cg27365208 | 19 | 19778986 | -0.329312143 | ZNF101 | cg26220419 | 11 | 107880052 | -0.328401256 | CUL5 |

Figure 16-10

| | | | | | | | | | |
|---|---|---|---|---|---|---|---|---|---|
| cg01235203 | 3 | 187461998 | -0.32838375 | BCL6 | cg25025968 | 11 | 4116056 | -0.327515114 | RRM1 |
| cg02839220 | 16 | 4400790 | -0.328375714 | Magmas | cg18689253 | 9 | 82186806 | -0.327509054 | TLE4 |
| cg02773889 | 13 | 42615649 | -0.328371192 | | cg08723131 | 20 | 55043694 | -0.327474664 | C20orf43 |
| cg02220499 | 16 | 19729278 | -0.328293789 | IQCK | cg26162836 | 1 | 160232429 | -0.327447023 | DCAF8 |
| cg11618704 | 10 | 43904553 | -0.328267436 | HNRNPF | cg25755261 | 14 | 35591781 | -0.32744401 | PPP2R3C |
| cg24513224 | 17 | 10102439 | -0.328139158 | GAS7 | cg05882878 | 2 | 37458821 | -0.327331685 | CEBPZ |
| cg16604136 | 1 | 163291493 | -0.328115915 | NUF2 | cg18766912 | 15 | 25683909 | -0.327305865 | UBE3A |
| cg15009698 | 5 | 77590494 | -0.328108638 | AP3B1 | cg08536977 | 17 | 73780663 | -0.327288334 | UNK |
| cg12619880 | 1 | 44172798 | -0.328100592 | ST3GAL3 | cg01423820 | 14 | 77228690 | -0.32726969 | VASH1 |
| cg07856758 | 19 | 37861652 | -0.328098838 | ZNF527 | cg05637795 | 15 | 72978746 | -0.327263727 | HIGD2B |
| cg03231960 | 19 | 49139050 | -0.328072515 | DBP | cg24465118 | 20 | 47895107 | -0.327263437 | C20orf199 |
| cg06745507 | 15 | 44085196 | -0.328061446 | SERF2 | cg04223844 | 8 | 42128868 | -0.327242973 | IKBKB |
| cg14586630 | 6 | 74171590 | -0.327999254 | MTO1 | cg08417687 | 6 | 108582627 | -0.327228651 | SNX3 |
| cg15546754 | 11 | 68065392 | -0.327980846 | | cg26960647 | 6 | 138188928 | -0.327209843 | TNFAIP3 |
| cg25525207 | 4 | 57843836 | -0.327976954 | C4orf14 | cg05954989 | 10 | 135191962 | -0.327160735 | PAOX |
| cg06575763 | 20 | 25604643 | -0.327960038 | NANP | cg10663973 | 4 | 6642559 | -0.327154714 | MRFAP1 |
| cg07006042 | 3 | 141595655 | -0.327941469 | ATP1B3 | cg08739576 | 7 | 44144360 | -0.32714863 | AEBP1 |
| cg23267217 | 1 | 26496298 | -0.327918017 | ZNF593 | cg18545992 | 2 | 133013028 | -0.327148475 | NCRNA00164 |
| cg13276752 | 17 | 57970287 | -0.32790782 | TUBD1 | cg03786924 | 6 | 73331680 | -0.327139314 | KCNQ5 |
| cg11021200 | 13 | 21750354 | -0.327902494 | SKA3 | cg12441052 | 11 | 66313700 | -0.327094082 | ZDHHC24 |
| cg22197033 | 17 | 8649004 | -0.327888032 | CCDC42 | cg11739541 | 12 | 49582842 | -0.327085762 | TUBA1A |
| cg10537699 | 11 | 60897371 | -0.327887751 | | cg00947019 | 7 | 44887958 | -0.32706042 | H2AFV |
| cg07169535 | 18 | 34408654 | -0.327864501 | KIAA1328 | cg08863539 | 19 | 2841394 | -0.327052768 | ZNF555 |
| cg07704495 | 21 | 43916519 | -0.327839196 | RSPH1 | cg07987262 | 19 | 19314408 | -0.327052731 | NR2C2AP |
| cg18108022 | 8 | 103666233 | -0.327827313 | KLF10 | cg12133425 | 1 | 247494926 | -0.327046135 | ZNF496 |
| cg21740452 | 21 | 34143691 | -0.327816254 | C21orf66 | cg02704927 | 5 | 65440543 | -0.327018464 | SFRS12 |
| cg17206034 | 3 | 38206839 | -0.327753182 | OXSR1 | cg21308020 | 4 | 99182242 | -0.327002081 | RAP1GDS1 |
| cg23145622 | 1 | 206859650 | -0.327722951 | MAPKAPK2 | cg04350249 | 20 | 18488833 | -0.326998367 | SEC23B |
| cg26396617 | 9 | 133815188 | -0.327682279 | FIBCD1 | cg27482856 | 7 | 99214447 | -0.326933242 | ZNF498 |
| cg07842594 | 10 | 43278214 | -0.327675781 | BMS1 | cg05776084 | 3 | 133293427 | -0.326924191 | CDV3 |
| cg09852199 | 1 | 203764897 | -0.327674089 | ZC3H11A | cg10767909 | 19 | 36980702 | -0.326913918 | ZNF566 |
| cg15229153 | 17 | 5323805 | -0.327666371 | RPAIN | cg09951650 | 15 | 51200814 | -0.326852007 | AP4E1 |
| cg04575467 | 8 | 41997444 | -0.327651604 | | cg00296291 | 4 | 129733887 | -0.32679224 | PHF17 |
| cg07939768 | 17 | 27621433 | -0.327641156 | NUFIP2 | cg17662034 | 8 | 74207518 | -0.326787073 | RDH10 |
| cg14153722 | 1 | 206858799 | -0.327638869 | MAPKAPK2 | cg00994924 | 20 | 25388641 | -0.326735039 | GINS1 |
| cg22664368 | 17 | 4634740 | -0.327607095 | MED11 | cg02226697 | 8 | 126010266 | -0.326718448 | SQLE |
| cg15094636 | 3 | 125094397 | -0.327599062 | ZNF148 | cg09742170 | 7 | 25021208 | -0.32671761 | OSBPL3 |
| cg18452324 | 22 | 37882397 | -0.327582078 | MFNG | cg00292047 | 11 | 33279899 | -0.326698839 | HIPK3 |
| cg23162983 | 17 | 63119174 | -0.327577993 | | cg11655486 | 1 | 85156638 | -0.326677398 | SSX2IP |
| cg05867307 | 4 | 144106066 | -0.327549394 | USP38 | cg10141938 | 7 | 26240087 | -0.326676366 | HNRNPA2B1 |
| cg11792664 | 19 | 1605706 | -0.327521905 | UQCR | cg00832928 | 3 | 150329458 | -0.326674246 | SELT |

Figure 16-11

| | | | | | | | | | |
|---|---|---|---|---|---|---|---|---|---|
| cg07458698 | 2 | 67624494 | -0.326664717 | ETAA1 | cg07274776 | 2 | 203241322 | -0.325916478 | BMPR2 |
| cg22293500 | 3 | 186544871 | -0.326626025 | | cg00061769 | 1 | 155658843 | -0.325909633 | YY1AP1 |
| cg14428767 | 6 | 149867359 | -0.326613523 | PPIL4 | cg07163173 | 2 | 67624373 | -0.325876814 | ETAA1 |
| ch.4.3837399F | 4 | 3867601 | -0.326602828 | | cg01109633 | 17 | 30263774 | -0.325871175 | SUZ12 |
| cg02250900 | 15 | 51915395 | -0.326596709 | DMXL2 | cg12245040 | 16 | 2009320 | -0.325848855 | NDUFB10 |
| cg03177631 | 11 | 18415927 | -0.326537506 | LDHA | cg08576658 | 19 | 56098601 | -0.32584852 | |
| cg21122725 | 4 | 123843781 | -0.326511587 | NUDT6 | cg13782561 | 9 | 94185786 | -0.325844458 | NFIL3 |
| cg22139878 | 10 | 91174299 | -0.326508301 | IFIT5 | cg26549029 | 12 | 133286883 | -0.32583593 | PGAM5 |
| cg25521086 | 2 | 113341977 | -0.326504199 | CHCHD5 | cg26100149 | 5 | 173315151 | -0.325811 | CPEB4 |
| cg16898066 | 6 | 25726437 | -0.326474446 | HIST1H2BA | cg21452766 | 1 | 70877088 | -0.325729334 | CTH |
| cg02625641 | 15 | 59041175 | -0.326464363 | ADAM10 | cg12222460 | 6 | 14211743 | -0.325704805 | |
| cg00900054 | 1 | 46016580 | -0.326437671 | AKR1A1 | cg18908981 | 3 | 43732200 | -0.325700868 | ABHD5 |
| cg01392184 | 15 | 41099692 | -0.326402001 | ZFYVE19 | cg16783819 | 6 | 122720842 | -0.32568702 | HSF2 |
| cg08764805 | 12 | 95867684 | -0.326382203 | METAP2 | cg19543987 | 2 | 73460508 | -0.325679713 | CCT7 |
| cg12637942 | 11 | 65190225 | -0.32637818 | NEAT1 | cg01773306 | 2 | 85555458 | -0.325670208 | TGOLN2 |
| cg09293387 | 8 | 6565827 | -0.326374531 | AGPAT5 | cg15355859 | 11 | 79149352 | -0.325611789 | ODZ4 |
| cg11995741 | 6 | 166797367 | -0.326329012 | BRP44L | cg09358454 | 2 | 157198726 | -0.325592413 | |
| cg12361356 | 1 | 200708503 | -0.326300131 | CAMSAP1L1 | cg08568987 | 19 | 56165234 | -0.32557561 | U2AF2 |
| cg07383443 | 12 | 118573736 | -0.32627295 | PEBP1 | cg16263943 | 2 | 144695179 | -0.325555557 | |
| cg26422134 | 7 | 43909318 | -0.326268066 | MRPS24 | cg10391629 | 13 | 42846072 | -0.325547228 | AKAP11 |
| cg22370633 | 10 | 70092255 | -0.326251124 | PBLD | cg11220663 | 2 | 70994863 | -0.325508551 | ADD2 |
| cg23069677 | 1 | 36863646 | -0.326247862 | LSM10 | cg24561572 | 17 | 43298813 | -0.325490933 | FMNL1 |
| cg22328771 | 22 | 50709822 | -0.326244795 | MAPK11 | cg16327326 | 16 | 1662895 | -0.325467769 | IFT140 |
| cg07399369 | 3 | 142838082 | -0.326236812 | CHST2 | cg27391780 | 16 | 30669108 | -0.325411698 | |
| cg03516836 | 12 | 57881693 | -0.326214124 | MARS | cg13406003 | 6 | 127535477 | -0.325387182 | |
| cg11355601 | 22 | 39096475 | -0.326122549 | JOSD1 | cg26528255 | 1 | 27652089 | -0.325367572 | TMEM222 |
| cg17211447 | 1 | 10490667 | -0.326090256 | APITD1 | cg24127244 | 3 | 133524572 | -0.325357658 | SRPRB |
| cg24236870 | 15 | 42264445 | -0.326088433 | EHD4 | cg04294412 | 4 | 7045720 | -0.325311963 | CCDC96 |
| cg19510484 | 12 | 95868044 | -0.326077218 | METAP2 | cg01822624 | 5 | 32710882 | -0.325290186 | NPR3 |
| cg27467005 | 19 | 17622279 | -0.326076207 | PGLS | cg22024876 | 11 | 105948183 | -0.325283912 | KBTBD3 |
| cg22048132 | 17 | 60005312 | -0.326062196 | INTS2 | cg05798608 | 1 | 202317770 | -0.325270152 | PPP1R12B |
| cg07001481 | 17 | 5389669 | -0.32606091 | DERL2 | cg19696333 | 10 | 124768261 | -0.32526046 | IKZF5 |
| cg14723664 | 6 | 34164073 | -0.326046424 | | cg26812503 | 16 | 75681495 | -0.325243431 | KARS |
| cg13727629 | 1 | 2232469 | -0.326031111 | SKI | cg14283194 | 7 | 91763737 | -0.32522297 | CYP51A1 |
| cg03888520 | 22 | 42978243 | -0.326021462 | RRP7B | cg19967433 | 17 | 7080988 | -0.325190516 | ASGR1 |
| cg20157484 | 12 | 46385525 | -0.32597696 | SFRS2IP | cg19906131 | 11 | 93862516 | -0.325184747 | PANX1 |
| cg06046434 | 11 | 57425242 | -0.325958922 | CLP1 | cg22411415 | 12 | 95228201 | -0.325083036 | MIR492 |
| cg27250139 | 8 | 9912632 | -0.325949679 | MSRA | cg25846022 | 1 | 78444909 | -0.325056366 | FUBP1 |
| cg13943141 | 9 | 93205862 | -0.325941895 | | cg01872295 | 6 | 32937388 | -0.325051757 | BRD2 |
| cg17859882 | 6 | 58287694 | -0.325939357 | GUSBL2 | cg12924408 | 22 | 37172025 | -0.325033384 | RABL4 |
| cg22272545 | 2 | 197036243 | -0.325939306 | STK17B | cg23834254 | 4 | 169931521 | -0.325031023 | CBR4 |

Figure 16-12

| | | | | | | | | | |
|---|---|---|---|---|---|---|---|---|---|
| cg01153132 | 6 | 119400114 | -0.325024366 | FAM184A | cg07617384 | 15 | 74392612 | -0.324232748 | |
| cg08674342 | 5 | 36152125 | -0.324988531 | LMBRD2 | cg22332388 | 8 | 64081173 | -0.324192609 | YTHDF3 |
| cg22280359 | 6 | 83903559 | -0.324982256 | PGM3 | ch.19.11524367R | 19 | 11663367 | -0.324190996 | |
| cg25449542 | 17 | 1957605 | -0.324965792 | HIC1 | cg08579753 | 1 | 39174525 | -0.324178189 | |
| cg14538868 | 2 | 37458838 | -0.32495014 | CEBPZ | cg16558358 | 17 | 80416024 | -0.324149559 | NARF |
| cg19921130 | 15 | 81294134 | -0.32493694 | MESDC1 | ch.1.3903344F | 1 | 201984137 | -0.324148319 | ELF3 |
| cg14555127 | 7 | 35841578 | -0.324857256 | 7-Sep | cg20952324 | 3 | 9773343 | -0.324123713 | BRPF1 |
| cg27132050 | 15 | 45021149 | -0.324809094 | | cg03100196 | 7 | 143077761 | -0.324118202 | ZYX |
| cg02972188 | 12 | 58165945 | -0.324789555 | METTL1 | cg07740989 | 6 | 74230681 | -0.324100074 | EEF1A1 |
| cg02508567 | 2 | 85361184 | -0.324776309 | TCF7L1 | cg02773756 | 6 | 27799308 | -0.324098135 | HIST1H4K |
| cg22164238 | 1 | 110162488 | -0.324766824 | AMPD2 | cg27573591 | 7 | 127672152 | -0.324089021 | SND1 |
| cg09131135 | 2 | 27886635 | -0.324748043 | SLC4A1AP | cg23109134 | 10 | 7830051 | -0.324027008 | ATP5C1 |
| cg07745102 | 7 | 111204826 | -0.324743251 | | cg24198128 | 19 | 18682398 | -0.323992027 | UBA52 |
| cg06564818 | 18 | 33162094 | -0.324742507 | | cg12110529 | 3 | 141030588 | -0.323968331 | |
| cg26477793 | 10 | 104262085 | -0.324725205 | ACTR1A | cg16987848 | 8 | 356385 | -0.323873848 | FBXO25 |
| cg26446827 | 20 | 18268978 | -0.324719315 | ZNF133 | cg13790879 | 2 | 239336104 | -0.323860169 | ASB1 |
| cg10698964 | 15 | 50647173 | -0.324710544 | FLJ10038 | cg23521964 | 10 | 127408065 | -0.323816189 | C10orf137 |
| cg27438040 | 6 | 136611664 | -0.324708659 | BCLAF1 | cg10922622 | 9 | 108210153 | -0.323814357 | FSD1L |
| cg08261858 | 1 | 246887303 | -0.324686816 | SCCPDH | cg23664192 | 6 | 34725288 | -0.323781194 | SNRPC |
| cg08908148 | 7 | 39606013 | -0.324672541 | C7orf36 | cg20617957 | 13 | 100085203 | -0.323779967 | |
| cg12018042 | 14 | 57735703 | -0.324662831 | MUDENG | cg07500976 | 19 | 13261292 | -0.323774553 | IER2 |
| cg04055703 | 5 | 39074730 | -0.324655194 | RICTOR | cg21522303 | 17 | 74581331 | -0.323701579 | ST6GALNAC2 |
| cg14140830 | 3 | 47020973 | -0.324586715 | NBEAL2 | cg22682162 | 6 | 97731065 | -0.323646018 | MIR548H3 |
| cg00143700 | 13 | 49107116 | -0.32457104 | RCBTB2 | cg04892170 | 10 | 128076910 | -0.323599224 | ADAM12 |
| cg15093003 | 10 | 123687697 | -0.324553876 | ATE1 | cg17718302 | 6 | 27858637 | -0.323594574 | HIST1H3J |
| cg01170099 | 14 | 82000431 | -0.324505423 | SEL1L | cg09084877 | 6 | 30181302 | -0.323571762 | TRIM26 |
| cg12429444 | 1 | 20988133 | -0.324491178 | DDOST | cg27574168 | 18 | 54318782 | -0.323523157 | WDR7 |
| cg14940636 | 12 | 56498092 | -0.324480936 | PA2G4 | cg08524221 | 17 | 74732291 | -0.323493781 | SFRS2 |
| cg23374376 | 19 | 39390198 | -0.324467272 | SIRT2 | cg23843362 | 10 | 104677600 | -0.323487052 | CNNM2 |
| cg04064611 | 7 | 72298987 | -0.324459461 | SBDSP | cg27326518 | 1 | 226187335 | -0.323484557 | C1orf55 |
| cg15203817 | 19 | 36980483 | -0.324456458 | ZNF566 | cg05105845 | 14 | 55369781 | -0.323476095 | GCH1 |
| cg26337884 | 10 | 52751119 | -0.324381202 | PRKG1 | cg15738138 | 17 | 40976420 | -0.323443222 | BECN1 |
| cg16302650 | 6 | 149867607 | -0.324375372 | PPIL4 | cg01446164 | 11 | 2421746 | -0.323419794 | |
| cg04798523 | 4 | 103749125 | -0.324368642 | UBE2D3 | cg25335190 | 6 | 27791899 | -0.323389975 | HIST1H4J |
| cg10916494 | 6 | 86388066 | -0.324357434 | SNHG5 | cg07720856 | 2 | 232572668 | -0.323317117 | PTMA |
| cg14907986 | 6 | 24645932 | -0.324349458 | KIAA0319 | cg04853151 | 1 | 54519244 | -0.323310252 | C1orf83 |
| cg10341991 | 3 | 48229869 | -0.324338049 | CDC25A | cg14795047 | 12 | 38710433 | -0.323262895 | ALG10B |
| cg18110359 | 2 | 45179970 | -0.324285248 | | cg21797405 | 5 | 139944339 | -0.323255048 | APBB3 |
| cg26633120 | 2 | 105654408 | -0.324261682 | MRPS9 | cg03299121 | 2 | 68384913 | -0.323209398 | PNO1 |
| cg12219045 | 22 | 44894262 | -0.32424612 | LDOC1L | cg18282264 | 7 | 6048883 | -0.323198034 | AIMP2 |
| cg02249930 | 10 | 70166207 | -0.32423633 | RUFY2 | cg05243144 | 19 | 46273434 | -0.323179055 | DMPK |

Figure 16-13

| | | | | | | | | | |
|---|---|---|---|---|---|---|---|---|---|
| cg04473235 | 5 | 77080995 | -0.32317354 | | cg19469297 | 7 | 45151440 | -0.322263518 | TBRG4 |
| cg22594055 | 5 | 131832675 | -0.323147221 | | cg04476741 | 1 | 11724884 | -0.322205816 | FBXO6 |
| cg01351869 | 15 | 80215929 | -0.323110631 | C15orf37 | cg00929855 | 6 | 31783364 | -0.322150938 | HSPA1A |
| cg25486143 | 3 | 50378527 | -0.323081941 | RASSF1 | cg05825950 | 1 | 207669576 | -0.322149922 | CR1 |
| cg01058931 | 16 | 25269641 | -0.323061952 | ZKSCAN2 | cg07575344 | 1 | 64055717 | -0.322125161 | |
| cg10130401 | 17 | 46970032 | -0.323052963 | ATP5G1 | cg13801946 | 17 | 61699522 | -0.322116732 | MAP3K3 |
| cg08699435 | 20 | 19997606 | -0.323042722 | NAA20 | cg22949637 | 1 | 109234813 | -0.322065257 | PRPF38B |
| cg13303229 | 5 | 154136254 | -0.323033169 | LARP1 | cg27463953 | 20 | 3451306 | -0.322063417 | ATRN |
| cg22311942 | 17 | 73201390 | -0.323032374 | NUP85 | cg22924867 | 7 | 94286834 | -0.322037174 | SGCE |
| cg01528792 | 9 | 73027862 | -0.323014216 | KLF9 | cg07233428 | 1 | 93646535 | -0.322020513 | TMED5 |
| cg11661269 | 1 | 39339371 | -0.322981793 | MYCBP | cg00453202 | 16 | 85482380 | -0.322018847 | |
| cg03162359 | 12 | 45610751 | -0.322961344 | ANO6 | cg14258555 | 19 | 50180725 | -0.322018282 | PRMT1 |
| cg07387199 | 17 | 62502055 | -0.322944049 | CCDC45 | cg22724132 | 16 | 81478990 | -0.322004356 | CMIP |
| cg02759489 | 4 | 55098483 | -0.322864602 | PDGFRA | cg21693780 | 2 | 15731793 | -0.321997128 | DDX1 |
| cg09881819 | 3 | 129034470 | -0.322863335 | H1FX | cg18299363 | 10 | 103816089 | -0.321994977 | C10orf76 |
| cg26689765 | 5 | 52083512 | -0.322837183 | ITGA1 | cg23129217 | 12 | 8551501 | -0.321942755 | |
| cg17998013 | 3 | 15643079 | -0.32282921 | HACL1 | cg13305652 | 7 | 138125259 | -0.321928381 | |
| cg13902357 | 6 | 31324280 | -0.322825841 | HLA-B | cg03449387 | 3 | 183736084 | -0.32189395 | ABCC5 |
| cg19672384 | 6 | 168132359 | -0.322815494 | | cg08202374 | 19 | 47164782 | -0.321877832 | DACT3 |
| cg25136709 | 7 | 143599409 | -0.322814727 | FAM115A | cg13386234 | 14 | 23058032 | -0.321863068 | DAD1 |
| cg10170443 | 5 | 72794209 | -0.322812808 | BTF3 | cg24170511 | 14 | 23341280 | -0.321857359 | LRP10 |
| cg08613513 | 1 | 52870060 | -0.322743742 | ORC1L | cg08923060 | 12 | 120884702 | -0.321852337 | TRIAP1 |
| cg09514055 | 1 | 43919573 | -0.322726322 | HYI | cg04121495 | 4 | 25162214 | -0.321845294 | SEPSECS |
| cg20427059 | 2 | 131851445 | -0.322721337 | FAM168B | cg27110129 | 4 | 15683224 | -0.321833927 | LOC285550 |
| cg18238734 | 12 | 26986119 | -0.32269329 | ITPR2 | cg21761776 | 11 | 58939272 | -0.321822163 | DTX4 |
| cg15660466 | 17 | 49230788 | -0.32267049 | NME1 | cg17386466 | 2 | 87035620 | -0.321816277 | CD8A |
| cg26805238 | 1 | 144931980 | -0.322666073 | PDE4DIP | cg05244136 | 10 | 75541665 | -0.32175145 | CHCHD1 |
| cg11543665 | 19 | 8373294 | -0.322633174 | CD320 | cg15451735 | 1 | 145209930 | -0.32174593 | NOTCH2NL |
| cg03761979 | 4 | 57843892 | -0.322632778 | C4orf14 | cg07867325 | 3 | 73159953 | -0.321722166 | |
| cg14919823 | 3 | 14166510 | -0.32263013 | TMEM43 | cg13113052 | 18 | 51796328 | -0.321686299 | POLI |
| cg26938153 | 7 | 137686926 | -0.32258273 | CREB3L2 | cg04119805 | 7 | 99102391 | -0.321676935 | ZKSCAN5 |
| cg06391926 | 16 | 1832733 | -0.322551841 | NUBP2 | cg17439023 | 12 | 132195732 | -0.321650788 | SFRS8 |
| cg12938135 | 13 | 20356591 | -0.322536412 | PSPC1 | cg09276355 | 13 | 50510822 | -0.32163652 | C13orf1 |
| cg27239157 | 3 | 183145817 | -0.322484551 | MCF2L2 | cg16240060 | 3 | 48956015 | -0.3216358 | ARIH2 |
| cg18912981 | 7 | 7222021 | -0.322438059 | C1GALT1 | cg10018272 | 1 | 67519814 | -0.32163229 | SLC35D1 |
| cg00597713 | 6 | 42947103 | -0.322377818 | PEX6 | cg02367949 | 11 | 94964516 | -0.321537357 | SESN3 |
| cg04771550 | 17 | 8079827 | -0.322358831 | TMEM107 | cg00607725 | 16 | 70380558 | -0.321504451 | DDX19A |
| cg18534872 | 10 | 58121066 | -0.322328227 | ZWINT | cg13863940 | 14 | 103799810 | -0.32150326 | EIF5 |
| cg05964952 | 12 | 51633050 | -0.322288042 | DAZAP2 | cg22083790 | 12 | 133532978 | -0.321453317 | ZNF605 |
| cg05091519 | 11 | 31839552 | -0.322284208 | PAX6 | cg14392031 | 9 | 107526202 | -0.321430955 | NIPSNAP3B |
| cg02167732 | 14 | 81687645 | -0.322281649 | GTF2A1 | cg14820927 | 18 | 34408166 | -0.32141394 | C18orf10 |

Figure 16-14

| | | | | | | | | | |
|---|---|---|---|---|---|---|---|---|---|
| cg13467399 | 9 | 133588111 | -0.32136029 | ABL1 | cg07909497 | 12 | 9600950 | -0.32062983 | DDX12 |
| cg27201871 | 17 | 79212816 | -0.32133625 | C17orf56 | cg05907029 | 1 | 197872227 | -0.320610732 | C1orf53 |
| cg18199720 | 1 | 115054041 | -0.321335395 | TRIM33 | cg03671660 | 21 | 40554907 | -0.320603863 | PSMG1 |
| cg23264557 | 5 | 89770687 | -0.321314646 | MBLAC2 | cg10029411 | 13 | 50746245 | -0.32059706 | FAM10A4 |
| cg14226747 | 4 | 657927 | -0.321302376 | PDE6B | cg03727342 | 9 | 6758683 | -0.320587997 | KDM4C |
| cg24966682 | 6 | 24666810 | -0.321297592 | ACOT13 | cg16989148 | 17 | 46125619 | -0.320578206 | NFE2L1 |
| cg05899183 | 16 | 66968638 | -0.321293986 | FAM96B | cg06591456 | 7 | 4814952 | -0.320569011 | KIAA0415 |
| ch.14.1499103R | 14 | 93412334 | -0.321275943 | ITPK1 | cg08278266 | 5 | 141071625 | -0.320560037 | |
| cg14210872 | 1 | 155294935 | -0.321249623 | RUSC1 | cg11225935 | 12 | 498478 | -0.320538087 | KDM5A |
| cg17323045 | 14 | 58764804 | -0.321247072 | FLJ31306 | cg20127188 | 22 | 21996426 | -0.320533792 | SDF2L1 |
| cg01547622 | 5 | 49962954 | -0.321241363 | PARP8 | cg19125715 | 8 | 67525489 | -0.320523485 | MYBL1 |
| cg11150308 | 17 | 74068434 | -0.321196292 | SRP68 | cg11337525 | 19 | 45418417 | -0.320450231 | APOC1 |
| cg00318899 | 3 | 50284137 | -0.321186065 | GNAI2 | cg26526379 | 7 | 26416184 | -0.320445104 | |
| cg09913796 | 17 | 27181988 | -0.321184802 | ERAL1 | cg15889838 | 5 | 131832312 | -0.320428934 | |
| cg15006843 | 1 | 205720633 | -0.321171607 | NUCKS1 | cg03323770 | 14 | 74960890 | -0.320393237 | NPC2 |
| cg19761211 | 16 | 70415365 | -0.321166532 | ST3GAL2 | cg07727872 | 19 | 33463030 | -0.320379934 | C19orf40 |
| cg23304339 | 19 | 37862045 | -0.321147788 | ZNF527 | cg17006779 | 17 | 27621172 | -0.320378565 | NUFIP2 |
| cg01911237 | 8 | 134582305 | -0.321000636 | ST3GAL1 | cg02318347 | 13 | 31735110 | -0.320378274 | HSPH1 |
| cg10101074 | 13 | 46961818 | -0.32096891 | C13orf18 | cg26623550 | 1 | 112281629 | -0.320374349 | C1orf183 |
| cg10234952 | 20 | 55926623 | -0.320929929 | RAE1 | cg18124201 | 20 | 46414952 | -0.32036769 | SULF2 |
| cg24909975 | 6 | 160147912 | -0.320926955 | WTAP | cg01657408 | 5 | 158634989 | -0.32036192 | RNF145 |
| cg02466926 | 10 | 127408000 | -0.320888054 | C10orf137 | cg20573831 | 16 | 89882393 | -0.320293448 | FANCA |
| cg15427567 | 14 | 21458055 | -0.320848398 | METT11D1 | cg17576719 | 12 | 46121221 | -0.320279495 | LOC400027 |
| cg02611874 | 10 | 46194725 | -0.320811407 | | cg02908709 | 3 | 111578238 | -0.320272316 | PHLDB2 |
| cg13390998 | 8 | 145670370 | -0.320810211 | NFKBIL2 | cg00270311 | 16 | 30366760 | -0.320264176 | CD2BP2 |
| cg25858682 | 3 | 48481793 | -0.320806895 | CCDC72 | cg05550371 | 3 | 49841167 | -0.320240443 | C3orf54 |
| cg15213114 | 10 | 74927623 | -0.320799709 | ECD | cg10998744 | 22 | 30685926 | -0.320178203 | GATSL3 |
| cg18841894 | 21 | 33031735 | -0.320796465 | SOD1 | cg08209724 | 17 | 30677138 | -0.320151273 | MIR632 |
| cg21618713 | 4 | 153701330 | -0.320791499 | ARFIP1 | cg23302316 | 11 | 22647430 | -0.320114875 | FANCF |
| cg07934604 | 4 | 139010141 | -0.320790128 | | cg14648311 | 17 | 17359737 | -0.320088258 | |
| cg17177829 | 19 | 50432927 | -0.320765551 | NUP62 | cg08310974 | 7 | 54827110 | -0.320069399 | SEC61G |
| cg25392269 | 19 | 13049289 | -0.320743229 | CALR | cg06527865 | 1 | 234746497 | -0.320046632 | IRF2BP2 |
| cg16410464 | 7 | 65215907 | -0.3206974 | CCT6P1 | cg06927280 | 8 | 29953601 | -0.320044476 | LEPROTL1 |
| cg05046597 | 7 | 148823741 | -0.320685163 | ZNF398 | cg13968953 | 3 | 97483466 | -0.320011219 | ARL6 |
| cg24953506 | 1 | 12079889 | -0.320673355 | MIIP | cg26207995 | 17 | 58045920 | -0.320010155 | |
| cg22126032 | 7 | 116166529 | -0.32064921 | CAV1 | cg04547425 | 17 | 73043127 | -0.319974067 | ATP5H |
| cg09964705 | 19 | 19030333 | -0.32064293 | DDX49 | cg01742905 | 11 | 88071023 | -0.319971303 | CTSC |
| cg01386121 | 16 | 22012560 | -0.320640591 | C16orf65 | cg01014179 | 2 | 230787137 | -0.319962207 | FBXO36 |
| cg01421963 | 19 | 11877743 | -0.320634917 | ZNF441 | cg15050398 | 6 | 28829182 | -0.319952016 | |
| cg05642446 | 12 | 117316716 | -0.32063475 | HRK | cg18352988 | 3 | 132136600 | -0.319945447 | DNAJC13 |
| cg04139300 | 20 | 40247070 | -0.320630349 | CHD6 | cg24134304 | 15 | 45003680 | -0.319937355 | B2M |

Figure 16-15

| | | | | | | | | | |
|---|---|---|---|---|---|---|---|---|---|
| cg24942186 | 3 | 55521373 | -0.319934646 | WNT5A | cg19909712 | 11 | 17374669 | -0.319280435 | DKFZp686O24 |
| cg03396809 | 3 | 48282488 | -0.319916354 | ZNF589 | cg27100316 | 1 | 151735804 | -0.319255246 | OAZ3 |
| cg11877577 | 6 | 133135687 | -0.319874698 | RPS12 | cg24041036 | 14 | 58711637 | -0.319250288 | PSMA3 |
| cg13452400 | 2 | 7006280 | -0.319819407 | CMPK2 | cg26929161 | 20 | 50701266 | -0.319246729 | ZFP64 |
| cg15916192 | 12 | 63025948 | -0.31981197 | | cg18039855 | 11 | 57434952 | -0.319226027 | ZDHHC5 |
| cg25072436 | 2 | 30454560 | -0.319811559 | LBH | cg07323055 | 20 | 3140559 | -0.319221291 | FASTKD5 |
| cg02580528 | 1 | 183441376 | -0.319795522 | SMG7 | cg04620101 | 15 | 101835123 | -0.319219805 | SNRPA1 |
| cg05639842 | 21 | 43639440 | -0.319782302 | ABCG1 | cg08452546 | 5 | 118323860 | -0.319216659 | DTWD2 |
| cg17903246 | 3 | 100053926 | -0.31977701 | NIT2 | cg07080177 | 17 | 75243417 | -0.319149171 | |
| ch.8.39446R | 8 | 1206157 | -0.319765689 | | cg03354957 | 1 | 246729501 | -0.319129299 | CNST |
| cg27394038 | 6 | 36562217 | -0.319752212 | SFRS3 | cg18251360 | 22 | 20067313 | -0.319127844 | DGCR8 |
| cg21753290 | 20 | 37376903 | -0.319721195 | ACTR5 | cg26998900 | 18 | 5238137 | -0.319115253 | C18orf18 |
| cg14535006 | 20 | 18448030 | -0.319712801 | C20orf12 | cg02342362 | 19 | 12792713 | -0.319074367 | DHPS |
| cg12144374 | 8 | 123793325 | -0.319694376 | ZHX2 | cg20173334 | 8 | 42698483 | -0.319056129 | THAP1 |
| cg14078059 | 12 | 65174660 | -0.319690859 | | cg01449415 | 16 | 3184811 | -0.319045677 | ZNF213 |
| cg26118675 | 2 | 96256841 | -0.319684739 | TRIM43 | cg09885409 | 21 | 34697563 | -0.319009414 | IFNAR1 |
| cg16970804 | 5 | 43042108 | -0.319666523 | LOC153684 | cg15305172 | 6 | 116892775 | -0.3189988 | RWDD1 |
| cg22149837 | 17 | 41150293 | -0.319651372 | RPL27 | cg10396609 | 4 | 89378025 | -0.318986561 | HERC5 |
| cg14714046 | 6 | 41341654 | -0.319643486 | | cg15884202 | 7 | 158649092 | -0.318963767 | WDR60 |
| cg00531307 | 14 | 50998683 | -0.319628429 | MAP4K5 | cg00046560 | 15 | 101835624 | -0.318953983 | SNRPA1 |
| cg15814736 | 11 | 63439115 | -0.319612295 | ATL3 | cg07315521 | 16 | 71929403 | -0.318926095 | KIAA0174 |
| cg12995162 | 2 | 129079641 | -0.319605245 | | cg08605641 | 8 | 96146723 | -0.31891987 | PLEKHF2 |
| cg15123824 | 2 | 85581917 | -0.319585923 | ELMOD3 | cg00125159 | 1 | 228290140 | -0.318919165 | C1orf35 |
| cg05468351 | 5 | 21459598 | -0.319580627 | LOC728411 | cg18976974 | 8 | 103990325 | -0.31886373 | |
| cg16273215 | 1 | 155100190 | -0.319572454 | EFNA1 | cg19478983 | 7 | 120590592 | -0.318846808 | ING3 |
| cg03214297 | 22 | 38453296 | -0.319539001 | PICK1 | cg03555836 | 8 | 41422764 | -0.318836096 | |
| cg08391020 | 5 | 74344779 | -0.319535462 | | cg09048062 | 11 | 129892327 | -0.318799468 | |
| cg11761572 | 19 | 39390455 | -0.319511445 | SIRT2 | cg25559069 | 6 | 33134799 | -0.31878808 | COL11A2 |
| cg16895948 | 1 | 145610875 | -0.319500108 | POLR3C | cg02252000 | 7 | 130792943 | -0.318754447 | FLJ43663 |
| cg09914581 | 2 | 11606494 | -0.31942943 | E2F6 | cg26020585 | 1 | 235491765 | -0.318725294 | GGPS1 |
| cg18745406 | 8 | 134309938 | -0.319428293 | NDRG1 | cg11656992 | 17 | 79818741 | -0.318708371 | P4HB |
| cg14123153 | 12 | 6602654 | -0.319396147 | NCAPD2 | cg17572663 | 8 | 27950635 | -0.318703702 | ELP3 |
| cg06872176 | 1 | 68697386 | -0.319374869 | GPR177 | cg17424134 | 2 | 27616206 | -0.318700799 | FTHL3 |
| cg23006223 | 4 | 57843834 | -0.319363247 | C4orf14 | cg01476820 | 2 | 86333266 | -0.318690077 | PTCD3 |
| cg04305134 | 10 | 75173374 | -0.319346905 | ANXA7 | cg03651680 | 2 | 46926842 | -0.318677691 | SOCS5 |
| cg21654379 | 3 | 32864307 | -0.319339391 | TRIM71 | cg03432151 | 15 | 89745000 | -0.318657951 | ABHD2 |
| cg04628413 | 16 | 28962222 | -0.319335418 | NFATC2IP | cg18296227 | 10 | 99205774 | -0.318632007 | ZDHHC16 |
| cg02447185 | 17 | 71228623 | -0.31931176 | C17orf80 | cg25784395 | 22 | 40742943 | -0.318619229 | ADSL |
| cg26450188 | 19 | 46850188 | -0.319299618 | PPP5C | cg11996632 | 16 | 70284893 | -0.318613349 | EXOSC6 |
| cg03436558 | 16 | 75657345 | -0.319293675 | ADAT1 | cg19402413 | 1 | 247453950 | -0.31859291 | |
| cg25495613 | 7 | 134895782 | -0.319290408 | WDR91 | cg06029050 | 11 | 74660429 | -0.318592152 | SPCS2 |

Figure 16-16

| | | | | | | | | | |
|---|---|---|---|---|---|---|---|---|---|
| cg06233552 | 17 | 5322836 | -0.318583811 | RPAIN | cg17323493 | 7 | 151573944 | -0.31782972 | PRKAG2 |
| cg00666849 | 2 | 85839032 | -0.318581343 | C2orf68 | cg20546928 | 8 | 27167985 | -0.317788159 | PTK2B |
| cg02772905 | 2 | 203484258 | -0.318571577 | | cg23483707 | 13 | 44453835 | -0.317758439 | C13orf31 |
| cg10203523 | 4 | 6711606 | -0.318556894 | MRFAP1L1 | cg10502884 | 10 | 125852315 | -0.317724567 | |
| cg26151531 | 22 | 19842652 | -0.318547473 | GNB1L | cg26856330 | 19 | 19314312 | -0.317722426 | NR2C2AP |
| cg11072373 | 4 | 100485070 | -0.318511974 | RG9MTD2 | cg23587005 | 12 | 9600941 | -0.31769931 | DDX12 |
| cg19294125 | 20 | 25604737 | -0.318503772 | NANP | cg06820286 | 22 | 29664179 | -0.317667424 | EWSR1 |
| cg14834466 | 11 | 67981677 | -0.318490985 | SUV420H1 | cg20423427 | 18 | 67873036 | -0.317644484 | RTTN |
| cg03410722 | 16 | 85588815 | -0.318393771 | | cg03773681 | 2 | 63815918 | -0.317634832 | MDH1 |
| cg10451977 | 15 | 45507901 | -0.318385842 | | cg07917842 | 17 | 29672644 | -0.317620083 | NF1 |
| cg16427488 | 8 | 86132835 | -0.318362584 | C8orf59 | cg05025913 | 11 | 7539248 | -0.317603976 | PPFIBP2 |
| cg01458420 | 20 | 48532416 | -0.3183503 | SPATA2 | cg07500433 | 5 | 63986130 | -0.317557954 | FAM159B |
| cg08643953 | 3 | 132379052 | -0.318333507 | UBA5 | cg00343022 | 3 | 38178135 | -0.317549845 | ACAA1 |
| cg07509872 | 17 | 26574551 | -0.318321054 | PPY2 | cg18633432 | 3 | 135915556 | -0.317535357 | MSL2 |
| cg26624026 | 19 | 18416001 | -0.318312224 | | cg11332388 | 1 | 42922083 | -0.317508674 | PPCS |
| cg21056475 | 5 | 110428269 | -0.318302024 | WDR36 | cg11792281 | 17 | 26443366 | -0.317503456 | NLK |
| cg05396178 | 6 | 27833129 | -0.318283962 | HIST1H2AL | cg00023288 | 2 | 44223284 | -0.317498439 | LRPPRC |
| cg21071625 | 19 | 39217605 | -0.318281465 | ACTN4 | cg19423311 | 16 | 27413904 | -0.317490447 | IL21R |
| cg07979357 | 19 | 14142353 | -0.318257333 | IL27RA | cg23665065 | 14 | 102781012 | -0.317487681 | |
| cg02600494 | 17 | 73257794 | -0.318232739 | MRPS7 | cg04402021 | 19 | 1094921 | -0.317487072 | POLR2E |
| cg15254860 | 3 | 167813494 | -0.318226119 | GOLIM4 | cg04722620 | 19 | 54982598 | -0.317485236 | CDC42EP5 |
| cg04671334 | 19 | 35224921 | -0.318225653 | ZNF181 | cg24603490 | 12 | 47473995 | -0.317483244 | AMIGO2 |
| cg15139906 | 19 | 48018631 | -0.318220403 | NAPA | cg12188830 | 3 | 57741926 | -0.31747084 | SLMAP |
| cg05526438 | 5 | 174350112 | -0.318206885 | | cg10035607 | 16 | 30366449 | -0.317464299 | CD2BP2 |
| cg22822383 | 19 | 58987261 | -0.31819855 | ZNF446 | cg16861047 | 1 | 116518978 | -0.317460593 | SLC22A15 |
| cg08686311 | 20 | 825052 | -0.318162649 | FAM110A | cg03831869 | 16 | 3508546 | -0.317446036 | NAT15 |
| cg02653800 | 10 | 60095305 | -0.318124029 | UBE2D1 | cg26759552 | 7 | 139877471 | -0.317432117 | LOC10013422 |
| cg05171480 | 13 | 32420488 | -0.318108464 | EEF1DP3 | cg08582555 | 22 | 21356051 | -0.317405036 | FLJ39582 |
| cg22396798 | 15 | 43478022 | -0.318098867 | CCNDBP1 | cg17055717 | 20 | 32700280 | -0.317358429 | EIF2S2 |
| cg04295991 | 13 | 21348012 | -0.318095056 | N6AMT2 | cg10541361 | 1 | 235667946 | -0.317336445 | B3GALNT2 |
| cg21120664 | 21 | 44299807 | -0.318080906 | WDR4 | cg20303592 | 10 | 116697907 | -0.317311403 | TRUB1 |
| cg03774520 | 1 | 32238105 | -0.318032599 | | cg23572376 | 6 | 1610120 | -0.317305549 | FOXC1 |
| cg23515325 | 19 | 1194462 | -0.318024235 | | cg18238491 | 18 | 47901440 | -0.317274509 | SKA1 |
| cg08713543 | 16 | 75575906 | -0.317988903 | TMEM231 | cg01718711 | 8 | 8860266 | -0.317265628 | ERI1 |
| cg03860054 | 16 | 55691102 | -0.317985928 | SLC6A2 | cg09823679 | 13 | 53425813 | -0.317185343 | |
| cg09001528 | 5 | 65440474 | -0.31795392 | SFRS12 | cg15993873 | 15 | 44719935 | -0.317175926 | CTDSPL2 |
| cg06207852 | 22 | 41033162 | -0.317880418 | MKL1 | cg16015499 | 1 | 159888603 | -0.317167085 | TAGLN2 |
| cg12858075 | 2 | 11606497 | -0.317863207 | E2F6 | cg11041264 | 20 | 33872554 | -0.317160612 | EIF6 |
| cg15575339 | 22 | 21272441 | -0.317842899 | CRKL | cg18611281 | 2 | 27805844 | -0.317100457 | ZNF512 |
| cg05279707 | 20 | 49547986 | -0.317842816 | ADNP | cg26455541 | 4 | 26321238 | -0.317087024 | RBPJ |
| cg08098619 | 11 | 3818841 | -0.317839785 | PGAP2 | cg11432034 | 3 | 13520913 | -0.3170766 | HDAC11 |

Figure 16-17

| cg00477061 | 18 | 77794585 | -0.317073557 | C18orf22 | cg17976065 | 17 | 15902694 | -0.316587368 | ZSWIM7 |
|---|---|---|---|---|---|---|---|---|---|
| cg14162457 | 13 | 113444243 | -0.317066079 | ATP11A | cg27308130 | 3 | 126422683 | -0.316577097 | CHCHD6 |
| cg02303317 | 10 | 135122580 | -0.317048209 | TUBGCP2 | cg13402292 | 21 | 37667921 | -0.316576392 | |
| cg08875433 | 6 | 29604148 | -0.317044591 | | cg11229390 | 6 | 32122082 | -0.316571087 | PPT2 |
| cg02063458 | 16 | 48190773 | -0.317041547 | | cg25825740 | 17 | 80036910 | -0.316562865 | FASN |
| cg09746604 | 3 | 15919583 | -0.317015865 | | cg00028636 | 12 | 6876321 | -0.316561751 | PTMS |
| cg03801946 | 16 | 4303664 | -0.317012306 | | cg04931453 | 9 | 101983720 | -0.316538558 | ALG2 |
| cg23048068 | 8 | 82192604 | -0.317002317 | FABP5 | cg05797656 | 17 | 61851352 | -0.316534057 | DDX42 |
| cg06790069 | 1 | 40203513 | -0.31698387 | PPIE | cg06329143 | 18 | 48556512 | -0.316532328 | SMAD4 |
| cg04122974 | 22 | 39916495 | -0.316977852 | ATF4 | cg26473728 | 6 | 33359147 | -0.316511087 | KIFC1 |
| cg02164516 | 15 | 41576100 | -0.316975036 | LOC729082 | cg00367659 | 17 | 33288544 | -0.31651086 | CCT6B |
| cg15345154 | 10 | 16563586 | -0.316973964 | C1QL3 | cg11726572 | 18 | 658602 | -0.316501562 | TYMS |
| cg07557355 | 1 | 155904306 | -0.316970418 | KIAA0907 | cg13643774 | 9 | 132176807 | -0.316451603 | |
| cg17415239 | 16 | 29937734 | -0.316963136 | KCTD13 | cg17996757 | 7 | 131013207 | -0.316443626 | MKLN1 |
| cg04757284 | 17 | 18585734 | -0.316959024 | ZNF286B | cg06148997 | 2 | 107084783 | -0.316432183 | RGPD3 |
| cg05964529 | 12 | 110906245 | -0.316956112 | GPN3 | cg00461978 | 15 | 75661184 | -0.316418729 | MAN2C1 |
| cg20872579 | 4 | 6643098 | -0.316929638 | MRFAP1 | cg06083525 | 1 | 27216957 | -0.316411254 | GPN2 |
| cg18803079 | 1 | 64014643 | -0.316900309 | EFCAB7 | cg06005571 | 3 | 52188725 | -0.316350406 | WDR51A |
| cg22167498 | 19 | 8451051 | -0.31689544 | | cg02775353 | 7 | 101814109 | -0.316345726 | CUX1 |
| cg19484299 | 2 | 234775274 | -0.316893115 | MSL3L2 | cg06578951 | 19 | 19030513 | -0.316344214 | DDX49 |
| cg03324837 | 17 | 61044407 | -0.316888657 | | cg06020459 | 5 | 64858893 | -0.316340679 | CENPK |
| cg27072387 | 2 | 33171699 | -0.316854653 | LTBP1 | cg07951488 | 4 | 41992560 | -0.316324269 | SLC30A9 |
| cg03017824 | 1 | 227915338 | -0.316851439 | LOC100130093 | cg06548512 | 1 | 146522492 | -0.316319221 | |
| cg19461392 | 12 | 26349002 | -0.316848597 | SSPN | cg24001556 | 20 | 5591874 | -0.316312757 | RP5-1022P6.2 |
| cg11976407 | 1 | 33814857 | -0.316848549 | PHC2 | cg24079591 | 14 | 103851511 | -0.316308634 | MARK3 |
| cg04347624 | 3 | 101498377 | -0.316817908 | FAM55C | cg03314080 | 2 | 178129903 | -0.316303911 | NFE2L2 |
| cg22512322 | 3 | 64009096 | -0.316777866 | PSMD6 | cg10826045 | 19 | 36631318 | -0.316302248 | CAPNS1 |
| cg22211971 | 17 | 73257917 | -0.316770696 | GGA3 | ch.19.1004238R | 19 | 30753371 | -0.316289741 | |
| cg20632873 | 1 | 155948126 | -0.316760195 | ARHGEF2 | cg23371542 | 6 | 31334738 | -0.316285184 | |
| cg27049318 | 5 | 68514098 | -0.316758021 | MRPS36 | cg12745769 | 19 | 21579993 | -0.31625756 | ZNF493 |
| cg11575912 | 19 | 5828299 | -0.316747049 | NRTN | cg14385337 | 7 | 113726252 | -0.316204654 | |
| cg09227150 | 10 | 102475578 | -0.316746332 | | cg00645922 | 5 | 114962179 | -0.316195809 | TMED7 |
| cg10470489 | 8 | 41686324 | -0.316694877 | ANK1 | cg17255450 | 4 | 5710372 | -0.316190761 | EVC2 |
| cg17212073 | 17 | 7818956 | -0.316694101 | LOC284023 | cg04940109 | 2 | 203240432 | -0.316185543 | BMPR2 |
| cg25142954 | 15 | 41245554 | -0.316692394 | CHAC1 | cg13195185 | 17 | 16875596 | -0.316183199 | TNFRSF13B |
| cg04729371 | 11 | 111637213 | -0.316645245 | PPP2R1B | cg06024111 | 6 | 43597558 | -0.316151626 | MAD2L1BP |
| cg27287791 | 15 | 49103304 | -0.316644621 | CEP152 | cg26428889 | 7 | 116311825 | -0.316147795 | MET |
| cg12722217 | 15 | 44487545 | -0.316627014 | FRMD5 | cg10055227 | 16 | 58768320 | -0.316145339 | GOT2 |
| cg24691578 | 11 | 45869488 | -0.316624188 | CRY2 | cg02725437 | 6 | 90348314 | -0.316145138 | LYRM2 |
| cg08316775 | 2 | 73964643 | -0.316617024 | TPRKB | cg03768106 | 11 | 111957237 | -0.316134758 | TIMM8B |
| cg18515171 | 17 | 58156344 | -0.316609868 | HEATR6 | ch.19.683370F | 19 | 16239180 | -0.31608497 | RAB8A |

Figure 16-18

| | | | | | | | | | |
|---|---|---|---|---|---|---|---|---|---|
| cg04233747 | 5 | 145214971 | -0.316038752 | PRELID2 | cg16859906 | 16 | 68298978 | -0.315462252 | SLC7A6 |
| cg18078305 | 2 | 65215753 | -0.316028995 | SLC1A4 | cg17513693 | 6 | 32122084 | -0.315449268 | PPT2 |
| cg26548134 | 22 | 41185283 | -0.316006968 | SLC25A17 | cg06329197 | 16 | 27214832 | -0.315441256 | JMJD5 |
| cg11227637 | 4 | 103749288 | -0.316003535 | UBE2D3 | cg24000232 | 1 | 166808428 | -0.315423291 | POGK |
| cg26330063 | 5 | 14614735 | -0.315981747 | FAM105A | cg01117273 | 3 | 112738650 | -0.315411432 | C3orf17 |
| cg13111374 | 4 | 17812581 | -0.315974869 | NCAPG | cg07885039 | 3 | 143690495 | -0.315404499 | C3orf58 |
| cg10063260 | 14 | 104181875 | -0.315972665 | XRCC3 | cg16750914 | 2 | 55646622 | -0.315317218 | CCDC88A |
| cg16579347 | 3 | 155572233 | -0.315961605 | SLC33A1 | cg22124117 | 15 | 43028932 | -0.315260277 | CDAN1 |
| cg02881434 | 3 | 101394920 | -0.315949831 | LOC100009676 | cg04907171 | 5 | 139135794 | -0.315247374 | |
| cg20332930 | 11 | 82997207 | -0.315941074 | CCDC90B | cg13129888 | 1 | 28415099 | -0.315219116 | EYA3 |
| cg04372675 | 8 | 107283146 | -0.315934161 | OXR1 | cg04252558 | 8 | 74884436 | -0.315191576 | TCEB1 |
| cg16222848 | 13 | 42846088 | -0.315914052 | AKAP11 | cg12052812 | 1 | 230778592 | -0.31517789 | COG2 |
| cg13546538 | 9 | 111754815 | -0.315884772 | CTNNAL1 | cg03511311 | 6 | 33385541 | -0.315147746 | CUTA |
| cg23639257 | 17 | 73663270 | -0.315880044 | RECQL5 | cg12538597 | 11 | 85906334 | -0.315146266 | |
| cg14460708 | 3 | 172428874 | -0.315879175 | NCEH1 | cg08390021 | 18 | 51884793 | -0.315136993 | C18orf54 |
| cg20433014 | 15 | 75018583 | -0.31585114 | CYP1A1 | cg16232504 | 1 | 99127707 | -0.315131026 | SNX7 |
| cg02005549 | 4 | 106629965 | -0.315840601 | GSTCD | cg10740670 | 14 | 65453617 | -0.315107181 | FNTB |
| cg03841667 | 22 | 41986013 | -0.315835653 | PMM1 | cg02006147 | 2 | 74734710 | -0.315100834 | PCGF1 |
| cg26258330 | 8 | 82633130 | -0.315829806 | ZFAND1 | cg20053981 | 10 | 70091610 | -0.315090558 | HNRNPH3 |
| cg13657659 | 2 | 208632393 | -0.315778484 | FZD5 | cg26996201 | 11 | 77122864 | -0.315084387 | PAK1 |
| cg06536503 | 6 | 42750688 | -0.31575931 | | cg06118578 | 18 | 67872897 | -0.31505969 | RTTN |
| cg00672574 | 17 | 79669841 | -0.315752305 | MRPL12 | cg12876333 | 18 | 55710995 | -0.315031304 | NEDD4L |
| cg02854226 | 6 | 33385965 | -0.315725102 | CUTA | cg09865173 | 10 | 104952209 | -0.31502791 | NT5C2 |
| cg05909891 | 12 | 19565983 | -0.315712495 | | cg21286626 | 6 | 33290780 | -0.315016935 | DAXX |
| cg02522757 | 12 | 48298992 | -0.315702476 | VDR | cg18877635 | 1 | 229643817 | -0.315015701 | NUP133 |
| cg21374864 | 9 | 132586569 | -0.315701176 | TOR1A | cg02753865 | 7 | 56119046 | -0.314966372 | CCT6A |
| cg04971263 | 1 | 27227008 | -0.315675891 | GPATCH3 | cg14563732 | 8 | 143474839 | -0.314949027 | TSNARE1 |
| cg14235783 | 11 | 65420518 | -0.315670955 | | cg16145821 | 11 | 66056771 | -0.314932065 | YIF1A |
| cg02501334 | 17 | 66508232 | -0.315653515 | PRKAR1A | cg09622330 | 16 | 10205262 | -0.314929743 | GRIN2A |
| cg17782025 | 3 | 23958698 | -0.315632621 | NKIRAS1 | cg00718440 | 9 | 21995312 | -0.314910696 | CDKN2BAS |
| cg12531328 | 13 | 31192104 | -0.315619562 | USPL1 | cg02640306 | 2 | 191745287 | -0.314900072 | GLS |
| cg01456571 | 8 | 23021325 | -0.315615915 | TNFRSF10D | cg27367554 | 20 | 5930982 | -0.314896239 | MCM8 |
| cg22320000 | 1 | 245027629 | -0.315589973 | HNRNPU | cg21549639 | 19 | 45394156 | -0.314877216 | TOMM40 |
| cg13380562 | 6 | 143832576 | -0.315571447 | FUCA2 | cg15639469 | 5 | 79596224 | -0.314866565 | LOC644936 |
| cg05060949 | 7 | 156798581 | -0.315567652 | MNX1 | cg07483245 | 15 | 23034598 | -0.314854594 | NIPA2 |
| cg14115740 | 9 | 98054883 | -0.315557555 | FANCC | cg04303571 | 17 | 25680876 | -0.314848503 | |
| cg24448326 | 1 | 85930306 | -0.31553667 | DDAH1 | cg21240492 | 17 | 7476105 | -0.314798367 | EIF4A1 |
| cg17859081 | 1 | 173446963 | -0.315523547 | PRDX6 | cg22852149 | 19 | 36980565 | -0.314795593 | ZNF566 |
| cg20705565 | 1 | 154580699 | -0.315522085 | ADAR | cg07837434 | 6 | 52149679 | -0.314787095 | MCM3 |
| cg18685883 | 3 | 51705045 | -0.315493148 | TEX264 | cg24667363 | 3 | 158362181 | -0.314777556 | GFM1 |
| cg20025072 | 10 | 126480608 | -0.315482712 | METTL10 | cg18350792 | 12 | 112563442 | -0.314760904 | TRAFD1 |

Figure 16-19

| | | | | | | | | | |
|---|---|---|---|---|---|---|---|---|---|
| cg20122548 | 15 | 45694411 | -0.3147572 | SPATA5L1 | cg27479693 | 17 | 17495173 | -0.314115064 | PEMT |
| cg05236391 | 19 | 6361348 | -0.314740074 | CLPP | cg02847589 | 1 | 22778394 | -0.314093777 | ZBTB40 |
| cg10427040 | 17 | 74261306 | -0.314713728 | FAM100B | cg11699826 | 1 | 26438425 | -0.314091519 | PDIK1L |
| cg20116574 | 20 | 44718168 | -0.314695262 | NCOA5 | cg24382801 | 6 | 37665291 | -0.314080732 | MDGA1 |
| cg03101422 | 2 | 136876737 | -0.314683549 | CXCR4 | cg23818142 | 2 | 170550784 | -0.314080047 | C2orf77 |
| cg25053079 | 6 | 31778519 | -0.31468268 | HSPA1L | cg03162131 | 11 | 82905106 | -0.31406978 | ANKRD42 |
| cg15642758 | 15 | 83876612 | -0.314675343 | HDGFRP3 | cg00347862 | 15 | 71184758 | -0.314065904 | LRRC49 |
| cg24354901 | 1 | 202777590 | -0.314667965 | KDM5B | cg02015280 | 7 | 134671225 | -0.314061078 | AGBL3 |
| cg02234820 | 1 | 85358327 | -0.314630703 | LPAR3 | cg06911282 | 8 | 11660733 | -0.314024935 | FDFT1 |
| cg10009297 | 17 | 34890195 | -0.314630019 | MYO19 | cg11213348 | 3 | 38206830 | -0.313946753 | OXSR1 |
| cg13301155 | 15 | 82338574 | -0.314620159 | MEX3B | cg04464219 | 8 | 98657199 | -0.313939983 | MTDH |
| cg03099492 | 10 | 94833214 | -0.314584322 | CYP26A1 | cg17171485 | 6 | 138725799 | -0.313937011 | HEBP2 |
| cg05447186 | 20 | 3869454 | -0.314580771 | PANK2 | cg12856612 | 22 | 42228819 | -0.313929974 | SREBF2 |
| cg04417028 | 11 | 110583882 | -0.31457063 | ARHGAP20 | ch.20.54687769F | 20 | 55254362 | -0.313916315 | |
| cg19556901 | 15 | 25414769 | -0.314559251 | SNORD115-1 | cg05614346 | 5 | 176858608 | -0.313897293 | GRK6 |
| cg18418962 | 18 | 2571633 | -0.31454915 | METTL4 | cg25486979 | 13 | 50510739 | -0.31384795 | C13orf1 |
| cg13694772 | 3 | 9773336 | -0.31453798 | BRPF1 | cg07751641 | 5 | 134826244 | -0.313809214 | |
| cg26068292 | 18 | 57360307 | -0.314530589 | CCBE1 | cg00590869 | 8 | 37962609 | -0.313805501 | ASH2L |
| cg07586906 | 1 | 160250600 | -0.314518743 | PEX19 | cg00087098 | 4 | 76598919 | -0.313789221 | G3BP2 |
| cg19236745 | 11 | 33182890 | -0.314496307 | CSTF3 | cg00935782 | 12 | 56498920 | -0.313782479 | PA2G4 |
| cg01209943 | 14 | 54863601 | -0.314481719 | CDKN3 | cg24565496 | 16 | 1021302 | -0.313744641 | LMF1 |
| cg07206840 | 1 | 110949893 | -0.314480105 | HBXIP | cg06627361 | 12 | 498468 | -0.313740268 | KDM5A |
| cg26490839 | 19 | 49999468 | -0.314471008 | RPS11 | cg04965811 | 10 | 101492459 | -0.313724711 | COX15 |
| ch.11.2738269F | 11 | 130342732 | -0.314470238 | ADAMTS15 | cg17738494 | 3 | 9773251 | -0.313702376 | BRPF1 |
| cg10266188 | 1 | 32645867 | -0.314461336 | TXLNA | cg04882175 | 6 | 131122610 | -0.313695633 | |
| cg25287247 | 2 | 86946958 | -0.31444225 | RMND5A | cg10313675 | 1 | 209957739 | -0.313693084 | C1orf74 |
| cg09977865 | 6 | 33385582 | -0.314428286 | CUTA | cg22094042 | 11 | 450123 | -0.313671343 | PTDSS2 |
| cg01049274 | 8 | 146228340 | -0.31441972 | ZNF252 | cg09225973 | 6 | 150232183 | -0.3136569 | |
| cg17490921 | 11 | 116658887 | -0.314408635 | ZNF259 | cg12091642 | 14 | 61104566 | -0.313648862 | |
| cg06784830 | 17 | 7486996 | -0.314406881 | MPDU1 | cg04680209 | 2 | 1941133 | -0.313647679 | MYT1L |
| cg12039286 | 8 | 143533193 | -0.314406393 | | cg04599631 | 4 | 84256200 | -0.313631727 | HPSE |
| cg03182819 | 17 | 63053327 | -0.314403563 | GNA13 | cg09214920 | 1 | 108743318 | -0.313623682 | SLC25A24 |
| cg10460130 | 2 | 242625978 | -0.314376936 | DTYMK | cg12581035 | 12 | 9067477 | -0.31358959 | PHC1 |
| cg06588087 | 4 | 36245610 | -0.314371059 | ARAP2 | cg23677570 | 7 | 74489617 | -0.313564664 | WBSCR16 |
| cg07831432 | 5 | 179125659 | -0.31434941 | CANX | cg21372200 | 3 | 50375735 | -0.313555931 | RASSF1 |
| cg08127941 | 6 | 30293955 | -0.314304646 | TRIM39 | cg07911523 | 22 | 32871416 | -0.313424356 | FBXO7 |
| cg11545360 | 12 | 96793417 | -0.314278106 | CDK17 | cg16193765 | 21 | 45527559 | -0.313408896 | PWP2 |
| cg02228207 | 1 | 244998759 | -0.314267612 | FAM36A | cg06177002 | 6 | 31370956 | -0.313382674 | MICA |
| cg12751733 | 1 | 38157745 | -0.314249719 | CDCA8 | cg04865575 | 10 | 27443031 | -0.31336713 | YME1L1 |
| cg16766889 | 17 | 48637951 | -0.314168303 | CACNA1G | cg14968603 | 10 | 102046143 | -0.313357898 | BLOC1S2 |
| cg02921269 | 14 | 75894323 | -0.314157785 | JDP2 | cg24861394 | 8 | 11141871 | -0.313341739 | MTMR9 |

Figure 16-20

| | | | | | | | | | |
|---|---|---|---|---|---|---|---|---|---|
| cg03538717 | 3 | 79068441 | -0.313318939 | ROBO1 | cg19011063 | 5 | 170171465 | -0.312604099 | |
| cg07185974 | 3 | 18485529 | -0.313291446 | | cg19406117 | 4 | 77228196 | -0.31260208 | STBD1 |
| cg11674773 | 1 | 54518492 | -0.313273236 | TMEM59 | cg02768471 | 1 | 155231827 | -0.312597618 | SCAMP3 |
| cg14157947 | 18 | 20513080 | -0.313271394 | RBBP8 | cg26890010 | 1 | 70876953 | -0.312584027 | CTH |
| cg16854524 | 4 | 83931902 | -0.313267561 | LIN54 | cg25230151 | 11 | 35441107 | -0.312575367 | SLC1A2 |
| cg12399453 | 1 | 27648454 | -0.313253477 | TMEM222 | cg09295542 | 6 | 88986071 | -0.312573243 | |
| cg04791162 | 14 | 62331287 | -0.313204112 | | cg02283836 | 14 | 52118711 | -0.312573076 | FRMD6 |
| cg13249876 | 10 | 32217968 | -0.313203077 | ARHGAP12 | cg20549080 | 10 | 103892662 | -0.312572442 | PPRC1 |
| cg08602689 | 13 | 103452535 | -0.313201285 | BIVM | cg26567249 | 8 | 97247842 | -0.312567105 | UQCRB |
| cg06039171 | 20 | 57599526 | -0.313182948 | TUBB1 | cg00459078 | 17 | 43024659 | -0.31254579 | KIF18B |
| cg17092583 | 11 | 735575 | -0.31316707 | | cg07066932 | 1 | 24285945 | -0.312525345 | PNRC2 |
| cg01936270 | 2 | 38303680 | -0.313163724 | CYP1B1 | cg09134840 | 1 | 235530680 | -0.31252441 | TBCE |
| cg12391087 | 1 | 244012456 | -0.313092666 | | cg23908998 | 10 | 22292698 | -0.312508657 | DNAJC1 |
| cg08451517 | 8 | 125383826 | -0.313067357 | TMEM65 | cg13612958 | 19 | 18303626 | -0.312432183 | MPV17L2 |
| cg10029427 | 6 | 31778258 | -0.313063644 | HSPA1L | cg12955252 | 20 | 32891324 | -0.312402774 | AHCY |
| cg23955684 | 3 | 16555288 | -0.313041653 | RFTN1 | cg15142485 | 2 | 240323713 | -0.3123785 | HDAC4 |
| cg08184792 | 12 | 48592270 | -0.313031799 | | cg04530460 | 6 | 42858550 | -0.312373143 | C6orf226 |
| cg15309223 | 1 | 54519091 | -0.31303093 | TMEM59 | cg02657830 | 1 | 27152905 | -0.312331236 | ZDHHC18 |
| cg07509420 | 16 | 740472 | -0.312997001 | WDR24 | cg10639412 | 2 | 33824684 | -0.312321857 | FAM98A |
| cg01997230 | 3 | 13937190 | -0.312992094 | | cg22846149 | 20 | 56064151 | -0.312319239 | HMGB1L1 |
| cg10210086 | 16 | 84837307 | -0.312990249 | | cg01430870 | 2 | 99954399 | -0.312310125 | EIF5B |
| cg24334002 | 22 | 42087946 | -0.3129473 | C22orf46 | ch.12.78471492F | 12 | 79947361 | -0.31228268 | |
| cg04583149 | 19 | 1207124 | -0.312938042 | STK11 | cg07639697 | 19 | 11850005 | -0.312259286 | ZNF823 |
| cg12380209 | 10 | 120515094 | -0.312919137 | C10orf46 | cg12835684 | 12 | 53645647 | -0.312259282 | MFSD5 |
| cg07335234 | 3 | 185304496 | -0.312901017 | SENP2 | cg01320614 | 2 | 86115591 | -0.312256233 | ST3GAL5 |
| cg21144673 | 22 | 42017783 | -0.312828234 | PPPDE2 | cg10122474 | 14 | 88459471 | -0.312253961 | GALC |
| cg10553894 | 11 | 68550534 | -0.312815938 | CPT1A | cg00483446 | 3 | 67048774 | -0.312227391 | KBTBD8 |
| cg21542094 | 10 | 6243955 | -0.312812907 | PFKFB3 | cg21610999 | 17 | 8661909 | -0.312214307 | SPDYE4 |
| cg08591058 | 17 | 25681106 | -0.31277814 | | cg02470625 | 7 | 39453784 | -0.312195627 | POU6F2 |
| cg23317683 | 7 | 99698554 | -0.312748966 | MCM7 | cg10261819 | 16 | 22448417 | -0.312186035 | RRN3P3 |
| cg25252777 | 19 | 56709056 | -0.31274811 | | cg12569089 | 20 | 35724525 | -0.312175162 | RBL1 |
| cg16317734 | 11 | 94822598 | -0.312726255 | ENDOD1 | cg22256960 | 15 | 77711686 | -0.312152953 | |
| cg01488306 | 1 | 197037504 | -0.312717361 | F13B | cg09774198 | 13 | 33160713 | -0.312129442 | PDS5B |
| cg06995565 | 16 | 75590339 | -0.312709713 | TMEM231 | cg15901997 | 18 | 48723744 | -0.312126192 | MEX3C |
| cg19438583 | 5 | 1585122 | -0.31266495 | SDHAP3 | cg04731813 | 4 | 2043086 | -0.312109391 | C4orf48 |
| cg12712846 | 1 | 181058068 | -0.312653477 | IER5 | cg11748640 | 19 | 5691196 | -0.312087368 | RPL36 |
| cg08346494 | 11 | 70049962 | -0.312649574 | FADD | cg16080746 | 4 | 87928530 | -0.312082237 | AFF1 |
| cg18882576 | 2 | 191184621 | -0.312640816 | HIBCH | cg03931027 | 5 | 138609848 | -0.312077003 | SNHG4 |
| cg17476752 | 19 | 24184762 | -0.312629479 | | cg08439970 | 6 | 74230786 | -0.312049726 | EEF1A1 |
| cg04529582 | 20 | 30697510 | -0.312615295 | TM9SF4 | cg18436128 | 14 | 65439236 | -0.31204719 | RAB15 |
| cg09463047 | 17 | 36104218 | -0.312604493 | HNF1B | cg15032638 | 10 | 51565035 | -0.312010206 | NCOA4 |

Figure 16-21

| | | | | | | | | | |
|---|---|---|---|---|---|---|---|---|---|
| cg23063986 | 4 | 128886308 | -0.312010108 | MFSD8 | cg23361901 | 6 | 4019100 | -0.311457675 | |
| cg01741121 | 14 | 24701991 | -0.311995322 | GMPR2 | cg04122790 | 1 | 229762148 | -0.31145005 | URB2 |
| cg10006762 | 11 | 65342202 | -0.311993608 | EHBP1L1 | cg20232119 | 6 | 31778558 | -0.311434108 | HSPA1L |
| cg16257334 | 6 | 30881842 | -0.311990634 | GTF2H4 | cg03700218 | 16 | 1832709 | -0.311425685 | SPSB3 |
| cg17145587 | 2 | 230579435 | -0.311956796 | DNER | cg26196213 | 6 | 29617956 | -0.311419256 | |
| cg26258108 | 2 | 232329189 | -0.311904844 | NCL | cg03503975 | 22 | 46518455 | -0.311408219 | |
| cg18423859 | 18 | 60986742 | -0.311896537 | BCL2 | cg04564312 | 5 | 102456179 | -0.311406209 | GIN1 |
| cg20099147 | 19 | 56652066 | -0.311876004 | ZNF444 | cg01913958 | 14 | 24658184 | -0.311394684 | IPO4 |
| cg24622726 | 9 | 91926624 | -0.311872136 | CKS2 | cg16228804 | 1 | 89150099 | -0.311383786 | PKN2 |
| cg03512355 | 12 | 121837704 | -0.311856927 | RNF34 | cg21641552 | 12 | 88535903 | -0.311363177 | TMTC3 |
| cg11368578 | 7 | 150754936 | -0.311833839 | CDK5 | cg11177179 | 14 | 65381159 | -0.311359427 | CHURC1 |
| cg14868663 | 14 | 77923968 | -0.311807926 | C14orf133 | cg19764048 | 4 | 5053152 | -0.311354382 | STK32B |
| cg12654140 | 17 | 46842970 | -0.311804284 | TTLL6 | cg12720152 | 14 | 91087476 | -0.311342047 | TTC7B |
| cg22063259 | 15 | 74428820 | -0.311800399 | ISLR2 | cg17834180 | 10 | 124768240 | -0.311338609 | IKZF5 |
| cg10553515 | 7 | 5013490 | -0.311790555 | RNF216L | cg01765930 | 22 | 37881422 | -0.311336552 | MFNG |
| cg23480499 | 12 | 95867566 | -0.311774415 | METAP2 | cg27575217 | 12 | 51984358 | -0.311336453 | SCN8A |
| cg06330324 | 22 | 31031670 | -0.311744645 | SLC35E4 | cg15411280 | 6 | 84747508 | -0.311334544 | MRAP2 |
| cg17983571 | 10 | 65186953 | -0.311742516 | JMJD1C | cg20546810 | 20 | 2489835 | -0.311326468 | ZNF343 |
| cg11723896 | 17 | 34136427 | -0.311708393 | TAF15 | cg01665633 | 15 | 29562142 | -0.311315041 | NDNL2 |
| cg23639922 | 10 | 103892660 | -0.311690979 | PPRC1 | cg20762182 | 15 | 69727293 | -0.311298714 | KIF23 |
| cg11371394 | 2 | 105946583 | -0.311684665 | TGFBRAP1 | cg13088939 | 1 | 155659111 | -0.311282538 | DAP3 |
| cg22786826 | 16 | 2564780 | -0.311664077 | ATP6V0C | cg24631920 | 11 | 108535736 | -0.311244961 | DDX10 |
| cg07033880 | 15 | 85923739 | -0.311661358 | AKAP13 | cg07937578 | 4 | 25487481 | -0.311230164 | |
| cg04270788 | 1 | 89356964 | -0.311646715 | GTF2B | ch.3.21287957F | 3 | 21312953 | -0.31122769 | |
| cg25902627 | 11 | 88071152 | -0.311636913 | CTSC | cg03573109 | 16 | 85849619 | -0.311221409 | |
| cg02568557 | 11 | 129288930 | -0.311633811 | BARX2 | cg22685123 | 19 | 35168238 | -0.311173235 | ZNF302 |
| cg25966751 | 14 | 74098320 | -0.311632275 | | cg26791985 | 3 | 52008971 | -0.311170877 | ABHD14A |
| cg09150633 | 5 | 148206173 | -0.311612062 | ADRB2 | cg20275462 | 17 | 60501228 | -0.311163602 | METTL2A |
| cg23243994 | 7 | 139045033 | -0.311590734 | LUC7L2 | cg24403497 | 1 | 146644500 | -0.311156458 | PRKAB2 |
| cg08027110 | 12 | 57082200 | -0.311589665 | PTGES3 | cg10463708 | 1 | 90309205 | -0.311154244 | LRRC8D |
| cg26278858 | 15 | 40401256 | -0.311565525 | BMF | cg18539474 | 1 | 113933413 | -0.311152994 | MAGI3 |
| cg08817965 | 17 | 38574364 | -0.311557758 | TOP2A | cg24643211 | 18 | 11851603 | -0.311144325 | GNAL |
| cg21930443 | 17 | 28443747 | -0.31155749 | CCDC55 | cg12968077 | 2 | 231921504 | -0.311139178 | PSMD1 |
| cg25781121 | 3 | 48282641 | -0.31153991 | ZNF589 | cg14240963 | 22 | 36925312 | -0.311137139 | EIF3D |
| cg12353549 | 17 | 30771552 | -0.31150551 | PSMD11 | cg00367327 | 22 | 44419885 | -0.311113281 | PARVB |
| cg10282920 | 2 | 95831790 | -0.311493502 | ZNF2 | cg17030981 | 4 | 205522 | -0.311081963 | ZNF876P |
| cg16497340 | 5 | 180601183 | -0.311491519 | | cg06060673 | 22 | 39268830 | -0.311053017 | CBX6 |
| cg24451858 | 11 | 75379620 | -0.311487056 | MAP6 | cg19882663 | 3 | 180308459 | -0.311051901 | |
| cg11739675 | 12 | 104852151 | -0.311467348 | CHST11 | cg15124560 | 10 | 112327767 | -0.311006881 | SMC3 |
| cg08965527 | 16 | 84178213 | -0.311458198 | HSDL1 | cg24926253 | 6 | 110799072 | -0.310993498 | SLC22A16 |
| cg16720880 | 9 | 33265144 | -0.311457945 | SUGT1P1 | cg04381122 | 14 | 59655332 | -0.310993018 | DAAM1 |

Figure 16-22

| | | | | | | | | | |
|---|---|---|---|---|---|---|---|---|---|
| cg04010712 | 3 | 42003234 | -0.310971927 | ULK4 | cg15485323 | 6 | 26234460 | -0.31040183 | HIST1H1D |
| cg12760261 | 5 | 122758659 | -0.310954843 | CEP120 | cg26974158 | 5 | 118788130 | -0.310394783 | HSD17B4 |
| cg01902998 | 14 | 65346633 | -0.310954012 | | cg25882709 | 1 | 224517832 | -0.310381947 | NVL |
| cg00098718 | 15 | 81072600 | -0.310943813 | KIAA1199 | cg20295040 | 1 | 192778396 | -0.310376629 | RGS2 |
| cg21119375 | 2 | 44393385 | -0.310941186 | | cg08118646 | 4 | 99850258 | -0.310362001 | EIF4E |
| cg27158084 | 6 | 149813350 | -0.310880851 | | cg04696149 | 2 | 37552545 | -0.310354955 | |
| cg06867829 | 12 | 24715508 | -0.310855578 | SOX5 | cg20259594 | 3 | 15920154 | -0.310314802 | |
| cg07195197 | 16 | 1662150 | -0.310851937 | IFT140 | cg15906409 | 17 | 17685582 | -0.310307309 | RAI1 |
| cg10700459 | 6 | 30231675 | -0.31084726 | HLA-L | cg05501276 | 7 | 23571514 | -0.310304828 | TRA2A |
| cg16050957 | 16 | 24550743 | -0.310839405 | RBBP6 | cg14219630 | 1 | 45987336 | -0.310282221 | PRDX1 |
| cg16223510 | 6 | 136610388 | -0.31083644 | BCLAF1 | cg00615550 | 6 | 109703901 | -0.310266408 | CD164 |
| cg13260314 | 6 | 3900192 | -0.310809318 | | cg03423968 | 10 | 124914448 | -0.310265171 | BUB3 |
| cg23465426 | 6 | 32847377 | -0.310804367 | PPP1R2P1 | cg06929872 | 15 | 65322164 | -0.310263064 | MTFMT |
| cg19138325 | 12 | 129429698 | -0.310787979 | GLT1D1 | cg05759182 | 12 | 132195987 | -0.310256508 | SFRS8 |
| cg09928842 | 8 | 135845050 | -0.310785667 | | cg18133008 | 2 | 70056632 | -0.310253914 | GMCL1 |
| cg21950493 | 12 | 110907285 | -0.310767027 | GPN3 | cg11310299 | 12 | 14923421 | -0.310237641 | |
| cg26014017 | 1 | 38019849 | -0.310757279 | SNIP1 | cg10371306 | 11 | 8985977 | -0.310234835 | TMEM9B |
| cg04210100 | 2 | 9614471 | -0.310757023 | IAH1 | cg08967200 | 11 | 28129733 | -0.310224134 | KIF18A |
| cg05732749 | 22 | 42467120 | -0.310710639 | NAGA | cg02738677 | 3 | 133265129 | -0.310220997 | |
| cg01199952 | 13 | 25591486 | -0.310694165 | | cg03863549 | 9 | 33474004 | -0.310183401 | NOL6 |
| cg13615109 | 9 | 27610826 | -0.310682333 | | cg04078251 | 16 | 29802448 | -0.310169295 | KIF22 |
| cg01245284 | 12 | 76426035 | -0.310653084 | PHLDA1 | cg07538747 | 8 | 94753418 | -0.310151829 | RBM12B |
| cg07660645 | 19 | 17392438 | -0.310651422 | ANKLE1 | cg20560182 | 5 | 140700478 | -0.310149367 | TAF7 |
| cg09986574 | 9 | 135544256 | -0.310637644 | DDX31 | cg25110245 | 2 | 191209022 | -0.310146761 | INPP1 |
| cg04982748 | 12 | 66696283 | -0.310592246 | HELB | cg09118169 | 16 | 1833616 | -0.310123881 | NUBP2 |
| cg18105335 | 19 | 37019307 | -0.310590173 | ZNF260 | cg19102035 | 6 | 28864611 | -0.310122362 | |
| cg14128369 | 6 | 34231203 | -0.310584514 | | cg02717437 | 18 | 14132207 | -0.3101214 | ZNF519 |
| cg12124647 | 19 | 20749738 | -0.310578389 | ZNF737 | cg00049253 | 1 | 231473541 | -0.310118095 | EXOC8 |
| cg02200456 | 11 | 2923436 | -0.310577221 | SLC22A18AS | cg12091641 | 8 | 145180933 | -0.310103328 | |
| cg26406994 | 4 | 99182798 | -0.310540847 | RAP1GDS1 | cg27429194 | 17 | 3099847 | -0.310092412 | OR1A2 |
| cg00164500 | 2 | 132416160 | -0.310538722 | | cg11726911 | 1 | 6241120 | -0.310084667 | CHD5 |
| cg26473844 | 5 | 37834909 | -0.310508489 | GDNF | cg03820909 | 10 | 127407979 | -0.310062111 | C10orf137 |
| cg00314018 | 20 | 3776260 | -0.310498132 | CDC25B | cg12790134 | 8 | 67578787 | -0.310052978 | VCPIP1 |
| cg06058395 | 18 | 13726784 | -0.310496038 | C18orf19 | cg25134231 | 2 | 122288051 | -0.310038735 | CLASP1 |
| ch.4.8394628F | 4 | 8343728 | -0.310490626 | | cg14377370 | 4 | 17812264 | -0.310022859 | NCAPG |
| cg25826526 | 20 | 61426675 | -0.310461276 | C20orf20 | cg13603859 | 5 | 145827007 | -0.310022832 | TCERG1 |
| cg13929053 | 6 | 3068474 | -0.310439582 | | cg07730007 | 12 | 107377277 | -0.310017507 | MTERFD3 |
| cg07353572 | 1 | 91966518 | -0.310426926 | CDC7 | cg06576783 | 6 | 53572893 | -0.309998009 | |
| cg01092811 | 3 | 131100455 | -0.31041985 | NUDT16 | cg25498327 | 5 | 68389852 | -0.30999672 | SLC30A5 |
| cg16063617 | 5 | 128430663 | -0.310416734 | ISOC1 | cg09063111 | 22 | 31503870 | -0.309973367 | SELM |
| cg17308959 | 3 | 15643111 | -0.31040967 | HACL1 | cg03082763 | 19 | 12662438 | -0.309973248 | ZNF564 |

Figure 16-23

| | | | | | | | | | |
|---|---|---|---|---|---|---|---|---|---|
| cg02718464 | 13 | 41384019 | -0.309964545 | SUGT1L1 | cg11356029 | 5 | 72112729 | -0.309328399 | TNPO1 |
| cg24669932 | 1 | 8877431 | -0.309957815 | RERE | cg04576025 | 5 | 1386550 | -0.309317824 | |
| cg10239816 | 10 | 101190596 | -0.309953822 | GOT1 | cg24427993 | 6 | 30418847 | -0.309316734 | |
| cg22048948 | 2 | 99225318 | -0.309889634 | C2orf64 | cg16576664 | 19 | 51611660 | -0.309309 | CTU1 |
| cg00208412 | 10 | 99609481 | -0.309882282 | GOLGA7B | cg09978545 | 11 | 66035829 | -0.309288893 | RAB1B |
| cg11488569 | 9 | 130186546 | -0.309874293 | ZNF79 | cg14064229 | 2 | 42588497 | -0.309275025 | COX7A2L |
| cg26112390 | 12 | 100550390 | -0.309863508 | GOLGA2L1 | cg21410080 | 21 | 43639862 | -0.309263997 | ABCG1 |
| cg09843086 | 7 | 131013189 | -0.309842788 | MKLN1 | cg11819799 | 10 | 105452339 | -0.30926266 | SH3PXD2A |
| cg20850195 | 17 | 62223337 | -0.309805432 | SNORA76 | cg02971882 | 4 | 71554083 | -0.309258765 | UTP3 |
| cg26796563 | 16 | 68344861 | -0.309784497 | PRMT7 | cg17574857 | 5 | 147763476 | -0.309251558 | FBXO38 |
| cg20054027 | 11 | 66610720 | -0.309783946 | RCE1 | cg20951334 | 2 | 86669446 | -0.309238473 | KDM3A |
| cg16501572 | 11 | 71934660 | -0.309781631 | INPPL1 | cg07391436 | 5 | 145214979 | -0.309233064 | PRELID2 |
| cg16147336 | 1 | 51435387 | -0.30975064 | CDKN2C | cg14553224 | 17 | 56084507 | -0.309205101 | SFRS1 |
| cg04974899 | 20 | 25177027 | -0.309749165 | ENTPD6 | cg19675288 | 6 | 166582206 | -0.30919056 | T |
| cg09281539 | 20 | 20693126 | -0.309738063 | RALGAPA2 | cg00267325 | 6 | 29691936 | -0.309184837 | HLA-F |
| cg08037327 | 7 | 150211061 | -0.309728585 | GIMAP7 | cg12610061 | 1 | 40916055 | -0.309183854 | ZNF643 |
| cg12349683 | 15 | 68133070 | -0.309720432 | | cg17896229 | 20 | 5294595 | -0.30917879 | PROKR2 |
| cg01557883 | 1 | 70820063 | -0.309719717 | HHLA3 | cg05092885 | 4 | 106629795 | -0.309169309 | INTS12 |
| cg00403457 | 7 | 77166947 | -0.309712411 | PTPN12 | ch.15.99448522F | 15 | 101630999 | -0.309168091 | |
| cg00933696 | 16 | 11327141 | -0.309672325 | | cg22350160 | 1 | 46016574 | -0.309166433 | AKR1A1 |
| cg24568842 | 10 | 90967160 | -0.309661868 | CH25H | cg04970352 | 11 | 44327399 | -0.309165028 | ALX4 |
| cg07699084 | 3 | 123307740 | -0.30964294 | | cg25478109 | 3 | 179322476 | -0.30915821 | NDUFB5 |
| cg08358671 | 1 | 185286807 | -0.309610866 | IVNS1ABP | cg24947163 | 15 | 23086952 | -0.309135818 | NIPA1 |
| cg20768342 | 1 | 85483948 | -0.309605089 | MCOLN3 | cg00215350 | 17 | 6555120 | -0.309093776 | C17orf100 |
| cg00966077 | 16 | 1401335 | -0.309556153 | C16orf42 | cg21411757 | 12 | 93771484 | -0.309089927 | NUDT4 |
| cg11733478 | 11 | 88071037 | -0.309540219 | CTSC | cg06449906 | 5 | 77072222 | -0.309075428 | TBCA |
| cg26507704 | 15 | 25314647 | -0.30953877 | SNORD116-8 | cg25993851 | 11 | 46722334 | -0.309066398 | ARHGAP1 |
| cg07515367 | 17 | 45401150 | -0.309530681 | C17orf57 | cg10001590 | 17 | 21729117 | -0.309047162 | |
| cg11676109 | 11 | 118992413 | -0.309529962 | HINFP | cg19510792 | 5 | 16935695 | -0.309042736 | MYO10 |
| cg14870242 | 14 | 55034646 | -0.309508258 | SAMD4A | cg09356401 | 2 | 64068331 | -0.309038662 | UGP2 |
| cg22984041 | 3 | 161090118 | -0.309445163 | C3orf57 | cg24152845 | 15 | 25414763 | -0.309009332 | SNORD115-1 |
| cg15799959 | 10 | 38146444 | -0.309426878 | ZNF248 | cg27518692 | 17 | 61627470 | -0.30897399 | DCAF7 |
| cg07968927 | 13 | 115080364 | -0.309416353 | ZNF828 | cg14256840 | 7 | 64197047 | -0.308966434 | |
| cg16513467 | 10 | 28822500 | -0.309390525 | WAC | cg19501543 | 1 | 35875651 | -0.308951201 | ZMYM4 |
| cg16341592 | 3 | 112931182 | -0.30938636 | BOC | cg17159242 | 2 | 3623060 | -0.30891525 | RPS7 |
| cg06160898 | 3 | 45187312 | -0.309383291 | CDCP1 | cg07793810 | 10 | 101989373 | -0.308892578 | CHUK |
| cg14621103 | 7 | 1178041 | -0.30938325 | C7orf50 | cg00734724 | 15 | 41408630 | -0.308881017 | INO80 |
| cg17131070 | 1 | 243418713 | -0.30935382 | SDCCAG8 | cg16989797 | 9 | 139378060 | -0.30887793 | C9orf163 |
| cg16056849 | 7 | 35225695 | -0.30934228 | | cg27026509 | 1 | 36348944 | -0.30886745 | EIF2C1 |
| cg10585870 | 19 | 14530314 | -0.309333683 | DDX39 | cg26053083 | 11 | 14995770 | -0.308860659 | |
| cg00533084 | 1 | 156698170 | -0.309330586 | C1orf66 | cg08400563 | 2 | 201729555 | -0.308853596 | CLK1 |

Figure 16-24

| | | | | |
|---|---|---|---|---|
| cg12271800 | 19 | 59028764 | -0.308817426 | ZBTB45 |
| cg20908993 | 14 | 67826378 | -0.308811976 | EIF2S1 |
| cg14094460 | 4 | 43900946 | -0.308803308 | |
| cg27659478 | 17 | 73891062 | -0.308782907 | TRIM65 |
| cg14407698 | 9 | 34458886 | -0.308776983 | C9orf25 |
| cg03218988 | 11 | 62341521 | -0.308770933 | EEF1G |
| cg24726668 | 14 | 39736238 | -0.308756003 | CTAGE5 |
| cg02566518 | 10 | 75531971 | -0.30872194 | FUT11 |
| cg17001531 | 1 | 16825540 | 0.309175372 | |
| cg08524474 | 10 | 49813208 | 0.309188516 | ARHGAP22 |
| cg11566832 | 10 | 88659593 | 0.309358545 | BMPR1A |
| cg26164151 | 11 | 44749353 | 0.309778003 | |
| cg12586707 | 4 | 74738902 | 0.309811367 | |
| cg01266707 | 17 | 37824461 | 0.310151696 | PNMT |
| cg10274208 | 13 | 41351044 | 0.31049244 | |
| ch.8.2353618R | 8 | 119282796 | 0.310724538 | SAMD12 |
| cg11964099 | 17 | 3905835 | 0.31085308 | |
| cg01194336 | 12 | 66627997 | 0.310951911 | IRAK3 |
| cg03183745 | 19 | 17577087 | 0.311037602 | |
| cg08541880 | 3 | 137833983 | 0.311204357 | DZIP1L |
| cg23869307 | 17 | 42297441 | 0.311749709 | UBTF |
| cg02850329 | 1 | 24829455 | 0.3119366 | RCAN3 |
| cg26547359 | 10 | 16859530 | 0.312483668 | RSU1 |
| cg17105206 | 16 | 67211972 | 0.312769436 | KIAA0895L |
| cg17079026 | 2 | 95858880 | 0.312782194 | |
| cg17847344 | 5 | 158478734 | 0.313906358 | EBF1 |
| cg16704344 | 5 | 141616127 | 0.315140712 | |
| cg08529748 | 19 | 52407630 | 0.315600775 | ZNF649 |
| cg01806195 | 14 | 102701850 | 0.316556217 | RAGE |
| cg07930620 | 12 | 96431556 | 0.316776736 | |
| cg18362448 | 19 | 18544419 | 0.316786853 | SSBP4 |
| cg07212416 | 16 | 28385626 | 0.320695478 | |
| cg08293303 | 5 | 176731731 | 0.321332977 | PRELID1 |
| cg00742472 | 14 | 31889912 | 0.322585238 | |

Figure 16-25

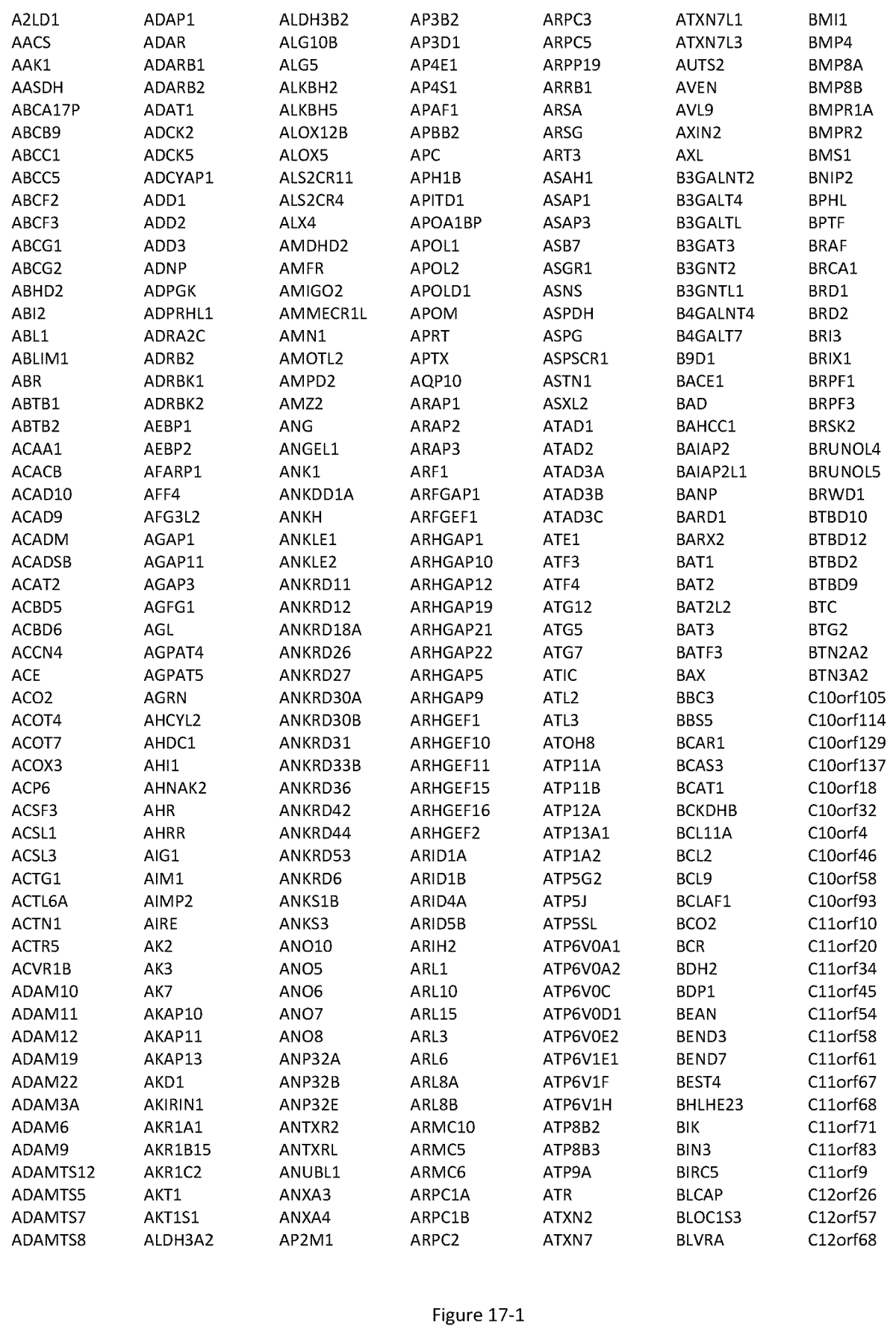

A2LD1
AACS
AAK1
AASDH
ABCA17P
ABCB9
ABCC1
ABCC5
ABCF2
ABCF3
ABCG1
ABCG2
ABHD2
ABI2
ABL1
ABLIM1
ABR
ABTB1
ABTB2
ACAA1
ACACB
ACAD10
ACAD9
ACADM
ACADSB
ACAT2
ACBD5
ACBD6
ACCN4
ACE
ACO2
ACOT4
ACOT7
ACOX3
ACP6
ACSF3
ACSL1
ACSL3
ACTG1
ACTL6A
ACTN1
ACTR5
ACVR1B
ADAM10
ADAM11
ADAM12
ADAM19
ADAM22
ADAM3A
ADAM6
ADAM9
ADAMTS12
ADAMTS5
ADAMTS7
ADAMTS8
ADAP1
ADAR
ADARB1
ADARB2
ADAT1
ADCK2
ADCK5
ADCYAP1
ADD1
ADD2
ADD3
ADNP
ADPGK
ADPRHL1
ADRA2C
ADRB2
ADRBK1
ADRBK2
AEBP1
AEBP2
AFARP1
AFF4
AFG3L2
AGAP1
AGAP11
AGAP3
AGFG1
AGL
AGPAT4
AGPAT5
AGRN
AHCYL2
AHDC1
AHI1
AHNAK2
AHR
AHRR
AIG1
AIM1
AIMP2
AIRE
AK2
AK3
AK7
AKAP10
AKAP11
AKAP13
AKD1
AKIRIN1
AKR1A1
AKR1B15
AKR1C2
AKT1
AKT1S1
ALDH3A2
ALDH3B2
ALG10B
ALG5
ALKBH2
ALKBH5
ALOX12B
ALOX5
ALS2CR11
ALS2CR4
ALX4
AMDHD2
AMFR
AMIGO2
AMMECR1L
AMN1
AMOTL2
AMPD2
AMZ2
ANG
ANGEL1
ANK1
ANKDD1A
ANKH
ANKLE1
ANKLE2
ANKRD11
ANKRD12
ANKRD18A
ANKRD26
ANKRD27
ANKRD30A
ANKRD30B
ANKRD31
ANKRD33B
ANKRD36
ANKRD42
ANKRD44
ANKRD53
ANKRD6
ANKS1B
ANKS3
ANO10
ANO5
ANO6
ANO7
ANO8
ANP32A
ANP32B
ANP32E
ANTXR2
ANTXRL
ANUBL1
ANXA3
ANXA4
AP2M1
AP3B2
AP3D1
AP4E1
AP4S1
APAF1
APBB2
APC
APH1B
APITD1
APOA1BP
APOL1
APOL2
APOLD1
APOM
APRT
APTX
AQP10
ARAP1
ARAP2
ARAP3
ARF1
ARFGAP1
ARFGEF1
ARHGAP1
ARHGAP10
ARHGAP12
ARHGAP19
ARHGAP21
ARHGAP22
ARHGAP5
ARHGAP9
ARHGEF1
ARHGEF10
ARHGEF11
ARHGEF15
ARHGEF16
ARHGEF2
ARID1A
ARID1B
ARID4A
ARID5B
ARIH2
ARL1
ARL10
ARL15
ARL3
ARL6
ARL8A
ARL8B
ARMC10
ARMC5
ARMC6
ARPC1A
ARPC1B
ARPC2
ARPC3
ARPC5
ARPP19
ARRB1
ARSA
ARSG
ART3
ASAH1
ASAP1
ASAP3
ASB7
ASGR1
ASNS
ASPDH
ASPG
ASPSCR1
ASTN1
ASXL2
ATAD1
ATAD2
ATAD3A
ATAD3B
ATAD3C
ATE1
ATF3
ATF4
ATG12
ATG5
ATG7
ATIC
ATL2
ATL3
ATOH8
ATP11A
ATP11B
ATP12A
ATP13A1
ATP1A2
ATP5G2
ATP5J
ATP5SL
ATP6V0A1
ATP6V0A2
ATP6V0C
ATP6V0D1
ATP6V0E2
ATP6V1E1
ATP6V1F
ATP6V1H
ATP8B2
ATP8B3
ATP9A
ATR
ATXN2
ATXN7
ATXN7L1
ATXN7L3
AUTS2
AVEN
AVL9
AXIN2
AXL
B3GALNT2
B3GALT4
B3GALTL
B3GAT3
B3GNT2
B3GNTL1
B4GALNT4
B4GALT7
B9D1
BACE1
BAD
BAHCC1
BAIAP2
BAIAP2L1
BANP
BARD1
BARX2
BAT1
BAT2
BAT2L2
BAT3
BATF3
BAX
BBC3
BBS5
BCAR1
BCAS3
BCAT1
BCKDHB
BCL11A
BCL2
BCL9
BCLAF1
BCO2
BCR
BDH2
BDP1
BEAN
BEND3
BEND7
BEST4
BHLHE23
BIK
BIN3
BIRC5
BLCAP
BLOC1S3
BLVRA
BMI1
BMP4
BMP8A
BMP8B
BMPR1A
BMPR2
BMS1
BNIP2
BPHL
BPTF
BRAF
BRCA1
BRD1
BRD2
BRI3
BRIX1
BRPF1
BRPF3
BRSK2
BRUNOL4
BRUNOL5
BRWD1
BTBD10
BTBD12
BTBD2
BTBD9
BTC
BTG2
BTN2A2
BTN3A2
C10orf105
C10orf114
C10orf129
C10orf137
C10orf18
C10orf32
C10orf4
C10orf46
C10orf58
C10orf93
C11orf10
C11orf20
C11orf34
C11orf45
C11orf54
C11orf58
C11orf61
C11orf67
C11orf68
C11orf71
C11orf83
C11orf9
C12orf26
C12orf57
C12orf68

Figure 17-1

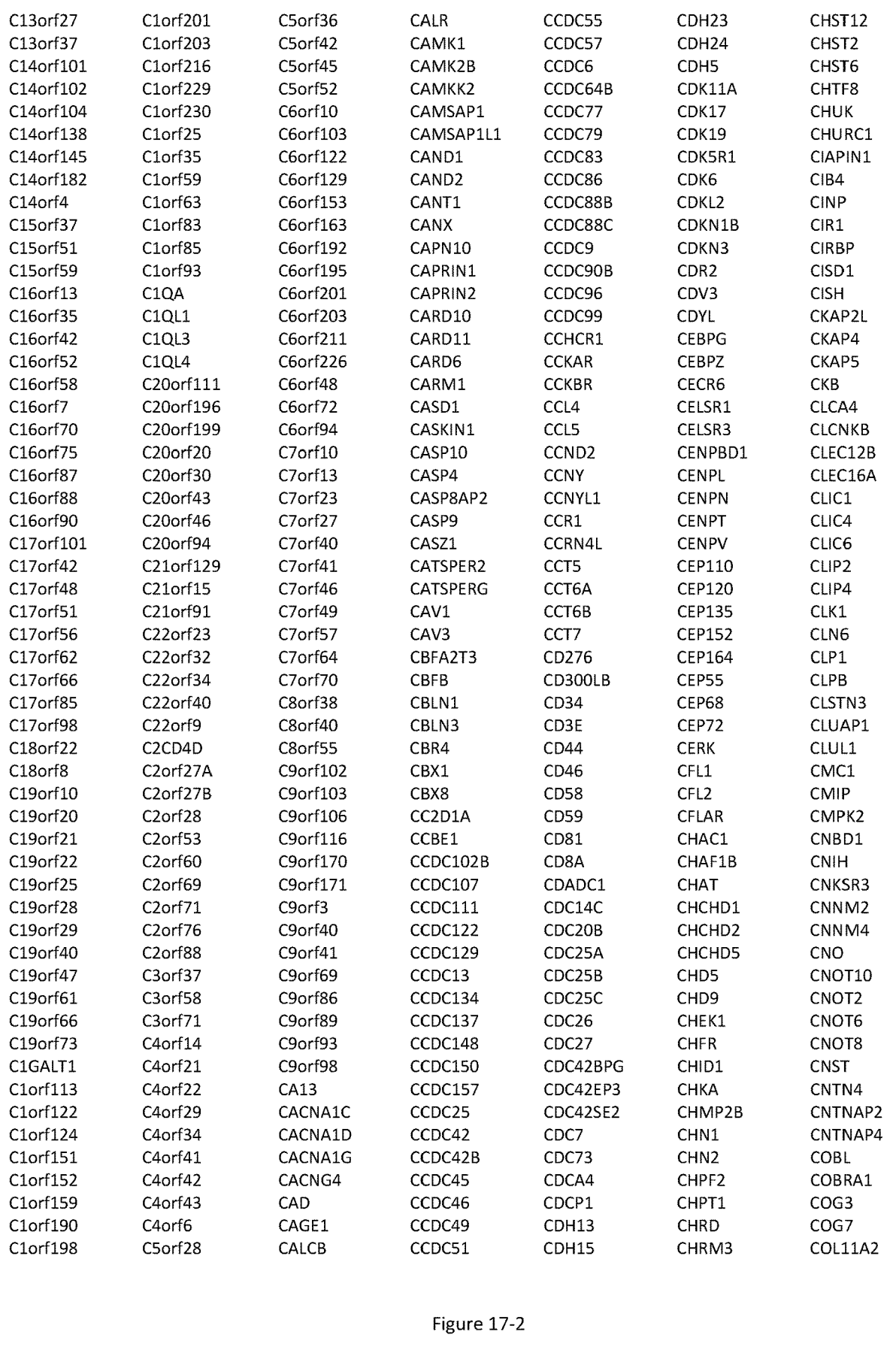

C13orf27
C13orf37
C14orf101
C14orf102
C14orf104
C14orf138
C14orf145
C14orf182
C14orf4
C15orf37
C15orf51
C15orf59
C16orf13
C16orf35
C16orf42
C16orf52
C16orf58
C16orf7
C16orf70
C16orf75
C16orf87
C16orf88
C16orf90
C17orf101
C17orf42
C17orf48
C17orf51
C17orf56
C17orf62
C17orf66
C17orf85
C17orf98
C18orf22
C18orf8
C19orf10
C19orf20
C19orf21
C19orf22
C19orf25
C19orf28
C19orf29
C19orf40
C19orf47
C19orf61
C19orf66
C19orf73
C1GALT1
C1orf113
C1orf122
C1orf124
C1orf151
C1orf152
C1orf159
C1orf190
C1orf198
C1orf201
C1orf203
C1orf216
C1orf229
C1orf230
C1orf25
C1orf35
C1orf59
C1orf63
C1orf83
C1orf85
C1orf93
C1QA
C1QL1
C1QL3
C1QL4
C20orf111
C20orf196
C20orf199
C20orf20
C20orf30
C20orf43
C20orf46
C20orf94
C21orf129
C21orf15
C21orf91
C22orf23
C22orf32
C22orf34
C22orf40
C22orf9
C2CD4D
C2orf27A
C2orf27B
C2orf28
C2orf53
C2orf60
C2orf69
C2orf71
C2orf76
C2orf88
C3orf37
C3orf58
C3orf71
C4orf14
C4orf21
C4orf22
C4orf29
C4orf34
C4orf41
C4orf42
C4orf43
C4orf6
C5orf28
C5orf36
C5orf42
C5orf45
C5orf52
C6orf10
C6orf103
C6orf122
C6orf129
C6orf153
C6orf163
C6orf192
C6orf195
C6orf201
C6orf203
C6orf211
C6orf226
C6orf48
C6orf72
C6orf94
C7orf10
C7orf13
C7orf23
C7orf27
C7orf40
C7orf41
C7orf46
C7orf49
C7orf57
C7orf64
C7orf70
C8orf38
C8orf40
C8orf55
C9orf102
C9orf103
C9orf106
C9orf116
C9orf170
C9orf171
C9orf3
C9orf40
C9orf41
C9orf69
C9orf86
C9orf89
C9orf93
C9orf98
CA13
CACNA1C
CACNA1D
CACNA1G
CACNG4
CAD
CAGE1
CALCB
CALR
CAMK1
CAMK2B
CAMKK2
CAMSAP1
CAMSAP1L1
CAND1
CAND2
CANT1
CANX
CAPN10
CAPRIN1
CAPRIN2
CARD10
CARD11
CARD6
CARM1
CASD1
CASKIN1
CASP10
CASP4
CASP8AP2
CASP9
CASZ1
CATSPER2
CATSPERG
CAV1
CAV3
CBFA2T3
CBFB
CBLN1
CBLN3
CBR4
CBX1
CBX8
CC2D1A
CCBE1
CCDC102B
CCDC107
CCDC111
CCDC122
CCDC129
CCDC13
CCDC134
CCDC137
CCDC148
CCDC150
CCDC157
CCDC25
CCDC42
CCDC42B
CCDC45
CCDC46
CCDC49
CCDC51
CCDC55
CCDC57
CCDC6
CCDC64B
CCDC77
CCDC79
CCDC83
CCDC86
CCDC88B
CCDC88C
CCDC9
CCDC90B
CCDC96
CCDC99
CCHCR1
CCKAR
CCKBR
CCL4
CCL5
CCND2
CCNY
CCNYL1
CCR1
CCRN4L
CCT5
CCT6A
CCT6B
CCT7
CD276
CD300LB
CD34
CD3E
CD44
CD46
CD58
CD59
CD81
CD8A
CDADC1
CDC14C
CDC20B
CDC25A
CDC25B
CDC25C
CDC26
CDC27
CDC42BPG
CDC42EP3
CDC42SE2
CDC7
CDC73
CDCA4
CDCP1
CDH13
CDH15
CDH23
CDH24
CDH5
CDK11A
CDK17
CDK19
CDK5R1
CDK6
CDKL2
CDKN1B
CDKN3
CDR2
CDV3
CDYL
CEBPG
CEBPZ
CECR6
CELSR1
CELSR3
CENPBD1
CENPL
CENPN
CENPT
CENPV
CEP110
CEP120
CEP135
CEP152
CEP164
CEP55
CEP68
CEP72
CERK
CFL1
CFL2
CFLAR
CHAC1
CHAF1B
CHAT
CHCHD1
CHCHD2
CHCHD5
CHD5
CHD9
CHEK1
CHFR
CHID1
CHKA
CHMP2B
CHN1
CHN2
CHPF2
CHPT1
CHRD
CHRM3
CHST12
CHST2
CHST6
CHTF8
CHUK
CHURC1
CIAPIN1
CIB4
CINP
CIR1
CIRBP
CISD1
CISH
CKAP2L
CKAP4
CKAP5
CKB
CLCA4
CLCNKB
CLEC12B
CLEC16A
CLIC1
CLIC4
CLIC6
CLIP2
CLIP4
CLK1
CLN6
CLP1
CLPB
CLSTN3
CLUAP1
CLUL1
CMC1
CMIP
CMPK2
CNBD1
CNIH
CNKSR3
CNNM2
CNNM4
CNO
CNOT10
CNOT2
CNOT6
CNOT8
CNST
CNTN4
CNTNAP2
CNTNAP4
COBL
COBRA1
COG3
COG7
COL11A2

Figure 17-2

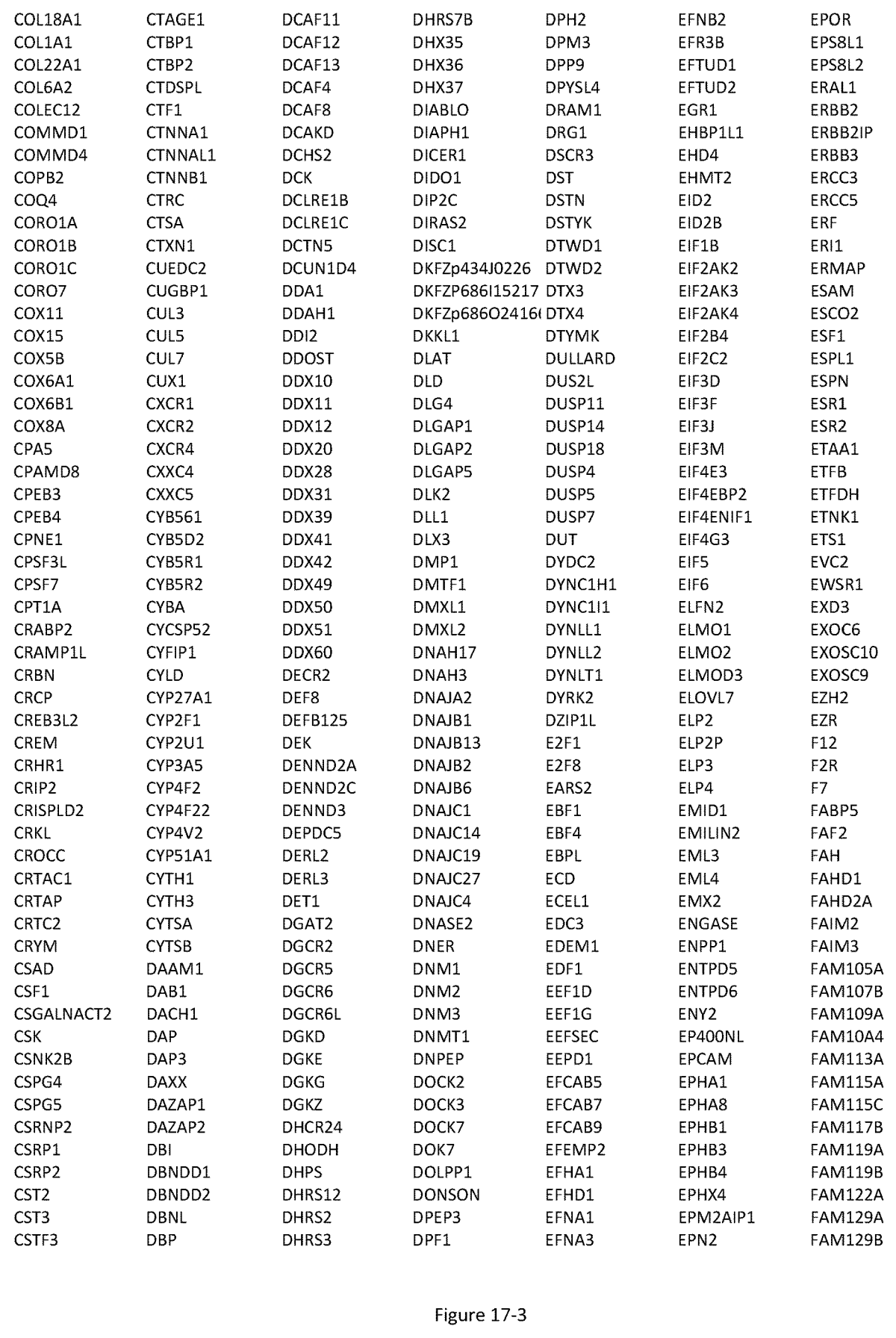

COL18A1
COL1A1
COL22A1
COL6A2
COLEC12
COMMD1
COMMD4
COPB2
COQ4
CORO1A
CORO1B
CORO1C
CORO7
COX11
COX15
COX5B
COX6A1
COX6B1
COX8A
CPA5
CPAMD8
CPEB3
CPEB4
CPNE1
CPSF3L
CPSF7
CPT1A
CRABP2
CRAMP1L
CRBN
CRCP
CREB3L2
CREM
CRHR1
CRIP2
CRISPLD2
CRKL
CROCC
CRTAC1
CRTAP
CRTC2
CRYM
CSAD
CSF1
CSGALNACT2
CSK
CSNK2B
CSPG4
CSPG5
CSRNP2
CSRP1
CSRP2
CST2
CST3
CSTF3
CTAGE1
CTBP1
CTBP2
CTDSPL
CTF1
CTNNA1
CTNNAL1
CTNNB1
CTRC
CTSA
CTXN1
CUEDC2
CUGBP1
CUL3
CUL5
CUL7
CUX1
CXCR1
CXCR2
CXCR4
CXXC4
CXXC5
CYB561
CYB5D2
CYB5R1
CYB5R2
CYBA
CYCSP52
CYFIP1
CYLD
CYP27A1
CYP2F1
CYP2U1
CYP3A5
CYP4F2
CYP4F22
CYP4V2
CYP51A1
CYTH1
CYTH3
CYTSA
CYTSB
DAAM1
DAB1
DACH1
DAP
DAP3
DAXX
DAZAP1
DAZAP2
DBI
DBNDD1
DBNDD2
DBNL
DBP
DCAF11
DCAF12
DCAF13
DCAF4
DCAF8
DCAKD
DCHS2
DCK
DCLRE1B
DCLRE1C
DCTN5
DCUN1D4
DDA1
DDAH1
DDI2
DDOST
DDX10
DDX11
DDX12
DDX20
DDX28
DDX31
DDX39
DDX41
DDX42
DDX49
DDX50
DDX51
DDX60
DECR2
DEF8
DEFB125
DEK
DENND2A
DENND2C
DENND3
DEPDC5
DERL2
DERL3
DET1
DGAT2
DGCR2
DGCR5
DGCR6
DGCR6L
DGKD
DGKE
DGKG
DGKZ
DHCR24
DHODH
DHPS
DHRS12
DHRS2
DHRS3
DHRS7B
DHX35
DHX36
DHX37
DIABLO
DIAPH1
DICER1
DIDO1
DIP2C
DIRAS2
DISC1
DKFZp434J0226
DKFZP686I15217
DKFZp686O2416(
DKKL1
DLAT
DLD
DLG4
DLGAP1
DLGAP2
DLGAP5
DLK2
DLL1
DLX3
DMP1
DMTF1
DMXL1
DMXL2
DNAH17
DNAH3
DNAJA2
DNAJB1
DNAJB13
DNAJB2
DNAJB6
DNAJC1
DNAJC14
DNAJC19
DNAJC27
DNAJC4
DNASE2
DNER
DNM1
DNM2
DNM3
DNMT1
DNPEP
DOCK2
DOCK3
DOCK7
DOK7
DOLPP1
DONSON
DPEP3
DPF1
DPH2
DPM3
DPP9
DPYSL4
DRAM1
DRG1
DSCR3
DST
DSTN
DSTYK
DTWD1
DTWD2
DTX3
DTX4
DTYMK
DULLARD
DUS2L
DUSP11
DUSP14
DUSP18
DUSP4
DUSP5
DUSP7
DUT
DYDC2
DYNC1H1
DYNC1I1
DYNLL1
DYNLL2
DYNLT1
DYRK2
DZIP1L
E2F1
E2F8
EARS2
EBF1
EBF4
EBPL
ECD
ECEL1
EDC3
EDEM1
EDF1
EEF1D
EEF1G
EEFSEC
EEPD1
EFCAB5
EFCAB7
EFCAB9
EFEMP2
EFHA1
EFHD1
EFNA1
EFNA3
EFNB2
EFR3B
EFTUD1
EFTUD2
EGR1
EHBP1L1
EHD4
EHMT2
EID2
EID2B
EIF1B
EIF2AK2
EIF2AK3
EIF2AK4
EIF2B4
EIF2C2
EIF3D
EIF3F
EIF3J
EIF3M
EIF4E3
EIF4EBP2
EIF4ENIF1
EIF4G3
EIF5
EIF6
ELFN2
ELMO1
ELMO2
ELMOD3
ELOVL7
ELP2
ELP2P
ELP3
ELP4
EMID1
EMILIN2
EML3
EML4
EMX2
ENGASE
ENPP1
ENTPD5
ENTPD6
ENY2
EP400NL
EPCAM
EPHA1
EPHA8
EPHB1
EPHB3
EPHB4
EPHX4
EPM2AIP1
EPN2
EPOR
EPS8L1
EPS8L2
ERAL1
ERBB2
ERBB2IP
ERBB3
ERCC3
ERCC5
ERF
ERI1
ERMAP
ESAM
ESCO2
ESF1
ESPL1
ESPN
ESR1
ESR2
ETAA1
ETFB
ETFDH
ETNK1
ETS1
EVC2
EWSR1
EXD3
EXOC6
EXOSC10
EXOSC9
EZH2
EZR
F12
F2R
F7
FABP5
FAF2
FAH
FAHD1
FAHD2A
FAIM2
FAIM3
FAM105A
FAM107B
FAM109A
FAM10A4
FAM113A
FAM115A
FAM115C
FAM117B
FAM119A
FAM119B
FAM122A
FAM129A
FAM129B

Figure 17-3

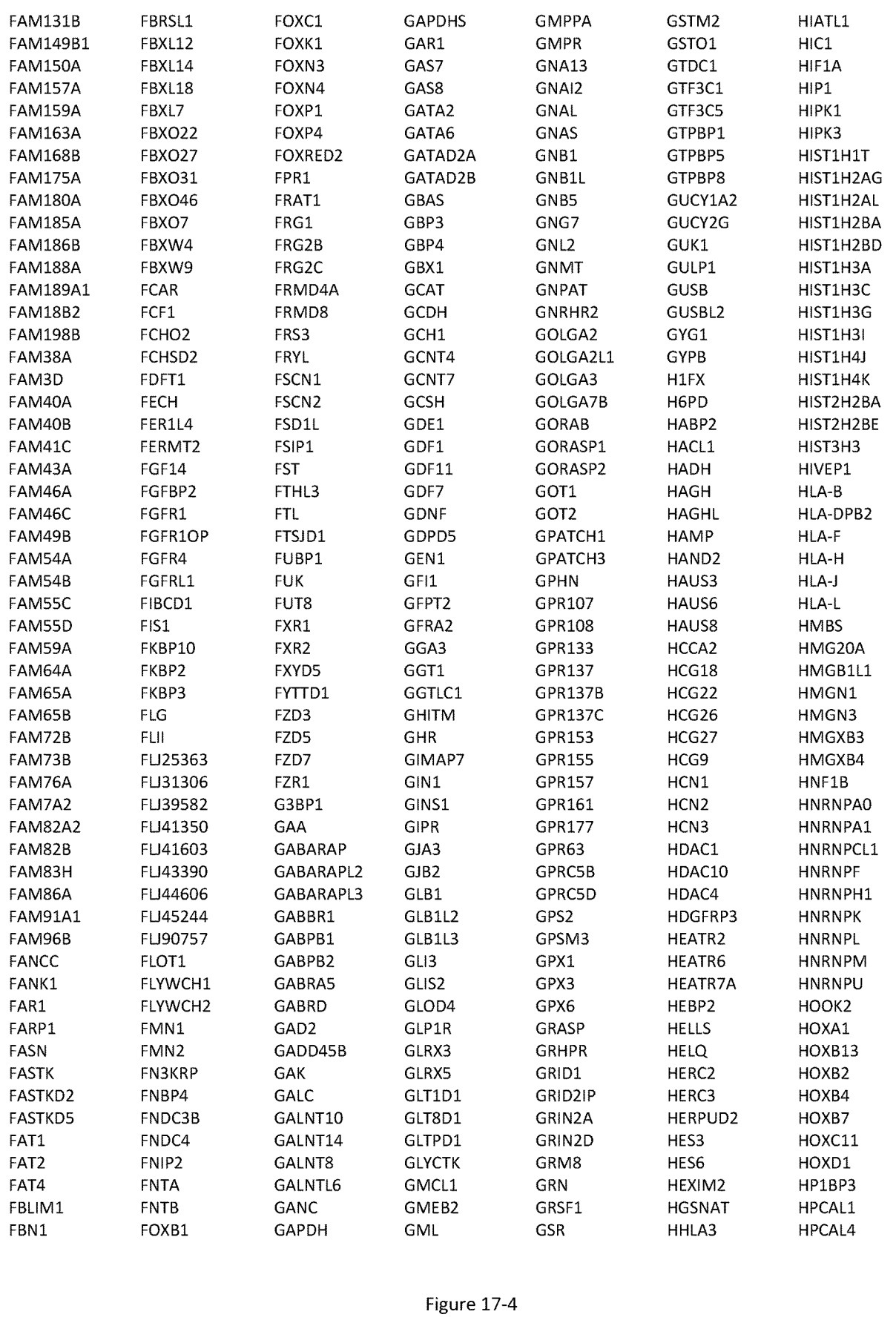

FAM131B
FAM149B1
FAM150A
FAM157A
FAM159A
FAM163A
FAM168B
FAM175A
FAM180A
FAM185A
FAM186B
FAM188A
FAM189A1
FAM18B2
FAM198B
FAM38A
FAM3D
FAM40A
FAM40B
FAM41C
FAM43A
FAM46A
FAM46C
FAM49B
FAM54A
FAM54B
FAM55C
FAM55D
FAM59A
FAM64A
FAM65A
FAM65B
FAM72B
FAM73B
FAM76A
FAM7A2
FAM82A2
FAM82B
FAM83H
FAM86A
FAM91A1
FAM96B
FANCC
FANK1
FAR1
FARP1
FASN
FASTK
FASTKD2
FASTKD5
FAT1
FAT2
FAT4
FBLIM1
FBN1
FBRSL1
FBXL12
FBXL14
FBXL18
FBXL7
FBXO22
FBXO27
FBXO31
FBXO46
FBXO7
FBXW4
FBXW9
FCAR
FCF1
FCHO2
FCHSD2
FDFT1
FECH
FER1L4
FERMT2
FGF14
FGFBP2
FGFR1
FGFR1OP
FGFR4
FGFRL1
FIBCD1
FIS1
FKBP10
FKBP2
FKBP3
FLG
FLII
FLJ25363
FLJ31306
FLJ39582
FLJ41350
FLJ41603
FLJ43390
FLJ44606
FLJ45244
FLJ90757
FLOT1
FLYWCH1
FLYWCH2
FMN1
FMN2
FN3KRP
FNBP4
FNDC3B
FNDC4
FNIP2
FNTA
FNTB
FOXB1
FOXC1
FOXK1
FOXN3
FOXN4
FOXP1
FOXP4
FOXRED2
FPR1
FRAT1
FRG1
FRG2B
FRG2C
FRMD4A
FRMD8
FRS3
FRYL
FSCN1
FSCN2
FSD1L
FSIP1
FST
FTHL3
FTL
FTSJD1
FUBP1
FUK
FUT8
FXR1
FXR2
FXYD5
FYTTD1
FZD3
FZD5
FZD7
FZR1
G3BP1
GAA
GABARAP
GABARAPL2
GABARAPL3
GABBR1
GABPB1
GABPB2
GABRA5
GABRD
GAD2
GADD45B
GAK
GALC
GALNT10
GALNT14
GALNT8
GALNTL6
GANC
GAPDH
GAPDHS
GAR1
GAS7
GAS8
GATA2
GATA6
GATAD2A
GATAD2B
GBAS
GBP3
GBP4
GBX1
GCAT
GCDH
GCH1
GCNT4
GCNT7
GCSH
GDE1
GDF1
GDF11
GDF7
GDNF
GDPD5
GEN1
GFI1
GFPT2
GFRA2
GGA3
GGT1
GGTLC1
GHITM
GHR
GIMAP7
GIN1
GINS1
GIPR
GJA3
GJB2
GLB1
GLB1L2
GLB1L3
GLI3
GLIS2
GLOD4
GLP1R
GLRX3
GLRX5
GLT1D1
GLT8D1
GLTPD1
GLYCTK
GMCL1
GMEB2
GML
GMPPA
GMPR
GNA13
GNAI2
GNAL
GNAS
GNB1
GNB1L
GNB5
GNG7
GNL2
GNMT
GNPAT
GNRHR2
GOLGA2
GOLGA2L1
GOLGA3
GOLGA7B
GORAB
GORASP1
GORASP2
GOT1
GOT2
GPATCH1
GPATCH3
GPHN
GPR107
GPR108
GPR133
GPR137
GPR137B
GPR137C
GPR153
GPR155
GPR157
GPR161
GPR177
GPR63
GPRC5B
GPRC5D
GPS2
GPSM3
GPX1
GPX3
GPX6
GRASP
GRHPR
GRID1
GRID2IP
GRIN2A
GRIN2D
GRM8
GRN
GRSF1
GSR
GSTM2
GSTO1
GTDC1
GTF3C1
GTF3C5
GTPBP1
GTPBP5
GTPBP8
GUCY1A2
GUCY2G
GUK1
GULP1
GUSB
GUSBL2
GYG1
GYPB
H1FX
H6PD
HABP2
HACL1
HADH
HAGH
HAGHL
HAMP
HAND2
HAUS3
HAUS6
HAUS8
HCCA2
HCG18
HCG22
HCG26
HCG27
HCG9
HCN1
HCN2
HCN3
HDAC1
HDAC10
HDAC4
HDGFRP3
HEATR2
HEATR6
HEATR7A
HEBP2
HELLS
HELQ
HERC2
HERC3
HERPUD2
HES3
HES6
HEXIM2
HGSNAT
HHLA3
HIATL1
HIC1
HIF1A
HIP1
HIPK1
HIPK3
HIST1H1T
HIST1H2AG
HIST1H2AL
HIST1H2BA
HIST1H2BD
HIST1H3A
HIST1H3C
HIST1H3G
HIST1H3I
HIST1H4J
HIST1H4K
HIST2H2BA
HIST2H2BE
HIST3H3
HIVEP1
HLA-B
HLA-DPB2
HLA-F
HLA-H
HLA-J
HLA-L
HMBS
HMG20A
HMGB1L1
HMGN1
HMGN3
HMGXB3
HMGXB4
HNF1B
HNRNPA0
HNRNPA1
HNRNPCL1
HNRNPF
HNRNPH1
HNRNPK
HNRNPL
HNRNPM
HNRNPU
HOOK2
HOXA1
HOXB13
HOXB2
HOXB4
HOXB7
HOXC11
HOXD1
HP1BP3
HPCAL1
HPCAL4

Figure 17-4

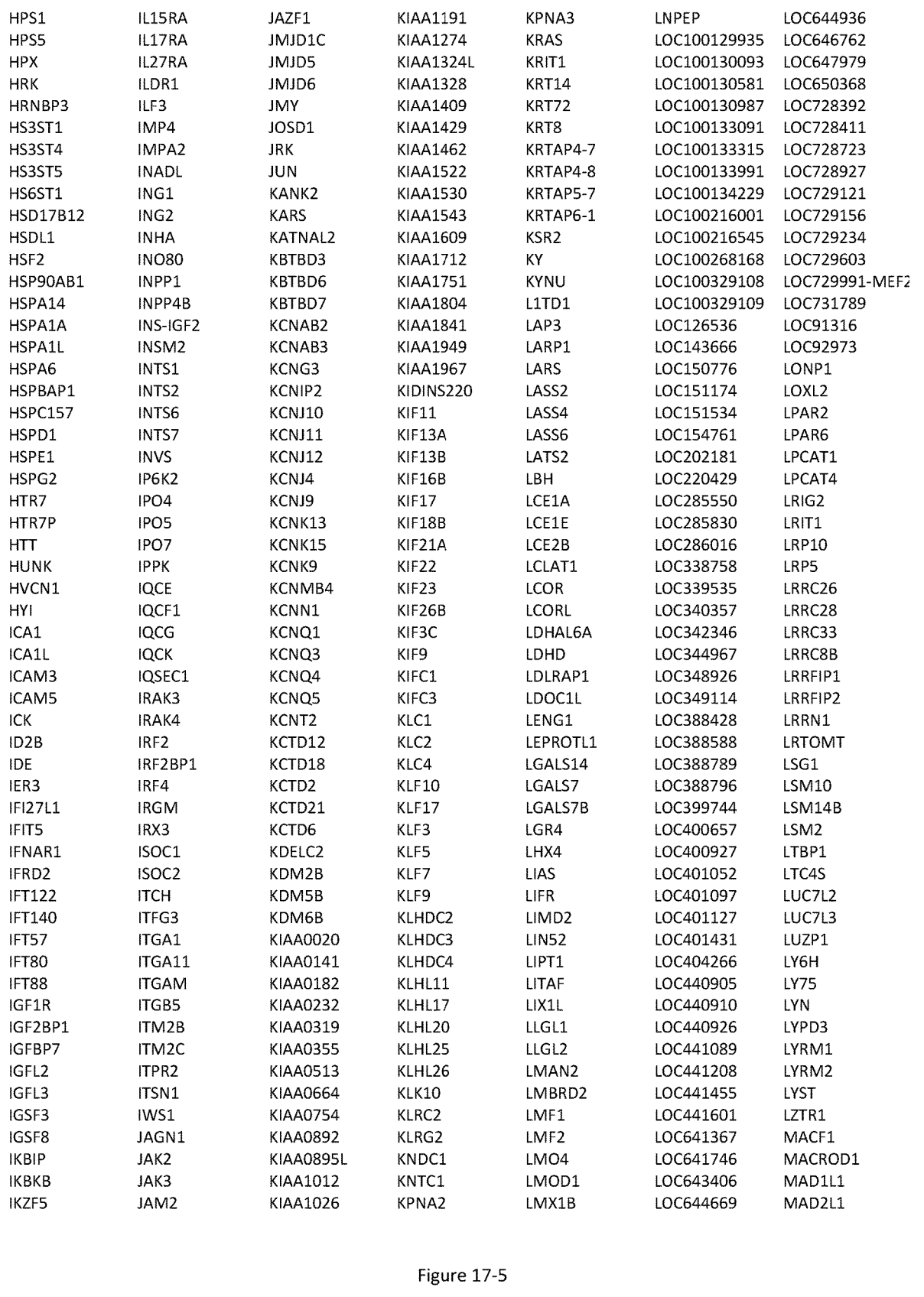

HPS1
HPS5
HPX
HRK
HRNBP3
HS3ST1
HS3ST4
HS3ST5
HS6ST1
HSD17B12
HSDL1
HSF2
HSP90AB1
HSPA14
HSPA1A
HSPA1L
HSPA6
HSPBAP1
HSPC157
HSPD1
HSPE1
HSPG2
HTR7
HTR7P
HTT
HUNK
HVCN1
HYI
ICA1
ICA1L
ICAM3
ICAM5
ICK
ID2B
IDE
IER3
IFI27L1
IFIT5
IFNAR1
IFRD2
IFT122
IFT140
IFT57
IFT80
IFT88
IGF1R
IGF2BP1
IGFBP7
IGFL2
IGFL3
IGSF3
IGSF8
IKBIP
IKBKB
IKZF5
IL15RA
IL17RA
IL27RA
ILDR1
ILF3
IMP4
IMPA2
INADL
ING1
ING2
INHA
INO80
INPP1
INPP4B
INS-IGF2
INSM2
INTS1
INTS2
INTS6
INTS7
INVS
IP6K2
IPO4
IPO5
IPO7
IPPK
IQCE
IQCF1
IQCG
IQCK
IQSEC1
IRAK3
IRAK4
IRF2
IRF2BP1
IRF4
IRGM
IRX3
ISOC1
ISOC2
ITCH
ITFG3
ITGA1
ITGA11
ITGAM
ITGB5
ITM2B
ITM2C
ITPR2
ITSN1
IWS1
JAGN1
JAK2
JAK3
JAM2
JAZF1
JMJD1C
JMJD5
JMJD6
JMY
JOSD1
JRK
JUN
KANK2
KARS
KATNAL2
KBTBD3
KBTBD6
KBTBD7
KCNAB2
KCNAB3
KCNG3
KCNIP2
KCNJ10
KCNJ11
KCNJ12
KCNJ4
KCNJ9
KCNK13
KCNK15
KCNK9
KCNMB4
KCNN1
KCNQ1
KCNQ3
KCNQ4
KCNQ5
KCNT2
KCTD12
KCTD18
KCTD2
KCTD21
KCTD6
KDELC2
KDM2B
KDM5B
KDM6B
KIAA0020
KIAA0141
KIAA0182
KIAA0232
KIAA0319
KIAA0355
KIAA0513
KIAA0664
KIAA0754
KIAA0892
KIAA0895L
KIAA1012
KIAA1026
KIAA1191
KIAA1274
KIAA1324L
KIAA1328
KIAA1409
KIAA1429
KIAA1462
KIAA1522
KIAA1530
KIAA1543
KIAA1609
KIAA1712
KIAA1751
KIAA1804
KIAA1841
KIAA1949
KIAA1967
KIDINS220
KIF11
KIF13A
KIF13B
KIF16B
KIF17
KIF18B
KIF21A
KIF22
KIF23
KIF26B
KIF3C
KIF9
KIFC1
KIFC3
KLC1
KLC2
KLC4
KLF10
KLF17
KLF3
KLF5
KLF7
KLF9
KLHDC2
KLHDC3
KLHDC4
KLHL11
KLHL17
KLHL20
KLHL25
KLHL26
KLK10
KLRC2
KLRG2
KNDC1
KNTC1
KPNA2
KPNA3
KRAS
KRIT1
KRT14
KRT72
KRT8
KRTAP4-7
KRTAP4-8
KRTAP5-7
KRTAP6-1
KSR2
KY
KYNU
L1TD1
LAP3
LARP1
LARS
LASS2
LASS4
LASS6
LATS2
LBH
LCE1A
LCE1E
LCE2B
LCLAT1
LCOR
LCORL
LDHAL6A
LDHD
LDLRAP1
LDOC1L
LENG1
LEPROTL1
LGALS14
LGALS7
LGALS7B
LGR4
LHX4
LIAS
LIFR
LIMD2
LIN52
LIPT1
LITAF
LIX1L
LLGL1
LLGL2
LMAN2
LMBRD2
LMF1
LMF2
LMO4
LMOD1
LMX1B
LNPEP
LOC100129935
LOC100130093
LOC100130581
LOC100130987
LOC100133091
LOC100133315
LOC100133991
LOC100134229
LOC100216001
LOC100216545
LOC100268168
LOC100329108
LOC100329109
LOC126536
LOC143666
LOC150776
LOC151174
LOC151534
LOC154761
LOC202181
LOC220429
LOC285550
LOC285830
LOC286016
LOC338758
LOC339535
LOC340357
LOC342346
LOC344967
LOC348926
LOC349114
LOC388428
LOC388588
LOC388789
LOC388796
LOC399744
LOC400657
LOC400927
LOC401052
LOC401097
LOC401127
LOC401431
LOC404266
LOC440905
LOC440910
LOC440926
LOC441089
LOC441208
LOC441455
LOC441601
LOC641367
LOC641746
LOC643406
LOC644669
LOC644936
LOC646762
LOC647979
LOC650368
LOC728392
LOC728411
LOC728723
LOC728927
LOC729121
LOC729156
LOC729234
LOC729603
LOC729991-MEF2
LOC731789
LOC91316
LOC92973
LONP1
LOXL2
LPAR2
LPAR6
LPCAT1
LPCAT4
LRIG2
LRIT1
LRP10
LRP5
LRRC26
LRRC28
LRRC33
LRRC8B
LRRFIP1
LRRFIP2
LRRN1
LRTOMT
LSG1
LSM10
LSM14B
LSM2
LTBP1
LTC4S
LUC7L2
LUC7L3
LUZP1
LY6H
LY75
LYN
LYPD3
LYRM1
LYRM2
LYST
LZTR1
MACF1
MACROD1
MAD1L1
MAD2L1

Figure 17-5

MAD2L1BP
MAD2L2
MAFG
MAFK
MAGI1
MAGI3
Magmas
MAN2B2
MAN2C1
MANEAL
MAP1S
MAP2K4
MAP3K1
MAP3K11
MAP3K12
MAP3K14
MAP3K6
MAP4
MAP4K1
MAPK1
MAPK11
MAPK8IP1
MAPK8IP2
MAPKAPK2
MAPKAPK5
MAPRE2
MAPRE3
MAPT
MARK3
MAST3
MAT2B
MATK
MATN1
MAVS
MBLAC1
MBLAC2
MBNL1
MBOAT2
MBOAT7
MBP
MBTD1
MCAM
MCART1
MCART3P
MCC
MCCD1
MCF2L
MCHR1
MCL1
MCM10
MCM3AP
MCM3APAS
MCM6
MCM7
MCM8
MCOLN1
MCOLN3
MDGA2
MDK
MDM2
MDN1
ME2
MEA1
MECOM
MED1
MED13
MED24
MED8
MED9
MEGF10
MEGF11
MEGF6
MEIS2
MEP1A
MEPCE
MESDC1
MESP1
METRNL
METT10D
METTL13
METTL2A
METTL2B
MEX3B
MEX3C
MEX3D
MFAP2
MFI2
MFSD10
MFSD2A
MFSD5
MFSD8
MGA
MGAT4A
MGAT4C
MGC23284
MGLL
MGMT
MIA
MICA
MICAL1
MICAL3
MICALCL
MICALL2
MICB
MIIP
MIOS
MIR1253
MIR1275
MIR1297
MIR1307
MIR142
MIR1470
MIR17HG
MIR1908
MIR210
MIR24-2
MIR375
MIR492
MIR517A
MIR517B
MIR517C
MIR518A1
MIR518A2
MIR518F
MIR519A1
MIR519C
MIR520A
MIR596
MIR618
MIR632
MIR636
MIR639
MIS12
MITF
MKI67IP
MKL2
MKNK2
MKRN1
MLKL
MLLT1
MLLT10
MLLT6
MLX
MMP19
MMP21
MNX1
MOBKL3
MOCS2
MOGS
MORG1
MORN3
MORN4
MOV10
MOXD1
MPDU1
MPL
MPPE1
MPV17L2
MRAP2
MRC2
MRE11A
MRFAP1
MRPL12
MRPL16
MRPL18
MRPL37
MRPL38
MRPL44
MRPS17
MRPS24
MRPS28
MRPS31
MRPS7
MRPS9
MRS2P2
MS4A10
MSH3
MSH5
MSH6
MSI2
MSL1
MSL2
MSRB3
MST1P2
MSTO2P
MT4
MTA1
MTA2
MTCH1
MTDH
MTERFD3
MTF2
MTFMT
MTHFD2
MTHFD2L
MTHFSD
MTL5
MTO1
MTR
MTRF1L
MTUS2
MUC1
MUDENG
MUTYH
MVP
MXD3
MYADM
MYADML2
MYBL1
MYC
MYCNOS
MYH10
MYH9
MYL12A
MYNN
MYO10
MYO19
MYO1G
MYO5A
MYO9B
MYRIP
MYST3
MYST4
MYT1L
MZF1
N4BP2
N6AMT2
NAA20
NAA30
NAAA
NAALADL1
NACAP1
NANOS1
NANP
NAP1L4
NAP1L5
NAPA
NARF
NARG2
NARS
NAT2
NBL1
NBN
NBPF1
NBPF14
NBPF16
NBPF3
NBPF9
NBR1
NCAM1
NCAPD2
NCAPD3
NCAPG
NCAPH2
NCBP2
NCEH1
NCF1C
NCK1
NCKIPSD
NCL
NCOA5
NCRNA00115
NCRNA00164
NCRNA00171
NCRNA00173
NCRNA00189
NDE1
NDEL1
NDN
NDRG1
NDUFA2
NDUFA3
NDUFA6
NDUFAB1
NDUFB5
NDUFB6
NEAT1
NEDD4L
NEDD8
NEFH
NEU1
NEURL
NEUROG1
NF1
NF2
NFATC1
NFATC2
NFATC2IP
NFATC4
NFE2L1
NFIC
NFIL3
NFKB2
NFKBIA
NFKBIE
NFKBIL1
NFKBIL2
NFYC
NGF
NGLY1
NHEDC2
NHLH1
NHLRC3
NHP2L1
NIF3L1
NINJ2
NIPA1
NIPA2
NIPSNAP3B
NIT2
NKAIN2
NKAIN3
NKD2
NKIRAS1
NKX2-8
NLK
NLRP7
NMB
NME1
NMNAT1
NMNAT2
NMT1
NMT2
NMU
NOL11
NOL7
NOM1
NOS3
NOSTRIN
NOTCH3
NPBWR1
NPC1
NPC2
NPFFR1
NPHP4
NPM1
NPR1
NPR3
NQO2
NR1D1
NR2C1
NR2C2AP
NR2F1
NRBF2
NRIP2
NRN1
NRTN
NSD1
NSMAF
NSMCE4A
NSUN2
NT5DC3
NT5M
NTF4
NTM
NTN4
NUBP2
NUCKS1
NUDT22
NUDT3
NUDT6
NUDT8
NUDT9
NUFIP1
NUFIP2
NUP133
NUP153
NUP188
NUP210
NUP93
NUS1
NVL
NXF1
NXN
OAS1
OAS3
OAT
OAZ2
OAZ3
OBFC1
OBSL1
OCEL1
OCIAD1
OCIAD2
ODC1

Figure 17-6

| | | | | | | |
|---|---|---|---|---|---|---|
| ODF2 | PAPPA2 | PFDN1 | PLCD1 | PON2 | PRDX3 | PSMG1 |
| ODZ4 | PARD6G | PFKFB3 | PLCH2 | POP1 | PRDX5 | PSMG2 |
| OGDH | PARP1 | PFKP | PLD2 | POU2F1 | PRDX6 | PSPC1 |
| OGFOD1 | PARP11 | PFN2 | PLD3 | POU3F2 | PRDXDD1P | PTBP2 |
| OGG1 | PARP15 | PGAM1 | PLEC1 | PP14571 | PRELID1 | PTCH1 |
| OLFM2 | PARVB | PGAP2 | PLEKHA1 | PPA1 | PRELID2 | PTCH2 |
| OLFML2B | PATE2 | PGBD2 | PLEKHA5 | PPAPDC1A | PREX1 | PTEN |
| OMP | PATE4 | PGD | PLEKHA6 | PPARGC1B | PRHOXNB | PTGES |
| ONECUT2 | PAX2 | PGLS | PLEKHA7 | PPCDC | PRIC285 | PTGES2 |
| OPTN | PAX5 | PGM1 | PLEKHB1 | PPCS | PRICKLE1 | PTGES3 |
| OR10G8 | PAX6 | PGM3 | PLEKHG4 | PPFIA1 | PRIM1 | PTGFRN |
| OR12D2 | PAX7 | PGS1 | PLEKHG6 | PPFIBP2 | PRKACA | PTH1R |
| OR1A2 | PCBP2 | PHAX | PLEKHH1 | PPHLN1 | PRKAG2 | PTK2 |
| OR2L8 | PCDH15 | PHC1 | PLEKHH3 | PPIB | PRKCA | PTMA |
| OR2M2 | PCDH21 | PHC2 | PLEKHM1 | PPIE | PRKCB | PTMS |
| OR2V2 | PCDP1 | PHF10 | PLEKHO2 | PPIL2 | PRKCD | PTPMT1 |
| OR52H1 | PCGF3 | PHF13 | PLGLA | PPIL4 | PRKCG | PTPN1 |
| OR5H1 | PCGF6 | PHF14 | PLIN3 | PPM1F | PRKCQ | PTPN12 |
| OR6P1 | PCM1 | PHF15 | PLK4 | PPM1J | PRKCZ | PTPN22 |
| OR8S1 | PCMT1 | PHF17 | PLXNA1 | PPM1K | PRKD1 | PTPN6 |
| ORC6L | PCMTD1 | PHF19 | PLXNA2 | PPM1L | PRKRA | PTPN7 |
| ORMDL3 | PCNP | PHF21A | PLXNA4 | PPM1M | PRKRIR | PTPRG |
| OSBPL11 | PCNT | PHF21B | PLXNC1 | PPP1CC | PRMT1 | PTPRJ |
| OSBPL2 | PCOTH | PHLDB1 | PLXND1 | PPP1R12B | PRND | PTPRN2 |
| OSBPL9 | PCTP | PHLPP2 | PMAIP1 | PPP1R12C | PROCA1 | PUM1 |
| OSCAR | PCYT1A | PHPT1 | PMS2 | PPP1R14B | PROKR2 | PURA |
| OSGIN1 | PDCD2L | PHTF2 | PMS2L3 | PPP1R15B | PROSC | PURB |
| OSTCL | PDCD6 | PI4K2B | PMS2L5 | PPP1R16B | PRPF3 | PURG |
| OTOP2 | PDCD6IP | PI4KAP2 | PNKD | PPP1R2P1 | PRPF31 | PUS1 |
| OTUB1 | PDCD7 | PIBF1 | PNKP | PPP1R3B | PRPF38B | PUS10 |
| OTUD1 | PDE2A | PICK1 | PNLIP | PPP1R3E | PRPF40B | PUS7 |
| OTUD3 | PDE3B | PIGG | PNMT | PPP1R9B | PRPF6 | PVRL1 |
| OVOL1 | PDE4DIP | PIGO | PNN | PPP2CA | PRR11 | PVRL2 |
| OXSR1 | PDE6D | PIGP | PNPLA2 | PPP2R3C | PRR14 | PVRL3 |
| P2RX2 | PDE7A | PIGT | PNPLA7 | PPP2R5A | PRR3 | PVT1 |
| P2RX4 | PDGFA | PIGV | PNPLA8 | PPP2R5C | PRR5 | PWWP2B |
| P2RY1 | PDGFRL | PIGX | PODXL | PPP3CB | PRRC1 | PXMP3 |
| P4HA3 | PDK2 | PIGY | POGK | PPP3CC | PRRT2 | PYCRL |
| P4HB | PDLIM1 | PIK3AP1 | POLD1 | PPP3R1 | PRRT4 | PYGB |
| PA2G4 | PDLIM5 | PIK3R5 | POLD3 | PPP4C | PRSS1 | PYY |
| PABPC4 | PDPK1 | PILRB | POLDIP2 | PPP4R4 | PRSS48 | QKI |
| PABPN1 | PDX1 | PIN1 | POLDIP3 | PPP5C | PSAT1 | QPCTL |
| PACS2 | PDXDC1 | PINK1 | POLR2C | PPPDE1 | PSD3 | QRICH1 |
| PACSIN1 | PDXDC2 | PION | POLR2E | PPPDE2 | PSD4 | QRSL1 |
| PACSIN3 | PDXK | PIP5K1A | POLR2G | PPT2 | PSG3 | QSOX1 |
| PAG1 | PDZD8 | PITPNB | POLR2I | PPTC7 | PSG6 | QTRT1 |
| PAIP2B | PEBP1 | PITRM1 | POLR3C | PPY2 | PSIP1 | RAB11FIP1 |
| PAK1 | PELI2 | PKD2 | POLR3D | PQLC1 | PSMA3 | RAB11FIP5 |
| PALM | PEPD | PKDCC | POLR3K | PQLC3 | PSMB1 | RAB12 |
| PAN2 | PER2 | PKM2 | POLRMT | PRAGMIN | PSMC4 | RAB14 |
| PANK2 | PET117 | PKN1 | POM121C | PRAMEF22 | PSMC5 | RAB18 |
| PANX1 | PEX10 | PKNOX2 | POM121L10P | PRC1 | PSMD1 | RAB1A |
| PANX2 | PEX19 | PLAGL1 | POMC | PRDM16 | PSMD11 | RAB1B |
| PAOX | PEX26 | PLAU | POMT2 | PRDM2 | PSMD4 | RAB27A |
| PAPOLA | PEX7 | PLCB1 | POMZP3 | PRDX1 | PSME3 | RAB2A |

Figure 17-7

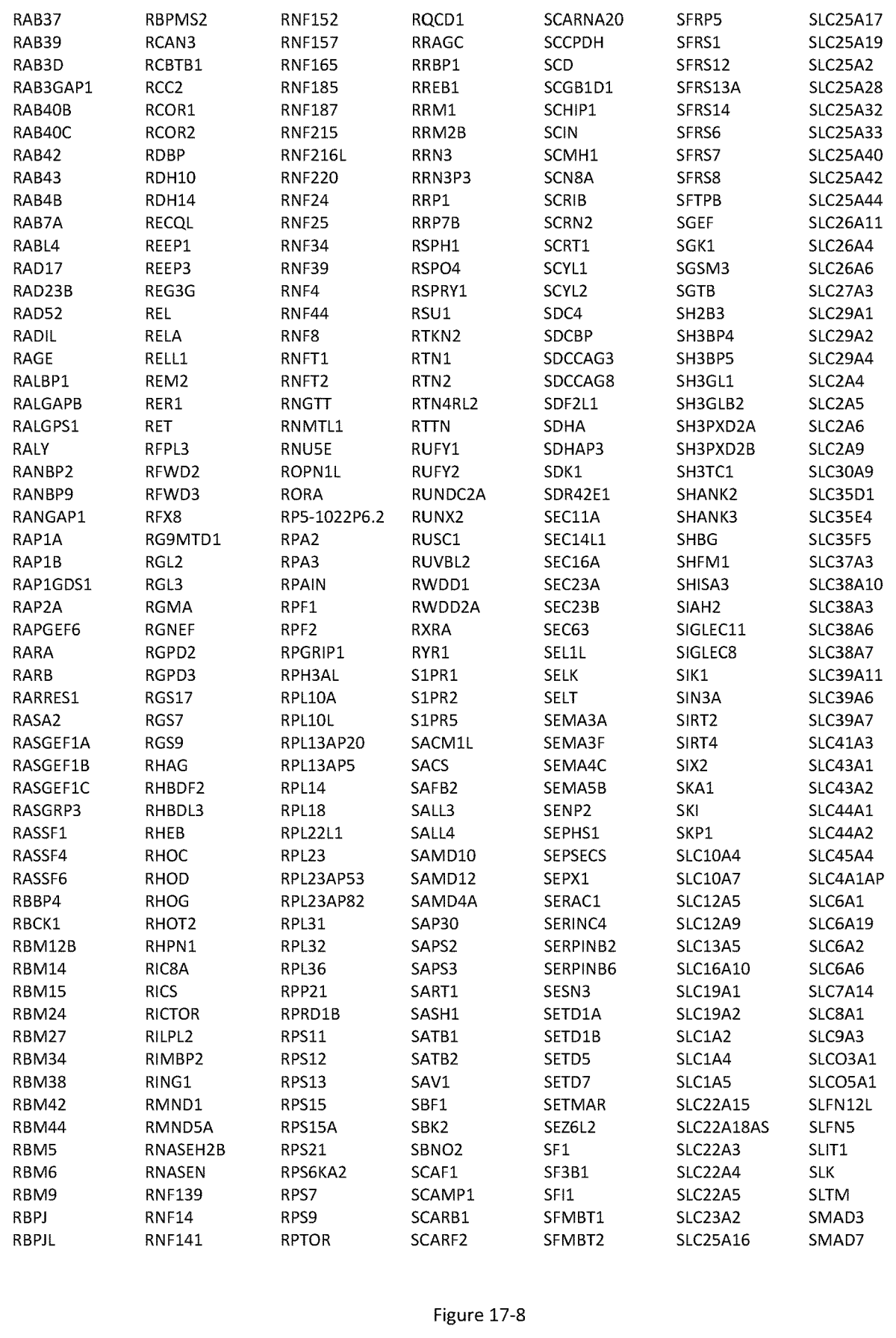

RAB37
RAB39
RAB3D
RAB3GAP1
RAB40B
RAB40C
RAB42
RAB43
RAB4B
RAB7A
RABL4
RAD17
RAD23B
RAD52
RADIL
RAGE
RALBP1
RALGAPB
RALGPS1
RALY
RANBP2
RANBP9
RANGAP1
RAP1A
RAP1B
RAP1GDS1
RAP2A
RAPGEF6
RARA
RARB
RARRES1
RASA2
RASGEF1A
RASGEF1B
RASGEF1C
RASGRP3
RASSF1
RASSF4
RASSF6
RBBP4
RBCK1
RBM12B
RBM14
RBM15
RBM24
RBM27
RBM34
RBM38
RBM42
RBM44
RBM5
RBM6
RBM9
RBPJ
RBPJL
RBPMS2
RCAN3
RCBTB1
RCC2
RCOR1
RCOR2
RDBP
RDH10
RDH14
RECQL
REEP1
REEP3
REG3G
REL
RELA
RELL1
REM2
RER1
RET
RFPL3
RFWD2
RFWD3
RFX8
RG9MTD1
RGL2
RGL3
RGMA
RGNEF
RGPD2
RGPD3
RGS17
RGS7
RGS9
RHAG
RHBDF2
RHBDL3
RHEB
RHOC
RHOD
RHOG
RHOT2
RHPN1
RIC8A
RICS
RICTOR
RILPL2
RIMBP2
RING1
RMND1
RMND5A
RNASEH2B
RNASEN
RNF139
RNF14
RNF141
RNF152
RNF157
RNF165
RNF185
RNF187
RNF215
RNF216L
RNF220
RNF24
RNF25
RNF34
RNF39
RNF4
RNF44
RNF8
RNFT1
RNFT2
RNGTT
RNMTL1
RNU5E
ROPN1L
RORA
RP5-1022P6.2
RPA2
RPA3
RPAIN
RPF1
RPF2
RPGRIP1
RPH3AL
RPL10A
RPL10L
RPL13AP20
RPL13AP5
RPL14
RPL18
RPL22L1
RPL23
RPL23AP53
RPL23AP82
RPL31
RPL32
RPL36
RPP21
RPRD1B
RPS11
RPS12
RPS13
RPS15
RPS15A
RPS21
RPS6KA2
RPS7
RPS9
RPTOR
RQCD1
RRAGC
RRBP1
RREB1
RRM1
RRM2B
RRN3
RRN3P3
RRP1
RRP7B
RSPH1
RSPO4
RSPRY1
RSU1
RTKN2
RTN1
RTN2
RTN4RL2
RTTN
RUFY1
RUFY2
RUNDC2A
RUNX2
RUSC1
RUVBL2
RWDD1
RWDD2A
RXRA
RYR1
S1PR1
S1PR2
S1PR5
SACM1L
SACS
SAFB2
SALL3
SALL4
SAMD10
SAMD12
SAMD4A
SAP30
SAPS2
SAPS3
SART1
SASH1
SATB1
SATB2
SAV1
SBF1
SBK2
SBNO2
SCAF1
SCAMP1
SCARB1
SCARF2
SCARNA20
SCCPDH
SCD
SCGB1D1
SCHIP1
SCIN
SCMH1
SCN8A
SCRIB
SCRN2
SCRT1
SCYL1
SCYL2
SDC4
SDCBP
SDCCAG3
SDCCAG8
SDF2L1
SDHA
SDHAP3
SDK1
SDR42E1
SEC11A
SEC14L1
SEC16A
SEC23A
SEC23B
SEC63
SEL1L
SELK
SELT
SEMA3A
SEMA3F
SEMA4C
SEMA5B
SENP2
SEPHS1
SEPSECS
SEPX1
SERAC1
SERINC4
SERPINB2
SERPINB6
SESN3
SETD1A
SETD1B
SETD5
SETD7
SETMAR
SEZ6L2
SF1
SF3B1
SFI1
SFMBT1
SFMBT2
SFRP5
SFRS1
SFRS12
SFRS13A
SFRS14
SFRS6
SFRS7
SFRS8
SFTPB
SGEF
SGK1
SGSM3
SGTB
SH2B3
SH3BP4
SH3BP5
SH3GL1
SH3GLB2
SH3PXD2A
SH3PXD2B
SH3TC1
SHANK2
SHANK3
SHBG
SHFM1
SHISA3
SIAH2
SIGLEC11
SIGLEC8
SIK1
SIN3A
SIRT2
SIRT4
SIX2
SKA1
SKI
SKP1
SLC10A4
SLC10A7
SLC12A5
SLC12A9
SLC13A5
SLC16A10
SLC19A1
SLC19A2
SLC1A2
SLC1A4
SLC1A5
SLC22A15
SLC22A18AS
SLC22A3
SLC22A4
SLC22A5
SLC23A2
SLC25A16
SLC25A17
SLC25A19
SLC25A2
SLC25A28
SLC25A32
SLC25A33
SLC25A40
SLC25A42
SLC25A44
SLC26A11
SLC26A4
SLC26A6
SLC27A3
SLC29A1
SLC29A2
SLC29A4
SLC2A4
SLC2A5
SLC2A6
SLC2A9
SLC30A9
SLC35D1
SLC35E4
SLC35F5
SLC37A3
SLC38A10
SLC38A3
SLC38A6
SLC38A7
SLC39A11
SLC39A6
SLC39A7
SLC41A3
SLC43A1
SLC43A2
SLC44A1
SLC44A2
SLC45A4
SLC4A1AP
SLC6A1
SLC6A19
SLC6A2
SLC6A6
SLC7A14
SLC8A1
SLC9A3
SLCO3A1
SLCO5A1
SLFN12L
SLFN5
SLIT1
SLK
SLTM
SMAD3
SMAD7

Figure 17-8

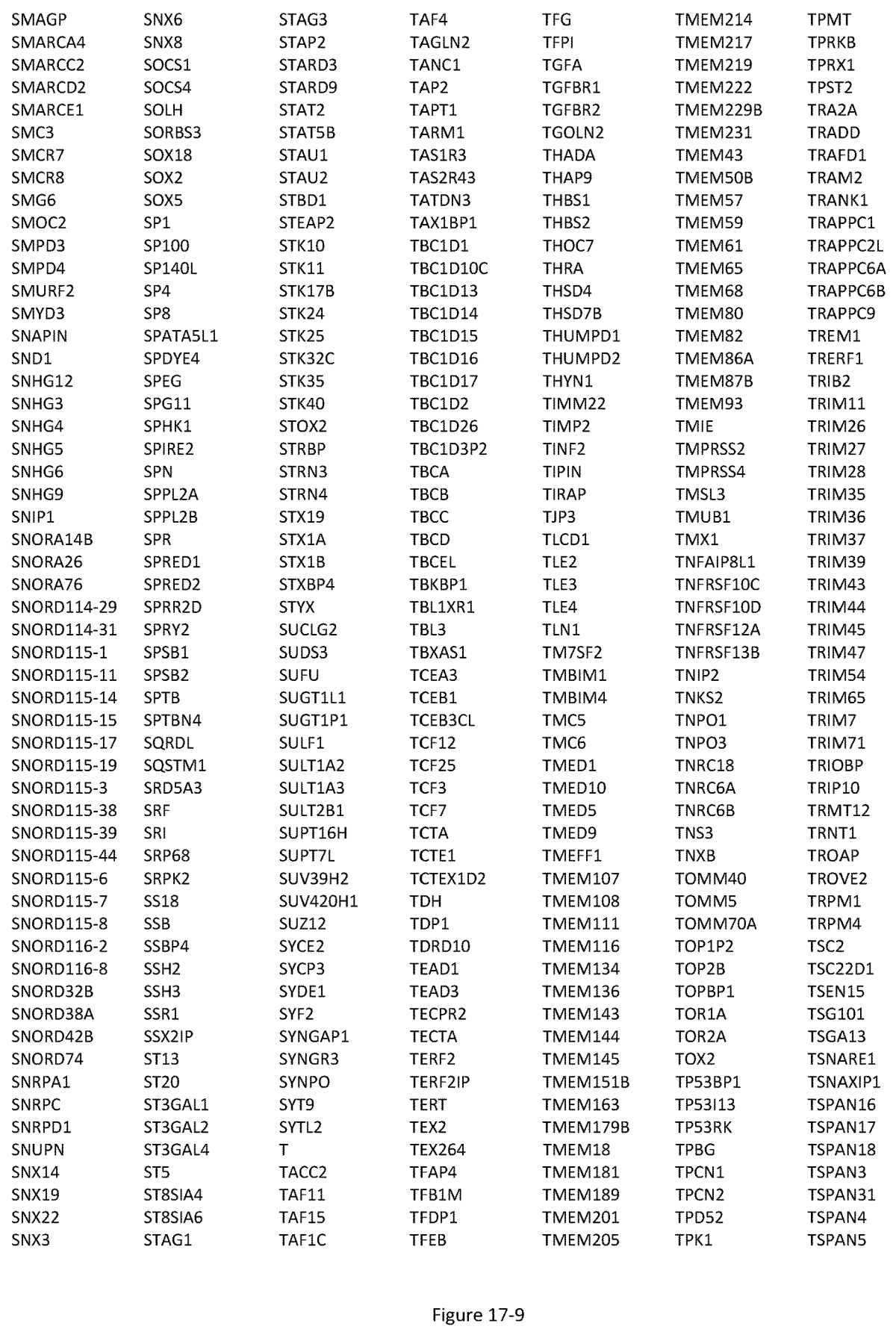

SMAGP
SMARCA4
SMARCC2
SMARCD2
SMARCE1
SMC3
SMCR7
SMCR8
SMG6
SMOC2
SMPD3
SMPD4
SMURF2
SMYD3
SNAPIN
SND1
SNHG12
SNHG3
SNHG4
SNHG5
SNHG6
SNHG9
SNIP1
SNORA14B
SNORA26
SNORA76
SNORD114-29
SNORD114-31
SNORD115-1
SNORD115-11
SNORD115-14
SNORD115-15
SNORD115-17
SNORD115-19
SNORD115-3
SNORD115-38
SNORD115-39
SNORD115-44
SNORD115-6
SNORD115-7
SNORD115-8
SNORD116-2
SNORD116-8
SNORD32B
SNORD38A
SNORD42B
SNORD74
SNRPA1
SNRPC
SNRPD1
SNUPN
SNX14
SNX19
SNX22
SNX3
SNX6
SNX8
SOCS1
SOCS4
SOLH
SORBS3
SOX18
SOX2
SOX5
SP1
SP100
SP140L
SP4
SP8
SPATA5L1
SPDYE4
SPEG
SPG11
SPHK1
SPIRE2
SPN
SPPL2A
SPPL2B
SPR
SPRED1
SPRED2
SPRR2D
SPRY2
SPSB1
SPSB2
SPTB
SPTBN4
SQRDL
SQSTM1
SRD5A3
SRF
SRI
SRP68
SRPK2
SS18
SSB
SSBP4
SSH2
SSH3
SSR1
SSX2IP
ST13
ST20
ST3GAL1
ST3GAL2
ST3GAL4
ST5
ST8SIA4
ST8SIA6
STAG1
STAG3
STAP2
STARD3
STARD9
STAT2
STAT5B
STAU1
STAU2
STBD1
STEAP2
STK10
STK11
STK17B
STK24
STK25
STK32C
STK35
STK40
STOX2
STRBP
STRN3
STRN4
STX19
STX1A
STX1B
STXBP4
STYX
SUCLG2
SUDS3
SUFU
SUGT1L1
SUGT1P1
SULF1
SULT1A2
SULT1A3
SULT2B1
SUPT16H
SUPT7L
SUV39H2
SUV420H1
SUZ12
SYCE2
SYCP3
SYDE1
SYF2
SYNGAP1
SYNGR3
SYNPO
SYT9
SYTL2
T
TACC2
TAF11
TAF15
TAF1C
TAF4
TAGLN2
TANC1
TAP2
TAPT1
TARM1
TAS1R3
TAS2R43
TATDN3
TAX1BP1
TBC1D1
TBC1D10C
TBC1D13
TBC1D14
TBC1D15
TBC1D16
TBC1D17
TBC1D2
TBC1D26
TBC1D3P2
TBCA
TBCB
TBCC
TBCD
TBCEL
TBKBP1
TBL1XR1
TBL3
TBXAS1
TCEA3
TCEB1
TCEB3CL
TCF12
TCF25
TCF3
TCF7
TCTA
TCTE1
TCTEX1D2
TDH
TDP1
TDRD10
TEAD1
TEAD3
TECPR2
TECTA
TERF2
TERF2IP
TERT
TEX2
TEX264
TFAP4
TFB1M
TFDP1
TFEB
TFG
TFPI
TGFA
TGFBR1
TGFBR2
TGOLN2
THADA
THAP9
THBS1
THBS2
THOC7
THRA
THSD4
THSD7B
THUMPD1
THUMPD2
THYN1
TIMM22
TIMP2
TINF2
TIPIN
TIRAP
TJP3
TLCD1
TLE2
TLE3
TLE4
TLN1
TM7SF2
TMBIM1
TMBIM4
TMC5
TMC6
TMED1
TMED10
TMED5
TMED9
TMEFF1
TMEM107
TMEM108
TMEM111
TMEM116
TMEM134
TMEM136
TMEM143
TMEM144
TMEM145
TMEM151B
TMEM163
TMEM179B
TMEM18
TMEM181
TMEM189
TMEM201
TMEM205
TMEM214
TMEM217
TMEM219
TMEM222
TMEM229B
TMEM231
TMEM43
TMEM50B
TMEM57
TMEM59
TMEM61
TMEM65
TMEM68
TMEM80
TMEM82
TMEM86A
TMEM87B
TMEM93
TMIE
TMPRSS2
TMPRSS4
TMSL3
TMUB1
TMX1
TNFAIP8L1
TNFRSF10C
TNFRSF10D
TNFRSF12A
TNFRSF13B
TNIP2
TNKS2
TNPO1
TNPO3
TNRC18
TNRC6A
TNRC6B
TNS3
TNXB
TOMM40
TOMM5
TOMM70A
TOP1P2
TOP2B
TOPBP1
TOR1A
TOR2A
TOX2
TP53BP1
TP53I13
TP53RK
TPBG
TPCN1
TPCN2
TPD52
TPK1
TPMT
TPRKB
TPRX1
TPST2
TRA2A
TRADD
TRAFD1
TRAM2
TRANK1
TRAPPC1
TRAPPC2L
TRAPPC6A
TRAPPC6B
TRAPPC9
TREM1
TRERF1
TRIB2
TRIM11
TRIM26
TRIM27
TRIM28
TRIM35
TRIM36
TRIM37
TRIM39
TRIM43
TRIM44
TRIM45
TRIM47
TRIM54
TRIM65
TRIM7
TRIM71
TRIOBP
TRIP10
TRMT12
TRNT1
TROAP
TROVE2
TRPM1
TRPM4
TSC2
TSC22D1
TSEN15
TSG101
TSGA13
TSNARE1
TSNAXIP1
TSPAN16
TSPAN17
TSPAN18
TSPAN3
TSPAN31
TSPAN4
TSPAN5

Figure 17-9

| | | | | | | |
|---|---|---|---|---|---|---|
| TSR1 | UBLCP1 | VPS37D | YAP1 | ZMPSTE24 | ZNF429 | ZNF643 |
| TSSC1 | UBP1 | VPS52 | YARS | ZMYM4 | ZNF431 | ZNF649 |
| TSSC4 | UBR3 | VPS54 | YBX2 | ZMYM5 | ZNF433 | ZNF653 |
| TSSK2 | UBTD2 | VRK1 | YIPF5 | ZNF10 | ZNF436 | ZNF662 |
| TTC14 | UBTF | VSNL1 | YLPM1 | ZNF100 | ZNF439 | ZNF664 |
| TTC22 | UBXN1 | VTA1 | YPEL1 | ZNF101 | ZNF440 | ZNF665 |
| TTC28 | UBXN11 | VTI1B | YPEL3 | ZNF107 | ZNF441 | ZNF669 |
| TTC30A | UBXN6 | WASF1 | YTHDF3 | ZNF12 | ZNF444 | ZNF689 |
| TTC31 | UCK1 | WASH3P | YWHAH | ZNF133 | ZNF462 | ZNF7 |
| TTC39A | UCRC | WASH5P | YWHAQ | ZNF14 | ZNF467 | ZNF70 |
| TTC7B | UFC1 | WASL | YWHAZ | ZNF141 | ZNF480 | ZNF701 |
| TTK | UFSP2 | WBSCR22 | YY1 | ZNF143 | ZNF484 | ZNF702P |
| TTLL1 | UGGT1 | WDR20 | YY1AP1 | ZNF146 | ZNF485 | ZNF703 |
| TTLL6 | UGT1A10 | WDR26 | ZAR1L | ZNF148 | ZNF487 | ZNF705D |
| TTPAL | UHRF1BP1 | WDR27 | ZBBX | ZNF184 | ZNF490 | ZNF706 |
| TTR | ULBP2 | WDR34 | ZBED5 | ZNF195 | ZNF491 | ZNF709 |
| TTYH3 | ULBP3 | WDR4 | ZBTB1 | ZNF20 | ZNF493 | ZNF716 |
| TUB | ULK1 | WDR47 | ZBTB12 | ZNF207 | ZNF496 | ZNF717 |
| TUBA1A | UMPS | WDR51A | ZBTB17 | ZNF213 | ZNF498 | ZNF718 |
| TUBA1B | UNC80 | WDR52 | ZBTB2 | ZNF219 | ZNF511 | ZNF735 |
| TUBA3C | UNC84A | WDR53 | ZBTB4 | ZNF22 | ZNF514 | ZNF737 |
| TUBA3D | UNKL | WDR55 | ZBTB40 | ZNF224 | ZNF521 | ZNF738 |
| TUBA4B | UPK3B | WDR59 | ZBTB41 | ZNF229 | ZNF527 | ZNF747 |
| TUBB | UQCR | WDR60 | ZBTB42 | ZNF235 | ZNF528 | ZNF749 |
| TUBB1 | URB2 | WDR62 | ZBTB45 | ZNF236 | ZNF530 | ZNF761 |
| TUBB4 | USF2 | WDR65 | ZBTB46 | ZNF252 | ZNF534 | ZNF764 |
| TUBB6 | USP1 | WDR7 | ZBTB7A | ZNF254 | ZNF540 | ZNF766 |
| TUBD1 | USP15 | WDR70 | ZBTB9 | ZNF257 | ZNF541 | ZNF768 |
| TUBGCP2 | USP18 | WDR73 | ZC3H11A | ZNF259 | ZNF543 | ZNF777 |
| TUBGCP6 | USP19 | WDR74 | ZC3H12C | ZNF26 | ZNF547 | ZNF784 |
| TXLNA | USP2 | WDR8 | ZC3HAV1L | ZNF264 | ZNF549 | ZNF787 |
| TXNIP | USP32 | WDR82 | ZCCHC14 | ZNF267 | ZNF550 | ZNF788 |
| TXNL4A | USP33 | WDTC1 | ZCCHC2 | ZNF276 | ZNF555 | ZNF8 |
| TXNRD1 | USP34 | WDYHV1 | ZCCHC24 | ZNF28 | ZNF557 | ZNF80 |
| TYK2 | USP36 | WEE1 | ZDHHC1 | ZNF280B | ZNF559 | ZNF808 |
| TYMS | USP4 | WHAMM | ZDHHC16 | ZNF286B | ZNF562 | ZNF813 |
| TYRO3 | USP42 | WHSC1 | ZDHHC19 | ZNF295 | ZNF564 | ZNF814 |
| TYROBP | USP43 | WHSC2 | ZDHHC23 | ZNF3 | ZNF565 | ZNF816A |
| U2AF2 | USP49 | WIZ | ZDHHC3 | ZNF311 | ZNF566 | ZNF821 |
| UAP1 | USP53 | WNK4 | ZDHHC4 | ZNF317 | ZNF57 | ZNF826 |
| UBA5 | USP7 | WNT11 | ZDHHC5 | ZNF321 | ZNF570 | ZNF827 |
| UBA52 | UTP15 | WNT3A | ZDHHC7 | ZNF322B | ZNF578 | ZNF829 |
| UBASH3B | UTP3 | WNT5A | ZEB1 | ZNF323 | ZNF583 | ZNF83 |
| UBB | UTRN | WRB | ZFAND2B | ZNF324 | ZNF584 | ZNF837 |
| UBC | VAC14 | WRN | ZFAND3 | ZNF335 | ZNF589 | ZNF839 |
| UBD | VAPA | WRNIP1 | ZFHX3 | ZNF33A | ZNF593 | ZNF845 |
| UBE2H | VARS | WSCD2 | ZFP1 | ZNF33B | ZNF594 | ZNF860 |
| UBE2I | VASH1 | WTAP | ZFP36L2 | ZNF354A | ZNF605 | ZNF876P |
| UBE2K | VCPIP1 | WWC1 | ZFP64 | ZNF358 | ZNF609 | ZNF880 |
| UBE2Q1 | VDAC3 | XAB2 | ZFYVE19 | ZNF366 | ZNF610 | ZNF90 |
| UBE3A | VGLL4 | XBP1 | ZFYVE9 | ZNF384 | ZNF611 | ZNF98 |
| UBIAD1 | VIPR2 | XKR5 | ZHX2 | ZNF385A | ZNF618 | ZNHIT1 |
| UBL3 | VKORC1L1 | XRCC3 | ZKSCAN1 | ZNF385B | ZNF619 | ZNHIT3 |
| UBL5 | VPS18 | XRN1 | ZKSCAN5 | ZNF395 | ZNF627 | ZSCAN2 |
| UBL7 | VPS37C | YAF2 | ZMIZ1 | ZNF397 | ZNF638 | ZSCAN29 |

Figure 17-10

ZSCAN5B
ZSWIM1
ZSWIM7
ZWILCH
ZWINT
ZXDC
ZYX

Figure 17-11

| Illumina Probe | Chr | Mapinfo | Correlation | Gene |
|---|---|---|---|---|
| cg27209395 | 6 | 26172397 | -0.185834649 | |
| cg07842594 | 10 | 43278214 | -0.172882298 | BMS1 |
| cg27551078 | 6 | 34191979 | -0.172168945 | |
| cg03130180 | 6 | 30312857 | 0.17081525 | RPP21 |
| cg10319399 | 8 | 145018285 | 0.170417571 | PLEC1 |
| cg04988187 | 15 | 80445147 | 0.166645603 | FAH |
| cg25861340 | 5 | 524683 | 0.165587106 | SLC9A3 |
| cg01778450 | 5 | 92920498 | 0.165290855 | NR2F1 |
| cg12163415 | 2 | 27906671 | 0.165117862 | SLC4A1AP |
| cg23267217 | 1 | 26496298 | -0.16388116 | ZNF593 |
| cg18354764 | 22 | 31064165 | -0.163879852 | DUSP18 |
| cg24170511 | 14 | 23341280 | -0.162761622 | LRP10 |
| cg23044564 | 5 | 126853253 | 0.162356683 | PRRC1 |
| cg05531134 | 21 | 19192027 | 0.162213611 | C21orf91 |
| cg02625745 | 2 | 37458728 | -0.161405725 | CEBPZ |
| cg06618254 | 22 | 20307980 | -0.161241262 | DGCR6L |
| cg16302458 | 11 | 68228228 | -0.161035122 | SAPS3 |
| cg16491046 | 1 | 247494983 | -0.1610061 | ZNF496 |
| cg09909775 | 12 | 45610071 | -0.16087252 | ANO6 |
| cg26789489 | 1 | 16941426 | -0.160580305 | NBPF1 |
| cg06341189 | 6 | 31831876 | 0.160442832 | NEU1 |
| cg11574094 | 10 | 14921550 | -0.16042562 | SUV39H2 |
| cg19456996 | 6 | 29600642 | 0.160263001 | GABBR1 |
| cg12972275 | 4 | 122722461 | -0.160131027 | EXOSC9 |
| cg18781817 | 6 | 33217368 | -0.159960915 | |
| cg07743799 | 20 | 2821434 | -0.159883389 | FAM113A |
| cg08800530 | 5 | 175788722 | -0.159808113 | KIAA1191 |
| cg13993673 | 1 | 3447740 | -0.159767459 | MEGF6 |
| cg04565464 | 8 | 145669602 | 0.15965711 | NFKBIL2 |
| cg05898754 | 1 | 805102 | 0.159570325 | FAM41C |
| cg26220419 | 11 | 107880052 | -0.159465263 | CUL5 |
| cg26807935 | 5 | 139028606 | 0.159406457 | CXXC5 |
| cg19759549 | 3 | 128211096 | -0.159405023 | GATA2 |
| cg02842104 | 19 | 12251201 | 0.159339878 | ZNF20 |
| cg19363916 | 11 | 67034540 | 0.159131526 | ADRBK1 |
| cg15012981 | 1 | 11741009 | -0.158916423 | MAD2L2 |
| cg20699036 | 5 | 38556796 | 0.158619383 | LIFR |
| cg19127541 | 7 | 63392087 | -0.15846813 | |
| cg05736120 | 6 | 170125165 | -0.158465591 | PHF10 |
| cg10762109 | 1 | 48463113 | 0.158350786 | |

| Illumina Probe | Chr | Mapinfo | Correlation | Gene |
|---|---|---|---|---|
| cg11728900 | 10 | 13203459 | -0.158183678 | MCM10 |
| cg19827148 | 1 | 1260496 | -0.158077141 | GLTPD1 |
| cg21243939 | 14 | 55033137 | -0.15796925 | SAMD4A |
| cg11677260 | 10 | 43361618 | 0.157968394 | |
| cg06703062 | 1 | 31191648 | -0.157826226 | MATN1 |
| cg06293099 | 11 | 67745999 | -0.157753658 | |
| cg23932846 | 6 | 31165843 | -0.157753366 | HCG27 |
| cg16755220 | 16 | 12070685 | 0.157619259 | RUNDC2A |
| cg06235246 | 3 | 195380764 | 0.15730284 | |
| cg05185519 | 16 | 2972941 | -0.15715639 | FLYWCH1 |
| cg02455615 | 11 | 33183110 | -0.156891668 | CSTF3 |
| cg09821533 | 6 | 13712174 | 0.156886635 | RANBP9 |
| cg01392184 | 15 | 41099692 | -0.156885196 | ZFYVE19 |
| cg07893813 | 15 | 52861112 | -0.15688342 | ARPP19 |
| cg11017226 | 10 | 61666667 | -0.156802852 | CCDC6 |
| cg24714709 | 7 | 95064397 | 0.156799443 | PON2 |
| cg27118062 | 17 | 27053269 | 0.156755573 | TLCD1 |
| cg02276269 | 1 | 161122156 | -0.156626247 | UFC1 |
| ch.4.113910337F | 4 | 113690888 | 0.156541726 | |
| cg27203090 | 3 | 33138513 | -0.156537909 | GLB1 |
| cg12275723 | 1 | 10856739 | 0.156406513 | CASZ1 |
| cg02307130 | 19 | 40030840 | -0.156119654 | EID2 |
| cg18095404 | 7 | 65338716 | 0.156111043 | VKORC1L1 |
| cg20744217 | 11 | 67211017 | 0.156106431 | CORO1B |
| cg25285186 | 19 | 54202347 | -0.156054823 | MIR518F |
| cg03017824 | 1 | 227915338 | -0.155978128 | LOC10013009 |
| cg05593182 | 5 | 142092835 | 0.155859829 | |
| cg20418818 | 12 | 11244939 | -0.15573673 | TAS2R43 |
| cg21881859 | 17 | 3749224 | 0.155647707 | C17orf85 |
| cg12504415 | 17 | 74722752 | 0.155558463 | JMJD6 |
| cg24199599 | 20 | 62681243 | 0.155458296 | SOX18 |
| cg00292851 | 21 | 44300012 | 0.155442677 | WDR4 |
| cg07713066 | 2 | 220363586 | -0.155385813 | GMPPA |
| cg12309030 | 3 | 40950037 | -0.155247556 | |
| cg15884202 | 7 | 158649092 | -0.155225225 | WDR60 |
| cg05731183 | 15 | 68132796 | -0.155050672 | |
| cg10495084 | 15 | 96889416 | 0.154937677 | |
| cg10896616 | 5 | 1295267 | 0.154921571 | TERT |
| cg26151531 | 22 | 19842652 | -0.154916257 | GNB1L |
| cg19294125 | 20 | 25604737 | -0.154890478 | NANP |

Figure 18-1

| | | | | |
|---|---|---|---|---|
| cg25270498 | 17 | 81037414 | 0.154850868 | METRNL |
| cg16246252 | 11 | 119535621 | 0.154835931 | PVRL1 |
| cg07483273 | 19 | 2901388 | 0.15482523 | ZNF57 |
| cg14116162 | 11 | 64052260 | 0.154813114 | BAD |
| cg16326998 | 7 | 5553266 | 0.154742278 | FBXL18 |
| cg02445395 | 7 | 157659455 | -0.154741029 | PTPRN2 |
| cg19731367 | 10 | 95256484 | 0.15469021 | CEP55 |
| cg02994863 | 1 | 64059297 | -0.154659001 | PGM1 |
| cg11855759 | 17 | 9548802 | 0.154602589 | USP43 |
| cg12822074 | 11 | 57243865 | 0.154588285 | RTN4RL2 |
| cg14694896 | 8 | 104427370 | -0.154578413 | SLC25A32 |
| cg26105280 | 1 | 11159908 | -0.15440444 | EXOSC10 |
| cg25753024 | 11 | 67070913 | 0.154332796 | SSH3 |
| cg02881082 | 14 | 101694374 | -0.154218759 | |
| cg23048068 | 8 | 82192604 | -0.154203444 | FABP5 |
| cg18545992 | 2 | 133013028 | -0.154183608 | NCRNA00164 |
| cg08700690 | 15 | 60884630 | -0.154106201 | RORA |
| cg22100652 | 6 | 28834404 | 0.154011378 | |
| cg07172256 | 5 | 65220910 | -0.153896215 | ERBB2IP |
| cg09951650 | 15 | 51200814 | -0.153867717 | AP4E1 |
| cg05882878 | 2 | 37458821 | -0.153736187 | CEBPZ |
| cg21535156 | 7 | 1499152 | 0.153696744 | MICALL2 |
| cg04246357 | 6 | 158589294 | 0.153694605 | SERAC1 |
| cg25825740 | 17 | 80036910 | -0.153670657 | FASN |
| cg18765439 | 11 | 65343343 | -0.153582145 | EHBP1L1 |
| cg12815918 | 13 | 28498544 | 0.153549663 | PDX1 |
| cg20630812 | 8 | 87877422 | -0.153539903 | CNBD1 |
| cg06945456 | 19 | 50887879 | 0.153532538 | POLD1 |
| cg06039171 | 20 | 57599526 | -0.153500523 | TUBB1 |
| cg10462593 | 15 | 79042505 | -0.153481813 | |
| cg00977301 | 15 | 25427487 | -0.15347267 | SNORD115-7 |
| cg15105252 | 17 | 17295483 | 0.153472309 | |
| cg10990665 | 14 | 102522832 | -0.153463291 | |
| cg13841901 | 1 | 45805975 | -0.153408611 | MUTYH |
| cg12895810 | 8 | 142138638 | 0.153379282 | DENND3 |
| cg02765496 | 9 | 71393662 | -0.153268715 | FAM122A |
| cg09951433 | 7 | 101843287 | 0.153226233 | CUX1 |
| cg18396041 | 7 | 149571256 | -0.153173819 | LOC401431 |
| cg17607973 | 7 | 100027408 | -0.153115784 | MEPCE |
| cg04453241 | 17 | 76374567 | -0.153081865 | PGS1 |
| cg09491948 | 11 | 62446595 | -0.153066122 | UBXN1 |

| | | | | |
|---|---|---|---|---|
| cg11675492 | 20 | 60640074 | 0.153055593 | TAF4 |
| cg05874913 | 2 | 160569340 | 0.153047444 | 7-Mar |
| cg22037798 | 1 | 231473786 | -0.153018104 | C1orf124 |
| cg09319020 | 17 | 7304467 | -0.152929383 | |
| cg14276772 | 2 | 10588646 | 0.15290302 | ODC1 |
| cg22704520 | 2 | 200820451 | -0.152868301 | C2orf60 |
| cg12459358 | 17 | 7199896 | 0.152866944 | |
| cg23572228 | 7 | 4923575 | 0.152850265 | RADIL |
| cg15994267 | 1 | 805352 | 0.152794359 | FAM41C |
| cg25653296 | 15 | 35413975 | -0.152764061 | |
| cg04479472 | 7 | 1231443 | -0.152726596 | |
| cg10945667 | 13 | 91999862 | -0.152718728 | MIR17HG |
| cg26520012 | 10 | 42672589 | 0.152701062 | |
| cg14804635 | 15 | 75747750 | -0.152687177 | SIN3A |
| cg01043997 | 6 | 30689219 | 0.152650354 | TUBB |
| cg23966123 | 14 | 105886028 | 0.152642204 | MTA1 |
| cg16063617 | 5 | 128430663 | -0.152641525 | ISOC1 |
| cg13854983 | 2 | 136875315 | -0.152597109 | CXCR4 |
| cg08224208 | 19 | 15218165 | 0.152595494 | SYDE1 |
| cg10041390 | 10 | 89623018 | -0.152572899 | PTEN |
| cg01026613 | 2 | 27255450 | 0.152543587 | TMEM214 |
| cg15062310 | 7 | 100450120 | -0.152532561 | SLC12A9 |
| cg18190323 | 4 | 113486291 | 0.152467613 | C4orf21 |
| cg25964984 | 22 | 30783371 | 0.152440628 | RNF215 |
| cg13468174 | 19 | 58919984 | -0.152435099 | ZNF584 |
| cg17428043 | 1 | 180200104 | -0.152423454 | LHX4 |
| cg12576688 | 1 | 2344112 | 0.152423351 | PEX10 |
| cg25632648 | 11 | 77899776 | -0.152399685 | KCTD21 |
| cg04407579 | 13 | 99228509 | 0.152394376 | STK24 |
| cg26633120 | 2 | 105654408 | -0.152372242 | MRPS9 |
| cg23473419 | 17 | 74732838 | 0.152313596 | MIR636 |
| cg02951344 | 11 | 85522279 | 0.152262611 | SYTL2 |
| cg27572074 | 19 | 42419406 | 0.152251113 | |
| cg11508669 | 12 | 6643545 | -0.152244554 | GAPDH |
| cg16310717 | 12 | 4383619 | -0.152207064 | CCND2 |
| cg18069309 | 15 | 42867567 | -0.152075913 | STARD9 |
| cg04286540 | 6 | 29944636 | 0.152072306 | HCG9 |
| cg04194728 | 6 | 150232017 | -0.152035648 | |
| cg13662093 | 20 | 33865505 | 0.152016464 | |
| cg12375025 | 18 | 67873125 | -0.152003547 | RTTN |
| cg26097011 | 13 | 103046943 | -0.152001466 | FGF14 |

Figure 18-2

| | | | | |
|---|---|---|---|---|
| cg26192815 | 2 | 240722597 | -0.151988227 | |
| cg06327849 | 3 | 129035119 | 0.151974022 | H1FX |
| cg13972460 | 20 | 1165703 | 0.151963336 | C20orf46 |
| cg06361278 | 17 | 25783929 | 0.151933678 | |
| cg08391321 | 5 | 112630695 | 0.151846152 | MCC |
| cg16600432 | 14 | 64970085 | 0.151762215 | ZBTB1 |
| cg13129662 | 17 | 48227708 | -0.151661424 | PPP1R9B |
| cg13550107 | 18 | 32558066 | -0.151648823 | MAPRE2 |
| cg08916879 | 7 | 2946518 | 0.151629537 | CARD11 |
| cg19169976 | 17 | 48071254 | 0.151611041 | DLX3 |
| cg23737366 | 1 | 9149026 | -0.15160714 | SLC2A5 |
| cg27367469 | 5 | 100239529 | 0.151604881 | ST8SIA4 |
| cg09695652 | 3 | 139108473 | -0.151596807 | COPB2 |
| cg16527939 | 1 | 1253970 | -0.151510937 | CPSF3L |
| cg05337192 | 1 | 108113367 | -0.15150932 | |
| cg21956150 | 19 | 1438388 | 0.151462566 | RPS15 |
| cg05585551 | 6 | 167314745 | -0.151421935 | |
| cg12586596 | 12 | 53645731 | -0.151387904 | MFSD5 |
| cg20806085 | 8 | 22108223 | -0.151379731 | POLR3D |
| cg16328462 | 8 | 36636824 | -0.151367967 | |
| cg02036077 | 22 | 35653364 | -0.151317152 | HMGXB4 |
| cg18877635 | 1 | 229643817 | -0.151285503 | NUP133 |
| cg18157915 | 17 | 61852003 | -0.151278011 | DDX42 |
| cg00900124 | 2 | 69969033 | 0.151173458 | ANXA4 |
| cg22933020 | 5 | 77072365 | 0.151118739 | TBCA |
| cg12152193 | 5 | 175954583 | -0.151112219 | RNF44 |
| cg18116217 | 10 | 3215066 | -0.151105762 | PITRM1 |
| cg27218469 | 2 | 7005960 | 0.151096478 | CMPK2 |
| cg13195185 | 17 | 16875596 | -0.151084988 | TNFRSF13B |
| cg05717050 | 12 | 20935811 | -0.151072047 | |
| cg06995549 | 1 | 43282720 | 0.151050549 | ERMAP |
| cg12930714 | 14 | 24835006 | 0.151015028 | NFATC4 |
| cg27664881 | 5 | 179234149 | 0.151014383 | SQSTM1 |
| cg16226300 | 6 | 133136135 | 0.151001866 | RPS12 |
| cg08602604 | 2 | 198364282 | -0.150957472 | HSPD1 |
| cg16504641 | 6 | 137143711 | 0.150918302 | PEX7 |
| cg10069734 | 2 | 120124354 | 0.150897259 | DBI |
| cg26681912 | 1 | 169455321 | -0.150884714 | SLC19A2 |
| cg06439489 | 5 | 176044620 | -0.15085924 | |
| cg04099813 | 11 | 2422520 | -0.150844198 | TSSC4 |
| cg03860054 | 16 | 55691102 | -0.150839379 | SLC6A2 |

| | | | | |
|---|---|---|---|---|
| cg09833174 | 7 | 143059591 | 0.150834506 | FAM131B |
| cg10241701 | 1 | 117113180 | -0.150829598 | CD58 |
| cg26528255 | 1 | 27652089 | -0.150820246 | TMEM222 |
| cg10955633 | 7 | 957950 | -0.150813737 | ADAP1 |
| cg14563732 | 8 | 143474839 | -0.150801927 | TSNARE1 |
| cg22995176 | 7 | 76139470 | 0.150745944 | UPK3B |
| cg17154187 | 17 | 18163844 | -0.150744467 | SMCR7 |
| cg16609139 | 11 | 23962902 | -0.150726414 | |
| cg05947570 | 10 | 89623020 | -0.150713259 | PTEN |
| cg24654547 | 16 | 68057165 | -0.150704372 | DUS2L |
| cg01485266 | 19 | 2476132 | -0.150699276 | GADD45B |
| cg12314527 | 22 | 19110193 | 0.150555397 | DGCR2 |
| cg06352483 | 1 | 28052575 | 0.150468906 | FAM76A |
| cg16968115 | 1 | 27560829 | -0.150466659 | WDTC1 |
| cg21035471 | 17 | 77005669 | 0.150428762 | CANT1 |
| cg06117184 | 2 | 113522207 | -0.150396687 | CKAP2L |
| cg06099276 | 16 | 49315812 | 0.1503915 | CBLN1 |
| ch.8.2353618R | 8 | 119282796 | 0.150370073 | SAMD12 |
| cg24363298 | 3 | 50242671 | 0.150302309 | SLC38A3 |
| cg18735798 | 3 | 194392871 | 0.150186096 | LSG1 |
| cg04607442 | 13 | 21872219 | 0.150166347 | |
| cg20368463 | 18 | 77673604 | 0.150153225 | PQLC1 |
| cg08526140 | 19 | 53693063 | -0.150119594 | ZNF665 |
| cg16221634 | 6 | 73332885 | -0.150092848 | KCNQ5 |
| cg26805238 | 1 | 144931980 | -0.150090824 | PDE4DIP |
| cg17001531 | 1 | 16825540 | 0.150086507 | |
| cg04063589 | 5 | 134871973 | 0.150084505 | NEUROG1 |
| cg02628801 | 1 | 101701963 | -0.150081278 | S1PR1 |
| cg18268492 | 10 | 99185986 | 0.1500765 | PGAM1 |
| cg05217468 | 6 | 30689475 | -0.150076046 | TUBB |
| cg20917554 | 6 | 110012378 | 0.150042794 | AKD1 |
| cg09852107 | 11 | 57226342 | 0.150036158 | |
| cg15365536 | 6 | 16266181 | -0.150015549 | GMPR |
| cg17115147 | 6 | 45345601 | 0.15001509 | RUNX2 |
| cg05005023 | 5 | 54469138 | 0.150011061 | CDC20B |
| cg04022891 | 19 | 17836889 | -0.149999536 | MAP1S |
| cg05882699 | 10 | 126840591 | 0.149983516 | CTBP2 |
| cg15649111 | 7 | 129988860 | -0.149884514 | CPA5 |
| cg23091255 | 6 | 64345855 | -0.149860681 | |
| cg03974286 | 2 | 201980638 | 0.149842516 | CFLAR |
| cg05762326 | 10 | 92591168 | -0.149770187 | HTR7 |

Figure 18-3

| | | | | |
|---|---|---|---|---|
| cg21028463 | 17 | 74733682 | -0.149757537 | MIR636 |
| cg11175310 | 10 | 16859107 | -0.149755971 | RSU1 |
| cg08264848 | 12 | 120740020 | 0.149741428 | SIRT4 |
| cg13364389 | 13 | 112876974 | -0.14971626 | |
| cg09044296 | 5 | 176739296 | 0.14966717 | MXD3 |
| cg15389153 | 3 | 42819341 | -0.149656056 | |
| cg13390975 | 5 | 34915890 | -0.149649837 | BRIX1 |
| cg10282371 | 8 | 38854376 | -0.149644383 | ADAM9 |
| cg07951488 | 4 | 41992560 | -0.149640297 | SLC30A9 |
| cg22017132 | 6 | 42927199 | -0.149632595 | GNMT |
| cg06207460 | 9 | 4741011 | 0.149573639 | AK3 |
| cg14376275 | 1 | 171810570 | 0.149515353 | DNM3 |
| cg22852149 | 19 | 36980565 | -0.149501651 | ZNF566 |
| cg10157951 | 12 | 122108328 | -0.149488889 | MORN3 |
| cg02656441 | 13 | 111367915 | -0.149484667 | ING1 |
| cg23540765 | 19 | 1173635 | 0.149467405 | SBNO2 |
| cg27564108 | 1 | 150585651 | 0.149431297 | |
| cg22860534 | 11 | 68813585 | -0.149420958 | |
| cg16249355 | 17 | 76310516 | 0.14939609 | |
| cg06646346 | 11 | 6280988 | 0.149368024 | CCKBR |
| cg24475210 | 4 | 6642433 | -0.149348708 | MRFAP1 |
| cg09220050 | 20 | 48770642 | 0.149347117 | TMEM189 |
| cg11177179 | 14 | 65381159 | -0.149283356 | CHURC1 |
| cg11949866 | 1 | 10754891 | 0.149280852 | CASZ1 |
| cg20919306 | 17 | 11924526 | 0.149272336 | MAP2K4 |
| cg26300597 | 3 | 128840676 | 0.149264485 | RAB43 |
| cg07370464 | 17 | 43394456 | 0.149260284 | MAP3K14 |
| cg05112967 | 7 | 63353492 | -0.149240706 | |
| cg17391518 | 19 | 59028285 | -0.149221852 | ZBTB45 |
| cg14229247 | 9 | 100745139 | -0.149199219 | ANP32B |
| cg09664684 | 4 | 38665613 | 0.149115513 | KLF3 |
| cg07928105 | 7 | 75368414 | 0.149108155 | HIP1 |
| cg22591103 | 3 | 159944037 | -0.149088107 | LOC401097 |
| cg26164151 | 11 | 44749353 | 0.14908218 | |
| cg00045190 | 6 | 33216612 | -0.149081913 | |
| cg25629442 | 17 | 77070844 | 0.149072973 | ENGASE |
| cg01532694 | 8 | 8243576 | -0.149068077 | |
| cg26976888 | 7 | 12628091 | -0.149064685 | SCIN |
| cg14036868 | 2 | 38604442 | -0.14906092 | ATL2 |
| cg23193446 | 10 | 15210836 | 0.149017758 | NMT2 |
| cg09011732 | 2 | 74730507 | 0.14900727 | LOC151534 |
| cg04215179 | 7 | 23719682 | 0.148995326 | C7orf46 |
| cg20382057 | 2 | 69969052 | 0.14898319 | ANXA4 |
| cg22813744 | 11 | 77899778 | -0.14890876 | KCTD21 |
| cg08984586 | 5 | 175963618 | -0.148907793 | RNF44 |
| cg16174274 | 7 | 148679906 | 0.148894155 | |
| cg05719877 | 11 | 114271629 | -0.14884886 | C11orf71 |
| cg13676204 | 14 | 61447818 | -0.148843602 | SLC38A6 |
| cg09634134 | 5 | 321681 | 0.148839064 | AHRR |
| cg16105080 | 1 | 239806917 | -0.148817779 | CHRM3 |
| cg11336323 | 19 | 41946040 | 0.148807561 | ATP5SL |
| cg14119392 | 14 | 95623926 | -0.148806362 | FLJ45244 |
| cg21347733 | 2 | 220306674 | 0.148797663 | SPEG |
| cg02772905 | 2 | 203484258 | -0.148796864 | |
| cg06756227 | 15 | 77712488 | 0.148794181 | HMG20A |
| cg11059266 | 4 | 48782139 | 0.14877356 | FRYL |
| cg16458507 | 12 | 113376293 | 0.148763956 | OAS3 |
| cg24951396 | 12 | 125473687 | -0.148763294 | DHX37 |
| cg26507704 | 15 | 25314647 | -0.148729954 | SNORD116-8 |
| cg02357877 | 7 | 56032049 | -0.148728823 | GBAS |
| cg15825725 | 11 | 82905263 | 0.148715548 | ANKRD42 |
| cg09127400 | 6 | 30712331 | -0.148685932 | IER3 |
| cg13834567 | 19 | 42817981 | 0.148665613 | TMEM145 |
| cg05300158 | 4 | 140477727 | -0.148640487 | SETD7 |
| cg04407100 | 10 | 133729658 | 0.14863168 | |
| cg03392679 | 3 | 71773917 | -0.148602006 | EIF4E3 |
| cg06928982 | 1 | 36851566 | 0.148587241 | STK40 |
| cg07179693 | 11 | 32605281 | -0.14858278 | EIF3M |
| cg06330324 | 22 | 31031670 | -0.148580156 | SLC35E4 |
| cg06366345 | 14 | 101459591 | -0.148574915 | SNORD114-3: |
| cg17753475 | 2 | 180477963 | -0.148564496 | ZNF385B |
| cg16704344 | 5 | 141616127 | 0.14855801 | |
| cg23387220 | 4 | 53578496 | 0.148481521 | SNORA26 |
| cg15408407 | 19 | 1438438 | -0.148464886 | RPS15 |
| cg13455597 | 9 | 2844149 | -0.148462079 | KIAA0020 |
| cg14397361 | 9 | 140149997 | -0.148402564 | COBRA1 |
| cg09200668 | 13 | 31773954 | 0.148378923 | B3GALTL |
| cg01196996 | 4 | 39481740 | -0.148338225 | LOC401127 |
| cg05544840 | 13 | 44716513 | -0.148331982 | |
| cg17324887 | 11 | 18720217 | 0.148297822 | TMEM86A |
| cg09706833 | 21 | 46824938 | 0.148289888 | COL18A1 |
| cg16591054 | 19 | 50145354 | -0.148289371 | SCAF1 |

Figure 18-4

| | | | | |
|---|---|---|---|---|
| cg27642943 | 19 | 11457439 | 0.148286047 | TMEM205 |
| cg02350644 | 2 | 133111454 | -0.148266521 | |
| cg22690046 | 1 | 36863663 | -0.148265602 | LSM10 |
| cg27275634 | 20 | 37590967 | -0.148263529 | DHX35 |
| cg00934735 | 5 | 180582587 | -0.148252309 | OR2V2 |
| cg14443077 | 11 | 68606701 | 0.148202821 | CPT1A |
| cg20363309 | 17 | 57184465 | -0.148191888 | TRIM37 |
| cg00226085 | 6 | 58172067 | -0.148186913 | |
| cg12013492 | 11 | 46143011 | 0.148176619 | PHF21A |
| cg08117032 | 8 | 38325144 | 0.148141221 | FGFR1 |
| cg27109030 | 19 | 2702898 | 0.14811743 | GNG7 |
| cg26258108 | 2 | 232329189 | -0.148113939 | NCL |
| cg18915437 | 12 | 62654245 | -0.148107202 | USP15 |
| cg03371986 | 5 | 138089103 | 0.148102031 | CTNNA1 |
| cg07661849 | 4 | 146686236 | -0.148082645 | ZNF827 |
| cg26115276 | 5 | 178977181 | 0.148058168 | RUFY1 |
| cg10734432 | 8 | 145180544 | -0.148048134 | |
| cg01176150 | 16 | 31519952 | -0.148044789 | C16orf58 |
| cg15233292 | 22 | 32340329 | -0.148043181 | YWHAH |
| cg25211006 | 1 | 43971496 | -0.148026322 | |
| cg14494313 | 8 | 18248453 | -0.14801893 | NAT2 |
| cg23955334 | 1 | 1543828 | -0.148008444 | |
| cg03989244 | 15 | 72523736 | -0.147993159 | PKM2 |
| cg27649653 | 19 | 58789751 | 0.147977673 | ZNF8 |
| cg18604876 | 3 | 5164258 | 0.147973745 | ARL8B |
| cg16250722 | 6 | 31478166 | -0.147964231 | MICB |
| cg26929161 | 20 | 50701266 | -0.147950104 | ZFP64 |
| cg25658641 | 17 | 19557814 | -0.147938892 | ALDH3A2 |
| cg00014203 | 17 | 7757969 | 0.147909582 | KDM6B |
| cg02918483 | 4 | 84406202 | 0.147891149 | FAM175A |
| cg03631596 | 13 | 73301985 | -0.147889449 | C13orf37 |
| cg15692992 | 13 | 112710428 | 0.147881968 | |
| cg20965255 | 17 | 37607625 | -0.147871346 | MED1 |
| cg20423427 | 18 | 67873036 | -0.147868534 | RTTN |
| cg27102918 | 6 | 20024152 | 0.147853428 | |
| cg17064520 | 10 | 98591758 | 0.147817311 | LCOR |
| cg12266953 | 2 | 20866261 | -0.14780131 | GDF7 |
| cg08502759 | 11 | 10562853 | 0.147777139 | RNF141 |
| cg03982544 | 11 | 17036042 | 0.147771177 | PLEKHA7 |
| cg11523350 | 11 | 117171073 | 0.147762515 | BACE1 |
| cg04364194 | 1 | 202114085 | -0.147739331 | ARL8A |

| | | | | |
|---|---|---|---|---|
| cg26487629 | 16 | 19418116 | -0.147739286 | |
| cg08187779 | 8 | 102217898 | 0.147702744 | ZNF706 |
| cg18818993 | 14 | 91087882 | -0.14769999 | TTC7B |
| cg16020249 | 1 | 27930640 | 0.147684057 | AHDC1 |
| cg15889649 | 15 | 79055693 | -0.147668507 | ADAMTS7 |
| cg04936382 | 20 | 36662003 | -0.147661501 | RPRD1B |
| cg27619163 | 17 | 7982806 | -0.1476506 | ALOX12B |
| cg08977130 | 3 | 176915099 | 0.147646178 | TBL1XR1 |
| cg14902146 | 15 | 90294607 | -0.147634919 | MESP1 |
| cg11975206 | 10 | 135192160 | -0.14760049 | PAOX |
| cg08557876 | 16 | 81130217 | 0.147593758 | GCSH |
| cg06100147 | 7 | 143059260 | 0.147576716 | FAM131B |
| cg11224423 | 12 | 56136943 | 0.147552317 | GDF11 |
| cg04323979 | 2 | 220306667 | 0.147546626 | SPEG |
| cg16370446 | 4 | 15683284 | -0.147533266 | LOC285550 |
| cg13979277 | 9 | 129388281 | 0.14753005 | LMX1B |
| cg11070069 | 6 | 105389370 | 0.147527638 | |
| cg23060872 | 2 | 71205685 | 0.147509904 | ANKRD53 |
| cg09141413 | 16 | 19896246 | 0.147501869 | GPRC5B |
| cg24517252 | 1 | 249200781 | 0.147484551 | PGBD2 |
| cg17598704 | 4 | 148885518 | -0.14746688 | ARHGAP10 |
| cg17734983 | 15 | 25456897 | -0.147459422 | SNORD115-1! |
| cg16203711 | 3 | 169491183 | -0.14744457 | MYNN |
| cg16263627 | 15 | 100339283 | -0.147430448 | C15orf51 |
| cg05938683 | 1 | 85156187 | 0.147394476 | SSX2IP |
| cg08342588 | 6 | 34494976 | 0.14739182 | PACSIN1 |
| cg24692716 | 6 | 133119484 | -0.147371456 | C6orf192 |
| cg04977109 | 17 | 46125622 | -0.147360657 | NFE2L1 |
| cg11983363 | 2 | 32578646 | -0.147349467 | |
| cg26548134 | 22 | 41185283 | -0.147312649 | SLC25A17 |
| cg11654179 | 12 | 57998762 | 0.147310319 | DTX3 |
| cg05102651 | 8 | 28351601 | 0.147237007 | FZD3 |
| cg09990596 | 14 | 102227939 | 0.147212069 | PPP2R5C |
| cg24152238 | 15 | 26327408 | 0.147206306 | |
| cg18436758 | 1 | 21113190 | 0.147196044 | HP1BP3 |
| cg20568408 | 14 | 90425050 | -0.147186139 | TDP1 |
| cg02416013 | 16 | 11891051 | 0.147177449 | |
| cg11228874 | 1 | 1813727 | -0.147129492 | GNB1 |
| cg24085655 | 6 | 35436189 | -0.147075727 | RPL10A |
| cg16989332 | 4 | 175216323 | 0.147059924 | KIAA1712 |
| cg14170181 | 9 | 5114002 | -0.147057911 | JAK2 |

Figure 18-5

| | | | | | | | | | |
|---|---|---|---|---|---|---|---|---|---|
| cg01249134 | 18 | 577110 | -0.147007892 | | cg02866761 | 22 | 17565664 | 0.146504678 | IL17RA |
| cg19385725 | 18 | 21166173 | 0.147003965 | NPC1 | cg23459174 | 14 | 82295989 | -0.146501189 | |
| cg17414733 | 19 | 21688647 | 0.146998767 | ZNF429 | cg25704749 | 2 | 241526252 | 0.146490289 | CAPN10 |
| cg07987587 | 22 | 42486991 | -0.146993117 | NDUFA6 | cg25559069 | 6 | 33134799 | -0.146488868 | COL11A2 |
| cg23271318 | 20 | 44509620 | 0.146976731 | ZSWIM1 | cg12078510 | 19 | 53030774 | 0.146463725 | ZNF808 |
| cg16834212 | 3 | 67706500 | 0.146967171 | SUCLG2 | cg03083562 | 8 | 126007153 | -0.146451536 | |
| cg23059868 | 1 | 1649451 | 0.146903206 | CDK11A | cg01266707 | 17 | 37824461 | 0.146424743 | PNMT |
| cg16458021 | 21 | 43430507 | -0.146878634 | ZNF295 | cg26450188 | 19 | 46850188 | -0.146423466 | PPP5C |
| cg24839520 | 3 | 129749648 | -0.14687072 | | cg05170366 | 10 | 34063213 | -0.146398386 | |
| cg14128369 | 6 | 34231203 | -0.146865351 | | cg19447629 | 12 | 82766859 | -0.146394834 | C12orf26 |
| cg16041611 | 6 | 43139680 | -0.146858375 | SRF | cg16868190 | 18 | 12377377 | 0.146394378 | AFG3L2 |
| cg21161069 | 7 | 32768311 | 0.146847352 | LOC441208 | cg16170495 | 6 | 30042626 | 0.146376432 | RNF39 |
| cg06183820 | 6 | 2972097 | -0.146833498 | SERPINB6 | cg25818882 | 19 | 12886379 | 0.146371446 | HOOK2 |
| cg22199361 | 20 | 5081567 | 0.146831171 | C20orf30 | cg11818149 | 2 | 132795839 | 0.146362461 | |
| cg22885777 | 19 | 15947555 | 0.146807253 | | cg24203851 | 6 | 111136481 | 0.146359632 | CDK19 |
| cg05256172 | 2 | 26139506 | 0.146805524 | | cg22345896 | 2 | 173399001 | -0.146339284 | |
| cg01438737 | 20 | 42086396 | -0.14680045 | SFRS6 | cg14382318 | 22 | 46646383 | -0.146331275 | C22orf40 |
| cg08142571 | 14 | 104096390 | 0.146793709 | KLC1 | cg25299201 | 13 | 22178312 | 0.146325742 | EFHA1 |
| cg19837214 | 12 | 133402551 | -0.146741638 | GOLGA3 | cg17575113 | 10 | 43186868 | -0.146294783 | |
| cg05982271 | 4 | 76555948 | -0.146715608 | CDKL2 | cg02718200 | 6 | 31324269 | 0.146286938 | HLA-B |
| cg13896783 | 2 | 159313876 | 0.146714173 | CCDC148 | cg26841507 | 12 | 56583252 | 0.146274253 | SMARCC2 |
| cg13144783 | 3 | 46249795 | 0.146710472 | CCR1 | cg15290081 | 7 | 76254647 | -0.146270174 | POMZP3 |
| cg25587211 | 3 | 43663662 | -0.146704921 | ANO10 | cg25490276 | 19 | 12992844 | 0.146248054 | DNASE2 |
| cg07100957 | 19 | 58982330 | -0.146683061 | ZNF324 | cg09933058 | 12 | 47473799 | 0.1462361 | AMIGO2 |
| cg10730421 | 3 | 186078847 | -0.146680082 | DGKG | cg22506343 | 3 | 127173672 | -0.146233006 | |
| cg19954613 | 22 | 22020219 | -0.146668083 | PPIL2 | cg08555160 | 16 | 69166339 | 0.146214468 | CHTF8 |
| cg06832605 | 20 | 26319303 | -0.14666373 | | cg12390003 | 1 | 160068671 | 0.14619861 | IGSF8 |
| cg17687970 | 8 | 22462467 | 0.146651288 | KIAA1967 | cg03056129 | 1 | 89593910 | -0.146183951 | |
| cg02360300 | 16 | 577976 | 0.146646328 | SOLH | cg21961512 | 4 | 8692854 | -0.146144174 | |
| cg25261764 | 18 | 55288998 | -0.146644714 | NARS | cg02095553 | 9 | 134428624 | -0.146111046 | |
| cg13717023 | 5 | 53606639 | -0.146634461 | ARL15 | cg19696333 | 10 | 124768261 | -0.146096847 | IKZF5 |
| cg14766646 | 19 | 20187337 | -0.146607817 | ZNF90 | cg07212416 | 16 | 28385626 | 0.146072461 | |
| cg22672078 | 12 | 132628386 | 0.146593884 | DDX51 | cg10824802 | 8 | 70747252 | -0.146035521 | SLCO5A1 |
| cg22160784 | 2 | 73460416 | -0.146590936 | CCT7 | cg05588757 | 2 | 95825608 | 0.146019956 | ZNF514 |
| cg13467399 | 9 | 133588111 | -0.146587138 | ABL1 | cg25020699 | 4 | 25247397 | -0.146009634 | PI4K2B |
| cg27248073 | 17 | 6347727 | 0.146579927 | FAM64A | cg18509719 | 11 | 1469746 | 0.146001258 | BRSK2 |
| cg16903217 | 1 | 201915950 | 0.146572934 | LMOD1 | cg01243297 | 6 | 33160292 | 0.145999539 | COL11A2 |
| cg08532569 | 22 | 36424620 | 0.146562289 | RBM9 | cg00260647 | 6 | 30524003 | 0.145993935 | PRR3 |
| cg16757281 | 16 | 685785 | 0.146532775 | C16orf13 | cg08855361 | 16 | 58718334 | 0.145979776 | SLC38A7 |
| cg04751069 | 16 | 89787483 | -0.146530595 | ZNF276 | cg07003055 | 20 | 3776921 | -0.145976739 | CDC25B |
| cg21605986 | 5 | 175788725 | -0.146527533 | KIAA1191 | cg06642177 | 6 | 134496341 | -0.145968281 | SGK1 |

Figure 18-6

| | | | | | | | | | |
|---|---|---|---|---|---|---|---|---|---|
| cg08293303 | 5 | 176731731 | 0.145960531 | PRELID1 | cg09238957 | 16 | 46723420 | -0.145535827 | ORC6L |
| cg11737710 | 19 | 37959864 | -0.145958036 | ZNF570 | cg04584087 | 3 | 129159014 | -0.145534147 | IFT122 |
| cg17092583 | 11 | 735575 | -0.145931918 | | cg19545258 | 7 | 73703601 | 0.145521537 | CLIP2 |
| cg00161367 | 6 | 153323552 | 0.145925226 | MTRF1L | cg14780883 | 15 | 25466402 | -0.145511238 | SNORD115-1! |
| cg20390253 | 18 | 77793812 | 0.14592137 | C18orf22 | cg09887955 | 1 | 202129854 | 0.145506281 | PTPN7 |
| cg08779779 | 2 | 200322566 | 0.14589524 | SATB2 | cg03657031 | 19 | 54385215 | 0.145500388 | PRKCG |
| cg11232610 | 5 | 140027381 | -0.145872418 | NDUFA2 | cg20681747 | 7 | 66949602 | 0.145499417 | |
| cg15617768 | 10 | 101492447 | -0.145866683 | COX15 | cg11532971 | 6 | 106676381 | -0.145493496 | ATG5 |
| cg04200362 | 2 | 73341598 | -0.14585801 | RAB11FIP5 | cg23983067 | 10 | 43277941 | -0.1454877 | BMS1 |
| cg12646754 | 1 | 2574751 | -0.145836637 | | cg15057823 | 6 | 42981704 | 0.145448952 | MEA1 |
| cg01245787 | 4 | 71859630 | -0.145833742 | DCK | cg05047465 | 10 | 27793441 | -0.145445233 | RAB18 |
| cg17508063 | 12 | 53298678 | -0.14582112 | KRT8 | cg10370564 | 19 | 39522418 | 0.1454394 | FBXO27 |
| cg13452400 | 2 | 7006280 | -0.145813123 | CMPK2 | cg02113521 | 15 | 22892956 | 0.145426434 | CYFIP1 |
| cg12673840 | 5 | 133193418 | -0.14580572 | | cg16943083 | 18 | 500817 | 0.145421286 | COLEC12 |
| cg05776084 | 3 | 133293427 | -0.145799061 | CDV3 | cg09293387 | 8 | 6565827 | -0.145417185 | AGPAT5 |
| cg03031660 | 17 | 73257791 | -0.145794474 | MRPS7 | cg06260874 | 8 | 6010288 | -0.145412078 | |
| cg10964421 | 8 | 23021093 | 0.145788903 | TNFRSF10D | cg20012885 | 18 | 12377404 | 0.145409524 | AFG3L2 |
| cg24500304 | 1 | 235291357 | 0.145779595 | SNORA14B | cg20284698 | 3 | 48956327 | 0.145396196 | C3orf71 |
| cg16008009 | 3 | 47620532 | 0.145774457 | CSPG5 | cg14102005 | 14 | 56645376 | -0.145391458 | PELI2 |
| cg04901121 | 13 | 25321731 | -0.145769462 | | cg02466749 | 9 | 98054877 | -0.145380955 | FANCC |
| cg13137533 | 17 | 43973292 | -0.145765755 | MAPT | cg05956803 | 5 | 137666464 | -0.145374184 | CDC25C |
| cg23627909 | 14 | 60337760 | -0.14576489 | RTN1 | cg07804735 | 3 | 113157476 | -0.145352523 | WDR52 |
| cg21914984 | 2 | 37899464 | -0.145750906 | CDC42EP3 | cg09744376 | 3 | 53080176 | 0.145351412 | SFMBT1 |
| cg26260369 | 14 | 68141723 | -0.145750822 | VTI1B | cg17043191 | 11 | 79968672 | -0.145346972 | |
| cg24589549 | 3 | 49391282 | -0.145739237 | | cg15050398 | 6 | 28829182 | -0.14532152 | |
| cg05865161 | 7 | 97557134 | 0.145735851 | | cg07455051 | 2 | 128051853 | -0.145316194 | ERCC3 |
| cg16168311 | 1 | 156561947 | 0.145732033 | APOA1BP | cg16884295 | 22 | 21018314 | -0.145308823 | |
| cg00090619 | 6 | 33160286 | 0.145723342 | COL11A2 | cg17430214 | 6 | 41246904 | 0.145250217 | TREM1 |
| cg11572675 | 2 | 86155952 | 0.14571672 | | cg00311921 | 22 | 19119464 | -0.145208327 | TSSK2 |
| cg09075525 | 13 | 25940208 | -0.145716233 | | cg04223844 | 8 | 42128868 | -0.14519515 | IKBKB |
| cg24294159 | 1 | 150947566 | -0.145699521 | LASS2 | cg23213688 | 1 | 231473791 | -0.14518404 | C1orf124 |
| cg27018005 | 7 | 134249247 | -0.145685962 | AKR1B15 | cg06046629 | 3 | 53698952 | -0.145171704 | CACNA1D |
| cg17847344 | 5 | 158478734 | 0.145651466 | EBF1 | cg07786668 | 16 | 73092391 | -0.145161769 | ZFHX3 |
| cg02611874 | 10 | 46194725 | -0.145649318 | | cg12198254 | 3 | 11521788 | -0.145160379 | ATG7 |
| cg08573907 | 13 | 101628998 | -0.145646169 | | cg12575136 | 18 | 32820987 | 0.145142575 | ZNF397 |
| cg09564990 | 10 | 113748602 | -0.145626619 | | cg23281018 | 1 | 944789 | 0.145140116 | |
| cg20275462 | 17 | 60501228 | -0.145620732 | METTL2A | cg07135388 | 1 | 160040411 | -0.14511769 | KCNJ10 |
| cg19722371 | 12 | 102271755 | 0.145616081 | DRAM1 | cg25495217 | 7 | 6048875 | -0.145117516 | PMS2 |
| cg01409734 | 12 | 112563185 | 0.145600525 | TRAFD1 | cg06551493 | 7 | 77166702 | 0.145111403 | PTPN12 |
| cg16613143 | 17 | 2415359 | -0.145596296 | METT10D | cg10700459 | 6 | 30231675 | -0.145109586 | HLA-L |
| cg23377236 | 6 | 3809610 | -0.145590335 | | cg07195197 | 16 | 1662150 | -0.145100701 | IFT140 |

Figure 18-7

| | | | | |
|---|---|---|---|---|
| cg13947043 | 9 | 88141545 | -0.145099533 | |
| cg16340159 | 2 | 240322705 | -0.145078412 | HDAC4 |
| cg12442236 | 22 | 37823644 | 0.145070768 | ELFN2 |
| cg17371350 | 17 | 655677 | 0.145023974 | ELP2P |
| cg25932599 | 4 | 1005201 | 0.145023631 | FGFRL1 |
| cg14537800 | 4 | 15964950 | 0.145009257 | FGFBP2 |
| cg22468803 | 18 | 9136381 | -0.145006366 | ANKRD12 |
| cg11027325 | 2 | 239148674 | 0.145003153 | HES6 |
| cg13741289 | 4 | 17578858 | -0.14499938 | LAP3 |
| cg09599399 | 6 | 32121843 | -0.144988081 | PPT2 |
| cg14284925 | 22 | 42315998 | 0.144986058 | |
| cg06536503 | 6 | 42750688 | -0.144978543 | |
| cg10101463 | 1 | 202780506 | -0.144936548 | |
| cg02568557 | 11 | 129288930 | -0.144914637 | BARX2 |
| cg24274354 | 1 | 13034580 | -0.14490222 | PRAMEF22 |
| cg25798026 | 22 | 32149910 | 0.144886889 | DEPDC5 |
| cg26937912 | 16 | 89945578 | -0.144875539 | TCF25 |
| cg01240047 | 14 | 91224692 | 0.144849038 | TTC7B |
| cg01289140 | 6 | 41862737 | 0.144840768 | USP49 |
| cg23868848 | 8 | 128806661 | 0.144835314 | PVT1 |
| cg19226007 | 17 | 43045068 | 0.14481882 | C1QL1 |
| cg24448326 | 1 | 85930306 | -0.144814465 | DDAH1 |
| cg25352856 | 1 | 180472145 | -0.144808397 | ACBD6 |
| cg25696485 | 21 | 38445943 | -0.144804471 | PIGP |
| cg19367232 | 2 | 68478649 | 0.14478426 | PPP3R1 |
| cg01400712 | 2 | 25352206 | 0.144779628 | EFR3B |
| cg17895522 | 10 | 44788915 | 0.144766133 | |
| cg02153829 | 12 | 119034267 | -0.14476336 | |
| cg17841838 | 19 | 3626645 | 0.144749137 | C19orf29 |
| cg20769334 | 22 | 50913335 | 0.144745105 | SBF1 |
| cg09197288 | 14 | 94550812 | -0.144737186 | IFI27L1 |
| cg25966751 | 14 | 74098320 | -0.144732878 | |
| cg13668025 | 3 | 67706320 | 0.144721538 | SUCLG2 |
| cg13637402 | 9 | 139009863 | 0.144718052 | C9orf69 |
| cg10446401 | 2 | 101619230 | 0.14471167 | RPL31 |
| cg10753423 | 7 | 143318009 | 0.144709219 | FAM115C |
| cg00494761 | 2 | 86564659 | 0.14470112 | REEP1 |
| cg12502155 | 15 | 85201891 | 0.1447 | NMB |
| cg22167498 | 19 | 8451051 | -0.144680036 | |
| cg06456464 | 1 | 9352752 | 0.144677234 | SPSB1 |
| cg04533881 | 14 | 50583218 | -0.144667878 | C14orf138 |
| cg06221470 | 7 | 2353869 | 0.144667213 | SNX8 |
| cg11974096 | 2 | 233470647 | -0.144663044 | EFHD1 |
| cg17452570 | 5 | 179886642 | -0.144645355 | |
| cg13754687 | 2 | 40573036 | -0.14463748 | SLC8A1 |
| cg03926050 | 12 | 111020225 | 0.144636428 | PPTC7 |
| cg19197523 | 8 | 124428674 | 0.144635607 | WDYHV1 |
| cg05168344 | 22 | 21340160 | 0.144634469 | LZTR1 |
| cg15605011 | 1 | 110162477 | 0.144633593 | AMPD2 |
| cg04510639 | 17 | 74722764 | 0.14463114 | JMJD6 |
| cg15272186 | 6 | 29709610 | -0.144621593 | LOC285830 |
| cg19945078 | 4 | 16944288 | -0.144603269 | |
| cg09392386 | 17 | 63557887 | 0.144596393 | AXIN2 |
| cg11038081 | 19 | 44810637 | -0.144588905 | ZNF235 |
| cg01606770 | 1 | 97279796 | 0.144586107 | PTBP2 |
| cg01950479 | 22 | 23528162 | 0.144584154 | BCR |
| cg05844625 | 6 | 29976071 | -0.144572468 | HLA-J |
| cg20676350 | 1 | 22961885 | -0.144570767 | C1QA |
| cg14172283 | 9 | 37592468 | -0.144566093 | TOMM5 |
| cg13956095 | 17 | 81037419 | 0.144559264 | METRNL |
| cg10274208 | 13 | 41351044 | 0.144549353 | |
| cg13806031 | 10 | 103454441 | 0.14453662 | FBXW4 |
| cg23727520 | 3 | 121741145 | 0.14453208 | ILDR1 |
| cg18622281 | 20 | 43977112 | 0.144489422 | SDC4 |
| cg27479418 | 10 | 126107594 | 0.144486055 | OAT |
| cg00556514 | 3 | 38066524 | 0.144483144 | PLCD1 |
| cg11228480 | 12 | 133066511 | 0.144474531 | FBRSL1 |
| cg10685336 | 3 | 149688848 | 0.144470583 | PFN2 |
| cg05516746 | 10 | 5884061 | -0.144460997 | |
| cg06691810 | 8 | 27168883 | -0.144459918 | TRIM35 |
| cg23924753 | 14 | 81979997 | -0.144447173 | SEL1L |
| cg26036626 | 1 | 16085597 | 0.14444652 | FBLIM1 |
| cg13433446 | 9 | 128170534 | -0.144430504 | |
| cg06384413 | 17 | 46671215 | 0.144418991 | LOC404266 |
| cg03610000 | 11 | 128392383 | 0.144414893 | ETS1 |
| cg20611850 | 19 | 41284006 | 0.144411711 | RAB4B |
| cg22031336 | 4 | 89079809 | -0.144411092 | ABCG2 |
| cg07959380 | 16 | 89894648 | 0.144408344 | SPIRE2 |
| cg07022554 | 16 | 1993481 | 0.144399564 | SEPX1 |
| cg05445051 | 6 | 107349292 | -0.144394343 | C6orf203 |
| cg22201516 | 19 | 32715740 | 0.144392486 | |
| cg19146902 | 11 | 47516584 | -0.144349217 | CUGBP1 |

Figure 18-8

| | | | | | | | | | |
|---|---|---|---|---|---|---|---|---|---|
| cg06936779 | 1 | 151171405 | 0.144346412 | PIP5K1A | cg19707448 | 17 | 25779279 | -0.143980789 | |
| cg10252138 | 17 | 58120427 | -0.144343746 | | cg07084801 | 15 | 66648876 | 0.143975257 | TIPIN |
| cg06708122 | 5 | 64969231 | -0.144326784 | SGTB | cg02100343 | 1 | 31538517 | -0.143974948 | PUM1 |
| cg11877270 | 2 | 65658583 | -0.144326086 | SPRED2 | cg11673391 | 1 | 10459052 | -0.143972279 | PGD |
| cg14551186 | 9 | 131012492 | 0.144306766 | DNM1 | cg08580796 | 6 | 79943404 | -0.143966736 | HMGN3 |
| cg15481483 | 19 | 23299728 | 0.144302895 | | cg26789283 | 22 | 41682348 | -0.143911495 | RANGAP1 |
| cg20521389 | 8 | 21645509 | 0.144299686 | GFRA2 | cg07591229 | 2 | 241922908 | 0.143907587 | |
| cg21871583 | 3 | 15374148 | 0.144294533 | SH3BP5 | cg09913796 | 17 | 27181988 | -0.143903324 | ERAL1 |
| cg00631837 | 22 | 45404212 | 0.144293286 | PHF21B | cg01444712 | 7 | 150210785 | -0.143896834 | GIMAP7 |
| cg12525736 | 1 | 228269915 | 0.144287586 | ARF1 | cg14910854 | 2 | 132254702 | -0.143880243 | LOC150776 |
| cg09172423 | 11 | 62446602 | -0.144280739 | UBXN1 | cg13614812 | 17 | 21254058 | -0.14387046 | |
| cg08213444 | 5 | 784871 | 0.144268688 | | cg18416950 | 17 | 46620413 | 0.143847756 | HOXB2 |
| cg23069677 | 1 | 36863646 | -0.14424909 | LSM10 | cg03183872 | 20 | 3140552 | -0.14384028 | FASTKD5 |
| cg16710791 | 1 | 193028559 | -0.144244488 | TROVE2 | cg15312192 | 3 | 125412355 | -0.143836547 | |
| cg26387966 | 8 | 144503421 | -0.144239401 | | cg03907612 | 6 | 41703314 | 0.143794968 | TFEB |
| cg26561207 | 5 | 171615258 | 0.144224081 | STK10 | cg17436327 | 6 | 170863443 | -0.143765511 | PSMB1 |
| cg09046255 | 16 | 30662126 | 0.144212928 | PRR14 | cg19034708 | 8 | 17780168 | -0.143750386 | PCM1 |
| cg02874321 | 11 | 94166952 | -0.144199147 | MRE11A | cg16538289 | 6 | 41703332 | 0.143744694 | TFEB |
| cg21501096 | 14 | 24454443 | -0.144181828 | | cg12449510 | 7 | 97910870 | 0.143737786 | BRI3 |
| cg10341991 | 3 | 48229869 | -0.144178374 | CDC25A | cg23645831 | 1 | 15944060 | 0.143735139 | DDI2 |
| cg01069104 | 3 | 18467441 | 0.144163346 | SATB1 | cg07899263 | 13 | 99293508 | -0.143725785 | |
| cg19340909 | 1 | 1821422 | -0.144161502 | GNB1 | cg11582617 | 6 | 158589302 | 0.14370099 | SERAC1 |
| cg00636124 | 16 | 27215281 | -0.144151508 | JMJD5 | cg12644885 | 1 | 154297985 | 0.143692522 | ATP8B2 |
| cg18517677 | 9 | 131799243 | 0.144149085 | FAM73B | cg24875440 | 1 | 27986375 | 0.143692289 | |
| cg13657659 | 2 | 208632393 | -0.144135344 | FZD5 | cg27035087 | 6 | 28834254 | 0.143678491 | |
| cg07646714 | 11 | 34378884 | 0.144119567 | ABTB2 | cg24684520 | 10 | 120543329 | -0.143673806 | |
| cg08411512 | 20 | 25846519 | 0.144113136 | | cg26674132 | 19 | 9434637 | 0.14367065 | ZNF559 |
| cg03215858 | 10 | 15025727 | -0.144112377 | | cg11527367 | 1 | 144612646 | -0.143653884 | C1orf152 |
| cg15617548 | 2 | 171785815 | 0.144108409 | GORASP2 | cg24631920 | 11 | 108535736 | -0.143653819 | DDX10 |
| cg02918146 | 7 | 99725667 | 0.144100791 | MBLAC1 | cg03020271 | 19 | 4867550 | 0.143636953 | PLIN3 |
| cg02330114 | 3 | 43663594 | 0.144080811 | ANO10 | cg12991976 | 12 | 83053192 | -0.143636883 | |
| cg09905732 | 16 | 928154 | -0.144074294 | LMF1 | cg13601636 | 19 | 55385010 | -0.143633914 | FCAR |
| cg11199036 | 3 | 129325693 | 0.144055593 | PLXND1 | cg26511840 | 5 | 137827785 | 0.143632918 | |
| cg27310761 | 14 | 90798393 | 0.144054452 | C14orf102 | cg08975295 | 12 | 37936063 | -0.143628507 | |
| cg01559663 | 8 | 53852274 | -0.144040189 | NPBWR1 | cg04903936 | 11 | 19262692 | -0.143612358 | E2F8 |
| cg01698167 | 4 | 11430908 | -0.144033258 | HS3ST1 | cg09691861 | 4 | 77870047 | -0.143597049 | 11-Sep |
| cg15318396 | 21 | 38593284 | -0.144026267 | | cg06462174 | 17 | 30813688 | 0.143583845 | CDK5R1 |
| cg12361356 | 1 | 200708503 | -0.144024427 | CAMSAP1L1 | cg03793778 | 19 | 39264720 | -0.1435794 | LGALS7 |
| cg11396746 | 16 | 1877632 | 0.143998564 | FAHD1 | cg10827434 | 1 | 84944976 | 0.1435725 | RPF1 |
| cg05954989 | 10 | 135191962 | -0.14399806 | PAOX | cg07033880 | 15 | 85923739 | -0.143563052 | AKAP13 |
| cg16120422 | 12 | 113590924 | -0.143985496 | CCDC42B | cg23924007 | 4 | 140099401 | -0.143549456 | |

Figure 18-9

| | | | | | | | | | |
|---|---|---|---|---|---|---|---|---|---|
| cg00544901 | 19 | 49999417 | -0.143546047 | RPS11 | cg21922468 | 19 | 42417238 | 0.143163113 | |
| cg00997262 | 16 | 19421265 | -0.143545731 | TMC5 | cg04473235 | 5 | 77080995 | -0.143153178 | |
| cg13241807 | 11 | 33757992 | 0.143532971 | CD59 | cg05941299 | 14 | 23095661 | -0.143153023 | |
| cg06910299 | 4 | 2758074 | 0.143528707 | TNIP2 | cg05157470 | 6 | 28937310 | -0.143136263 | |
| cg18574403 | 17 | 77070839 | 0.143517544 | ENGASE | cg18732869 | 19 | 6739680 | 0.143133536 | TRIP10 |
| cg18471460 | 14 | 54863582 | -0.143503877 | CDKN3 | cg23084309 | 19 | 6280164 | 0.143129689 | MLLT1 |
| cg21799605 | 6 | 42713881 | -0.143495991 | TBCC | cg26932860 | 7 | 75938875 | -0.14311066 | |
| cg08328124 | 16 | 28251274 | -0.143486281 | | cg04836154 | 11 | 62439314 | -0.143108776 | C11orf83 |
| cg09020181 | 22 | 46467123 | 0.143466327 | | cg18045461 | 22 | 29601862 | 0.143102873 | EMID1 |
| cg16840889 | 6 | 107077549 | 0.143443188 | QRSL1 | cg19038917 | 10 | 106014565 | 0.143094361 | GSTO1 |
| cg24104633 | 14 | 67999913 | 0.143425776 | PLEKHH1 | cg11575912 | 19 | 5828299 | -0.143078231 | NRTN |
| cg21216828 | 19 | 15560076 | 0.143413768 | MIR1470 | cg27621528 | 2 | 241392617 | 0.143077502 | PP14571 |
| cg06510563 | 19 | 11308259 | 0.143411473 | KANK2 | cg17700415 | 8 | 145901039 | 0.14307031 | |
| cg15786664 | 6 | 28917329 | -0.14340202 | | cg07575812 | 5 | 138883510 | -0.143066702 | |
| cg19149264 | 3 | 187571176 | 0.143398382 | | cg11724493 | 6 | 33168040 | 0.143061784 | SLC39A7 |
| cg07559730 | 19 | 53497048 | 0.143397989 | ZNF702P | cg25486143 | 3 | 50378527 | -0.143055206 | RASSF1 |
| cg20856750 | 15 | 41444887 | -0.143397234 | | cg25923207 | 11 | 62192276 | 0.14305433 | |
| cg21422400 | 1 | 1747243 | -0.143393336 | GNB1 | cg24106894 | 15 | 48623432 | -0.143046805 | DUT |
| cg01218180 | 6 | 168079427 | 0.143367827 | | cg17053098 | 6 | 33137183 | -0.143031785 | COL11A2 |
| cg14162034 | 15 | 78112026 | 0.143365993 | | cg25221281 | 11 | 106698622 | -0.14301587 | GUCY1A2 |
| cg18075720 | 19 | 45349207 | 0.143360144 | PVRL2 | cg13249096 | 3 | 48670922 | 0.14300549 | SLC26A6 |
| cg23717752 | 17 | 21360435 | 0.143353962 | | cg27121095 | 18 | 77155145 | 0.142999981 | NFATC1 |
| cg21285133 | 1 | 150209464 | -0.143344346 | ANP32E | cg07416975 | 4 | 699435 | 0.142996122 | PCGF3 |
| cg02775353 | 7 | 101814109 | -0.14330473 | CUX1 | cg14303778 | 8 | 1616111 | -0.142988403 | DLGAP2 |
| cg08249899 | 16 | 20975258 | 0.143298089 | DNAH3 | cg16040094 | 14 | 52240877 | -0.14298482 | |
| cg06305175 | 2 | 228337254 | -0.143271754 | AGFG1 | cg15209934 | 19 | 52800385 | 0.142978259 | ZNF480 |
| cg01353139 | 8 | 124170018 | 0.143267543 | | cg10122932 | 7 | 99698990 | -0.142963883 | MCM7 |
| cg22229470 | 6 | 168107104 | 0.143264081 | | cg19255053 | 1 | 184944109 | -0.142957611 | FAM129A |
| cg05598205 | 16 | 46723426 | -0.143255291 | ORC6L | cg11786428 | 2 | 132560627 | -0.142954203 | C2orf27B |
| cg14860917 | 8 | 18871440 | 0.143254218 | PSD3 | cg14162457 | 13 | 113444243 | -0.142953758 | ATP11A |
| cg05990936 | 9 | 95858257 | 0.14324035 | C9orf89 | cg00303723 | 19 | 18304398 | 0.142945962 | MPV17L2 |
| cg14654948 | 6 | 36164803 | 0.143237102 | BRPF3 | cg03238901 | 19 | 10047197 | 0.14293808 | OLFM2 |
| cg24015081 | 14 | 105144033 | -0.143235808 | | cg18751306 | 15 | 81294292 | -0.142925444 | MESDC1 |
| cg24297454 | 6 | 30689211 | 0.143228083 | TUBB | cg12429444 | 1 | 20988133 | -0.142916935 | DDOST |
| cg18782651 | 7 | 65969785 | -0.143222905 | | cg09275602 | 7 | 66370330 | -0.142909278 | |
| cg10616859 | 7 | 2586532 | -0.143215146 | C7orf27 | cg13738615 | 9 | 109624741 | 0.142894432 | ZNF462 |
| cg13985271 | 9 | 97140681 | -0.143195614 | HIATL1 | cg13140465 | 15 | 23085026 | -0.142879507 | NIPA1 |
| cg02861733 | 1 | 153930593 | 0.143169875 | CRTC2 | cg00710870 | 7 | 102793411 | -0.142865435 | |
| cg08348387 | 2 | 242158123 | 0.143168425 | ANO7 | cg01779076 | 2 | 201980642 | 0.142863153 | CFLAR |
| cg08163906 | 14 | 102227932 | 0.143165814 | PPP2R5C | cg03951132 | 20 | 5931305 | -0.142846926 | MCM8 |
| cg21352959 | 17 | 62340143 | -0.14316438 | TEX2 | cg24131747 | 14 | 68141730 | -0.142827403 | VTI1B |

Figure 18-10

| | | | | |
|---|---|---|---|---|
| cg23783768 | 10 | 45454944 | -0.14281714 | RASSF4 |
| cg16436509 | 12 | 120875898 | -0.142804624 | COX6A1 |
| cg02083412 | 8 | 1649758 | 0.142804564 | DLGAP2 |
| cg19071627 | 7 | 98923091 | 0.142802756 | ARPC1A |
| cg06793377 | 22 | 51112536 | 0.142800765 | SHANK3 |
| cg25290175 | 2 | 71248774 | -0.142795628 | |
| cg18715525 | 5 | 179223116 | 0.142782785 | LTC4S |
| cg22223655 | 18 | 67872902 | -0.142779322 | RTTN |
| cg06012509 | 6 | 43027269 | -0.142776386 | KLC4 |
| cg10757027 | 7 | 150783788 | 0.142767561 | AGAP3 |
| cg04956913 | 6 | 30712436 | -0.142759546 | IER3 |
| cg27226043 | 11 | 1770394 | 0.142757482 | HCCA2 |
| cg23488616 | 6 | 159065864 | 0.142744978 | DYNLT1 |
| cg10534439 | 2 | 69969029 | 0.142716442 | ANXA4 |
| cg04887335 | 3 | 196044632 | -0.142713408 | TCTEX1D2 |
| cg23806411 | 16 | 49890167 | 0.14270233 | |
| cg09013204 | 13 | 79183513 | 0.142701032 | |
| cg18451256 | 2 | 128284158 | -0.142672764 | IWS1 |
| cg08661899 | 6 | 132722664 | 0.142671747 | MOXD1 |
| cg24385902 | 6 | 144617301 | -0.14265619 | UTRN |
| cg08163160 | 12 | 7052390 | -0.142654223 | C12orf57 |
| cg04553410 | 7 | 150864885 | -0.142645841 | GBX1 |
| cg01283712 | 14 | 106919294 | -0.142644348 | |
| cg15967188 | 4 | 2470700 | -0.142630041 | RNF4 |
| cg02283811 | 11 | 576060 | 0.142628062 | LOC143666 |
| cg08007338 | 1 | 180123948 | 0.142626313 | QSOX1 |
| cg14870242 | 14 | 55034646 | -0.142620511 | SAMD4A |
| cg02436290 | 12 | 130877573 | -0.142616715 | |
| cg14732699 | 8 | 128750039 | 0.142608737 | MYC |
| cg18511212 | 10 | 38715824 | -0.14259973 | LOC399744 |
| cg14385738 | 1 | 114414340 | 0.142588711 | PTPN22 |
| cg27502066 | 17 | 74380231 | 0.142573972 | SPHK1 |
| cg21121496 | 19 | 55592930 | 0.142573836 | EPS8L1 |
| cg24122991 | 12 | 6985221 | -0.142557538 | |
| cg06791151 | 3 | 37034956 | -0.14255306 | EPM2AIP1 |
| cg12856433 | 11 | 44084185 | -0.14255263 | |
| cg04599297 | 10 | 26505442 | 0.142551284 | GAD2 |
| cg03326059 | 11 | 13690160 | -0.142538135 | FAR1 |
| cg09607178 | 6 | 29978432 | -0.142522516 | NCRNA00171 |
| cg14858951 | 17 | 38257028 | -0.142518626 | NR1D1 |
| cg22611419 | 17 | 77070824 | 0.142517668 | ENGASE |

| | | | | |
|---|---|---|---|---|
| cg01712432 | 6 | 28480974 | -0.142512411 | GPX6 |
| cg06895436 | 8 | 82434543 | -0.142507543 | |
| cg25876975 | 15 | 77363192 | 0.142506067 | TSPAN3 |
| cg08377569 | 16 | 30538014 | 0.142502767 | ZNF768 |
| cg11399053 | 11 | 130781648 | -0.142501298 | SNX19 |
| cg08283318 | 19 | 51859473 | -0.1424988 | ETFB |
| cg23762487 | 6 | 31165673 | 0.142497893 | HCG27 |
| cg15813550 | 20 | 62221886 | -0.14249465 | GMEB2 |
| cg04792380 | 12 | 105162318 | -0.142481018 | |
| cg04383836 | 17 | 9559049 | -0.142479059 | USP43 |
| cg20632863 | 12 | 99038768 | -0.142476177 | APAF1 |
| cg10515630 | 1 | 248342467 | -0.142472392 | OR2M2 |
| cg14368881 | 9 | 21396078 | -0.142471663 | |
| cg19366591 | 1 | 92951355 | -0.142470941 | GFI1 |
| cg10772238 | 7 | 11013365 | 0.142467978 | PHF14 |
| cg10392378 | 6 | 90348606 | -0.142467808 | LYRM2 |
| cg25245266 | 22 | 38349536 | -0.142465333 | C22orf23 |
| cg05621343 | 11 | 134146253 | 0.142441131 | GLB1L3 |
| cg21926875 | 2 | 47596410 | 0.142412816 | EPCAM |
| cg08782481 | 6 | 27839916 | 0.142406517 | HIST1H3I |
| cg25406872 | 5 | 172385821 | 0.142402108 | LOC1002681( |
| cg05832051 | 19 | 54369469 | 0.142386925 | MYADM |
| cg20627546 | 1 | 1451383 | -0.142376434 | ATAD3A |
| cg15172514 | 6 | 31478236 | -0.14237425 | MICB |
| cg08485259 | 3 | 196590644 | -0.14235179 | |
| cg23917680 | 4 | 323517 | -0.142345395 | |
| cg22852134 | 11 | 71618618 | -0.142344736 | LOC10013331 |
| cg23945273 | 4 | 120987944 | 0.142343661 | MAD2L1 |
| cg21981298 | 11 | 1824157 | -0.142337353 | |
| cg04474988 | 10 | 131770171 | 0.142315488 | |
| cg01013595 | 16 | 3130324 | -0.142310554 | |
| cg26094752 | 14 | 35099088 | -0.142310546 | SNX6 |
| cg04041474 | 2 | 219187843 | 0.142308846 | PNKD |
| cg13171979 | 16 | 57497010 | -0.142303606 | POLR2C |
| cg06717289 | 15 | 75978121 | -0.14229569 | CSPG4 |
| cg19415767 | 6 | 7108058 | 0.142276348 | RREB1 |
| cg26014952 | 3 | 196366994 | -0.142237153 | LRRC33 |
| cg05712126 | 22 | 29601860 | 0.14222413 | EMID1 |
| cg01289656 | 12 | 51984945 | 0.142213782 | SCN8A |
| cg18500714 | 14 | 100706288 | -0.142201896 | YY1 |
| cg06412409 | 21 | 43426532 | -0.14219949 | ZNF295 |

Figure 18-11

| | | | | | | | | | |
|---|---|---|---|---|---|---|---|---|---|
| cg25004737 | 2 | 204209718 | -0.142197125 | ABI2 | cg04738301 | 12 | 96184580 | -0.141935596 | NTN4 |
| cg12814147 | 7 | 142375072 | -0.142192922 | | cg01204669 | 15 | 101176097 | -0.141935058 | ASB7 |
| cg27159032 | 19 | 9272145 | -0.142191574 | ZNF317 | cg04293891 | 19 | 53239200 | -0.141920287 | ZNF611 |
| cg21938149 | 5 | 107746626 | -0.142176772 | | cg27505348 | 4 | 8441964 | 0.141913942 | ACOX3 |
| cg01547051 | 7 | 150777654 | -0.142172982 | FASTK | cg11450546 | 19 | 43965012 | -0.141888269 | LYPD3 |
| cg19695335 | 20 | 25604759 | -0.142171678 | NANP | cg13406003 | 6 | 127535477 | -0.14188261 | |
| cg03027379 | 6 | 31462183 | 0.142170333 | | cg16807577 | 16 | 22019998 | 0.141871988 | C16orf52 |
| cg11427898 | 15 | 38544983 | 0.142170114 | SPRED1 | cg10260072 | 6 | 42421084 | 0.141871489 | TRERF1 |
| cg19678315 | 6 | 168760112 | -0.142165811 | | cg07244326 | 1 | 161360101 | 0.141865317 | |
| cg03797305 | 16 | 30209202 | -0.14215647 | SULT1A3 | cg16406226 | 20 | 42086458 | 0.141856851 | SFRS6 |
| cg24066601 | 6 | 26271455 | 0.14215023 | HIST1H3G | cg15072612 | 6 | 32862352 | -0.14185641 | |
| cg00531400 | 12 | 125348358 | 0.142133097 | SCARB1 | cg03324464 | 1 | 116022091 | -0.1418497 | |
| cg23322777 | 8 | 145215781 | -0.142130657 | HEATR7A | cg02759005 | 3 | 53925912 | -0.141844314 | SELK |
| cg01383268 | 17 | 71088868 | 0.142127037 | SLC39A11 | cg27272293 | 12 | 76531007 | -0.141842382 | |
| cg07478100 | 17 | 5389857 | -0.14211707 | MIS12 | cg26460378 | 19 | 36545594 | -0.141835413 | WDR62 |
| cg06695833 | 19 | 18220682 | 0.142114498 | MAST3 | cg12774559 | 11 | 68519071 | 0.141833839 | MTL5 |
| cg21840888 | 18 | 33709847 | -0.142085542 | ELP2 | cg25916505 | 18 | 32820654 | 0.141824258 | ZNF397 |
| cg24147024 | 3 | 40526345 | -0.142082431 | ZNF619 | cg00715047 | 17 | 73522054 | -0.141821991 | LLGL2 |
| cg10003974 | 7 | 47552912 | -0.142079527 | TNS3 | cg02125554 | 16 | 90238222 | -0.141816151 | |
| cg18590611 | 1 | 40745926 | -0.142075841 | ZMPSTE24 | cg16792258 | 2 | 239631449 | -0.141797001 | |
| cg14664575 | 19 | 40476624 | -0.142074211 | PSMC4 | cg26054336 | 11 | 47586799 | -0.141779422 | PTPMT1 |
| cg07636117 | 2 | 237072957 | 0.142058112 | | cg10912077 | 1 | 87794075 | -0.14177516 | LMO4 |
| cg07290865 | 4 | 187053574 | -0.142039486 | | cg20395128 | 19 | 4243436 | -0.141773642 | |
| cg13795627 | 1 | 157015873 | 0.142034642 | ARHGEF11 | cg24647506 | 10 | 130366835 | -0.141772232 | |
| cg24909975 | 6 | 160147912 | -0.14203111 | WTAP | cg08290850 | 6 | 44238228 | 0.141767615 | TMEM151B |
| cg14645856 | 6 | 18368844 | -0.142030473 | | cg23946709 | 14 | 23527317 | 0.141757281 | CDH24 |
| cg10583683 | 15 | 23034700 | -0.142022398 | NIPA2 | cg23409587 | 3 | 128840680 | 0.141754097 | RAB43 |
| cg01708236 | 6 | 44233446 | 0.142022054 | NFKBIE | cg18335034 | 6 | 31922445 | -0.141748701 | RDBP |
| cg02785793 | 19 | 16125592 | -0.142018398 | LOC126536 | cg04337618 | 16 | 777215 | 0.141742206 | HAGHL |
| cg21898708 | 6 | 31802157 | 0.142015279 | C6orf48 | cg00080118 | 6 | 31126173 | -0.141736423 | CCHCR1 |
| cg27267227 | 16 | 29888023 | 0.142015148 | SEZ6L2 | cg10977398 | 3 | 124606490 | -0.14173491 | ITGB5 |
| cg04611493 | 2 | 100863359 | -0.142013888 | | cg26973045 | 18 | 77711805 | 0.141731284 | PQLC1 |
| cg00591353 | 16 | 83670892 | 0.142012139 | CDH13 | cg15413566 | 7 | 8301971 | 0.14172299 | ICA1 |
| cg17436946 | 4 | 39699568 | 0.141994616 | UBE2K | cg26668872 | 16 | 3546216 | -0.141722347 | C16orf90 |
| cg08867249 | 12 | 9067433 | 0.141991897 | PHC1 | cg16144447 | 1 | 36184773 | 0.141718692 | C1orf216 |
| cg10831504 | 12 | 69005104 | -0.141978329 | RAP1B | cg00223042 | 2 | 65126816 | -0.141718172 | |
| cg04912466 | 11 | 63742028 | -0.1419616 | COX8A | cg14712964 | 3 | 9773672 | 0.141713337 | BRPF1 |
| cg23971381 | 11 | 58736000 | -0.141957257 | | cg21290290 | 1 | 2518275 | 0.141711404 | C1orf93 |
| cg00848394 | 3 | 52188768 | -0.141943752 | WDR51A | cg11162385 | 20 | 25604740 | -0.141705047 | NANP |
| cg13353472 | 19 | 39343117 | 0.141940595 | HNRNPL | cg10318313 | 11 | 3014937 | -0.141700008 | NAP1L4 |
| cg04515258 | 17 | 78825412 | -0.141938228 | RPTOR | cg12242204 | 11 | 62607811 | 0.141681385 | WDR74 |

Figure 18-12

| cg10637425 | 17 | 79008593 | 0.141677728 | BAIAP2 |
|---|---|---|---|---|
| cg07377675 | 1 | 62901875 | -0.141672587 | USP1 |
| cg10709925 | 3 | 149768629 | -0.141669894 | |
| cg26910867 | 11 | 68228179 | 0.141669732 | SAPS3 |
| cg13260314 | 6 | 3900192 | -0.141668974 | |
| cg15646967 | 7 | 43795266 | -0.141661539 | |
| cg21811549 | 7 | 63667594 | -0.141657689 | ZNF735 |
| cg17251379 | 20 | 55966551 | 0.141657407 | RBM38 |
| cg08120389 | 17 | 19881268 | 0.141644612 | AKAP10 |
| cg22183232 | 11 | 9406733 | -0.141639999 | IPO7 |
| cg04310649 | 10 | 35416472 | -0.141639965 | CREM |
| cg20977357 | 19 | 24184933 | -0.141634699 | |
| cg27110132 | 16 | 3661765 | -0.141628529 | BTBD12 |
| cg27084994 | 5 | 175875161 | -0.141626706 | FAF2 |
| cg07867325 | 3 | 73159953 | -0.141616613 | |
| cg01436664 | 3 | 128997925 | 0.141614884 | C3orf37 |
| cg04140754 | 12 | 124196328 | 0.141609326 | ATP6V0A2 |
| cg23411981 | 14 | 105940377 | -0.141607704 | CRIP2 |

Figure 18-13

| | | | | | | |
|---|---|---|---|---|---|---|
| A2BP1 | AKAP13 | ATOH8 | C10orf137 | C2orf60 | CCRN4L | CKAP2L |
| AASDHPPT | AKAP8 | ATP13A1 | C10orf78 | C2orf68 | CCT6P1 | CKS2 |
| AATF | AKNA | ATP1B1 | C10orf95 | C3orf18 | CCT7 | CLK1 |
| ABCA7 | ALDH3B1 | ATP1B3 | C11orf21 | C3orf21 | CD34 | CLN8 |
| ABCB9 | ALDH5A1 | ATP5C1 | C11orf34 | C3orf54 | CD44 | CLU |
| ABCD3 | ALDOA | ATP6V0E2 | C11orf41 | C3orf57 | CD58 | CMIP |
| ABCF3 | ALG12 | ATPGD1 | C11orf83 | C3orf63 | CD59 | CN5H6.4 |
| ABCG1 | ALG6 | ATR | C11orf93 | C3orf71 | CD9 | CNKSR3 |
| ABCG2 | ALKBH4 | ATRN | C12orf26 | C4orf10 | CDAN1 | CNNM2 |
| ABL1 | ALKBH5 | AVIL | C12orf61 | C4orf34 | CDC20 | CNOT6 |
| ABLIM1 | ALOX12B | AZI1 | C13orf31 | C4orf41 | CDC25A | COBRA1 |
| ABLIM2 | AMIGO1 | AZU1 | C13orf37 | C4orf48 | CDC25B | COG2 |
| ABR | AMOTL1 | B3GALNT2 | C14orf133 | C5orf24 | CDC42EP4 | COG8 |
| ABTB2 | AMT | B9D1 | C14orf138 | C5orf43 | CDC42SE2 | COL18A1 |
| ACAA1 | AMZ2 | BAHCC1 | C14orf174 | C6orf27 | CDC73 | COL23A1 |
| ACBD6 | ANK1 | BAIAP2L1 | C15orf37 | C6orf81 | CDCA4 | COL7A1 |
| ACCN3 | ANKH | BAIAP3 | C16orf13 | C7orf50 | CDH23 | COMMD3 |
| ACOT2 | ANKRD12 | BAMBI | C16orf42 | C7orf51 | CDK13 | COMMD6 |
| ACOT4 | ANKRD16 | BANP | C16orf57 | C7orf70 | CDK2AP1 | COPS8 |
| ACOT7 | ANKRD26 | BBS5 | C16orf59 | C8orf73 | CDK6 | COQ6 |
| ACP1 | ANKRD27 | BCAM | C16orf87 | C9orf106 | CDKN1B | CORO7 |
| ACSL1 | ANKRD39 | BCAP29 | C16orf89 | C9orf139 | CDKN1C | COX18 |
| ACSL3 | ANP32B | BCAS3 | C17orf42 | C9orf140 | CDNF | COX19 |
| ACTN4 | ANXA5 | BCCIP | C17orf48 | C9orf69 | CEACAM8 | COX5B |
| ACTR5 | AP2A2 | BCL2 | C17orf57 | C9orf98 | CEBPE | COX8A |
| ACVR2A | AP3B1 | BCL2L11 | C17orf59 | CA5A | CEBPG | CPEB1 |
| ADAD1 | AP3D1 | BCR | C17orf70 | CABC1 | CECR2 | CPEB3 |
| ADAL | AP3M2 | BDP1 | C17orf89 | CACNA1C | CECR4 | CPNE1 |
| ADAM10 | AP4S1 | BECN1 | C17orf91 | CACNA2D4 | CELSR1 | CPT2 |
| ADAM22 | APP | BEND3 | C17orf95 | CACYBP | CELSR3 | CR2 |
| ADAM30 | AREG | BICC1 | C17orf96 | CALHM1 | CENPA | CRADD |
| ADCY3 | ARFGAP3 | BICD1 | C18orf18 | CALHM2 | CENPN | CREB3L2 |
| ADCY4 | ARHGAP26 | BICD2 | C18orf19 | CALM2 | CEP170 | CRNKL1 |
| ADD2 | ARHGAP27 | BID | C18orf22 | CALN1 | CEP63 | CROT |
| ADHFE1 | ARHGAP5 | BLM | C18orf55 | CALR | CEP72 | CRTC2 |
| ADNP | ARHGEF3 | BMF | C19orf10 | CAMK1D | CEP78 | CRYM |
| ADORA2B | ARID1B | BMP1 | C19orf25 | CAMTA1 | CGGBP1 | CSF1 |
| ADRB2 | ARL15 | BMP8A | C19orf29 | CANX | CGRRF1 | CSGALNACT2 |
| AFF1 | ARL2 | BMPR2 | C1orf106 | CARD14 | CH25H | CSNK1E |
| AGA | ARL8A | BMS1 | C1orf124 | CATSPERG | CHCHD1 | CSNK1G3 |
| AGAP1 | ARMC8 | BOC | C1orf216 | CBFA2T3 | CHD6 | CTBP1 |
| AGPAT2 | ARNTL | BRD1 | C1orf53 | CBFB | CHEK1 | CTDP1 |
| AGPAT5 | ARPP-21 | BRD4 | C1orf59 | CCDC12 | CHERP | CTDSPL |
| AGRN | ASB1 | BRIX1 | C1orf95 | CCDC148 | CHKB | CTF1 |
| AGTRAP | ASB13 | BRP44 | C1orf97 | CCDC33 | CHKB-CPT1B | CTNS |
| AHCY | ASB6 | BRP44L | C1QL1 | CCDC40 | CHMP6 | CTPS |
| AHCYL1 | ASGR1 | BRPF1 | C1R | CCDC41 | CHN1 | CUTA |
| AHDC1 | ASXL2 | BRWD1 | C1S | CCDC6 | CHN2 | CUX1 |
| AHNAK | ATAD2 | BSN | C20orf117 | CCDC72 | CHPF2 | CUX2 |
| AIFM2 | ATF3 | BSPRY | C20orf27 | CCDC85A | CHRAC1 | CXCR1 |
| AIM1 | ATG12 | BTBD10 | C20orf43 | CCDC90A | CHSY1 | CXCR2 |
| AK2 | ATG16L2 | BTBD12 | C21orf59 | CCDC96 | CHSY3 | CXXC5 |
| AKAP1 | ATHL1 | BTNL9 | C21orf66 | CCHCR1 | CIB1 | CYB5R3 |
| AKAP10 | ATL2 | BTRC | C22orf32 | CCND3 | CITED2 | CYFIP1 |
| AKAP11 | ATL3 | BZW2 | C2orf15 | CCNL2 | CKAP2 | CYP1B1 |

Figure 19-1

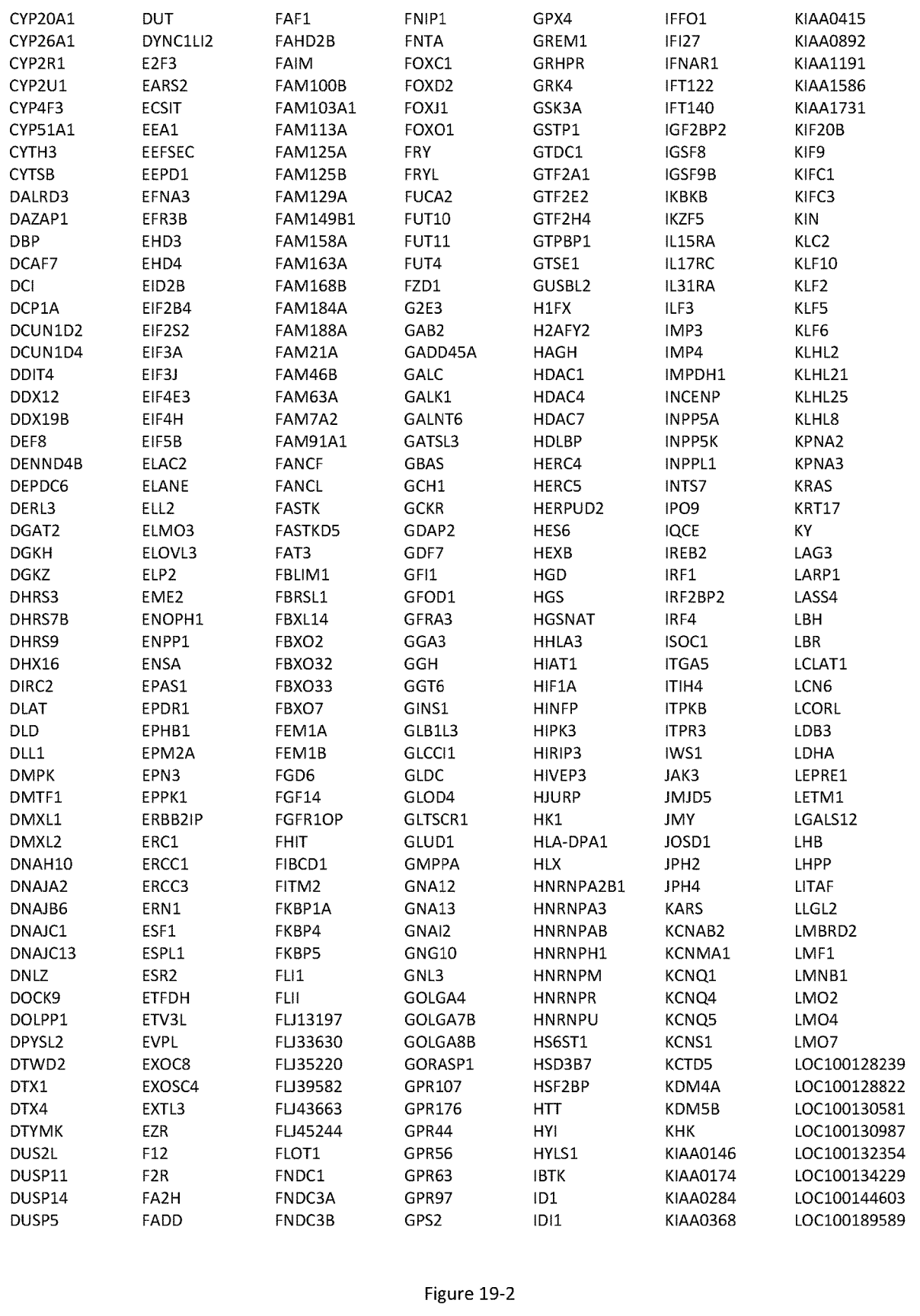

CYP20A1
CYP26A1
CYP2R1
CYP2U1
CYP4F3
CYP51A1
CYTH3
CYTSB
DALRD3
DAZAP1
DBP
DCAF7
DCI
DCP1A
DCUN1D2
DCUN1D4
DDIT4
DDX12
DDX19B
DEF8
DENND4B
DEPDC6
DERL3
DGAT2
DGKH
DGKZ
DHRS3
DHRS7B
DHRS9
DHX16
DIRC2
DLAT
DLD
DLL1
DMPK
DMTF1
DMXL1
DMXL2
DNAH10
DNAJA2
DNAJB6
DNAJC1
DNAJC13
DNLZ
DOCK9
DOLPP1
DPYSL2
DTWD2
DTX1
DTX4
DTYMK
DUS2L
DUSP11
DUSP14
DUSP5
DUT
DYNC1LI2
E2F3
EARS2
ECSIT
EEA1
EEFSEC
EEPD1
EFNA3
EFR3B
EHD3
EHD4
EID2B
EIF2B4
EIF2S2
EIF3A
EIF3J
EIF4E3
EIF4H
EIF5B
ELAC2
ELANE
ELL2
ELMO3
ELOVL3
ELP2
EME2
ENOPH1
ENPP1
ENSA
EPAS1
EPDR1
EPHB1
EPM2A
EPN3
EPPK1
ERBB2IP
ERC1
ERCC1
ERCC3
ERN1
ESF1
ESPL1
ESR2
ETFDH
ETV3L
EVPL
EXOC8
EXOSC4
EXTL3
EZR
F12
F2R
FA2H
FADD
FAF1
FAHD2B
FAIM
FAM100B
FAM103A1
FAM113A
FAM125A
FAM125B
FAM129A
FAM149B1
FAM158A
FAM163A
FAM168B
FAM184A
FAM188A
FAM21A
FAM46B
FAM63A
FAM7A2
FAM91A1
FANCF
FANCL
FASTK
FASTKD5
FAT3
FBLIM1
FBRSL1
FBXL14
FBXO2
FBXO32
FBXO33
FBXO7
FEM1A
FEM1B
FGD6
FGF14
FGFR1OP
FHIT
FIBCD1
FITM2
FKBP1A
FKBP4
FKBP5
FLI1
FLII
FLJ13197
FLJ33630
FLJ35220
FLJ39582
FLJ43663
FLJ45244
FLOT1
FNDC1
FNDC3A
FNDC3B
FNIP1
FNTA
FOXC1
FOXD2
FOXJ1
FOXO1
FRY
FRYL
FUCA2
FUT10
FUT11
FUT4
FZD1
G2E3
GAB2
GADD45A
GALC
GALK1
GALNT6
GATSL3
GBAS
GCH1
GCKR
GDAP2
GDF7
GFI1
GFOD1
GFRA3
GGA3
GGH
GGT6
GINS1
GLB1L3
GLCCI1
GLDC
GLOD4
GLTSCR1
GLUD1
GMPPA
GNA12
GNA13
GNAI2
GNG10
GNL3
GOLGA4
GOLGA7B
GOLGA8B
GORASP1
GPR107
GPR176
GPR44
GPR56
GPR63
GPR97
GPS2
GPX4
GREM1
GRHPR
GRK4
GSK3A
GSTP1
GTDC1
GTF2A1
GTF2E2
GTF2H4
GTPBP1
GTSE1
GUSBL2
H1FX
H2AFY2
HAGH
HDAC1
HDAC4
HDAC7
HDLBP
HERC4
HERC5
HERPUD2
HES6
HEXB
HGD
HGS
HGSNAT
HHLA3
HIAT1
HIF1A
HINFP
HIPK3
HIRIP3
HIVEP3
HJURP
HK1
HLA-DPA1
HLX
HNRNPA2B1
HNRNPA3
HNRNPAB
HNRNPH1
HNRNPM
HNRNPR
HNRNPU
HS6ST1
HSD3B7
HSF2BP
HTT
HYI
HYLS1
IBTK
ID1
IDI1
IFFO1
IFI27
IFNAR1
IFT122
IFT140
IGF2BP2
IGSF8
IGSF9B
IKBKB
IKZF5
IL15RA
IL17RC
IL31RA
ILF3
IMP3
IMP4
IMPDH1
INCENP
INPP5A
INPP5K
INPPL1
INTS7
IPO9
IQCE
IREB2
IRF1
IRF2BP2
IRF4
ISOC1
ITGA5
ITIH4
ITPKB
ITPR3
IWS1
JAK3
JMJD5
JMY
JOSD1
JPH2
JPH4
KARS
KCNAB2
KCNMA1
KCNQ1
KCNQ4
KCNQ5
KCNS1
KCTD5
KDM4A
KDM5B
KHK
KIAA0146
KIAA0174
KIAA0284
KIAA0368
KIAA0415
KIAA0892
KIAA1191
KIAA1586
KIAA1731
KIF20B
KIF9
KIFC1
KIFC3
KIN
KLC2
KLF10
KLF2
KLF5
KLF6
KLHL2
KLHL21
KLHL25
KLHL8
KPNA2
KPNA3
KRAS
KRT17
KY
LAG3
LARP1
LASS4
LBH
LBR
LCLAT1
LCN6
LCORL
LDB3
LDHA
LEPRE1
LETM1
LGALS12
LHB
LHPP
LITAF
LLGL2
LMBRD2
LMF1
LMNB1
LMO2
LMO4
LMO7
LOC100128239
LOC100128822
LOC100130581
LOC100130987
LOC100132354
LOC100134229
LOC100144603
LOC100189589

Figure 19-2

LOC100270710
LOC151534
LOC153684
LOC202181
LOC253724
LOC25845
LOC283404
LOC284023
LOC284837
LOC285830
LOC389033
LOC401431
LOC647121
LOC728264
LOC728411
LOC730755
LOC93622
LOXHD1
LPAR1
LPAR5
LRBA
LRP5
LRRC26
LRRC28
LRRC3
LRRC56
LRRC8A
LRRC8D
LRRFIP2
LSP1
LUC7L3
LYPLA1
LYRM4
LYST
LZTS2
MACF1
MACROD1
MAD2L1BP
MAEA
MAFF
MAFG
MAG
Magmas
MAN2A1
MAN2C1
MANF
MAP3K1
MAP3K11
MAP3K12
MAP3K3
MAP3K6
MAP3K8
MAP6
MAPK1
MAPK11
MAPK1IP1L
MAPKAPK2
MAPKBP1
MARCO
MARK2
MARK3
MAT2A
MBLAC2
MCAM
MCC
MCCC2
MCF2L
MCF2L2
MCM2
MCM5
MCM6
MCM7
MCM8
MDGA1
MDH2
MDK
MDN1
MED12L
MEN1
MESDC1
METAP1
METTL9
MEX3C
MFSD1
MFSD3
MFSD4
MGA
MGAT5B
MGRN1
MIB2
MICAL2
MIR146B
MIR17HG
MIR191
MIR24-2
MIRLET7I
MIS12
MKRN2
MLLT1
MMAB
MMRN2
MOGS
MORN1
MORN2
MPG
MPHOSPH6
MPO
MPRIP
MPV17L2
MRP63
MRPL20
MRPS24
MRS2
MSH3
MSL2
MTERFD1
MTHFD1L
MTHFD2
MTIF3
MTMR10
MTO1
MTRF1L
MTX1
MUM1
MUTYH
MX1
MXD3
MYBL1
MYL12B
MYO15A
MYST2
N4BP2
N6AMT2
NAA35
NAAA
NADK
NANP
NAP1L4
NARF
NBPF1
NCAPG
NCBP2
NCK1
NCKAP5L
NCL
NCOA5
NCOR1
NCOR2
NCRNA00115
NDFIP1
NDUFA10
NDUFA6
NDUFAF2
NDUFS2
NDUFS6
NDUFV1
NEIL3
NEK11
NEK3
NEK9
NEO1
NEURL
NF2
NFIC
NFKB1
NFKBIA
NGLY1
NHLRC4
NHP2L1
NHSL1
NID2
NIPA2
NIPSNAP3B
NKIRAS1
NLGN2
NOB1
NOL7
NOM1
NOSTRIN
NPAT
NPC2
NPHP4
NPLOC4
NR1H2
NR1H3
NRSN2
NRXN2
NSMAF
NT5DC1
NTN1
NTN3
NTN4
NUBP2
NUDT16L1
NUDT3
NUDT4
NUDT6
NUP153
NUP210
NXT1
OAS2
OAT
OAZ1
OCIAD1
OGFRL1
ORAOV1
ORC6L
OSBPL1A
OSBPL5
OSCAR
OTUD4
OTUD7B
P2RX4
P2RY2
P4HB
PABPC1
PANK4
PANX1
PAOX
PAQR7
PARD3B
PARP12
PARP8
PARVB
PAXIP1
PBX3
PCGF1
PCID2
PCK2
PCM1
PCMT1
PCNT
PCSK7
PDCD11
PDCD5
PDE3B
PDIA4
PDIK1L
PDP2
PDPK1
PDS5B
PDXDC1
PDXK
PEBP1
PEBP4
PECI
PER2
PFKL
PGAP2
PGD
PGLYRP4
PGM1
PGP
PGS1
PHACTR3
PHC2
PHF15
PHKG1
PHLDA1
PHLPP1
PIGY
PILRB
PIM3
PITPNB
PITPNC1
PKD1
PKIG
PKM2
PKNOX1
PKNOX2
PLAUR
PLBD2
PLCL1
PLD1
PLEC1
PLEKHA6
PLEKHG3
PLEKHG6
PLEKHO1
PLK4
PLXNA2
PMS2L2
PNN
PNPLA8
POGK
POLR1B
POM121L2
POU2F1
PPARA
PPARGC1B
PPBPL1
PPHLN1
PPIF
PPIL2
PPIL4
PPP1CC
PPP1R12C
PPP1R14B
PPP1R7
PPP1R9B
PPP2R2A
PPP2R2B
PPP2R3C
PPP3CA
PPP4C
PPPDE1
PRDM14
PRDM15
PRDM2
PRDX1
PRDX6
PREP
PRICKLE1
PRKAG2
PRKCA
PRKD2
PROSC
PRPF8
PRR3
PRRX2
PRSS8
PRTN3
PSD4
PSMB9
PSMD1
PSMD11
PSMD6
PSMG1
PSMG2
PSPC1
PTAFR
PTCH2
PTDSS2
PTEN
PTGER2
PTGER4
PTGS1
PTK2B
PTPN23
PTPN5
PTPRE
PTRH1
PTTG1
PUF60
PUM1
PUSL1
PVRL3
PVRL4
PWWP2A
PXMP2
PXMP3
PXN
PYCR2
QKI
QPCTL
QPRT
QRICH1
RAB10
RAB11FIP3
RAB11FIP4
RAB12
RAB32
RAB5C
RAD23A
RAET1K
RAGE
RAI1
RALB
RALGAPB
RALY
RANBP2
RAP1B
RAP1GDS1
RAP2B
RAPH1
RASA1
RASA3
RASGEF1B
RASSF1
RASSF10
RASSF4
RB1CC1
RBBP6
RBM14
RBX1

Figure 19-3

RCAN3
RCOR1
RDH10
RDH13
REEP3
RELT
REPS1
RET
REV3L
RFC4
RFTN1
RFWD2
RGS17
RGS6
RHOB
RHOF
RICTOR
RILPL1
RNASE12
RNASE2
RNASEH2B
RNF11
RNF126
RNF14
RNF149
RNF168
RNF187
RNF4
RNF8
RNH1
RNU5E
ROGDI
RORA
RP5-1022P6.2
RPAIN
RPL10A
RPLP0
RPP40
RPS11
RPS15
RPS21
RPS3A
RPTOR
RPUSD1
RRAGC
RRBP1
RREB1
RRN3P3
RRS1
RTKN
RTTN
RUFY2
RUNX3
RUSC1
RWDD1
RXRA
S100A11
S1PR4
SACM1L
SAMD13
SAMD4A
SAP130
SARS
SAV1
SBNO2
SC65
SCAMP1
SCAMP4
SCAND1
SCARF1
SCD
SCLY
SCN2B
SCN8A
SCT
SDCBP
SDCBP2
SEC1
SEC23B
SEC31A
SEC31B
SEMA4C
SEMA5B
SENP2
SENP3
SEPHS1
SERBP1
SERPINB13
SESN3
SETD2
SETD3
SETD7
SETD8
SF3A1
SFMBT1
SFMBT2
SFRS2IP
SFRS4
SFRS8
SFXN5
SGCE
SGK1
SGK196
SGMS2
SGSM3
SH3D20
SH3GL1
SHC1
SIDT1
SIGLEC9
SIK3
SIKE1
SILV
SIM2
SIN3A
SIRT2
SIT1
SIVA1
SKA1
SKI
SLC11A2
SLC12A9
SLC16A1
SLC16A3
SLC1A5
SLC22A18AS
SLC22A4
SLC25A13
SLC25A16
SLC25A18
SLC25A29
SLC25A4
SLC25A42
SLC26A2
SLC27A1
SLC27A3
SLC2A1
SLC2A11
SLC2A6
SLC33A1
SLC35E1
SLC35F1
SLC36A4
SLC37A3
SLC39A4
SLC43A2
SLC45A4
SLC46A2
SLC46A3
SLC6A6
SLC7A5
SLC7A6
SLC7A7
SLFN12L
SMAD4
SMARCA4
SMCR5
SMCR7
SMPD4
SNAPC2
SNCG
SND1
SNHG12
SNHG7
SNHG9
SNORA30
SNRPA1
SNRPF
SNX10
SNX14
SNX17
SNX20
SNX24
SP4
SPAG4
SPATA13
SPATA20
SPCS3
SPEN
SPOPL
SPTBN5
SREBF1
SREBF2
SRF
SRGAP3
SRRT
SS18
SS18L1
SSB
SSH3
ST3GAL2
ST6GALNAC4
STARD5
STARD7
STARD9
STAT5A
STIM2
STK17B
STK36
STRADB
STX1B
STYXL1
SUGT1L1
SUSD1
SYF2
SYNGR2
SYNJ2
SYNPO
TAF15
TAF4
TAP2
TBC1D10B
TBC1D14
TBCD
TCEA2
TCEA3
TCF12
TCF25
TCF7L1
TCN2
TCTA
TEAD3
TECPR1
TENC1
TERF2
TES
TGFB3
TGFBI
TGFBR1
THAP11
THBS1
THRA
TIGD3
TIMM13
TIMM22
TIMP2
TJP2
TLE3
TM2D3
TMCC3
TMEM105
TMEM127
TMEM146
TMEM14B
TMEM150A
TMEM175
TMEM18
TMEM2
TMEM201
TMEM22
TMEM231
TMEM43
TMEM64
TMEM65
TMEM79
TMEM93
TMEM9B
TMTC4
TNFAIP3
TNPO1
TOB2
TOLLIP
TOMM40
TOMM5
TOP3A
TRA2A
TRAM1
TRAM2
TRANK1
TRAPPC3
TRIM17
TRIM25
TRIM26
TRIM27
TRIM28
TRIM33
TRIM37
TRIM52
TRIM59
TRIM7
TRIM71
TROVE2
TRPV4
TSEN2
TSKU
TSPAN18
TSTD2
TTC15
TTC30A
TTC36
TTC7B
TTLL1
TTLL4
TUBA1B
TUBA3E
TUBG2
TUBGCP2
TUBGCP3
TUBGCP6
TUFM
TUSC2
TXLNA
TXNDC12
TXNDC15
TXNDC16
TYK2
TYMS
U2AF1
U2AF2
UBE2E2
UBE2J2
UBE2L3
UBE3A
UBLCP1
UHRF1BP1
UIMC1
UNC45A
UQCR
URB2
USP1
USP14
USP21
USP3
USP36
USP38
USP39
USP46
UVRAG
VAPA
VAV2
VDR
VKORC1
VPS13C
VPS16
VPS29
VPS52
VRK1
VTI1B
VTRNA1-3
VWA1
VWCE
WDFY2
WDR27
WDR4
WDR51B
WDR60
WDR76
WDR81
WHAMM
WHAMML1
WNT3
WNT5A
WRNIP1
WSCD2
WTAP
XRN2
YAF2
YARS
YIF1A
YIPF2
YPEL3
YTHDF3
YWHAH
YWHAQ
YY1
ZADH2
ZBP1
ZBTB1
ZBTB16
ZBTB2
ZBTB25
ZBTB4
ZBTB42
ZBTB48
ZBTB7B
ZC3H12C
ZC3H18
ZC3H6
ZCCHC10
ZCCHC2
ZDHHC3
ZDHHC5
ZEB2
ZFHX3
ZFP161

Figure 19-4

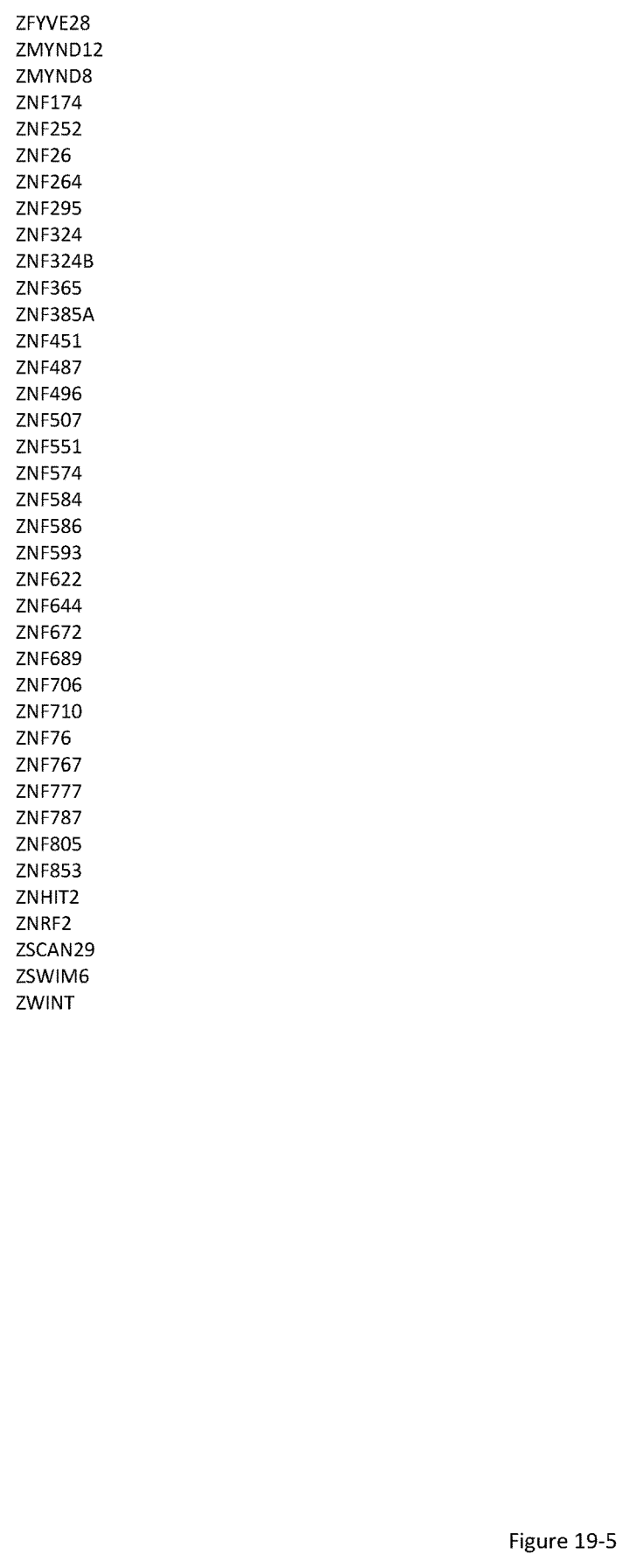

ZFYVE28
ZMYND12
ZMYND8
ZNF174
ZNF252
ZNF26
ZNF264
ZNF295
ZNF324
ZNF324B
ZNF365
ZNF385A
ZNF451
ZNF487
ZNF496
ZNF507
ZNF551
ZNF574
ZNF584
ZNF586
ZNF593
ZNF622
ZNF644
ZNF672
ZNF689
ZNF706
ZNF710
ZNF76
ZNF767
ZNF777
ZNF787
ZNF805
ZNF853
ZNHIT2
ZNRF2
ZSCAN29
ZSWIM6
ZWINT

Figure 19-5

| Illumina Probe | Chr | Mapinfo | Correlation | Gene |
|---|---|---|---|---|
| cg09099697 | 10 | 65281856 | -0.193379401 | REEP3 |
| cg19679281 | 2 | 58468512 | -0.185685097 | FANCL |
| cg25840850 | 2 | 237994627 | -0.185054516 | COPS8 |
| cg08503002 | 3 | 183903768 | -0.184334999 | ABCF3 |
| cg15147060 | 3 | 88108213 | -0.181815672 | CGGBP1 |
| cg07249227 | 21 | 43430503 | -0.178346706 | ZNF295 |
| cg14157244 | 2 | 170655474 | -0.175330946 | SSB |
| cg25072436 | 2 | 30454560 | -0.174710628 | LBH |
| cg10122474 | 14 | 88459471 | -0.173252955 | GALC |
| cg01493617 | 17 | 79650915 | -0.172916428 | HGS |
| cg14167673 | 15 | 63796729 | -0.172333193 | USP3 |
| cg18845832 | 1 | 184943573 | -0.171089644 | FAM129A |
| cg14092529 | 5 | 21459600 | -0.171049555 | LOC728411 |
| cg18022279 | 1 | 231473268 | -0.170919895 | C1orf124 |
| cg20366603 | 17 | 7218821 | -0.17014871 | GPS2 |
| cg07852756 | 4 | 152021104 | -0.169669026 | RPS3A |
| cg00477061 | 18 | 77794585 | -0.169560714 | C18orf22 |
| cg01910197 | 22 | 35796030 | -0.169135137 | MCM5 |
| cg20116574 | 20 | 44718168 | -0.169087579 | NCOA5 |
| cg09531225 | 4 | 82393079 | -0.169005298 | RASGEF1B |
| cg04396495 | 5 | 60626910 | -0.168951894 | ZSWIM6 |
| cg17813364 | 7 | 149321879 | -0.168877571 | ZNF767 |
| cg01446164 | 11 | 2421746 | -0.168532183 | |
| cg14374980 | 8 | 29397161 | 0.167331051 | |
| cg09730697 | 2 | 96931861 | -0.16727242 | TMEM127 |
| cg06753281 | 1 | 6086652 | -0.167253216 | KCNAB2 |
| cg02276695 | 19 | 19774628 | -0.166913495 | ATP13A1 |
| cg26223989 | 18 | 60189751 | -0.166720544 | ZCCHC2 |
| cg05907029 | 1 | 197872227 | -0.165768203 | C1orf53 |
| cg25937832 | 3 | 23958525 | -0.165467301 | NKIRAS1 |
| cg17019204 | 6 | 86303781 | -0.165254339 | SNX14 |
| cg25371036 | 11 | 94500749 | 0.165007581 | AMOTL1 |
| cg10391629 | 13 | 42846072 | -0.164969318 | AKAP11 |
| cg11075316 | 3 | 160167725 | -0.164835814 | TRIM59 |
| cg04613791 | 20 | 1373260 | -0.164725767 | FKBP1A |
| cg21545849 | 20 | 40247209 | -0.164421404 | CHD6 |
| cg09185754 | 10 | 1095081 | -0.164167608 | IDI1 |
| cg08925142 | 4 | 18023851 | -0.163893057 | LCORL |
| cg17329534 | 1 | 154980743 | 0.163804997 | ZBTB7B |
| cg07730301 | 11 | 67777952 | 0.163310193 | ALDH3B1 |

| Illumina Probe | Chr | Mapinfo | Correlation | Gene |
|---|---|---|---|---|
| cg05639842 | 21 | 43639440 | -0.163110259 | ABCG1 |
| cg00911981 | 3 | 142297824 | -0.16303639 | ATR |
| cg04875007 | 16 | 2014871 | -0.162049943 | SNHG9 |
| cg10122932 | 7 | 99698990 | -0.161865279 | MCM7 |
| cg09089230 | 17 | 1588195 | -0.161658514 | PRPF8 |
| cg17491846 | 19 | 19431584 | -0.161623054 | KIAA0892 |
| cg09693228 | 4 | 2965311 | -0.161609044 | GRK4 |
| cg13875899 | 6 | 5004148 | -0.161551284 | RPP40 |
| cg10035432 | 14 | 39644345 | -0.161504145 | PNN |
| cg00329447 | 8 | 145028170 | 0.16145763 | PLEC1 |
| cg07326074 | 16 | 2510388 | -0.161334732 | C16orf59 |
| cg22929219 | 22 | 35796023 | -0.161015227 | MCM5 |
| cg19594691 | 2 | 20646743 | -0.160915427 | RHOB |
| cg23635560 | 2 | 27473369 | 0.160806621 | |
| cg09682913 | 2 | 30455589 | -0.160789982 | LBH |
| cg16643542 | 19 | 827843 | 0.160786219 | AZU1 |
| cg03754076 | 1 | 232766254 | -0.160692897 | |
| cg21122725 | 4 | 123843781 | -0.16062274 | NUDT6 |
| cg21120249 | 9 | 139921971 | 0.160105625 | C9orf139 |
| cg24919790 | 10 | 90967918 | -0.160034928 | CH25H |
| cg20966828 | 9 | 74384075 | -0.160020427 | TMEM2 |
| cg22094042 | 11 | 450123 | -0.159993886 | PTDSS2 |
| cg18565702 | 13 | 113241891 | -0.15987487 | TUBGCP3 |
| cg23474794 | 1 | 182584178 | -0.159554489 | |
| cg09537354 | 17 | 19266363 | -0.159538084 | B9D1 |
| cg24275354 | 2 | 240964415 | -0.159497264 | NDUFA10 |
| cg02787772 | 8 | 26435434 | -0.159492158 | DPYSL2 |
| cg11198734 | 3 | 53381585 | -0.159099556 | DCP1A |
| cg08308556 | 6 | 157342734 | -0.158975294 | ARID1B |
| cg10849092 | 15 | 40574697 | -0.158964065 | |
| cg19764539 | 21 | 44394723 | -0.158881867 | PKNOX1 |
| cg05884522 | 6 | 13615538 | -0.158869514 | NOL7 |
| cg08439468 | 9 | 95526812 | -0.158781541 | BICD2 |
| cg21610516 | 6 | 151186758 | -0.1587097 | MTHFD1L |
| cg23962478 | 22 | 50354086 | -0.158709561 | PIM3 |
| cg14931122 | 17 | 20059106 | -0.15870089 | CYTSB |
| cg07006042 | 3 | 141595655 | -0.158690134 | ATP1B3 |
| cg00126034 | 17 | 44896162 | -0.158665168 | WNT3 |
| cg04891053 | 1 | 161053558 | 0.158627481 | PVRL4 |
| cg24909975 | 6 | 160147912 | -0.158614432 | WTAP |

Figure 20-1

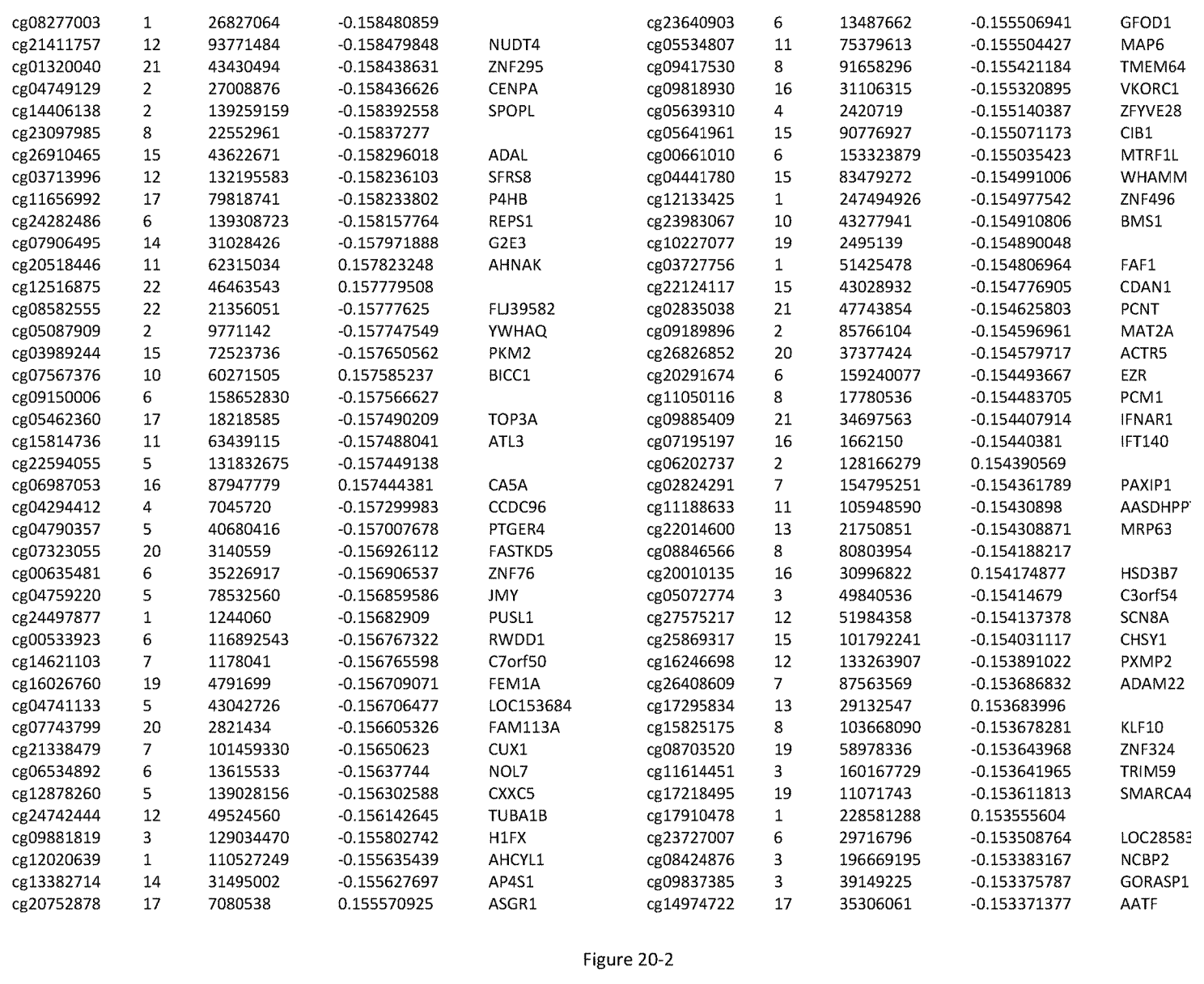

| | | | | |
|---|---|---|---|---|
| cg08277003 | 1 | 26827064 | -0.158480859 | |
| cg21411757 | 12 | 93771484 | -0.158479848 | NUDT4 |
| cg01320040 | 21 | 43430494 | -0.158438631 | ZNF295 |
| cg04749129 | 2 | 27008876 | -0.158436626 | CENPA |
| cg14406138 | 2 | 139259159 | -0.158392558 | SPOPL |
| cg23097985 | 8 | 22552961 | -0.15837277 | |
| cg26910465 | 15 | 43622671 | -0.158296018 | ADAL |
| cg03713996 | 12 | 132195583 | -0.158236103 | SFRS8 |
| cg11656992 | 17 | 79818741 | -0.158233802 | P4HB |
| cg24282486 | 6 | 139308723 | -0.158157764 | REPS1 |
| cg07906495 | 14 | 31028426 | -0.157971888 | G2E3 |
| cg20518446 | 11 | 62315034 | 0.157823248 | AHNAK |
| cg12516875 | 22 | 46463543 | 0.157779508 | |
| cg08582555 | 22 | 21356051 | -0.15777625 | FLJ39582 |
| cg05087909 | 2 | 9771142 | -0.157747549 | YWHAQ |
| cg03989244 | 15 | 72523736 | -0.157650562 | PKM2 |
| cg07567376 | 10 | 60271505 | 0.157585237 | BICC1 |
| cg09150006 | 6 | 158652830 | -0.157566627 | |
| cg05462360 | 17 | 18218585 | -0.157490209 | TOP3A |
| cg15814736 | 11 | 63439115 | -0.157488041 | ATL3 |
| cg22594055 | 5 | 131832675 | -0.157449138 | |
| cg06987053 | 16 | 87947779 | 0.157444381 | CA5A |
| cg04294412 | 4 | 7045720 | -0.157299983 | CCDC96 |
| cg04790357 | 5 | 40680416 | -0.157007678 | PTGER4 |
| cg07323055 | 20 | 3140559 | -0.156926112 | FASTKD5 |
| cg00635481 | 6 | 35226917 | -0.156906537 | ZNF76 |
| cg04759220 | 5 | 78532560 | -0.156859586 | JMY |
| cg24497877 | 1 | 1244060 | -0.15682909 | PUSL1 |
| cg00533923 | 6 | 116892543 | -0.156767322 | RWDD1 |
| cg14621103 | 7 | 1178041 | -0.156765598 | C7orf50 |
| cg16026760 | 19 | 4791699 | -0.156709071 | FEM1A |
| cg04741133 | 5 | 43042726 | -0.156706477 | LOC153684 |
| cg07743799 | 20 | 2821434 | -0.156605326 | FAM113A |
| cg21338479 | 7 | 101459330 | -0.15650623 | CUX1 |
| cg06534892 | 6 | 13615533 | -0.15637744 | NOL7 |
| cg12878260 | 5 | 139028156 | -0.156302588 | CXXC5 |
| cg24742444 | 12 | 49524560 | -0.156142645 | TUBA1B |
| cg09881819 | 3 | 129034470 | -0.155802742 | H1FX |
| cg12020639 | 1 | 110527249 | -0.155635439 | AHCYL1 |
| cg13382714 | 14 | 31495002 | -0.155627697 | AP4S1 |
| cg20752878 | 17 | 7080538 | 0.155570925 | ASGR1 |

| | | | | |
|---|---|---|---|---|
| cg23640903 | 6 | 13487662 | -0.155506941 | GFOD1 |
| cg05534807 | 11 | 75379613 | -0.155504427 | MAP6 |
| cg09417530 | 8 | 91658296 | -0.155421184 | TMEM64 |
| cg09818930 | 16 | 31106315 | -0.155320895 | VKORC1 |
| cg05639310 | 4 | 2420719 | -0.155140387 | ZFYVE28 |
| cg05641961 | 15 | 90776927 | -0.155071173 | CIB1 |
| cg00661010 | 6 | 153323879 | -0.155035423 | MTRF1L |
| cg04441780 | 15 | 83479272 | -0.154991006 | WHAMM |
| cg12133425 | 1 | 247494926 | -0.154977542 | ZNF496 |
| cg23983067 | 10 | 43277941 | -0.154910806 | BMS1 |
| cg10227077 | 19 | 2495139 | -0.154890048 | |
| cg03727756 | 1 | 51425478 | -0.154806964 | FAF1 |
| cg22124117 | 15 | 43028932 | -0.154776905 | CDAN1 |
| cg02835038 | 21 | 47743854 | -0.154625803 | PCNT |
| cg09189896 | 2 | 85766104 | -0.154596961 | MAT2A |
| cg26826852 | 20 | 37377424 | -0.154579717 | ACTR5 |
| cg20291674 | 6 | 159240077 | -0.154493667 | EZR |
| cg11050116 | 8 | 17780536 | -0.154483705 | PCM1 |
| cg09885409 | 21 | 34697563 | -0.154407914 | IFNAR1 |
| cg07195197 | 16 | 1662150 | -0.15440381 | IFT140 |
| cg06202737 | 2 | 128166279 | 0.154390569 | |
| cg02824291 | 7 | 154795251 | -0.154361789 | PAXIP1 |
| cg11188633 | 11 | 105948590 | -0.15430898 | AASDHPP |
| cg22014600 | 13 | 21750851 | -0.154308871 | MRP63 |
| cg08846566 | 8 | 80803954 | -0.154188217 | |
| cg20010135 | 16 | 30996822 | 0.154174877 | HSD3B7 |
| cg05072774 | 3 | 49840536 | -0.15414679 | C3orf54 |
| cg27575217 | 12 | 51984358 | -0.154137378 | SCN8A |
| cg25869317 | 15 | 101792241 | -0.154031117 | CHSY1 |
| cg16246698 | 12 | 133263907 | -0.153891022 | PXMP2 |
| cg26408609 | 7 | 87563569 | -0.153686832 | ADAM22 |
| cg17295834 | 13 | 29132547 | 0.153683996 | |
| cg15825175 | 8 | 103668090 | -0.153678281 | KLF10 |
| cg08703520 | 19 | 58978336 | -0.153643968 | ZNF324 |
| cg11614451 | 3 | 160167729 | -0.153641965 | TRIM59 |
| cg17218495 | 19 | 11071743 | -0.153611813 | SMARCA4 |
| cg17910478 | 1 | 228581288 | 0.153555604 | |
| cg23727007 | 6 | 29716796 | -0.153508764 | LOC28583 |
| cg08424876 | 3 | 196669195 | -0.153383167 | NCBP2 |
| cg09837385 | 3 | 39149225 | -0.153375787 | GORASP1 |
| cg14974722 | 17 | 35306061 | -0.153371377 | AATF |

Figure 20-2

| | | | | | | | | | |
|---|---|---|---|---|---|---|---|---|---|
| cg14397361 | 9 | 140149997 | -0.153309057 | COBRA1 | cg04123995 | 17 | 71308339 | -0.150918461 | CDC42EP4 |
| cg06123753 | 2 | 60593185 | 0.153281414 | | cg16859906 | 16 | 68298978 | -0.150914093 | SLC7A6 |
| cg16710791 | 1 | 193028559 | -0.153267263 | TROVE2 | cg11204983 | 6 | 82957301 | -0.150911872 | IBTK |
| cg18221226 | 12 | 124997487 | 0.153261211 | NCOR2 | cg07642705 | 16 | 2014817 | -0.150831191 | SNHG9 |
| cg17727929 | 21 | 38069338 | -0.153254996 | | cg23092788 | 4 | 949558 | 0.150827511 | TMEM175 |
| cg00232265 | 5 | 1814816 | -0.153252737 | NDUFS6 | cg23706268 | 13 | 51484060 | -0.150779916 | RNASEH2B |
| cg00248174 | 10 | 43600239 | -0.153169685 | RET | cg01025283 | 3 | 138327728 | -0.15077408 | FAIM |
| cg02249648 | 12 | 1703181 | -0.153117313 | FBXL14 | cg17978996 | 6 | 107436496 | -0.150653997 | BEND3 |
| cg05501276 | 7 | 23571514 | -0.152912497 | TRA2A | cg15901997 | 18 | 48723744 | -0.150636021 | MEX3C |
| cg05468351 | 5 | 21459598 | -0.152911507 | LOC728411 | cg12570942 | 2 | 242626270 | -0.150572219 | DTYMK |
| cg12922931 | 21 | 33984727 | -0.152902343 | C21orf59 | cg14945578 | 20 | 3776324 | -0.150567537 | CDC25B |
| cg24395307 | 7 | 39990042 | -0.152765999 | CDK13 | cg24640588 | 4 | 1283718 | -0.150530252 | MAEA |
| cg06912282 | 1 | 1563001 | 0.152708218 | MIB2 | cg19804488 | 17 | 73760363 | 0.150502464 | GALK1 |
| cg01943813 | 6 | 24495061 | -0.152647113 | ALDH5A1 | cg01102854 | 11 | 63605717 | 0.150488304 | MARK2 |
| cg16007497 | 4 | 74713356 | 0.152454835 | PPBPL1 | cg22043361 | 14 | 64970199 | -0.15047175 | ZBTB1 |
| cg10786622 | 6 | 17706560 | -0.152409545 | NUP153 | cg16971831 | 5 | 56110935 | -0.150460325 | MAP3K1 |
| cg11075994 | 15 | 102192790 | -0.152309844 | TM2D3 | cg22332388 | 8 | 64081173 | -0.150359955 | YTHDF3 |
| cg12133664 | 12 | 94217493 | 0.152046022 | CRADD | cg26541587 | 10 | 43950885 | -0.150328936 | ZNF487 |
| cg05669853 | 6 | 107435226 | 0.152011974 | BEND3 | cg24085655 | 6 | 35436189 | -0.150295392 | RPL10A |
| cg17626178 | 2 | 205410273 | -0.151976152 | PARD3B | cg15818008 | 11 | 112126170 | 0.15028977 | C11orf34 |
| cg08884209 | 5 | 73981306 | -0.151931335 | HEXB | cg15684661 | 5 | 1795014 | 0.150277861 | |
| cg26337430 | 1 | 43232221 | -0.151895538 | LEPRE1 | cg16395133 | 6 | 150326394 | -0.150241954 | RAET1K |
| cg06478398 | 19 | 1479426 | -0.151864871 | C19orf25 | cg20890156 | 8 | 53627208 | -0.150238928 | RB1CC1 |
| cg18455653 | 20 | 17662865 | -0.151859378 | RRBP1 | cg10414829 | 10 | 88719259 | 0.15017174 | SNCG |
| cg10338848 | 16 | 7701595 | 0.151809987 | A2BP1 | cg21753290 | 20 | 37376903 | -0.150140034 | ACTR5 |
| cg25609649 | 2 | 19547730 | -0.151784709 | | cg02043083 | 6 | 150070997 | -0.150111476 | PCMT1 |
| cg19847945 | 17 | 60783784 | 0.151708191 | 10-Mar | cg02006147 | 2 | 74734710 | -0.150089989 | PCGF1 |
| cg06764670 | 1 | 110052490 | -0.151705335 | AMIGO1 | cg01049274 | 8 | 146228340 | -0.150047572 | ZNF252 |
| cg11967952 | 1 | 52498983 | -0.151696194 | TXNDC12 | cg16811230 | 3 | 39149235 | -0.149965796 | GORASP1 |
| cg08096946 | 3 | 122514224 | -0.151585448 | DIRC2 | cg18613834 | 7 | 65215902 | -0.149929372 | CCT6P1 |
| cg02357725 | 15 | 75932598 | -0.151580256 | IMP3 | cg24781737 | 11 | 66034681 | 0.149919889 | KLC2 |
| cg05180153 | 19 | 11039414 | -0.15157422 | YIPF2 | cg18199720 | 1 | 115054041 | -0.149877242 | TRIM33 |
| cg24298255 | 19 | 58280994 | -0.151430693 | ZNF586 | cg04081402 | 22 | 31003587 | 0.149871454 | TCN2 |
| cg03647327 | 6 | 28891109 | -0.151357238 | TRIM27 | cg02631957 | 5 | 122847966 | -0.149774738 | CSNK1G3 |
| cg04410161 | 6 | 116892488 | -0.151305719 | RWDD1 | cg27193080 | 3 | 129160612 | 0.14976515 | IFT122 |
| cg04794887 | 4 | 1858231 | -0.151286531 | LETM1 | cg26745551 | 6 | 97285260 | -0.149685651 | GPR63 |
| cg03519303 | 4 | 139936796 | -0.15122989 | CCRN4L | cg07793203 | 2 | 9771347 | -0.149655797 | YWHAQ |
| cg03966045 | 2 | 202316319 | -0.151183333 | STRADB | cg12359279 | 21 | 42797953 | -0.149655305 | MX1 |
| cg20137586 | 12 | 95043552 | -0.151125738 | TMCC3 | cg23955684 | 3 | 16555288 | -0.149647391 | RFTN1 |
| cg09840736 | 3 | 47205788 | -0.150944043 | SETD2 | cg05988158 | 22 | 51021418 | -0.14964072 | CHKB-CPT |
| cg19080138 | 7 | 35734733 | -0.150935037 | HERPUD2 | cg04258457 | 17 | 62207789 | -0.149635563 | ERN1 |

Figure 20-3

| | | | | |
|---|---|---|---|---|
| cg16103421 | 15 | 102068632 | 0.149520412 | |
| cg10972821 | 17 | 55163212 | -0.149514625 | AKAP1 |
| cg11909217 | 16 | 23569246 | -0.149498547 | EARS2 |
| cg08629647 | 22 | 46692562 | -0.14949374 | GTSE1 |
| cg22084410 | 3 | 51987688 | 0.149484748 | |
| cg09841203 | 13 | 52733292 | -0.14947635 | NEK3 |
| cg02110858 | 8 | 145028222 | 0.149448761 | PLEC1 |
| cg25296860 | 13 | 20702426 | -0.149415589 | |
| cg13267195 | 11 | 67777215 | 0.149414279 | ALDH3B1 |
| cg05001598 | 9 | 114246158 | -0.149291453 | KIAA0368 |
| cg05500574 | 19 | 58962884 | -0.149286244 | ZNF324B |
| cg10480239 | 22 | 23522307 | 0.149217989 | BCR |
| cg19656070 | 17 | 3571978 | -0.149217902 | TMEM93 |
| cg19761211 | 16 | 70415365 | -0.149210318 | ST3GAL2 |
| cg02818189 | 1 | 25173236 | 0.149159776 | |
| cg24904084 | 5 | 14653382 | -0.149150582 | |
| cg26975609 | 7 | 150777587 | -0.149148473 | FASTK |
| cg24106894 | 15 | 48623432 | -0.149130669 | DUT |
| cg04584087 | 3 | 129159014 | -0.14912679 | IFT122 |
| cg11688696 | 1 | 155052192 | 0.149031833 | EFNA3 |
| cg03231960 | 19 | 49139050 | -0.149009914 | DBP |
| cg26758863 | 19 | 57752111 | -0.148965348 | ZNF805 |
| cg01134297 | 16 | 90014983 | -0.148947814 | DEF8 |
| cg22984041 | 3 | 161090118 | -0.148900293 | C3orf57 |
| cg21308020 | 4 | 99182242 | -0.148888958 | RAP1GDS1 |
| cg27236973 | 17 | 39781997 | 0.148859457 | KRT17 |
| cg16263943 | 2 | 144695179 | -0.148838578 | |
| cg03631596 | 13 | 73301985 | -0.14879802 | C13orf37 |
| cg05129930 | 21 | 45719797 | -0.148776087 | PFKL |
| cg11017226 | 10 | 61666667 | -0.148766615 | CCDC6 |
| cg04706880 | 19 | 40023151 | -0.148758074 | EID2B |
| cg02016753 | 1 | 249132838 | -0.148746861 | ZNF672 |
| cg25467336 | 7 | 2757616 | 0.148681857 | |
| cg16257334 | 6 | 30881842 | -0.148652748 | GTF2H4 |
| cg18473162 | 19 | 56631888 | -0.148616405 | ZNF787 |
| cg05663418 | 16 | 3451086 | -0.148552528 | ZNF174 |
| cg25589651 | 6 | 28891121 | -0.148551078 | TRIM27 |
| cg06793581 | 16 | 46865077 | -0.148541202 | C16orf87 |
| cg18764107 | 1 | 225615669 | -0.148444024 | LBR |
| cg14244577 | 16 | 70332878 | 0.148366225 | DDX19B |
| cg08655589 | 3 | 14444175 | -0.148293474 | SLC6A6 |

| | | | | |
|---|---|---|---|---|
| cg05738924 | 2 | 144995448 | 0.14829255 | GTDC1 |
| cg17154187 | 17 | 18163844 | -0.148283886 | SMCR7 |
| cg06058395 | 18 | 13726784 | -0.148280468 | C18orf19 |
| cg02357877 | 7 | 56032049 | -0.148259756 | GBAS |
| cg23320649 | 3 | 50604613 | 0.148240924 | C3orf18 |
| cg12100751 | 1 | 109203672 | -0.148232565 | C1orf59 |
| cg27414860 | 16 | 4852427 | -0.148207496 | ROGDI |
| cg15967188 | 4 | 2470700 | -0.148189045 | RNF4 |
| cg12243976 | 12 | 133563125 | -0.148089896 | ZNF26 |
| cg24097153 | 12 | 122231765 | -0.147940216 | RHOF |
| cg24848615 | 19 | 3368396 | 0.147907846 | NFIC |
| cg17024199 | 17 | 74881747 | 0.147840184 | MGAT5B |
| cg18770186 | 8 | 141521259 | -0.14783855 | CHRAC1 |
| cg02932736 | 1 | 67896194 | -0.147837458 | SERBP1 |
| cg25562925 | 2 | 25110049 | 0.147817341 | ADCY3 |
| cg23018091 | 1 | 32758168 | 0.147772105 | HDAC1 |
| cg21442773 | 1 | 236029828 | -0.147753262 | LYST |
| cg12962778 | 12 | 54778312 | 0.147736731 | ZNF385A |
| cg01385795 | 11 | 14913124 | -0.147717124 | CYP2R1 |
| cg15541611 | 10 | 104211319 | 0.147692866 | C10orf95 |
| cg22512633 | 4 | 39640549 | -0.147683986 | C4orf34 |
| cg00049253 | 1 | 231473541 | -0.147665885 | EXOC8 |
| cg22796393 | 3 | 50375250 | -0.1476625 | RASSF1 |
| cg25753024 | 11 | 67070913 | 0.147655116 | SSH3 |
| cg16664617 | 19 | 17607007 | 0.147639896 | SLC27A1 |
| cg06186940 | 12 | 93322861 | -0.147610253 | EEA1 |
| cg19906131 | 11 | 93862516 | -0.14760571 | PANX1 |
| cg01318248 | 1 | 226736816 | -0.147569449 | C1orf95 |
| cg14319655 | 19 | 15490716 | -0.147489505 | AKAP8 |
| cg14235783 | 11 | 65420518 | -0.147480169 | |
| cg18070593 | 12 | 53891718 | 0.147478964 | MAP3K12 |
| cg10620680 | 1 | 178025100 | 0.14747724 | |
| cg05380793 | 13 | 73301995 | -0.147471604 | C13orf37 |
| cg10393416 | 4 | 128802077 | -0.147435391 | PLK4 |
| cg06994657 | 5 | 77656066 | -0.147364293 | SCAMP1 |
| cg04275707 | 20 | 20033092 | -0.147318515 | CRNKL1 |
| cg18357736 | 6 | 35705549 | 0.147287498 | C6orf81 |
| cg20952324 | 3 | 9773343 | -0.147279052 | BRPF1 |
| cg05573699 | 3 | 52720067 | -0.147278181 | GNL3 |
| cg25953341 | 14 | 24610919 | -0.147276991 | FAM158A |
| cg16512867 | 3 | 136581189 | -0.147259919 | NCK1 |

Figure 20-4

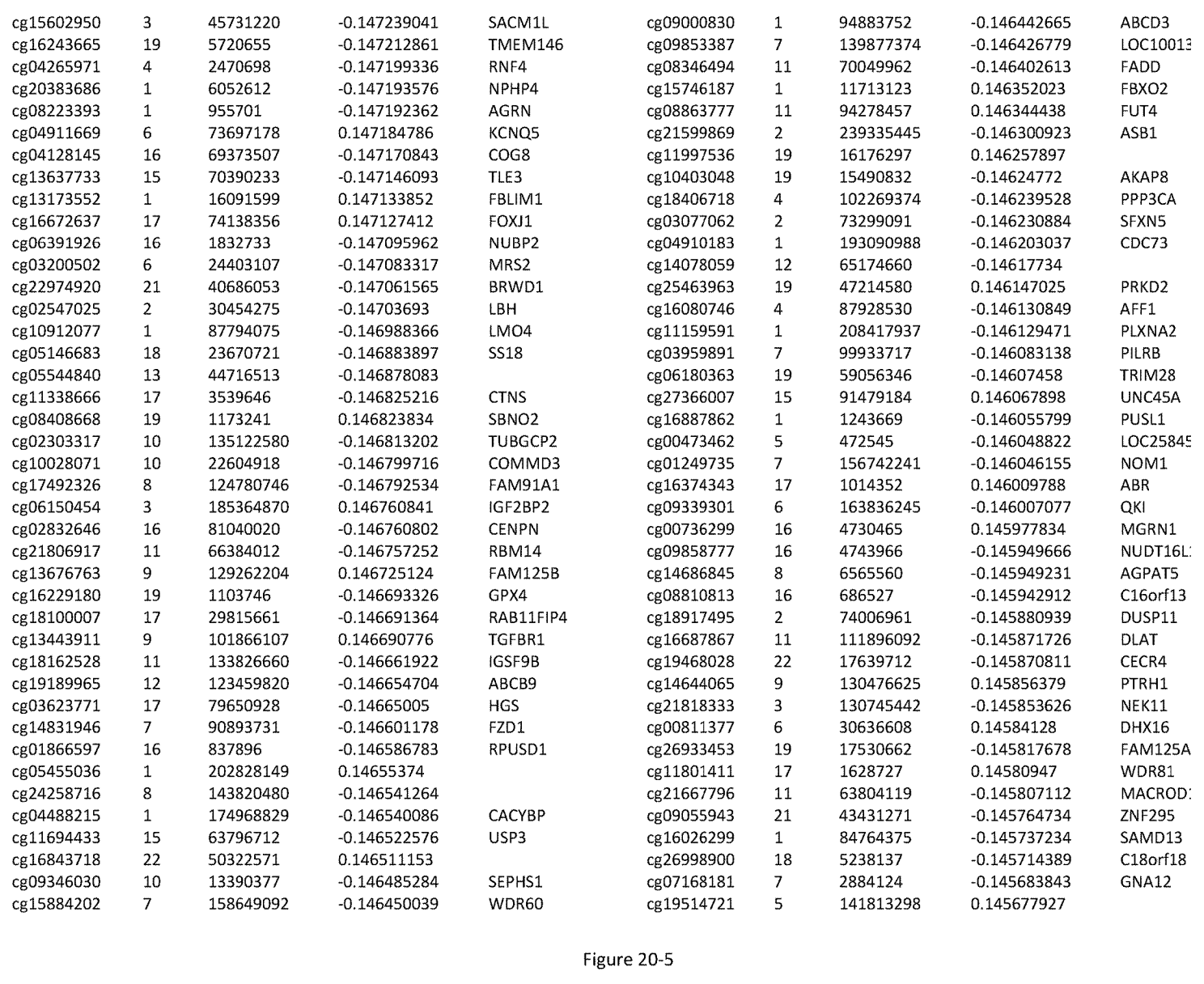

| | | | | | | | | | |
|---|---|---|---|---|---|---|---|---|---|
| cg15602950 | 3 | 45731220 | -0.147239041 | SACM1L | cg09000830 | 1 | 94883752 | -0.146442665 | ABCD3 |
| cg16243665 | 19 | 5720655 | -0.147212861 | TMEM146 | cg09853387 | 7 | 139877374 | -0.146426779 | LOC10013 |
| cg04265971 | 4 | 2470698 | -0.147199336 | RNF4 | cg08346494 | 11 | 70049962 | -0.146402613 | FADD |
| cg20383686 | 1 | 6052612 | -0.147193576 | NPHP4 | cg15746187 | 1 | 11713123 | 0.146352023 | FBXO2 |
| cg08223393 | 1 | 955701 | -0.147192362 | AGRN | cg08863777 | 11 | 94278457 | 0.146344438 | FUT4 |
| cg04911669 | 6 | 73697178 | 0.147184786 | KCNQ5 | cg21599869 | 2 | 239335445 | -0.146300923 | ASB1 |
| cg04128145 | 16 | 69373507 | -0.147170843 | COG8 | cg11997536 | 19 | 16176297 | 0.146257897 | |
| cg13637733 | 15 | 70390233 | -0.147146093 | TLE3 | cg10403048 | 19 | 15490832 | -0.14624772 | AKAP8 |
| cg13173552 | 1 | 16091599 | 0.147133852 | FBLIM1 | cg18406718 | 4 | 102269374 | -0.146239528 | PPP3CA |
| cg16672637 | 17 | 74138356 | 0.147127412 | FOXJ1 | cg03077062 | 2 | 73299091 | -0.146230884 | SFXN5 |
| cg06391926 | 16 | 1832733 | -0.147095962 | NUBP2 | cg04910183 | 1 | 193090988 | -0.146203037 | CDC73 |
| cg03200502 | 6 | 24403107 | -0.147083317 | MRS2 | cg14078059 | 12 | 65174660 | -0.14617734 | |
| cg22974920 | 21 | 40686053 | -0.147061565 | BRWD1 | cg25463963 | 19 | 47214580 | 0.146147025 | PRKD2 |
| cg02547025 | 2 | 30454275 | -0.14703693 | LBH | cg16080746 | 4 | 87928530 | -0.146130849 | AFF1 |
| cg10912077 | 1 | 87794075 | -0.146988366 | LMO4 | cg11159591 | 1 | 208417937 | -0.146129471 | PLXNA2 |
| cg05146683 | 18 | 23670721 | -0.146883897 | SS18 | cg03959891 | 7 | 99933717 | -0.146083138 | PILRB |
| cg05544840 | 13 | 44716513 | -0.146878083 | | cg06180363 | 19 | 59056346 | -0.14607458 | TRIM28 |
| cg11338666 | 17 | 3539646 | -0.146825216 | CTNS | cg27366007 | 15 | 91479184 | 0.146067898 | UNC45A |
| cg08408668 | 19 | 1173241 | 0.146823834 | SBNO2 | cg16887862 | 1 | 1243669 | -0.146055799 | PUSL1 |
| cg02303317 | 10 | 135122580 | -0.146813202 | TUBGCP2 | cg00473462 | 5 | 472545 | -0.146048822 | LOC25845 |
| cg10028071 | 10 | 22604918 | -0.146799716 | COMMD3 | cg01249735 | 7 | 156742241 | -0.146046155 | NOM1 |
| cg17492326 | 8 | 124780746 | -0.146792534 | FAM91A1 | cg16374343 | 17 | 1014352 | 0.146009788 | ABR |
| cg06150454 | 3 | 185364870 | 0.146760841 | IGF2BP2 | cg09339301 | 6 | 163836245 | -0.146007077 | QKI |
| cg02832646 | 16 | 81040020 | -0.146760802 | CENPN | cg00736299 | 16 | 4730465 | 0.145977834 | MGRN1 |
| cg21806917 | 11 | 66384012 | -0.146757252 | RBM14 | cg09858777 | 16 | 4743966 | -0.145949666 | NUDT16L |
| cg13676763 | 9 | 129262204 | 0.146725124 | FAM125B | cg14686845 | 8 | 6565560 | -0.145949231 | AGPAT5 |
| cg16229180 | 19 | 1103746 | -0.146693326 | GPX4 | cg08810813 | 16 | 686527 | -0.145942912 | C16orf13 |
| cg18100007 | 17 | 29815661 | -0.146691364 | RAB11FIP4 | cg18917495 | 2 | 74006961 | -0.145880939 | DUSP11 |
| cg13443911 | 9 | 101866107 | 0.146690776 | TGFBR1 | cg16687867 | 11 | 111896092 | -0.145871726 | DLAT |
| cg18162528 | 11 | 133826660 | -0.146661922 | IGSF9B | cg19468028 | 22 | 17639712 | -0.145870811 | CECR4 |
| cg19189965 | 12 | 123459820 | -0.146654704 | ABCB9 | cg14644065 | 9 | 130476625 | 0.145856379 | PTRH1 |
| cg03623771 | 17 | 79650928 | -0.14665005 | HGS | cg21818333 | 3 | 130745442 | -0.145853626 | NEK11 |
| cg14831946 | 7 | 90893731 | -0.146601178 | FZD1 | cg00811377 | 6 | 30636608 | 0.14584128 | DHX16 |
| cg01866597 | 16 | 837896 | -0.146586783 | RPUSD1 | cg26933453 | 19 | 17530662 | -0.145817678 | FAM125A |
| cg05455036 | 1 | 202828149 | 0.14655374 | | cg11801411 | 17 | 1628727 | 0.14580947 | WDR81 |
| cg24258716 | 8 | 143820480 | -0.146541264 | | cg21667796 | 11 | 63804119 | -0.145807112 | MACROD |
| cg04488215 | 1 | 174968829 | -0.146540086 | CACYBP | cg09055943 | 21 | 43431271 | -0.145764734 | ZNF295 |
| cg11694433 | 15 | 63796712 | -0.146522576 | USP3 | cg16026299 | 1 | 84764375 | -0.145737234 | SAMD13 |
| cg16843718 | 22 | 50322571 | 0.146511153 | | cg26998900 | 18 | 5238137 | -0.145714389 | C18orf18 |
| cg09346030 | 10 | 13390377 | -0.146485284 | SEPHS1 | cg07168181 | 7 | 2884124 | -0.145683843 | GNA12 |
| cg15884202 | 7 | 158649092 | -0.146450039 | WDR60 | cg19514721 | 5 | 141813298 | 0.145677927 | |

Figure 20-5

| | | | | | | | | | |
|---|---|---|---|---|---|---|---|---|---|
| cg01313966 | 18 | 47901443 | -0.145649922 | SKA1 | cg16788234 | 11 | 108093338 | -0.144584744 | NPAT |
| cg24001556 | 20 | 5591874 | -0.145636981 | RP5-1022P6.2 | cg02016838 | 11 | 109963531 | -0.144564254 | ZC3H12C |
| cg07617384 | 15 | 74392612 | -0.145606454 | | cg01259782 | 16 | 21313973 | 0.144545051 | CRYM |
| cg13430225 | 1 | 53662423 | -0.145427102 | CPT2 | cg08133912 | 19 | 47747483 | -0.144533911 | |
| cg21243939 | 14 | 55033137 | -0.145400717 | SAMD4A | cg11436767 | 11 | 46401422 | 0.144518118 | MDK |
| cg00421624 | 1 | 153746588 | 0.145345528 | SLC27A3 | cg23659250 | 22 | 50174065 | 0.144496308 | BRD1 |
| cg01574390 | 16 | 21623651 | 0.145328826 | METTL9 | cg25372103 | 6 | 170599661 | -0.144484397 | DLL1 |
| cg19591588 | 3 | 45730799 | -0.145316484 | SACM1L | cg16928487 | 17 | 17741425 | 0.144471087 | SREBF1 |
| cg24000232 | 1 | 166808428 | -0.145293301 | POGK | cg10463708 | 1 | 90309205 | -0.144457118 | LRRC8D |
| cg03512248 | 1 | 28517610 | 0.145288929 | PTAFR | cg20227213 | 3 | 37284559 | -0.144454047 | GOLGA4 |
| cg03236816 | 19 | 36618904 | -0.145262962 | | cg05867307 | 4 | 144106066 | -0.144441974 | USP38 |
| cg23408670 | 17 | 36831499 | -0.145247503 | C17orf96 | cg07535605 | 18 | 158294 | -0.144410067 | USP14 |
| cg18794664 | 1 | 42922694 | -0.145191673 | ZMYND12 | cg21740452 | 21 | 34143691 | -0.144386437 | C21orf66 |
| cg18925864 | 17 | 48624421 | -0.145180463 | SPATA20 | cg07097722 | 20 | 43247325 | -0.144373596 | PKIG |
| cg01693598 | 1 | 47998637 | 0.145157565 | | cg01406317 | 16 | 4397291 | 0.144364867 | Magmas |
| cg08285587 | 7 | 152161197 | -0.145141416 | LOC100128822 | cg04569651 | 5 | 177956199 | 0.144299333 | COL23A1 |
| cg12124516 | 2 | 136634144 | -0.145097583 | MCM6 | cg07471962 | 14 | 55368706 | -0.144297295 | GCH1 |
| cg25414605 | 11 | 67182672 | 0.145069327 | ATPGD1 | cg21160472 | 1 | 212782112 | -0.144296979 | ATF3 |
| cg11464438 | 2 | 113957041 | 0.145052514 | PSD4 | cg15441731 | 14 | 74036128 | -0.144240375 | ACOT2 |
| cg24331354 | 3 | 14444067 | -0.145018838 | SLC6A6 | cg10101470 | 1 | 90286633 | -0.144223979 | LRRC8D |
| cg13190306 | 11 | 18415923 | -0.144959234 | LDHA | cg17338544 | 11 | 44559989 | 0.144210963 | |
| cg19916323 | 19 | 16653199 | -0.144953856 | CHERP | cg04690289 | 3 | 45017999 | -0.144200383 | ZDHHC3 |
| cg22320000 | 1 | 245027629 | -0.144947456 | HNRNPU | cg10298855 | 14 | 35874025 | -0.14418808 | NFKBIA |
| cg19696103 | 5 | 132354130 | 0.144938565 | ZCCHC10 | cg03183872 | 20 | 3140552 | -0.144150199 | FASTKD5 |
| cg26449680 | 22 | 38714272 | 0.144934305 | CSNK1E | cg09527615 | 11 | 94883350 | 0.144140151 | |
| cg20080702 | 10 | 74046947 | 0.144867036 | | cg00367327 | 22 | 44419885 | -0.144127129 | PARVB |
| cg26761504 | 19 | 49140601 | -0.144863958 | SEC1 | cg24099956 | 11 | 113907379 | 0.14411921 | |
| cg08723131 | 20 | 55043694 | -0.144850307 | C20orf43 | cg19240052 | 22 | 42475693 | -0.144112873 | C22orf32 |
| cg17290332 | 10 | 14880008 | -0.144849792 | CDNF | cg07315521 | 16 | 71929403 | -0.144070658 | KIAA0174 |
| cg02569115 | 17 | 76922138 | 0.144810669 | TIMP2 | cg27637895 | 1 | 118472247 | -0.143998043 | GDAP2 |
| cg13189086 | 15 | 23034679 | -0.144801106 | NIPA2 | cg23959009 | 4 | 83352458 | -0.143981513 | ENOPH1 |
| cg05978546 | 5 | 131132739 | -0.144799677 | FNIP1 | cg08136416 | 21 | 44060833 | 0.143980372 | |
| cg08802167 | 14 | 74959978 | -0.144795178 | NPC2 | cg19529645 | 17 | 79196743 | -0.143977208 | AZI1 |
| cg14871856 | 8 | 30515337 | -0.144786495 | GTF2E2 | cg21403330 | 7 | 1178030 | -0.143965672 | C7orf50 |
| cg26215227 | 14 | 55518143 | -0.144776671 | MAPK1IP1L | cg21012061 | 1 | 205568557 | 0.143952643 | MFSD4 |
| cg27564108 | 1 | 150585651 | 0.144764715 | | cg25123308 | 2 | 113300087 | -0.143919987 | POLR1B |
| cg11826961 | 17 | 38221639 | 0.144763914 | THRA | cg06233552 | 17 | 5322836 | -0.143905247 | RPAIN |
| cg16048537 | 5 | 39074780 | -0.144750624 | RICTOR | cg03725309 | 1 | 109757585 | 0.143897155 | SARS |
| cg09932345 | 1 | 1710561 | -0.144653677 | NADK | cg19426773 | 6 | 139309558 | -0.143892848 | REPS1 |
| cg00957688 | 1 | 36183672 | 0.14464267 | C1orf216 | cg12586707 | 4 | 74738902 | 0.143822018 | |
| cg02244204 | 5 | 625213 | 0.144640223 | CEP72 | cg01733795 | 17 | 7465439 | -0.14381146 | SENP3 |

Figure 20-6

| | | | | | | | | | |
|---|---|---|---|---|---|---|---|---|---|
| cg10080401 | 22 | 22210635 | 0.143800265 | MAPK1 | cg10107890 | 2 | 44314289 | 0.143254484 | |
| cg16573386 | 1 | 1334508 | -0.14378666 | CCNL2 | cg10393931 | 7 | 95951432 | -0.143252546 | SLC25A13 |
| cg20102034 | 2 | 74653166 | 0.143758904 | RTKN | cg06177860 | 15 | 60884785 | -0.143249002 | RORA |
| cg05048680 | 1 | 1342566 | -0.143758879 | MRPL20 | cg00715047 | 17 | 73522054 | -0.143246665 | LLGL2 |
| cg04593445 | 16 | 2265125 | -0.143750317 | PGP | cg04928693 | 1 | 155178248 | 0.14323694 | MTX1 |
| cg10427040 | 17 | 74261306 | -0.143731837 | FAM100B | cg13639083 | 9 | 100957746 | 0.143236274 | |
| cg09456216 | 2 | 175870288 | -0.143721701 | CHN1 | cg07851008 | 2 | 109335747 | -0.14322934 | RANBP2 |
| cg13380562 | 6 | 143832576 | -0.143704172 | FUCA2 | cg22766770 | 17 | 18218566 | -0.143180143 | TOP3A |
| cg06003169 | 4 | 103422460 | -0.143675707 | NFKB1 | cg00608540 | 5 | 180627973 | 0.143164608 | TRIM7 |
| cg10093594 | 1 | 206858754 | -0.14366241 | MAPKAPK2 | cg24014462 | 17 | 12921391 | -0.143160808 | ELAC2 |
| cg06329143 | 18 | 48556512 | -0.143662321 | SMAD4 | cg04309350 | 8 | 67341294 | -0.14314686 | RRS1 |
| cg13807549 | 9 | 116444721 | 0.143653248 | | cg01332181 | 19 | 47290716 | -0.143143759 | SLC1A5 |
| cg24694913 | 19 | 58978210 | -0.14362171 | ZNF324 | cg13801946 | 17 | 61699522 | -0.14313367 | MAP3K3 |
| cg23908998 | 10 | 22292698 | -0.143614577 | DNAJC1 | cg08700690 | 15 | 60884630 | -0.143048803 | RORA |
| cg11723896 | 17 | 34136427 | -0.143574196 | TAF15 | cg14592933 | 7 | 26416122 | -0.14302871 | |
| cg20835353 | 7 | 99698988 | -0.143554889 | MCM7 | cg10051414 | 22 | 38598733 | -0.143026203 | MAFF |
| cg09039698 | 16 | 30007384 | -0.143550055 | HIRIP3 | cg27579771 | 5 | 142431272 | 0.143019345 | ARHGAP2 |
| cg00533407 | 7 | 150745278 | 0.14354925 | ACCN3 | cg19594024 | 19 | 58919948 | -0.14295505 | ZNF584 |
| cg08161931 | 8 | 145028402 | 0.143530309 | PLEC1 | cg07536998 | 4 | 178363522 | -0.142939512 | AGA |
| cg16588137 | 4 | 186064512 | -0.143516018 | SLC25A4 | cg17923377 | 22 | 50174057 | 0.1429254 | BRD1 |
| cg15686615 | 4 | 6781565 | 0.14351396 | | cg18167179 | 14 | 74058881 | -0.142923356 | ACOT4 |
| cg12445422 | 11 | 113920436 | 0.143508166 | | cg15783696 | 16 | 68564277 | -0.142916685 | |
| cg26952697 | 6 | 148881461 | 0.143506126 | | cg02505296 | 8 | 63951123 | -0.142910631 | GGH |
| cg13883202 | 3 | 47422330 | -0.14350314 | PTPN23 | cg10604550 | 5 | 43001210 | 0.142904319 | |
| cg10124993 | 14 | 105478712 | 0.143441685 | CDCA4 | cg26752655 | 20 | 23331282 | -0.14289375 | NXT1 |
| cg08451517 | 8 | 125383826 | -0.143430215 | TMEM65 | cg06704539 | 7 | 102105256 | -0.142870548 | ALKBH4 |
| cg20468415 | 8 | 41592973 | 0.143423115 | ANK1 | cg11673391 | 1 | 10459052 | -0.142813926 | PGD |
| cg26775866 | 5 | 159849193 | 0.143406385 | PTTG1 | cg11210652 | 12 | 32260091 | -0.142812635 | BICD1 |
| cg01305745 | 16 | 31106788 | 0.143398108 | VKORC1 | cg08915922 | 1 | 42127381 | -0.142801393 | HIVEP3 |
| cg21279955 | 1 | 153747551 | 0.143392101 | SLC27A3 | cg00929964 | 6 | 30879921 | 0.142783337 | GTF2H4 |
| cg01437482 | 14 | 100772378 | -0.14338621 | SLC25A29 | cg23054379 | 1 | 176176226 | -0.142772794 | RFWD2 |
| cg27605748 | 5 | 42951711 | -0.143378774 | | cg12143717 | 8 | 145133263 | -0.142764142 | EXOSC4 |
| cg01905773 | 17 | 79297618 | 0.143374854 | TMEM105 | cg13371705 | 12 | 2452955 | 0.142736454 | CACNA1C |
| cg03029755 | 17 | 76265444 | 0.143353737 | | cg18045172 | 6 | 32801648 | -0.142733855 | TAP2 |
| cg22666115 | 6 | 30182186 | -0.143347521 | TRIM26 | cg02839220 | 16 | 4400790 | -0.142727983 | Magmas |
| cg01307174 | 3 | 35722556 | 0.143306493 | ARPP-21 | cg10648908 | 22 | 43253189 | -0.142655385 | ARFGAP3 |
| cg06708720 | 12 | 1099075 | 0.143301954 | ERC1 | cg14461650 | 2 | 101925089 | -0.142625869 | RNF149 |
| cg15420687 | 5 | 159546321 | -0.143293962 | PWWP2A | cg27661869 | 17 | 61627703 | -0.142616659 | DCAF7 |
| cg03361810 | 8 | 42010162 | -0.143289592 | AP3M2 | cg23044186 | 5 | 141228416 | 0.142608028 | |
| cg21550006 | 2 | 97760606 | -0.143273409 | FAHD2B | cg15444566 | 15 | 63796413 | -0.142599782 | USP3 |
| cg14815005 | 22 | 22222162 | -0.143256624 | MAPK1 | cg03240232 | 12 | 113448327 | 0.142569771 | OAS2 |

Figure 20-7

| | | | | | | | | | |
|---|---|---|---|---|---|---|---|---|---|
| cg05289892 | 11 | 67070816 | 0.142568423 | SSH3 | cg10277631 | 14 | 53019580 | -0.142036723 | TXNDC16 |
| cg20669049 | 19 | 55573572 | 0.142560169 | RDH13 | cg03536846 | 8 | 120886254 | -0.142033842 | DEPDC6 |
| cg16235860 | 1 | 62902122 | -0.142547332 | USP1 | cg04792715 | 3 | 49058577 | -0.142024737 | MIR191 |
| cg26478485 | 10 | 112257641 | -0.142529671 | DUSP5 | cg27413118 | 2 | 238969595 | -0.142023689 | SCLY |
| cg24899068 | 19 | 49999470 | -0.142527579 | RPS11 | cg12616531 | 4 | 8160892 | -0.142000222 | ABLIM2 |
| cg02141084 | 12 | 8834151 | 0.142487773 | | cg13309513 | 17 | 40811520 | -0.141993264 | TUBG2 |
| cg00798281 | 6 | 33041697 | 0.142451642 | HLA-DPA1 | cg07188523 | 6 | 44528793 | 0.141982609 | |
| cg16501572 | 11 | 71934660 | -0.142432178 | INPPL1 | cg06372654 | 7 | 128044655 | 0.141964604 | IMPDH1 |
| cg23651356 | 6 | 153452954 | 0.142417229 | RGS17 | cg17959183 | 2 | 26297671 | 0.141872897 | RAB10 |
| cg11355601 | 22 | 39096475 | -0.142413325 | JOSD1 | cg19254163 | 11 | 60623782 | 0.141865552 | GPR44 |
| cg12700464 | 11 | 78128424 | -0.142339 | GAB2 | cg16679302 | 16 | 85622276 | 0.141858724 | |
| cg14183540 | 11 | 3175007 | 0.142321201 | OSBPL5 | cg26789400 | 15 | 43663318 | -0.141845397 | ZSCAN29 |
| cg02271677 | 2 | 130939252 | -0.142314268 | SMPD4 | cg26902127 | 16 | 88513285 | 0.141838083 | |
| cg23572376 | 6 | 1610120 | -0.142308491 | FOXC1 | cg17029062 | 3 | 32859445 | -0.141837757 | TRIM71 |
| cg23233742 | 5 | 139077894 | 0.142308414 | | cg06654628 | 5 | 150018914 | 0.141829279 | SYNPO |
| cg10341991 | 3 | 48229869 | -0.142298724 | CDC25A | cg01896926 | 17 | 685509 | -0.141827087 | GLOD4 |
| cg09504873 | 16 | 66774626 | 0.142286216 | DYNC1LI2 | cg03327386 | 18 | 8609878 | -0.141798651 | RAB12 |
| cg03182688 | 17 | 33825300 | 0.142276211 | SLFN12L | cg07485181 | 2 | 131851172 | -0.141787096 | FAM168B |
| cg24347098 | 1 | 113456650 | 0.142266323 | SLC16A1 | cg00881254 | 18 | 657522 | -0.141784809 | TYMS |
| cg12707346 | 12 | 64960957 | 0.142266268 | | cg24231804 | 15 | 67316861 | 0.141781051 | |
| cg08339208 | 1 | 115323327 | -0.142265519 | SIKE1 | cg02956542 | 1 | 153321421 | 0.141771061 | PGLYRP4 |
| cg25794819 | 19 | 55629097 | -0.142249393 | PPP1R12C | cg03666053 | 4 | 2765951 | -0.141764691 | |
| cg08382497 | 2 | 232469534 | -0.142239341 | | cg02003202 | 9 | 116111459 | 0.141745034 | BSPRY |
| cg16250856 | 12 | 133563128 | -0.142224566 | ZNF26 | cg01701959 | 1 | 51443542 | -0.141710805 | |
| cg04175957 | 15 | 23207925 | -0.142211301 | WHAMML1 | cg01196404 | 5 | 53606491 | -0.141701685 | ARL15 |
| cg04366628 | 4 | 26290463 | 0.142208378 | | cg24953179 | 7 | 37960251 | -0.141698998 | EPDR1 |
| cg09060789 | 11 | 1884988 | 0.142206128 | LSP1 | cg01067849 | 6 | 2765587 | -0.141662958 | WRNIP1 |
| cg12276904 | 3 | 129035177 | -0.142193542 | H1FX | cg22512536 | 5 | 154134507 | -0.141608708 | LARP1 |
| cg17663101 | 3 | 49131524 | -0.142177838 | QRICH1 | cg19696333 | 10 | 124768261 | -0.141598301 | IKZF5 |
| cg17323243 | 5 | 141488153 | -0.142177803 | NDFIP1 | cg27316808 | 1 | 6453995 | -0.141587484 | ACOT7 |
| cg09771049 | 17 | 66031798 | -0.142169758 | KPNA2 | cg27560367 | 13 | 114144049 | 0.141549134 | DCUN1D2 |
| cg06699484 | 5 | 132166328 | -0.142138577 | | cg09129050 | 11 | 64478374 | 0.141521271 | NRXN2 |
| cg08263040 | 1 | 43824491 | -0.142123673 | CDC20 | cg26812503 | 16 | 75681495 | -0.141501297 | KARS |
| cg26161024 | 1 | 27693840 | 0.142122906 | MAP3K6 | cg26937389 | 1 | 12677975 | -0.141468946 | DHRS3 |
| cg17985418 | 17 | 66031785 | -0.142106255 | KPNA2 | cg25962774 | 5 | 176831364 | -0.141442173 | F12 |
| cg09802818 | 12 | 52604609 | 0.142096244 | LOC283404 | cg14971597 | 6 | 159590578 | -0.141422488 | FNDC1 |
| cg10250355 | 22 | 43045158 | -0.142086732 | CYB5R3 | cg24452366 | 12 | 42719850 | -0.141402578 | PPHLN1 |
| cg09580608 | 17 | 63052483 | -0.142086287 | GNA13 | cg06635946 | 22 | 46470016 | 0.141376824 | |
| cg05434655 | 2 | 178078121 | -0.142084203 | HNRNPA3 | cg25861458 | 8 | 42948482 | -0.141313584 | SGK196 |
| cg13353389 | 7 | 73609617 | 0.142056986 | EIF4H | cg01550445 | 11 | 72929983 | 0.141308444 | P2RY2 |
| cg01162436 | 10 | 15902292 | -0.142039844 | FAM188A | cg09317239 | 10 | 21818060 | 0.141301174 | |

Figure 20-8

| | | | | |
|---|---|---|---|---|
| cg00355829 | 3 | 128326679 | 0.141284711 | |
| cg14389547 | 19 | 3398778 | 0.141281524 | NFIC |
| cg02463426 | 19 | 16683387 | -0.14127762 | SLC35E1 |
| cg02775028 | 4 | 184580387 | -0.141272302 | C4orf41 |
| cg08116711 | 7 | 101596218 | 0.141271838 | CUX1 |
| cg12665973 | 15 | 42867875 | -0.141268104 | STARD9 |
| cg04888030 | 2 | 113033033 | -0.141257674 | ZC3H6 |
| cg14428767 | 6 | 149867359 | -0.141255695 | PPIL4 |
| cg24798115 | 7 | 149157735 | -0.141232962 | ZNF777 |
| cg26490839 | 19 | 49999468 | -0.14121366 | RPS11 |
| cg22162404 | 19 | 8273842 | -0.141213142 | LASS4 |
| cg01411894 | 6 | 86303454 | -0.141204473 | SNX14 |
| cg00666849 | 2 | 85839032 | -0.14118894 | C2orf68 |
| cg08669096 | 11 | 121229765 | 0.141179606 | |
| cg26904702 | 1 | 153746899 | 0.14117201 | SLC27A3 |
| cg23267217 | 1 | 26496298 | -0.141171116 | ZNF593 |
| cg27203184 | 7 | 100081966 | 0.141163475 | C7orf51 |
| cg11690666 | 17 | 80415469 | 0.141067206 | NARF |
| cg03399927 | 11 | 64036876 | -0.141064683 | |
| cg02793948 | 11 | 68095662 | 0.141047963 | LRP5 |
| cg07383443 | 12 | 118573736 | -0.141036051 | PEBP1 |
| cg01153872 | 2 | 240323819 | -0.14101712 | HDAC4 |
| cg13567813 | 19 | 50879636 | -0.141011242 | NR1H2 |
| cg09864245 | 11 | 33746426 | 0.141011047 | CD59 |
| cg26987179 | 17 | 40307119 | -0.140992169 | RAB5C |
| cg20107653 | 22 | 42228989 | -0.140975054 | SREBF2 |
| cg22111723 | 13 | 21872664 | -0.140965278 | |
| cg13717023 | 5 | 53606639 | -0.14095761 | ARL15 |
| cg13672514 | 12 | 123869502 | 0.140948561 | SETD8 |
| cg08527566 | 12 | 95611432 | -0.140939378 | FGD6 |
| cg05465755 | 9 | 91926196 | -0.140914728 | CKS2 |
| cg16001977 | 22 | 32340332 | -0.140909322 | YWHAH |
| cg20288129 | 3 | 122745632 | -0.140901438 | SEMA5B |
| cg00779206 | 12 | 2914519 | 0.140898497 | FKBP4 |
| cg20577878 | 16 | 66914781 | -0.140887469 | PDP2 |
| cg14426371 | 9 | 113714986 | -0.140880317 | LPAR1 |
| cg14156905 | 1 | 17193979 | 0.140877411 | |
| cg03071793 | 16 | 11682634 | 0.140835067 | LITAF |
| cg00286773 | 11 | 12207449 | 0.140831425 | MICAL2 |
| cg07326768 | 15 | 86337453 | -0.140827552 | KLHL25 |
| cg26896160 | 1 | 6454004 | -0.140799114 | ACOT7 |

| | | | | |
|---|---|---|---|---|
| cg13850871 | 9 | 139583773 | 0.140769543 | |
| cg14553881 | 17 | 79361650 | 0.14076785 | |
| cg22033189 | 1 | 28908551 | -0.140764715 | SNHG12 |
| cg17457912 | 17 | 1617102 | 0.140762759 | C17orf91 |
| cg00164196 | 2 | 162095477 | -0.140757784 | |
| cg25347941 | 22 | 43486472 | 0.140741734 | TTLL1 |
| cg03954150 | 18 | 71815372 | -0.140736768 | C18orf55 |
| cg25213720 | 5 | 176734343 | 0.140693163 | MXD3 |
| cg25021247 | 3 | 49460162 | 0.140685924 | AMT |
| cg01035038 | 14 | 88459686 | -0.140684248 | GALC |
| cg02197392 | 19 | 13049544 | -0.140650309 | CALR |
| cg14031414 | 20 | 13765665 | -0.140607259 | ESF1 |
| cg14229247 | 9 | 100745139 | -0.140572797 | ANP32B |
| cg03646967 | 3 | 61196428 | -0.140569709 | FHIT |
| cg18001714 | 5 | 14871894 | -0.140563924 | ANKH |
| cg25944720 | 6 | 106958640 | -0.140512105 | AIM1 |
| cg18751306 | 15 | 81294292 | -0.140504767 | MESDC1 |
| cg13475822 | 3 | 9210116 | -0.140498751 | SRGAP3 |
| cg05729480 | 17 | 75276428 | 0.140490295 | 9-Sep |
| cg13752043 | 9 | 131644109 | -0.140487766 | LRRC8A |
| cg18467978 | 19 | 47134906 | 0.140469522 | |
| cg23281075 | 1 | 31538727 | -0.14045366 | PUM1 |
| cg24668150 | 10 | 27389076 | -0.14043479 | ANKRD26 |
| cg17665608 | 10 | 43633793 | -0.140424471 | CSGALNA( |
| cg15440973 | 14 | 24610792 | -0.140422901 | FAM158A |
| cg13053396 | 12 | 7168545 | 0.1404228 | C1S |
| cg12419348 | 17 | 54991398 | -0.140408612 | TRIM25 |
| cg15238008 | 12 | 9600875 | -0.14038581 | DDX12 |
| cg04468671 | 12 | 132337407 | 0.14032159 | |
| cg05006942 | 16 | 69776039 | 0.140302667 | NOB1 |
| cg26227101 | 1 | 14075870 | -0.140293274 | PRDM2 |
| cg11162385 | 20 | 25604740 | -0.140288363 | NANP |
| cg04426007 | 4 | 166129241 | -0.140279294 | KLHL2 |
| cg03295933 | 19 | 1479358 | -0.140261436 | C19orf25 |
| cg08092393 | 14 | 64970675 | -0.140255646 | ZBTB25 |
| cg17341174 | 7 | 97923834 | 0.140240012 | BAIAP2L1 |
| cg02385710 | 11 | 64884962 | -0.14022812 | ZNHIT2 |
| cg02130266 | 22 | 17078353 | -0.140180673 | |
| cg07945480 | 4 | 2964972 | -0.140170738 | GRK4 |
| cg00431050 | 10 | 103985730 | 0.140165615 | ELOVL3 |
| cg20310071 | 8 | 77912528 | -0.140140087 | PXMP3 |

Figure 20-9

| | | | | | | | | | |
|---|---|---|---|---|---|---|---|---|---|
| cg07172256 | 5 | 65220910 | -0.140124048 | ERBB2IP | cg15102777 | 10 | 127511674 | -0.139766363 | BCCIP |
| cg05914712 | 19 | 33864373 | -0.140108759 | CEBPG | cg02083189 | 1 | 100503813 | -0.139761249 | HIAT1 |
| cg23684603 | 4 | 185747386 | -0.140107225 | ACSL1 | cg04159215 | 10 | 126182324 | 0.139755036 | LHPP |
| cg25039902 | 14 | 103063148 | -0.140103012 | RCOR1 | cg26580576 | 4 | 6675790 | -0.139743417 | LOC93622 |
| cg18176482 | 1 | 161128720 | 0.140094983 | USP21 | cg17193921 | 22 | 50683583 | -0.139738644 | TUBGCP6 |
| cg15500658 | 1 | 16174610 | -0.14007385 | SPEN | cg07810106 | 5 | 131630122 | -0.139734148 | SLC22A4 |
| cg02070289 | 5 | 43066798 | -0.14005195 | | cg01377696 | 20 | 32581542 | -0.139731316 | RALY |
| cg00509610 | 3 | 12528629 | 0.140050677 | TSEN2 | cg04705952 | 1 | 160066587 | 0.139712804 | IGSF8 |
| cg01398415 | 1 | 226309536 | -0.140048 | | cg00594118 | 9 | 140150000 | -0.139707838 | COBRA1 |
| cg25136353 | 10 | 44185896 | -0.140047889 | | cg02999224 | 14 | 23284559 | 0.139700564 | SLC7A7 |
| cg27234239 | 2 | 121010047 | -0.140014512 | RALB | cg24608684 | 6 | 130686865 | -0.139682436 | |
| cg01441777 | 22 | 38714416 | 0.140013072 | CSNK1E | cg02994588 | 1 | 24828970 | -0.139670677 | RCAN3 |
| cg22499237 | 16 | 2587546 | -0.140001227 | PDPK1 | cg17442852 | 17 | 1478889 | 0.139662547 | SLC43A2 |
| cg17526741 | 5 | 126366741 | -0.139982332 | 3-Mar | cg10610348 | 19 | 2427956 | -0.139661366 | TIMM13 |
| cg26260386 | 4 | 140477698 | -0.139979578 | SETD7 | cg23872935 | 5 | 130599536 | -0.139649183 | CDC42SE2 |
| cg03576863 | 16 | 69415422 | 0.139973796 | TERF2 | cg07274776 | 2 | 203241322 | -0.139639797 | BMPR2 |
| cg20521685 | 17 | 10600763 | -0.139971177 | C17orf48 | cg10287970 | 6 | 7115345 | 0.139628123 | RREB1 |
| cg27467996 | 5 | 179921670 | -0.139956085 | CNOT6 | cg20670292 | 2 | 131099506 | -0.139620627 | IMP4 |
| cg22248011 | 6 | 52442381 | -0.139946299 | TRAM2 | cg24534743 | 1 | 27884345 | 0.139607926 | AHDC1 |
| cg09048062 | 11 | 129892327 | -0.13994208 | | cg11429664 | 15 | 91260578 | -0.139605859 | BLM |
| cg17418708 | 2 | 204400358 | -0.139939352 | RAPH1 | cg24732796 | 11 | 133907497 | -0.139594535 | LOC10012 |
| cg07824483 | 17 | 79882042 | 0.139934863 | MAFG | cg16185365 | 3 | 196230308 | -0.139589869 | RNF168 |
| cg15638207 | 6 | 5261560 | -0.139934528 | LYRM4 | cg00536939 | 11 | 47279352 | 0.139589455 | NR1H3 |
| cg04738301 | 12 | 96184580 | -0.139933106 | NTN4 | cg08502703 | 21 | 45138838 | -0.139570156 | PDXK |
| cg00484122 | 2 | 20579065 | 0.139926336 | | cg08794928 | 6 | 144537264 | -0.139564831 | |
| cg02093647 | 2 | 148602395 | -0.139916596 | ACVR2A | cg04296257 | 2 | 219536679 | -0.139554224 | STK36 |
| cg08867893 | 10 | 64134160 | -0.139904822 | ZNF365 | cg02178957 | 16 | 85964200 | 0.139546843 | |
| cg05105845 | 14 | 55369781 | -0.139904698 | GCH1 | cg24312792 | 1 | 27337638 | 0.139519683 | FAM46B |
| cg19695335 | 20 | 25604759 | -0.139843104 | NANP | cg00763768 | 14 | 99947408 | -0.1395129 | SETD3 |
| cg03479527 | 8 | 145637966 | 0.139835399 | SLC39A4 | cg24537993 | 1 | 204275926 | 0.139488917 | PLEKHA6 |
| cg03951132 | 20 | 5931305 | -0.13983285 | MCM8 | cg00019301 | 4 | 123843794 | -0.139481422 | NUDT6 |
| cg00546897 | 21 | 45232232 | 0.139824625 | LOC284837 | cg03638642 | 16 | 1877211 | -0.139461012 | HAGH |
| cg16340159 | 2 | 240322705 | -0.139814047 | HDAC4 | cg25699034 | 17 | 74721824 | 0.139455215 | C17orf95 |
| cg11357670 | 13 | 114143948 | 0.139813506 | DCUN1D2 | cg19442470 | 8 | 27470225 | 0.139449051 | CLU |
| cg25365783 | 7 | 108166722 | -0.139803966 | PNPLA8 | cg19044674 | 1 | 43232628 | -0.139412398 | LEPRE1 |
| cg08452546 | 5 | 118323860 | -0.139797182 | DTWD2 | cg01881062 | 1 | 6660403 | 0.139406873 | KLHL21 |
| cg23535768 | 15 | 68570349 | -0.139787616 | FEM1B | cg11515196 | 15 | 44829065 | -0.139404162 | EIF3J |
| cg15543443 | 6 | 33386036 | -0.139783399 | CUTA | cg07321171 | 2 | 74692645 | -0.139397731 | MOGS |
| cg01854842 | 20 | 49547693 | -0.1397828 | ADNP | cg03598938 | 2 | 191502738 | 0.139395724 | |
| cg00083188 | 10 | 79314844 | 0.13977793 | KCNMA1 | cg10945667 | 13 | 91999862 | -0.139385185 | MIR17HG |
| cg03926751 | 4 | 88140261 | 0.139772908 | KLHL8 | cg12995410 | 6 | 151712734 | -0.139358518 | ZBTB2 |

Figure 20-10

| | | | | |
|---|---|---|---|---|
| cg00443276 | 17 | 15848206 | -0.139346001 | ADORA2B |
| cg27286107 | 3 | 88108209 | -0.139307682 | CGGBP1 |
| cg26188571 | 5 | 179050811 | -0.139300554 | HNRNPH1 |
| cg10646145 | 2 | 9235600 | 0.139272066 | |
| cg26712763 | 17 | 21030248 | -0.13924529 | DHRS7B |
| cg03499675 | 6 | 31744339 | 0.13923966 | C6orf27 |
| cg06014792 | 17 | 7382760 | -0.139213431 | ZBTB4 |
| cg10045354 | 11 | 111169427 | 0.139206535 | C11orf93 |
| cg19698084 | 10 | 91461284 | -0.13920132 | KIF20B |
| cg09384035 | 8 | 104131768 | 0.139195976 | |
| cg04624363 | 5 | 176433907 | -0.13917953 | UIMC1 |
| cg06656994 | 1 | 179713176 | -0.139155881 | FAM163A |
| cg01015663 | 1 | 23729692 | 0.139153583 | TCEA3 |
| cg00816008 | 16 | 82203996 | -0.139136639 | MPHOSPH6 |
| cg06875162 | 1 | 28184973 | 0.13913165 | |
| cg01313320 | 2 | 46526265 | -0.13912913 | EPAS1 |
| cg15494556 | 20 | 56196212 | 0.139107576 | ZBP1 |
| cg15787552 | 7 | 21467063 | -0.139085932 | SP4 |
| cg26900616 | 4 | 159593389 | -0.139073229 | ETFDH |
| cg16772514 | 17 | 43046872 | 0.139070601 | C1QL1 |
| cg06395692 | 6 | 28891945 | -0.139070023 | TRIM27 |
| cg15408407 | 19 | 1438438 | -0.139035451 | RPS15 |
| cg01165297 | 16 | 475440 | -0.139033611 | RAB11FIP3 |
| cg18730422 | 6 | 4135609 | -0.139019655 | PECI |
| cg14567424 | 11 | 67349598 | 0.138979769 | GSTP1 |
| cg05209463 | 4 | 2935884 | -0.13897162 | C4orf10 |
| cg07187585 | 17 | 10600923 | -0.138968833 | C17orf48 |
| cg11699826 | 1 | 26438425 | -0.138966568 | PDIK1L |
| cg26349332 | 9 | 37592199 | -0.138957679 | TOMM5 |
| cg13423282 | 19 | 19174731 | -0.138952777 | SLC25A42 |
| cg24431349 | 17 | 18218572 | -0.138947622 | TOP3A |
| cg05251190 | 10 | 104196206 | 0.138946207 | MIR146B |
| cg22512322 | 3 | 64009096 | -0.138937161 | PSMD6 |
| cg17735043 | 5 | 21459472 | -0.13892543 | LOC728411 |
| cg12410310 | 11 | 63275838 | 0.138913747 | LGALS12 |
| cg05051152 | 8 | 124408913 | -0.138912109 | ATAD2 |
| cg04497885 | 19 | 42747008 | -0.138906723 | GSK3A |
| cg03621988 | 3 | 113251716 | -0.138892334 | SIDT1 |
| cg00993543 | 2 | 159313345 | -0.138885239 | CCDC148 |
| cg01620248 | 14 | 105265453 | 0.138877746 | ZBTB42 |
| cg18482175 | 6 | 10747728 | -0.13887497 | TMEM14B |

| | | | | |
|---|---|---|---|---|
| cg01811416 | 1 | 227127838 | -0.138869417 | CABC1 |
| cg14694952 | 4 | 3076907 | -0.138855297 | HTT |
| cg01422009 | 16 | 125896 | 0.138854555 | MPG |
| cg01089095 | 10 | 75541668 | -0.138838044 | CHCHD1 |
| cg01794932 | 1 | 1209696 | -0.138827943 | UBE2J2 |
| cg05954120 | 1 | 156254757 | 0.138823075 | TMEM79 |
| cg26336164 | 19 | 4791680 | -0.138807544 | FEM1A |
| cg17892917 | 3 | 107823424 | 0.138806082 | |
| cg14804635 | 15 | 75747750 | -0.138802427 | SIN3A |
| cg19256675 | 7 | 74988891 | -0.138763337 | PMS2L2 |
| cg11826708 | 3 | 115502895 | -0.138755663 | |
| cg14631910 | 8 | 10590511 | -0.138752046 | |
| cg23251057 | 14 | 69480702 | 0.138750491 | |
| cg12582330 | 1 | 2473224 | 0.138744956 | |
| cg02201963 | 18 | 12702795 | -0.138741927 | PSMG2 |
| cg16722292 | 10 | 7830180 | -0.138735291 | KIN |
| cg25998745 | 8 | 142028625 | 0.138730232 | |
| cg14315992 | 4 | 48833004 | -0.138712052 | OCIAD1 |
| cg00583733 | 16 | 30075102 | 0.138694408 | ALDOA |
| cg10603824 | 17 | 48943588 | -0.138687412 | |
| cg00965795 | 2 | 27957843 | 0.138679328 | |
| cg05713474 | 20 | 60718893 | -0.138678366 | SS18L1 |
| cg20874785 | 2 | 74612674 | 0.138674288 | LOC10018 |
| cg09378756 | 14 | 24569543 | 0.138666023 | PCK2 |
| cg14283194 | 7 | 91763737 | -0.138635504 | CYP51A1 |
| cg15971879 | 2 | 3467236 | 0.138623752 | TTC15 |
| cg00967073 | 1 | 244443687 | 0.138622679 | |
| cg26433102 | 6 | 391441 | -0.138609316 | IRF4 |
| cg10264529 | 14 | 24562064 | 0.138607106 | PCK2 |
| cg01012242 | 7 | 140043078 | 0.138602232 | SLC37A3 |
| cg22951727 | 7 | 127292125 | -0.138594467 | SND1 |
| cg08491025 | 1 | 113498799 | -0.138593326 | SLC16A1 |
| cg05049628 | 11 | 72525270 | -0.138588931 | ATG16L2 |
| cg15062310 | 7 | 100450120 | -0.13858048 | SLC12A9 |
| cg12923613 | 4 | 83812206 | -0.138580184 | SEC31A |
| cg01547051 | 7 | 150777654 | -0.138555847 | FASTK |
| cg21497607 | 2 | 74425593 | -0.13854892 | MTHFD2 |
| cg08996788 | 3 | 194992260 | -0.138528886 | C3orf21 |
| cg07414961 | 17 | 70587753 | -0.138526223 | |
| cg09238598 | 5 | 14871908 | -0.138525044 | ANKH |
| cg14702655 | 14 | 72398920 | -0.138498344 | RGS6 |

Figure 20-11

| | | | | |
|---|---|---|---|---|
| cg14284211 | 6 | 35570224 | 0.138495526 | FKBP5 |
| cg01098651 | 18 | 77439095 | -0.138486195 | CTDP1 |
| cg04355250 | 12 | 113796401 | -0.138484317 | PLBD2 |
| cg19925518 | 10 | 90851787 | 0.138475989 | |
| cg21937128 | 1 | 150971889 | 0.138454318 | FAM63A |
| cg22512377 | 22 | 42475683 | -0.13842818 | C22orf32 |
| cg13390332 | 17 | 78971641 | 0.138420336 | CHMP6 |
| cg03949755 | 7 | 26437999 | -0.138410898 | |
| cg27241907 | 3 | 23244637 | -0.138410397 | UBE2E2 |
| cg07388806 | 6 | 7108895 | -0.138389639 | RREB1 |
| cg19114543 | 3 | 46996484 | 0.138383862 | CCDC12 |
| cg01719220 | 16 | 58035188 | -0.13838198 | C16orf57 |
| cg27108047 | 17 | 73257286 | -0.138375664 | GGA3 |
| cg21289924 | 10 | 120839943 | -0.138345419 | EIF3A |
| cg22396980 | 8 | 146228348 | -0.138336171 | ZNF252 |
| cg19971804 | 2 | 39102883 | -0.138334169 | MORN2 |
| cg22546696 | 15 | 41952645 | -0.138325776 | MGA |
| cg22407744 | 2 | 136634157 | -0.138294936 | MCM6 |
| cg19673549 | 5 | 54916621 | 0.138272725 | |
| cg12455363 | 7 | 27200671 | -0.138269405 | |
| cg25678231 | 1 | 157069611 | 0.138259653 | ETV3L |
| cg15223102 | 19 | 33166151 | -0.138236403 | ANKRD27 |
| cg00858400 | 16 | 87904580 | 0.138224791 | SLC7A5 |
| cg13810234 | 9 | 139622243 | -0.138161929 | SNHG7 |
| cg23921523 | 21 | 45876245 | 0.138157575 | LRRC3 |
| cg21826784 | 1 | 11795937 | 0.138148466 | AGTRAP |
| cg20687038 | 3 | 127317259 | -0.138143028 | MCM2 |
| cg14195992 | 8 | 48265917 | 0.138140171 | KIAA0146 |
| cg19198358 | 8 | 1725179 | 0.138122524 | CLN8 |
| cg11975206 | 10 | 135192160 | -0.138102579 | PAOX |
| cg03209127 | 1 | 235668099 | -0.138097688 | B3GALNT2 |
| cg10971750 | 14 | 97264166 | -0.138089169 | VRK1 |
| cg00982830 | 12 | 82752388 | -0.138082947 | C12orf26 |
| cg09030452 | 3 | 64008884 | -0.138077091 | PSMD6 |
| cg14569415 | 2 | 220363584 | -0.138074785 | GMPPA |
| cg02676144 | 1 | 25174677 | -0.138073265 | |
| cg03156112 | 10 | 22630065 | -0.138061452 | |
| cg02367949 | 11 | 94964516 | -0.138053063 | SESN3 |
| cg19306970 | 1 | 221055097 | 0.138052194 | HLX |
| cg02294302 | 1 | 47906276 | 0.138051433 | FOXD2 |
| cg03691549 | 12 | 53443911 | 0.138049721 | TENC1 |

| | | | | |
|---|---|---|---|---|
| cg22992588 | 18 | 74207551 | -0.138023751 | |
| cg23067438 | 22 | 42228994 | -0.138001194 | SREBF2 |
| cg06218044 | 6 | 105851256 | -0.137979885 | PREP |
| cg17661220 | 20 | 3693179 | 0.137957723 | |
| cg19117777 | 5 | 109024969 | -0.137954855 | MAN2A1 |
| cg03633458 | 19 | 852284 | 0.137914434 | ELANE |
| cg18307957 | 1 | 9649516 | -0.137905494 | TMEM201 |
| cg10502957 | 12 | 123757070 | 0.137897352 | CDK2AP1 |
| cg16041611 | 6 | 43139680 | -0.137893849 | SRF |
| cg04005943 | 10 | 73350048 | 0.137890391 | CDH23 |
| cg09572053 | 6 | 34360501 | -0.137846377 | NUDT3 |
| cg25140066 | 2 | 30670679 | -0.137844293 | LCLAT1 |
| cg22916109 | 15 | 78730334 | -0.137843807 | IREB2 |
| cg10460130 | 2 | 242625978 | -0.137838585 | DTYMK |
| cg23459643 | 5 | 149109544 | -0.137834001 | PPARGC1I |
| cg20153322 | 12 | 120703977 | 0.137819343 | PXN |
| cg23483707 | 13 | 44453835 | -0.1378172 | C13orf31 |
| cg05824432 | 16 | 2301222 | -0.137811767 | DCI |
| cg21120664 | 21 | 44299807 | -0.137809884 | WDR4 |
| cg17501485 | 22 | 24191984 | -0.137809769 | |
| cg06818484 | 8 | 145051287 | -0.137800965 | PLEC1 |
| cg22032626 | 12 | 50203811 | 0.137791607 | NCKAP5L |
| cg02508567 | 2 | 85361184 | -0.137764112 | TCF7L1 |
| cg14766148 | 2 | 128786246 | -0.13776139 | SAP130 |
| cg00395632 | 22 | 50709221 | -0.137753647 | MAPK11 |
| cg21656600 | 12 | 111181027 | -0.137744367 | PPP1CC |
| cg25976786 | 12 | 53662079 | -0.137736289 | ESPL1 |
| cg03222009 | 2 | 129077232 | 0.137734333 | HS6ST1 |
| cg07517005 | 1 | 6051606 | -0.137725508 | NPHP4 |
| cg08522087 | 5 | 14871910 | -0.137724723 | ANKH |
| cg11070000 | 14 | 64805073 | -0.137719025 | ESR2 |
| cg23890469 | 10 | 88715317 | 0.137709708 | MMRN2 |
| cg27024417 | 1 | 32645813 | -0.137703766 | TXLNA |
| cg16405432 | 14 | 95973710 | 0.137657788 | |
| cg26337070 | 2 | 85999873 | 0.137657072 | ATOH8 |
| cg04482628 | 1 | 36581751 | 0.137652192 | |
| cg01231779 | 14 | 52535887 | -0.137644363 | NID2 |
| cg08767710 | 7 | 149570989 | -0.137623136 | ATP6V0E2 |
| cg13304638 | 17 | 80834089 | 0.137583066 | TBCD |
| cg18130076 | 11 | 66384026 | -0.137581855 | RBM14 |
| cg10069121 | 1 | 152009711 | 0.137577548 | S100A11 |

Figure 20-12

| | | | | |
|---|---|---|---|---|
| cg21369679 | 16 | 47007757 | -0.137565628 | DNAJA2 |
| cg07556261 | 20 | 35484900 | 0.137558735 | C20orf117 |
| cg14306819 | 2 | 128052889 | 0.137543739 | ERCC3 |
| cg20752795 | 2 | 20866407 | -0.137542736 | GDF7 |
| cg16252717 | 19 | 39390344 | -0.137536146 | SIRT2 |
| cg10588135 | 17 | 59329903 | 0.137518966 | BCAS3 |
| cg14143241 | 3 | 14166563 | -0.137514663 | TMEM43 |
| cg24714742 | 1 | 91487571 | -0.137513992 | ZNF644 |
| cg06642177 | 6 | 134496341 | -0.137496047 | SGK1 |
| cg10129391 | 4 | 54582825 | 0.137489435 | |
| cg08211967 | 15 | 85923708 | -0.137488614 | AKAP13 |
| cg12363903 | 5 | 134526269 | 0.13746002 | |
| cg03456512 | 7 | 107531689 | -0.137455535 | DLD |
| cg13393276 | 11 | 13484763 | -0.137447544 | BTBD10 |
| cg12938135 | 13 | 20356591 | -0.137438874 | PSPC1 |
| cg13573745 | 9 | 97405553 | 0.137433787 | |
| cg02640604 | 16 | 29690271 | 0.137421976 | QPRT |
| cg23508052 | 10 | 102106811 | -0.13740472 | SCD |

Figure 20-13

| SNP | ChiSquare p value | SNP | ChiSquare p value | SNP | ChiSquare p value | SNP | ChiSquare p value |
|---|---|---|---|---|---|---|---|
| rs6418712 | 2.18E-08 | rs756827 | 9.32E-06 | rs4240151 | 2.72E-05 | rs5925800 | 4.98E-05 |
| rs11924095 | 1.42E-07 | rs7049377 | 9.44E-06 | rs5972323 | 2.74E-05 | rs11066587 | 5.01E-05 |
| rs3889602 | 1.63E-07 | rs5949715 | 9.49E-06 | rs4625170 | 2.79E-05 | rs601300 | 5.08E-05 |
| rs4358964 | 5.01E-07 | rs5980073 | 9.57E-06 | rs7061674 | 2.83E-05 | rs1416244 | 5.13E-05 |
| rs7888371 | 5.16E-07 | rs12390162 | 9.59E-06 | rs5907076 | 2.86E-05 | rs2864894 | 5.15E-05 |
| rs3131441 | 6.21E-07 | rs5957709 | 9.83E-06 | rs5943627 | 2.90E-05 | rs4748099 | 5.18E-05 |
| rs5932058 | 7.58E-07 | rs2056491 | 1.00E-05 | rs12689291 | 2.93E-05 | rs1285582 | 5.24E-05 |
| rs5933886 | 9.11E-07 | rs12393815 | 1.02E-05 | rs5910006 | 2.94E-05 | rs4830819 | 5.28E-05 |
| rs6640916 | 1.12E-06 | rs10881990 | 1.03E-05 | rs572249 | 2.94E-05 | rs6525672 | 5.46E-05 |
| rs6457816 | 1.23E-06 | rs582132 | 1.07E-05 | rs5925762 | 2.96E-05 | rs1906321 | 5.49E-05 |
| rs12690204 | 1.51E-06 | rs7884737 | 1.08E-05 | rs6616265 | 2.97E-05 | rs7882491 | 5.51E-05 |
| rs1875619 | 1.82E-06 | rs806643 | 1.12E-05 | rs1582412 | 3.01E-05 | rs205828 | 5.53E-05 |
| rs5972470 | 1.82E-06 | rs1040474 | 1.12E-05 | rs222108 | 3.07E-05 | rs6528055 | 5.60E-05 |
| rs17365948 | 1.84E-06 | rs2027822 | 1.18E-05 | rs321034 | 3.11E-05 | rs12688712 | 5.72E-05 |
| rs5929410 | 1.86E-06 | rs4830923 | 1.19E-05 | rs644429 | 3.11E-05 | rs8031759 | 5.81E-05 |
| rs1540705 | 1.95E-06 | rs4497115 | 1.21E-05 | rs2100684 | 3.41E-05 | rs5934763 | 5.87E-05 |
| rs2239431 | 2.15E-06 | rs17337541 | 1.22E-05 | rs5921682 | 3.42E-05 | rs4358925 | 5.91E-05 |
| rs6608067 | 2.40E-06 | rs1986011 | 1.24E-05 | rs5936019 | 3.44E-05 | rs5918514 | 5.99E-05 |
| rs1073274 | 2.61E-06 | rs203995 | 1.28E-05 | rs5970907 | 3.49E-05 | rs6623334 | 6.00E-05 |
| rs6638536 | 2.63E-06 | rs4475664 | 1.32E-05 | rs2407769 | 3.52E-05 | rs2830582 | 6.06E-05 |
| rs5932609 | 2.66E-06 | rs5969461 | 1.33E-05 | rs6523640 | 3.52E-05 | rs2048637 | 6.07E-05 |
| rs4240003 | 2.76E-06 | rs5942191 | 1.33E-05 | rs5916610 | 3.53E-05 | rs5928121 | 6.15E-05 |
| rs5908325 | 3.03E-06 | rs5929657 | 1.39E-05 | rs5910831 | 3.58E-05 | rs2233048 | 6.16E-05 |
| rs6866970 | 3.13E-06 | rs5920401 | 1.43E-05 | rs11094849 | 3.61E-05 | rs6641786 | 6.20E-05 |
| rs1268602 | 3.23E-06 | rs5937156 | 1.44E-05 | rs2190567 | 3.65E-05 | rs12706350 | 6.24E-05 |
| rs41359256 | 3.43E-06 | rs1425843 | 1.46E-05 | rs17341595 | 3.65E-05 | rs5949779 | 6.31E-05 |
| rs3747276 | 3.48E-06 | rs914936 | 1.50E-05 | rs760580 | 3.66E-05 | rs10514576 | 6.40E-05 |
| rs5961804 | 3.61E-06 | rs2858278 | 1.51E-05 | rs1894571 | 3.71E-05 | rs9927211 | 6.54E-05 |
| rs5972354 | 3.73E-06 | rs6640037 | 1.52E-05 | rs2066364 | 3.74E-05 | rs1937567 | 6.56E-05 |
| rs5968401 | 3.85E-06 | rs9325663 | 1.53E-05 | rs484369 | 3.77E-05 | rs1980775 | 6.69E-05 |
| rs6834019 | 3.90E-06 | rs16995825 | 1.53E-05 | rs16998872 | 3.84E-05 | rs12127143 | 6.74E-05 |
| rs3827468 | 3.95E-06 | rs17377726 | 1.55E-05 | rs4825213 | 3.84E-05 | rs5966508 | 6.75E-05 |
| rs1016824 | 4.00E-06 | rs5985781 | 1.56E-05 | rs5933350 | 3.85E-05 | rs5978240 | 6.79E-05 |
| rs7830923 | 5.42E-06 | rs1474804 | 1.61E-05 | rs1230820 | 3.99E-05 | rs7884069 | 6.83E-05 |
| rs1004991 | 5.59E-06 | rs10521847 | 1.70E-05 | rs3935725 | 4.02E-05 | rs1012454 | 6.83E-05 |
| rs10496147 | 5.89E-06 | rs981780 | 1.71E-05 | rs6629434 | 4.03E-05 | rs4844071 | 6.95E-05 |
| rs16994895 | 6.16E-06 | rs5972463 | 1.71E-05 | rs7052935 | 4.11E-05 | rs762875 | 7.03E-05 |
| rs4421510 | 6.33E-06 | rs5927921 | 1.74E-05 | rs807185 | 4.24E-05 | rs16985984 | 7.18E-05 |
| rs10783884 | 6.65E-06 | rs5971598 | 1.74E-05 | rs4131420 | 4.31E-05 | rs17390 | 7.27E-05 |
| rs5974336 | 6.82E-06 | rs5950604 | 1.84E-05 | rs5974239 | 4.36E-05 | rs2961375 | 7.29E-05 |
| rs9813811 | 6.84E-06 | rs5945723 | 1.96E-05 | rs4829909 | 4.37E-05 | rs2224048 | 7.31E-05 |
| rs6640079 | 7.13E-06 | rs7050981 | 2.03E-05 | rs1448514 | 4.49E-05 | rs5939895 | 7.33E-05 |
| rs6631703 | 7.15E-06 | rs2316179 | 2.10E-05 | rs6530108 | 4.51E-05 | rs6631847 | 7.43E-05 |
| rs2223315 | 7.53E-06 | rs5976289 | 2.10E-05 | rs2842687 | 4.54E-05 | rs10856497 | 7.51E-05 |
| rs7882576 | 7.53E-06 | rs2131927 | 2.27E-05 | rs10863224 | 4.59E-05 | rs2742587 | 7.82E-05 |
| rs17312192 | 8.18E-06 | rs5929842 | 2.30E-05 | rs176034 | 4.63E-05 | rs5972314 | 7.95E-05 |
| rs6619299 | 8.44E-06 | rs1837943 | 2.32E-05 | rs10081857 | 4.71E-05 | rs5941725 | 7.97E-05 |
| rs6609614 | 8.73E-06 | rs5921205 | 2.39E-05 | rs5991450 | 4.74E-05 | rs1019089 | 8.04E-05 |
| rs1866934 | 8.77E-06 | rs5990899 | 2.42E-05 | rs1203564 | 4.78E-05 | rs1478550 | 8.04E-05 |
| rs10275666 | 8.99E-06 | rs5980078 | 2.49E-05 | rs5926901 | 4.83E-05 | rs5970748 | 8.13E-05 |
| rs16856394 | 9.07E-06 | rs1031914 | 2.51E-05 | rs5987947 | 4.84E-05 | rs1378389 | 8.15E-05 |
| rs9018 | 9.11E-06 | rs6540394 | 2.55E-05 | rs5941511 | 4.88E-05 | rs2611019 | 8.16E-05 |
| rs2369786 | 9.27E-06 | rs6634590 | 2.59E-05 | rs5908093 | 4.97E-05 | rs11796000 | 8.18E-05 |

Figure 21-1

| | | | | | | | |
|---|---|---|---|---|---|---|---|
| rs5970768 | 8.20E-05 | rs5961787 | 0.0001163 | rs9996437 | 0.0001552 | rs5908994 | 0.00019894 |
| rs2214180 | 8.23E-05 | rs952836 | 0.0001178 | rs6525581 | 0.0001559 | rs7881785 | 0.00019919 |
| rs633203 | 8.23E-05 | rs5922641 | 0.0001178 | rs7392062 | 0.0001561 | rs17261572 | 0.00019993 |
| rs5915507 | 8.30E-05 | rs4826673 | 0.0001179 | rs6744831 | 0.0001567 | rs16966903 | 0.00020151 |
| rs12008641 | 8.32E-05 | rs12950579 | 0.0001195 | rs11865044 | 0.0001575 | rs287771 | 0.00020449 |
| rs797252 | 8.32E-05 | rs5953410 | 0.0001205 | rs225048 | 0.0001593 | rs12868476 | 0.00020535 |
| rs677066 | 8.45E-05 | rs4074209 | 0.0001219 | rs10521585 | 0.0001604 | rs5934025 | 0.00020568 |
| rs3747687 | 8.45E-05 | rs196356 | 0.000122 | rs1602407 | 0.0001608 | rs10999786 | 0.00020737 |
| rs2014867 | 8.48E-05 | rs3126111 | 0.0001225 | rs5906156 | 0.0001622 | rs12065003 | 0.00021065 |
| rs6528845 | 8.54E-05 | rs10511632 | 0.0001231 | rs1005911 | 0.0001645 | rs10506534 | 0.00021266 |
| rs12842964 | 8.56E-05 | rs766118 | 0.0001232 | rs5935270 | 0.0001645 | rs5942608 | 0.00021305 |
| rs5965947 | 8.56E-05 | rs2800662 | 0.0001234 | rs5910616 | 0.0001648 | rs1029454 | 0.00021385 |
| rs28201 | 8.59E-05 | rs17250761 | 0.0001241 | rs16910276 | 0.0001651 | rs6521151 | 0.00021455 |
| rs234491 | 8.65E-05 | rs5979707 | 0.0001249 | rs9906017 | 0.0001654 | rs1949951 | 0.00021598 |
| rs11864276 | 8.65E-05 | rs1795577 | 0.0001253 | rs715171 | 0.0001659 | rs8169 | 0.00021632 |
| rs11079344 | 8.66E-05 | rs2889001 | 0.0001255 | rs4655316 | 0.0001704 | rs17317628 | 0.00021656 |
| rs10507930 | 8.80E-05 | rs6637507 | 0.0001259 | rs12007404 | 0.0001704 | rs6643887 | 0.00021728 |
| rs7061270 | 8.89E-05 | rs5956542 | 0.0001264 | rs16828505 | 0.0001711 | rs1463435 | 0.00021845 |
| rs2719873 | 8.89E-05 | rs12559140 | 0.0001276 | rs1324823 | 0.0001714 | rs11572381 | 0.00021978 |
| rs3781383 | 9.14E-05 | rs9324789 | 0.0001277 | rs6609302 | 0.0001725 | rs2025580 | 0.00022028 |
| rs4828210 | 9.23E-05 | rs5917513 | 0.0001285 | rs5908542 | 0.0001732 | rs620787 | 0.00022055 |
| rs1115361 | 9.26E-05 | rs5934731 | 0.0001291 | rs10500548 | 0.0001739 | rs5915785 | 0.00022097 |
| rs1656651 | 9.28E-05 | rs17145430 | 0.0001292 | rs41451152 | 0.0001749 | rs4460557 | 0.00022105 |
| rs6527243 | 9.32E-05 | rs2787566 | 0.0001295 | rs5935573 | 0.0001749 | rs17505622 | 0.00022175 |
| rs178715 | 9.37E-05 | rs5974714 | 0.0001298 | rs1015825 | 0.0001753 | rs6645778 | 0.000222 |
| rs5961648 | 9.42E-05 | rs2312984 | 0.00013 | rs10509870 | 0.0001759 | rs5934137 | 0.0002221 |
| rs3126289 | 9.47E-05 | rs16989935 | 0.0001311 | rs2238917 | 0.0001771 | rs5927057 | 0.00022234 |
| rs4844224 | 9.55E-05 | rs10220201 | 0.0001317 | rs5971556 | 0.0001774 | rs5974808 | 0.00022543 |
| rs831167 | 9.66E-05 | rs722847 | 0.0001332 | rs12836051 | 0.0001794 | rs7296677 | 0.00022642 |
| rs6621132 | 9.69E-05 | rs7879492 | 0.000134 | rs1072149 | 0.0001802 | rs5974406 | 0.00022652 |
| rs6616008 | 9.81E-05 | rs979848 | 0.0001344 | rs5944269 | 0.0001825 | rs7056902 | 0.00022687 |
| rs3095633 | 9.87E-05 | rs5910248 | 0.0001353 | rs17108506 | 0.0001831 | rs4129094 | 0.0002275 |
| rs5937126 | 9.90E-05 | rs2254392 | 0.0001356 | rs11942278 | 0.000184 | rs225041 | 0.00022965 |
| rs5935292 | 9.94E-05 | rs41356547 | 0.0001357 | rs6653828 | 0.0001849 | rs6522693 | 0.00023004 |
| rs2316351 | 1.00E-04 | rs1546885 | 0.0001368 | rs1977059 | 0.0001858 | rs9948310 | 0.00023122 |
| rs6654427 | 0.0001012 | rs1609538 | 0.0001375 | rs12852982 | 0.0001868 | rs5984750 | 0.00023273 |
| rs11795905 | 0.0001028 | rs5984526 | 0.0001399 | rs1869562 | 0.0001882 | rs5989582 | 0.00023303 |
| rs5927267 | 0.0001037 | rs1033388 | 0.0001409 | rs2266910 | 0.0001882 | rs6603421 | 0.00023331 |
| rs3125579 | 0.0001039 | rs10173586 | 0.0001424 | rs11096119 | 0.0001885 | rs1361651 | 0.00023409 |
| rs6530045 | 0.0001047 | rs7062414 | 0.0001427 | rs3828983 | 0.0001886 | rs5957470 | 0.00023523 |
| rs17541189 | 0.0001065 | rs12391688 | 0.0001427 | rs7527017 | 0.0001889 | rs2748475 | 0.00023607 |
| rs4830233 | 0.0001065 | rs17020606 | 0.000143 | rs11094826 | 0.0001899 | rs1529405 | 0.0002374 |
| rs4830335 | 0.0001073 | rs2903676 | 0.0001434 | rs11095248 | 0.0001902 | rs5955303 | 0.00023785 |
| rs5943240 | 0.0001092 | rs5949319 | 0.0001445 | rs7631725 | 0.0001915 | rs5956460 | 0.00023913 |
| rs17013157 | 0.0001097 | rs7061076 | 0.0001449 | rs3772601 | 0.0001916 | rs5905768 | 0.00023913 |
| rs6520412 | 0.0001098 | rs5918075 | 0.0001453 | rs17341330 | 0.000192 | rs477233 | 0.00024383 |
| rs11549009 | 0.0001102 | rs6847617 | 0.0001457 | rs6523584 | 0.0001921 | rs5972363 | 0.00024529 |
| rs12014135 | 0.0001123 | rs7879771 | 0.0001482 | rs4826634 | 0.0001921 | rs6528142 | 0.0002455 |
| rs5907551 | 0.0001125 | rs1322199 | 0.0001498 | rs845122 | 0.0001923 | rs473838 | 0.00024605 |
| rs4759438 | 0.0001128 | rs331345 | 0.0001512 | rs17758599 | 0.0001925 | rs9894417 | 0.00024623 |
| rs991256 | 0.0001131 | rs6636113 | 0.0001523 | rs978390 | 0.000196 | rs6418754 | 0.00024754 |
| rs5986271 | 0.0001133 | rs1263913 | 0.0001527 | rs13403523 | 0.000197 | rs942459 | 0.00024803 |
| rs5919700 | 0.0001138 | rs6654492 | 0.000153 | rs6627910 | 0.000198 | rs6641022 | 0.00024868 |
| rs1906299 | 0.0001159 | rs41495649 | 0.0001533 | rs17120381 | 0.0001985 | rs6530511 | 0.00024868 |
| rs17034357 | 0.000116 | rs13158981 | 0.0001552 | rs6611276 | 0.0001989 | rs12307589 | 0.00025279 |

Figure 21-2

| | | | | | | | |
|---|---|---|---|---|---|---|---|
| rs7738055 | 0.0002545 | rs10470321 | 0.0003026 | rs10880022 | 0.0003503 | rs6624074 | 0.00040852 |
| rs5972240 | 0.000255 | rs500879 | 0.0003028 | rs7663471 | 0.0003504 | rs5950893 | 0.00040955 |
| rs17004107 | 0.000257 | rs7776126 | 0.000303 | rs1293919 | 0.0003531 | rs17321050 | 0.00040995 |
| rs17597375 | 0.0002606 | rs5926307 | 0.0003041 | rs2025278 | 0.0003532 | rs4240155 | 0.00041035 |
| rs8126456 | 0.0002615 | rs17650556 | 0.0003048 | rs5932574 | 0.0003535 | rs2902210 | 0.00041373 |
| rs850635 | 0.0002615 | rs1726206 | 0.0003049 | rs4787348 | 0.0003541 | rs707289 | 0.00041472 |
| rs4447684 | 0.0002623 | rs16970170 | 0.0003056 | rs12325649 | 0.0003545 | rs4829035 | 0.00041524 |
| rs5910867 | 0.0002634 | rs1882354 | 0.000306 | rs4526506 | 0.0003556 | rs10765861 | 0.00042006 |
| rs2192276 | 0.0002646 | rs2199809 | 0.0003087 | rs11252547 | 0.0003564 | rs5911622 | 0.00042111 |
| rs9552517 | 0.0002657 | rs900450 | 0.0003092 | rs5981268 | 0.0003579 | rs736818 | 0.00042362 |
| rs821038 | 0.0002669 | rs1353456 | 0.0003092 | rs1158755 | 0.0003594 | rs4826609 | 0.00042385 |
| rs12687579 | 0.0002671 | rs7707177 | 0.0003101 | rs12513356 | 0.0003598 | rs5936684 | 0.00042754 |
| rs2127064 | 0.000268 | rs2979322 | 0.0003104 | rs4425925 | 0.0003599 | rs975166 | 0.00042873 |
| rs10483818 | 0.0002683 | rs12489946 | 0.0003105 | rs7909677 | 0.0003624 | rs5990013 | 0.00042922 |
| rs2588288 | 0.0002696 | rs682176 | 0.0003119 | rs11899367 | 0.0003626 | rs11218131 | 0.00042925 |
| rs6984890 | 0.0002696 | rs16861267 | 0.0003121 | rs9698796 | 0.0003626 | rs7952006 | 0.00042961 |
| rs7891415 | 0.0002699 | rs5916520 | 0.0003124 | rs2926458 | 0.000365 | rs1204399 | 0.00043114 |
| rs5951458 | 0.0002704 | rs5940942 | 0.0003145 | rs17159801 | 0.000366 | rs5916245 | 0.00043141 |
| rs4307646 | 0.0002706 | rs7577881 | 0.0003149 | rs400439 | 0.0003666 | rs11092739 | 0.00043174 |
| rs16923297 | 0.0002707 | rs178685 | 0.0003151 | rs35906400 | 0.0003668 | rs4969661 | 0.00043509 |
| rs964528 | 0.0002716 | rs41376146 | 0.0003152 | rs6943487 | 0.000367 | rs10459940 | 0.00043593 |
| rs233655 | 0.0002722 | rs17076490 | 0.000317 | rs12159204 | 0.0003684 | rs1858934 | 0.00043806 |
| rs5972177 | 0.0002727 | rs4844164 | 0.0003173 | rs12007523 | 0.0003694 | rs17542763 | 0.00043984 |
| rs5927923 | 0.0002728 | rs6825299 | 0.0003177 | rs41477549 | 0.0003702 | rs13385578 | 0.00044122 |
| rs4623700 | 0.0002731 | rs11092309 | 0.0003186 | rs4825158 | 0.0003711 | rs979127 | 0.00044359 |
| rs815869 | 0.0002755 | rs5990540 | 0.0003186 | rs4474149 | 0.0003725 | rs2521385 | 0.00044378 |
| rs11169170 | 0.0002758 | rs5916657 | 0.00032 | rs4288315 | 0.0003741 | rs17300926 | 0.00044465 |
| rs1703946 | 0.0002765 | rs17019491 | 0.0003209 | rs9806181 | 0.0003746 | rs2051727 | 0.00044614 |
| rs5915287 | 0.0002766 | rs5906161 | 0.0003213 | rs845188 | 0.0003796 | rs376165 | 0.00044636 |
| rs5923929 | 0.0002785 | rs6964079 | 0.0003219 | rs1018794 | 0.0003811 | rs41333050 | 0.00044645 |
| rs5935153 | 0.0002791 | rs12320268 | 0.000323 | rs9988299 | 0.0003831 | rs1125142 | 0.00044666 |
| rs17035686 | 0.0002794 | rs10498926 | 0.0003234 | rs5936963 | 0.000384 | rs3128282 | 0.00044785 |
| rs6590392 | 0.0002796 | rs5934746 | 0.0003248 | rs5926173 | 0.0003851 | rs5915856 | 0.00044819 |
| rs10961079 | 0.0002801 | rs2428447 | 0.0003255 | rs4262422 | 0.0003856 | rs228392 | 0.00044905 |
| rs7190458 | 0.0002815 | rs4733372 | 0.0003258 | rs6551290 | 0.0003857 | rs5979977 | 0.00045173 |
| rs454992 | 0.0002818 | rs5942185 | 0.0003269 | rs7853273 | 0.0003864 | rs1380722 | 0.00045353 |
| rs4330825 | 0.0002819 | rs5910842 | 0.0003269 | rs6624381 | 0.0003874 | rs4072191 | 0.00045626 |
| rs7718116 | 0.0002845 | rs1007942 | 0.000329 | rs5919772 | 0.0003877 | rs1342321 | 0.00045872 |
| rs5923736 | 0.0002854 | rs4679029 | 0.0003291 | rs11797927 | 0.0003881 | rs11209241 | 0.00046002 |
| rs5917288 | 0.0002874 | rs161630 | 0.0003316 | rs12558359 | 0.0003889 | rs17148289 | 0.00046048 |
| rs17259400 | 0.0002877 | rs7225465 | 0.000332 | rs11051643 | 0.0003898 | rs763696 | 0.00046106 |
| rs1268027 | 0.0002883 | rs2238973 | 0.0003321 | rs6527192 | 0.0003907 | rs119301 | 0.00046154 |
| rs5908591 | 0.0002906 | rs1980789 | 0.0003322 | rs653618 | 0.0003912 | rs4892897 | 0.00046276 |
| rs1116372 | 0.000292 | rs4969659 | 0.000334 | rs11091070 | 0.0003928 | rs5974275 | 0.00046481 |
| rs5973375 | 0.0002929 | rs10944520 | 0.0003345 | rs331347 | 0.000393 | rs7138534 | 0.00046643 |
| rs4828959 | 0.0002933 | rs6894882 | 0.0003347 | rs194293 | 0.0003947 | rs5981088 | 0.00046668 |
| rs2805962 | 0.0002946 | rs1368769 | 0.0003387 | rs12398801 | 0.000397 | rs16981858 | 0.00046792 |
| rs2266790 | 0.0002954 | rs5911136 | 0.0003396 | rs6630002 | 0.0004003 | rs4080381 | 0.00046951 |
| rs17134173 | 0.0002965 | rs5906947 | 0.0003405 | rs10161783 | 0.0004012 | rs5966774 | 0.00046957 |
| rs4829169 | 0.0002979 | rs11265318 | 0.0003409 | rs5918081 | 0.0004023 | rs5010471 | 0.00047054 |
| rs5924002 | 0.0002984 | rs400586 | 0.0003423 | rs1540301 | 0.000403 | rs6829976 | 0.00047179 |
| rs5916870 | 0.0002984 | rs16901105 | 0.0003441 | rs5968948 | 0.0004052 | rs9803580 | 0.00047386 |
| rs17575611 | 0.0002986 | rs12037400 | 0.0003464 | rs11943130 | 0.0004057 | rs623695 | 0.00047778 |
| rs7325627 | 0.0002995 | rs5930036 | 0.0003484 | rs4829934 | 0.0004057 | rs17411883 | 0.00047844 |
| rs2632086 | 0.0003 | rs765304 | 0.0003497 | rs2451678 | 0.0004074 | rs568707 | 0.00048002 |

Figure 21-3

| | | | | | | | |
|---|---|---|---|---|---|---|---|
| rs6639416 | 0.0004815 | rs17254207 | 0.0005789 | rs4291390 | 0.0007037 | rs12526341 | 0.00081451 |
| rs5922023 | 0.0004871 | rs5971110 | 0.0005803 | rs5934442 | 0.0007097 | rs13027348 | 0.00081934 |
| rs4573436 | 0.0004873 | rs4827600 | 0.0005816 | rs5929803 | 0.00071 | rs11122275 | 0.00082208 |
| rs7553222 | 0.0004896 | rs107621 | 0.0005817 | rs5906073 | 0.0007102 | rs10126138 | 0.00082342 |
| rs5935138 | 0.0004924 | rs5982635 | 0.0005822 | rs6619657 | 0.0007102 | rs12560013 | 0.00082359 |
| rs16905445 | 0.000494 | rs10467741 | 0.0005836 | rs6641050 | 0.0007117 | rs11071467 | 0.0008263 |
| rs12661742 | 0.0004942 | rs206050 | 0.0005856 | rs17219483 | 0.0007146 | rs4824228 | 0.00082668 |
| rs4844477 | 0.0004953 | rs9887051 | 0.0005859 | rs12844438 | 0.0007152 | rs1650590 | 0.00082727 |
| rs5956652 | 0.0004953 | rs11125548 | 0.0005869 | rs16975213 | 0.000717 | rs17481221 | 0.00082949 |
| rs17278485 | 0.0004981 | rs1620574 | 0.0005872 | rs719499 | 0.0007192 | rs6617632 | 0.00083014 |
| rs5918494 | 0.0004989 | rs4893429 | 0.0005916 | rs206599 | 0.0007203 | rs1926114 | 0.00083271 |
| rs4827622 | 0.0005006 | rs1454500 | 0.0005939 | rs7166105 | 0.0007227 | rs7534148 | 0.00083301 |
| rs5973843 | 0.000501 | rs11152555 | 0.0006033 | rs7585736 | 0.0007258 | rs10521956 | 0.00083588 |
| rs41536847 | 0.0005023 | rs1999923 | 0.0006051 | rs5935385 | 0.0007272 | rs16985419 | 0.00083752 |
| rs17097997 | 0.0005037 | rs4827618 | 0.0006064 | rs292199 | 0.0007285 | rs7475474 | 0.00084211 |
| rs41525448 | 0.0005061 | rs5959364 | 0.0006094 | rs10521981 | 0.000729 | rs10522007 | 0.00084988 |
| rs6628810 | 0.0005151 | rs2436065 | 0.0006113 | rs4503229 | 0.0007333 | rs8077332 | 0.00085439 |
| rs661342 | 0.0005164 | rs6632790 | 0.0006121 | rs2858222 | 0.0007341 | rs10505725 | 0.00085591 |
| rs10091938 | 0.0005199 | rs5951580 | 0.0006157 | rs6633000 | 0.0007345 | rs1948558 | 0.00085744 |
| rs4830677 | 0.0005234 | rs6526513 | 0.0006165 | rs5908778 | 0.000737 | rs588427 | 0.00085768 |
| rs11083957 | 0.0005258 | rs659521 | 0.0006173 | rs17190904 | 0.0007407 | rs11120869 | 0.00086064 |
| rs16994558 | 0.0005259 | rs1935404 | 0.0006215 | rs2040416 | 0.0007449 | rs1453329 | 0.00086212 |
| rs10855477 | 0.0005266 | rs9493709 | 0.0006253 | rs6636518 | 0.000749 | rs2540769 | 0.00086341 |
| rs7827160 | 0.0005307 | rs987017 | 0.0006288 | rs16870514 | 0.0007502 | rs5972873 | 0.00086447 |
| rs6420139 | 0.0005313 | rs7719299 | 0.0006294 | rs5930699 | 0.0007511 | rs6694388 | 0.00086642 |
| rs1159223 | 0.0005332 | rs5978122 | 0.0006311 | rs4830633 | 0.0007512 | rs12710568 | 0.00086771 |
| rs12012009 | 0.0005348 | rs4571411 | 0.0006315 | rs5904763 | 0.0007571 | rs17835106 | 0.00086787 |
| rs871156 | 0.0005352 | rs10820175 | 0.0006335 | rs9450829 | 0.0007574 | rs2179049 | 0.00086814 |
| rs1029308 | 0.0005371 | rs7826323 | 0.0006341 | rs601552 | 0.0007607 | rs6641173 | 0.00086901 |
| rs2224095 | 0.000538 | rs4300782 | 0.0006386 | rs17325827 | 0.000763 | rs12854960 | 0.00087142 |
| rs6528940 | 0.0005402 | rs12848856 | 0.000639 | rs2561435 | 0.0007671 | rs1581706 | 0.00087214 |
| rs533054 | 0.0005411 | rs5974183 | 0.0006394 | rs3920502 | 0.0007711 | rs10983233 | 0.00087462 |
| rs719199 | 0.0005414 | rs10498670 | 0.00065 | rs10867945 | 0.000772 | rs2570306 | 0.00087673 |
| rs11092138 | 0.0005426 | rs12557389 | 0.0006557 | rs7066452 | 0.0007721 | rs1482821 | 0.00087723 |
| rs367985 | 0.0005428 | rs5955132 | 0.0006559 | rs3752627 | 0.0007733 | rs3819662 | 0.00087727 |
| rs5927035 | 0.0005436 | rs1937561 | 0.0006571 | rs5921731 | 0.0007735 | rs2521651 | 0.00087842 |
| rs2150010 | 0.0005491 | rs17315366 | 0.0006586 | rs4829829 | 0.0007749 | rs177680 | 0.00087873 |
| rs2806022 | 0.0005492 | rs4816165 | 0.0006598 | rs2499416 | 0.0007751 | rs4306056 | 0.00088598 |
| rs5922797 | 0.0005526 | rs4545218 | 0.0006607 | rs5942091 | 0.0007773 | rs9892139 | 0.00088887 |
| rs9501885 | 0.0005543 | rs10948714 | 0.0006631 | rs1879610 | 0.0007783 | rs5971421 | 0.00090017 |
| rs5916284 | 0.0005549 | rs9539143 | 0.0006638 | rs5921690 | 0.0007815 | rs12594048 | 0.000905 |
| rs1937178 | 0.0005553 | rs6756191 | 0.0006687 | rs10521556 | 0.0007822 | rs4957169 | 0.00090574 |
| rs6633864 | 0.0005566 | rs2534697 | 0.000669 | rs5979463 | 0.0007844 | rs972655 | 0.00090696 |
| rs4457887 | 0.0005566 | rs6641482 | 0.0006705 | rs603315 | 0.0007877 | rs5918053 | 0.00090798 |
| rs12855563 | 0.000557 | rs4826184 | 0.0006735 | rs11167418 | 0.0007897 | rs2731014 | 0.00090985 |
| rs17333127 | 0.0005586 | rs6634857 | 0.0006768 | rs5945977 | 0.0007901 | rs9556491 | 0.00091076 |
| rs2106913 | 0.0005588 | rs17133347 | 0.0006835 | rs6610918 | 0.0007913 | rs6527730 | 0.00091126 |
| rs5972512 | 0.0005591 | rs5936657 | 0.0006842 | rs5958482 | 0.0007936 | rs4805410 | 0.00091207 |
| rs845445 | 0.0005609 | rs6629310 | 0.0006887 | rs4826217 | 0.0007957 | rs2269466 | 0.00091562 |
| rs1929363 | 0.0005655 | rs954911 | 0.0006927 | rs12689414 | 0.0008024 | rs6520724 | 0.0009168 |
| rs1493061 | 0.0005677 | rs7026753 | 0.0006931 | rs6629756 | 0.0008031 | rs7064695 | 0.00091999 |
| rs41516347 | 0.0005749 | rs629846 | 0.000696 | rs919037 | 0.0008037 | rs12556842 | 0.00092038 |
| rs4811738 | 0.0005754 | rs11055460 | 0.0006964 | rs6685296 | 0.0008042 | rs7880724 | 0.00092092 |
| rs2519196 | 0.0005787 | rs5978787 | 0.0007027 | rs17017422 | 0.000806 | rs5980419 | 0.00092491 |
| rs4240068 | 0.0005788 | rs5928378 | 0.0007027 | rs9321951 | 0.0008092 | rs2858769 | 0.00093018 |

Figure 21-4

| | | | | | | | |
|---|---|---|---|---|---|---|---|
| rs6608501 | 0.0009307 | rs2595146 | 0.0010466 | rs6624219 | 0.0011488 | rs17270765 | 0.00129065 |
| rs4826225 | 0.0009321 | rs17721991 | 0.0010499 | rs4824580 | 0.0011488 | rs5922289 | 0.00129082 |
| rs6634178 | 0.0009336 | rs1336832 | 0.0010509 | rs1409134 | 0.0011522 | rs5967919 | 0.0012912 |
| rs2050979 | 0.0009391 | rs1195395 | 0.0010554 | rs2227142 | 0.001155 | rs5931583 | 0.0012916 |
| rs4830507 | 0.0009416 | rs1115799 | 0.001057 | rs5950978 | 0.0011578 | rs16936151 | 0.00129237 |
| rs11925620 | 0.0009444 | rs17057631 | 0.0010576 | rs4365962 | 0.001158 | rs5951426 | 0.00129292 |
| rs17069764 | 0.0009485 | rs6675190 | 0.0010581 | rs2238149 | 0.0011589 | rs17127885 | 0.00129522 |
| rs1126140 | 0.000952 | rs13328515 | 0.001059 | rs2225969 | 0.0011607 | rs1540281 | 0.00129564 |
| rs6034572 | 0.0009538 | rs12454155 | 0.0010668 | rs1318833 | 0.0011673 | rs17627141 | 0.00129723 |
| rs16945163 | 0.0009598 | rs5909509 | 0.0010698 | rs5934013 | 0.0011696 | rs3926503 | 0.00130058 |
| rs532856 | 0.0009605 | rs2855259 | 0.0010721 | rs7526407 | 0.0011725 | rs556111 | 0.00130131 |
| rs5926763 | 0.0009627 | rs5979403 | 0.0010745 | rs2109563 | 0.0011798 | rs2050775 | 0.00130267 |
| rs1414073 | 0.000964 | rs217932 | 0.0010747 | rs10494345 | 0.0011812 | rs3918084 | 0.00130515 |
| rs2188133 | 0.0009669 | rs6527577 | 0.0010799 | rs6568219 | 0.0011828 | rs6637465 | 0.0013055 |
| rs1556618 | 0.0009677 | rs555063 | 0.0010838 | rs1731475 | 0.0011854 | rs4643744 | 0.00131142 |
| rs5972174 | 0.0009691 | rs2807171 | 0.0010871 | rs1921938 | 0.0011871 | rs12198920 | 0.00131572 |
| rs12556700 | 0.000974 | rs5980285 | 0.0010881 | rs5918486 | 0.0011888 | rs2242903 | 0.00132036 |
| rs3865999 | 0.0009746 | rs1876415 | 0.0010892 | rs6539020 | 0.0011913 | rs5934628 | 0.00132716 |
| rs1795594 | 0.0009772 | rs5937005 | 0.0010927 | rs5934039 | 0.001192 | rs1898271 | 0.00132906 |
| rs5927141 | 0.0009772 | rs6710956 | 0.0010931 | rs2804591 | 0.0011987 | rs17333065 | 0.00133026 |
| rs4923429 | 0.0009788 | rs2838246 | 0.0010953 | rs5927105 | 0.0011996 | rs17388907 | 0.00133253 |
| rs5931086 | 0.0009797 | rs11027538 | 0.0010957 | rs9550218 | 0.0012001 | rs11245246 | 0.00133309 |
| rs12623857 | 0.0009827 | rs5935784 | 0.0010957 | rs10491777 | 0.0012044 | rs17329378 | 0.00133565 |
| rs5977273 | 0.0009846 | rs6953339 | 0.0010984 | rs7772349 | 0.0012062 | rs6568048 | 0.00133669 |
| rs17222293 | 0.0009871 | rs12861218 | 0.0010989 | rs7888015 | 0.0012082 | rs2748855 | 0.00133812 |
| rs1788244 | 0.0009883 | rs5926757 | 0.0010991 | rs1207469 | 0.0012085 | rs1921944 | 0.00134784 |
| rs12489983 | 0.000991 | rs6528766 | 0.0010996 | rs823066 | 0.0012129 | rs5972815 | 0.00134984 |
| rs5935925 | 0.0009926 | rs858079 | 0.0011001 | rs3127080 | 0.0012149 | rs848622 | 0.00135153 |
| rs4304064 | 0.0009931 | rs17031214 | 0.0011027 | rs5927572 | 0.0012169 | rs5920040 | 0.00135298 |
| rs5979606 | 0.0009936 | rs11094371 | 0.001103 | rs5940848 | 0.0012173 | rs7885172 | 0.0013536 |
| rs5963786 | 0.0009941 | rs2660006 | 0.001103 | rs10491766 | 0.0012186 | rs1482832 | 0.00135902 |
| rs3095571 | 0.0009943 | rs209990 | 0.0011066 | rs6636303 | 0.001222 | rs7884783 | 0.00135948 |
| rs12689742 | 0.0009958 | rs5910840 | 0.0011078 | rs1859168 | 0.0012221 | rs7055913 | 0.00136155 |
| rs11204227 | 0.0009971 | rs2182285 | 0.0011081 | rs11773573 | 0.0012258 | rs16990063 | 0.00136575 |
| rs5910186 | 0.0010018 | rs7864957 | 0.001109 | rs5920671 | 0.0012272 | rs7296488 | 0.00136746 |
| rs4824801 | 0.0010032 | rs7876945 | 0.0011093 | rs11215380 | 0.0012315 | rs7541884 | 0.00137536 |
| rs5942617 | 0.0010088 | rs4586824 | 0.0011095 | rs868117 | 0.0012316 | rs10033375 | 0.00137654 |
| rs11265310 | 0.0010127 | rs12427587 | 0.001111 | rs12488162 | 0.0012335 | rs12689966 | 0.00137944 |
| rs6609568 | 0.0010133 | rs11091237 | 0.001113 | rs5935787 | 0.0012355 | rs17807973 | 0.00138259 |
| rs2117234 | 0.0010147 | rs1736649 | 0.0011138 | rs5933842 | 0.0012355 | rs283446 | 0.00138287 |
| rs2027803 | 0.0010149 | rs539181 | 0.0011167 | rs6942273 | 0.0012407 | rs5907830 | 0.00138383 |
| rs5972224 | 0.0010172 | rs4912577 | 0.0011168 | rs175737 | 0.001243 | rs209234 | 0.0013862 |
| rs7683566 | 0.0010222 | rs41483250 | 0.0011192 | rs6461569 | 0.0012451 | rs1397169 | 0.00138675 |
| rs6081140 | 0.0010227 | rs3176595 | 0.0011224 | rs2627530 | 0.0012473 | rs9644996 | 0.00139061 |
| rs41342947 | 0.0010265 | rs1436971 | 0.0011225 | rs2107528 | 0.0012481 | rs2071780 | 0.0013915 |
| rs5989532 | 0.0010268 | rs17576350 | 0.0011233 | rs3013028 | 0.001249 | rs5977928 | 0.00139204 |
| rs2904124 | 0.0010271 | rs11095630 | 0.0011237 | rs10906798 | 0.0012527 | rs6520655 | 0.0013922 |
| rs12568255 | 0.0010288 | rs17801315 | 0.0011241 | rs488163 | 0.0012555 | rs4484871 | 0.00139362 |
| rs1997481 | 0.0010294 | rs2057521 | 0.0011296 | rs4920416 | 0.0012609 | rs6608087 | 0.00139487 |
| rs13073001 | 0.0010296 | rs2050909 | 0.0011357 | rs10993042 | 0.0012658 | rs16999222 | 0.00139818 |
| rs943498 | 0.0010309 | rs6530556 | 0.0011377 | rs6418053 | 0.0012695 | rs11806541 | 0.00140033 |
| rs6520279 | 0.001034 | rs16962802 | 0.0011417 | rs6617714 | 0.0012709 | rs5920370 | 0.00140055 |
| rs11165120 | 0.0010392 | rs4903444 | 0.001146 | rs4824895 | 0.0012764 | rs923820 | 0.00140444 |
| rs1537720 | 0.0010433 | rs2746112 | 0.0011465 | rs1727451 | 0.0012792 | rs5957567 | 0.00140597 |
| rs12078096 | 0.0010453 | rs2264844 | 0.001147 | rs2474853 | 0.0012867 | rs9408314 | 0.00140658 |

Figure 21-5

| | | | | | | | |
|---|---|---|---|---|---|---|---|
| rs5922256 | 0.0014107 | rs17114702 | 0.0015632 | rs5943053 | 0.0017117 | rs7250197 | 0.00186604 |
| rs11652587 | 0.0014151 | rs7053403 | 0.0015636 | rs4870397 | 0.0017119 | rs16912030 | 0.00186738 |
| rs7063248 | 0.0014167 | rs6546227 | 0.0015637 | rs7338471 | 0.0017123 | rs10511264 | 0.00187045 |
| rs1927272 | 0.0014169 | rs845118 | 0.0015662 | rs17285811 | 0.0017147 | rs2001510 | 0.00187687 |
| rs7053410 | 0.0014268 | rs6639974 | 0.0015672 | rs6471286 | 0.0017158 | rs6110699 | 0.00188002 |
| rs9287640 | 0.0014272 | rs5934683 | 0.0015705 | rs154756 | 0.0017212 | rs17304062 | 0.00188456 |
| rs12876111 | 0.0014272 | rs5931630 | 0.0015745 | rs12468338 | 0.0017262 | rs11084878 | 0.001886 |
| rs7974374 | 0.0014275 | rs5920606 | 0.0015758 | rs9865038 | 0.0017279 | rs1470909 | 0.00188901 |
| rs6608592 | 0.0014275 | rs5950249 | 0.0015801 | rs10492879 | 0.0017306 | rs996058 | 0.00189152 |
| rs35091279 | 0.0014328 | rs12687753 | 0.0015821 | rs10521972 | 0.0017341 | rs12559003 | 0.00189466 |
| rs6639695 | 0.0014366 | rs16825798 | 0.0015822 | rs9813304 | 0.0017341 | rs16984818 | 0.00189607 |
| rs5908724 | 0.001437 | rs3911610 | 0.0015847 | rs12832235 | 0.0017387 | rs17108228 | 0.00189804 |
| rs2428720 | 0.0014416 | rs7018599 | 0.0015862 | rs6600090 | 0.0017404 | rs10121216 | 0.00189981 |
| rs4827044 | 0.0014425 | rs10519262 | 0.0015915 | rs202777 | 0.001743 | rs4376434 | 0.00190068 |
| rs2278945 | 0.0014439 | rs4828437 | 0.0015932 | rs5911660 | 0.0017449 | rs5906928 | 0.00190483 |
| rs2285633 | 0.0014448 | rs4830050 | 0.0015935 | rs16868212 | 0.0017461 | rs11062532 | 0.00190736 |
| rs7058159 | 0.0014463 | rs5981065 | 0.0015945 | rs536097 | 0.0017465 | rs743896 | 0.00191456 |
| rs17170955 | 0.0014534 | rs5917963 | 0.0016033 | rs4134051 | 0.0017497 | rs960066 | 0.00191551 |
| rs9678479 | 0.001459 | rs2292804 | 0.0016069 | rs10512989 | 0.0017533 | rs2594854 | 0.00191843 |
| rs16911103 | 0.0014627 | rs196580 | 0.0016091 | rs4478749 | 0.0017537 | rs2010606 | 0.00192018 |
| rs17160154 | 0.0014637 | rs2448853 | 0.001611 | rs7806810 | 0.0017562 | rs1944390 | 0.00192316 |
| rs5944690 | 0.0014675 | rs3895063 | 0.001613 | rs5909187 | 0.0017585 | rs5977298 | 0.00192621 |
| rs5909721 | 0.0014686 | rs378414 | 0.001615 | rs6548098 | 0.0017697 | rs6629277 | 0.00193512 |
| rs479036 | 0.0014713 | rs17131080 | 0.0016195 | rs5970645 | 0.0017727 | rs1003169 | 0.00193579 |
| rs6636107 | 0.0014741 | rs7684025 | 0.0016207 | rs4826690 | 0.0017746 | rs1342219 | 0.00193875 |
| rs17246141 | 0.0014745 | rs3117460 | 0.0016233 | rs5930020 | 0.0017758 | rs11048606 | 0.00193905 |
| rs2320009 | 0.0014802 | rs13102624 | 0.0016254 | rs2727184 | 0.0017819 | rs17276881 | 0.00194542 |
| rs5933743 | 0.0014819 | rs7069744 | 0.0016296 | rs482796 | 0.0017832 | rs7539893 | 0.00194681 |
| rs12387720 | 0.0014827 | rs815419 | 0.0016532 | rs11256530 | 0.0017877 | rs2748302 | 0.00194729 |
| rs11564026 | 0.0014856 | rs3008972 | 0.0016556 | rs16989995 | 0.001793 | rs7192139 | 0.00194778 |
| rs11052552 | 0.0014918 | rs10881582 | 0.0016567 | rs5908051 | 0.0017936 | rs17532490 | 0.00194952 |
| rs5950402 | 0.0014937 | rs12185961 | 0.0016569 | rs7644001 | 0.0017987 | rs10081808 | 0.00195023 |
| rs5916697 | 0.0014972 | rs41476844 | 0.0016573 | rs7699969 | 0.0018013 | rs134767 | 0.00195514 |
| rs33123 | 0.0015029 | rs12836085 | 0.0016577 | rs17517294 | 0.0018017 | rs4893622 | 0.00195681 |
| rs2010818 | 0.001516 | rs9988960 | 0.0016585 | rs1634347 | 0.0018019 | rs1493594 | 0.00195769 |
| rs2092909 | 0.0015183 | rs5920650 | 0.0016594 | rs2384424 | 0.0018025 | rs2612326 | 0.00195822 |
| rs10521922 | 0.0015189 | rs3746250 | 0.0016605 | rs5905013 | 0.0018053 | rs5974210 | 0.00195929 |
| rs959694 | 0.001522 | rs10168890 | 0.0016628 | rs1898810 | 0.0018267 | rs1216714 | 0.00196133 |
| rs7762850 | 0.0015233 | rs7669737 | 0.0016635 | rs1370865 | 0.0018291 | rs6645884 | 0.00196248 |
| rs7422689 | 0.0015278 | rs2335519 | 0.0016669 | rs916658 | 0.0018319 | rs7193282 | 0.00196351 |
| rs8024593 | 0.0015279 | rs5936438 | 0.0016672 | rs11163235 | 0.0018342 | rs11002824 | 0.00196678 |
| rs2281808 | 0.0015303 | rs5921608 | 0.0016688 | rs4759285 | 0.0018349 | rs6641732 | 0.00196842 |
| rs16950388 | 0.0015358 | rs2144732 | 0.0016707 | rs1016553 | 0.0018367 | rs617156 | 0.00197332 |
| rs1041236 | 0.0015406 | rs10521748 | 0.001672 | rs17726411 | 0.001837 | rs11150186 | 0.00197476 |
| rs5944691 | 0.0015407 | rs7403021 | 0.0016816 | rs11682110 | 0.0018404 | rs1592293 | 0.00198202 |
| rs7562854 | 0.0015416 | rs1978147 | 0.0016858 | rs10521352 | 0.0018423 | rs11597065 | 0.00198347 |
| rs2521413 | 0.0015448 | rs12010464 | 0.0016867 | rs4408025 | 0.0018454 | rs1986391 | 0.00198544 |
| rs2982104 | 0.0015459 | rs816971 | 0.0016878 | rs3803214 | 0.0018455 | rs5931020 | 0.00198622 |
| rs6087099 | 0.0015482 | rs1558089 | 0.0016902 | rs17584901 | 0.0018506 | rs12273505 | 0.0019876 |
| rs6637454 | 0.0015498 | rs5928685 | 0.0016944 | rs7879462 | 0.0018512 | rs407746 | 0.00198929 |
| rs13148770 | 0.0015528 | rs898249 | 0.0016961 | rs10521683 | 0.0018528 | rs2498044 | 0.00199083 |
| rs2129557 | 0.0015529 | rs2239477 | 0.0017006 | rs5937001 | 0.0018591 | rs7879064 | 0.00199267 |
| rs25699 | 0.001557 | rs2742899 | 0.0017085 | rs4889442 | 0.0018601 | rs5923840 | 0.00199562 |
| rs12338324 | 0.0015587 | rs7844594 | 0.0017097 | rs17300660 | 0.0018626 | rs10785219 | 0.00199979 |
| rs8044444 | 0.0015599 | rs1916827 | 0.00171 | rs6567560 | 0.0018643 | rs1033952 | 0.00200103 |

Figure 21-6

| | | | | | | | |
|---|---|---|---|---|---|---|---|
| rs5931055 | 0.0020028 | rs1237597 | 0.0021771 | rs5925658 | 0.0023131 | rs2984344 | 0.00246824 |
| rs12191972 | 0.002008 | rs5940217 | 0.002181 | rs2522942 | 0.0023136 | rs2074321 | 0.00247031 |
| rs5933686 | 0.0020202 | rs4830882 | 0.0021828 | rs3002415 | 0.0023155 | rs17594762 | 0.00247953 |
| rs1600705 | 0.0020212 | rs2205637 | 0.0021837 | rs6960667 | 0.0023205 | rs3763496 | 0.00248049 |
| rs1277992 | 0.0020237 | rs41393746 | 0.002184 | rs2428212 | 0.0023236 | rs821931 | 0.00248293 |
| rs1293888 | 0.002026 | rs17745898 | 0.0021873 | rs2312033 | 0.0023243 | rs7602129 | 0.00248309 |
| rs6676084 | 0.0020293 | rs13111857 | 0.0021882 | rs2271688 | 0.0023296 | rs875494 | 0.00248916 |
| rs17280555 | 0.002033 | rs35731709 | 0.0021926 | rs7034379 | 0.0023315 | rs2373571 | 0.00248984 |
| rs12672637 | 0.0020338 | rs814953 | 0.0021952 | rs12396885 | 0.0023329 | rs7062292 | 0.00249602 |
| rs17338737 | 0.0020338 | rs5974063 | 0.0021968 | rs1563295 | 0.0023346 | rs5953564 | 0.00250443 |
| rs11698063 | 0.002034 | rs4844144 | 0.0022003 | rs17421554 | 0.0023381 | rs1839148 | 0.00250556 |
| rs17191803 | 0.0020384 | rs5970756 | 0.0022013 | rs1194565 | 0.0023395 | rs2971381 | 0.00251669 |
| rs5961501 | 0.002039 | rs5920654 | 0.0022092 | rs4784307 | 0.00234 | rs2294456 | 0.0025179 |
| rs461011 | 0.0020393 | rs11077573 | 0.0022125 | rs4431713 | 0.0023405 | rs217994 | 0.00251793 |
| rs10975141 | 0.0020444 | rs5923649 | 0.0022151 | rs5952630 | 0.0023424 | rs12285681 | 0.00252214 |
| rs7563563 | 0.0020447 | rs17589482 | 0.0022165 | rs5926145 | 0.0023439 | rs3812243 | 0.00252829 |
| rs2702239 | 0.0020457 | rs850638 | 0.0022191 | rs10282982 | 0.0023469 | rs17520378 | 0.00252979 |
| rs2237785 | 0.0020475 | rs10736703 | 0.0022224 | rs1011624 | 0.002357 | rs41456245 | 0.00253124 |
| rs5927077 | 0.0020518 | rs12012062 | 0.0022238 | rs1366934 | 0.0023595 | rs7988462 | 0.00253455 |
| rs1354504 | 0.0020574 | rs12625924 | 0.0022256 | rs2782669 | 0.002361 | rs905362 | 0.00253683 |
| rs7334189 | 0.0020581 | rs1924680 | 0.0022269 | rs10521427 | 0.002361 | rs10848161 | 0.00253872 |
| rs12013728 | 0.0020647 | rs5910937 | 0.0022306 | rs2071191 | 0.0023637 | rs10745676 | 0.0025398 |
| rs2694710 | 0.0020746 | rs2833537 | 0.0022321 | rs2231496 | 0.0023638 | rs16831204 | 0.00254301 |
| rs10495660 | 0.0020749 | rs17316731 | 0.0022339 | rs7844288 | 0.0023654 | rs11147630 | 0.0025433 |
| rs1942598 | 0.0020759 | rs10502407 | 0.0022349 | rs16956948 | 0.0023699 | rs1933405 | 0.00255057 |
| rs35209885 | 0.0020815 | rs12450386 | 0.0022371 | rs5972687 | 0.0023713 | rs5925593 | 0.00255282 |
| rs7431265 | 0.0020884 | rs985703 | 0.0022383 | rs13110602 | 0.0023725 | rs4811792 | 0.00255362 |
| rs9444074 | 0.0020914 | rs5907001 | 0.0022385 | rs4825511 | 0.0023805 | rs4825476 | 0.00255601 |
| rs5931595 | 0.0020952 | rs3130076 | 0.0022438 | rs4467269 | 0.002381 | rs2642589 | 0.0025603 |
| rs9851426 | 0.0020977 | rs4240057 | 0.0022439 | rs3118077 | 0.0023811 | rs17552796 | 0.00256075 |
| rs17246029 | 0.0020978 | rs4839775 | 0.0022529 | rs318168 | 0.0023861 | rs199638 | 0.0025622 |
| rs12852223 | 0.0021021 | rs17694541 | 0.0022531 | rs17800362 | 0.0023866 | rs41329849 | 0.00256368 |
| rs1607653 | 0.0021044 | rs16989447 | 0.0022536 | rs2091648 | 0.0023886 | rs4300141 | 0.00257031 |
| rs980494 | 0.0021102 | rs5971790 | 0.0022545 | rs1382410 | 0.0023923 | rs5972809 | 0.00257265 |
| rs256003 | 0.0021111 | rs9546325 | 0.0022554 | rs7653913 | 0.0023932 | rs5962299 | 0.00257416 |
| rs5910841 | 0.0021176 | rs10033826 | 0.0022562 | rs11766540 | 0.0023952 | rs203644 | 0.0025798 |
| rs32274 | 0.0021198 | rs1841135 | 0.0022586 | rs10021331 | 0.0023986 | rs333910 | 0.00258065 |
| rs5951582 | 0.0021202 | rs4782854 | 0.0022705 | rs6917645 | 0.0023996 | rs4499720 | 0.00258417 |
| rs1742852 | 0.002123 | rs5750467 | 0.0022741 | rs7894582 | 0.0024021 | rs7061865 | 0.00258863 |
| rs12525343 | 0.0021258 | rs2316997 | 0.0022782 | rs2960660 | 0.0024043 | rs4636358 | 0.0025911 |
| rs1926282 | 0.0021268 | rs1345320 | 0.0022796 | rs2614578 | 0.0024048 | rs41464946 | 0.00259324 |
| rs527174 | 0.0021283 | rs1284440 | 0.0022822 | rs12327672 | 0.0024061 | rs7500985 | 0.00259625 |
| rs17794389 | 0.0021286 | rs641284 | 0.0022834 | rs10991736 | 0.0024147 | rs17155887 | 0.00259717 |
| rs960230 | 0.0021297 | rs1921946 | 0.0022847 | rs6017996 | 0.0024217 | rs10031347 | 0.00259808 |
| rs2984915 | 0.0021299 | rs2804356 | 0.0022851 | rs202273 | 0.0024224 | rs17210369 | 0.00259939 |
| rs41494755 | 0.0021301 | rs1962051 | 0.0022871 | rs13264791 | 0.0024225 | rs17404243 | 0.00259966 |
| rs6610466 | 0.0021361 | rs5925749 | 0.0022889 | rs10333 | 0.0024249 | rs4755454 | 0.00260627 |
| rs11105027 | 0.0021466 | rs3121454 | 0.0022892 | rs16999801 | 0.002425 | rs4595494 | 0.00260748 |
| rs7746596 | 0.0021479 | rs819558 | 0.0022917 | rs213535 | 0.0024416 | rs7302566 | 0.00260924 |
| rs12687206 | 0.0021508 | rs741928 | 0.0022934 | rs41464344 | 0.0024428 | rs10811434 | 0.00261524 |
| rs7878715 | 0.0021513 | rs17353229 | 0.0022942 | rs1997480 | 0.0024462 | rs7056866 | 0.00261615 |
| rs3860829 | 0.0021528 | rs13265492 | 0.0023063 | rs2201665 | 0.0024515 | rs959931 | 0.00261706 |
| rs5957111 | 0.0021589 | rs5935593 | 0.002309 | rs17731407 | 0.0024533 | rs1025952 | 0.00261784 |
| rs5922247 | 0.0021674 | rs1553690 | 0.0023098 | rs4281059 | 0.0024544 | rs17280621 | 0.00261818 |
| rs12851930 | 0.0021722 | rs5970981 | 0.0023109 | rs5905163 | 0.0024547 | rs808517 | 0.00262687 |

Figure 21-7

| | | | | | | | |
|---|---|---|---|---|---|---|---|
| rs12333603 | 0.0026322 | rs5964314 | 0.0027994 | rs17537048 | 0.0029885 | rs240188 | 0.00320274 |
| rs5973570 | 0.0026351 | rs16864788 | 0.0028088 | rs239757 | 0.0029912 | rs9365789 | 0.00320424 |
| rs7882753 | 0.002646 | rs1551343 | 0.0028097 | rs237150 | 0.002998 | rs2460488 | 0.0032044 |
| rs1918560 | 0.0026505 | rs6638777 | 0.002815 | rs5747353 | 0.0030026 | rs13389178 | 0.00321331 |
| rs7885928 | 0.0026556 | rs17794578 | 0.0028154 | rs4697350 | 0.0030033 | rs1020256 | 0.00321663 |
| rs10028553 | 0.0026571 | rs10118551 | 0.002822 | rs1999270 | 0.0030053 | rs4696645 | 0.00321765 |
| rs679327 | 0.0026622 | rs12690384 | 0.0028235 | rs10435425 | 0.0030055 | rs7882055 | 0.00322128 |
| rs10961168 | 0.0026708 | rs7867360 | 0.0028295 | rs1277767 | 0.0030107 | rs5927962 | 0.00322171 |
| rs1839436 | 0.0026752 | rs9559772 | 0.0028322 | rs4503268 | 0.0030114 | rs4787053 | 0.00322545 |
| rs9348837 | 0.0026794 | rs2064652 | 0.0028358 | rs6625472 | 0.0030162 | rs12851954 | 0.00322738 |
| rs11948744 | 0.0026817 | rs5945705 | 0.0028361 | rs5928187 | 0.0030182 | rs7312853 | 0.00323082 |
| rs5944563 | 0.0026828 | rs1565471 | 0.0028392 | rs3744760 | 0.0030249 | rs9501975 | 0.0032327 |
| rs5910718 | 0.0026838 | rs6636538 | 0.0028403 | rs869738 | 0.0030287 | rs10522017 | 0.00323398 |
| rs1857853 | 0.0026868 | rs4826780 | 0.0028414 | rs7611544 | 0.00303 | rs12688897 | 0.00323836 |
| rs2869076 | 0.0026872 | rs10860397 | 0.0028427 | rs4526502 | 0.003033 | rs4633929 | 0.00324201 |
| rs3775121 | 0.0026903 | rs2158536 | 0.0028451 | rs9503670 | 0.003041 | rs10999085 | 0.00324237 |
| rs878073 | 0.0026919 | rs779984 | 0.0028482 | rs6535220 | 0.0030427 | rs2146951 | 0.00324626 |
| rs4396581 | 0.0026921 | rs2925175 | 0.0028662 | rs6715785 | 0.0030452 | rs7312700 | 0.00324792 |
| rs16911991 | 0.002695 | rs17219901 | 0.0028746 | rs2825603 | 0.0030486 | rs36047913 | 0.00324935 |
| rs4119090 | 0.0026975 | rs17399240 | 0.0028751 | rs721431 | 0.0030507 | rs747145 | 0.00324975 |
| rs2172693 | 0.0026975 | rs16876827 | 0.0028758 | rs7963886 | 0.0030538 | rs2060978 | 0.00326257 |
| rs1898799 | 0.002701 | rs17002433 | 0.0028809 | rs9350228 | 0.0030559 | rs6658076 | 0.00327437 |
| rs9520124 | 0.0027101 | rs5979643 | 0.0028809 | rs5953847 | 0.0030565 | rs2016751 | 0.0032874 |
| rs5905042 | 0.0027104 | rs5949507 | 0.0028931 | rs2248314 | 0.003059 | rs3772505 | 0.00328972 |
| rs4107962 | 0.0027118 | rs3744758 | 0.0028934 | rs2290674 | 0.0030597 | rs7822711 | 0.00329723 |
| rs12849629 | 0.0027188 | rs761685 | 0.0029 | rs2595479 | 0.003063 | rs5945546 | 0.00329999 |
| rs17337757 | 0.0027215 | rs6520623 | 0.0029025 | rs909379 | 0.0030663 | rs12559632 | 0.00330103 |
| rs17245537 | 0.0027239 | rs7179956 | 0.0029038 | rs12516361 | 0.0030664 | rs1965009 | 0.00330437 |
| rs728340 | 0.0027251 | rs3771685 | 0.0029054 | rs11151771 | 0.003069 | rs5927408 | 0.00331134 |
| rs4917653 | 0.0027278 | rs916352 | 0.0029217 | rs316720 | 0.0030696 | rs1874274 | 0.00331507 |
| rs1558690 | 0.0027309 | rs1547396 | 0.0029277 | rs115571 | 0.0030791 | rs2748312 | 0.00331579 |
| rs5909876 | 0.0027353 | rs12618771 | 0.0029313 | rs2049661 | 0.0030804 | rs3027369 | 0.00331871 |
| rs2238971 | 0.0027371 | rs16960253 | 0.0029335 | rs5924031 | 0.0030854 | rs1169081 | 0.00332104 |
| rs696975 | 0.0027412 | rs7325885 | 0.0029382 | rs1354269 | 0.0030862 | rs938661 | 0.0033234 |
| rs11800756 | 0.0027475 | rs1032075 | 0.0029391 | rs1037104 | 0.0030947 | rs2290376 | 0.00332458 |
| rs5928271 | 0.0027514 | rs6573309 | 0.0029434 | rs10470297 | 0.0030975 | rs7622802 | 0.00332616 |
| rs7095944 | 0.002752 | rs4844364 | 0.0029462 | rs17324835 | 0.0030986 | rs34985771 | 0.00332852 |
| rs16894192 | 0.0027534 | rs3764763 | 0.0029476 | rs7989613 | 0.0030997 | rs6638361 | 0.00332862 |
| rs11796631 | 0.0027545 | rs1921152 | 0.0029485 | rs5918463 | 0.0031039 | rs2471105 | 0.00332998 |
| rs9526447 | 0.0027545 | rs5981241 | 0.0029486 | rs12134393 | 0.0031045 | rs3135154 | 0.00333373 |
| rs2206684 | 0.0027591 | rs2842772 | 0.00295 | rs1055919 | 0.0031067 | rs196987 | 0.00333595 |
| rs7641386 | 0.0027595 | rs1218124 | 0.0029549 | rs6609303 | 0.0031183 | rs17104169 | 0.00334024 |
| rs6527779 | 0.0027613 | rs17338057 | 0.0029584 | rs11103505 | 0.0031232 | rs942602 | 0.00334173 |
| rs12431261 | 0.0027632 | rs2030253 | 0.0029594 | rs317089 | 0.0031419 | rs418544 | 0.00334287 |
| rs6908911 | 0.0027649 | rs7779937 | 0.0029604 | rs1457608 | 0.0031596 | rs6748518 | 0.00334315 |
| rs6619699 | 0.0027657 | rs4631605 | 0.0029626 | rs9315031 | 0.0031601 | rs5911634 | 0.00334528 |
| rs2840811 | 0.0027668 | rs7868409 | 0.0029658 | rs34745199 | 0.0031648 | rs2144497 | 0.00335158 |
| rs2162919 | 0.002776 | rs6100719 | 0.0029684 | rs1915601 | 0.0031654 | rs7201592 | 0.00335163 |
| rs1351260 | 0.0027817 | rs2820694 | 0.0029693 | rs9922955 | 0.0031654 | rs9399704 | 0.00335386 |
| rs1581286 | 0.0027844 | rs10483477 | 0.0029695 | rs6112546 | 0.003171 | rs2236153 | 0.00336477 |
| rs10826588 | 0.0027849 | rs768198 | 0.0029717 | rs2156975 | 0.0031727 | rs17091245 | 0.00336891 |
| rs5966755 | 0.0027926 | rs418886 | 0.0029749 | rs6128676 | 0.0031732 | rs4826897 | 0.0033848 |
| rs4825731 | 0.0027933 | rs16953757 | 0.0029769 | rs17319056 | 0.0031795 | rs4749305 | 0.00338501 |
| rs2836503 | 0.0027944 | rs5973160 | 0.0029799 | rs7584187 | 0.0031913 | rs798159 | 0.00339438 |
| rs4318894 | 0.0027961 | rs6609257 | 0.0029843 | rs2611605 | 0.0031928 | rs5934551 | 0.0033963 |

Figure 21-8

| | | | | | | | |
|---|---|---|---|---|---|---|---|
| rs4452953 | 0.0034007 | rs11796660 | 0.0035869 | rs1034461 | 0.0038374 | rs10511568 | 0.00401354 |
| rs7222649 | 0.0034017 | rs5933309 | 0.0035929 | rs384225 | 0.0038424 | rs12007973 | 0.00401441 |
| rs17081893 | 0.0034026 | rs2211221 | 0.0035955 | rs4830299 | 0.0038435 | rs8050204 | 0.0040171 |
| rs4363313 | 0.0034081 | rs6575728 | 0.0036085 | rs16833171 | 0.0038452 | rs4655643 | 0.00402414 |
| rs8060992 | 0.0034106 | rs7919211 | 0.0036099 | rs17805883 | 0.0038454 | rs4484340 | 0.00402587 |
| rs9937119 | 0.0034108 | rs4939921 | 0.0036148 | rs12613322 | 0.0038462 | rs11915789 | 0.00403255 |
| rs1198723 | 0.0034179 | rs3128809 | 0.003615 | rs865525 | 0.0038514 | rs4345730 | 0.0040398 |
| rs5927062 | 0.0034254 | rs2875248 | 0.0036185 | rs4240039 | 0.0038606 | rs6633866 | 0.00404001 |
| rs16997510 | 0.0034354 | rs41391344 | 0.0036234 | rs2992177 | 0.0038645 | rs2267592 | 0.00405032 |
| rs1544867 | 0.0034376 | rs7202180 | 0.0036311 | rs5919988 | 0.0038663 | rs10498850 | 0.0040597 |
| rs1554310 | 0.0034386 | rs7826857 | 0.0036348 | rs11676482 | 0.0038678 | rs110133 | 0.00406725 |
| rs2238993 | 0.003439 | rs5954822 | 0.0036367 | rs10521726 | 0.0038751 | rs5918362 | 0.00407197 |
| rs12852291 | 0.0034442 | rs5925924 | 0.003638 | rs17743398 | 0.0038885 | rs10893379 | 0.00407291 |
| rs1462811 | 0.0034484 | rs2291985 | 0.0036389 | rs11176397 | 0.0038945 | rs5954267 | 0.00407985 |
| rs2870758 | 0.0034486 | rs12976023 | 0.0036399 | rs633691 | 0.0039039 | rs17260618 | 0.00408233 |
| rs1537415 | 0.0034522 | rs7885942 | 0.0036463 | rs5927914 | 0.0039071 | rs4827023 | 0.00408343 |
| rs5962954 | 0.0034563 | rs4278071 | 0.003651 | rs7719176 | 0.0039074 | rs5921851 | 0.00408877 |
| rs4740583 | 0.0034579 | rs11619328 | 0.0036594 | rs7586131 | 0.0039101 | rs11580624 | 0.004096 |
| rs2429799 | 0.0034611 | rs403558 | 0.0036804 | rs17641840 | 0.0039134 | rs6033377 | 0.0040983 |
| rs6628825 | 0.003464 | rs17051672 | 0.0036873 | rs4828941 | 0.003918 | rs7278294 | 0.00409833 |
| rs2058655 | 0.0034653 | rs3008922 | 0.0036874 | rs11038227 | 0.0039192 | rs1017190 | 0.0041036 |
| rs34191540 | 0.003467 | rs5927678 | 0.0036882 | rs4593704 | 0.003922 | rs1882407 | 0.00410628 |
| rs5975291 | 0.0034672 | rs10521432 | 0.0036935 | rs2107425 | 0.0039248 | rs684573 | 0.00410707 |
| rs1021734 | 0.0034701 | rs13256218 | 0.0037045 | rs5982925 | 0.0039284 | rs9842287 | 0.00411098 |
| rs4277226 | 0.0034749 | rs5911548 | 0.0037078 | rs10085385 | 0.003929 | rs11129517 | 0.00411194 |
| rs1884694 | 0.0034765 | rs9522357 | 0.0037085 | rs9376702 | 0.0039316 | rs12621754 | 0.00411712 |
| rs4830775 | 0.0034838 | rs893465 | 0.0037086 | rs2961401 | 0.0039317 | rs6481864 | 0.00412961 |
| rs1864277 | 0.0034847 | rs5923658 | 0.0037116 | rs6676380 | 0.0039338 | rs4258586 | 0.00413439 |
| rs652582 | 0.0034849 | rs10808361 | 0.0037121 | rs7787946 | 0.003939 | rs9895315 | 0.00413935 |
| rs738085 | 0.0034905 | rs1277964 | 0.0037132 | rs17790821 | 0.0039407 | rs10454141 | 0.00414685 |
| rs5920949 | 0.0034914 | rs4827289 | 0.0037153 | rs5765532 | 0.0039423 | rs2092255 | 0.00415235 |
| rs1937076 | 0.0034916 | rs2765379 | 0.0037168 | rs5942880 | 0.0039443 | rs16899194 | 0.00415637 |
| rs17608192 | 0.0034931 | rs7708097 | 0.0037231 | rs2508420 | 0.0039498 | rs411751 | 0.00416171 |
| rs11156966 | 0.0034966 | rs2376973 | 0.003725 | rs1427087 | 0.003954 | rs2573668 | 0.00416774 |
| rs2103520 | 0.003498 | rs1152202 | 0.0037286 | rs5949581 | 0.003954 | rs10924848 | 0.00416907 |
| rs783404 | 0.0034986 | rs2908784 | 0.0037308 | rs6463443 | 0.0039581 | rs12949329 | 0.00417518 |
| rs376886 | 0.0034987 | rs851235 | 0.003742 | rs5938377 | 0.0039589 | rs8101738 | 0.00417741 |
| rs5905820 | 0.0035065 | rs36038231 | 0.003748 | rs10253752 | 0.0039603 | rs4524307 | 0.0041816 |
| rs5940034 | 0.0035147 | rs2164787 | 0.0037502 | rs823031 | 0.0039614 | rs5927693 | 0.00418473 |
| rs17122882 | 0.0035164 | rs10196963 | 0.0037513 | rs11013860 | 0.0039632 | rs5748307 | 0.0041927 |
| rs16855137 | 0.0035166 | rs12598492 | 0.0037552 | rs17273882 | 0.0039694 | rs903471 | 0.00421122 |
| rs952489 | 0.0035187 | rs5990571 | 0.0037712 | rs2157272 | 0.0039731 | rs6639205 | 0.00421309 |
| rs2568447 | 0.0035232 | rs17095458 | 0.0037738 | rs17239044 | 0.0039735 | rs11234201 | 0.00421742 |
| rs939348 | 0.0035232 | rs16974638 | 0.0037754 | rs579005 | 0.0039742 | rs5933374 | 0.00421821 |
| rs1181065 | 0.003524 | rs9394524 | 0.0037792 | rs917640 | 0.0039746 | rs1458961 | 0.00421919 |
| rs7975082 | 0.0035325 | rs1318761 | 0.0037818 | rs6637203 | 0.00398 | rs6726739 | 0.00422111 |
| rs5904980 | 0.003541 | rs10126799 | 0.0037993 | rs10504398 | 0.0039825 | rs754133 | 0.00422691 |
| rs7120805 | 0.0035481 | rs12557491 | 0.0038043 | rs6991826 | 0.0039872 | rs808802 | 0.00423544 |
| rs10184858 | 0.0035549 | rs2292893 | 0.0038051 | rs5963545 | 0.0039963 | rs17138834 | 0.00423809 |
| rs2225609 | 0.0035563 | rs5765558 | 0.0038059 | rs1840485 | 0.003999 | rs9730979 | 0.00423983 |
| rs8037065 | 0.0035572 | rs31465 | 0.0038093 | rs1124814 | 0.0040021 | rs17398001 | 0.00424094 |
| rs6812536 | 0.003568 | rs733099 | 0.0038105 | rs749516 | 0.0040037 | rs4734058 | 0.00424127 |
| rs1206920 | 0.0035713 | rs41491649 | 0.0038106 | rs2737424 | 0.0040079 | rs2562784 | 0.00424606 |
| rs6132672 | 0.0035746 | rs2952131 | 0.0038211 | rs5905498 | 0.0040083 | rs4957159 | 0.00424724 |
| rs2523990 | 0.003585 | rs981066 | 0.0038251 | rs6594805 | 0.0040101 | rs3113053 | 0.00424805 |

Figure 21-9

| | |
|---|---|
| rs8033429 | 0.004255 |
| rs2040577 | 0.0042552 |
| rs6718080 | 0.0042557 |
| rs17148800 | 0.0042603 |
| rs9950126 | 0.0042613 |
| rs232569 | 0.0042633 |
| rs17093688 | 0.0042635 |
| rs4940732 | 0.0042677 |
| rs5915280 | 0.0042691 |
| rs10151548 | 0.0042727 |
| rs12011691 | 0.0042742 |
| rs41408045 | 0.0042805 |
| rs2327951 | 0.0042865 |
| rs10193163 | 0.0042878 |
| rs5920962 | 0.0042885 |
| rs7052650 | 0.004293 |
| rs4076999 | 0.0042957 |
| rs13406485 | 0.0042981 |
| rs11217364 | 0.0043033 |
| rs5928184 | 0.0043047 |
| rs5928022 | 0.0043048 |
| rs7912575 | 0.004307 |
| rs1338097 | 0.0043073 |
| rs4300862 | 0.0043077 |
| rs5963436 | 0.0043151 |
| rs17103027 | 0.0043259 |
| rs236064 | 0.004332 |
| rs12394920 | 0.0043394 |

Figure 21-10

| SNP | ChiSquare P value | SNP | ChiSquare P value | SNP | ChiSquare P value |
|---|---|---|---|---|---|
| rs11007270 | 5.14E-19 | rs658339 | 1.18E-09 | rs7620921 | 1.91E-09 |
| rs17073262 | 2.61E-18 | rs11894357 | 1.19E-09 | rs17150942 | 1.92E-09 |
| rs7190657 | 1.58E-12 | rs7813492 | 1.19E-09 | rs7696347 | 1.93E-09 |
| rs2411130 | 1.74E-12 | rs10991286 | 1.25E-09 | rs17101921 | 1.93E-09 |
| rs1346861 | 6.09E-12 | rs17045475 | 1.28E-09 | rs17070374 | 1.93E-09 |
| rs2503730 | 1.28E-11 | rs10509275 | 1.30E-09 | rs17665636 | 1.93E-09 |
| rs773969 | 1.45E-11 | rs1026842 | 1.33E-09 | rs11016169 | 1.94E-09 |
| rs4448502 | 2.51E-11 | rs17135958 | 1.34E-09 | rs1800130 | 1.95E-09 |
| rs11935979 | 5.47E-11 | rs10521073 | 1.34E-09 | rs16945738 | 1.95E-09 |
| rs8066895 | 5.51E-11 | rs16829525 | 1.36E-09 | rs2116732 | 1.95E-09 |
| rs4837165 | 1.45E-10 | rs12809590 | 1.37E-09 | rs4544694 | 1.96E-09 |
| rs2122189 | 1.51E-10 | rs7236104 | 1.37E-09 | rs4832055 | 1.98E-09 |
| rs4743886 | 1.55E-10 | rs6016319 | 1.38E-09 | rs135080 | 2.01E-09 |
| rs9813883 | 2.18E-10 | rs13294648 | 1.38E-09 | rs341971 | 2.02E-09 |
| rs11902772 | 2.36E-10 | rs8048037 | 1.40E-09 | rs1391048 | 2.03E-09 |
| rs17041032 | 2.57E-10 | rs9893250 | 1.41E-09 | rs10033823 | 2.03E-09 |
| rs7949670 | 2.78E-10 | rs10000609 | 1.42E-09 | rs11063757 | 2.03E-09 |
| rs12716680 | 3.69E-10 | rs2707671 | 1.43E-09 | rs11882629 | 2.06E-09 |
| rs2139622 | 4.13E-10 | rs12058586 | 1.47E-09 | rs856127 | 2.07E-09 |
| rs17644677 | 4.38E-10 | rs16940712 | 1.47E-09 | rs12141445 | 2.08E-09 |
| rs10924674 | 4.44E-10 | rs1017329 | 1.52E-09 | rs9855339 | 2.12E-09 |
| rs1443903 | 4.90E-10 | rs17245098 | 1.52E-09 | rs441394 | 2.12E-09 |
| rs16907736 | 5.20E-10 | rs16954194 | 1.54E-09 | rs8069306 | 2.13E-09 |
| rs2458707 | 5.73E-10 | rs12679740 | 1.57E-09 | rs3135679 | 2.14E-09 |
| rs1488831 | 5.98E-10 | rs3731194 | 1.59E-09 | rs16839691 | 2.18E-09 |
| rs17058945 | 6.22E-10 | rs10989383 | 1.60E-09 | rs10746431 | 2.25E-09 |
| rs41524446 | 6.36E-10 | rs12481485 | 1.62E-09 | rs11158527 | 2.25E-09 |
| rs1862725 | 6.38E-10 | rs4140637 | 1.65E-09 | rs1545653 | 2.28E-09 |
| rs12405213 | 6.49E-10 | rs459289 | 1.67E-09 | rs2898097 | 2.29E-09 |
| rs16873285 | 6.91E-10 | rs17223923 | 1.69E-09 | rs7612956 | 2.32E-09 |
| rs16969423 | 7.46E-10 | rs10469061 | 1.70E-09 | rs9428247 | 2.42E-09 |
| rs17084123 | 7.60E-10 | rs1974880 | 1.72E-09 | rs17071555 | 2.50E-09 |
| rs41358349 | 7.69E-10 | rs16986733 | 1.73E-09 | rs6972733 | 2.72E-09 |
| rs2365177 | 7.78E-10 | rs7664613 | 1.76E-09 | rs6849870 | 2.87E-09 |
| rs10081321 | 7.84E-10 | rs17459522 | 1.77E-09 | rs2664089 | 3.07E-09 |
| rs13226886 | 7.98E-10 | rs953216 | 1.77E-09 | rs17127235 | 3.15E-09 |
| rs10116858 | 8.37E-10 | rs11028121 | 1.78E-09 | rs2064873 | 3.29E-09 |
| rs16996744 | 8.45E-10 | rs17130723 | 1.78E-09 | rs1397706 | 3.79E-09 |
| rs9968025 | 8.53E-10 | rs10847143 | 1.78E-09 | rs9511646 | 4.49E-09 |
| rs2114656 | 8.98E-10 | rs17129180 | 1.79E-09 | rs10507779 | 4.91E-09 |
| rs12427758 | 9.10E-10 | rs11973158 | 1.80E-09 | rs16977815 | 5.00E-09 |
| rs1893912 | 9.10E-10 | rs7325039 | 1.81E-09 | rs12645640 | 5.04E-09 |
| rs7616638 | 9.38E-10 | rs7746075 | 1.83E-09 | rs3828983 | 5.06E-09 |
| rs17701478 | 9.66E-10 | rs16877066 | 1.84E-09 | rs10272660 | 5.09E-09 |
| rs4736240 | 9.80E-10 | rs2833537 | 1.84E-09 | rs9673539 | 5.66E-09 |
| rs6071448 | 1.09E-09 | rs17305183 | 1.84E-09 | rs16828720 | 5.74E-09 |
| rs10272511 | 1.09E-09 | rs1003106 | 1.85E-09 | rs17198456 | 1.44E-08 |
| rs17134173 | 1.10E-09 | rs2595146 | 1.87E-09 | rs12424995 | 2.75E-08 |
| rs10514526 | 1.14E-09 | rs7231918 | 1.88E-09 | rs8175963 | 2.94E-08 |
| rs222809 | 1.15E-09 | rs6801556 | 1.88E-09 | rs7329263 | 3.06E-08 |
| rs12166759 | 1.16E-09 | rs11892351 | 1.89E-09 | rs17154065 | 3.36E-08 |
| rs4140425 | 1.16E-09 | rs16899203 | 1.89E-09 | rs17125102 | 5.31E-08 |
| rs11109787 | 1.17E-09 | rs1215834 | 1.89E-09 | rs10161762 | 8.14E-08 |

Figure 22-1

| | | | | | |
|---|---|---|---|---|---|
| rs874511 | 9.81E-08 | rs7792701 | 5.42E-06 | rs159619 | 2.06E-05 |
| rs4906417 | 1.13E-07 | rs4751881 | 5.44E-06 | rs6867140 | 2.08E-05 |
| rs16894463 | 1.48E-07 | rs7601609 | 5.45E-06 | rs4899628 | 2.08E-05 |
| rs2220197 | 1.69E-07 | rs7561649 | 5.46E-06 | rs7081304 | 2.09E-05 |
| rs11082879 | 1.86E-07 | rs17447468 | 5.62E-06 | rs4145262 | 2.09E-05 |
| rs2702894 | 1.94E-07 | rs6907667 | 5.67E-06 | rs3010711 | 2.11E-05 |
| rs3101089 | 2.26E-07 | rs41385047 | 5.81E-06 | rs9896209 | 2.12E-05 |
| rs17322650 | 2.77E-07 | rs16868514 | 5.95E-06 | rs12100022 | 2.16E-05 |
| rs7995725 | 2.78E-07 | rs1461698 | 5.96E-06 | rs7148698 | 2.18E-05 |
| rs11245373 | 2.95E-07 | rs17213769 | 6.05E-06 | rs10483600 | 2.20E-05 |
| rs16850673 | 3.27E-07 | rs7048449 | 6.07E-06 | rs9362046 | 2.23E-05 |
| rs777805 | 3.33E-07 | rs10159565 | 6.11E-06 | rs7746931 | 2.26E-05 |
| rs2137873 | 3.55E-07 | rs4476905 | 6.45E-06 | rs16861032 | 2.31E-05 |
| rs7083512 | 3.63E-07 | rs10252992 | 6.67E-06 | rs606670 | 2.33E-05 |
| rs1374778 | 3.78E-07 | rs2493215 | 6.74E-06 | rs1978147 | 2.34E-05 |
| rs2845573 | 4.19E-07 | rs1353645 | 7.32E-06 | rs4748946 | 2.37E-05 |
| rs2374506 | 4.67E-07 | rs17135053 | 8.44E-06 | rs2879725 | 2.44E-05 |
| rs11249163 | 4.86E-07 | rs7814691 | 8.82E-06 | rs2136781 | 2.54E-05 |
| rs17488361 | 4.97E-07 | rs13235564 | 8.83E-06 | rs4425537 | 2.56E-05 |
| rs11230550 | 5.37E-07 | rs6708183 | 9.80E-06 | rs3124736 | 2.57E-05 |
| rs4257980 | 5.80E-07 | rs10838120 | 1.01E-05 | rs7775112 | 2.60E-05 |
| rs17247907 | 6.88E-07 | rs2642556 | 1.04E-05 | rs17827168 | 2.64E-05 |
| rs16975213 | 9.37E-07 | rs9864435 | 1.04E-05 | rs993250 | 2.65E-05 |
| rs4687113 | 1.08E-06 | rs4239555 | 1.08E-05 | rs7527246 | 2.67E-05 |
| rs12997980 | 1.11E-06 | rs7221984 | 1.08E-05 | rs13178377 | 2.67E-05 |
| rs17027550 | 1.12E-06 | rs17294110 | 1.11E-05 | rs1936763 | 2.71E-05 |
| rs11824839 | 1.16E-06 | rs17109825 | 1.12E-05 | rs41415147 | 2.71E-05 |
| rs1076725 | 1.17E-06 | rs10929654 | 1.17E-05 | rs4455878 | 2.72E-05 |
| rs12395234 | 1.18E-06 | rs3852823 | 1.21E-05 | rs12788831 | 2.73E-05 |
| rs7030479 | 1.20E-06 | rs2657475 | 1.22E-05 | rs17059620 | 2.76E-05 |
| rs2305885 | 1.27E-06 | rs4689349 | 1.27E-05 | rs9829645 | 2.81E-05 |
| rs6924108 | 1.39E-06 | rs7673636 | 1.34E-05 | rs11961118 | 2.81E-05 |
| rs9646957 | 1.52E-06 | rs6437301 | 1.38E-05 | rs31887 | 2.82E-05 |
| rs17055923 | 1.56E-06 | rs6005515 | 1.38E-05 | rs16975860 | 2.88E-05 |
| rs9302221 | 1.84E-06 | rs7828571 | 1.39E-05 | rs1359140 | 2.89E-05 |
| rs9568130 | 2.01E-06 | rs1413254 | 1.39E-05 | rs1341140 | 2.89E-05 |
| rs3934577 | 2.33E-06 | rs16980981 | 1.48E-05 | rs17347454 | 2.91E-05 |
| rs17172689 | 2.39E-06 | rs7249111 | 1.49E-05 | rs9820153 | 2.92E-05 |
| rs4852262 | 2.44E-06 | rs7814667 | 1.51E-05 | rs9287767 | 2.93E-05 |
| rs13142375 | 3.25E-06 | rs4300229 | 1.59E-05 | rs6925493 | 2.93E-05 |
| rs995385 | 3.78E-06 | rs1446216 | 1.63E-05 | rs10489643 | 2.96E-05 |
| rs6716674 | 3.83E-06 | rs6547193 | 1.64E-05 | rs17169595 | 3.01E-05 |
| rs1152934 | 4.14E-06 | rs2785173 | 1.72E-05 | rs6760222 | 3.04E-05 |
| rs8098902 | 4.43E-06 | rs11778669 | 1.76E-05 | rs2496331 | 3.04E-05 |
| rs12064275 | 4.48E-06 | rs29426 | 1.82E-05 | rs12447986 | 3.07E-05 |
| rs1005427 | 4.54E-06 | rs9609441 | 1.83E-05 | rs1978949 | 3.12E-05 |
| rs11066699 | 4.57E-06 | rs41497849 | 1.84E-05 | rs3135806 | 3.13E-05 |
| rs13338089 | 4.58E-06 | rs735311 | 1.85E-05 | rs2778913 | 3.17E-05 |
| rs17777478 | 4.71E-06 | rs41478351 | 1.92E-05 | rs41353849 | 3.20E-05 |
| rs16952725 | 4.94E-06 | rs12232279 | 1.92E-05 | rs9577246 | 3.20E-05 |
| rs1571362 | 4.94E-06 | rs135439 | 1.96E-05 | rs2998734 | 3.24E-05 |
| rs9954459 | 5.23E-06 | rs17652855 | 2.00E-05 | rs17003277 | 3.24E-05 |
| rs1962511 | 5.24E-06 | rs7660043 | 2.00E-05 | rs7905885 | 3.25E-05 |
| rs886206 | 5.36E-06 | rs16952975 | 2.03E-05 | rs16872626 | 3.26E-05 |
| rs9573196 | 5.41E-06 | rs9592510 | 2.05E-05 | rs17071212 | 3.27E-05 |

Figure 22-2

| | | | | | |
|---|---|---|---|---|---|
| rs7290510 | 3.31E-05 | rs2089051 | 4.57E-05 | rs17081073 | 6.33E-05 |
| rs2489386 | 3.33E-05 | rs10851713 | 4.58E-05 | rs16946234 | 6.33E-05 |
| rs17136184 | 3.39E-05 | rs6072574 | 4.62E-05 | rs1966049 | 6.33E-05 |
| rs6112602 | 3.41E-05 | rs1338007 | 4.62E-05 | rs41390551 | 6.33E-05 |
| rs7258075 | 3.42E-05 | rs774507 | 4.66E-05 | rs6813350 | 6.34E-05 |
| rs4894094 | 3.44E-05 | rs2115055 | 4.78E-05 | rs2470592 | 6.39E-05 |
| rs16867583 | 3.46E-05 | rs726085 | 4.96E-05 | rs17248007 | 6.41E-05 |
| rs735665 | 3.47E-05 | rs4378299 | 5.00E-05 | rs11113904 | 6.57E-05 |
| rs17078168 | 3.49E-05 | rs2363768 | 5.01E-05 | rs909966 | 6.57E-05 |
| rs9635390 | 3.52E-05 | rs16955607 | 5.03E-05 | rs10492479 | 6.58E-05 |
| rs16964764 | 3.57E-05 | rs17190037 | 5.07E-05 | rs11200820 | 6.61E-05 |
| rs17434013 | 3.58E-05 | rs10957260 | 5.08E-05 | rs2588153 | 6.64E-05 |
| rs16980975 | 3.61E-05 | rs13231718 | 5.08E-05 | rs6061414 | 6.64E-05 |
| rs11014853 | 3.63E-05 | rs2848872 | 5.13E-05 | rs17037858 | 6.65E-05 |
| rs1517440 | 3.64E-05 | rs1441492 | 5.17E-05 | rs17088891 | 6.67E-05 |
| rs12323400 | 3.65E-05 | rs10019120 | 5.17E-05 | rs2075005 | 6.69E-05 |
| rs17600829 | 3.67E-05 | rs17130391 | 5.18E-05 | rs11256896 | 6.70E-05 |
| rs11971669 | 3.74E-05 | rs16853335 | 5.18E-05 | rs3751609 | 6.71E-05 |
| rs328389 | 3.74E-05 | rs1402982 | 5.24E-05 | rs17110716 | 6.72E-05 |
| rs7511818 | 3.75E-05 | rs8021182 | 5.24E-05 | rs17738584 | 6.72E-05 |
| rs17063661 | 3.76E-05 | rs17104310 | 5.25E-05 | rs16945302 | 6.75E-05 |
| rs17009821 | 3.76E-05 | rs41431549 | 5.27E-05 | rs742058 | 6.76E-05 |
| rs735183 | 3.83E-05 | rs777831 | 5.31E-05 | rs6947391 | 6.77E-05 |
| rs17161652 | 3.84E-05 | rs4448295 | 5.35E-05 | rs11066417 | 6.79E-05 |
| rs11780949 | 3.86E-05 | rs4693997 | 5.44E-05 | rs7540790 | 6.86E-05 |
| rs2035882 | 3.88E-05 | rs8037800 | 5.47E-05 | rs361386 | 6.87E-05 |
| rs2127388 | 3.88E-05 | rs6456652 | 5.49E-05 | rs2506363 | 6.91E-05 |
| rs9397087 | 3.92E-05 | rs12102352 | 5.53E-05 | rs6930572 | 6.95E-05 |
| rs16991630 | 3.93E-05 | rs16860778 | 5.55E-05 | rs17143029 | 6.97E-05 |
| rs2203428 | 3.94E-05 | rs12419474 | 5.57E-05 | rs17359763 | 7.00E-05 |
| rs618393 | 3.96E-05 | rs16943976 | 5.64E-05 | rs7753282 | 7.00E-05 |
| rs138465 | 3.98E-05 | rs16934126 | 5.65E-05 | rs11934409 | 7.01E-05 |
| rs16855587 | 3.99E-05 | rs822519 | 5.67E-05 | rs2127994 | 7.03E-05 |
| rs17684354 | 4.01E-05 | rs12603217 | 5.70E-05 | rs16926940 | 7.04E-05 |
| rs7197514 | 4.03E-05 | rs17028456 | 5.70E-05 | rs11802583 | 7.05E-05 |
| rs6739610 | 4.03E-05 | rs1325350 | 5.71E-05 | rs6564988 | 7.05E-05 |
| rs2672458 | 4.06E-05 | rs2824903 | 5.74E-05 | rs17019886 | 7.07E-05 |
| rs10514852 | 4.10E-05 | rs12489946 | 5.81E-05 | rs6725530 | 7.07E-05 |
| rs17738653 | 4.13E-05 | rs9928871 | 5.83E-05 | rs17644551 | 7.08E-05 |
| rs10956341 | 4.18E-05 | rs1980789 | 5.89E-05 | rs4553462 | 7.09E-05 |
| rs17828913 | 4.19E-05 | rs9882757 | 5.90E-05 | rs11049300 | 7.10E-05 |
| rs3744951 | 4.20E-05 | rs2112626 | 5.91E-05 | rs17162892 | 7.10E-05 |
| rs6956087 | 4.25E-05 | rs17144649 | 6.00E-05 | rs379387 | 7.11E-05 |
| rs7556491 | 4.25E-05 | rs10242657 | 6.03E-05 | rs11978507 | 7.12E-05 |
| rs7176139 | 4.27E-05 | rs16837404 | 6.16E-05 | rs41421146 | 7.12E-05 |
| rs6711283 | 4.29E-05 | rs10927530 | 6.16E-05 | rs9643874 | 7.13E-05 |
| rs9327170 | 4.32E-05 | rs2010905 | 6.17E-05 | rs1392481 | 7.15E-05 |
| rs900501 | 4.32E-05 | rs7284708 | 6.19E-05 | rs17076068 | 7.15E-05 |
| rs10166067 | 4.36E-05 | rs16902902 | 6.19E-05 | rs13335336 | 7.15E-05 |
| rs11239131 | 4.37E-05 | rs12248406 | 6.21E-05 | rs34442697 | 7.16E-05 |
| rs10985431 | 4.40E-05 | rs7952006 | 6.22E-05 | rs11988203 | 7.16E-05 |
| rs10521469 | 4.42E-05 | rs6461068 | 6.25E-05 | rs2834567 | 7.16E-05 |
| rs9296758 | 4.43E-05 | rs17011669 | 6.27E-05 | rs11077913 | 7.18E-05 |
| rs1861269 | 4.49E-05 | rs821585 | 6.27E-05 | rs167901 | 7.20E-05 |
| rs10498889 | 4.53E-05 | rs12592927 | 6.31E-05 | rs1333345 | 7.20E-05 |

Figure 22-3

| | | | | | |
|---|---|---|---|---|---|
| rs16863892 | 7.23E-05 | rs11698155 | 0.0001198 | rs4278478 | 0.0001867 |
| rs6967655 | 7.24E-05 | rs4690374 | 0.0001207 | rs7465564 | 0.0001868 |
| rs3118205 | 7.25E-05 | rs6127676 | 0.0001266 | rs4499448 | 0.0001873 |
| rs17135109 | 7.25E-05 | rs4669573 | 0.0001271 | rs11601059 | 0.0001893 |
| rs16871387 | 7.27E-05 | rs524811 | 0.0001279 | rs2610808 | 0.0001928 |
| rs6534884 | 7.29E-05 | rs7034055 | 0.0001302 | rs11117209 | 0.0001941 |
| rs925219 | 7.29E-05 | rs4524459 | 0.0001307 | rs708436 | 0.0001942 |
| rs13439821 | 7.32E-05 | rs2410200 | 0.0001359 | rs10503636 | 0.000197 |
| rs10944520 | 7.32E-05 | rs17807611 | 0.0001363 | rs7847263 | 0.0001996 |
| rs16842165 | 7.36E-05 | rs8050204 | 0.0001381 | rs7084614 | 0.0002045 |
| rs17103118 | 7.38E-05 | rs7157772 | 0.0001407 | rs4435942 | 0.0002056 |
| rs17021261 | 7.38E-05 | rs6534890 | 0.0001408 | rs183805 | 0.000207 |
| rs7560153 | 7.39E-05 | rs7224403 | 0.0001413 | rs2729547 | 0.0002085 |
| rs1774929 | 7.39E-05 | rs4856008 | 0.0001428 | rs6698441 | 0.0002088 |
| rs12381471 | 7.44E-05 | rs587952 | 0.000143 | rs4670949 | 0.0002096 |
| rs9590070 | 7.49E-05 | rs1629888 | 0.0001438 | rs16882008 | 0.0002123 |
| rs17195435 | 7.51E-05 | rs10516697 | 0.0001442 | rs4307284 | 0.0002203 |
| rs6855048 | 7.55E-05 | rs1174305 | 0.0001444 | rs10514492 | 0.0002206 |
| rs6887404 | 7.56E-05 | rs17675810 | 0.0001447 | rs12402548 | 0.0002215 |
| rs1526959 | 7.62E-05 | rs10492314 | 0.0001456 | rs2032821 | 0.0002294 |
| rs7776218 | 7.73E-05 | rs17212829 | 0.0001458 | rs4045515 | 0.0002337 |
| rs17157380 | 7.83E-05 | rs8057123 | 0.0001472 | rs1659284 | 0.0002349 |
| rs11143178 | 7.87E-05 | rs869901 | 0.0001474 | rs10964337 | 0.0002365 |
| rs9910447 | 8.21E-05 | rs9477397 | 0.000148 | rs9873736 | 0.0002378 |
| rs16824224 | 8.35E-05 | rs3744171 | 0.0001515 | rs1451890 | 0.0002379 |
| rs10845920 | 8.44E-05 | rs10487884 | 0.0001548 | rs608665 | 0.000239 |
| rs6868941 | 8.53E-05 | rs6974087 | 0.0001574 | rs1078324 | 0.0002399 |
| rs9357123 | 8.54E-05 | rs9365114 | 0.0001577 | rs1020723 | 0.0002419 |
| rs17181606 | 8.61E-05 | rs7611795 | 0.0001593 | rs4784805 | 0.0002426 |
| rs639595 | 8.79E-05 | rs501213 | 0.0001603 | rs10505446 | 0.0002446 |
| rs9427477 | 8.88E-05 | rs10490000 | 0.0001605 | rs1370138 | 0.0002482 |
| rs10175061 | 9.04E-05 | rs16904805 | 0.0001665 | rs13279286 | 0.0002494 |
| rs11581227 | 9.08E-05 | rs911225 | 0.0001671 | rs9352838 | 0.0002507 |
| rs17666079 | 9.23E-05 | rs17666735 | 0.0001672 | rs4872206 | 0.0002528 |
| rs9313810 | 9.52E-05 | rs17378053 | 0.0001682 | rs10804866 | 0.0002548 |
| rs1489170 | 9.62E-05 | rs7907913 | 0.0001691 | rs4325261 | 0.000259 |
| rs943327 | 9.63E-05 | rs9946486 | 0.0001695 | rs10737025 | 0.0002599 |
| rs7776583 | 9.71E-05 | rs6824902 | 0.0001696 | rs41347750 | 0.0002648 |
| rs16938000 | 9.83E-05 | rs6066395 | 0.0001699 | rs17619264 | 0.0002691 |
| rs9570793 | 9.99E-05 | rs10515813 | 0.000171 | rs12757377 | 0.0002699 |
| rs17432461 | 0.0001015 | rs6747341 | 0.000171 | rs1448809 | 0.0002703 |
| rs6046762 | 0.0001078 | rs4557033 | 0.0001715 | rs11188759 | 0.0002709 |
| rs7978045 | 0.0001093 | rs34379411 | 0.0001729 | rs17642885 | 0.0002714 |
| rs437518 | 0.0001093 | rs1156942 | 0.000174 | rs4499238 | 0.0002733 |
| rs1407877 | 0.0001105 | rs12147724 | 0.0001743 | rs10492055 | 0.0002779 |
| rs6112481 | 0.0001116 | rs7739957 | 0.0001743 | rs12418818 | 0.0002783 |
| rs16929898 | 0.0001117 | rs9689350 | 0.0001748 | rs6936494 | 0.0002808 |
| rs3929907 | 0.0001139 | rs253910 | 0.0001749 | rs9544230 | 0.0002824 |
| rs16929280 | 0.0001142 | rs16823725 | 0.0001762 | rs930655 | 0.0002839 |
| rs2476163 | 0.0001142 | rs10490665 | 0.0001779 | rs35653399 | 0.000289 |
| rs17172341 | 0.0001159 | rs2219652 | 0.0001781 | rs11234429 | 0.0002891 |
| rs16937734 | 0.0001163 | rs17508331 | 0.0001814 | rs17167995 | 0.0002915 |
| rs7248144 | 0.0001174 | rs4774941 | 0.0001837 | rs16918784 | 0.0002918 |
| rs6584984 | 0.0001179 | rs2895 | 0.0001864 | rs6794287 | 0.0002943 |
| rs10458204 | 0.0001197 | rs16995302 | 0.0001866 | rs10839595 | 0.0002982 |

Figure 22-4

| | | | | | |
|---|---|---|---|---|---|
| rs10510819 | 0.0002997 | rs6086496 | 0.0004182 | rs341497 | 0.0005481 |
| rs4668298 | 0.0003002 | rs883010 | 0.00042 | rs6714881 | 0.0005487 |
| rs4833840 | 0.000304 | rs1432693 | 0.0004234 | rs572609 | 0.0005498 |
| rs16892009 | 0.0003071 | rs17011927 | 0.0004273 | rs10811539 | 0.0005498 |
| rs11192252 | 0.0003075 | rs12755278 | 0.0004316 | rs12676658 | 0.0005499 |
| rs11215482 | 0.0003078 | rs3113053 | 0.0004351 | rs17044304 | 0.0005512 |
| rs6508341 | 0.0003125 | rs7574709 | 0.0004373 | rs1407214 | 0.0005585 |
| rs841779 | 0.000315 | rs4839801 | 0.0004382 | rs17146892 | 0.0005586 |
| rs2457715 | 0.0003166 | rs13030985 | 0.000439 | rs196580 | 0.0005607 |
| rs9398226 | 0.0003177 | rs11080775 | 0.0004419 | rs17425397 | 0.0005622 |
| rs7646819 | 0.0003186 | rs40590 | 0.0004455 | rs16866574 | 0.0005627 |
| rs6063367 | 0.000324 | rs666051 | 0.0004468 | rs17031621 | 0.0005635 |
| rs6862877 | 0.000328 | rs7149693 | 0.0004497 | rs277094 | 0.0005648 |
| rs1523074 | 0.0003322 | rs10755055 | 0.0004586 | rs10503493 | 0.0005655 |
| rs2175465 | 0.0003338 | rs12156924 | 0.0004593 | rs10856827 | 0.0005656 |
| rs10860877 | 0.000336 | rs750571 | 0.0004594 | rs851023 | 0.0005688 |
| rs6990760 | 0.0003398 | rs6994723 | 0.0004604 | rs41496150 | 0.0005693 |
| rs1996671 | 0.0003421 | rs7925366 | 0.0004616 | rs13388047 | 0.0005708 |
| rs2198207 | 0.0003433 | rs1076884 | 0.0004623 | rs665036 | 0.0005732 |
| rs12127407 | 0.0003433 | rs4418560 | 0.0004657 | rs12467020 | 0.0005735 |
| rs17561681 | 0.000346 | rs9893321 | 0.000466 | rs17651026 | 0.000574 |
| rs1891987 | 0.0003481 | rs17811677 | 0.0004686 | rs16870976 | 0.0005745 |
| rs3821285 | 0.0003514 | rs11675929 | 0.0004705 | rs6133374 | 0.0005762 |
| rs17458000 | 0.0003541 | rs1583646 | 0.0004717 | rs1607807 | 0.0005794 |
| rs7091524 | 0.0003556 | rs11751618 | 0.0004718 | rs1684674 | 0.0005814 |
| rs2828789 | 0.0003569 | rs6107483 | 0.000473 | rs5995594 | 0.0005863 |
| rs12423492 | 0.0003573 | rs628606 | 0.0004731 | rs11265310 | 0.0005888 |
| rs388 | 0.0003589 | rs670271 | 0.0004745 | rs2105158 | 0.0005916 |
| rs13265557 | 0.0003619 | rs816546 | 0.0004764 | rs17745803 | 0.0005919 |
| rs17123864 | 0.0003631 | rs6854741 | 0.0004783 | rs17642119 | 0.0005948 |
| rs1978300 | 0.0003643 | rs4440674 | 0.0004846 | rs10885348 | 0.0005974 |
| rs9942632 | 0.0003647 | rs10514444 | 0.0004861 | rs9371388 | 0.0005983 |
| rs16936184 | 0.0003647 | rs834130 | 0.0004911 | rs1564048 | 0.0006011 |
| rs973009 | 0.000369 | rs12174997 | 0.000494 | rs9492415 | 0.0006066 |
| rs11218313 | 0.0003748 | rs41339754 | 0.0004951 | rs16893890 | 0.0006078 |
| rs6066693 | 0.0003757 | rs10503795 | 0.0005005 | rs10910443 | 0.0006089 |
| rs17824132 | 0.0003766 | rs6934260 | 0.0005008 | rs12061312 | 0.000613 |
| rs1239904 | 0.0003776 | rs6458330 | 0.0005077 | rs16966632 | 0.0006247 |
| rs11820515 | 0.0003832 | rs6490506 | 0.0005078 | rs3024676 | 0.0006305 |
| rs6736779 | 0.0003847 | rs16856202 | 0.0005188 | rs4595229 | 0.000641 |
| rs4240446 | 0.000385 | rs10974007 | 0.0005192 | rs868928 | 0.0006452 |
| rs6963233 | 0.000385 | rs11653617 | 0.0005212 | rs41445146 | 0.0006465 |
| rs947919 | 0.0003857 | rs41386450 | 0.0005225 | rs2819820 | 0.0006552 |
| rs6874596 | 0.0003894 | rs10839585 | 0.0005264 | rs9621532 | 0.0006578 |
| rs1005948 | 0.0003944 | rs4754276 | 0.0005297 | rs1856107 | 0.00066 |
| rs7725377 | 0.0003958 | rs17816553 | 0.0005306 | rs283027 | 0.0006608 |
| rs7772387 | 0.0003996 | rs6446391 | 0.0005307 | rs753725 | 0.0006672 |
| rs10850171 | 0.0004014 | rs9941114 | 0.0005334 | rs7223092 | 0.0006677 |
| rs326141 | 0.0004072 | rs3748006 | 0.0005335 | rs4076124 | 0.00067 |
| rs17119912 | 0.0004112 | rs4942165 | 0.0005352 | rs7172232 | 0.0006747 |
| rs10047208 | 0.000413 | rs12351443 | 0.0005375 | rs16892504 | 0.0006747 |
| rs2527853 | 0.0004133 | rs11859738 | 0.0005394 | rs6995938 | 0.0006757 |
| rs705970 | 0.000414 | rs2272094 | 0.0005437 | rs7926940 | 0.0006759 |
| rs1399358 | 0.0004153 | rs12447958 | 0.0005439 | rs6977788 | 0.0006857 |
| rs7010545 | 0.0004174 | rs7744512 | 0.0005441 | rs9813811 | 0.0006857 |

Figure 22-5

| | | | | | |
|---|---|---|---|---|---|
| rs12454921 | 0.0006911 | rs12701006 | 0.0008747 | rs16897892 | 0.0010566 |
| rs6435822 | 0.0006916 | rs7967638 | 0.0008837 | rs11216466 | 0.0010593 |
| rs34918490 | 0.0006962 | rs1943387 | 0.0008857 | rs17653411 | 0.0010645 |
| rs10431282 | 0.0007071 | rs2350415 | 0.0009072 | rs17190412 | 0.0010676 |
| rs4370778 | 0.0007108 | rs7123782 | 0.0009079 | rs2065968 | 0.0010685 |
| rs12135026 | 0.0007119 | rs6727051 | 0.0009098 | rs10491598 | 0.0010703 |
| rs16932063 | 0.0007151 | rs4717229 | 0.0009108 | rs7001472 | 0.0010726 |
| rs1574399 | 0.0007183 | rs4695345 | 0.000918 | rs7713655 | 0.0010729 |
| rs12925964 | 0.0007184 | rs2297154 | 0.0009184 | rs6923835 | 0.0010763 |
| rs1764416 | 0.0007226 | rs2268389 | 0.0009197 | rs751625 | 0.0010872 |
| rs1439025 | 0.0007248 | rs400214 | 0.0009244 | rs11158850 | 0.0010917 |
| rs6512152 | 0.0007266 | rs16981495 | 0.0009295 | rs10519971 | 0.0010921 |
| rs6936315 | 0.0007285 | rs8026993 | 0.0009325 | rs2067589 | 0.0010937 |
| rs10458732 | 0.0007287 | rs2044538 | 0.0009331 | rs7221278 | 0.0010952 |
| rs4936823 | 0.0007297 | rs7320986 | 0.0009354 | rs1672989 | 0.0010955 |
| rs247355 | 0.0007312 | rs6805279 | 0.0009396 | rs10880010 | 0.0010979 |
| rs17072878 | 0.0007328 | rs1605864 | 0.0009411 | rs11807765 | 0.0010987 |
| rs6602515 | 0.0007376 | rs11074481 | 0.0009431 | rs17089826 | 0.001102 |
| rs1888140 | 0.0007377 | rs12404945 | 0.0009483 | rs10492719 | 0.0011062 |
| rs17011839 | 0.000739 | rs442208 | 0.0009528 | rs3024994 | 0.0011064 |
| rs4774725 | 0.0007543 | rs17101811 | 0.0009555 | rs1317928 | 0.0011076 |
| rs4291550 | 0.0007576 | rs1647646 | 0.0009579 | rs11101085 | 0.0011197 |
| rs2785245 | 0.0007588 | rs12024134 | 0.0009588 | rs355127 | 0.0011241 |
| rs6482455 | 0.0007589 | rs11135418 | 0.0009669 | rs17363431 | 0.0011276 |
| rs1998927 | 0.0007607 | rs10767929 | 0.0009692 | rs1417676 | 0.0011281 |
| rs5917746 | 0.0007615 | rs2170057 | 0.0009794 | rs16837190 | 0.0011287 |
| rs6732885 | 0.0007662 | rs11892488 | 0.0009795 | rs12718224 | 0.001129 |
| rs16927476 | 0.0007694 | rs10517845 | 0.0009808 | rs16834810 | 0.0011294 |
| rs10510233 | 0.0007768 | rs2099305 | 0.0009821 | rs10140983 | 0.0011323 |
| rs17227203 | 0.0007793 | rs10762774 | 0.0009884 | rs1613776 | 0.0011362 |
| rs6421008 | 0.0007923 | rs7155312 | 0.0009919 | rs6556757 | 0.0011415 |
| rs17830967 | 0.0007929 | rs2034598 | 0.0009937 | rs7800059 | 0.0011432 |
| rs11929326 | 0.0007939 | rs7753049 | 0.000995 | rs17084040 | 0.001147 |
| rs11215936 | 0.000798 | rs9868264 | 0.0010095 | rs7633800 | 0.0011488 |
| rs6766260 | 0.0008037 | rs4671694 | 0.0010108 | rs7324489 | 0.0011521 |
| rs305423 | 0.0008071 | rs4797092 | 0.0010121 | rs384134 | 0.0011541 |
| rs10951911 | 0.0008096 | rs9890514 | 0.0010122 | rs16940610 | 0.0011616 |
| rs11606886 | 0.0008134 | rs3848110 | 0.001014 | rs17610832 | 0.0011618 |
| rs16966835 | 0.0008154 | rs10509052 | 0.0010218 | rs12632003 | 0.0011628 |
| rs2179307 | 0.0008163 | rs10437704 | 0.0010223 | rs7986406 | 0.001168 |
| rs3852545 | 0.0008236 | rs2337251 | 0.0010246 | rs4481316 | 0.0011694 |
| rs17232873 | 0.0008254 | rs41508049 | 0.001025 | rs11574637 | 0.001174 |
| rs17284999 | 0.000827 | rs16948360 | 0.0010304 | rs11199375 | 0.0011742 |
| rs6998419 | 0.0008284 | rs16983057 | 0.0010324 | rs11005278 | 0.0011743 |
| rs700228 | 0.0008378 | rs16823172 | 0.0010367 | rs2830993 | 0.00118 |
| rs1337645 | 0.0008446 | rs3806402 | 0.0010371 | rs1628891 | 0.0011818 |
| rs4979807 | 0.000848 | rs17669038 | 0.001039 | rs7787896 | 0.0011831 |
| rs9360049 | 0.0008518 | rs12611846 | 0.0010391 | rs2084903 | 0.0011837 |
| rs6979341 | 0.0008523 | rs703602 | 0.001047 | rs8078588 | 0.0011842 |
| rs1742852 | 0.0008621 | rs9904198 | 0.0010488 | rs12048640 | 0.0011878 |
| rs7794464 | 0.0008634 | rs41514051 | 0.0010493 | rs7296488 | 0.0011924 |
| rs735173 | 0.0008641 | rs1163760 | 0.0010496 | rs4140577 | 0.0011967 |
| rs4468514 | 0.0008711 | rs6779915 | 0.0010534 | rs10850536 | 0.0012037 |
| rs964745 | 0.0008731 | rs1405217 | 0.0010548 | rs638191 | 0.0012061 |
| rs7182710 | 0.0008735 | rs17747953 | 0.0010553 | rs11212290 | 0.001208 |

Figure 22-6

| | |
|---|---|
| rs16965693 | 0.0012129 |
| rs1354308 | 0.0012129 |
| rs3923096 | 0.0012137 |
| rs12142665 | 0.0012186 |
| rs6718149 | 0.0012323 |
| rs2277176 | 0.0012361 |
| rs8089224 | 0.001239 |
| rs765336 | 0.0012403 |
| rs16872733 | 0.0012421 |
| rs17393206 | 0.001245 |
| rs17710558 | 0.001246 |
| rs1212595 | 0.001247 |
| rs11037407 | 0.0012477 |
| rs353206 | 0.0012559 |
| rs11122414 | 0.0012644 |
| rs994769 | 0.0012645 |

Figure 22-7

| SNP | ChiSquare p value | SNP | ChiSquare p value | SNP | ChiSquare p value |
|---|---|---|---|---|---|
| rs10833199 | 8.83E-19 | rs7696347 | 3.56E-09 | rs4132421 | 6.38E-09 |
| rs11728055 | 2.87E-17 | rs4899015 | 3.85E-09 | rs7129236 | 6.41E-09 |
| rs16901105 | 4.52E-17 | rs11219832 | 3.99E-09 | rs3096660 | 6.44E-09 |
| rs12325649 | 4.92E-17 | rs222809 | 4.01E-09 | rs2303723 | 6.55E-09 |
| rs2632086 | 1.68E-16 | rs4306358 | 4.11E-09 | rs7547381 | 6.57E-09 |
| rs997860 | 7.91E-12 | rs35005996 | 4.14E-09 | rs7868409 | 6.57E-09 |
| rs10277013 | 1.16E-11 | rs11160571 | 4.21E-09 | rs16883001 | 6.57E-09 |
| rs17154797 | 1.18E-11 | rs16949908 | 4.27E-09 | rs10510498 | 6.57E-09 |
| rs17055141 | 1.52E-11 | rs2896061 | 4.33E-09 | rs7006266 | 6.58E-09 |
| rs17586131 | 1.54E-11 | rs17654944 | 4.40E-09 | rs1904928 | 6.58E-09 |
| rs11729371 | 1.85E-11 | rs2862116 | 4.43E-09 | rs6100719 | 6.59E-09 |
| rs4300782 | 1.91E-11 | rs2296066 | 4.45E-09 | rs17116121 | 6.64E-09 |
| rs8139654 | 2.25E-11 | rs9321466 | 4.46E-09 | rs10868851 | 6.69E-09 |
| rs9552517 | 2.53E-11 | rs17191803 | 4.51E-09 | rs16996490 | 6.78E-09 |
| rs2815732 | 2.70E-11 | rs7188054 | 4.57E-09 | rs17174407 | 6.79E-09 |
| rs11626422 | 2.83E-11 | rs17701478 | 4.69E-09 | rs17148966 | 6.79E-09 |
| rs7069744 | 4.87E-11 | rs12111154 | 4.71E-09 | rs41472047 | 6.91E-09 |
| rs10773005 | 1.85E-10 | rs297779 | 4.86E-09 | rs6100783 | 6.99E-09 |
| rs13429130 | 3.55E-10 | rs1413512 | 4.87E-09 | rs11935748 | 7.02E-09 |
| rs9312755 | 3.99E-10 | rs10044755 | 4.95E-09 | rs16983712 | 7.02E-09 |
| rs1039119 | 4.30E-10 | rs4568238 | 4.97E-09 | rs17015855 | 7.03E-09 |
| rs17155293 | 5.16E-10 | rs1497169 | 4.99E-09 | rs16827988 | 7.04E-09 |
| rs2449539 | 6.97E-10 | rs41388249 | 5.00E-09 | rs7934354 | 7.05E-09 |
| rs268299 | 1.07E-09 | rs1439332 | 5.01E-09 | rs3962573 | 7.06E-09 |
| rs9979508 | 1.15E-09 | rs1198006 | 5.05E-09 | rs17043686 | 7.08E-09 |
| rs2048495 | 1.24E-09 | rs41386447 | 5.15E-09 | rs17836464 | 7.08E-09 |
| rs10991581 | 1.30E-09 | rs6589527 | 5.26E-09 | rs16893391 | 7.10E-09 |
| rs13176869 | 1.47E-09 | rs1821542 | 5.28E-09 | rs16847237 | 7.10E-09 |
| rs11787939 | 1.60E-09 | rs415208 | 5.29E-09 | rs17524193 | 7.10E-09 |
| rs17128560 | 1.61E-09 | rs2725663 | 5.33E-09 | rs17065451 | 7.11E-09 |
| rs8022177 | 1.64E-09 | rs1915462 | 5.35E-09 | rs7137705 | 7.13E-09 |
| rs960078 | 2.18E-09 | rs17121606 | 5.35E-09 | rs7648240 | 7.15E-09 |
| rs4320103 | 2.20E-09 | rs16910061 | 5.36E-09 | rs17017662 | 7.27E-09 |
| rs2711493 | 2.36E-09 | rs12694400 | 5.42E-09 | rs10957818 | 7.27E-09 |
| rs5026429 | 2.50E-09 | rs6517876 | 5.54E-09 | rs17834140 | 7.33E-09 |
| rs7119574 | 2.53E-09 | rs17080859 | 5.57E-09 | rs2154399 | 7.40E-09 |
| rs17713163 | 2.54E-09 | rs7210897 | 5.58E-09 | rs1782786 | 7.40E-09 |
| rs41524446 | 2.57E-09 | rs17023472 | 5.62E-09 | rs6441299 | 7.51E-09 |
| rs10280397 | 2.63E-09 | rs2279023 | 5.63E-09 | rs9828738 | 7.54E-09 |
| rs10053788 | 2.84E-09 | rs42772 | 5.67E-09 | rs7982110 | 7.56E-09 |
| rs8015614 | 2.84E-09 | rs4740238 | 5.68E-09 | rs4837165 | 7.56E-09 |
| rs6858024 | 2.84E-09 | rs12059815 | 5.70E-09 | rs6481454 | 7.59E-09 |
| rs16986733 | 2.85E-09 | rs1017931 | 5.70E-09 | rs17128992 | 7.66E-09 |
| rs8021182 | 2.89E-09 | rs355954 | 5.72E-09 | rs16931982 | 7.85E-09 |
| rs11562945 | 2.96E-09 | rs16956948 | 5.81E-09 | rs16839691 | 8.05E-09 |
| rs10748449 | 2.99E-09 | rs9385824 | 5.81E-09 | rs9513390 | 8.18E-09 |
| rs3187141 | 3.00E-09 | rs7923915 | 6.01E-09 | rs9428247 | 8.26E-09 |
| rs1341994 | 3.09E-09 | rs17660851 | 6.11E-09 | rs12509766 | 8.44E-09 |
| rs9992080 | 3.17E-09 | rs17326067 | 6.21E-09 | rs7735510 | 8.82E-09 |
| rs11106069 | 3.19E-09 | rs1932637 | 6.28E-09 | rs10509275 | 8.99E-09 |
| rs955943 | 3.22E-09 | rs3866687 | 6.30E-09 | rs16904515 | 9.01E-09 |
| rs2830017 | 3.31E-09 | rs4503463 | 6.32E-09 | rs7204905 | 9.84E-09 |
| rs7718362 | 3.43E-09 | rs2022105 | 6.35E-09 | rs17033273 | 9.85E-09 |

Figure 23-1

| | | | | | |
|---|---|---|---|---|---|
| rs996793 | 1.01E-08 | rs6989128 | 2.21E-06 | rs10880288 | 2.24E-05 |
| rs4839854 | 1.06E-08 | rs12608629 | 2.30E-06 | rs9609775 | 2.25E-05 |
| rs17770834 | 1.07E-08 | rs957434 | 2.66E-06 | rs10768703 | 2.34E-05 |
| rs4743886 | 1.11E-08 | rs3929907 | 2.81E-06 | rs1539400 | 2.43E-05 |
| rs245675 | 1.12E-08 | rs6663174 | 2.86E-06 | rs10515762 | 2.45E-05 |
| rs17000486 | 1.15E-08 | rs6560752 | 3.40E-06 | rs7840975 | 2.51E-05 |
| rs16856394 | 1.30E-08 | rs4401694 | 3.88E-06 | rs4745006 | 2.57E-05 |
| rs41465145 | 1.34E-08 | rs2427995 | 4.11E-06 | rs11259475 | 2.69E-05 |
| rs10850269 | 1.45E-08 | rs7822802 | 4.16E-06 | rs138465 | 2.71E-05 |
| rs9591488 | 1.55E-08 | rs10434137 | 4.40E-06 | rs1786734 | 2.85E-05 |
| rs41456546 | 1.57E-08 | rs7711505 | 4.41E-06 | rs735311 | 2.86E-05 |
| rs9511646 | 1.57E-08 | rs10431210 | 4.64E-06 | rs727190 | 2.95E-05 |
| rs6957661 | 1.74E-08 | rs10490904 | 5.65E-06 | rs1423616 | 2.97E-05 |
| rs502518 | 1.76E-08 | rs4691370 | 5.74E-06 | rs10267502 | 3.05E-05 |
| rs7978453 | 1.77E-08 | rs2722552 | 5.92E-06 | rs16988320 | 3.12E-05 |
| rs7634813 | 1.82E-08 | rs17769092 | 5.94E-06 | rs10935018 | 3.20E-05 |
| rs13479 | 2.01E-08 | rs17045404 | 6.09E-06 | rs9577481 | 3.28E-05 |
| rs9384060 | 2.41E-08 | rs2043265 | 6.56E-06 | rs3852528 | 3.38E-05 |
| rs1009295 | 2.50E-08 | rs17063761 | 6.76E-06 | rs4752432 | 3.41E-05 |
| rs850942 | 2.67E-08 | rs10509376 | 6.91E-06 | rs17528635 | 3.44E-05 |
| rs1077747 | 2.93E-08 | rs12158070 | 7.34E-06 | rs12644895 | 3.45E-05 |
| rs6722636 | 3.17E-08 | rs17114703 | 8.07E-06 | rs12901876 | 3.46E-05 |
| rs17212829 | 3.65E-08 | rs6135697 | 8.20E-06 | rs6765656 | 3.47E-05 |
| rs41348748 | 4.25E-08 | rs13220654 | 9.17E-06 | rs9436667 | 3.56E-05 |
| rs1021379 | 4.41E-08 | rs12260362 | 9.29E-06 | rs17676550 | 3.57E-05 |
| rs10975141 | 5.00E-08 | rs6034984 | 9.39E-06 | rs6665865 | 3.70E-05 |
| rs10733352 | 5.47E-08 | rs17801458 | 9.86E-06 | rs16912196 | 3.78E-05 |
| rs1248551 | 7.65E-08 | rs12110175 | 1.02E-05 | rs2301857 | 4.02E-05 |
| rs16922192 | 7.86E-08 | rs1493506 | 1.12E-05 | rs879428 | 4.10E-05 |
| rs10777800 | 2.49E-07 | rs1254703 | 1.24E-05 | rs6994642 | 4.29E-05 |
| rs10494170 | 2.69E-07 | rs16931326 | 1.29E-05 | rs2689132 | 4.30E-05 |
| rs16919123 | 2.97E-07 | rs17124464 | 1.29E-05 | rs6494165 | 4.39E-05 |
| rs11860355 | 2.98E-07 | rs9552533 | 1.31E-05 | rs7737968 | 4.43E-05 |
| rs10495153 | 4.27E-07 | rs4592605 | 1.33E-05 | rs1423304 | 4.46E-05 |
| rs1254672 | 6.04E-07 | rs1492689 | 1.34E-05 | rs9497352 | 4.75E-05 |
| rs17652341 | 6.09E-07 | rs503554 | 1.36E-05 | rs9302577 | 4.75E-05 |
| rs11187403 | 6.29E-07 | rs4772416 | 1.38E-05 | rs17514618 | 4.86E-05 |
| rs9959126 | 6.98E-07 | rs11193528 | 1.38E-05 | rs1927272 | 4.91E-05 |
| rs17324835 | 7.02E-07 | rs9532930 | 1.40E-05 | rs10490898 | 4.94E-05 |
| rs17541562 | 7.61E-07 | rs17330898 | 1.42E-05 | rs17141840 | 5.01E-05 |
| rs7595832 | 7.72E-07 | rs2154704 | 1.44E-05 | rs6850330 | 5.09E-05 |
| rs35805164 | 7.81E-07 | rs17156145 | 1.49E-05 | rs1950851 | 5.14E-05 |
| rs16884886 | 8.18E-07 | rs1594424 | 1.52E-05 | rs5969903 | 5.19E-05 |
| rs10511116 | 8.94E-07 | rs661149 | 1.59E-05 | rs1446216 | 5.24E-05 |
| rs10882332 | 9.16E-07 | rs11043229 | 1.60E-05 | rs9328948 | 5.31E-05 |
| rs13158321 | 9.55E-07 | rs10004741 | 1.65E-05 | rs1872043 | 5.41E-05 |
| rs11122825 | 9.57E-07 | rs4355718 | 1.67E-05 | rs7504430 | 5.43E-05 |
| rs1522779 | 9.85E-07 | rs711826 | 1.67E-05 | rs11052464 | 5.46E-05 |
| rs1123595 | 1.06E-06 | rs11146539 | 1.72E-05 | rs1523648 | 5.56E-05 |
| rs9298792 | 1.16E-06 | rs11252747 | 1.86E-05 | rs9296344 | 5.61E-05 |
| rs9287482 | 1.21E-06 | rs16871320 | 1.91E-05 | rs13374152 | 5.68E-05 |
| rs897656 | 1.57E-06 | rs10902933 | 2.01E-05 | rs383855 | 5.79E-05 |
| rs2389883 | 1.71E-06 | rs2977537 | 2.19E-05 | rs16920386 | 5.80E-05 |
| rs7628803 | 1.82E-06 | rs570880 | 2.22E-05 | rs17009291 | 5.84E-05 |
| rs16918253 | 1.84E-06 | rs17564083 | 2.22E-05 | rs16929074 | 6.08E-05 |

Figure 23-2

| | | | | | |
|---|---|---|---|---|---|
| rs13399239 | 6.10E-05 | rs17004068 | 8.42E-05 | rs4476905 | 0.000106 |
| rs7540790 | 6.11E-05 | rs13334391 | 8.45E-05 | rs17655252 | 0.0001063 |
| rs7302965 | 6.11E-05 | rs12430149 | 8.46E-05 | rs10107255 | 0.000107 |
| rs6503858 | 6.14E-05 | rs2131247 | 8.57E-05 | rs2838484 | 0.0001081 |
| rs3826149 | 6.16E-05 | rs9302218 | 8.58E-05 | rs1286220 | 0.0001081 |
| rs4575739 | 6.31E-05 | rs4509408 | 8.60E-05 | rs9950823 | 0.0001087 |
| rs2887208 | 6.33E-05 | rs17757989 | 8.60E-05 | rs4296747 | 0.0001088 |
| rs7895335 | 6.38E-05 | rs6436168 | 8.63E-05 | rs16912743 | 0.0001091 |
| rs17010429 | 6.50E-05 | rs6757928 | 8.70E-05 | rs17066406 | 0.0001094 |
| rs11139727 | 6.51E-05 | rs16952642 | 8.73E-05 | rs12381471 | 0.0001111 |
| rs3940202 | 6.52E-05 | rs17300991 | 8.78E-05 | rs17168413 | 0.0001115 |
| rs11007270 | 6.55E-05 | rs4751276 | 8.79E-05 | rs6925493 | 0.000112 |
| rs16903084 | 6.60E-05 | rs11065386 | 8.81E-05 | rs17125701 | 0.0001125 |
| rs590732 | 6.66E-05 | rs4241471 | 8.82E-05 | rs7786553 | 0.000113 |
| rs824211 | 6.68E-05 | rs2429010 | 8.83E-05 | rs11925269 | 0.0001135 |
| rs7018599 | 6.69E-05 | rs10927510 | 8.88E-05 | rs871387 | 0.0001139 |
| rs16962248 | 6.72E-05 | rs7986574 | 8.90E-05 | rs12820818 | 0.0001142 |
| rs6590743 | 6.79E-05 | rs11607727 | 8.99E-05 | rs470029 | 0.0001145 |
| rs41425044 | 6.79E-05 | rs7914927 | 9.09E-05 | rs17084772 | 0.0001146 |
| rs435945 | 6.94E-05 | rs17232035 | 9.23E-05 | rs7076586 | 0.0001149 |
| rs17143392 | 6.95E-05 | rs17777477 | 9.23E-05 | rs17145374 | 0.0001152 |
| rs16894744 | 6.97E-05 | rs17744902 | 9.24E-05 | rs6597472 | 0.0001157 |
| rs17631686 | 6.98E-05 | rs10976785 | 9.24E-05 | rs3889602 | 0.000116 |
| rs1971603 | 7.01E-05 | rs189509 | 9.28E-05 | rs17044733 | 0.0001162 |
| rs12416804 | 7.11E-05 | rs1116864 | 9.32E-05 | rs17083131 | 0.0001168 |
| rs16966786 | 7.18E-05 | rs17073748 | 9.32E-05 | rs10174991 | 0.0001169 |
| rs11673919 | 7.22E-05 | rs10159565 | 9.33E-05 | rs2101210 | 0.000117 |
| rs17758987 | 7.27E-05 | rs3739216 | 9.33E-05 | rs4461205 | 0.0001171 |
| rs1514589 | 7.34E-05 | rs6836600 | 9.41E-05 | rs131390 | 0.0001171 |
| rs1229670 | 7.39E-05 | rs1445871 | 9.43E-05 | rs7095435 | 0.0001174 |
| rs7116979 | 7.49E-05 | rs17144393 | 9.48E-05 | rs1355554 | 0.0001177 |
| rs6538486 | 7.52E-05 | rs7525079 | 9.56E-05 | rs475842 | 0.0001178 |
| rs10447132 | 7.56E-05 | rs17016123 | 9.66E-05 | rs4335774 | 0.0001179 |
| rs2526565 | 7.58E-05 | rs2888686 | 9.71E-05 | rs16954432 | 0.0001181 |
| rs7115217 | 7.63E-05 | rs4284619 | 9.74E-05 | rs12430547 | 0.0001182 |
| rs4979530 | 7.73E-05 | rs16886698 | 9.79E-05 | rs17804486 | 0.000119 |
| rs17069212 | 7.96E-05 | rs12159204 | 9.84E-05 | rs6684802 | 0.000119 |
| rs1333345 | 7.98E-05 | rs6964079 | 9.85E-05 | rs833986 | 0.0001193 |
| rs2423672 | 7.99E-05 | rs16875172 | 9.98E-05 | rs2658072 | 0.0001195 |
| rs7342882 | 8.00E-05 | rs1426284 | 9.99E-05 | rs17101993 | 0.0001197 |
| rs10930700 | 8.04E-05 | rs17155568 | 0.0001012 | rs2266910 | 0.0001199 |
| rs562907 | 8.05E-05 | rs17046231 | 0.0001014 | rs10505414 | 0.0001203 |
| rs34277810 | 8.05E-05 | rs10250922 | 0.0001015 | rs7832507 | 0.000121 |
| rs17732220 | 8.09E-05 | rs9495484 | 0.0001033 | rs4469890 | 0.0001214 |
| rs11239303 | 8.18E-05 | rs6456652 | 0.0001037 | rs412841 | 0.0001218 |
| rs1389750 | 8.23E-05 | rs9930732 | 0.000104 | rs4402410 | 0.000122 |
| rs7921998 | 8.24E-05 | rs7236945 | 0.000104 | rs7115657 | 0.0001222 |
| rs17427680 | 8.26E-05 | rs1469488 | 0.0001042 | rs9565932 | 0.0001225 |
| rs8007742 | 8.28E-05 | rs546528 | 0.0001042 | rs4405320 | 0.0001226 |
| rs10521469 | 8.29E-05 | rs10073428 | 0.0001043 | rs10966485 | 0.0001236 |
| rs16842165 | 8.29E-05 | rs3791320 | 0.0001043 | rs16954906 | 0.0001239 |
| rs17450699 | 8.32E-05 | rs879362 | 0.0001043 | rs12406698 | 0.0001239 |
| rs10895889 | 8.33E-05 | rs17215946 | 0.0001045 | rs6571823 | 0.0001248 |
| rs6413523 | 8.36E-05 | rs9957971 | 0.0001058 | rs1512432 | 0.0001252 |
| rs9289448 | 8.41E-05 | rs4742424 | 0.000106 | rs11074925 | 0.0001258 |

Figure 23-3

| | | | | | |
|---|---|---|---|---|---|
| rs1937934 | 0.0001261 | rs2422677 | 0.000137 | rs11831258 | 0.0001739 |
| rs11068096 | 0.0001268 | rs17014869 | 0.000137 | rs17505435 | 0.0001744 |
| rs10087433 | 0.0001269 | rs1393355 | 0.0001371 | rs959454 | 0.0001754 |
| rs11935340 | 0.0001269 | rs157673 | 0.0001372 | rs442332 | 0.0001767 |
| rs3934900 | 0.000127 | rs1737502 | 0.0001373 | rs4845016 | 0.0001774 |
| rs17446338 | 0.0001273 | rs41477845 | 0.0001381 | rs11022250 | 0.0001778 |
| rs9402750 | 0.0001275 | rs6862763 | 0.0001381 | rs16848847 | 0.0001782 |
| rs16920467 | 0.0001276 | rs17088255 | 0.0001382 | rs4720801 | 0.0001846 |
| rs6881226 | 0.0001277 | rs9924092 | 0.000139 | rs1485591 | 0.0001854 |
| rs1448127 | 0.0001286 | rs17143671 | 0.0001392 | rs7792597 | 0.0001886 |
| rs4932976 | 0.000129 | rs17122763 | 0.0001396 | rs11870481 | 0.0001892 |
| rs16944056 | 0.0001292 | rs904317 | 0.0001398 | rs2068929 | 0.0001916 |
| rs11862196 | 0.0001292 | rs3096378 | 0.0001398 | rs9568232 | 0.0001927 |
| rs11184329 | 0.0001293 | rs10256108 | 0.0001399 | rs7321954 | 0.0001948 |
| rs16892989 | 0.0001296 | rs1346861 | 0.0001401 | rs13101295 | 0.0001967 |
| rs28607918 | 0.0001297 | rs2939967 | 0.0001401 | rs10919966 | 0.0002021 |
| rs11864276 | 0.0001308 | rs4932445 | 0.0001408 | rs17069141 | 0.0002026 |
| rs3206354 | 0.0001309 | rs17348537 | 0.0001409 | rs837727 | 0.0002044 |
| rs1893836 | 0.0001312 | rs6481313 | 0.0001413 | rs7604415 | 0.0002056 |
| rs7611514 | 0.0001312 | rs2824903 | 0.0001416 | rs1927551 | 0.0002094 |
| rs8110995 | 0.0001312 | rs7776126 | 0.0001417 | rs2165565 | 0.0002099 |
| rs10437704 | 0.0001315 | rs2681314 | 0.0001418 | rs17058450 | 0.000214 |
| rs41461646 | 0.0001317 | rs2963794 | 0.0001421 | rs1546914 | 0.0002156 |
| rs17109410 | 0.0001318 | rs7540706 | 0.0001424 | rs3915055 | 0.000216 |
| rs11219735 | 0.0001327 | rs9358928 | 0.0001432 | rs11081336 | 0.000216 |
| rs8109860 | 0.0001328 | rs920967 | 0.000144 | rs16978425 | 0.0002169 |
| rs9615766 | 0.0001334 | rs10518794 | 0.0001451 | rs17322057 | 0.000221 |
| rs2962249 | 0.0001336 | rs565742 | 0.0001462 | rs10828685 | 0.0002227 |
| rs740553 | 0.0001337 | rs994638 | 0.0001463 | rs17728260 | 0.0002245 |
| rs6453220 | 0.0001337 | rs643099 | 0.0001472 | rs7858066 | 0.0002247 |
| rs4600958 | 0.0001338 | rs2996368 | 0.0001472 | rs4993355 | 0.0002284 |
| rs10920462 | 0.0001339 | rs7938742 | 0.0001477 | rs6124562 | 0.0002344 |
| rs972178 | 0.0001339 | rs6035213 | 0.0001485 | rs896186 | 0.0002403 |
| rs6467723 | 0.0001341 | rs12555797 | 0.0001502 | rs10736996 | 0.000243 |
| rs11645072 | 0.0001343 | rs10491116 | 0.0001502 | rs173389 | 0.0002444 |
| rs4072879 | 0.0001348 | rs11644455 | 0.000153 | rs673471 | 0.0002482 |
| rs2879725 | 0.0001352 | rs17162823 | 0.0001539 | rs16846246 | 0.0002538 |
| rs9928871 | 0.0001354 | rs9838009 | 0.000154 | rs17653822 | 0.0002549 |
| rs3027209 | 0.0001355 | rs6951874 | 0.0001544 | rs7182308 | 0.0002611 |
| rs376535 | 0.0001358 | rs9943843 | 0.0001556 | rs746385 | 0.0002618 |
| rs2025278 | 0.000136 | rs2218066 | 0.0001557 | rs11245257 | 0.0002623 |
| rs2140756 | 0.0001361 | rs4778099 | 0.0001577 | rs7613256 | 0.0002656 |
| rs6912037 | 0.0001361 | rs4676312 | 0.0001598 | rs1421346 | 0.0002666 |
| rs16872626 | 0.0001361 | rs4917745 | 0.0001614 | rs4880511 | 0.00027 |
| rs16914121 | 0.0001363 | rs11247377 | 0.0001628 | rs33157 | 0.0002727 |
| rs2445174 | 0.0001363 | rs10225776 | 0.0001633 | rs1617936 | 0.0002737 |
| rs1482619 | 0.0001364 | rs6132977 | 0.0001637 | rs10936578 | 0.000274 |
| rs1906969 | 0.0001364 | rs16994140 | 0.0001647 | rs6563177 | 0.0002806 |
| rs10509148 | 0.0001366 | rs2344752 | 0.0001655 | rs313161 | 0.0002865 |
| rs544789 | 0.0001367 | rs11677881 | 0.0001672 | rs8463 | 0.0002865 |
| rs750339 | 0.0001367 | rs6598912 | 0.0001673 | rs16926787 | 0.0002915 |
| rs16981660 | 0.0001367 | rs7811465 | 0.0001674 | rs7959960 | 0.0002921 |
| rs17674478 | 0.0001367 | rs699181 | 0.0001694 | rs1536945 | 0.0002997 |
| rs245957 | 0.0001368 | rs948173 | 0.0001698 | rs35241893 | 0.000301 |
| rs12257536 | 0.000137 | rs10884039 | 0.000172 | rs1372540 | 0.0003014 |

Figure 23-4

| | | | | | |
|---|---|---|---|---|---|
| rs17165412 | 0.0003014 | rs9263597 | 0.0004274 | rs5976816 | 0.0005863 |
| rs496190 | 0.000302 | rs1976192 | 0.0004299 | rs4603275 | 0.0005939 |
| rs2243544 | 0.000305 | rs4689915 | 0.0004302 | rs274035 | 0.0005981 |
| rs10183197 | 0.0003062 | rs4978438 | 0.0004313 | rs17415059 | 0.0006031 |
| rs4072661 | 0.0003069 | rs41509648 | 0.0004315 | rs4757064 | 0.0006039 |
| rs10816972 | 0.0003081 | rs7969825 | 0.0004402 | rs2043778 | 0.0006071 |
| rs1603199 | 0.0003087 | rs2281649 | 0.0004419 | rs12312105 | 0.0006094 |
| rs719926 | 0.0003103 | rs16921893 | 0.0004459 | rs4750048 | 0.0006109 |
| rs16915382 | 0.0003104 | rs12083416 | 0.0004498 | rs17033398 | 0.0006125 |
| rs7324589 | 0.0003108 | rs11982286 | 0.0004505 | rs4505340 | 0.0006159 |
| rs9865234 | 0.000312 | rs7772922 | 0.0004526 | rs2024788 | 0.0006173 |
| rs4264593 | 0.0003184 | rs17184428 | 0.0004541 | rs11220051 | 0.0006216 |
| rs17092188 | 0.0003187 | rs10873349 | 0.0004553 | rs10772075 | 0.0006226 |
| rs315782 | 0.0003194 | rs7973206 | 0.0004597 | rs11165315 | 0.0006341 |
| rs9830956 | 0.0003245 | rs1836655 | 0.0004617 | rs2287045 | 0.0006353 |
| rs7141908 | 0.000326 | rs10032829 | 0.0004706 | rs4242340 | 0.0006359 |
| rs16931010 | 0.0003286 | rs8060064 | 0.0004715 | rs1735469 | 0.0006364 |
| rs6690583 | 0.0003311 | rs4869890 | 0.0004759 | rs2070334 | 0.0006367 |
| rs12359591 | 0.0003337 | rs534150 | 0.0004793 | rs11615777 | 0.0006371 |
| rs911782 | 0.000337 | rs6008573 | 0.0004818 | rs2445333 | 0.0006415 |
| rs12026625 | 0.0003379 | rs10256786 | 0.0004823 | rs1893791 | 0.0006426 |
| rs2211011 | 0.0003382 | rs9586181 | 0.0004839 | rs6981251 | 0.0006439 |
| rs4243965 | 0.0003397 | rs7955585 | 0.0004923 | rs10860097 | 0.0006564 |
| rs7357322 | 0.0003426 | rs1340048 | 0.0004928 | rs349973 | 0.0006567 |
| rs1934020 | 0.0003429 | rs6705877 | 0.0004943 | rs2199154 | 0.0006583 |
| rs4132554 | 0.0003435 | rs1598745 | 0.0004965 | rs8078261 | 0.0006608 |
| rs17168361 | 0.0003492 | rs10247439 | 0.000497 | rs16958089 | 0.0006622 |
| rs10518891 | 0.0003498 | rs9856242 | 0.0004983 | rs7324699 | 0.0006777 |
| rs12610253 | 0.0003506 | rs6501834 | 0.0004994 | rs2237961 | 0.0006782 |
| rs4637494 | 0.0003535 | rs28606996 | 0.0005122 | rs248848 | 0.0006785 |
| rs2279018 | 0.0003544 | rs1631596 | 0.000513 | rs2685468 | 0.0006841 |
| rs12262851 | 0.0003613 | rs10767075 | 0.0005132 | rs17684734 | 0.0006854 |
| rs16898687 | 0.0003621 | rs11913750 | 0.0005147 | rs10170236 | 0.0006928 |
| rs772443 | 0.0003665 | rs12927476 | 0.0005158 | rs283735 | 0.0006937 |
| rs41521048 | 0.0003685 | rs6465381 | 0.0005167 | rs9405232 | 0.0006972 |
| rs7599985 | 0.0003689 | rs1861710 | 0.0005173 | rs6047797 | 0.0006977 |
| rs4935838 | 0.0003747 | rs7524430 | 0.0005207 | rs17282840 | 0.0006988 |
| rs104664 | 0.0003766 | rs10860397 | 0.0005231 | rs7882576 | 0.0007015 |
| rs6724110 | 0.0003779 | rs4782712 | 0.0005253 | rs488156 | 0.000706 |
| rs2461202 | 0.0003815 | rs8126456 | 0.0005342 | rs4242245 | 0.000707 |
| rs1869176 | 0.0003819 | rs4776292 | 0.0005368 | rs17007695 | 0.000707 |
| rs7594094 | 0.0003849 | rs879872 | 0.0005368 | rs17169771 | 0.0007073 |
| rs7022605 | 0.0003888 | rs10283737 | 0.0005375 | rs2674885 | 0.0007106 |
| rs17566231 | 0.000395 | rs41468946 | 0.0005382 | rs6892850 | 0.0007118 |
| rs1939631 | 0.0003952 | rs41376144 | 0.0005547 | rs7327101 | 0.0007174 |
| rs2600960 | 0.000399 | rs4930027 | 0.0005572 | rs11928296 | 0.000723 |
| rs2811608 | 0.0004022 | rs5952804 | 0.0005598 | rs7480288 | 0.0007352 |
| rs323451 | 0.0004025 | rs447136 | 0.0005663 | rs7772387 | 0.0007353 |
| rs333165 | 0.0004027 | rs12805072 | 0.0005709 | rs17001349 | 0.0007355 |
| rs7199063 | 0.0004042 | rs185435 | 0.0005719 | rs10512441 | 0.0007379 |
| rs7563563 | 0.0004058 | rs10977348 | 0.0005724 | rs1818806 | 0.0007399 |
| rs464466 | 0.0004069 | rs3843718 | 0.0005733 | rs11002432 | 0.0007409 |
| rs6996216 | 0.0004086 | rs16862435 | 0.0005739 | rs41440247 | 0.0007441 |
| rs7921993 | 0.0004112 | rs11611673 | 0.0005797 | rs12508229 | 0.0007458 |
| rs17296412 | 0.0004139 | rs1436879 | 0.0005849 | rs16929280 | 0.0007491 |

Figure 23-5

| | | | | | |
|---|---|---|---|---|---|
| rs7913128 | 0.000751 | rs4695881 | 0.0009128 | rs9576072 | 0.0010531 |
| rs16912372 | 0.0007512 | rs11189359 | 0.0009171 | rs12757377 | 0.0010626 |
| rs2387595 | 0.0007568 | rs2286720 | 0.0009182 | rs3791624 | 0.0010643 |
| rs7089591 | 0.0007576 | rs2973488 | 0.0009184 | rs11071385 | 0.0010647 |
| rs12990870 | 0.0007577 | rs4628973 | 0.0009205 | rs206910 | 0.0010665 |
| rs9922955 | 0.0007662 | rs329235 | 0.0009205 | rs7303167 | 0.0010678 |
| rs4921698 | 0.0007719 | rs2241520 | 0.0009276 | rs10509810 | 0.0010686 |
| rs7951875 | 0.0007774 | rs11071467 | 0.0009349 | rs1980775 | 0.0010769 |
| rs319301 | 0.0007778 | rs12540569 | 0.0009355 | rs4430519 | 0.001082 |
| rs16964802 | 0.0007843 | rs1011624 | 0.0009419 | rs4463179 | 0.0010827 |
| rs671873 | 0.0007878 | rs16989701 | 0.0009455 | rs1740720 | 0.0010887 |
| rs17029241 | 0.0007884 | rs7875389 | 0.0009459 | rs12637343 | 0.0010895 |
| rs11130377 | 0.0007908 | rs17822462 | 0.0009467 | rs2439631 | 0.0010896 |
| rs12601491 | 0.0007919 | rs6595788 | 0.0009474 | rs4761615 | 0.0010938 |
| rs834487 | 0.0007941 | rs1165207 | 0.0009474 | rs218815 | 0.0010944 |
| rs8113032 | 0.0007956 | rs1888924 | 0.0009476 | rs1449546 | 0.0010947 |
| rs10261536 | 0.0007962 | rs1882426 | 0.0009495 | rs17627078 | 0.0010981 |
| rs6887277 | 0.0007969 | rs17630766 | 0.0009523 | rs1153744 | 0.0011002 |
| rs4677259 | 0.0007972 | rs7316431 | 0.0009604 | rs7070722 | 0.0011011 |
| rs9843448 | 0.0007995 | rs237238 | 0.0009607 | rs244990 | 0.0011066 |
| rs16933168 | 0.0008038 | rs7324229 | 0.0009627 | rs12144146 | 0.0011132 |
| rs616749 | 0.0008058 | rs1322199 | 0.000963 | rs17306064 | 0.0011133 |
| rs9694859 | 0.0008099 | rs739104 | 0.0009636 | rs1607237 | 0.0011156 |
| rs7577271 | 0.0008165 | rs2833457 | 0.0009644 | rs16982350 | 0.0011172 |
| rs7311216 | 0.0008249 | rs11956184 | 0.0009715 | rs12490417 | 0.0011177 |
| rs7046184 | 0.0008262 | rs3851333 | 0.0009761 | rs6027005 | 0.0011216 |
| rs6741676 | 0.0008274 | rs2934118 | 0.000977 | rs2156646 | 0.0011284 |
| rs294711 | 0.0008291 | rs954882 | 0.0009792 | rs7591341 | 0.0011337 |
| rs6870006 | 0.0008321 | rs17728526 | 0.0009845 | rs12675500 | 0.0011392 |
| rs1023853 | 0.0008406 | rs12666205 | 0.0009875 | rs10507004 | 0.001147 |
| rs4789753 | 0.0008436 | rs670232 | 0.0009877 | rs2283029 | 0.0011492 |
| rs4131667 | 0.0008462 | rs41484050 | 0.0009882 | rs12201626 | 0.0011563 |
| rs764502 | 0.0008476 | rs314583 | 0.0009926 | rs6069285 | 0.0011628 |
| rs2306936 | 0.0008513 | rs1944469 | 0.0009945 | rs2472680 | 0.0011833 |
| rs654694 | 0.0008522 | rs6812348 | 0.0009949 | rs12705150 | 0.0011848 |
| rs782702 | 0.0008541 | rs7873050 | 0.0009979 | rs9650197 | 0.0011877 |
| rs2633019 | 0.0008565 | rs17016013 | 0.0010024 | rs16838718 | 0.001189 |
| rs4813377 | 0.0008587 | rs994813 | 0.0010033 | rs12247030 | 0.0011986 |
| rs11106868 | 0.0008596 | rs4622487 | 0.0010054 | rs16907322 | 0.0012026 |
| rs11602880 | 0.0008598 | rs7954351 | 0.0010078 | rs2046357 | 0.0012093 |
| rs754233 | 0.0008617 | rs1180657 | 0.0010107 | rs10038062 | 0.0012105 |
| rs4391826 | 0.0008645 | rs10079961 | 0.0010139 | rs6517304 | 0.0012118 |
| rs1982265 | 0.0008655 | rs17425397 | 0.0010142 | rs797252 | 0.0012201 |
| rs10812021 | 0.0008667 | rs2391214 | 0.0010222 | rs9864057 | 0.0012207 |
| rs3812704 | 0.000871 | rs9829295 | 0.0010249 | rs12463085 | 0.0012258 |
| rs13088856 | 0.0008736 | rs10515149 | 0.0010287 | rs2900476 | 0.001226 |
| rs12584035 | 0.0008756 | rs675893 | 0.0010342 | rs4890173 | 0.0012274 |
| rs17156347 | 0.0008757 | rs17356585 | 0.0010364 | rs4843632 | 0.0012278 |
| rs7087658 | 0.0008847 | rs17638906 | 0.0010394 | rs257962 | 0.0012362 |
| rs2518827 | 0.0008898 | rs11595510 | 0.0010401 | rs4750655 | 0.0012365 |
| rs9285163 | 0.0008931 | rs7869264 | 0.001042 | rs7220621 | 0.0012419 |
| rs17517294 | 0.0008973 | rs893460 | 0.0010453 | rs7495602 | 0.0012422 |
| rs33995980 | 0.000902 | rs150568 | 0.0010475 | rs192680 | 0.0012483 |
| rs2061840 | 0.0009095 | rs12212981 | 0.0010522 | rs4235441 | 0.0012524 |
| rs2285663 | 0.0009105 | rs3087684 | 0.0010522 | rs7527274 | 0.0012566 |

Figure 23-6

| | |
|---|---|
| rs13432866 | 0.0012592 |
| rs7047314 | 0.0012592 |
| rs943165 | 0.0012621 |
| rs6892944 | 0.0012664 |
| rs6963728 | 0.0012686 |
| rs4684269 | 0.0012721 |
| rs4775229 | 0.0012777 |
| rs11660443 | 0.0012777 |
| rs10106438 | 0.0012795 |
| rs4983243 | 0.0012818 |
| rs41460547 | 0.0012832 |
| rs10257375 | 0.0012834 |
| rs10884470 | 0.0012835 |
| rs11020149 | 0.0012901 |
| rs11698292 | 0.001294 |
| rs2451678 | 0.001295 |

Figure 23-7

COMPOSITIONS AND METHODS FOR DETECTING PREDISPOSITION TO CARDIOVASCULAR DISEASE

CROSS REFERENCE TO RELATED APPLICATIONS

This application is a National Phase application under 35 U.S.C. § 371 of PCT International Application number PCT/US2017/036555 filed Jun. 8, 2017, which claims the benefit of priority under 35 U.S.C. § 119(e) to U.S. Application No. 62/347,479 filed Jun. 8, 2016, and U.S. Application No. 62/455,468 filed Feb. 6, 2017. Each of these applications are incorporated herein in their entirety.

STATEMENT REGARDING FEDERALLY SPONSORED RESEARCH

This invention was made with government support under R01DA037648 and R44DA041014 awarded by the National Institutes of Health. The government has certain rights in the invention.

BACKGROUND OF THE INVENTION

Cardiovascular Disease (CVD), which consists of Coronary Heart Disease (CHD), Congestive Heart Failure (CHF) and Stoke, is the leading cause of death in the United States. Effective treatments to prevent morbidity and mortality of CVD exist, but their clinical implementation is hindered by inefficient screening techniques. In recent years, others and we have shown that DNA methylation signatures can infer the presence of a variety of disorders related to CVD such as smoking. Unfortunately, when these epigenetic techniques are applied to CVD itself, the power of these methods is diminished, thus limiting their clinical utility. One possible reason for these failures may be the obscuration of epigenetic signature of CVD by gene x methylation interaction effects.

A reliable laboratory test would be of practical value in clinical practice, for example, in assisting doctors in prescribing the appropriate treatment for their patients. Accordingly, methods of identifying subjects that have, or are at risk for developing, CVD are needed.

SUMMARY OF THE INVENTION

In certain embodiments, the present disclosure provides a kit for determining methylation status of at least one CpG dinucleotide and a genotype of at least one single-nucleotide polymorphism (SNP), the kit comprising at least one first nucleic acid primer at least 8 nucleotides in length that is complementary to a bisulfite-converted nucleic acid sequence comprising a CpG dinucleotide from a gene from FIG. 15 or a first CpG site from FIG. 16, or a second CpG site that is collinear (e.g., R>0.3) with a first CpG site from FIG. 16, wherein the at least one first nucleic acid primer detects an unmethylated CpG dinucleotide; and at least one second nucleic acid primer at least 8 nucleotides in length that is complementary to a DNA sequence or bisulfite converted DNA sequence of a first SNP from FIG. 21 or a second SNP in linkage disequilibrium with a first SNP from FIG. 21. In some embodiments, the linkage disequilibrium has a value of R>0.3.

In certain embodiments the present disclosure provides a kit for determining methylation status of at least one CpG dinucleotide and a genotype of at least one single-nucleotide polymorphism (SNP), the kit comprising at least one first nucleic acid primer at least 8 nucleotides in length that is complementary to a bisulfite-converted nucleic acid sequence comprising a gene from FIG. 17 or a first CpG dinucleotide from FIG. 18 or a second CpG dinucleotide collinear (e.g., R>0.3) with a first CpG site from FIG. 18, wherein the at least one first nucleic acid primer detects an unmethylated CpG dinucleotide; and at least one second nucleic acid primer at least 8 nucleotides in length that is complementary to a DNA sequence or bisulfite converted DNA sequence of a first SNP FIG. 22 or a second SNP in linkage disequilibrium with a first SNP from FIG. 22. In some embodiments, the linkage disequilibrium has a value of R>0.3.

In certain embodiments the present disclosure provides a kit for determining methylation status of at least one CpG dinucleotide and a genotype of at least one single-nucleotide polymorphism (SNP), the kit comprising at least one first nucleic acid primer at least 8 nucleotides in length that is complementary to a bisulfite-converted nucleic acid sequence comprising a CpG dinucleotide from a gene from FIG. 19 or a first CpG site in FIG. 20 or a second CpG dinucleotide collinear (R>0.3) with a first CpG site from FIG. 20, wherein the at least one first nucleic acid primer detects an unmethylated CpG dinucleotide; and at least one second nucleic acid primer at least 8 nucleotides in length that is complementary to a DNA sequence or bisulfite converted DNA sequence of a first SNP from FIG. 23 or a second SNP in linkage disequilibrium with a first SNP from FIG. 23. In some embodiments, the linkage disequilibrium has a value of R>0.3.

In certain embodiments, the present disclosure provides a kit for determining the methylation status of at least one CpG dinucleotide and the presence of at least one single-nucleotide polymorphism (SNP), the kit comprising at least one first nucleic acid primer at least 8 nucleotides in length that is complementary to a bisulfite-converted nucleic acid sequence comprising a CpG dinucleotide at position 92203667 of chromosome 1 within the Transforming Growth Factor, Beta Receptor III (TGFBR3) gene, wherein the at least one first nucleic acid primer detects the unmethylated CpG dinucleotide, and at least one second nucleic acid primer at least 8 nucleotides in length that is complementary to SNP rs347027.

In certain embodiments, the present disclosure provides a kit for determining the methylation status of at least one CpG dinucleotide and the presence of at least one single-nucleotide polymorphism (SNP), the kit comprising at least one first nucleic acid primer at least 8 nucleotides in length that is complementary to a bisulfite-converted nucleic acid sequence comprising a CpG dinucleotide at position 38364951 in an intergenic region of chromosome 15 wherein the at least one first nucleic acid primer detects the unmethylated CpG dinucleotide, and at least one second nucleic acid primer at least 8 nucleotides in length that is complementary to SNP rs4937276.

In certain embodiments, the present disclosure provides a kit for determining the methylation status of at least one CpG dinucleotide and the presence of at least one single-nucleotide polymorphism (SNP), the kit comprising at least one first nucleic acid primer at least 8 nucleotides in length that is complementary to a bisulfite-converted nucleic acid sequence comprising a CpG dinucleotide at position 84206068 of chromosome 4 in the Coenzyme Q2 4-Hydroxybenzoate Polyprenyltransferase (COQ2) gene, wherein the at least one first nucleic acid primer detects the unmethylated CpG dinucleotide, and at least one second nucleic acid primer at least 8 nucleotides in length that is complementary SNP rs17355663.

In certain embodiments, the present disclosure provides a kit for determining the methylation status of at least one CpG dinucleotide and the presence of at least one single-nucleotide polymorphism (SNP), the kit comprising at least one first nucleic acid primer at least 8 nucleotides in length that is complementary to a bisulfite-converted nucleic acid sequence comprising a CpG dinucleotide at position 26146070 of chromosome 16 in the Heparan Sulfate 3-O-Sulfotransferase 4 (HS3ST4) gene, wherein the at least one first nucleic acid primer detects the unmethylated CpG dinucleotide, and at least one second nucleic acid primer at least 8 nucleotides in length that is complementary to SNP rs235807.

In certain embodiments, the present disclosure provides a kit for determining the methylation status of at least one CpG dinucleotide and the presence of at least one single-nucleotide polymorphism (SNP), the kit comprising at least one first nucleic acid primer at least 8 nucleotides in length that is complementary to a bisulfite-converted nucleic acid sequence comprising a CpG dinucleotide at position 91171013 of an intergenic region of chromosome 1, wherein the at least one first nucleic acid primer detects the unmethylated CpG dinucleotide, and at least one second nucleic acid primer at least 8 nucleotides in length that is complementary to SNP rs11579814.

In certain embodiments, the present disclosure provides a kit for determining the methylation status of at least one CpG dinucleotide and the presence of at least one single-nucleotide polymorphism (SNP), the kit comprising at least one first nucleic acid primer at least 8 nucleotides in length that is complementary to a bisulfite-converted nucleic acid sequence comprising a CpG dinucleotide at position 39491936 of chromosome 1 in the NADH Dehydrogenase (Ubiquinone) Fe—S Protein 5 (NDUFS5) gene, wherein the at least one first nucleic acid primer detects the unmethylated CpG dinucleotide, and at least one second nucleic acid primer at least 8 nucleotides in length that is complementary to SNP rs2275187.

In certain embodiments, the present disclosure provides a kit for determining the methylation status of at least one CpG dinucleotide and the presence of at least one single-nucleotide polymorphism (SNP), the kit comprising at least one first nucleic acid primer at least 8 nucleotides in length that is complementary to a bisulfite-converted nucleic acid sequence comprising a CpG dinucleotide at position 186426136 mapping to chromosome 1 in the Phosducin gene, wherein the at least one first nucleic acid primer detects the unmethylated CpG dinucleotide, and at least one second nucleic acid primer at least 8 nucleotides in length that is complementary to SNP rs4336803.

In certain embodiments, the present disclosure provides a kit for determining the methylation status of at least one CpG dinucleotide and the presence of at least one single-nucleotide polymorphism (SNP), the kit comprising at least one first nucleic acid primer at least 8 nucleotides in length that is complementary to a bisulfite-converted nucleic acid sequence comprising a CpG dinucleotide at position 205475130 of chromosome 1 in the Cyclin-Dependent Kinase 18 (CDK18) gene, wherein the at least one first nucleic acid primer detects the unmethylated CpG dinucleotide, and at least one second nucleic acid primer at least 8 nucleotides in length that is complementary to SNP rs4951158.

In certain embodiments, the present disclosure provides a kit for determining the methylation status of at least one CpG dinucleotide and the presence of at least one single-nucleotide polymorphism (SNP), the kit comprising at least one first nucleic acid primer at least 8 nucleotides in length that is complementary to a bisulfite-converted nucleic acid sequence comprising a CpG dinucleotide at position 130614013 of chromosome 3 in the ATPase, Ca++ Transporting, Type 2C, Member 1 (ATP2C1) gene, wherein the at least one first nucleic acid primer detects the unmethylated CpG dinucleotide, and at least one second nucleic acid primer at least 8 nucleotides in length that is complementary to SNP rs925613.

In certain embodiments, the present disclosure provides a kit for determining the methylation status of at least one CpG dinucleotide, the kit comprising: at least one first nucleic acid primer at least 8 nucleotides in length that is complementary to a bisulfite-converted nucleic acid sequence comprising a CpG dinucleotide at position 92203667 of chromosome 1 within the Transforming Growth Factor, Beta Receptor III (TGFBR3) gene, wherein the at least one first nucleic acid primer comprises one or more nucleotide analogs or one or more synthetic or non-natural nucleotides, and wherein the at least one nucleic acid primer detects either the unmethylated CpG dinucleotide or the methylated CpG dinucleotide.

In certain embodiments, the present disclosure provides a kit for determining the methylation status of at least one CpG dinucleotide, the kit comprising: at least one first nucleic acid primer at least 8 nucleotides in length that is complementary to a bisulfite-converted nucleic acid sequence comprising a CpG dinucleotide at position 92203667 of chromosome 1 within the Transforming Growth Factor, Beta Receptor III (TGFBR3) gene, and wherein the at least one nucleic acid primer detects either the unmethylated CpG dinucleotide or the methylated CpG dinucleotide; and a detectable label selected from the group consisting of an enzyme label, a fluorescent label, and a colorimetric label.

In certain embodiments, the present disclosure provides a kit for determining the methylation status of at least one CpG dinucleotide, the kit comprising: at least one first nucleic acid primer at least 8 nucleotides in length that is complementary to a bisulfite-converted nucleic acid sequence comprising a CpG dinucleotide at position 92203667 of chromosome 1 within the Transforming Growth Factor, Beta Receptor III (TGFBR3) gene, and wherein the at least one nucleic acid primer detects either the unmethylated CpG dinucleotide or the methylated CpG dinucleotide; and a solid substrate to which the at least one first nucleic acid primer is bound.

In certain embodiments, the present disclosure provides a method for detecting that a subject is predisposed to or has coronary heart disease comprising: (a) providing a biological sample from the subject; (b) contacting DNA from the biological sample with bisulfite under alkaline conditions; (c) contacting the bisulfite-treated DNA with at least one first oligonucleotide probe at least 8 nucleotides in length that is complementary to a sequence that comprises a CpG dinucleotide at position 92203667 of chromosome 1 within the Transforming Growth Factor, Beta Receptor III (TGFBR3), wherein the at least one first oligonucleotide probe detects either the unmethylated CpG dinucleotide or the methylated CpG dinucleotide, (d) determining genotype at single nucleotide polymorphism rs347027; and (e) detecting either the unmethylated CpG dinucleotide or the methylated CpG dinucleotide, wherein methylation of the CpG dinucleotide at position 92203667 of chromosome 1 is associated with coronary heart disease when genotype of rs347027 is determined.

In certain embodiments, the present disclosure provides a method for measuring the presence of a biomarker in a biological sample from a patient, the improvement comprising (a) contacting DNA from the biological sample with bisulfite under alkaline conditions; and (b) contacting the bisulfite-treated DNA with at least one first oligonucleotide probe at least 8 nucleotides in length that is complementary to a sequence that comprises a CpG dinucleotide at position 92203667 of chromosome 1 within the Transforming Growth Factor, Beta Receptor III (TGFBR3 gene, wherein the at least one first oligonucleotide probe detects either the unmethylated CpG dinucleotide or the methylated CpG dinucleotide, for use in predicting that the patient has coronary heart disease or has an increased likelihood of developing coronary heart disease.

In certain embodiments, the present disclosure provides a method of predicting the presence of biomarkers associated with Cardiovascular Disease (CVD) in a biological sample from a patient, comprising (a) providing a first aliquot from the biological sample and contacting DNA from the first biological sample with bisulfite under alkaline conditions, and (b) providing a second aliquot from the biological sample; (c) contacting (i) the first aliquot with a first oligonucleotide probe at least 8 nucleotides in length that is complementary to a sequence that comprises a CpG dinucleotide at position 92203667 of chromosome 1 within the Transforming Growth Factor, Beta Receptor III (TGFBR3) gene, and the second aliquot with a nucleic acid primer at least 8 nucleotides in length that is complementary to SNP rs347027, (ii) the first aliquot with a first oligonucleotide probe at least 8 nucleotides in length that is complementary to a sequence that comprises a CpG dinucleotide at position 38364951 in an intergenic region of chromosome 15, and the second aliquot with a nucleic acid primer at least 8 nucleotides in length that is complementary to SNP rs4937276, (iii) the first aliquot with a first oligonucleotide probe at least 8 nucleotides in length that is complementary to a sequence that comprises a CpG dinucleotide at position 84206068 of chromosome 4 in the Coenzyme Q2 4-Hydroxybenzoate Polyprenyltransferase (COQ2) gene, and the second aliquot with a nucleic acid primer at least 8 nucleotides in length that is complementary to SNP rs17355663, (iv) the first aliquot with a first oligonucleotide probe at least 8 nucleotides in length that is complementary to a sequence that comprises a CpG dinucleotide at position 26146070 of chromosome 16 in the Heparan Sulfate 3-O-Sulfotransferase 4 (HS3ST4) gene, and the second aliquot with a nucleic acid primer at least 8 nucleotides in length that is complementary to SNP rs235807, (v) the first aliquot with a first oligonucleotide probe at least 8 nucleotides in length that is complementary to a sequence that comprises a CpG dinucleotide at position 91171013 of an intergenic region of chromosome 1, and the second aliquot with a nucleic acid primer at least 8 nucleotides in length that is complementary to SNP rs11579814, (vi) the first aliquot with a first oligonucleotide probe at least 8 nucleotides in length that is complementary to a sequence that comprises a CpG dinucleotide at position 39491936 of chromosome 1 in the NADH Dehydrogenase (Ubiquinone) Fe—S Protein 5 (NDUFS5) gene, and the second aliquot with a nucleic acid primer at least 8 nucleotides in length that is complementary to SNP rs2275187, (vii) the first aliquot with a first oligonucleotide probe at least 8 nucleotides in length that is complementary to a sequence that comprises a CpG dinucleotide at position 186426136 mapping to chromosome 1 in the Phosducin gene, and the second aliquot with a nucleic acid primer at least 8 nucleotides in length that is complementary to SNP rs4336803, (viii) the first aliquot with a first oligonucleotide probe at least 8 nucleotides in length that is complementary to a sequence that comprises a CpG dinucleotide at position 205475130 of chromosome 1 in the Cyclin-Dependent Kinase 18 (CDK18) gene, and the second aliquot with a nucleic acid primer at least 8 nucleotides in length that is complementary to SNP rs4951158, and/or (ix) the first aliquot with a first oligonucleotide probe at least 8 nucleotides in length that is complementary to a sequence that comprises a CpG dinucleotide at position 130614013 of chromosome 3 in the ATPase, Ca++ Transporting, Type 2C, Member 1 (ATP2C1) gene, and the second aliquot with a nucleic acid primer at least 8 nucleotides in length that is complementary to rs925613, wherein methylation of the CpG dinucleotide at position 92203667 of chromosome 1 within the TGFBR3 gene, cg20636912, cg16947947, cg05916059, cg04567738, cg16603713, cg05709437, cg12081870, and/or cg18070470, and a G at position 91618766 of chromosome 1, or polymorphisms in rs4937276, rs17355663, rs235807, rs11579814, rs2275187, rs4336803, rs4951158, and/or rs925613 is associated with CVD.

In certain embodiments, the biological sample is a saliva sample.

In certain embodiments, the present disclosure provides a method for detecting one or more copies of a G allele at rs347027 and methylation status at cg13078798 on a nucleic acid sample from a subject at risk for Cardiovascular Disease (CVD), comprising a) performing a genotyping assay on a nucleic acid sample of said human subject to detect the presence of one or more copies of a G allele of the rs347027 polymorphism, and b) performing a methylation assessment at cg13078798 on a nucleic acid sample of said human to detect methylation status to determine if cg13078798 is unmethylated.

In certain embodiments, the present disclosure provides a method of predicting the presence of biomarkers associated with Cardiovascular Disease (CVD) in a biological sample from a patient, comprising detecting one or more pairs of SNPs and CpGs in Table 3 (e.g., SNP rs347027 in conjunction with CpG cg13078798; SNP rs4937276 in conjunction with CpG cg20636912; SNP rs17355663 in conjunction with CpG cg16947947; SNP rs235807 in conjunction with CpG cg05916059; SNP rs11579814 in conjunction with CpG cg04567738; SNP rs2275187 in conjunction with CpG cg16603713; SNP rs4336803 in conjunction with CpG cg05709437; SNP rs4951158 in conjunction with CpG cg12081870; and/or SNP rs925613 in conjunction with CpG cg18070470).

In certain embodiments, the CVD is Coronary Heart Disease (CHD), Congestive Heart Failure (CHF) and/or Stoke.

In certain embodiments the present disclosure provides a method of determining the presence of a biomarker associated with CHD in a patient sample, the method comprising: (a) isolating nucleic acid sample from the patient sample, (b) performing a genotyping assay on a first aliquot of the nucleic acid sample to detect the presence of at least one SNP, wherein the SNP is selected from a first SNP in FIG. 21 and/or is a second SNP in linkage disequilibrium (e.g., R>0.3) with a first SNP from FIG. 21 to obtain genotype data; and/or (c) bisulfite converting the nucleic acid in a second aliquot of the nucleic acid and performing methylation assessment on a second aliquot of the nucleic acid sample to detect methylation status of at least one gene from FIG. 15 or a first CpG site from FIG. 16 and/or a second CpG site collinear (e.g., R>0.3) with a first CpG from FIG. 16 to obtain methylation data regarding whether a specific CpG residue is unmethylated; and (d) inputting genotype from step (b) and/or methylation data from step (c) into an algorithm that accounts for the contribution of at least one SNP main effect and/or at least one CpG main effect and/or at least one interaction effect (e.g., SNPxSNP, CpGxCpG, SNPxCpG). In some embodiments, the algorithm is Random Forest™ or another algorithm capable of accounting for linear and non-linear effects.

In certain embodiments the present disclosure provides a method of determining the presence of a biomarker associated with stroke in a patient sample, the method comprising: (a) isolating nucleic acid sample from the patient sample, (b) performing a genotyping assay on a first aliquot of the nucleic acid sample to detect the presence of at least one SNP, wherein the SNP is selected from a first SNP in FIG. 22 and/or a second SNP in linkage disequilibrium (e.g., R>0.3) with a first SNP from FIG. 22 to obtain genotype data; and/or (c) bisulfite converting the nucleic acid in a second aliquot of the nucleic acid and performing methylation assessment on a second aliquot of the nucleic acid sample to detect methylation status of at least one gene from FIG. 17 or a first CpG site from FIG. 18 and/or a second CpG site collinear (e.g., R>0.3) with a first CpG from FIG. 18 to obtain methylation data regarding whether a specific CpG residue is unmethylated; and (d) inputting genotype from step (b) and/or methylation data from step (c) into an algorithm that accounts for the contribution of at least one SNP main effect and/or at least one CpG main effect and/or at least one interaction effect (e.g., SNPxSNP, CpGxCpG, SNPxCpG). In some embodiments, the algorithm is Random Forest™ or another algorithm capable of accounting for linear and non-linear effects.

In certain embodiments the present disclosure provides a method of determining the presence of a biomarker associated with CHF in a patient sample, the method comprising: (a) isolating nucleic acid sample from the patient sample, (b) performing a genotyping assay on a first aliquot of the nucleic acid sample to detect the presence of at least one SNP, wherein the SNP is selected from a first SNP in FIG. 23 and/or a second SNP in linkage disequilibrium (e.g., R>0.3) with a first SNP from FIG. 23 to obtain genotype data; and/or (c) bisulfite converting the nucleic acid in a second aliquot of the nucleic acid and performing methylation assessment on a second aliquot of the nucleic acid sample to detect methylation status of at least one gene from FIG. 19 or a first CpG site from FIG. 20 and/or a second CpG site collinear (e.g., R>0.3) with a first CpG from FIG. 20 to obtain methylation data regarding whether a specific CpG residue is unmethylated; and (d) inputting genotype from step (b) and/or methylation data from step (c) into an algorithm that accounts for the contribution of at least one SNP main effect and/or at least one CpG main effect and/or at least one interaction effect (e.g., SNPxSNP, CpGxCpG, SNPxCpG). In some embodiments, the algorithm is Random Forest™ or another algorithm capable of accounting for linear and non-linear effects.

In certain embodiments, the result comprises a gene-environment interaction effect (SNPxCpG) between the second CpG site collinear (e.g., R>0.3) with the first CpG from FIG. 16 and the first SNP from FIG. 21 or the second SNP in linkage disequilibrium (e.g., R>0.3) with a first SNP from FIG. 21. In certain embodiments, the result comprises at least one environment-environment interaction effect (CpGxCpG) between at least two CpG sites from FIG. 16 and/or at least two genes from FIG. 15. In certain embodiments, the result comprises a at least one environment-environment interaction effect (CpGxCpG) between at least two CpG sites collinear with the first CpG site from FIG. 16. In certain embodiments, the result comprises a gene-environment interaction effect (SNPxCpG) between a CpG site collinear (e.g., R>0.3) with the first CpG from FIG. 18 and the first SNP from FIG. 22 or the second SNP in linkage disequilibrium (e.g., R>0.3) with the first SNP from FIG. 22. In certain embodiments, the result comprises at least one environment-environment interaction effect (CpGxCpG) between at least two CpG sites from FIG. 18 and/or genes from FIG. 17. In certain embodiments, the result comprises at least one environment-environment interaction effect (CpGxCpG) between at least two CpG sites collinear with the first CpG site from FIG. 18. In certain embodiments, the result comprises a gene-environment interaction effect (SNPxCpG) between the second CpG site collinear (e.g., R>0.3) with the first CpG from FIG. 20 and the first SNP from FIG. 23 or the second SNP in linkage disequilibrium (e.g., R>0.3) from the first SNP from FIG. 23. In certain embodiments, the result comprises at least one environment-environment interaction effect (CpGxCpG) between at least two CpG sites from FIG. 20 and/or genes from FIG. 19. In certain embodiments, the result comprises at least one environment-environment interaction effect (CpGxCpG) between at least two CpG sites collinear with the first CpG site from FIG. 20.

In certain embodiments of the present disclosure, the blood cell is a lymphocyte, such as a monocyte, a basophil, an eosinophil, and/or a neutrophil. In certain embodiments the lymphocyte type is a B-lymphocyte. In certain embodiments, the B-lymphocytes have been immortalized. In certain embodiments, the blood cell type is a mixture of peripheral white blood cells. In certain embodiments, the peripheral blood cell has been transformed into a cell line.

In certain embodiments, the analytical process comprises comparing the obtained profile with a reference profile. In certain embodiments, the reference profile comprises data obtained from one or more healthy control subjects, or comprises data obtained from one or more subjects diagnosed with a substance use disorder. In certain embodiments, the method further comprises obtaining a statistical measure of a similarity of the obtained profile to the reference profile. In certain embodiments, the blood cell or blood cell derivative is a peripheral blood cell. In certain embodiments, the profile is obtained by sequencing of methylated DNA, such as by digital sequencing.

In certain embodiments, the current disclosure can also take the form of a PCR (polymerize chain reaction) assay. In some cases, this will take the form of real time PCR assays (RTPCR) or digital PCR assays. In certain embodiments of these PCR assays, a kit may contain two primers that specifically amplify a region of a target gene and a gene-specific probe that selectively recognizes the amplified region. Together, the primers and the gene specific probes are referred to as a primer-probe set. By measuring the amount of gene specific probe that has hybridized to an amplified segment at a given point of the PCR reaction or throughout the PCR reaction, one who is skilled in the art can infer the amount of nucleic acid originally present at the start of the reaction. In some cases, the amount of probe hybridized is measured through fluorescence spectrophotometry. The number of primer-probe sets can be any integer between 1 and 10,000 probes, such as 1, 2, 3, 4, 5, 6, 7, 8, 9, 10, . . . 9997, 9998, 9999, 10,000. In one kit, all of the probes may be physically located in a single reaction well or in multiple reaction wells. The probes may be in dry or in liquid form. They may be used in a single reaction or in a series of reactions. In certain embodiments, the probe is an oligonucleotide probe. In certain embodiments, the probe is a nucleic acid derivative probe.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

BRIEF DESCRIPTION OF DRAWINGS

FIG. 15. List of genes whose methylation is associated with CHD.

FIG. 16. List of CpGs whose methylation is associated with CHD.

FIG. 17. List of genes whose methylation is associated with stroke.

FIG. 18. List of CpGs whose methylation is associated with stroke.

FIG. 19. List of genes whose methylation is associated with CHF.

FIG. 20. List of CpGs whose methylation is associated with CHF.

FIG. 21. List of SNPs associated with CHD.

FIG. 22. List of SNPs associated with stroke.

FIG. 23. List of SNPs associated with CHF.

DETAILED DESCRIPTION OF THE INVENTION

Figure 1A:
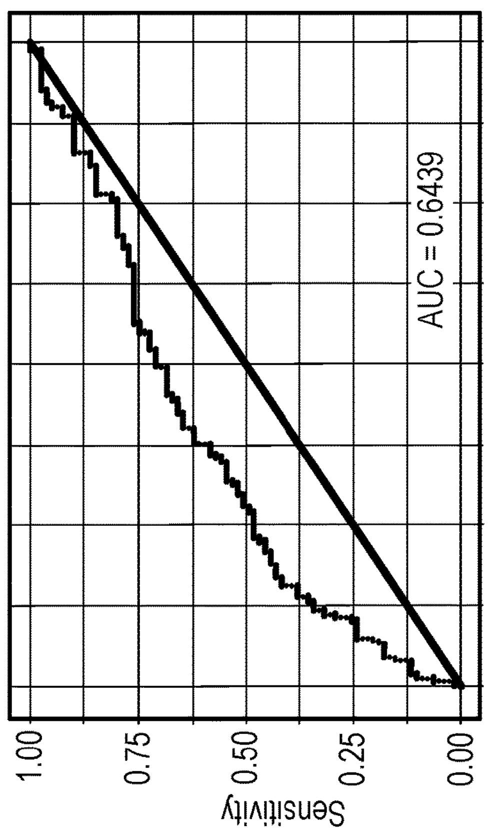
FIGS. 1A-ID. Area under the receiver operating characteristic curve for cg05575921 (A), age+gender+batch+cg05575921 (B), self-reported smoking status (C) and age+gender+batch+self-reported smoking status (D).
Figure 1B:
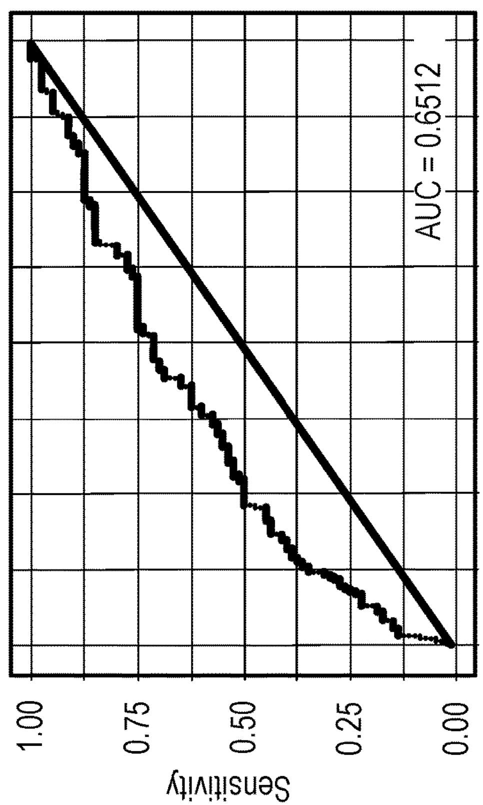
Figure 1C:
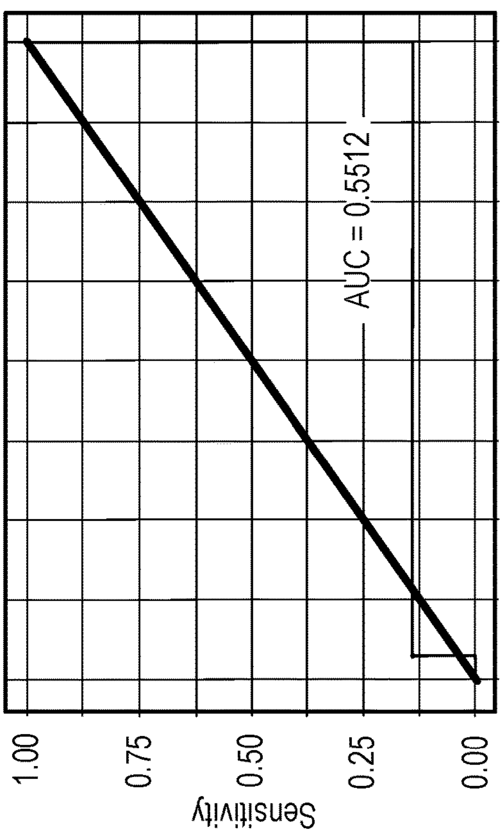
Figure 1D:
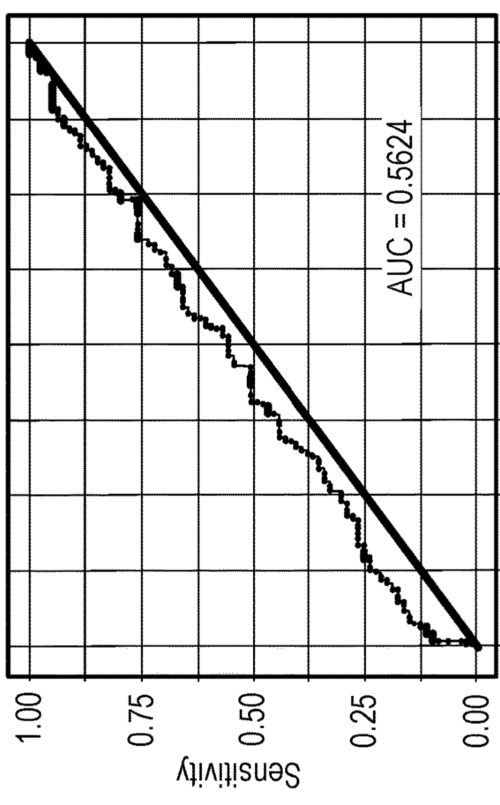

The present disclosure provides methods and kits for determining whether a subject has a predisposition to, or likelihood of having or developing cardiovascular disease (CVD). As shown herein, the methylation status of one or more CpG dinucleotides, alone, or in combination with the genotype and/or the interaction between the genotype and the methylation status (e.g., CH3xSNP), is associated with CVD. As used herein, the term "predisposition" is defined as a tendency or susceptibility for a subject to manifest a condition. For example, a subject is more likely to manifest a condition than is a control subject.

DNA Methylation

DNA does not exist as naked molecules in the cell. For example, DNA is associated with proteins called histones to form a complex substance known as chromatin. Chemical modifications of the DNA or the histones alter the structure of the chromatin without changing the nucleotide sequence of the DNA. Such modifications are described as "epigenetic" modifications of the DNA. Changes to the structure of the chromatin can have a profound influence on gene expression. If the chromatin is condensed, factors involved in gene expression may not have access to the DNA, and the genes will be switched off. Conversely, if the chromatin is "open," the genes can be switched on. Some important forms of epigenetic modification are DNA methylation and histone deacetylation. DNA methylation is a chemical modification of the DNA molecule itself and is carried out by an enzyme called DNA methyltransferase. Methylation can directly switch off gene expression by preventing transcription factors binding to promoters. A more general effect is the attraction of methyl-binding domain (MBD) proteins. These are associated with further enzymes called histone deacetylases (HDACs), which function to chemically modify histones and change chromatin structure. Chromatin-containing acetylated histones are open and accessible to transcription factors, and the genes are potentially active. Histone deacetylation causes the condensation of chromatin, making it inaccessible to transcription factors and causing the silencing of genes.

CpG islands are short stretches of DNA in which the frequency of the CpG sequence is higher than other regions. The "p" in the term CpG indicates that cysteine ("C") and guanine ("G") are connected by a phosphodiester bond. CpG islands are often located around promoters of housekeeping genes and many regulated genes. At these locations, the CG sequence is not methylated. By contrast, the CG sequences in inactive genes are usually methylated to suppress their expression.

As used herein, the term "methylation status" means the determination whether a certain target DNA, such as a CpG dinucleotide, is methylated. As used herein the term "CpG dinucleotide repeat motif" means a series of two or more CpG dinucleotides positioned in a DNA sequence.

About 56% of human genes and 47% of mouse genes are associated with CpG islands. Often, CpG islands overlap the promoter and extend about 1000 base pairs downstream into the transcription unit. Identification of potential CpG islands during sequence analysis helps to define the extreme 5' ends of genes, something that is notoriously difficult with cDNA-based approaches. The methylation of a CpG island can be determined by a skilled artisan using any method suitable to determine such methylation. For example, the skilled artisan can use a bisulfite reaction-based method for determining such methylation.

The present disclosure provides methods to determine the nucleic acid methylation of TGFBR3 of a patient in order to predict the clinical course and eventual outcome of patients suspected of being predisposed or of having a CHD.

In particular, in certain embodiments of the disclosure, the methods may be practiced as follows. A sample, such as a blood sample, is taken from a patient. In certain embodiments, a single cell type, e.g., lymphocytes, basophils, or monocytes isolated from the blood, may be isolated for further testing. The DNA is harvested from the sample and examined to determine if the TGFBR3 region is methylated. For example, the DNA of interest can be treated with bisulfite to deaminate unmethylated cytosine residues to uracil. Since uracil base pairs with adenosine, thymidines are incorporated into subsequent DNA strands in the place of unmethylated cytosine residues during subsequence PCR amplifications. Next, the target sequence is amplified by PCR, and probed with a TGFBR3-specific probe. Only DNA from the patient that was methylated will bind to the probe. A specific profile associates with a specific condition.

Methods of determining the patient nucleic acid profile are well known to the art worker and include any of the well-known detection methods. Various PCR methods are described, for example, in *PCR Primer: A Laboratory Manual*, Dieffenbach 7 Dveksler, Eds., Cold Spring Harbor Laboratory Press, 1995. Other analysis methods include, but are not limited to, nucleic acid quantification, restriction enzyme digestion, DNA sequencing, hybridization technologies, such as Southern Blotting, etc., amplification methods such as Ligase Chain Reaction (LCR), Nucleic Acid Sequence Based Amplification (NASBA), Self-sustained Sequence Replication (SSR or 3SR), Strand Displacement Amplification (SDA), and Transcription Mediated Amplification (TMA), Quantitative PCR (qPCR), or other DNA analyses, as well as RT-PCR, in vitro translation, Northern blotting, and other RNA analyses. In another embodiment, hybridization on a microarray is used.

Single Nucleotide Polymorphism (SNP) Genotyping

Traditional methods for the screening of heritable diseases have depended on either the identification of abnormal gene products (e.g., sickle cell anemia) or an abnormal phenotype (e.g., mental retardation). With the development of simple and inexpensive genetic screening methodology, it is now possible to identify polymorphisms that indicate a propensity to develop disease, even when the disease is of polygenic origin.

Single nucleotide polymorphism (SNP) genotyping measures genetic variations of SNPs between members of a species. A SNP is a single base pair mutation at a specific locus, usually consisting of two alleles (where the rare allele frequency is >1%), and is very common. Because SNPs are conserved during evolution, they have been proposed as markers for use in quantitative trait loci (QTL) analysis and in association studies in place of microsatellites. Many different SNP genotyping methods are known, including hybridization-based methods (such as Dynamic allele-specific hybridization, molecular beacons, and SNP microarrays) enzyme-based methods (including restriction fragment length polymorphism, PCR-based methods, flap endonuclease, primer extension, 5'-nuclease, and oligonucleotide ligation assay), other post-amplification methods based on physical properties of DNA (such as single strand conformation polymorphism, temperature gradient gel electrophoresis, denaturing high performance liquid chromatography, high-resolution melting of the entire amplicon, use of DNA mismatch-binding proteins, SNPlex and surveyor nuclease assay), and sequencing (such as "next generation" sequencing). See, e.g., U.S. Pat. No. 7,972,779.

A plurality of alleles having distinct organ-functionality (e.g., high and low levels of expression in the heart, or, e.g., high, moderate and low levels of expression in the heart) can arise from one or more polymorphisms in a region of a gene that encodes a polypeptide or can be in a regulatory control sequence that affects expression of the polypeptide, such as a promoter or polyadenylation sequence. Alternatively, relevant alleles can arise from one or more polymorphism at a locus distal to a gene having a direct effect in the identified behavior, wherein the product of that distal locus has an indirect effect on the behavior. A relevant allele can affect a polypeptide at a transcriptional or a translational level and can affect a polypeptide's transcription rate, translation rate, degradation rate, or activity. Differences between alleles at a brain-functional gene can be characterized in a sample from a subject or from a plurality of subjects by methods for assaying any of the foregoing that are well-known to the skilled artisan. Such methods can include, but are not limited to measuring an amount of an encoded polypeptide and measuring the potential for a polynucleotide sequence to be expressed. Assay methods can detect proteins or nucleic acids directly or indirectly. One can evaluate the suitability of an upstream promoter region for directing transcription of a coding region of the polynucleotide that encodes a polypeptide or can evaluate the suitability of the coding region for encoding a functional polypeptide. The assay methods are specifically contemplated to include screening for the presence of particular sequences or structures of nucleic acids or polypeptides using, e.g., any of various known microarray technologies.

It will be fully appreciated by the skilled artisan that the allele need not have previously been shown to have had any link or association with the disorder phenotype. Instead, an allele and a pathogenic environmental risk factor can interact to predict a predisposition to a disorder phenotype even when neither the allele nor the risk factor bears any direct relation to the disorder phenotype.

Genetic screening (also called genotyping or molecular screening), can be broadly defined as testing to determine if a patient has mutations (or alleles or polymorphisms) that either cause a disease state or are "linked" to the mutation causing a disease state. Linkage refers to the phenomenon that DNA sequences which are close together in the genome have a tendency to be inherited together. Two sequences may be linked because of some selective advantage of co-inheritance. More typically, however, two polymorphic sequences are co-inherited because of the relative infrequency with which meiotic recombination events occur within the region between the two polymorphisms. The co-inherited polymorphic alleles are said to be in "linkage disequilibrium" with one another because, in a given population, they tend to either both occur together or else not occur at all in any particular member of the population. Indeed, where multiple polymorphisms in a given chromosomal region are found to be in linkage disequilibrium with one another, they define a quasi-stable genetic "haplotype." In contrast, recombination events occurring between two polymorphic loci cause them to become separated onto distinct homologous chromosomes. If meiotic recombination between two physically linked polymorphisms occurs frequently enough, the two polymorphisms will appear to segregate independently and are said to be in linkage equilibrium.

It would be understood that linkage equilibrium/disequilibrium can be quantitated (using, for example, the Pearson correlation (R) or co-inheritance of alleles (D')). For example, a low level of linkage can be reflected in a correlation (e.g., R value) of about 0.1 or less, a moderate level of linkage is reflected in a R value of about 0.3, while a high level of linkage is reflected in a R value of 0.5 or greater. It also would be understood that, when referring to methylation (i.e. CpGs), collinearity (with an R value) is used as a determination of the linear strength of the association between two CpGs (e.g., a low level of collinearity can be reflected by an R value of about 0.1 or less; a moderate level of collinearity can be reflected by an R value of about 0.3; and a high level of collinearity can be reflected by an R value of about 0.5 or greater).

While the frequency of meiotic recombination between two markers is generally proportional to the physical distance between them on the chromosome, the occurrence of "hot spots" as well as regions of repressed chromosomal recombination can result in discrepancies between the physical and recombinational distance between two markers. Thus, in certain chromosomal regions, multiple polymorphic loci spanning a broad chromosomal domain may be in linkage disequilibrium with one another, and thereby define a broad-spanning genetic haplotype. Furthermore, where a disease-causing mutation is found within or in linkage with this haplotype, one or more polymorphic alleles of the haplotype can be used as a diagnostic or prognostic indicator of the likelihood of developing the disease. This association between otherwise benign polymorphisms and a disease-causing polymorphism occurs if the disease mutation arose in the recent past, so that sufficient time has not elapsed for equilibrium to be achieved through recombination events. Therefore, identification of a haplotype that spans or is linked to a disease-causing mutational change serves as a predictive measure of an individual's likelihood of having inherited that disease-causing mutation. Such prognostic or diagnostic procedures can be utilized without necessitating the identification and isolation of the actual disease-causing lesion. This is significant because the precise determination of the molecular defect involved in a disease process can be difficult and laborious, especially in the case of multifactorial diseases.

The statistical correlation between a disorder and a polymorphism does not necessarily indicate that the polymorphism directly causes the disorder. Rather the correlated polymorphism may be a benign allelic variant which is linked to (i.e., in linkage disequilibrium with) a disorder-causing mutation that has occurred in the recent evolutionary past, so that sufficient time has not elapsed for equilibrium to be achieved through recombination events in the intervening chromosomal segment. Thus, for the purposes of diagnostic and prognostic assays for a particular disease, detection of a polymorphic allele associated with that disease can be utilized without consideration of whether the polymorphism is directly involved in the etiology of the disease. Furthermore, where a given benign polymorphic locus is in linkage disequilibrium with an apparent disease-causing polymorphic locus, still other polymorphic loci which are in linkage disequilibrium with the benign polymorphic locus are also likely to be in linkage disequilibrium with the disease-causing polymorphic locus. Thus these other polymorphic loci will also be prognostic or diagnostic of the likelihood of having inherited the disease-causing polymorphic locus. A broad-spanning haplotype (describing the typical pattern of co-inheritance of alleles of a set of linked polymorphic markers) can be targeted for diagnostic purposes once an association has been drawn between a particular disease or condition and a corresponding haplotype. Thus, the determination of an individual's likelihood for developing a particular disease of condition can be made by characterizing one or more disease-associated polymorphic alleles (or even one or more disease-associated haplotypes) without necessarily determining or characterizing the causative genetic variation.

Many methods are available for detecting specific alleles at polymorphic loci. Certain methods for detecting a specific polymorphic allele will depend, in part, upon the molecular nature of the polymorphism. For example, the various allelic forms of the polymorphic locus may differ by a single base-pair of the DNA. Such single nucleotide polymorphisms (or SNPs) are major contributors to genetic variation, comprising some 80% of all known polymorphisms, and their density in the genome is estimated to be on average 1 per 1,000 base pairs. SNPs are most frequently bi-allelic, or occurring in only two different forms (although up to four different forms of an SNP, corresponding to the four different nucleotide bases occurring in DNA, are theoretically possible). Nevertheless, SNPs are mutationally more stable than other polymorphisms, making them suitable for association studies in which linkage disequilibrium between markers and an unknown variant is used to map disease-causing mutations. In addition, because SNPs typically have only two alleles, they can be genotyped by a simple plus/minus assay rather than a length measurement, making them more amenable to automation.

In one embodiment, allelic profiling can be accomplished using a nucleic acid microarray, which can also be commercialized alone or in combination with one or more kit components. The genetic testing field is rapidly evolving and, as such, the skilled artisan will appreciate that a wide range of profiling tests exist, and will be developed, to determine the allelic profile of individuals in accord with the disclosure.

Nucleic Acids and Polypeptides

The term "nucleic acid" refers to deoxyribonucleotides or ribonucleotides and polymers thereof in either single- or double-stranded form, made of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. The terms "nucleic acid," "nucleic acid molecule," or "polynucleotide" are used interchangeably and may also be used interchangeably with gene, cDNA, DNA and/or RNA encoded by a gene.

The term "nucleotide sequence" refers to a polymer of DNA or RNA which can be single-stranded or double-stranded, optionally containing synthetic, non-natural or altered nucleotide bases capable of incorporation into DNA or RNA polymers. A DNA molecule or polynucleotide is a polymer of deoxyribonucleotides (A, G, C, and T), and an RNA molecule or polynucleotide is a polymer of ribonucleotides (A, G, C and U).

A "gene," for the purposes of the present disclosure, includes a DNA region encoding a gene product, as well as all DNA regions which regulate the production of the gene product, whether or not such regulatory sequences are adjacent to coding and/or transcribed sequences. The term "gene" is used broadly to refer to any segment of nucleic acid associated with a biological function. Genes include coding sequences and/or the regulatory sequences required for their expression. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. For example, "gene" refers to a nucleic acid fragment that expresses mRNA, functional RNA, or specific protein, including regulatory sequences. "Functional RNA" refers to sense RNA, antisense RNA, ribozyme RNA, siRNA, or other RNA that may not be translated but yet has an effect on at least one cellular process. "Genes" also include non-expressed DNA segments that, for example, form recognition sequences for other proteins. "Genes" can be obtained from a variety of sources, including cloning from a source of interest or synthesizing from known or predicted sequence information, and may include sequences designed to have desired parameters.

"Gene expression" refers to the conversion of the information, contained in a gene, into a gene product. It refers to the transcription and/or translation of an endogenous gene, heterologous gene or nucleic acid segment, or a transgene in cells. In addition, expression refers to the transcription and stable accumulation of sense (mRNA) or functional RNA. Expression may also refer to the production of protein. The term "altered level of expression" refers to the level of expression in transgenic cells or organisms that differs from that of normal or untransformed cells or organisms.

A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs, which are modified, by processes such as capping, polyadenylation, methylation, and editing, and proteins modified by, for example, methylation, acetylation, phosphorylation, ubiquitination, ADP-ribosylation, myristilation, and glycosylation. The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA. "Functional RNA" refers to sense RNA, antisense RNA, ribozyme RNA, siRNA, or other RNA that may not be translated but yet has an effect on at least one cellular process.

A "coding sequence," or a sequence that "encodes" a selected polypeptide, is a nucleic acid molecule that is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral (e.g., DNA viruses and retroviruses) or prokaryotic DNA, and especially synthetic DNA sequences. A transcription termination sequence may be located 3' to the coding sequence.

Certain embodiments of the disclosure encompass isolated or substantially purified nucleic acid compositions. In the context of the present disclosure, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

By "fragment" is intended a polypeptide consisting of only a part of the intact full-length polypeptide sequence and structure. The fragment can include a C-terminal deletion an N-terminal deletion, and/or an internal deletion of the native polypeptide. A fragment of a protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, or any integer between 5 amino acids and the full-length sequence.

Certain embodiments of the disclosure encompass isolated or substantially purified nucleic acid compositions. In the context of the present disclosure, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule is substantially free of other cellular material or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

"Naturally occurring" is used to describe a composition that can be found in nature as distinct from being artificially produced. For example, a nucleotide sequence present in an organism, which can be isolated from a source in nature and which has not been intentionally modified by a person in the laboratory, is naturally occurring.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences.

A "5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency. A "3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor. The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

A "promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. "Constitutive expression" refers to expression using a constitutive promoter. "Conditional" and "regulated expression" refer to expression controlled by a regulated promoter.

"Operably-linked" refers to the association of nucleic acid sequences on a single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. In addition, expression refers to the transcription and stable accumulation of sense (mRNA) or functional RNA. Expression may also refer to the production of protein. The term "altered level of expression" refers to the level of expression in cells or organisms that differs from that of normal cells or organisms.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

The following terms are used to describe the sequence relationships between two or more nucleic acids or polynucleotides: (a) "reference sequence," (b) "comparison window," (c) "sequence identity," (d) "percentage of sequence identity," and (e) "substantial identity." As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence. As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm. Non-limiting examples of such mathematical algorithms are the algorithm of Myers and Miller (Myers and Miller, CABIOS, 4, 11 (1988)); the local homology algorithm of Smith et al. (Smith et al., Adv. Appl. Math., 2, 482 (1981)); the homology alignment algorithm of Needleman and Wunsch (Needleman and Wunsch, JMB, 48, 443 (1970)); the search-for-similarity-method of Pearson and Lipman (Pearson and Lipman, Proc. Natl. Acad. Sci. USA, 85, 2444 (1988)); the algorithm of Karlin and Altschul (Karlin and Altschul, Proc. Natl. Acad. Sci. USA, 87, 2264 (1990)), modified as in Karlin and Altschul (Karlin and Altschul, Proc. Natl. Acad. Sci. USA 90, 5873 (1993)).

Computer implementations of these mathematical algorithms can be utilized for comparison of sequences to determine sequence identity. Such implementations include, but are not limited to: CLUSTAL® in the PC/Gene program (available from Intelligenetics, Mountain View, Calif.); the ALIGN® program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL® program is well described by Higgins et al. (Higgins et al., CABIOS, 5, 151 (1989)); Corpet et al. (Corpet et al., Nucl. Acids Res., 16, 10881 (1988)); Huang et al. (Huang et al., CABIOS, 8, 155 (1992)); and Pearson et al. (Pearson et al., Meth. Mol. Biol., 24, 307 (1994)). The ALIGN® program is based on the algorithm of Myers and Miller, supra. The BLAST® programs of Altschul et al. (Altschul et al., JMB, 215, 403 (1990)) are based on the algorithm of Karlin and Altschul supra.

Software for performing BLAST® analyses is publicly available through the National Center for Biotechnology Information. This algorithm involves first identifying high scoring sequence pairs (HSPs) by identifying short words of length "W" in the query sequence, which either match or satisfy some positive-valued threshold score T when aligned with a word of the same length in a database sequence. "T" is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters "M" (reward score for a pair of matching residues; always >0) and "N" (penalty score for mismatching residues; always <0). For amino acid sequences, a scoring matrix is used to calculate the cumulative score. Extension of the word hits in each direction are halted when the cumulative alignment score falls off by the quantity "X" from its maximum achieved value, the cumulative score goes to zero or below due to the accumulation of one or more negative-scoring residue alignments, or the end of either sequence is reached.

In addition to calculating percent sequence identity, the BLAST® algorithm also performs a statistical analysis of the similarity between two sequences. One measure of similarity provided by the BLAST® algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST® (in BLAST® 2.0) can be utilized. Alternatively, PSI-BLAST® (in BLAST® 2.0) can be used to perform an iterated search that detects distant relationships between molecules. When utilizing BLAST®, Gapped BLAST®, PSI-BLAST®, the default parameters of the respective programs (e.g., BLASTN® for nucleotide sequences, BLASTX® for proteins) can be used. The BLASTN® program (for nucleotide sequences) uses as defaults a wordlength (W) of 11, an expectation (E) of 10, a cutoff of 100, M=5, N=−4, and a comparison of both strands. For amino acid sequences, the BLASTP® program uses as defaults a wordlength (W) of 3, an expectation (E) of 10, and the BLOSUM62 scoring matrix. Alignment may also be performed manually by inspection.

For purposes of the present disclosure, comparison of nucleotide sequences for determination of percent sequence identity to the promoter sequences disclosed herein may be made using the BLASTN® program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the program.

As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics™, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70%, 71%, 72%, 73%, 74%, 75%, 76%, 77%, 78%, 79%, 80%, 81%, 82%, 83%, 84%, 85%, 86%, 87%, 88%, 89%0, 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, 80%, 90%, or even at least 95%.

The term "substantial identity" in the context of a peptide indicates that a peptide comprises a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even 95%, 96%, 97%, 98% or 99%, sequence identity to the reference sequence over a specified comparison window. In certain embodiments, optimal alignment is conducted using the homology alignment algorithm of Needleman and Wunsch (Needleman and Wunsch, JMB, 48, 443 (1970)). An indication that two peptide sequences are substantially identical is that one peptide is immunologically reactive with antibodies raised against the second peptide. Thus, a peptide is substantially identical to a second peptide, for example, where the two peptides differ only by a conservative substitution. Thus, the disclosure also provides nucleic acid molecules and peptides that are substantially identical to the nucleic acid molecules and peptides presented herein.

Another indication that nucleotide sequences are substantially identical is if two molecules hybridize to each other under stringent conditions. Hybridization of nucleic acids is discussed in more detail below.

Oligonucleotide Probes

As used herein, "primer," "probe," and "oligonucleotide" are used interchangeably. The term "nucleic acid probe" or a "probe specific for" a nucleic acid refers to a nucleic acid sequence that has at least about 80%, e.g., at least about 90%, e.g., at least about 95% contiguous sequence identity or homology to the nucleic acid sequence encoding the targeted sequence of interest. A probe (or oligonucleotide or primer) of the disclosure is at least about 8 nucleotides in length (e.g., at least about 8-50 nucleotides in length, e.g., at least about 10-40, e.g., at least about 15-35 nucleotides in length). The oligonucleotide probes or primers of the disclosure may comprise at least about eight nucleotides at the 3' of the oligonucleotide that have at least about 80%, e.g., at least about 85%, e.g., at least about 90% contiguous identity to the targeted sequence of interest.

Primer pairs are useful for determination of the nucleotide sequence of a particular SNP using PCR. The pairs of single-stranded DNA primers can be annealed to sequences within or surrounding the SNP in order to prime amplifying DNA synthesis of the SNP itself.

The first step of the process involves contacting a physiological sample obtained from a patient, which sample contains nucleic acid, with an oligonucleotide probe to form a hybridized DNA. The oligonucleotide probes that are useful in the methods of the present disclosure can be any probe comprised of between about 4 or 6 bases up to about 80 or 100 bases or more. In one embodiment of the present disclosure, the probes are between about 10 and about 20 bases.

The primers themselves can be synthesized using techniques that are well known in the art. Generally, the primers can be made using oligonucleotide synthesizing machines that are commercially available.

The primers or probes of the present disclosure can be labeled using techniques known to those of skill in the art. For example, the labels used in the assays of disclosure can be primary labels (where the label comprises an element that is detected directly) or secondary labels (where the detected label binds to a primary label, e.g., as is common in immunological labeling). An introduction to labels (also called "tags"), tagging or labeling procedures, and detection of labels is found in Polak and Van Noorden (1997) Introduction to Immunocytochemistry, second edition, Springer Verlag, N.Y. and in Haugland (1996) Handbook of Fluorescent Probes and Research Chemicals, a combined handbook and catalogue Published by Molecular Probes, Inc®, Eugene, Oreg. Primary and secondary labels can include undetected elements as well as detected elements. Useful primary and secondary labels in the present disclosure can include spectral labels such as fluorescent dyes (e.g., fluorescein and derivatives such as fluorescein isothiocyanate (FITC) and Oregon Green™, rhodamine and derivatives (e.g., Texas Red®, tetramethylrhodamine isothiocyanate (TRITC), etc.), digoxigenin, biotin, phycoerythrin, AMCA, CyDyes™, and the like), radiolabels (e.g., $^{3}H$, $^{125}I$, $^{35}S$, $^{14}C$, $^{32}P$, $^{33}P$), enzymes (e.g., horse-radish peroxidase, alkaline phosphatase) spectral colorimetric labels such as colloidal gold or colored glass or plastic (e.g., polystyrene, polypropylene, latex) beads. The label may be coupled directly or indirectly to a component of the detection assay (e.g., the labeled nucleic acid) according to methods well known in the art. As indicated above, a wide variety of labels may be used, with the choice of label depending on sensitivity required, ease of conjugation with the compound, stability requirements, available instrumentation, and disposal provisions.

In general, a detector that monitors a probe-substrate nucleic acid hybridization is adapted to the particular label that is used. Typical detectors include spectrophotometers, phototubes and photodiodes, microscopes, scintillation counters, cameras, film and the like, as well as combinations thereof. Examples of suitable detectors are widely available from a variety of commercial sources known to persons of skill. Commonly, an optical image of a substrate comprising bound labeled nucleic acids is digitized for subsequent computer analysis.

Preferred labels include those that use (1) chemiluminescence (using Horseradish Peroxidase and/or Alkaline Phosphatase with substrates that produce photons as breakdown products) with kits being available, e.g., from Molecular Probes®, Amersham®, Boehringer-Mannheim®, and Life Technologies/Gibco BRL®; (2) color production (using both Horseradish Peroxidase and/or Alkaline Phosphatase with substrates that produce a colored precipitate) (kits available from Life Technologies/Gibco BRL®, and Boehringer-Mannheim®); (3) hemifluorescence using, e.g., Alkaline Phosphatase and the substrate AttoPhos (Amersham) or other substrates that produce fluorescent products, (4) fluorescence (e.g., using Cy-5™ (Amersham®), fluorescein, and other fluorescent labels); (5) radioactivity using kinase enzymes or other end-labeling approaches, nick translation, random priming, or PCR to incorporate radioactive molecules into the labeled nucleic acid. Other methods for labeling and detection will be readily apparent to one skilled in the art.

Fluorescent labels can be used and have the advantage of requiring fewer precautions in handling, and being amendable to high-throughput visualization techniques (optical analysis including digitization of the image for analysis in an integrated system comprising a computer). Preferred labels are typically characterized by one or more of the following: high sensitivity, high stability, low background, low environmental sensitivity and high specificity in labeling. Fluorescent moieties, which are incorporated into the labels of the disclosure, are generally are known, including Texas red, dixogenin, biotin, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes, flavin and many others. Many fluorescent labels are commercially available from the SIGMA® Chemical Company (Saint Louis, Mo.), Molecular Probes®, R&D Systems® (Minneapolis, Minn.), Pharmacia LKB Biotechnology® (Piscataway, N.J.), CLONTECH® Laboratories, Inc. (Palo Alto, Calif.), Chem Genes Corp., Aldrich® Chemical Company (Milwaukee, Wis.), Glen Research, Inc., GIBCO® BRL® Life Technologies, Inc.® (Gaithersberg, Md.), Fluka ChemicaBiochemika Analytika (Fluka Chemie AG, Buchs, Switzerland), and Applied Biosystems™ (Foster City, Calif.), as well as many other commercial sources known to one of skill.

Means of detecting and quantifying labels are well known to those of skill in the art. Thus, for example, where the label is a radioactive label, means for detection include a scintillation counter or photographic film as in autoradiography. Where the label is optically detectable, typical detectors include microscopes, cameras, phototubes and photodiodes and many other detection systems that are widely available.

Oligonucleotide probes may be prepared having any of a wide variety of base sequences according to techniques that are well known in the art. Suitable bases for preparing the oligonucleotide probe may be selected from naturally occurring nucleotide bases such as adenine, cytosine, guanine, uracil, and thymine; and non-naturally occurring or "synthetic" nucleotide bases such as 7-deaza-guanine 8-oxo-guanine, 6-mercaptoguanine, 4-acetylcytidine, 5-(carboxyhydroxyethyl)uridine, 2'-O-methylcytidine, 5-carboxymethylamino-methyl-2-thioridine, 5-carboxymethylaminomethyluridine, dihydrouridine, 2'-O-methylpseudouridine, β,D-galactosylqueosine, 2'-O-methylguanosine, inosine, N6-isopentenyladenosine, 1-methyladenosine, 1-methylpseeudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylamninomethyluridine, 5-methoxyaminomethyl-2-thiouridine, β,D-mannosylqueosine, 5-methloxycarbonylmethyluridine, 5-methoxyuridine, 2-methyltio-N6-isopentenyladenosine, N-((9-β-D-ribofuranosyl-2-methylthiopurine-6-yl)carbamoyl)threonine, N-((9-β-D-ribofuranosylpurine-6-yl)N-methyl-carbamoyl)threonine, uridine-5-oxyacetic acid methylester, uridine-5-oxy acetic acid, wybutoxosine, pseudouridine, queosine, 2-thiocytidine, 5-methyl-2-thiouridine, 2-thiouridine, 2-thiouridine, 5-Methylurdine, N-((9-beta-D-ribofuranosylpurine-6-yl)carbamoyl)threonine, 2'-O-methyl-5-methyluridine, 2'-O-methylurdine, wybutosine, and 3-(3-amino-3-carboxypropyl)uridine. Any oligonucleotide backbone may be employed, including DNA, RNA (although RNA is less preferred than DNA), modified sugars such as carbocycles, and sugars containing 2' substitutions such as fluoro and methoxy. The oligonucleotides may be oligonucleotides wherein at least one, or all, of the internucleotide bridging phosphate residues are modified phosphates, such as methyl phosphonates, methyl phosphonotlioates, phosphoroinorpholidates, phosphoropiperazidates and phosplioramidates (for example, every other one of the internucleotide bridging phosphate residues may be modified as described). The oligonucleotide may be a "peptide nucleic acid" such as described in Nielsen et al., Science, 254:1497-1500 (1991).

As used herein, a "single base pair extension probe" is a nucleic acid that selectively recognizes a single nucleotide polymorphism (i.e., either the A or the G of an A/G polymorphism). Generally, these probes take the form of a DNA primer (e.g., as in PCR primers) that are modified so that incorporation of the primer releases a fluorophore. One example of this is a Taqman® probe that uses the 5' exonuclease activity of the enzyme Taq Polymerase for measuring the amount of target sequences in the samples. TaqMan® probes consist of a 18-22 bp oligonucleotide probe, which is labeled with a reporter fluorophore at the 5' end, and a quencher fluorophore at the 3' end. Incorporation of the probe molecule into a PCR chain (which occurs because the probe set is contained in a mixture of PCR primers) liberates the reporter fluorophore from the effects of the quencher. The primer must be able to recognize the target binding site. Some primer extension probes can be "activated" directly by DNA polymerase without a full PCR extension cycle.

The only requirement is that the oligonucleotide probe should possess a sequence at least a portion of which is capable of binding to a known portion of the sequence of the DNA sample. The nucleic acid probes provided by the present disclosure are useful for a number of purposes.

Methods of Detecting Nucleic Acids

A. Amplification

According to the methods of the present disclosure, the amplification of DNA present in a physiological sample may be carried out by any means known to the art. Examples of suitable amplification techniques include, but are not limited to, polymerase chain reaction (including, for RNA amplification, reverse-transcriptase polymerase chain reaction), ligase chain reaction, strand displacement amplification, transcription-based amplification, self-sustained sequence replication (or "3SR"), the Qbeta replicase system, nucleic acid sequence-based amplification (or "NASBA"), the repair chain reaction (or "RCR"), and boomerang DNA amplification (or "BDA").

The bases incorporated into the amplification product may be natural or modified bases (modified before or after amplification), and the bases may be selected to optimize subsequent electrochemical detection steps.

Polymerase chain reaction (PCR) may be carried out in accordance with known techniques. See, e.g., U.S. Pat. Nos. 4,683,195; 4,683,202; 4,800,159; and 4,965,188. In general, PCR involves, first, treating a nucleic acid sample (e.g., in the presence of a heat stable DNA polymerase) with one oligonucleotide primer for each strand of the specific sequence to be detected under hybridizing conditions so that an extension product of each primer is synthesized that is complementary to each nucleic acid strand, with the primers sufficiently complementary to each strand of the specific sequence to hybridize therewith so that the extension product synthesized from each primer, when it is separated from its complement, can serve as a template for synthesis of the extension product of the other primer, and then treating the sample under denaturing conditions to separate the primer extension products from their templates if the sequence or sequences to be detected are present. These steps are cyclically repeated until the desired degree of amplification is obtained. Detection of the amplified sequence may be carried out by adding, to the reaction product, an oligonucleotide probe capable of hybridizing to the reaction product (e.g., an oligonucleotide probe of the present disclosure), the probe carrying a detectable label, and then detecting the label in accordance with known techniques. Various labels that can be incorporated into or operably linked to nucleic acids are well known in the art, such as radioactive, enzymatic, and florescent labels. Where the nucleic acid to be amplified is RNA, amplification may be carried out by initial conversion to DNA by reverse transcriptase in accordance with known techniques.

Strand displacement amplification (SDA) may be carried out in accordance with known techniques. For example, SDA may be carried out with a single amplification primer or a pair of amplification primers, with exponential amplification being achieved with the latter. In general, SDA amplification primers comprise, in the 5' to 3' direction, a flanking sequence (the DNA sequence of which is noncritical), a restriction site for the restriction enzyme employed in the reaction, and an oligonucleotide sequence (e.g., an oligonucleotide probe of the present disclosure) that hybridizes to the target sequence to be amplified and/or detected. The flanking sequence, which serves to facilitate binding of the restriction enzyme to the recognition site and provides a DNA polymerase priming site after the restriction site has been nicked, is about 15 to 20 nucleotides in length in one embodiment. The restriction site is functional in the SDA reaction. The oligonucleotide probe portion is about 13 to 15 nucleotides in length in one embodiment of the disclosure.

Ligase chain reaction (LCR) also can be carried out in accordance with known techniques. In general, the reaction is carried out with two pairs of oligonucleotide probes: one pair binds to one strand of the sequence to be detected; the other pair binds to the other strand of the sequence to be detected. Each pair together completely overlaps the strand to which it corresponds. The reaction is carried out by, first, denaturing (e.g., separating) the strands of the sequence to be detected, then reacting the strands with the two pairs of oligonucleotide probes in the presence of a heat stable ligase so that each pair of oligonucleotide probes is ligated together, then separating the reaction product, and then cyclically repeating the process until the sequence has been amplified to the desired degree. Detection may then be carried out in like manner as described above with respect to PCR.

According to the methods of the present disclosure, a particular SNP at this locus is detected. Techniques that are useful in the methods of the disclosure include, but are not limited to direct DNA sequencing, PFGE analysis, allele-specific oligonucleotide (ASO), dot blot analysis and denaturing gradient gel electrophoresis, and are well known to a skilled artisan.

There are several methods that can be used to detect DNA sequence variation. Direct DNA sequencing, either manual sequencing or automated fluorescent sequencing can detect sequence variation. Another approach is the single-stranded conformation polymorphism assay (SSCA). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments that have shifted mobility on SSCA gels are then sequenced to determine the exact nature of the DNA sequence variation. Other approaches based on the detection of mismatches between the two complementary DNA strands include clamped denaturing gel electrophoresis (CDGE), heteroduplex analysis (HA) and chemical mismatch cleavage (CMC). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result.

Detection of SNPs may be accomplished by sequencing the desired target region using techniques well known in the art. Alternatively, the gene sequences can be amplified directly from a genomic DNA preparation from patient tissue, using known techniques. The DNA sequence of the amplified sequences can then be determined.

There are six well known methods for a more complete, yet still indirect, test for confirming the presence of a mutant allele: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. For allele-specific PCR, primers are used which hybridize at their 3' ends to a particular DNM1 mutation. If the particular mutation is not present, an amplification product is not observed. Amplification Refractory Mutation System (ARMS) can also be used. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Other techniques for detecting insertions and deletions as known in the art can be used.

In the first three methods (SSCA, DGGE and RNase protection assay), a new electrophoretic band appears. SSCA detects a band that migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present disclosure, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. The riboprobe and either mRNA or DNA isolated from the tumor tissue are annealed (hybridized) together and subsequently digested with the enzyme RNase A that is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the DNM1 mRNA or gene but can be a segment of either. If the riboprobe comprises only a segment of the DNM1 mRNA or gene, it will be desirable to use a number of these probes to screen the whole mRNA sequence for mismatches.

In similar fashion, DNA probes can be used to detect mismatches, through enzymatic or chemical cleavage. Alternatively, mismatches can be detected by shifts in the electrophoretic mobility of mismatched duplexes relative to matched duplexes. With either riboprobes or DNA probes, the cellular mRNA or DNA that might contain a mutation can be amplified using PCR before hybridization.

B. Hybridization

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

"Stringent conditions" are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.10% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS. Other examples of stringent conditions are well known in the art.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point (Tm) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984); $T_m$ 81.5° C.+16.6 (log M)+0.41 (% GC) −0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), the SSC concentration is increased so that a higher temperature can be used. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. For short nucleotide sequences (e.g., about 10 to 50 nucleotides), stringent conditions typically involve salt concentrations of less than about 1.5 M, less than about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2×(or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids that have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

"Northern analysis" or "Northern blotting" is a method used to identify RNA sequences that hybridize to a known probe such as an oligonucleotide, DNA fragment, cDNA or fragment thereof, or RNA fragment. The probe can be labeled with a radioisotope such as $^{32}P$, by biotinylation or with an enzyme. The RNA to be analyzed can be usually electrophoretically separated on an agarose or polyacrylamide gel, transferred to nitrocellulose, nylon, or other suitable membrane, and hybridized with the probe, using standard techniques well known in the art.

Nucleic acid sample may be contacted with an oligonucleotide probe in any suitable manner known to those skilled in the art. For example, the DNA sample may be solubilized in solution, and contacted with the oligonucleotide probe by solubilizing the oligonucleotide probe in solution with the DNA sample under conditions that permit hybridization. Suitable conditions are well known to those skilled in the art. Alternatively, the DNA sample may be solubilized in solution with the oligonucleotide probe immobilized on a solid support, whereby the DNA sample may be contacted with the oligonucleotide probe by immersing the solid support having the oligonucleotide probe immobilized thereon in the solution containing the DNA sample.

The term "substrate" refers to any solid support to which the probes may be attached. The substrate material may be modified, covalently or otherwise, with coatings or functional groups to facilitate binding of probes. Suitable substrate materials include polymers, glasses, semiconductors, papers, metals, gels and hydrogels among others. Substrates may have any physical shape or size, e.g., plates, strips, or microparticles. The term "spot" refers to a distinct location on a substrate to which probes of known sequence or sequences are attached. A spot may be an area on a planar substrate, or it may be, for example, a microparticle distinguishable from other microparticles. The term "bound" means affixed to the solid substrate. A spot is "bound" to the solid substrate when it is affixed in a particular location on the substrate for purposes of the screening assay.

In certain embodiments of the present disclosure, the substrate is a polymer, glass, semiconductor, paper, metal, gel or hydrogel. In certain embodiments of the present disclosure, a kit can further include a solid substrate and at least one control probe, wherein the at least one control probe is bound onto the substrate in a distinct spot.

In certain embodiments of the present disclosure, the solid substrate is a microarray. An "array" or "microarray" is used synonymously herein to refer to a plurality of probes attached to one or more distinguishable spots on a substrate. A microarray may include a single substrate or a plurality of substrates, for example a plurality of beads or microspheres. A "copy" of a microarray contains the same types and arrangements of probes.

Methods for Detecting Coronary Heart Disease

The present disclosure provides a method using bisulfite treated DNA for determining whether a subject has the likelihood of having a CVD by determining methylation status of a CpG dinucleotide repeat or CpG dinucleotide repeat motif region, where the methylation status of the CpG dinucleotide is associated with CVD. In certain embodiments, the method determines the methylation status of a plurality (e.g., any integer between 1 and 10,000, such as at least 100) of CpG dinucleotide repeat motif regions.

Various techniques and reagents find use in the methods of the present disclosure. In one embodiment of the disclosure, blood samples, or samples derived from blood, e.g. plasma, circulating, peripheral, lymphocytes, etc. are assayed for the presence of one or more SNPs and/or the methylation status of one or more CpG dinucleotides. A biological sample also can be saliva. Typically, a biological sample that contains nucleic acids is provided and tested.

As used herein, the term "healthy" means that a subject does not manifest a particular condition, and is no more likely than at random to be susceptible to a particular condition.

In certain embodiments, the present disclosure provides a method for detecting that a subject is predisposed to or has coronary heart disease. Such a method typically includes providing a biological sample from the subject; contacting DNA from the biological sample with bisulfite under alkaline conditions; contacting the bisulfite-treated DNA with at least one first oligonucleotide probe at least 8 nucleotides in length that is complementary to a sequence that comprises a CpG dinucleotide, wherein the at least one first oligonucleotide probe detects either the unmethylated CpG dinucleotide or the methylated CpG dinucleotide, and detecting either the unmethylated CpG dinucleotide or the methylated CpG dinucleotide, wherein methylation of the CpG dinucleotide is associated with coronary heart disease. Such a method can further include determining the genotype of a single nucleotide polymorphism (SNP) (e.g., rs347027).

In certain embodiments, the method further comprises contacting the bisulfite-treated DNA with at least one second oligonucleotide probe at least 8 nucleotides in length that is complementary to a sequence that comprises a CpG dinucleotide, where the at least one second oligonucleotide probe detects either the unmethylated CpG dinucleotide or the methylated CpG dinucleotide, whichever is not detected by the at least one first oligonucleotide probe.

In certain embodiments, the method further comprises determining the ratio of methylated CpG dinucleotides to unmethylated CpG dinucleotides. In certain embodiments, the method can include an amplifying step after the contacting step. In certain embodiments, the method can include a sequencing step after the contacting step.

In certain embodiments, a method for measuring the presence of a biomarker in a biological sample from a patient is provided. Such a method can include contacting DNA from the biological sample with bisulfite under alkaline conditions; and contacting the bisulfite-treated DNA with at least one first oligonucleotide probe at least 8 nucleotides in length that is complementary to a sequence that comprises a CpG dinucleotide, where the at least one first oligonucleotide probe detects either the unmethylated CpG dinucleotide or the methylated CpG dinucleotide. Such a method can be used to predict whether or not the patient has coronary heart disease or has an increased likelihood of developing coronary heart disease.

In certain embodiments, a method of predicting the presence of biomarkers associated with Coronary Heart Disease (CHD) in a biological sample from a patient is provided. Such a method typically includes providing a first aliquot from a biological sample and contacting DNA from the first aliquot with bisulfite under alkaline conditions. Such a method also typically includes providing a second aliquot from the biological sample and contacting the bisulfite-treated first aliquot and the second aliquot with the following: (i) a first oligonucleotide probe at least 8 nucleotides in length that is complementary to a sequence that comprises a CpG dinucleotide at position 92203667 of chromosome 1 within the Transforming Growth Factor, Beta Receptor III (TGFBR3) gene, and the second aliquot with a nucleic acid primer at least 8 nucleotides in length that is complementary to SNP rs347027; (ii) the first aliquot with a first oligonucleotide probe at least 8 nucleotides in length that is complementary to a sequence that comprises a CpG dinucleotide at position 38364951 in an intergenic region of chromosome 15, and the second aliquot with a nucleic acid primer at least 8 nucleotides in length that is complementary to SNP rs4937276; (iii) the first aliquot with a first oligonucleotide probe at least 8 nucleotides in length that is complementary to a sequence that comprises a CpG dinucleotide at position 84206068 of chromosome 4 in the Coenzyme Q2 4-hydroxybenzoate poly-prenyl transferase (COQ2) gene, and the second aliquot with a nucleic acid primer at least 8 nucleotides in length that is complementary to SNP rs17355663; (iv) the first aliquot with a first oligonucleotide probe at least 8 nucleotides in length that is complementary to a sequence that comprises a CpG dinucleotide at position 26146070 of chromosome 16 in the Heparan Sulfate 3-O-Sulfotransferase 4 (HS3ST4) gene, and the second aliquot with a nucleic acid primer at least 8 nucleotides in length that is complementary to SNP rs235807; (v) the first aliquot with a first oligonucleotide probe at least 8 nucleotides in length that is complementary to a sequence that comprises a CpG dinucleotide at position 91171013 of an intergenic region of chromosome 1, and the second aliquot with a nucleic acid primer at least 8 nucleotides in length that is complementary to SNP rs11579814; (vi) the first aliquot with a first oligonucleotide probe at least 8 nucleotides in length that is complementary to a sequence that comprises a CpG dinucleotide at position 39491936 of chromosome 1 in the NADH Dehydrogenase (Ubiquinone) Fe—S Protein 5 (NDUFS5) gene, and the second aliquot with a nucleic acid primer at least 8 nucleotides in length that is complementary to SNP rs2275187; (vii) the first aliquot with a first oligonucleotide probe at least 8 nucleotides in length that is complementary to a sequence that comprises a CpG dinucleotide at position 186426136 mapping to chromosome 1 in the Phosducin gene, and the second aliquot with a nucleic acid primer at least 8 nucleotides in length that is complementary to SNP rs4336803; (viii) the first aliquot with a first oligonucleotide probe at least 8 nucleotides in length that is complementary to a sequence that comprises a CpG dinucleotide at position 205475130 of chromosome 1 in the Cyclin-Dependent Kinase 18 (CDK18) gene, and the second aliquot with a nucleic acid primer at least 8 nucleotides in length that is complementary to SNP rs4951158; and/or (ix) the first aliquot with a first oligonucleotide probe at least 8 nucleotides in length that is complementary to a sequence that comprises a CpG dinucleotide at position 130614013 of chromosome 3 in the ATPase, Ca++ Transporting, Type 2C, Member 1 (ATP2C1) gene, and the second aliquot with a nucleic acid primer at least 8 nucleotides in length that is complementary to rs925613.

In certain embodiments, the present disclosure provide a method for detecting one or more copies of a G allele at rs347027 and methylation status at cg13078798 on a nucleic acid sample from a subject at risk for Coronary Heart Disease (CHD), comprising a) performing a genotyping assay on a nucleic acid sample of said human subject to detect the presence of one or more copies of a G allele of the rs347027 polymorphism, and b) performing a methylation assessment at cg13078798 on a nucleic acid sample of said human to detect methylation status to determine if cg13078798 is unmethylated.

In such a method, methylation of the CpG dinucleotide at position 92203667 of chromosome 1 within the TGFBR3 gene, or at any of positions cg20636912, cg16947947, cg05916059, cg04567738, cg16603713, cg05709437, cg12081870, and/or cg18070470, along with a G at position 1618766 of chromosome 1 or polymorphisms in the SNPs at rs4937276, rs17355663, rs235807, rs11579814, rs2275187, rs4336803, rs4951158, and/or rs925613 are associated with CHD.

Kits for Detecting Coronary Heart Disease

In a further embodiment of the disclosure, there are provided articles of manufacture and kits containing probes, oligonucleotides or antibodies which can be used, for instance, for the applications described above. The article of manufacture comprises a container with a label. Suitable containers include, for example, bottles, vials, and test tubes. The containers may be formed from a variety of materials such as glass or plastic. The container holds a composition which includes one or more agents that are effective for practicing the methods described herein. The label on the container indicates that the composition can be used for a specific application. The kit of the disclosure will typically comprise the container described above and one or more other containers comprising materials desirable from a commercial and user standpoint, including buffers, diluents, filters and package inserts with instructions for use.

In certain embodiments, the present disclosure provides a kit for determining the methylation status of at least one CpG dinucleotide and the presence of at least one single-nucleotide polymorphism (SNP). In certain embodiments, a kit as described herein may contain a number of primers that is any integer between 1 and 10,000, such as 1, 2, 3, 4, 5, 6, 7, 8, 9, 10, . . . 9997, 9998, 9999, 10,000. As used herein, the term “nucleic acid primer” or “nucleic acid probes” or “oligonucleotide” encompasses both DNA and RNA primers. In certain embodiments, the primers or probes may be physically located on a single solid substrate or on multiple substrates.

A kit as described herein can include at least one first nucleic acid primer (e.g., at least 8 nucleotides in length) that is complementary to a bisulfite-converted nucleic acid sequence comprising a CpG dinucleotide (e.g., at position 92203667 of chromosome 1 within the Transforming Growth Factor, Beta Receptor III (TGFBR3) gene), and at least one second nucleic acid primer (e.g., at least 8 nucleotides in length) that is complementary to a SNP (e.g., SNP rs347027). In some embodiments, the at least one first nucleic acid primer detects the unmethylated CpG dinucleotide. In some embodiments, the at last one second nucleic acid primer has a sequence that detects a G nucleotide at SNP rs347027.

In some embodiments, a kit further can include at least one third nucleic acid primer (e.g., at least 8 nucleotides in length) that is complementary to a bisulfite-converted nucleic acid sequence comprising a CpG dinucleotide (e.g., at position 92203667 of chromosome 1 within the TGFBR gene), where the at least one third nucleic acid primer detects the methylated CpG dinucleotide.

A kit as described herein can include at least one first nucleic acid primer (e.g., at least 8 nucleotides in length) that is complementary to a bisulfite-converted nucleic acid sequence comprising a CpG dinucleotide (e.g., at position 38364951 in an intergenic region of chromosome 15), where the at least one first nucleic acid primer detects the unmethylated CpG dinucleotide, and at least one second nucleic acid primer (e.g., at least 8 nucleotides in length) that is complementary to a SNP (e.g., rs4937276).

In some embodiments, a kit further can include at least one third nucleic acid primer (e.g., at least 8 nucleotides in length) that is complementary to a bisulfite-converted nucleic acid sequence comprising a CpG dinucleotide (e.g., at position 38364951 in an intergenic region of chromosome 15), where the at least one second nucleic acid primer detects the methylated CpG dinucleotide.

A kit as described herein can include at least one first nucleic acid primer (e.g., at least 8 nucleotides in length) that is complementary to a bisulfite-converted nucleic acid sequence comprising a CpG dinucleotide (e.g., at position 84206068 of chromosome 4 in the Coenzyme Q2 4-Hydroxybenzoate Polyprenyltransferase (COQ2) gene), where the at least one first nucleic acid primer detects the unmethylated CpG dinucleotide, and at least one second nucleic acid primer (e.g., at least 8 nucleotides in length) that is complementary to a SNP (e.g., SNP rs17355663).

In some embodiments, the kit further can include at least one third nucleic acid primer (e.g., at least 8 nucleotides in length) that is complementary to a bisulfite-converted nucleic acid sequence comprising a CpG dinucleotide (e.g., at position 84206068 of chromosome 4 in the Coenzyme Q2 4-Hydroxybenzoate Polyprenyltransferase (COQ2) gene), where the at least one second nucleic acid primer detects the methylated CpG dinucleotide.

A kit as described herein can include at least one first nucleic acid primer (e.g., at least 8 nucleotides in length) that is complementary to a bisulfite-converted nucleic acid sequence comprising a CpG dinucleotide (e.g., at position 26146070 of chromosome 16 in the Heparan Sulfate 3-O-Sulfotransferase 4 (HS3ST4) gene), where the at least one first nucleic acid primer detects the unmethylated CpG dinucleotide, and at least one second nucleic acid primer (e.g., at least 8 nucleotides in length) that is complementary to a SNP (e.g., SNP rs235807).

In some embodiments, the kit further can include at least one third nucleic acid primer (e.g., at least 8 nucleotides in length) that is complementary to a bisulfite-converted nucleic acid sequence comprising a CpG dinucleotide (e.g., at position 26146070 of chromosome 16 in the Heparan Sulfate 3-O-Sulfotransferase 4 (HS3ST4) gene), where the at least one second nucleic acid primer detects the methylated CpG dinucleotide.

A kit as described herein can include at least one first nucleic acid primer (e.g., at least 8 nucleotides in length) that is complementary to a bisulfite-converted nucleic acid sequence comprising a CpG dinucleotide (e.g., at position 91171013 of an intergenic region of chromosome 1), where the at least one first nucleic acid primer detects the unmethylated CpG dinucleotide, and at least one second nucleic acid primer (e.g., at least 8 nucleotides in length) that is complementary to a SNP (e.g., SNP rs11579814).

In some embodiments, the kit further can include at least one third nucleic acid primer (e.g., at least 8 nucleotides in length) that is complementary to a bisulfite-converted nucleic acid sequence comprising a CpG dinucleotide (e.g., at position 91171013 of an intergenic region of chromosome 1), wherein the at least one second nucleic acid primer detects the methylated CpG dinucleotide.

A kit as described herein can include at least one first nucleic acid primer (e.g., at least 8 nucleotides in length) that is complementary to a bisulfite-converted nucleic acid sequence comprising a CpG dinucleotide (e.g., at position 39491936 of chromosome 1 in the NADH Dehydrogenase (Ubiquinone) Fe—S Protein 5 (NDUFS5) gene), where the at least one first nucleic acid primer detects the unmethylated CpG dinucleotide, and at least one second nucleic acid primer (e.g., at least 8 nucleotides in length) that is complementary to a SNP (e.g., SNP rs2275187).

In some embodiments, the kit further can include at least one third nucleic acid primer (e.g., at least 8 nucleotides in length) that is complementary to a bisulfite-converted nucleic acid sequence comprising a CpG dinucleotide (e.g., at position 39491936 of chromosome 1 in the NADH Dehydrogenase (Ubiquinone) Fe—S Protein 5 (NDUFS5) gene), wherein the at least one second nucleic acid primer detects the methylated CpG dinucleotide.

A kit as described herein can include at least one first nucleic acid primer (e.g., at least 8 nucleotides in length) that is complementary to a bisulfite-converted nucleic acid sequence comprising a CpG dinucleotide (e.g., at position 186426136 mapping to chromosome 1 in the Phosducin gene), where the at least one first nucleic acid primer detects the unmethylated CpG dinucleotide, and at least one second nucleic acid primer (e.g., at least 8 nucleotides in length) that is complementary to a SNP (e.g., SNP rs4336803).

In some embodiments, the kit further can include at least one third nucleic acid primer (e.g., at least 8 nucleotides in length) that is complementary to a bisulfite-converted nucleic acid sequence comprising a CpG dinucleotide (e.g., at position 186426136 mapping to chromosome 1 in the Phosducin gene), where the at least one second nucleic acid primer detects the methylated CpG dinucleotide.

A kit as described herein can include at least one first nucleic acid primer (e.g., at least 8 nucleotides in length) that is complementary to a bisulfite-converted nucleic acid sequence comprising a CpG dinucleotide (e.g., at position 205475130 of chromosome 1 in the Cyclin-Dependent Kinase 18 (CDK18) gene), where the at least one first nucleic acid primer detects the unmethylated CpG dinucleotide, and at least one second nucleic acid primer (e.g., at least 8 nucleotides in length) that is complementary to a SNP (e.g., SNP rs4951158).

In some embodiments, the kit further can include at least one third nucleic acid primer (e.g., at least 8 nucleotides in length) that is complementary to a bisulfite-converted nucleic acid sequence comprising a CpG dinucleotide (e.g., at position 205475130 of chromosome 1 in the Cyclin-Dependent Kinase 18 (CDK18) gene), where the at least one second nucleic acid primer detects the methylated CpG dinucleotide.

A kit as described herein can include at least one first nucleic acid primer (e.g., at least 8 nucleotides in length) that is complementary to a bisulfite-converted nucleic acid sequence comprising a CpG dinucleotide (e.g., at position 130614013 of chromosome 3 in the ATPase, Ca++ Transporting, Type 2C, Member 1 (ATP2C1) gene), where the at least one first nucleic acid primer detects the unmethylated CpG dinucleotide, and at least one second nucleic acid primer (e.g., at least 8 nucleotides in length) that is complementary to a SNP (e.g., SNP rs925613).

In some embodiments, the kit further can include at least one third nucleic acid primer (e.g., at least 8 nucleotides in length) that is complementary to a bisulfite-converted nucleic acid sequence comprising a CpG dinucleotide (e.g., at position 130614013 of chromosome 3 in the ATPase, Ca++ Transporting, Type 2C, Member 1 (ATP2C1) gene), where the at least one second nucleic acid primer detects the methylated CpG dinucleotide.

It would be appreciated that any of the nucleic acid primers, probes or oligonucleotides described herein can include one or more nucleotide analogs and/or one or more synthetic or non-natural nucleotides.

It also would be appreciated that any of the kits described herein can include a solid substrate. In some embodiments, one or more of the nucleic acid primers can be bound to the solid support. Examples of solid supports include, without limitation, polymers, glass, semiconductors, papers, metals, gels or hydrogels. Additional examples of solid supports include, without limitation, microarrays or microfluidics cards.

It also would be appreciated that any of the kits described herein can include one or more detectable labels. In some embodiments, one or more of the nucleic acid primers can be labeled with the one or more detectable labels. Representative detectable labels include, without limitation, an enzyme label, a fluorescent label, and a colorimetric label.

Algorithm for Predicting Post-Surgical Cardiac Events

Figure 14:
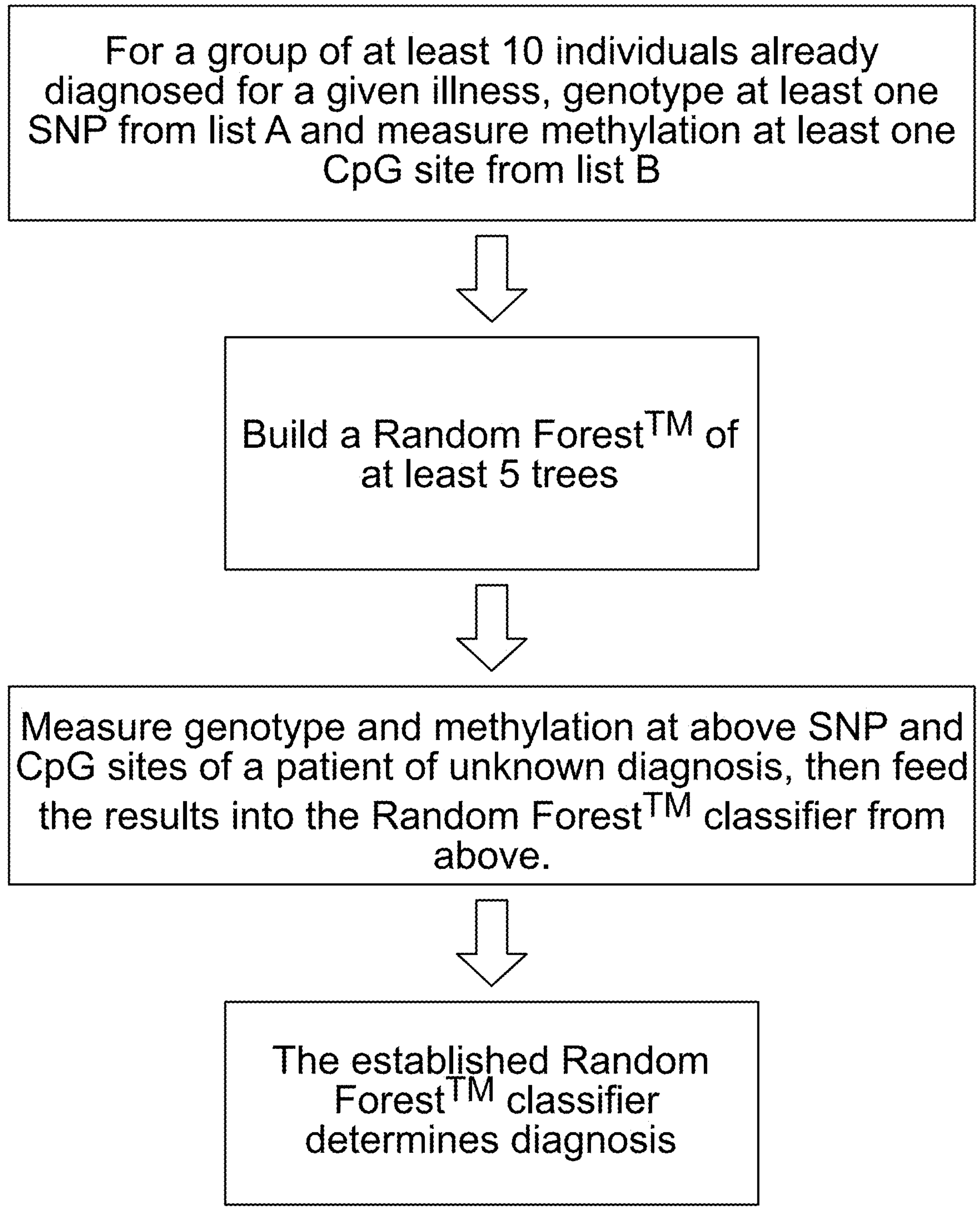
FIG. 14. Flow chart of certain embodiment of method of the invention.

Any number of algorithms that can capture linear effects (e.g., linear regression) or both linear and non-linear effects (e.g., Random Forest™, Gradient Boosting™, Neural Networks (e.g., deep neural network, extreme learning machine (ELM)), Support Vector Machine, Hidden Markov model)

can be used in the methods described herein. See, for example, McKinney et al., 2011, Appl. Bioinform., 5(2):77-88; Gunther et al., 2012, BMC Genet., 13:37; and Ogutu et al., 2011, BMC Proceedings, 5(Suppl 3):S11. Any type of machine learning algorithm or deep learning neural network algorithm (tuned or non-tuned) capable of capturing linear and/or non-linear contribution of traits for the prediction can be used. See, for example, FIG. 14. In some instances, a combination of algorithms (e.g., a combination or ensemble of multiple algorithms that capture linear and/or non-linear contributions of traits) is used.

Simply by way of example, Random Forest™ is a popular machine learning algorithm created by Breiman & Cutler for generating "classification trees" (see, for example, "stat-.berkeley.edu/~breiman/RandomiForests/cc_home.htm" on the World Wide Web). Using standard machine learning and predictive modeling techniques, a diagnostic classifier algorithm was written to be implemented in R and Python programming languages (though it can be implemented in many other programming languages), according to well described guidelines by Breiman & Cutler. A diagnostic classifier algorithm was generated using data from at least two traits (T) and the diagnosis of interest from that population. To determine the output (e.g., diagnosis) for a new individual, one simply determines values for the at least two traits (T) and inputs that information into an algorithm (e.g., the diagnostic classifier algorithm described herein or another algorithm discussed above) that is capable of capturing the linear and non-linear contributions of the traits.

As described herein, the inputs are at least one genotype (e.g., SNP) and the methylation status of at least one CpG dinucleotide, and the outcome can represent a positive or a negative probability (e.g., prediction or diagnosis) for CHD, CHF, stroke or other illnesses. The Traits (T) used to determine the outcome can represent the methylation status of at least one CpG dinucleotide or at least one genotype (e.g., of a SNP), but Traits (T) also can correspond to at least one interaction (e.g., between methylation status and genotype (CpGxSNP), between the methylation status of two different sites (CpGxCpG) or between two different genotypes (SNPxSNP)). It would be appreciated that any such interactions can be visualized using partial dependence plots.

It will be apparent that the present disclosure provides a skilled artisan the ability to construct a matrix in which the methylation status of one or more CpG dinucleotides and one or more genotypes (e.g., SNPs; e.g., at one or more alleles) can be evaluated as described herein, typically using a computer, to identify interactions and allow for prediction of a post-surgical cardiac event. Although such an analysis is complex, no undue experimentation is required as all necessary information is either readily available to the skilled artisan or can be acquired by experimentation as described herein.

The present invention is further detailed in the following Examples, which are offered by way of illustration and are not intended to limit the invention in any manner. Standard techniques well known in the art or the techniques specifically described below are utilized. All patent and literature references cited in the present specification are hereby incorporated by reference in their entirety.

EXAMPLE 1

Methylation and GxMethylation Effects in Predicting Cardiovascular Disease

Methylation-based biomarkers are gaining increasing clinical traction for use in guiding diagnosis and therapy. In attempts to identify CpG loci whose methylation status is predictive of cardiovascular disease, a number of investigators have used genome wide approaches combined with clinical diagnostics. In particular, Brenner and colleagues have identified F2RL3 residue cg03636183 as a biomarker for cardiovascular disease (Breitling et al., "Smoking, F2RL3 methylation, and prognosis in stable coronary heart disease," Eur. Heart J., 2012, 33:2841-8). Unfortunately, these analyses have been shown to have been completely confounded by incomplete knowledge of smoking status and did not consider possible confounding genetic variance. In fact, when using biomarker approaches that fully account for the intensity of smoking, the coronary heart disease signal at cg03636183 disappears. Furthermore, using a genome wide methylation and genetic analyses, combined with biomarker guided smoking assessments, we have recently analyzed data from a large cohort of subjects informative for cardiac disease. We demonstrate that independent of smoking intensity status, that the genetically contextual methylation status, as embodied by methylation-genotype interact (meQTLs) actually contribute better to the prediction of coronary heart disease and that the use of an algorithm that combines local genetic variation and methylation markedly improves prediction of coronary heart disease.

EXAMPLE 2

Incorporating Gene X Methylation Interactions Increases the Power to Predict the Presence of Coronary Heart Disease Abstract Coronary heart disease (CHD) is the leading cause of death in the United States. Effective treatments to prevent morbidity and mortality of CHD exist, but their clinical implementation is hindered by inefficient screening techniques. In recent years, others and we have shown that DNA methylation signatures can infer the presence of a variety of disorders related to CHD such as smoking. Unfortunately, when these epigenetic techniques are applied to CHD itself, the power of these methods is diminished, thus limiting their clinical utility. One possible reason for these failures may be the obscuration of epigenetic signature of CHD by gene x methylation interaction (meQTL) effects. In order to test this possibility, using a stepwise approach, we examined whether incorporation of meQTLs could be used to improve the predictive value of a prior methylation-based assessment by analyzing genetic and epigenetic data from the Framingham Heart Study. In our initial attempt, using Receiver Operator Characteristic (ROC) Area Under the Curve (AUC) analyses focused on F2RL3, we found that the addition of cis- and trans-meQTL at CpG residue cg13751927, which is near a locus previously described by Brenner and colleagues, significantly improved the capacity of a model that included smoking status alone to predict CHD in the training dataset. Subsequent genome-wide meQTL analyses identified a total of 3,265 cis-meQTLs at a FDR of 0.05 and 467,314 significant trans-meQTLs at a FDR of 0.1. Our preliminary analysis suggests that, the inclusion of six additional cis-meQTL further improved the AUC of the existing model with only the F2RL3 meQTL and smoking. This non-optimized model is capable of predicting CHD with 81.9% accuracy. We conclude that incorporating meQTL information in prediction algorithms can markedly improve their power to predict CHD and that further attempts to improve the ability of the model to predict CHD are possible through additional optimized machine learning models.

Introduction

Coronary Heart Disease (CHD) is the leading cause of death in the United States whose direct cost to the US economy was estimated to be 108 billion dollars in 2012.[1] Over the past fifty years, a number of medications and devices have been developed to treat CHD. Unfortunately, tens of thousands of Americans continue to die each year because the presence of CHD is not noted until a fatal cardiac event. Conceivably, more effective screening procedures for CHD could lead to the prevention of some of these deaths.[1] But at the current time, the cumbersomeness of certain techniques, such as fasting lipid panels, and/or the limited predictive ability of others such as electrocardiograms and C-reactive protein levels, limit the effectiveness of the current approaches in identifying CHD.[1-3]

A number of investigators have proposed that genetic approaches could provide another potential avenue through which to prevent CHD related morbidity and mortality.[4] Using whole exome and genome sequencing techniques, a number of variants predisposing to CHD have been identified. The relative risk conferred by of many of these variants is often considerable and their presence is sometimes useful for guiding prevention and treatment.[5] However, the large effect size variants tend to be rare and their presence is not pathognomonic of current disease.[4] Hence, at the current time, genetic approaches are not generally used for the assessment of the presence or absence of current CHD in general medical practice.

Alternatively, others have proposed that epigenetic techniques might be useful in assessing CHD.[6-8] Since replicated peripheral white blood cell DNA methylation signatures for the presence of type 2 diabetes, smoking and drinking have been developed,[9-12] this suggestion has strong face validity. Notably, using this approach, Brenner and colleagues have proposed that DNA methylation at cg03636183, a CpG residue found in Coagulation factor II (thrombin) receptor-like 3 (F2RL3), predicts risk for cardiac disease.[6,13] Although this is an extremely biologically plausible finding, their subsequent studies have demonstrated that the CHD related signal at cg03636183 completely co-segregates with smoking status as indicated by DNA methylation at cg05575921,[14] a CpG residue found in the aryl hydrocarbon receptor repressor (AHRR) whose strong predictive power with respect to smoking status has been demonstrated in dozens of studies.[15]

However, the failure of the initially intriguing cg03636183 findings to independently identify additional risk outside of that conferred by smoking alone does not mean that methylation approaches for assessing the presence of CHD are destined to fail. Instead, they suggest that successful approaches need to be more nuanced and that reconsideration of our conceptualization of relationship of methylation status to CHD is in order. For example, the findings by Brenner's group strongly suggest that methylation algorithms for the prediction of current CHD should include an indicator of smoking status. Given the fact that smoking is the largest preventable risk factor for CHD,[16] this is eminently logical. However, in addition, they may need to take into consideration that the long-term effects of exposure to environmental risk factors such as smoking or other cardiac risk factors such as hyperlipidemia may be obscured by gene-environment interactions.

The role of gene-environment interactions (GxE) effects in moderating vulnerability to illness is perhaps better appreciated in the behavioral sciences. The basic premise of GxE effects is that the influence of the environment during a developmentally sensitive period of time changes the biological properties of a system in a genetically contextual manner so that in the future-even in the absence of the environmental factor-enhanced vulnerability to illness is present.[17] Critically, because of confounding by the genetic variable, the direct effects of the environmental variable are generally not detectable. Rather, only when considered in the context of genetic variation can these be detected. Though the strength of some GxE findings are controversial, many investigators continue to stress the importance of these GxE effects in the pathogenesis of a variety of behavioral disorders such as depression, post-traumatic stress disorder and antisocial behavior.[18-20]

The physical basis for these GxE effects is thought to vary. For example, at the anatomical level, the GxE effects for behavioral disorders can be manifested by changes in synaptic structure.[21] However, at the molecular level, the physical manifestation of GxE effects is less certain. But a number of investigators have suggested that changes in DNA methylation may be one potential mechanism through which the physical effects of GxE effects are conveyed.[22]

Interestingly, the fact that behaviorally relevant changes in the environment can alter DNA methylation and that the degree of those changes is influenced by genetic variation has been known for many years. In our early candidate gene studies, we showed that smoking altered DNA methylation in the promoter region of monoamine oxidase A (MAOA), a key regulator of monoaminergic neurotransmission, and that genotype at the well-characterized promoter associated variable nucleotide repeat (VNTR) altered the percent methylation at the status in both the presence and absence of smoking.[23,24] Subsequently, methylation changes at those loci were shown to be functional by Volkow and colleagues.[25]

In current terminology, those effects of the VNTR on smoking or basal DNA methylation are now referred to genotype-methylation interaction or methylation quantitative trait locus (meQTL) effects. These MAOA meQTL effects had consequence on our ability to detect their relationship to smoking when we conducted our first genome wide studies. Despite the magnitude of the smoking induced change in DNA methylation in response to smoking, the probes surrounding the MAOA VNTR are not among the more highly ranked probes even in studies of DNA from subjects of only one gender. Other observations from those initial studies are equally instructive. First, the local methylation response to smoking was not homogenous. Factor analysis of the methylation status of the 88 CpG residues in the promoter associated islands showed that increases in methylation at one area of the island could be associated with demethylation at others.[26] Finally, the effects of smoking on DNA methylation were not static. After time, the signature tended to decay.[23] Hence, from those early studies, it was clear that at MAOA promoter, genetic variation could alter the effects of environmental factor on the local DNA methylation signature in a complex manner.

Subsequent studies suggest that many of these same complexities in response to smoking are evident at the genome wide level. For example, it is clear that at the genome wide level, genetic variation affects the magnitude of the methylation response, and that when attempting to replicate signatures from those of differing ancestries, those meQTL effects may impair the ability to replicate findings at a given locus in a subject pool of a different ancestry.[27,28] Second, and equally importantly, the reversion of the methylation signatures can be complex.[28,29] Guida and colleagues specifically examined the epigenomic response to smoking cessation in DNA from a collection of 745 subjects and found two classes of CpG sites, those whose methylation signature reverted with time and those that did not; and concluded that at the genome wide level the "dynamics of methylation changes following smoking cessation are driven by a differential and site specific magnitude of the smoking induced changes that is irrespective of the intensity and duration of smoking."[29] In summary, a substantial body of evidence suggests that the genome wide signature to smoking is only partially reversible and that a large chunk of the non-reversible changes may be complexly masked in meQTL effects.

Since smoking is a major risk factor for CHD, this also suggests that a portion of the smoking induced risk present in the epigenome that moderates the risk for CHD may be somewhat non-reversible and masked in meQTL responses. In addition, since smoking is only one of a number of factors can alter risk for CHD and these other factors also may have complex epigenetic signatures, it may well be that interrogation of peripheral WBC DNA methylation may reveal meQTL that moderate risk for CHD and are relatively stable. In this communication, we used regression analytical approaches and the epigenetic and genetic resources from 324 subjects who participated in the Framingham Heart Study to test whether the addition of meQTL effects can make a contribution to algorithms to predict CHD.

Methods

Framingham Heart Study. The data used in this study is derived from participants in the Framingham Heart Study (FHS).[30] FHS is a longitudinal study aimed at understanding the risks of cardiovascular disease (CVD) and consists of several cohorts including the Original Cohort, Offspring Cohort, Omni Cohort, Third Generation Cohort, New Offspring Spouse Cohort and Second Generation Omni Cohort. Specifically, the Offspring Cohort, initiated in 1971, consisting of the offspring of the Original Cohort and their spouses was used in this study. This cohort consists of 2,483 males and 2,641 females (total of 5,124).[31] The specific analyses described in this communication were approved by the University of Iowa Institutional Review Board.

Genome-wide DNA Methylation. Of the 5,124 individuals in the Offspring Cohort, only 2,567 individuals (duplicates removed) with DNA methylation data were considered. These individuals were included in the DNA methylation study because they attended the Framingham Offspring 8$^{th}$ exam, provided consent for genetic research, had a buffy coat sample, and had sufficient DNA quantity and quality for methylation profiling. Exam 8 took place between 2005 and 2008. Genomic DNA extracted from their white blood cells was bisulfite converted, then genome-wide DNA methylation was profiled using the Illumina HumanMethylation450 BeadChip (San Diego, Calif.) at either the University of Minnesota or Johns Hopkins University. The intensity data (IDAT) files of the samples alongside their slide and array information were used to perform the DASEN normalization using the MethyLumi™, WateRmelon™ and IlluminaHumanMethylation450k.db R™ packages.[32] The DASEN normalization performs probe filtering, background correction and adjustment for probe types. Samples were removed if they contained >1% of CpG sites with a detection p-value >0.05. CpG sites were removed if they had a bead count of <3 and/or >10% of samples had a detection p-value >0.05. After DASEN normalization, there were 2,560 samples and 484,241 sites remaining (484,125 CpG sites). CpG sites were grouped by chromosome. Methylation beta values were converted to M values using the beta2m R function in the Lumi package and subsequently converted to z-scores using an R script.[33]

Genome-wide Genotype. Of the 2,560 remaining individuals after DNA methylation quality control, 2,406 (1,100 males and 1,306 females) had genome-wide genotype data from the Affymetrix® GeneChip HumanMapping 500K Array Set® (Santa Clara, Calif.). This array is capable of profiling 500,568 SNPs in the genome. Quality control was performed at both the sample and SNP probe levels in PLINK. The initial quality control step involved identifying individuals with discordant sex information. None were identified. Next, individuals with a heterozygosity rate of greater or smaller than the mean±2SD and with a proportion of missing SNPs >0.03 were excluded. Related individuals were also excluded if the identity by descent value was >0.185 (halfway between second and third degree relatives). After performing these sample level quality control steps, 1,599 individuals remained (722 males and 877 females). On the probe level, SNPs with a minor allele frequency >1%, Hardy-Weinberg equilibrium p-value $>10^{-5}$ and SNP missing rate of <5% were retained. A total of 403,192 SNPs remained after these quality control steps. Using the recode option in PLINK,[34] genotypes were coded as 0, 1 or 2.

Phenotypes. In the methylation quantitative trait loci (meQTL) analysis, phenotypes that were considered include age, gender, batch, smoke exposure, and coronary heart disease (CHD) status. Among the 1,599 individuals that passed all quality control steps, 324 were recorded as having CHD at exam 8. These individuals were the training set. CHD was recorded as either prevalent or incident and an individual is diagnosed as having CHD if the Framingham Endpoint Review Committee (panel of three investigators) agrees that one of the following is present: myocardial infarction, coronary insufficiency, angina pectoris, sudden death from CHD, non-sudden death from CHD. For the analysis, CHD was coded as 1 if an individual had either prevalent and/or incident CHD, or 0 otherwise. The age used was the age of an individual at exam 8. Batch was the methylation plate number and smoke exposure was the methylation level at the aryl hydrocarbon receptor repressor (AHRR) smoking biomarker, cg05575921. The demographics of the 324 individuals in the training set are summarized in Table 1.

TABLE 1

Demographic of the 324 individuals in the training set

| | CHD present | CHD absent |
|---|---|---|
| n | | |
| Male | 56 | 167 |
| Female | 23 | 78 |
| Age | | |
| Male | 70.9 ± 7.0 | 71.1 ± 7.8 |
| Female | 71.7 ± 9.2 | 72.7 ± 7.9 |
| cg05575921 | | |
| Male | −0.389 ± 1.41 | 0.277 ± 1.04 |
| Female | −0.218 ± 1.16 | 0.403 ± 0.90 |

The remaining 1275 individuals were the testing dataset. The CHD status of these individuals was coded as 0 if CHD was not present, and 1 otherwise. The demographics of these individuals are summarized in Table 2.

TABLE 2

Demographic of the 1275 individuals in the testing dataset

| | CHD present | CHD absent |
|---|---|---|
| n | | |
| Male | 52 | 447 |
| Female | 49 | 727 |
| Age | | |
| Male | 71.0 ± 8.5 | 65.0 ± 8.3 |
| Female | 72.2 ± 8.9 | 65.8 ± 8.4 |
| cg05575921 methylation (m-value) | | |
| Male | −0.269 ± 1.02 | −0.153 ± 1.02 |
| Female | −0.181 ± 1.00 | 0.055 ± 0.91 |

Methylation Quantitative Trait Loci. The meQTL analysis was performed in the training set using the MatrixeQTL package in R.[35] To determine significant effects of SNP on methylation (meQTL) given CHD status, the following model was interrogated:

$$Meth_i \alpha Age+Gender+Batch+cg05575921+SNP_j+CHD+SNP_j{*}CHD$$

Cis- and trans-meQTL with a significant $SNP_1$*CHD term were retained for prediction. The interaction term was of particular interest because the analysis was aimed at uncovering specific SNPs that significantly predicted specific methylation sites given CHD status, after controlling for age, gender, batch, smoke exposure and the main effects of SNP and CHD. In the MatrixeQTL package, this was achieved using the modelLINEAR_CROSS model type. The cis distance was chosen to be 500,000 on either side of the site and was performed at the chromosome level. The meQTL analysis was performed on a genome-wide level and for coagulation factor II receptor-like 3 (F2RL3) gene specifically. This was done to determine if there is other meQTL beyond those identified for F2RL3 that better predict CHD.

Receiver Operating Characteristic Curve. An R script was written to perform logistic regression of the models shown below and subsequently calculate the area under the curve (AUC) receiver operating characteristic (ROC)[36] using the pROC package in R. This was performed for significant cis-meQTL at a nominal 0.05 level and trans-meQTL at an FDR 0.1 level. In the models listed below, each meQTL is represented by the SNP*meth term.

$$CHD{\sim}Age+Gender+Batch+cg05575921+SNP_j+meth_i+SNP_j{*}meth_i$$

$$CHD{\sim}Age+Gender+Batch+cg05575921+SNP_j+meth_i+SNP_j{*}meth_i$$

Model Training. A model was trained on the training dataset consisting of 324 individuals. Variables in this model were chosen based on their individual area under the ROC curve (AUC) generated from models described above. A 10-fold cross-validation was performed to determine the logistic regression threshold for CHD classification. From the average accuracy, a classification threshold of 0.5 was chosen.

Model Testing. Once the training model parameters and the classification thresholds were determined, the trained model was applied on an independent testing dataset. The demographics of the individuals in the testing dataset were described above. Model testing was performed in R.

Results cg05575921 for smoking status. As discussed earlier, smoking is a major risk factor of CHD. While most studies in the past have used self-reported smoking measures, the reliability and informativeness of these measures is less than optimal. Therefore, in order to minimize the effects of unreliable self-report and to take advantage of the ability of a continuous metric to better capture the amount of smoking consumption, we used a well validated biomarker of smoking, cg05575921.[14,15,37] While cg05575921 is a strong predictor of self-reported smoking in the 324 individuals (p-value=8.71e-9, $R^2$=0.62), the strength of cg05575921 as a predictor of CHD outweighs self-reported smoking status (p-value=1.64e-5, R2=0.085 vs. p-value=0.00218, $R^2$=0.042). This demonstrates that the incorporation of cg05575921 to represent smoke exposure instead of self-reported smoking status would further strengthen the downstream model for CHD prediction.

Methylation quantitative trait loci. The importance of accounting for the confounding effects of interaction between methylation and genotype for CHD prediction was demonstrated by the genome-wide DNA methylation analysis as discussed in the methods section. After controlling for age, gender, batch and cg05575921, CHD was not significantly associated with any methylation CpG sites at an FDR significance level of 0.05. From the meQTL analysis, there were 5,458,462, 3,265, 2,025 and 1,227 significant cis-meQTL at the 0.05 nominal, 0.05 FDR, 0.01 FDR and 0.001 FDR significance levels, respectively. Similarly, there was 467,314 significant trans-meQTL at the 0.1 FDR significance levels. The importance of some of these meQTL is demonstrated using the area under the receiver operating characteristic curve.

Receiver Operator Curve (ROC) of core variables. A ROC curve depicts the tradeoff between the sensitivity and selectivity of a model. Before introducing genetic and epigenetic variables, we established the area under the ROC curve (AUC) for the core variables age, gender, batch, and cg05575921 used in the meQTL model. The AUC of age, gender, batch and cg05575921 were 0.52, 0.51, 0.50, and 0.64, respectively. Collectively, they resulted in an AUC of 0.65, which is almost equal to the AUC of just cg05575921. If self-reported smoking was used instead of cg05575921, its individual and collective AUC is 0.55 and 0.56, respectively. The ROC curves of these analyses are depicted in FIG. 1. Hence, only one core variable, cg05575921, was included in subsequent models.

Figure 2:
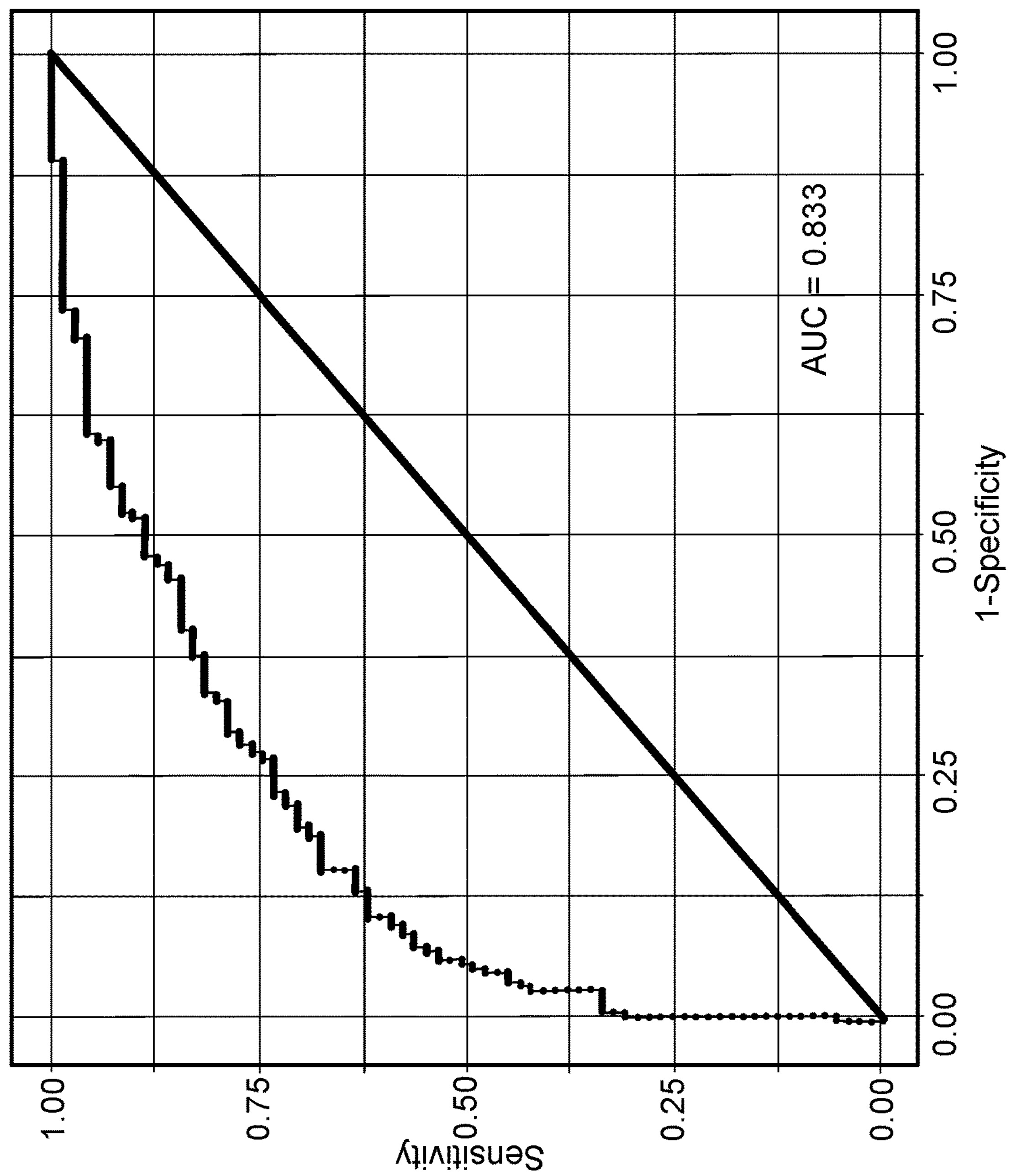
FIG. 2. Area under the receiver operating characteristic curve for the CHD prediction model (non-optimized).

ROC of CHD prediction in training data. Using cg05575921 and nine SNP-methylation interaction terms for CHD prediction, an AUC of ROC curve of 0.964 was obtained (see FIG. 2). The nine interaction terms and their respective AUC with and without the addition of cg05575921 to the model are summarized in Table 3.

TABLE 3

The list of the 9 meQTLs used to generate the Initial Prediction Model.

| SNP | CpG | meQTL AUC | meQTL + cg055 AUC |
|---|---|---|---|
| rs347027 | cg13078798 | 0.728 | 0.776 |
| rs4937276 | cg20636912 | 0.731 | 0.770 |
| rs17355663 | cg16947947 | 0.712 | 0.769 |
| rs235807 | cg05916059 | 0.698 | 0.765 |
| rs11579814 | cg04567738 | | |
| rs2275187 | cg16603713 | | |
| rs4336803 | cg05709437 | | |
| rs4951158 | cg12081870 | | |
| rs925613 | cg18070470 | 0.730 | 0.761 |

Prediction model. A preliminary logistic prediction model was used to predict CHD in the training data. After 10-fold cross-validation, the classification threshold was set to 0.5. Of the 324 individuals, 299 were included in the prediction due to absence of missing data. Of those 299 individuals, 73 and 226 do and do not have CHD, respectively. This means, if everyone were assigned the majority class (i.e. CHD absent), the prediction accuracy would be 75.6%. The average accuracy of this preliminary model after 10-fold cross-validation was 910%, which is much higher than the baseline.

Model testing. The trained model was used to predict CHD status in the independent testing dataset of 1275 individuals. The model was capable of predicting CHD with an 80% accuracy. This model is yet to be optimized.

Discussion

The results demonstrate that the presence of CHD can be inferred through the use of methylation-genotype interactions derived from meQTL. However, before the results can be discussed, it is important to note several limitations to the current study. First, the Framingham cohort is exclusively White and most subjects are in their mid to late sixties and seventies. Therefore, the current findings may not apply to those of other ethnicities or different age range. Second, outside of cg05575921, the validity of the M (or B-values) for the other probes has not been confirmed by an independent technique such as pyrosequencing. Third, the Illumina array used in the studies is no longer available. Because of changes in design or availability of probes in the new generation of array, the ability to replicate and extend may be affected.

The current results underscore the value of resources such as the Framingham Heart Study furthering our understanding heart disease. In fact, without this resource, it is fair to say that this type of work would be difficult if not impossible to conduct. Still, even given the current results using this unique data set, a great deal of additional work will be necessary before a screening test such as that described in the current communication can be employed clinically. Most obviously, the current results will have to be replicated and refined in other data sets, then re-tested in research populations representative of their intended future clinical application. The latter point is particularly important because even well-designed cohort studies that were originally epidemiologically sound suffer from retention biases that enrich the remaining pool for less serious illness. This is particularly true with respect to illnesses associated with substance use, because probands with high levels of substance use are more often lost to longitudinal follow-up.[38] In addition, because SNP frequencies can vary between ethnicities, the effect size of a given meQTL may also vary. Therefore, extensive testing and development in a variety of ethnically informative cohorts will be necessary.

There may be a hard ceiling for improvement of the AUC. Ironically, this has little to do with the quality or quantity of the epigenetic and genetic data. Rather, the limitation may be the uncertainty in the clinical characterizations. Sadly, even under the best conditions, clinically relevant CHD can remain undetected. This is true even for the FHS cohort. As a result, the "gold standard" itself in the current study is somewhat inaccurate with respect to the actual clinical state. Since this inaccuracy increases the error of even a biomarker that is exactly targeted on the relevant biology, our ability to improve the AUC may be dependent on our ability to derive a more accurate clinical assessment.[39]

Another limitation to the use this approach is the constantly evolving epidemiology of CHD. Whereas the genetic contribution to CHD is relatively fixed, diets and other environmental exposures continue to vary from generation to generation. Perhaps the best illustration of this limitation can be by considering contribution of smoking to the predictive power of this test in prior generations. Since tobacco was introduced to Europe from the New World in the early 1500s, we can confidently state that the contribution of smoking to CHD in medieval Europe was limited and therefore, the impact of the cg05575921 on predictive power would have be nil. In contrast, because over 40% of US adults smoked in the 1960s,[40] it is likely that the contribution of smoking behaviors, as captured by cg05575921, to the prediction of CHD would have been significantly greater in subjects from that era. However, smoking is not the only environmental factor that varies from generation to generation and from cohort to cohort. Over the past 20 years, there have been marked shifts in our understanding and public attitudes towards the amount of saturated and trans-fatty acids in a healthy diet. Since these environment factors also have strong influence on the likelihood of CHD, we would expect that the weighting of meQTLs loading on these dietary factors might vary with respect to age and ethnicity.

The improved predictive power of the smoking methylation biomarker cg05575921 as compared to self-reported smoking is not unexpected. In our initial studies, it has shown to be a potent indicator of current smoking status with an AUC of 0.99 in study that used well screened cases and controls.[37] Unreliable self-report for smoking, particularly in high risk cohorts, is a well-established phenomenon.[41-44] Furthermore, unlike cg05575921, categorical self-report does not capture the intensity of smoking.[37] Finally, many subjects who may have participated in the study may have previously smoked, but did not smoke at the Wave 8 interview but still had residual demethylation of AHRR. In each of these instance, the use of the continuous metric may capture additional vulnerability to CHD that is not captured by a dichotomous smoking variable.

Since alcoholism is also a risk for CHD,[1] we were somewhat surprised that our previously established and validated biomarker approach for assessing alcohol intake did not have a greater predictive impact.[10,45] In our initial models, the addition of methylation status at cg2313759 only improved AUC by 0.015. Although one reason for this failure to show the effect of alcohol use on risk for CHD may be that this marker is not as well validated as our smoking biomarker, there are other reasons as well. First and foremost, as opposed to methylation at cg05575921 which displays a tonic increasing risk for decreased life expectancies at all of levels of exposure, methylation at cg2313759 displays an inverted U-shaped distribution with respect to biological aging. Whether risk for CHD also follows a U shaped distribution with respect to alcohol intake is not known. But it does suggest that any successful algorithm incorporating the main effects of alcohol associated methylation cannot use a simple linear approach.

Our success in finding meQTLs predictive of CHD in the absence of genome wide significant main effects may have significant implications for the searches for marker sets for other common complex disorders of adulthood. Of the top 10 leading causes of death in the United States, using main effects, reliable methylation signatures have been developed only for type 2 diabetes and chronic obstructive pulmonary disease (COPD).[12,46] Because the ability to find a good biomarker for illness is highly contingent on the reliability of the clinical diagnosis, the success in these two instances may be secondary to the excellent diagnostic reliability of the methods used to diagnose these two disorders, namely the hemoglobin A1C and spirometry. Additionally, it is important to note that the diagnostic signature for T2DM largely maps to pathways affected by excessive glucose levels while the signature associated with COPD largely overlaps with that of smoking which contributes to 95% of all cases of COPD.[12,46] Still, because many of the risk factors for other major causes of death, such as stroke, overlap with those for CHD (e.g. smoking), we are optimistic that similar profiles can be generated using this approach.

Unfortunately, the vast majority of adult onset common complex disorders do not have good existing biomarkers or large effect size etiological factors. In these cases, an approach that incorporates meQTLs may be beneficial—the real question is why? Although speculative, based on our experience with local and genome wide data indicates that chronic exposure to cellular stressors leads to a reorganization of the epigenome, which may be only partially reversible. If that disorganization of the genome, regardless of how long it lasts, is causally associated with illness, it can be used as a biomarker for illness. Understanding the reversion time of each of these meQTLS may lead to additional insights. For example, pharmacological interventions may have effects at discrete subsets of these meQTLs. By understanding the relationship between reversion at these loci and therapeutic outcomes, it may be possible to optimize existing medications or more adroitly tailor new combination regimens.

The fact that no main effects of methylation are observed for CHD is not necessarily an indication of lack of epigenetic signature in WBCs. Rather, it speaks to the complexity of the overall genetic architecture. For example, although methylation status at thousands of CpG loci have been associated with smoking status (for review see[14,15]) the signal at cg05575921 is one of the few whose signal is not obscured by ethnic specific genetic differences in one population or another.[27] This communication shows that the epigenomic response to smoking also includes a plethora of meQTLs. But the necessity of measuring at least two values for each meQTL suggests that translating these findings to improvements in diagnosis, treatment or prevention may be more challenging.

In summary, we report that an algorithm that incorporates information from meQTLs can predict the presence of CHD in the FCS. We suggest that further studies to replicate and expand the generalizability the approach in cohorts of other ethnicities are indicated. We furthermore suggest that similar approaches may lead to the generation of methylation profiles for other common complex disorders such as stroke.

EXAMPLE 2 REFERENCES

1. Mozaffarian et al., Executive Summary: Heart Disease and Stroke Statistics-2016 Update: A Report From the American Heart Association. *Circulation* 133, 447-454 (2016)
2. Buckley et al., C-reactive protein as a risk factor for coronary heart disease: a systematic review and meta-analyses for the US Preventive Services Task Force. *Ann. Intern. Med.* 151, 483-495 (2009)
3. Auer et al., Association of major and minor ecg abnormalities with coronary heart disease events. *JAMA* 307, 1497-1505 (2012)
4. Paynter et al., Are Genetic Tests for Atherosclerosis Ready for Routine Clinical Use? *Circ. Res.* 118, 607-619 (2016)
5. Mega et al., Genetic risk, coronary heart disease events, and the clinical benefit of statin therapy: an analysis of primary and secondary prevention trials. *The Lancet* 385, 2264-2271
6. Breitling et al., Smoking, F2RL3 methylation, and prognosis in stable coronary heart disease. *Eur. Heart J.* 33, 2841-2848 (2012)
7. Sharma et al., Detection of altered global DNA methylation in coronary artery disease patients. *DNA Cell Biol.* 27, 357-365 (2008)
8. Gluckman et al., Epigenetic mechanisms that underpin metabolic and cardiovascular diseases. *Nat. Rev. Endocrinol.* 5, 401-408 (2009)
9. Monick et al., Coordinated changes in AHRR methylation in lymphoblasts and pulmonary macrophages from smokers. *Am. J Med Genet.* 159B, 141-151 (2012) 3318996.
10. Philibert et al., A pilot examination of the genome-wide DNA methylation signatures of subjects entering and exiting short-term alcohol dependence treatment programs. *Epigenetics* 9, 1-7 (2014)
11. Zeilinger et al., Tobacco smoking leads to extensive genome-wide changes in DNA methylation. *PLoS One* 8, e63812 (2013)
12. Toperoff et al., Genome-wide survey reveals predisposing diabetes type 2-related DNA methylation variations in human peripheral blood. *Hum. Mol. Genet.* 21, 371-383 (2012)
13. Zhang et al., F2RL3 methylation in blood DNA is a strong predictor of mortality. Int. J. Epidemiol. (2014)
14. Zhang et al., Smoking-Associated DNA Methylation Biomarkers and Their Predictive Value for All-Cause and Cardiovascular Mortality. *Environ. Health Perspect.* (2015)
15. Andersen et al., Current and Future Prospects for Epigenetic Biomarkers of Substance Use Disorders. *Genes* 6, 991-1022 (2015)
16. Center for Disease Control. Annual Smoking-Attributable Mortality, Years of Potential Life Lost, and Productivity Losses—United States, 1997-2001. MMWR 54, 625-628 (2005)
17. Yang et al., Evolving methods in genetic epidemiology. III. Gene-environment interaction in epidemiologic research. *Epidemiol. Rev.* 19, 33-43 (1997)
18. Caspi et al., Influence of life stress on depression: moderation by a polymorphism in the 5-HTT gene. *Science* 301, 386-389 (2003)
19. Caspi et al., Role of genotype in the cycle of violence in maltreated children. *Science* 297, 851-854 (2002)
20. Kolassa et al., Association study of trauma load and SLC6A4 promoter polymorphism in posttraumatic stress disorder: evidence from survivors of the Rwandan genocide. *J Clinical Psychiatry* 71, 543-547 (2010)
21. McEwen, Physiology and Neurobiology of Stress and Adaptation: Central Role of the Brain. *Physiol. Rev.* 87, 873-904 (2007)
22. Klengel et al., The role of DNA methylation in stress-related psychiatric disorders. *Neuropharmacology* 80, 115-132 (2014)
23. Philibert et al., The effect of smoking on MAOA promoter methylation in DNA prepared from lymphoblasts and whole blood. *Am. J Med. Genet.* 153B, 619-628 (2010)
24. Philibert et al., MAOA methylation is associated with nicotine and alcohol dependence in women. *Am. J. Med. Genet.* 147B, 565-570 (2008)

25. Shumay et al., Evidence that the methylation state of the monoamine oxidase A (MAOA) gene predicts brain activity of MAOA enzyme in healthy men. *Epigenetics* 7, 10-19 (2012)
26. Beach et al., Child maltreatment moderates the association of MAOA with symptoms of depression and antisocial personality disorder. *J. Fam. Psychol.* 24, 12-20 (2010) 2839928.
27. Dogan et al., Ethnicity and Smoking-Associated DNA Methylation Changes at HIV Co-Receptor GPR15. *Frontiers in psychiatry* 6(2015)
28. Tsaprouni et al., Cigarette smoking reduces DNA methylation levels at multiple genomic loci but the effect is partially reversible upon cessation. *Epigenetics* 9, 1382-1396 (2014)
29. Guida et al., Dynamics of Smoking-Induced Genome-Wide Methylation Changes with Time Since Smoking Cessation. *Hum. Mol. Genet*. (2015)
30. Dawber et al., An approach to longitudinal studies in a community: the Framingham Study. *Ann. N. Y. Acad. Sci.* 107, 539-556 (1963)
31. Mahmood et al., *The Framingham Heart Study* and the epidemiology of cardiovascular disease: a historical perspective. *The Lancet* 383, 999-1008 (2014)
32. Pidsley et al., A data-driven approach to preprocessing Illumina 450K methylation array data. *BMC Genomics* 14, 1-10 (2013)
33. Du et al., lumi: a pipeline for processing Illumina microarray. *Bioinformatics* 24, 1547-1548 (2008)
34. Purcell et al., PLINK: a tool set for whole-genome association and population-based linkage analyses. *The American Journal of Human Genetics* 81, 559-575 (2007)
35. Shabalin, Matrix eQTL: ultra fast eQTL analysis via large matrix operations. *Bioinformatics* 28, 1353-1358 (2012)
36. Beck et al., The use of relative operating characteristic (ROC) curves in test performance evaluation. *Arch. Pathol. Lab. Med.* 110, 13-20 (1986)
37. Philibert et al., A Quantitative Epigenetic Approach for the Assessment of Cigarette Consumption. *Front. Psychol.* 6(2015)
38. Wolke et al., Selective drop-out in longitudinal studies and non-biased prediction of behaviour disorders. *The British Journal of Psychiatry* 195, 249-256 (2009)
39. Philibert et al., The search for peripheral biomarkers for major depression: Benefiting from successes in the biology of smoking. *American Journal of Medical Genetics Part B: Neuropsychiatric Genetics* 165, 230-234 (2014)
40. Garrett et al., Control, C.f.D. & Prevention. *Cigarette smoking-United States,* 1965-2008. *MMWR Surveill. Summ.* 60, 109-113 (2011)
41. Caraballo et al., Self-reported cigarette smoking vs. serum cotinine among U.S. adolescents. *Nicotine & Tobacco Research* 6, 19-25 (2004)
42. Caraballo et al., Factors associated with discrepancies between self-reports on cigarette smoking and measured serum cotinine levels among persons aged 17 years or older: Third National Health and Nutrition Examination Survey, 1988-1994. *Am. J Epidemiol.* 153, 807-814 (2001)
43. Shipton et al., Reliability of self-reported smoking status by pregnant women for estimating smoking prevalence: a retrospective, cross sectional study, (2009).
44. Webb et al., The discrepancy between self-reported smoking status and urine continine levels among women enrolled in prenatal care at four publicly funded clinical sites. *J Public Health Manag. Pract.* 9, 322-325 (2003)
45. Brückmann et al., Validation of differential GDAP1 DNA methylation in alcohol dependence and its potential function as a biomarker for disease severity and therapy outcome. *Epigenetics,* 00-00 (2016)
46. Qiu et al., Variable DNA Methylation Is Associated with Chronic Obstructive Pulmonary Disease and Lung Function. *Am. J Respir. Crit. Care Med.* 185, 373-381 (2012)

EXAMPLE 3

Smoking Associated Methylation Quantitative Trait Loci Preferentially Map to Neurodevelopmental Pathways Smoking is the leading preventable cause of morbidity and mortality in the United States. Smoking exerts its effects indirectly by increasing susceptibility to common complex diseases such as coronary heart disease and coronary obstructive pulmonary disorder. While the association between these disorders and smoking are widely studied, our understanding of the molecular mechanisms through which smoking increasing vulnerability for complex diseases could still be improved. This is especially true for disorders than preferentially involve the central nervous system (CNS). Smoking is a known risk factor for the development of attention deficit hyperactivity disorder and panic disorder. Our study was designed to understand the effects of smoking on DNA methylation in the presence and absence of genetic context in the Framingham Heart Study (FHS). Specifically, data from 1599 individuals from the FHS Offspring cohort were used. These individuals were of European ancestry and were in their early to mid-sixties. The self-reported smoking rate among these individuals was 7.6%. Genome-wide DNA methylation was profiled using the Illumina HumanMethylation 450k BeadChip and the genome-wide SNP data was assessed using the Affymetrix GeneChip HumanMapping 500k Array Set. To understand the effects of smoking on DNA methylation in the absence of genetic variation, we regressed smoking against DNA methylation, controlling for age, gender and batch. After correction for multiple comparisons, methylation status at 525 sites was significant at a 0.05 level. Consistent with prior studies, the top-ranking probe was cg05575921 from the AHRR gene (p-value of $7.65\times10^{155}$). Subsequently, to determine the effects of smoking on DNA methylation in the presence of genetic variation, cis and trans-methylation quantitative trait loci (meQTL) analyses were conducted to determine the significant effects of SNP on DNA methylation given smoking status, controlling for age, gender and batch. A total of 126,369,511 cis and 195,068,554,297 trans analyses were performed. Of those, 5294 (0.00419%) and 422,623 (0.00022%) significant cis- and trans-meQTL were generated after correction for multiple comparisons at a 0.05 significance level. To better visualize and compare the connectivity and gene ontology (GO) enrichment between the results of both analyses, we generated protein-protein interaction (PPI) networks. While the DNA methylation analysis mapped to inflammatory pathways, the cis and trans-meQTL analyses mapped to neurodevelopmental pathways. These neurodevelopmental pathways could provide additional insight into the association of smoking to psychiatric disorders. Furthermore, this study demonstrates that combined genetic and epigenetic analyses may be crucial in better understanding the interplay between environmental variables such as smoking and pathophysiological outcomes.

EXAMPLE 4

Integrated Genetic and Epigenetic Prediction of Coronary Heart Disease in the Framingham Heart Study Abstract Background: Coronary Heart Disease (CHD) is the leading cause of mortality and morbidity in the United States. Unfortunately, the first sign of CHD for some patients is a fatal myocardial infarction. A sensitive method for detecting current CHD or risk for future cardiac events could prevent some of this mortality, but current biomarkers for asymptomatic CHD are both insensitive and non-specific. Recently, others and we have shown that array based DNA methylation assessments accurately predict the degree of cigarette consumption and the smoking associated risk for CHD. However, attempts to extract additional risk for CHD information from these genome wide assessments have not yet been successful.

Methods and Results: Building on the idea that CHD risk factors are a conglomeration of genetic and environmental factors, we use machine learning techniques and integrate genetic, epigenetic and phenotype data (n=2214) from the Framingham Heart Study to build and test a Random Forest™ classification model for risk for CHD. Our final classifier, was trained on n=1545 individuals and utilized four DNA methylation sites, two SNPs, age and gender, and was capable of predicting CHD status with 78% accuracy in the test set (n=669) and a sensitivity and specificity of 0.75 and 0.80, respectively. In contrast, a model using only CHD risk factors as predictors had an accuracy and sensitivity of only 65% and 0.41, respectively. The specificity was 0.89. Regression analyses of the individual clinical risk factors highlight the strong role of pathways moderated by smoking in CHD pathogenesis.

Conclusions: This study demonstrates the capability of integrated approaches for predicting symptomatic CHD status and suggests that further work could lead to the introduction of a sensitive, readily employable method for detecting asymptomatic CHD.

Introduction

Coronary Heart Disease (CHD) is the leading cause of death in United States.[1] Effective methods to prevent this mortality and the accompanying morbidity exist, but they are often employed ineffectively. In fact, sudden cardiac death is the initial presentation in 15% of patients with CHD.[2, 3]

In efforts to more effectively detect and treat CHD, a number of screening methods for both symptomatic (angina, myocardial infarction) and asymptomatic CHD have been developed. For asymptomatic patients, the intensity of the screening for CHD depends on the level of clinical suspicion. Though clinicians are wary of the potential for cardiac disease at any age, increased attention is paid to individuals with the classic risk factors for CHD defined in the Framingham Heart Study (FHS) including family history of CHD, smoking, elevated systolic blood pressure, diabetes, or anything resembling angina-like chest pain.[4,5] Depending on the level of suspicion for CHD, the initial examination typically includes a complete physical exam and a fasting lipid panel that includes low density lipoprotein (LDL), high density lipoprotein (HDL) and triglyceride levels.[5] The next level of response is normally an electrocardiogram (ECG) followed by more costly and invasive measures including stress testing and cardiac angiography.[6]

Sadly, the most clinically routine tests, the 12 lead ECG and serum lipid screening, are remarkably insensitive for CHD. For example, in a study of 479 patients admitted for acute chest pain with creatine kinase-MB isoenzyme (CK-MB) and troponin T (TnT) confirmed MI, 12 lead ECG were positive only 33% and 28% at admission and post-admission, respectively.[7] Likewise, serum lipid (cholesterol and triglyceride) screening has been employed for many years. Most relevantly, in the Framingham Heart Study (FHS), using a cutoff of 260 mg/dl, elevated serum cholesterol levels performed at intake failed to identify ⅔ of all the males who developed CHD over the subsequent four years. Hence, for the past decade there has been an increasing call for biomarkers for the prediction and diagnosis of CHD.

Spurred by the lack of sensitivity and specificity of standard procedures such as the ECG and lipid profile, a large number of investigators have attempted to identify biomarkers of asymptomatic CHD and cardiovascular disease (CVD), its closely related disease cluster. Although a variety of approaches, including imaging, mechanical and bio-electrical techniques have been used,[8-10] the vast majority of investigators have focused on blood based methods because of the 1) proof of principal provided by prior work with triglycerides and cholesterol, 2) clear involvement of blood components such as platelets and white blood cells in CHD and CVD pathogenesis and 3) the ease of integrating blood based approaches into current medical diagnostics.

The majority of these blood-based approaches have focused on circulating lipids and proteins (for review see[11, 12]) such as hemoglobin A1C (HbA1c), fibrinogen, vitamin D, C-reactive protein (CRP), apolipoprotein B (ApoB), apolipoprotein AI (ApoAI), and cholesterol (including high density and low density, HDL and LDL). When the appropriate cutoffs are employed in research settings, each of these markers is modestly informative (Odds or Relative Ratios of 1.5 to 2.5) with respect to the development of future illness.[11] In addition, for those with pre-existing disease, cardiac troponin (cTn) levels and high sensitivity (HsCRP) ratios can be informative about future risk.[11] However, each of these markers has challenges to their clinical implementation, such as lack of ease of measurement, ethnic variation or limitations in scope of prediction, that have precluded their routine implementation in CHD screening.

Seeking alternative means of creating more effective screening procedures, other investigators have used genetic procedures to identify risk associated variation including more recent genome wide association (GWAS) and exome/genome sequencing studies (Please see O'Donnell and Nabel, 2011 for review).[13] To date, these studies have isolated approximately 10% of the total genetic risk for CHD.[14, 15] Notably, many of these SNPs map to lipid and inflammation pathways, both of which are known to be important from prior studies of CHD.[15] Although these studies can predict who is potentially vulnerable to CHD, they do not actually indicate whether an individual has CHD and meta-analyses indicate that at best the contribution of pure genetic approaches to the prediction of CHD will be minimal.[16] As such, genetic approaches have not been incorporated into routine clinical practice.

Epigenetic approaches may provide a new avenue for assessing risk for CHD. It is already well established that epigenetic approaches can quantitatively assess cigarette consumption which may be the largest preventable cause of CHD.[17, 18] Notably, Hermann Brenner and colleagues have shown that DNA methylation at cg03636183 predicts not only smoking status but risk for MI.[19, 20] Unfortunately, the risk for CHD and smoking are not independent with their group also showing that the risk for MI connoted by cg03636183 is fully subsumed by smoking status as denoted by methylation at cg05575921, the best established epigenetic biomarker for smoking in all ethnic groups.[17, 21]

Critical to the current work is the observation that one of the reasons that methylation status markers such as cg03636183 and GPR15 marker cg19859270[22, 23] do not predict smoking status well in all populations is the presence of genetic confounding of methylation changes by local genetic variation.[22] Over the past several years, our understanding of these effects, which were originally described as relatively static interactions (GxMeth),[24] has been modified to show that a subset of these interactions can be contextual on the degree of smoking exposure.[22, 25, 26] In essence, these and other findings demonstrate that at the single locus level, methylation response to smoking can be better conceptualized as a product of both the degree of smoking exposure and genetic variation. These interaction effects appear to be widespread. Using a genome wide approach, we have recently shown these smoking contextual genetic effects on DNA methylation on a genome wide basis and have shown that nearly ¼ of all genes harbor genetically contextual changes in methylation in response to smoking (Dogan et al., in submission).

As opposed to the more easily conceptualized response of a single facet of the methylome to a single environmental factor (smoking), the entirety of the biological response of the peripheral white blood cells (WBC) to the diverse factors that contribute to CHD is likely to be more complex and difficult to reproducibly capture. For example, at the RNA level, significant signatures for micro-RNA[27, 28] and mRNA[29] prepared from blood have been described, but clear utility as clinical tools has not yet come to fruition. Still, their partial success to date indicates that nucleic acids prepared from peripheral WBC possess a larger biological signature that could be harvested through a more systematic approach.

In that hope, we detail the results of an integrated approach that incorporates commonly used machine learning algorithms in combination with both genome wide epigenetic and genetic data from the Framingham Heart Study.

Methods

Framingham Heart Study. The Framingham Heart Study (FHS) has been described in detail elsewhere.[30, 31] The clinical, genetic and epigenetic data included in this study is from the Offspring cohort. Specifically, this study included 2,741 of the 5,124 individuals in the Offspring cohort who 1) survived till the eighth examination cycle which was conducted between 2005 and 2008, 2) consented to genetics research, and 3) have peripheral blood genome-wide DNA methylation data. The FHS data was obtained through dbGAP (https://dbgap.ncbi.nlm.nih.gov). The University of Iowa Institutional Review Board approved all described analyses.

Genome Wide DNA Methylation. After removing duplicates, DNA methylation data was available for 2,567 individuals. Genome wide DNA methylation of the Offspring cohort was profiled using the Illumina Infinium HumanMethylation450 BeadChip[32] (San Diego, Calif.) array at either University of Minnesota or Johns Hopkins University. The 485,577 probes in this array cover 99% of RefSeq genes with an average of 17 CpG sites per gene within and outside of CpG islands.[32]

Probe filtering, background correction and adjustment for probe types were performed on the methylation intensity data (IDAT) files using the MethyLumi, WateRmelon and IlluminaHumanMethylation450k.db R packages.[33] Quality control was performed on the sample and probe levels. For samples, those with >1% CpG sites with a detection p-value >0.05 were removed while CpG sites with a bead count <3 and/or >1% samples with a detection p-value >0.05 were removed. After quality control, 2,560 unique samples and 484,125 CpG sites remained. Of those CpG sites, 472,822 mapped to autosomes. Due to the bounded nature of methylation beta values (0<=beta<=1), logistic transformation of beta values to M-values was conducted (−inf<M-value<inf) using the beta2m R package, and subsequently converted to z-scores using an R script.[34]

Genome Wide Genotype. Genome wide SNP data was profiled using the Affymetrix GeneChip HumanMapping 500K (Santa Clara, Calif.) array. Of the 2,560 individuals remaining after DNA methylation quality control, 2,406 (1,100 males and 1,306 females) had genotype data. Again, quality control was performed at the sample and probe levels. Using PLINK[35], samples were examined for discordant sex information, heterozygosity rate greater or smaller than two standard deviations from the mean, and proportion of missing SNPs >0.03. As a result, a total of 111 samples were removed. Population stratification was also performed and no individuals were excluded. Samples were also excluded if their identity by descent value was >0.1875, which is halfway in between second and third degree relatives to ensure that downstream analyses were not influenced by related individuals. As a result of this criterion, a total of 696 individuals were removed, leaving 1599 subjects (722 males and 877 females) for further analyses. Probes were retained if the minor allele frequency was >1%, the Hardy-Weinberg equilibrium p-value was $>10^{-5}$ and the missing rate was <5%. After quality control, 403,192 SNPs remained (472,822 mapped to autosomes). SNPs were coded as 0, 1, 2 per minor allele frequency.

Phenotypes. For each individual, the following data were extracted from the FHS dataset: age, gender, systolic blood pressure (SBP), high-density lipoprotein (HDL) cholesterol level, total cholesterol level, hemoglobin A1C (HbA1c) level, self-reported smoking status, CHD status and date of CHD established.

Data analysis. To identify CHD and conventional modifiable CHD risk factors associated genome wide DNA methylation changes, linear regression analyses were conducted in R as delineated in Equation 1:

$$\text{Meth}_1 \alpha \text{Age}+\text{Gender}+\text{Batch}+X \quad (1)$$

where X represents CHD or conventional modifiable CHD risk factors: SBP, smoking, HDL, total cholesterol and diabetes. Batch represented the DNA methylation laboratory batch.

The association between DNA methylation and CHD or each of the risk factors was determined while controlling for age, gender and batch effects. Bonferroni correction for multiple comparisons at a genome-wide $\alpha=0.05$ was performed for every regression analysis.[36] For each X, a total of 472,822 independent tests were conducted and therefore, only those with a nominal p-value of 1e-07 (0.05/472822) were considered to be significantly associated at the genome wide level.

Network Analysis: A network was generated and Gene Ontology (GO) pathways were identified using STRING Version 10 for symptomatic CHD.[37] The STRING database contains information on known and predicted physical (direct) and functional (indirect) associations between proteins. The network included genes with at least one significant main effect DNA methylation locus after genome wide Bonferroni correction for multiple comparisons. Networks were further reduced to include only nodes (proteins) with edges (interactions) with the highest confidence interaction scores of 0.9 or greater. The PPI figure includes nodes with at least one edge. STRING Version 10 was also used to determine the GO enrichment pathways of the network.

Training and Testing Datasets. The goal of this study was to develop an integrated genetic-epigenetic classifier to predict symptomatic CHD. To achieve this, training and testing datasets were prepared. As mentioned previously after DNA methylation and SNP quality control, 1599 subjects remained. However, based on the CHD status and eighth examination cycle dates, the number of individuals reduced from 1599 to 1545 (694 males and 851 females) and these individuals constituted the training set.

To assess the generalizability of the trained model, data from the 696 individuals removed due to relatedness (identity by descent >0.1875) were used. Similar to the individuals in the training dataset, the CHD status and the eighth examination cycle dates of the individuals in the test dataset were compared to ensure that only those with a CHD status date less than or equal to the eighth examination cycle date are retained. From doing so, the number of individuals in the test set reduced from 696 to 669 (314 males and 355 females).

Variable Reduction. The total number of genetic (SNP) and epigenetic (DNA methylation) probes remaining after quality control measures were 403,192 and 472,822, respectively. Due to the large number of variables (876,014 total, excluding phenotypes), we reduced the search space and minimized redundancy in the predictors as described below.

Linkage disequilibrium based SNP pruning was performed in PLINK[35] with a window size of 50 SNPs, window shift of 5 SNPs and a pairwise SNP-SNP LD threshold of 0.5. This reduced the number of SNPs from 403,192 to 161,474. To further reduce the number of SNPs, the chi-squared p-value was calculated between the remaining 161, 474 SNPs and CHD status. Those with a chi-squared p-value <0.1 were retained for model training, resulting in 17,532 SNPs (~4%).

To reduce the number of DNA methylation loci, first, the correlation was calculated between the 472,822 CpG sites and CHD status. CpG sites were retained if the point bi-serial correlation was at least 0.1. A total of 138,815 CpG sites remained. Subsequently, Pearson correlation between those 138,815 sites was calculated. If the Pearson correlation between two loci was at least 0.8, the loci with a smaller point bi-serial correlation was discarded. In the end, 107,799 DNA methylation loci (~23%) remained for model training.

Class Imbalance. Among the 1545 individuals in the training dataset, only 173 were diagnosed with symptomatic CHD. Therefore, the ratio of those with to those without symptomatic CHD is approximately 1:8 (173:1372). This means that if data from all 1545 individuals were to be utilized simultaneously, the baseline prediction accuracy where if all individuals are classified as not having CHD (majority class) will be ~89% (1372/1545). This depicts the major class imbalance in this dataset, which is quite common in medical datasets. It also suggests that accuracy would not be the ideal performance metric. To deal with class imbalance, under-sampling of those without CHD was performed.[38] The 1372 individuals without CHD were randomly assigned to eight datasets: 4 with 171 individuals and 4 with 172 individuals, totaling to 1372 individuals. All eight datasets also consisted of the same 173 individuals with CHD, which now balances the classes in each of the eight datasets to a 1:1 ratio (i.e. a 50% baseline accuracy).

Similarly, among the 669 test set individuals, only 71 were diagnosed with CHD, depicting class imbalance. Therefore, 71 individuals without CHD were randomly chosen to ensure the ratio between cases and controls was 1:1.

Model Training and Testing. Using a stratified 10-fold cross-validation approach, Random Forest™ (RF)[39] classification models were built independently using scikit-learn in Python[40] on all eight datasets consisting of genetic, epigenetic and phenotype data. SNPs with smaller chi-squared p-value and methylation sites with a larger correlation with respect to CHD were fed systematically to the model. Feature importance, accuracy and AUC of RF classifiers were used to select important variables for prediction. A grid search was employed to perform 10-fold cross-validation hyper-parameter tuning of the models. The performance metrics of the models were determined. The final model was saved for testing on the test dataset.

To compare the performance of our integrated genetic-epigenetic model to a model with conventional CHD risk factors as predictors, a similar approach was employed to build the model on the training data and subsequently test it on the test dataset.

An alternative approach was implemented in R using the RandomForest™ package. The "strata" and "sampsize" arguments were used to perform stratified sampling of the minority class. This is a simpler implementation of the undersampling approach described above. The number of trees (ntree) parameter of this alternative RF classifier was tuned. The same n=1545 training set and n=142 testing set were used to train and test this classifier.

Results

The clinical characteristics of the 1545 subjects used in the primary analyses in this study are given in Table 4. There were more females (n=851) than males (n=694) and they were all of Northern European ancestry. A total of 115 males (~17%) and 58 females (~7%) were diagnosed with symptomatic CHD. Those with symptomatic CHD on average tended to be older, in their early 70s, as opposed to those without symptomatic CHD who tended to be in their mid-60s.

TABLE 4

Demographic and CHD risk factors of 1545 individuals

| | CHD | No CHD |
|---|---|---|
| Gender (count) | | |
| Male | 115 | 579 |
| Female | 58 | 793 |
| Age (years) | | |
| Male | 71.1 ± 7.4 | 66.4 ± 8.5 |
| Female | 73.0 ± 8.7 | 66.4 ± 8.6 |
| Total Cholesterol (mg/dL) | | |
| Male | 154 ± 33 | 176 ± 33 |
| Female | 172 ± 35 | 199 ± 36 |

TABLE 4-continued

| Demographic and CHD risk factors of 1545 individuals | | |
|---|---|---|
| | CHD | No CHD |
| HDL Cholesterol (mg/dL) | | |
| Male | 45 ± 12 | 50 ± 14 |
| Female | 59 ± 17 | 65 ± 19 |
| HbA1c (%) | | |
| Male | 6.0 ± 0.9 | 5.7 ± 0.8 |
| Female | 6.0 ± 0.9 | 5.7 ± 0.5 |
| SBP (mmHg) | | |
| Male | 128 ± 19 | 130 ± 17 |
| Female | 135 ± 18 | 129 ± 18 |
| cg05575921 (z-score) | | |
| Male | −0.15 ± 1.19 | −0.07 ± 1.05 |
| Female | −0.12 ± 1.11 | 0.08 ± 0.92 |
| Smoker (count) | | |
| Male | 12 (10%) | 39 (7%) |
| Female | 2 (3%) | 64 (8%) |

SBP: systolic blood pressure
HbA1c: Hemoglobin A1c

The average HDL and total cholesterol levels were higher among females and those without symptomatic CHD. All total cholesterol averages were <200 mg/dL, but only females without symptomatic CHD had an HDL cholesterol level >60 mg/dL. More importantly, the ratio between the averages of HDL and total cholesterol were 1:3.4 and 1:3.5 for males with and without symptomatic CHD, respectively, and, 1:2.9 and 1:3.1 for females with and without symptomatic CHD, respectively. The target ratio between total and HDL cholesterol for cardiovascular disease prevention for men is <4.5 and <4.0 for women.[41]

Those diagnosed with symptomatic CHD had a higher HbA1c level (6%), on average, than those not diagnosed with symptomatic CHD (5.7%). However, while females with CHD had higher SBP than those without, the opposite was true for males. All SBP averages were larger than 120 mmHg.

Another well-known risk factor for CHD is smoking. Based on self-reported current smoking status, among the men, but not the women, proportionately there were more smokers with symptomatic CHD than without symptomatic CHD. However, methylation status at the smoking biomarker (cg05575921) indicates that both men and women with symptomatic CHD actually smoke more often than those without symptomatic CHD.

Regression Analyses. As a first step of the analyses, the CHD status of the 1545 subjects was regressed against age, gender, cg05575921, SBP, HDL cholesterol, total cholesterol, and percent HbA1c. The summary of the regression outputs with respect to each risk factor is shown in Table 5. The analyses suggest that all conventional risk factors except SBP and HDL cholesterol are significantly associated with CHD status at a 0.05 significance level. More importantly, the trend of slopes suggest that symptomatic CHD is more prevalent in 1) males, 2) older individuals, 3) those with lower total cholesterol, 4) those de-methylated

TABLE 5

Regression parameters of risk factors of CHD against symptomatic CHD

| Risk Factor | Beta | Standard Error | t-statistic | p-value |
|---|---|---|---|---|
| Gender | −0.0506 | 0.0173 | −2.933 | 3.41e−03 |
| Age | 0.0063 | 0.0009 | 6.670 | 3.57e−11 |
| SBP | −0.0006 | 0.0005 | −1.376 | 1.69e−01 |
| HDL Cholesterol | −0.0004 | 0.0005 | −0.890 | 3.73e−01 |
| Total Cholesterol | −0.0014 | 0.0002 | −5.889 | 4.75e−09 |
| cg05575921 | −0.0149 | 0.0077 | −1.932 | 5.36e−02 |
| HbA1c | 0.0465 | 0.0116 | 4.003 | 6.56e−05 |

SBP: systolic blood pressure
HbA1c: Hemoglobin A1c

As the next step, we conducted regression analyses of the relationship of symptomatic CHD to genome wide DNA methylation. After Bonferroni correction, 11,497 methylation sites (2.4%) remained significantly associated with symptomatic CHD. These methylation sites mapped to 6,319 genes. The top 30 sites are shown in Table 6. All significant sites are provided in FIG. 16.

TABLE 6

Top 30 significant CpG sites associated with symptomatic CHD

| CpG | Beta | Gene | Position | Island Status | Corrected p-value* |
|---|---|---|---|---|---|
| cg26910465 | 6.48E−01 | ADAL | TSS200 | Island | 8.01E−18 |
| cg13567813 | 6.60E−01 | NR1H2 | TSS200 | Island | 2.05E−17 |
| cg09238957 | 5.98E−01 | ORC6L | TSS200 | Island | 7.97E−17 |
| cg04099813 | 6.12E−01 | TSSC4 | TSS1500 | S_Shore | 1.45E−16 |
| cg07546106 | 6.29E−01 | TAP2 | 5'UTR | N_Shore | 2.40E−16 |
| cg20808462 | 6.01E−01 | HAUS3 | 5'UTR | Island | 5.42E−16 |
| cg16968115 | 5.92E−01 | WDTC1 | TSS200 | Island | 1.25E−15 |
| cg24475210 | 5.84E−01 | MRFAP1 | TSS200 | Island | 1.26E−15 |
| cg03031660 | 5.84E−01 | MRPS7 | 1stExon | Island | 1.45E−15 |
| cg22605179 | 5.97E−01 | EWSR1 | 5'UTR | Island | 3.81E−15 |
| cg02357877 | 5.71E−01 | GBAS | TSS1500 | Island | 4.04E−15 |
| cg22111723 | 5.65E−01 | | | Island | 4.57E−15 |
| cg06117184 | 5.67E−01 | CKAP2L | 1stExon | Island | 4.87E−15 |
| cg07478100 | 5.85E−01 | MIS12 | TSS1500 | Island | 5.36E−15 |
| cg15318396 | 5.83E−01 | | | Island | 5.52E−15 |
| cg00544901 | 5.76E−01 | RPS11 | TSS1500 | Island | 5.62E−15 |
| cg24478630 | 5.88E−01 | MOGS | TSS200 | S_Shore | 5.65E−15 |
| cg04022019 | 5.90E−01 | DCAF13 | 1stExon | Island | 5.86E−15 |
| cg12124516 | 5.81E−01 | MCM6 | TSS200 | Island | 6.41E−15 |
| cg20935862 | 5.96E−01 | C9orf41 | TSS1500 | Island | 6.62E−15 |
| cg07377675 | 6.00E−01 | USP1 | TSS200 | Island | 7.79E−15 |
| cg07734253 | 5.83E−01 | CORO1A | TSS1500 | N_Shore | 8.16E−15 |
| cg03699307 | 5.94E−01 | GABARAPL2 | TSS1500 | Island | 8.44E−15 |

TABLE 6-continued

Top 30 significant CpG sites associated with symptomatic CHD

| CpG | Beta | Gene | Position | Island Status | Corrected p-value* |
|---|---|---|---|---|---|
| cg17360140 | 5.79E−01 | C4orf29 | TSS1500 | Island | 9.10E−15 |
| cg25632648 | 6.06E−01 | KCTD21 | TSS200 | Island | 9.83E−15 |
| cg06339248 | 5.83E−01 | ZDHHC5 | 5'UTR | Island | 1.10E−14 |
| cg24275354 | 6.24E−01 | NDUFA10 | Body | N_Shore | 1.52E−14 |
| cg25261764 | 5.93E−01 | NARS | 1stExon | Island | 1.69E−14 |
| cg14172283 | 5.83E−01 | TOMM5 | 1stExon | Island | 2.00E−14 |
| cg01089095 | 5.69E−01 | CHCHD1 | TSS200 | Island | 2.02E−14 |

*All nominal p-values were adjusted for multiple comparisons by the Bonferroni method.

Figure 3:
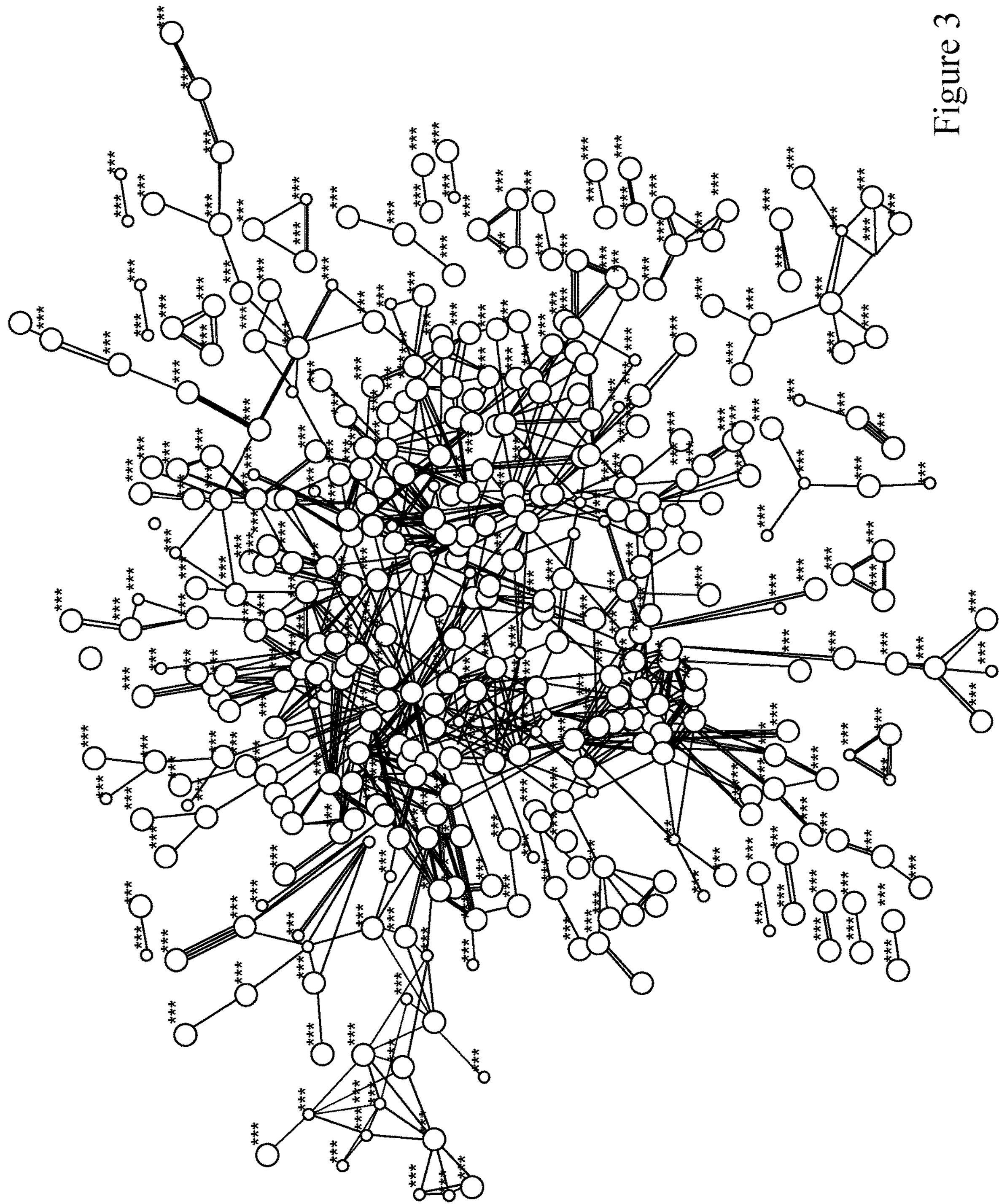
FIG. 3. Protein Protein Interactome of CHD. Network of top 1000 genes with at least one DNA methylation probe significantly associated with symptomatic CHD.

Due to the large number of genes, network and functional enrichment analyses of the network were performed using data from the top 1000 genes. The network consisted of 952 proteins represented by the nodes and 1,144 interactions represented by the edges. The expected number of edges was 634 with a PPI enrichment p-value of 0, suggesting that interactions between the proteins in the network are likely to have biological relevance. The average node degree and clustering coefficient were 2.4 and 0.85, respectively. This network is depicted in FIG. 3. The top 10 pathways of this network are shown in Table 7.

TABLE 7

Top 10 significant PPI network pathways associated with symptomatic CHD

| GO Pathway ID | Pathway Description | Observed Gene Count | False Discovery Rate |
|---|---|---|---|
| GO.0044260 | cellular macromolecule metabolic process | 414 | 4.53E−18 |
| GO.0043170 | macromolecule metabolic process | 435 | 6.54E−17 |
| GO.0044237 | cellular metabolic process | 476 | 5.41E−16 |

TABLE 7-continued

Top 10 significant PPI network pathways associated with symptomatic CHD

| GO Pathway ID | Pathway Description | Observed Gene Count | False Discovery Rate |
|---|---|---|---|
| GO.0006807 | nitrogen compound metabolic process | 351 | 8.54E−16 |
| GO.0034641 | cellular nitrogen compound metabolic process | 335 | 8.54E−16 |
| GO.0010467 | gene expression | 275 | 5.07E−15 |
| GO.0044238 | primary metabolic process | 474 | 1.64E−14 |
| GO.0090304 | nucleic acid metabolic process | 273 | 1.64E−14 |
| GO.0008152 | metabolic process | 516 | 2.97E−14 |
| GO.0071704 | organic substance metabolic process | 481 | 3.55E−14 |

PPI: protein-protein interaction

From the regression analyses, there were 44,108 (9.3%), 0, 32, 51 and 6 methylation sites significantly associated with cg05575921, SBP, HDL cholesterol, total cholesterol and HbA1c, respectively. The top results for cg05575921, HDL, total cholesterol and HbA1c analyses are given in Table 8 through Table 11.

TABLE 8

Top 30 significant CpG sites associated with cg05575921 after Bonferroni correction

| CpG | Beta | Gene | Position | Island Status | Corrected p-value* |
|---|---|---|---|---|---|
| cg21566642 | 7.10E−01 | | | Island | 2.74E−227 |
| cg03636183 | 7.01E−01 | F2RL3 | Body | N_Shore | 1.01E−223 |
| cg05951221 | 6.91E−01 | | | Island | 1.34E−208 |
| cg01940273 | 6.68E−01 | | | Island | 1.18E−196 |
| cg25648203 | 5.57E−01 | AHRR | Body | | 2.08E−119 |
| cg21161138 | 5.37E−01 | AHRR | Body | | 7.19E−113 |
| cg06126421 | 5.05E−01 | | | | 6.74E−108 |
| cg09935388 | 5.02E−01 | GFI1 | Body | Island | 2.91E−94 |
| cg06644428 | 4.85E−01 | | | Island | 7.76E−85 |
| cg15342087 | 4.73E−01 | | | | 1.44E−81 |
| cg03329539 | 4.61E−01 | | | N_Shore | 2.30E−76 |
| cg23079012 | 4.62E−01 | | | | 2.47E−76 |
| cg11660018 | 4.42E−01 | PRSS23 | TSS1500 | N_Shore | 1.15E−74 |
| cg23916896 | 4.31E−01 | AHRR | Body | N_Shore | 3.99E−65 |
| cg12876356 | 4.34E−01 | GFI1 | Body | Island | 4.30E−65 |
| cg05284742 | 4.27E−01 | ITPK1 | Body | | 2.41E−64 |
| cg19859270 | 4.29E−01 | GPR15 | 1stExon | | 7.30E−64 |
| cg14817490 | 4.24E−01 | AHRR | Body | | 7.27E−62 |
| cg26361535 | 4.22E−01 | ZC3H3 | Body | | 1.18E−61 |
| cg03991871 | 4.19E−01 | AHRR | Body | N_Shore | 1.19E−60 |
| cg26703534 | 4.15E−01 | AHRR | Body | S_Shelf | 5.17E−60 |
| cg24859433 | 3.95E−01 | | | | 1.24E−58 |
| cg12806681 | 4.08E−01 | AHRR | Body | N_Shore | 1.53E−56 |
| cg23771366 | 4.01E−01 | PRSS23 | TSS1500 | N_Shore | 2.12E−56 |

TABLE 8-continued

| Top 30 significant CpG sites associated with cg05575921 after Bonferroni correction | | | | | |
|---|---|---|---|---|---|
| CpG | Beta | Gene | Position | Island Status | Corrected p-value* |
| cg18146737 | 3.99E−01 | GFI1 | Body | Island | 2.59E−53 |
| cg13193840 | 3.93E−01 | | | Island | 1.03E−52 |
| cg27241845 | 3.73E−01 | | | N_Shore | 9.87E−52 |
| cg21322436 | 3.76E−01 | CNTNAP2 | TSS1500 | N_Shore | 2.94E−51 |
| cg25189904 | 3.89E−01 | GNG12 | TSS1500 | S_Shore | 1.23E−50 |
| cg04517079 | 3.83E−01 | FOXP4 | Body | | 5.18E−50 |

*All nominal p-values were adjusted for multiple comparisons by the Bonferroni method.

TABLE 9

| All 32 significant CpG sites associated with HDL cholesterol after Bonferroni correction | | | | | |
|---|---|---|---|---|---|
| CpG | Beta | Gene | Position | Island Status | Corrected p-value* |
| cg06500161 | −1.38E−02 | ABCG1 | Body | S_Shore | 1.63E−14 |
| cg17901584 | 1.33E−02 | DHCR24 | TSS1500 | S_Shore | 3.39E−13 |
| cg06560379 | 1.30E−02 | NFKBIE | Body | N_Shore | 2.36E−12 |
| cg12394289 | 8.78E−03 | EHMT2 | Body | N_Shore | 1.84E−04 |
| ch.14.1488981R | 8.94E−03 | RIN3 | Body | | 1.93E−04 |
| cg02076355 | 9.36E−03 | C10orf10 | TSS200 | | 2.39E−04 |
| cg03717755 | −9.16E−03 | MYLIP | Body | | 4.34E−04 |
| cg10375409 | −8.79E−03 | CD247 | Body | N_Shelf | 2.00E−03 |
| cg21669326 | 8.76E−03 | | | | 2.06E−03 |
| cg21139312 | −7.73E−03 | MSI2 | Body | | 2.36E−03 |
| cg11666534 | 8.60E−03 | IGLL1 | TSS200 | | 3.10E−03 |
| cg00144180 | −7.52E−03 | HDAC4 | 5'UTR | | 3.87E−03 |
| cg03078551 | 8.75E−03 | | | | 4.19E−03 |
| cg15878619 | 8.45E−03 | TUBB | TSS1500 | N_Shore | 4.48E−03 |
| cg25757877 | −8.58E−03 | UBE2O | Body | | 4.96E−03 |
| cg21205288 | −8.33E−03 | | | | 5.04E−03 |
| cg04557677 | 8.03E−03 | JAK3 | TSS1500 | S_Shore | 5.20E−03 |
| cg26313301 | −8.68E−03 | LDLR | Body | S_Shelf | 7.79E−03 |
| cg03290131 | 8.22E−03 | DUSP5 | Body | | 8.43E−03 |
| cg15989436 | 8.21E−03 | | | | 8.75E−03 |
| ch.2.207814544R | 7.97E−03 | | | | 1.12E−02 |
| cg08105590 | 8.28E−03 | FAM38A | Body | N_Shore | 1.21E−02 |
| cg18407309 | 7.88E−03 | CCL3 | TSS200 | | 1.52E−02 |
| ch.2.11889418R | 7.80E−03 | | | | 1.99E−02 |
| cg06007201 | 7.88E−03 | FAM38A | Body | Island | 2.06E−02 |
| cg00218409 | 8.13E−03 | | | | 2.37E−02 |
| cg13134297 | 8.08E−03 | | | | 2.86E−02 |
| cg04605590 | 7.69E−03 | | | | 2.97E−02 |
| cg03068497 | 8.02E−03 | GARS | Body | S_Shore | 3.24E−02 |
| cg21812670 | 8.15E−03 | SNORD45C | TSS1500 | | 3.53E−02 |
| ch.1.171672612F | 7.65E−03 | | | | 3.55E−02 |
| cg00004667 | 7.95E−03 | ZBTB17 | 5'UTR | | 4.11E−02 |

*All nominal p-values were adjusted for multiple comparisons by the Bonferroni method.

TABLE 10

| Top 30 significant CpG sites associated with total cholesterol after Bonferroni correction | | | | | |
|---|---|---|---|---|---|
| CpG | Beta | Gene | Position | Island Status | Corrected p-value* |
| cg17901584 | 6.14E−03 | DHCR24 | TSS1500 | S_Shore | 6.96E−12 |
| cg11840035 | −4.70E−03 | | | | 1.01E−05 |
| cg15989436 | 4.29E−03 | | | | 3.71E−04 |
| cg15428620 | 4.16E−03 | SFXN3 | Body | S_Shore | 8.57E−04 |
| cg16460860 | 4.31E−03 | | | S_Shore | 9.63E−04 |
| cg24405567 | 4.18E−03 | | | | 1.06E−03 |
| cg27407935 | 4.22E−03 | SREBF1 | Body | N_Shelf | 1.89E−03 |

TABLE 10-continued

Top 30 significant CpG sites associated with total cholesterol after Bonferroni correction

| CpG | Beta | Gene | Position | Island Status | Corrected p-value* |
|---|---|---|---|---|---|
| cg25536676 | 4.14E−03 | DHCR24 | TSS1500 | Island | 2.30E−03 |
| cg02560388 | 4.22E−03 | | | | 2.38E−03 |
| cg01400685 | 4.08E−03 | FADS2 | Body | S_Shore | 2.91E−03 |
| cg05932360 | 4.13E−03 | JARID2 | Body | | 2.98E−03 |
| cg04804052 | 4.14E−03 | SMARCA4 | TSS200 | N_Shelf | 3.15E−03 |
| cg01234420 | 3.80E−03 | LOC150381 | Body | N_Shelf | 4.03E−03 |
| cg22011731 | 3.95E−03 | SQLE | 1stExon | S_Shore | 4.27E−03 |
| cg21593001 | 4.05E−03 | DTX1 | Body | Island | 4.49E−03 |
| cg14208102 | 3.88E−03 | TREX1 | TSS200 | | 5.22E−03 |
| cg08690876 | 4.14E−03 | CYB5R3 | 5'UTR | | 5.33E−03 |
| cg25114611 | 4.05E−03 | FKBP5 | TSS1500 | S_Shore | 6.72E−03 |
| cg03113867 | 3.91E−03 | | | | 7.17E−03 |
| cg20519581 | 4.00E−03 | | | N_Shore | 8.11E−03 |
| cg11071448 | 3.98E−03 | SYT2 | 5'UTR | | 9.33E−03 |
| cg14254720 | 3.99E−03 | LRRC8C | TSS1500 | N_Shore | 1.07E−02 |
| cg21645268 | 3.96E−03 | FDFT1 | Body | N_Shelf | 1.12E−02 |
| cg21443274 | −4.10E−03 | ZFPM2 | Body | | 1.18E−02 |
| cg03440556 | 4.04E−03 | SCD | Body | S_Shore | 1.40E−02 |
| cg09682727 | 3.67E−03 | | | | 1.69E−02 |
| cg21108085 | 3.92E−03 | CD82 | 5'UTR | S_Shelf | 1.73E−02 |
| cg22164009 | 3.89E−03 | | | | 1.77E−02 |
| cg03611151 | 3.72E−03 | CNR2 | 5'UTR | S_Shore | 1.93E−02 |
| cg19696333 | −3.06E−03 | IKZF5 | 5'UTR | Island | 2.27E−02 |

*All nominal p-values were adjusted for multiple comparisons by the Bonferroni method.

TABLE 11

All 6 significant CpG sites associated with HbA1c after Bonferroni correction

| CpG | Beta | Gene | Position | Island Status | Corrected p-value* |
|---|---|---|---|---|---|
| cg19693031 | −3.63E−01 | TXNIP | 3'UTR | | 1.84E−17 |
| cg17901584 | −2.67E−01 | DHCR24 | TSS1500 | S_Shore | 2.65E−07 |
| cg06500161 | 2.31E−01 | ABCG1 | Body | S_Shore | 2.21E−04 |
| cg02420024 | −2.31E−01 | OCA2 | Body | | 3.08E−04 |
| cg04143120 | −2.20E−01 | | | | 2.39E−03 |
| cg04311230 | 2.05E−01 | SOD2 | TSS1500 | Island | 2.08E−02 |

*All nominal p-values were adjusted for multiple comparisons by the Bonferroni method.

Figure 4:
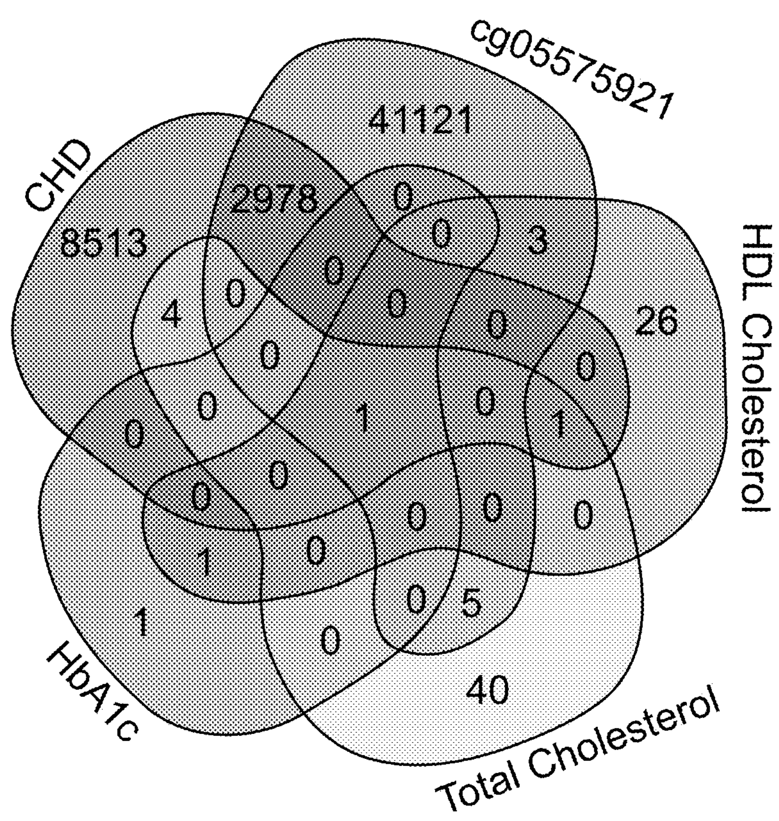
FIG. 4. Venn diagram of DNA methylation probes significantly associated with symptomatic CHD and its conventional modifiable risk factors.
Figure 5:
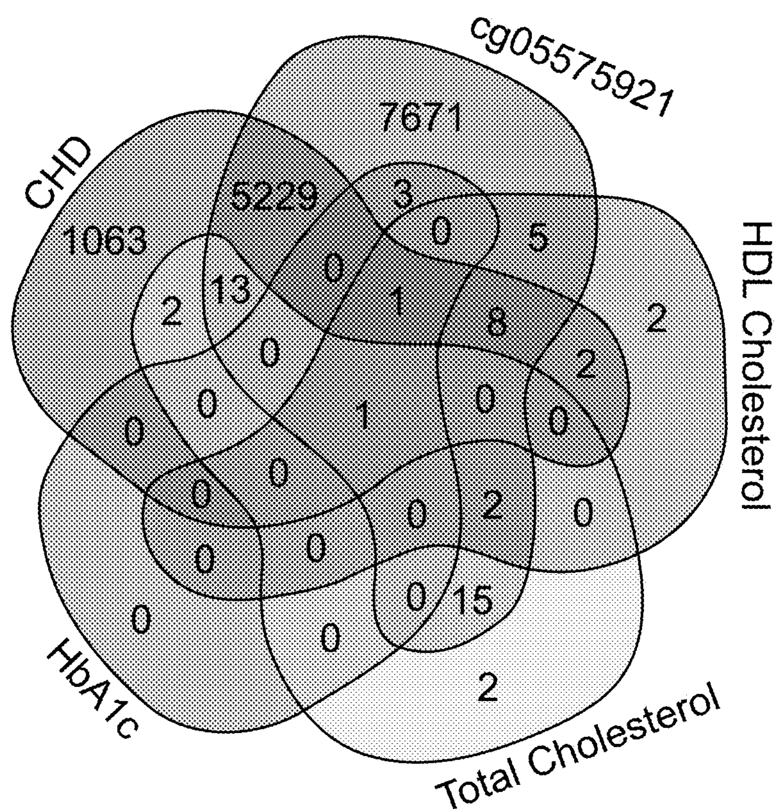
FIG. 5. Venn diagram of genes with at least one DNA methylation probe significantly associated with symptomatic CHD and its conventional modifiable risk factors.

To understand the mapping of significant symptomatic CHD DNA methylation sites to that of its risk factors, FIGS. 4 and 5 were generated. The Venn diagram in FIG. 4 shows the overlap in methylation probes between symptomatic CHD and its risk factors, while FIG. 5 depicts overlapping genes mapping to at least one of the probes. As shown in FIG. 5, the top three intersections in DNA methylation associated genes are between symptomatic CHD and smoking (5229), smoking and total cholesterol (15), and symptomatic CHD, smoking and total cholesterol (13). One gene, DHCR24, was significantly associated with symptomatic CHD and all risk factors.

Figure 6:
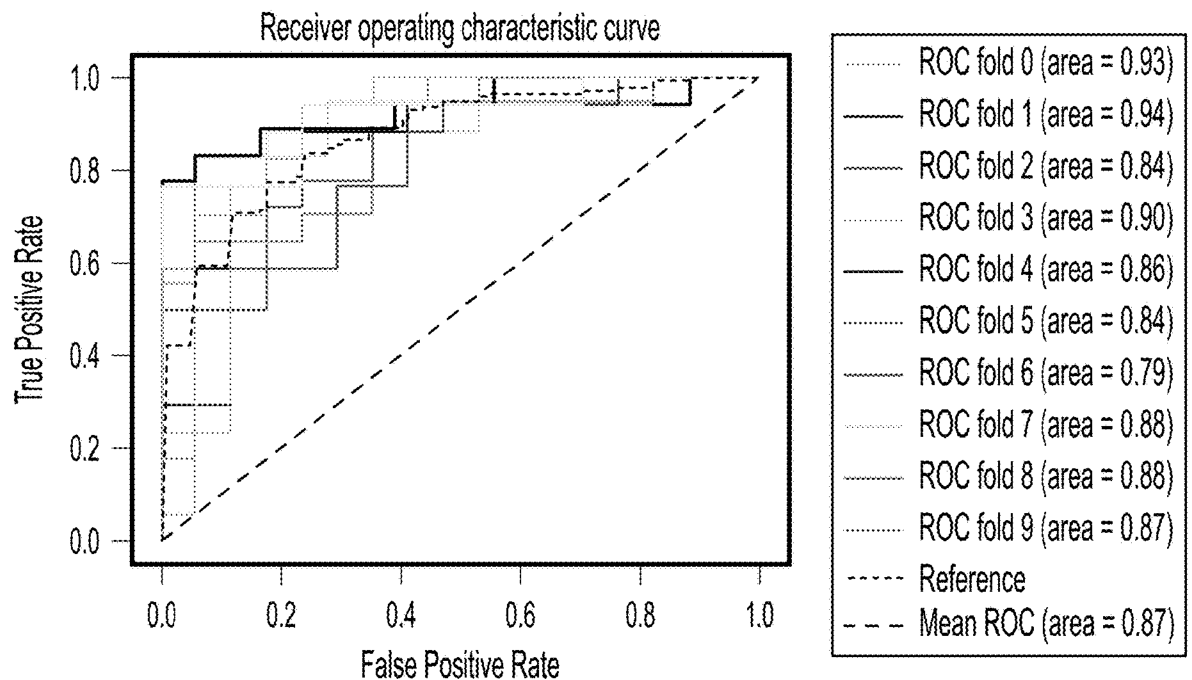
FIG. 6. ROC curve of the integrated genetic-epigenetic model with the highest average 10-fold cross-validation AUC value.

Integrated Genetic-Epigenetic Random Forest™ Analyses. Eight RF models were built on the eight datasets consisting of genetic, epigenetic, age and gender data from the 1545 subjects in the training dataset. Standard scikit-learn RF parameters were used to determine the important SNPs and DNA methylation loci. Based on the average accuracy and AUC of the eight classifiers and the Gini index of each variable, four CpG sites (cg26910465, cg11355601, cg16410464 and cg12091641), two SNPs (rs6418712 and rs10275666), age and gender were retained for prediction. Using the tuned parameters (maximum features, minimum samples for each split, information gain criterion, maximum tree depth, number of trees), all eight models were re-fitted to the training dataset. The performance metrics of these stratified 10-fold cross-validated models are shown in Table 12. As depicted in this table, the accuracy ranges from 70-80% between these eight models, which is between a 20-30% increase from the 50% accuracy baseline. More importantly, the sensitivity of the model ranged from 70-82%, while the specificity ranged from 70-79%. The ROC AUC of the eight models ranged from 0.77-0.87. The 10-fold ROC AUC of the best performing model (model 7) is shown in FIG. 6. All eight models were saved for testing on the test dataset.

TABLE 12

10-fold cross-validation performance metrics of the eight integrated genetic-epigenetic models

| Model | Accuracy | AUC | Sensitivity | Specificity |
|---|---|---|---|---|
| 1 | 0.78 ± 0.09 | 0.82 ± 0.09 | 0.79 ± 0.12 | 0.77 ± 0.08 |
| 2 | 0.75 ± 0.05 | 0.83 ± 0.06 | 0.78 ± 0.10 | 0.72 ± 0.08 |
| 3 | 0.79 ± 0.05 | 0.85 ± 0.07 | 0.83 ± 0.07 | 0.76 ± 0.08 |

TABLE 12-continued 10-fold cross-validation performance metrics of the eight integrated genetic-epigenetic models

| Model | Accuracy | AUC | Sensitivity | Specificity |
|---|---|---|---|---|
| 4 | 0.78 ± 0.07 | 0.84 ± 0.07 | 0.79 ± 0.12 | 0.76 ± 0.07 |
| 5 | 0.75 ± 0.06 | 0.78 ± 0.06 | 0.70 ± 0.09 | 0.79 ± 0.09 |
| 6 | 0.70 ± 0.05 | 0.77 ± 0.05 | 0.70 ± 0.12 | 0.70 ± 0.10 |
| 7 | 0.80 ± 0.06 | 0.87 ± 0.04 | 0.82 ± 0.08 | 0.77 ± 0.07 |
| 8 | 0.78 ± 0.06 | 0.85 ± 0.05 | 0.82 ± 0.07 | 0.74 ± 0.08 |

The demographics and CHD risk factors of the individuals in the testing dataset are summarized in Table 13. Of the 54 females and 88 males, 22 females (~41%) and 49 males (~56%) were diagnosed with symptomatic CHD. Those with symptomatic CHD on average tended to be older, males in their late 60s and females in their early 70s. Males and females without symptomatic CHD were on average in their late 50s and mid-60s, respectively. Unlike males, the average ages of females with and without symptomatic CHD were comparable between the training and test datasets.

TABLE 13

Demographics and CHD risk factors of 142 individuals in the test dataset

| | CHD | No CHD |
|---|---|---|
| Gender (count) | | |
| Male | 49 | 39 |
| Female | 22 | 32 |
| Age (years) | | |
| Male | 67.5 ± 8.4 | 59.6 ± 9.2 |
| Female | 72.5 ± 9.0 | 64.6 ± 10.8 |
| Total Cholesterol (mg/dL) | | |
| Male | 141 ± 25 | 191 ± 32 |
| Female | 180 ± 41 | 187 ± 35 |
| HDL Cholesterol (mg/dL) | | |
| Male | 46 ± 11 | 51 ± 15 |
| Female | 62 ± 18 | 61 ± 18 |
| HbA1c (%) | | |
| Male | 5.9 ± 0.9 | 5.9 ± 1.4 |
| Female | 6.3 ± 1.0 | 6.0 ± 1.0 |
| SBP (mmHg) | | |
| Male | 124 ± 19 | 127 ± 17 |
| Female | 136 ± 17 | 129 ± 15 |
| cg05575921 (z-score) | | |
| Male | −0.46 ± 1.43 | −0.26 ± 1.12 |
| Female | 0.10 ± 1.12 | −0.13 ± 0.93 |
| Smoker (count) | | |
| Male | 6 | 7 |
| Female | 1 | 4 |

SBP: systolic blood pressure
HbA1c: Hemoglobin A1c

All total cholesterol averages were <200 mg/dL and only females had average HDL cholesterol levels >60 mg/dL. The ratio between the averages of HDL and total cholesterol were 1:3.1 and 1:3.7 for males with and without symptomatic CHD, respectively, and, 1:2.9 and 1:3.1 for females with and without symptomatic CHD, respectively. Again, the ratios were more comparable between both datasets for females than males. However, the ratios were all lower than the target ratio between total and HDL cholesterol for cardiovascular disease prevention, which are <4.5 for men and <4.0 for women.[41]

In the test dataset, females tended to have higher HbA1c percentages than males. In addition, females with symptomatic CHD had an average HbA1c >6%. Females also had higher SBP than males. All SBP averages were >120 mmHg. Based on self-reported current smoking status, similar to the training dataset, there were more smokers without symptomatic CHD than with symptomatic CHD. However, when the smoking biomarker, cg05575921, is considered, males tended to be more demethylated than females.

An ensemble of the eight models was used to perform CHD classification in the test dataset. An individual was classified as having CHD if at least four of the eight models voted in favor of CHD. Of the 142 individuals (71 with and 71 without symptomatic CHD) in the test dataset, the CHD status of 110 individuals was predicted correctly, resulting in an accuracy of 77.5%. The confusion matrix of the prediction is shown in Table 14. The test set sensitivity and specificity of the ensemble was 0.75 and 0.80, respectively.

TABLE 14

Confusion matrix of the integrated genetic-epigenetic ensemble on the test dataset

| | Predicted | |
|---|---|---|
| TRUE | CHD absent | CHD present |
| CHD absent | 57 | 14 |
| CHD present | 18 | 53 |

Figure 7:
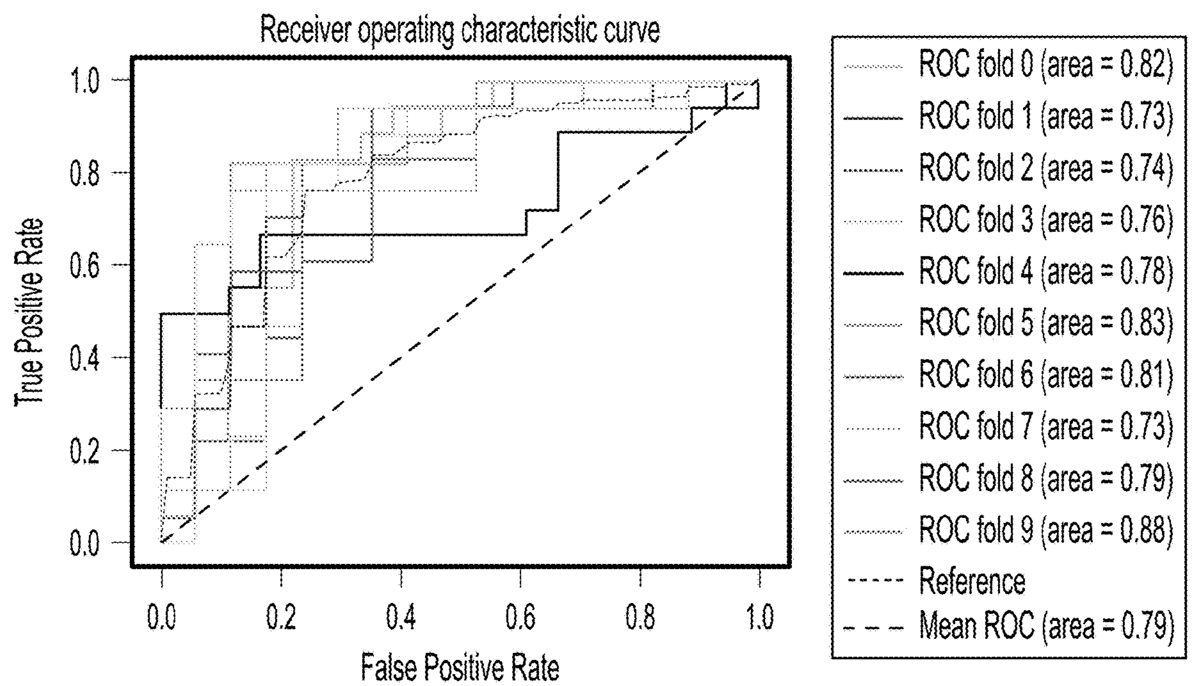
FIG. 7. ROC curve of the conventional risk factor model with the highest average 10-fold cross-validation AUC value.

Conventional CHD Risk Factor Model. To compare the performance of our integrated genetic-epigenetic model to the performance of conventional CHD risk factors in predicting CHD status, another eight RF models were built using age, gender, SBP, HbA1c, total cholesterol, self-reported smoking and HDL cholesterol as predictors. Again, using tuned parameters, the eight RF models were built on the training dataset and tested on the test dataset. The performance metrics of the eight models are summarized in Table 15. Accuracies of these models on their respective training datasets ranged from 70-76%, while the sensitivity and specificity ranges were 67-74% and 72-79%, respectively. The range of the ROC AUC was 0.72-0.79. While the accuracy and specificity is quite comparable with the integrated genetic-epigenetic models, the conventional risk factors models underperformed with respect to sensitivity and ROC AUC. The 10-fold ROC AUC of the best performing model (model 7) among the eight models is shown in FIG. 7. When the ensemble of the eight models was tested on the test dataset, the test accuracy was 64.8%, which is approximately 13% less than that of our integrated genetic-epigenetic ensemble. However, the more important metric is the sensitivity since it shows the degree to which a person with CHD is classified correctly. The sensitivity on the test dataset was only 41%, which is 24% less than that of our integrated genetic-epigenetic ensemble. However, the specificity of the conventional risk factor ensemble was 0.89. The confusion matrix is shown in Table 16.

TABLE 15

10-fold cross-validation performance metrics of the eight conventional risk factors models

| Model | Accuracy | AUC | Sensitivity | Specificity |
|---|---|---|---|---|
| 1 | 0.73 ± 0.03 | 0.77 ± 0.05 | 0.71 ± 0.07 | 0.75 ± 0.10 |
| 2 | 0.73 ± 0.07 | 0.75 ± 0.08 | 0.74 ± 0.08 | 0.72 ± 0.09 |

TABLE 15-continued

| 10-fold cross-validation performance metrics of the eight conventional risk factors models | | | | |
|---|---|---|---|---|
| Model | Accuracy | AUC | Sensitivity | Specificity |
| 3 | 0.75 ± 0.07 | 0.79 ± 0.06 | 0.73 ± 0.12 | 0.77 ± 0.10 |
| 4 | 0.70 ± 0.06 | 0.75 ± 0.08 | 0.68 ± 0.10 | 0.72 ± 0.07 |
| 5 | 0.70 ± 0.06 | 0.72 ± 0.08 | 0.67 ± 0.09 | 0.73 ± 0.10 |
| 6 | 0.71 ± 0.10 | 0.75 ± 0.10 | 0.68 ± 0.14 | 0.75 ± 0.10 |
| 7 | 0.76 ± 0.04 | 0.79 ± 0.05 | 0.73 ± 0.11 | 0.79 ± 0.09 |
| 8 | 0.71 ± 0.10 | 0.76 ± 0.12 | 0.68 ± 0.15 | 0.75 ± 0.11 |

TABLE 16

| Confusion matrix of the conventional risk factor ensemble on the test dataset | | |
|---|---|---|
| | Predicted | |
| TRUE | CHD absent | CHD present |
| CHD absent | 63 | 8 |
| CHD present | 42 | 29 |

Alternative Random Forest™ Model. To determine if our ensemble approach consisting of eight models performs better than a single RF model, as described in the methods, one RF model that includes stratified sampling based on the minority class was built in R. The model again included the same four CpGs, two SNPs, age and gender. The classifier was tuned and the classifier with the largest sensitivity was chosen (ntree=500). The training accuracy, AUC, sensitivity and specificity of this model were 82%, 0.83, 0.68 and 0.83, respectively. While the accuracy, AUC and specificity of this model is comparable to our ensemble model, clearly, the ensemble model provides better sensitivity. When tested on the test set, the single RF model performed with an accuracy, sensitivity and specificity of 76%, 0.66 and 0.86, respectively, demonstrating the increased sensitivity but not specificity provided by the ensemble approach. The comparison between this alternative approach and the ensemble approach is being done on the basis of sensitivity rather than specificity is because, given the application of the classifier in predicting CHD, it is rather important to maximize true positives than true negatives. In other words, the negative impact of having a false negative is much higher than a false positive. However, one of the reasons the sensitivity of the ensemble (ntree=170,000) may not be directly comparable to that of this single RF classifier (ntree=500) is the effective number of trees in the ensemble being much larger than this classifier. Nevertheless, a comparison can be made between one classifier within the ensemble with 20,000 trees and the alternative RF classifier with the same number of trees. The average accuracy, AUC, sensitivity and specificity of the classifier from the ensemble with 20,000 trees were 80%, 0.87, 0.82 and 0.77, respectively. Similarly, the accuracy, AUC, sensitivity and specificity of the alternative RF classifier with 20,000 trees were 82%, 0.83, 0.67 and 0.83. Similar to the prior comparison, the ensemble model performs better with respect to sensitivity than specificity.

While age and gender were included because they are the two non-modifiable risk factors of CHD, we re-fitted the single RF model without age and gender to demonstrate that the performance is not driven solely by these two factors. Without age and gender in the model, the training accuracy, AUC, sensitivity and specificity were 81%, 0.80, 0.65 and 0.83, respectively. On the test dataset, this model performed with an accuracy, sensitivity and specificity of 78%, 0.68 and 0.89, respectively. Therefore, age and gender are not single handedly responsible for the performance of the integrated genetic-epigenetic model. Using conventional risk factors from the training dataset, this alternative RF model performed with an accuracy, AUC, sensitivity and specificity of 77%, 0.77, 0.60 and 0.79, respectively. On the test dataset, it performed with an accuracy, sensitivity and specificity of 69%, 0.61 and 0.77, respectively.

Figure 8:
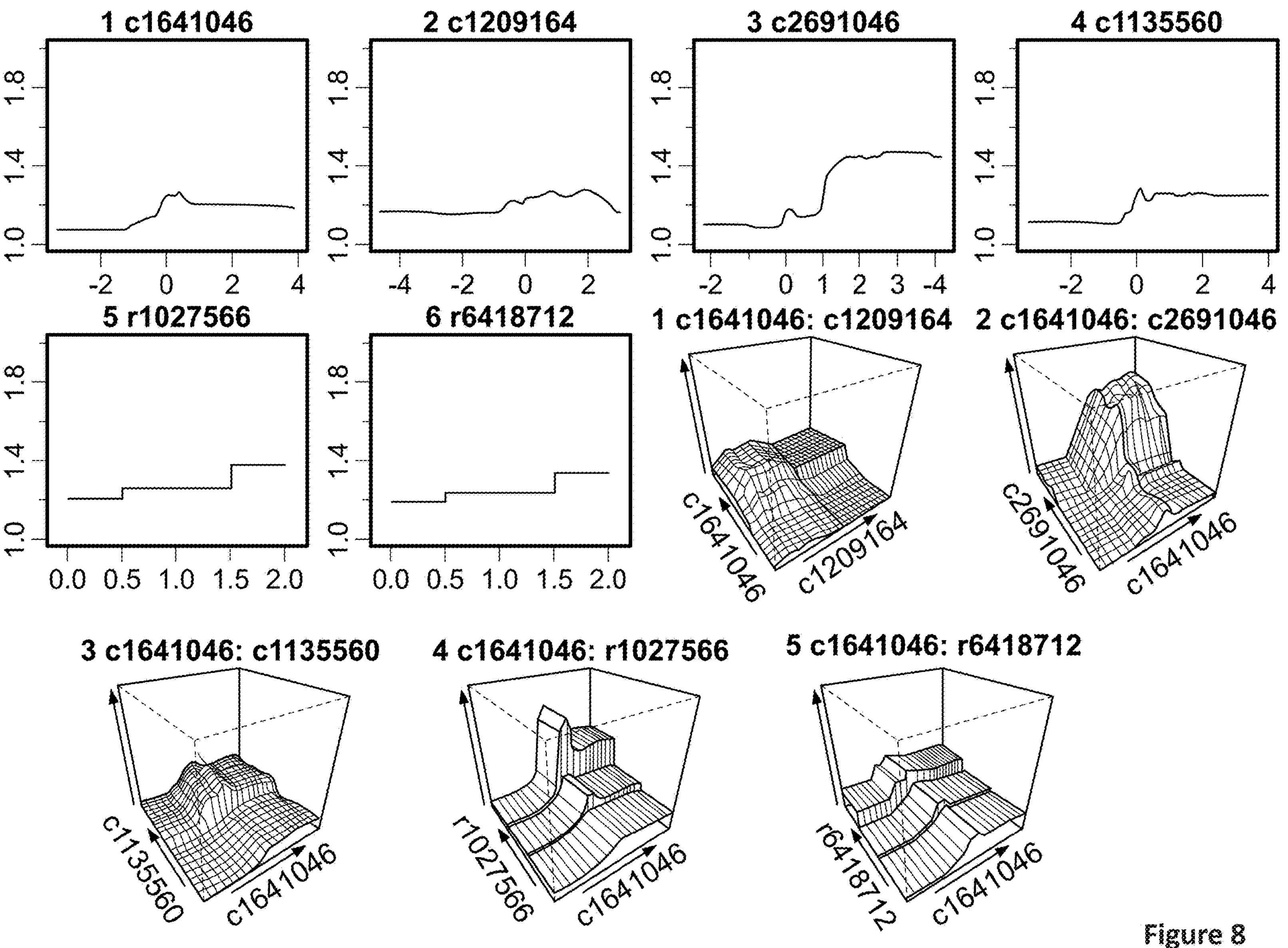
FIG. 8. Partial dependence plots of DNA methylation sites and SNPs.
Figure 8:
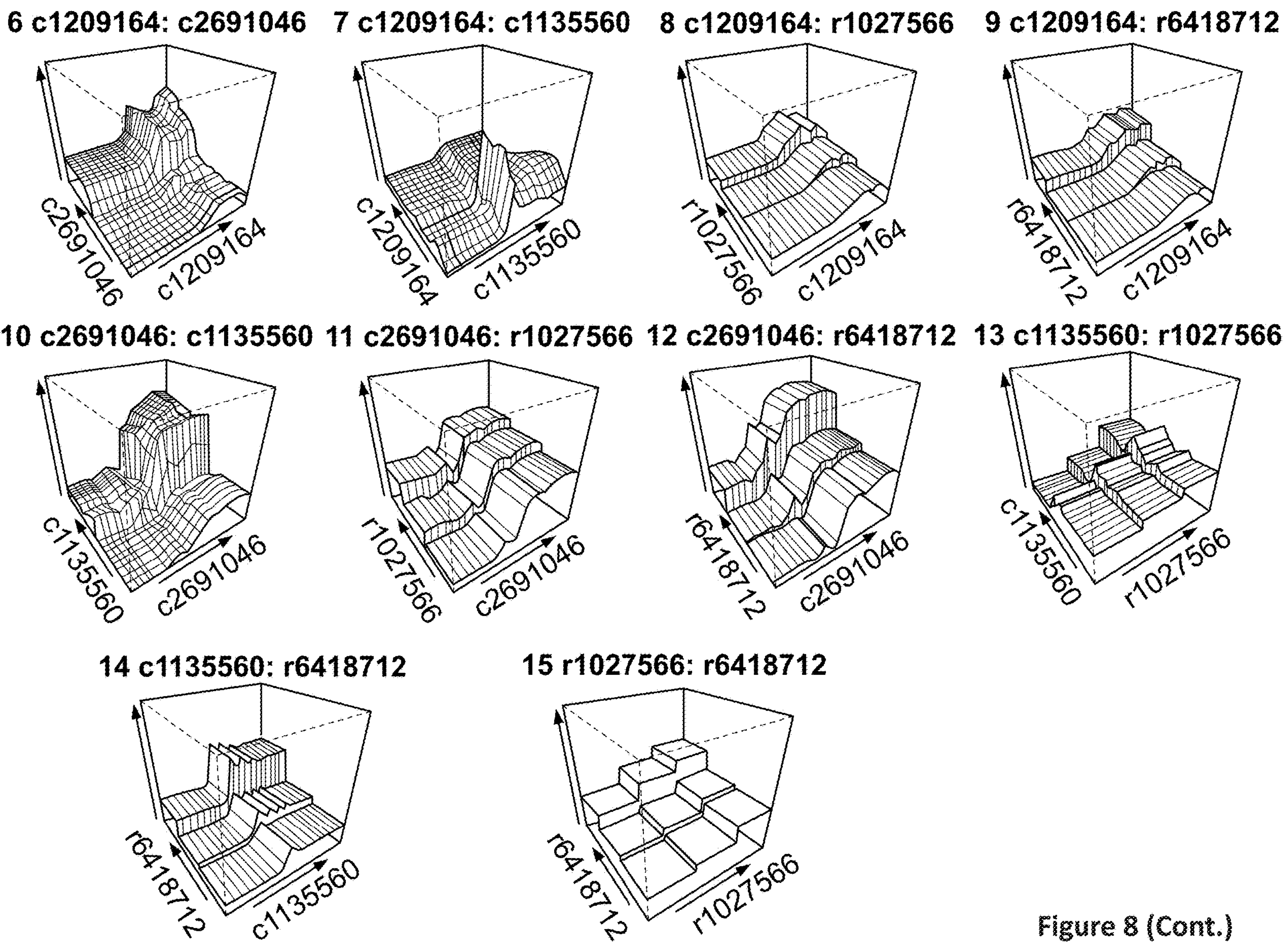
Figure 9:
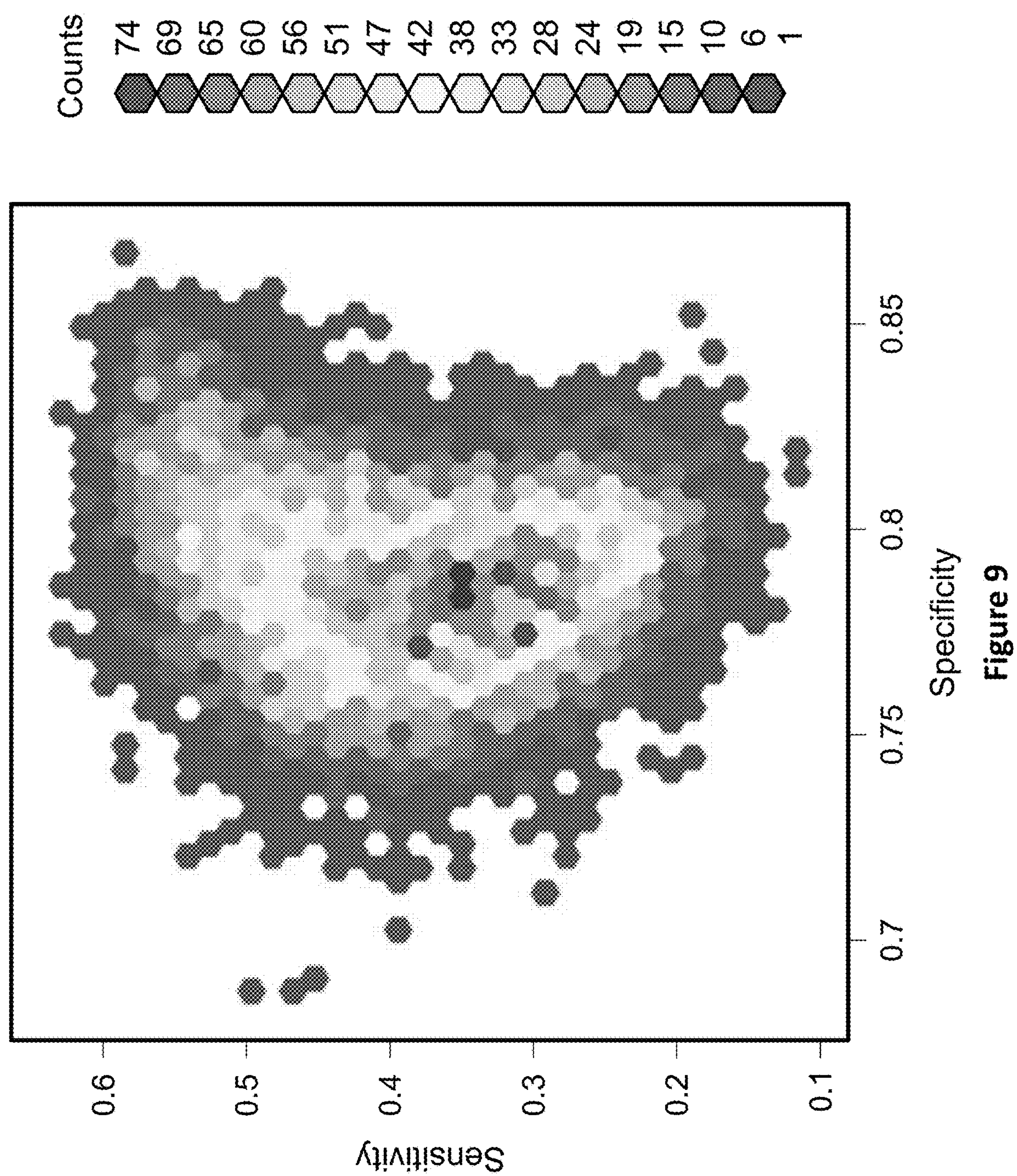
FIG. 9. Two-dimensional histogram of sensitivity and specificity of 10,000 permutations of DNA methylation sites and SNPs.

This genetic-epigenetic model was also used to show that the use of a RF model provides an added advantage in capturing possible GxM and MxM interactions, as depicted by the partial dependence plots in FIG. 8. Finally, permutation of DNA methylation sites and genotypes was performed to compare the performance of a model consisting of four randomly chosen CpG sites and two randomly chosen SNPs using the training dataset to our integrated model and the conventional risk factor model. A two-dimensional histogram of sensitivities and specificities of 10,000 permutations are shown in FIG. 9. The largest sensitivity and specificity among these permutations were 0.62 and 0.87, respectively. The training sensitivity and specificity of the single conventional risk factors model of 0.60 and 0.79, respectively, falls well within the sensitivity and specificity of the permutations. The training sensitivity and specificity of the single integrated genetic-epigenetic model of 0.68 and 0.83, respectively, suggests that sensitivity but not the specificity falls outside the permuted values.

Discussion

A better understanding of the relationship of epigenetic changes to the pathogenesis of cardiovascular diseases is essential for the development of improved diagnostics and therapeutics. To the best of our knowledge, we are the first group to examine the relationship between DNA methylation as quantified using the Illumina 450k array and CHD. Therefore, there are limited comparisons that can be made with our results. Nevertheless, our analyses demonstrate that epigenetic signatures with respect to CHD substantially overlap with that of cumulative smoking. This is consistent with the strong well-established relationship between smoking and risk for CHD, where approximately 30% of CHD related deaths in the US each year is attributed to cigarette smoking.[42, 43] This is not point made lightly. Smoking cessation may be one of the most beneficial, yet underutilized, general interventions in clinical medicine and has also been shown to substantially reduce mortality risk among those with CHD.[44, 45]

Interesting but not surprisingly, the DNA methylation analysis of all other risk factors described in our study show the wide spread effects of smoking in the remodeling of the epigenome. Prior investigations of the relationship between atherosclerosis and lipid levels, diabetes or hypertension have demonstrated the effect of smoking on these clinical measures.[46-48] Our analyses not only identified HDL cholesterol, total cholesterol and HbA1c associated changes in DNA methylation, but also delineated specific loci whose epigenetic signature is modified by smoking and associated with increased risk for CHD. Pending confirmation of the findings by others, the increased precision afforded by extension of the findings in subjects from a diverse set of ethnicities may aid in identifying specific therapeutic interventions for CHD at the individual level.

An additional application for methylation signatures of CHD and its risk factors is as an alternative approach to assess risk for CHD. This idea is particularly attractive given the challenges and limitations in using conventional risk factors to predict the risk for CHD. For instance, most studies use self-reported smoking status, which others and we have shown to be unreliable in more clinical/high risk populations.[49-52] These prior findings are especially relevant given the inconsistency between self-report and cg05575921 methylation in the Offspring cohort used in this study. Another test that is routinely conducted to assess risk for CHD is the fasting serum lipid panel, which assesses total cholesterol, HDL cholesterol, LDL cholesterol and triglyceride levels. While studies have shown that the ratio between total cholesterol and HDL cholesterol are especially predictive of risk for CHD[53, 54], others have also shown that information from additional markers such as C-reactive protein is needed to enhance the predictability.[55] Since these DNA methylation measures are more summative and less influenced by day to day fluctuations in diet, it is possible that they could more exactly constrain the relative contribution each of these metabolic/transcriptional pathways to CHD pathogenesis.

Over the years, the identification of conventional CHD risk factors has led to the development of a number of multivariate risk models. The Framingham Heart Study was a pioneer in this effort developing the Framingham Risk Score for CHD.[56] This algorithm uses the conventional risk factors (age, gender, total or LDL cholesterol, SBP, diabetes and current smoking) and was developed using the FHS cohort consisting of individuals of European ancestry. Therefore, as expected, this model performed well for white men and women, but hardly generalized to all other ethnic groups. Specifically, in a study that validated this algorithm in an ethnically diverse cohort, the prediction model held for black men and women, but overestimated risk of Japanese Americans, Hispanic men and Native American women.[57] Hence, there is a need for algorithms that can be used for all members of our society.

One plausible reason for the lack in generalizability is the possible confounding effects of genetic variation. The concept of the potential for genetic confounding of epigenetic signal is widely accepted.[58] Therefore, the goal of our study was to integrate genetic and epigenetic data to develop a classifier to predict CHD as an alternative to existing algorithms currently available. This approach that mines predictive signal from large and complex genetic and epigenetic datasets is made possible by the advancements in high performance computing systems. Computational techniques such as machine learning have been successfully employed in the fields of genomics and epigenomics.[59, 60] While logistic regression is the commonly used method for developing binary classification models in medical applications and have been used to analyze microarray data[61], it lacks the ability to capture implicit complex nonlinear relationships. Hence, algorithms capable of detecting complex relationships such as interactions between genetic variation and DNA methylation have an added advantage. In our study, the use of a Random Forest™ ensemble allowed for a highly accurate, sensitive and specific classification of individuals with CHD. However, since some genetic risk variants co-sort with ethic background and may not map to pathways associated with conventional risk factors, it will be necessary to build, test and extend these Random Forest™ approaches using subjects from all ethnic groups to develop the most generalizable prediction tools.[62]

While a similar integrated genetic and epigenetic study is not available for comparison, our integrated model clearly outperforms the classifier that uses the Framingham score risk factors. The conventional risk factors model demonstrates the limited predictive value of these risk factors as indicated by a number of studies.[63-65] Moreover, in a study consisting of over 2000 older black and white adults, the Framingham risk score was only capable of distinguishing those who experienced a CHD event versus those who did not after an eight year follow-up at a C-index of 0.577 and 0.583 in women and men, respectively.[66] The conventional risk factors may not perform as well due to hourly variations of factors such as serum cholesterol level and the use of a single blood pressure measurement instead of an average recorded throughout the day.[67, 68]

As demonstrated in this manuscript, there are several approaches to building classifiers. In comparing the two methods delineated in this manuscript, the ensemble model performed better than the single RF model with respect to sensitivity and vice versa for specificity. Our reason to favor a model with higher sensitivity is simple. For the classification of diseases such as CHD, a false positive would require further testing but a false negative result could be more detrimental to the patient. However, a test with high sensitivity and specificity is ideal. To achieve that, a larger sample consisting of diverse ethnic groups encompassing both genders is required. Also, while we used the RF algorithm, there are many other algorithms such as Support Vector Machines that can be used as the algorithm underlying a classifier. Nevertheless, our RF model clearly shows non-linearity between methylation sites and SNPs as depicted in the partial dependence plots. Yet, we would like to clarify that the combination of methylation sites and SNPs in our ensemble is only one of many possible combinations that are highly predictive. Based on the permutation results, we demonstrate that the variable reduction step undertaken to enrich for highly predictive methylation and SNP probes provide an edge with respect to sensitivity. However, as the pool of diverse samples increases, a highly predictive yet generalizable classifier will be required.

Our analyses did not take into account the possible effects of medications. This is notable because the current armamentarium of cholesterol lowering agents can have a dramatic effect on the levels of certain risk factors, such as serum cholesterol, that are associated with risk for CHD. Indeed, the presence of these medications may be the reason why the serum cholesterol level is actually lower in those in the training set who have CHD than in those in the training set without CHD. Unfortunately, it is very difficult to incorporate these types of data into the current analytical approach for a number of reasons. In addition, even if the subjects self-report of prescriptions were accurate, critical information needed to account for their effects, such as medication compliance and the treatment history length are not available. However, in the future, having data such as "pill count" and serum drug level information will be critical if we are to fully understand the effect of medical interventions on epigenetic signatures.

In addition, there are several other limitations in our study. First, our study includes only individuals of European ancestry. However, the incorporation of genetic variation in our model allows for the generalizability between ethnic groups. Nevertheless, additional studies are required to demonstrate this. Second, while our approach predicts symptomatic CHD, the goal is to use this study as a proof of concept towards building a multivariate model capable of forecasting risk for an initial CHD event and subsequently the risk of CHD event recurrence. Further exploration in prospectively biosampled cohorts will be necessary to achieve that goal. Yet, it is important to note that this integrated genetic-epigenetic approach has its advantages. The use of conventional risk factors in calculating risk requires cumbersome testing procedures, the collection of considerable amounts of blood and multiple lab tests. Conceivably, the need for these often cumbersome tests and procedures will be greatly reduced by using a single genetic-epigenetic assay procedure that uses a microgram or less of DNA. More importantly, the pathways associated with specific epigenetic loci with high predictive value could be very useful in guiding therapeutic interventions, management of risk factors and monitoring efficacy of treatments and lifestyle modifications.

EXAMPLE 4 REFERENCES

1. Centers for Disease Control and Prevention. Heart Disease and Stroke Prevention, Addressing the Nation's Leading Killers: At A Glance 2011.
2. Myerburg et al., Sudden cardiac death caused by coronary heart disease. *Circulation.* 2012; 125:1043-52.
3. Kannel et al., Precursors of sudden coronary death. Factors related to the incidence of sudden death. *Circulation.* 1975; 51:606-13.
4. Dawber et al., II. Coronary Heart Disease in the Framingham Study. *Int J Epidemiol.* 2015; 44:1767-1780.
5. Braunwald, Approach to the Patient with Heart Disease *Harrison's Principles of Internal Medicine,* 14th ed. New York: McGraw Hill; 1998: 1229-1231.
6. Chandrasekar et al., Complications of cardiac catheterization in the current era: a single-center experience. *Catheter Cardiovasc Interv.* 2001; 52:289-295.
7. Trägårdh et al., Detection of acute myocardial infarction using the 12-lead ECG plus inverted leads versus the 16-lead ECG (with additional posterior and right-sided chest electrodes). *Clin Physiol Funct Imaging.* 2007; 27:368-374.
8. Brant et al., Gender differences in the accuracy of time-dependent blood pressure indices for predicting coronary heart disease: A random-effects modeling approach. *Gend Med.* 2010; 7:616-627.
9. Stys et al., Current clinical applications of heart rate variability. *Clin Cardiol.* 1998; 21:719-724.
10. Nandalur et al., Diagnostic Performance of Stress Cardiac Magnetic Resonance Imaging in the Detection of Coronary Artery DiseaseA Meta-Analysis. *J Am Coll Cardiol.* 2007; 50:1343-1353.
11. van Holten et al., Circulating Biomarkers for Predicting Cardiovascular Disease Risk; a Systematic Review and Comprehensive Overview of Meta-Analyses. *PLoS One.* 2013; 8:e62080.
12. Manson et al., Biomarkers of cardiovascular disease risk in women. *Metabolism.* 2015; 64:S33-S39.
13. O'Donnell et al., Genomics of cardiovascular disease. *N Engl J Med.* 2011; 365:2098-2109.
14. Dehghan et al., Genome-wide association study for incident myocardial infarction and coronary heart disease in prospective cohort studies: the CHARGE consortium. *PLoS One.* 2016; 11:e0144997.
15. Deloukas et al., Large-scale association analysis identifies new risk loci for coronary artery disease. *Nat Genet.* 2013; 45:25-33.
16. Hernesniemi et al., Genetic profiling using genome-wide significant coronary artery disease risk variants does not improve the prediction of subclinical atherosclerosis: the cardiovascular risk in young Finns study, the bogalusa heart study and the health 2000 survey—a meta-analysis of three independent studies. *PLoS One.* 2012; 7:e28931.
17. Andersen et al., Current and Future Prospects for Epigenetic Biomarkers of Substance Use Disorders. *Genes.* 2015; 6:991-1022.
18. Gao et al., DNA methylation changes of whole blood cells in response to active smoking exposure in adults: a systematic review of DNA methylation studies. *Clin Epigenetics.* 2015; 7:113.
19. Breitling et al., Smoking, F2RL3 methylation, and prognosis in stable coronary heart disease. *Eur Heart J.* 2012.
20. Zhang et al., F2RL3 methylation in blood DNA is a strong predictor of mortality. *Int J Epidemiol.* 2014.
21. Zhang et al., Smoking-Associated DNA Methylation Biomarkers and Their Predictive Value for All-Cause and Cardiovascular Mortality. *Environ Health Perspect.* 2015.
22. Dogan et al., Ethnicity and Smoking-Associated DNA Methylation Changes at HIV Co-Receptor GPR15. *Frontiers in Psychiatry.* 2015; 6.
23. Dogan et al., The effect of smoking on DNA methylation of peripheral blood mononuclear cells from African American women. *BMC Genomics.* 2014; 15:151.
24. Gibbs et al., Abundant Quantitative Trait Loci Exist for DNA Methylation and Gene Expression in Human Brain. *PLoS Genet.* 2010; 6:e1000952.
25. Tsaprouni et al., Cigarette smoking reduces DNA methylation levels at multiple genomic loci but the effect is partially reversible upon cessation. *Epigenetics.* 2014; 9:1382-1396.
26. Philibert et al., The effect of smoking on MAOA promoter methylation in DNA prepared from lymphoblasts and whole blood. *Am J Med Genet.* 2010; 153B: 619-28.
27. Hoekstra et al., The peripheral blood mononuclear cell microRNA signature of coronary artery disease. *Biochem Biophys Res Commun.* 2010; 394:792-797.
28. Meder et al., MicroRNA signatures in total peripheral blood as novel biomarkers for acute myocardial infarction. *Basic Res Cardiol.* 2011; 106:13-23.
29. Aziz et al., Peripheral blood gene expression profiling for cardiovascular disease assessment. *Genomic Med.* 2007; 1:105-112.
30. Cupples et al., *The Framingham Heart Study*, Section 35. An Epidemiological Investigation of Cardiovascular Disease Survival Following Cardiovascular Events: 30 Year Follow-up. *Lung and Blood Institute.* 1988.
31. Dawber et al., An approach to longitudinal studies in a community: the Framingham Study. *Ann N Y Acad Sci.* 1963; 107:539-556.
32. Bibikova et al., High density DNA methylation array with single CpG site resolution. *Genomics.* 2011; 98:288-95.
33. Pidsley et al., A data-driven approach to preprocessing Illumina 450K methylation array data. *BMC Genomics.* 2013; 14:293.
34. Du et al., Comparison of Beta-value and M-value methods for quantifying methylation levels by microarray analysis. *BMC Bioinformatics.* 2010; 11:587.
35. Purcell et al., PLINK: a tool set for whole-genome association and population-based linkage analyses. *Am J Hum Genet.* 2007; 81:559-75.
36. Hochberg et al., *Multiple Comparison Procedures*. New York: Wiley; 1987.
37. Szklarczyk et al., *The STRING database in* 2011: functional interaction networks of proteins, globally integrated and scored. *Nucleic Acids Res.* 2011; 39:D561-8.
38. Chen et al., Using random forest to learn imbalanced data. *University of California, Berkeley.* 2004; 110.

39. Breiman, Random forests. *MLear.* 2001; 45:5-32.
40. Pedregosa et al., Scikit-learn: Machine Learning in Python. *Journal of Machine Learning Research.* 2011; 12:2825-2830.
41. Millan et al., Lipoprotein ratios: Physiological significance and clinical usefulness in cardiovascular prevention. *Vasc Health Risk Manag.* 2009; 5:757-65.
42. Neaton et al., Serum cholesterol, blood pressure, cigarette smoking, and death from coronary heart disease. Overall findings and differences by age for 316,099 white men.
Multiple Risk Factor Intervention Trial Research Group. *Arch Intern Med.* 1992; 152:56-64.
43. Ockene et al., Cigarette smoking, cardiovascular disease, and stroke: a statement for healthcare professionals from the American Heart Association. American Heart Association Task Force on Risk Reduction. *Circulation.* 1997; 96:3243-7.
44. Critchley et al., Mortality risk reduction associated with smoking cessation in patients with coronary heart disease: a systematic review. *JAMA.* 2003; 290:86-97.
45. Anczak et al., Tobacco cessation in primary care: maximizing intervention strategies. *Clin Med Res.* 2003; 1:201-216.
46. Garrison et al., Cigarette smoking and HDL cholesterol: the Framingham offspring study. *Atherosclerosis.* 1978; 30:17-25.
47. Kong et al., Smoking is associated with increased hepatic lipase activity, insulin resistance, dyslipidaemia and early atherosclerosis in Type 2 diabetes. *Atherosclerosis.* 2001; 156:373-8.
48. Wilhelmsen, Coronary heart disease: epidemiology of smoking and intervention studies of smoking. *Am Heart J.* 1988; 115:242-9.
49. Hilberink et al., Validation of smoking cessation self-reported by patients with chronic obstructive pulmonary disease. *Int J Gen Med.* 2011; 4:85.
50. Philibert et al., Reversion of AHRR Demethylation Is a Quantitative Biomarker of Smoking Cessation. *Frontiers in Psychiatry.* 2016; 7.
51. Britton et al., Comparison of self-reported smoking and urinary cotinine levels in a rural pregnant population. *J Obstet Gynecol Neonatal Nurs.* 2004; 33:306-11.
52. Andersen et al., Accuracy and Utility of an Epigenetic Biomarker for Smoking in Populations with Varying Rates of False Self-Report. in submission.
53. Kinosian et al., Cholesterol and coronary heart disease: predicting risks by levels and ratios. *Ann Intern Med.* 1994; 121:641-7.
54. Castelli et al., Lipids and risk of coronary heart disease. The Framingham Study. *Ann Epidemiol.* 1992; 2:23-8.
55. Ridker et al., C-reactive protein adds to the predictive value of total and HDL cholesterol in determining risk of first myocardial infarction. *Circulation.* 1998; 97:2007-11.
56. Wilson et al., Prediction of coronary heart disease using risk factor categories. *Circulation.* 1998; 97:1837-47.
57. D'Agostino et al., Validation of the Framingham coronary heart disease prediction scores: results of a multiple ethnic groups investigation. *JAMA.* 2001; 286:180-7.
58. Petronis, Human morbid genetics revisited: relevance of epigenetics. *Trends Genet.* 2001; 17:142-146.
59. Bock et al., Computational epigenetics. *Bioinformatics.* 2008; 24:1-10.
60. Libbrecht et al., Machine learning applications in genetics and genomics. *Nat Rev Genet.* 2015; 16:321-32.
61. Liao et al., Logistic regression for disease classification using microarray data: model selection in a large p and small n case. *Bioinformatics.* 2007; 23:1945-51.
62. Roberts, Genetics of coronary artery disease. *Circ Res.* 2014; 114:1890-903.
63. Bastuji-Garin et al., *Intervention as a Goal in Hypertension Treatment Study G.*
The Framingham prediction rule is not valid in a European population of treated hypertensive patients. *J Hypertens.* 2002; 20:1973-80.
64. Brindle et al., Predictive accuracy of the Framingham coronary risk score in British men: prospective cohort study. *BMJ.* 2003; 327:1267.
65. Liu et al., Predictive value for the Chinese population of the Framingham CHD risk assessment tool compared with the Chinese Multi-Provincial Cohort Study. *JAMA.* 2004; 291:2591-9.
66. Rodondi et al., Framingham risk score and alternatives for prediction of coronary heart disease in older adults. *PLoS One.* 2012; 7:e34287.
67. Peterson et al., Hourly variation in total serum cholesterol. *Circulation.* 1960; 22:247-53.
68. Staessen et al., Predicting cardiovascular risk using conventional vs ambulatory blood pressure in older patients with systolic hypertension. Systolic Hypertension in Europe Trial Investigators. *JAMA.* 1999; 282:539-46.

EXAMPLE 5

Methylation and Gxmethylation Effects in Predicting Cardiovascular Disease: Stroke and Congestive Heart Failure Methylation-based biomarkers are gaining increasing clinical traction for use in guiding diagnosis and therapy. Currently, Cologuard, an assay that quantifies DNA methylation in human DNA found in stool samples, is FDA approved for the detection of colon cancer (Lao and Grady 2011). In addition, Smoke Signature™, an DNA methylation assay that detects cigarettes consumption using DNA from blood (Philibert, Hollenbeck et al. 2016), is available for the research market and is being prepared for FDA submission. In attempts to identify CpG loci whose methylation status is predictive of cardiovascular disease, a number of investigators have used genome wide approaches combined with clinical diagnostics. In particular, Brenner and colleagues (Breitling, Salzmann et al. 2012) have identified F2RL3 residue cg03636183 as a biomarker for cardiovascular disease. Unfortunately, these analyses have been shown to have been completely confounded by incomplete knowledge of smoking status and did not consider possible confounding genetic variance. In fact, when using biomarker approaches that fully account for the intensity of smoking, the coronary heart disease signal at cg03636183 disappears (Zhang, Schöttker et al. 2015). Furthermore, using a genome wide methylation and genetic analyses, combined with biomarker guided smoking assessments, we have recently analyzed data from a large cohort of subjects informative for cardiac disease. We have shown that independent of smoking intensity status, that the genetically contextual methylation status, as embodied by methylation-genotype interact effects actually contribute better to the prediction of coronary heart disease and that the use of an algorithm that combines local genetic variation and methylation markedly improves prediction of coronary heart disease (CVD, Dogan et al., in submission).

However, CVD is only one of three major forms of Cardiovascular Disease (CVD). Stroke and congestive heart failure (CHF) are also prominent forms of CVD. In these examples, we extend our previous work with CVD to show how a combination of genetic variation, as embodied by SNPs, and epigenetic markers, as embodied by the Illumina methylation probes predicts Stroke or CHF.

Abstract

Congestive heart failure (CHF) and stroke are two of the three common types of cardiovascular disease (CVD). Both CHF and stroke affects a large numbers of Americans. While preventative measures such as avoiding smoking can be taken to reduce risk for stroke and CHF, limited options are available for early detection of risk for these diseases. However, in recent years, the field of epigenetics has provided an alternative approach to understanding complex illnesses. Specifically, DNA methylation signatures may present the opportunity to develop robust clinical tests for CHF and stroke prior to their occurrence. The ability to utilize only DNA methylation and generalize it to a diverse group of individuals could be limited by the presence of confounding genetic effects. Therefore, we integrated genetic and epigenetic data from the Framingham Heart Study to uncover SNPs and DNA methylation sites that collectively increase the predictability of CHF and stroke. Our preliminary analyses suggest that, the incorporation of three DNA methylation sites and three SNPs is capable of classifying CHF status with an area under the curve (AUC) of the receiver operating characteristic (ROC) curve of 0.78 and 0.81 in main effects and interaction effects models, respectively. In assessing the parameters of these models, we show that both DNA methylation and SNP are highly predictive of CHF status when implemented concurrently. Similarly, the AUC of the ROC curve of stroke at 0.85 and 0.86 for the main effects and interaction effects models, respectively, demonstrates the importance of integrating genetic and epigenetic effects. While these models are not optimized and were developed with a relatively small CHF and stroke sample size, we are certain that the more optimized version of this algorithm that accounts for genetic and epigenetic effects developed using a larger cohort could markedly improve our prediction capabilities of the risk for CHF and stroke prior to its occurrence. We are also confident that the presence of genetic information in the algorithm would allow its generalization to different ethnic groups.

Introduction

Cardiovascular Disease (CVD) includes three distinct diagnostic entities; coronary heart disease (CVD), stroke and congestive heart failure (CHF). By itself, CVD is the leading cause of death in the United States while stroke ranks fourth as a cause of mortality (Centers for Disease Control and Prevention). Over the past fifty years, a number of medications and devices have been developed to treat CVD. Unfortunately, hundreds of thousands of Americans continue to die each year because the presence of CVD is not noted until a fatal thromboembolic or cardiac event. Conceivably, more effective screening procedures for CVD could lead to the prevention of some of these deaths. (Mozaffarian, Benjamin et al. 2016) But at the current time, the cumbersomeness of certain techniques, such as fasting lipid panels, and/or the limited predictive ability of others such as electrocardiograms and C-reactive protein levels, limit the effectiveness of the current approaches in identifying CVD. (Buckley, Fu et al. 2009, Auer, Bauer et al. 2012, Mozaffarian, Benjamin et al. 2016)

A number of investigators have proposed that genetic approaches could provide another potential avenue through which to prevent CVD related morbidity and mortality. (Paynter, Ridker et al. 2016) Using whole exome and genome sequencing techniques, a number of variants predisposing to CVD have been identified. The relative risk conferred by of many of these variants is often considerable and their presence is sometimes useful for guiding prevention and treatment. (Mega, Stitziel et al.) However, with isolated exceptions, the large effect size variants tend to be rare, often population specific and their presence is not pathognomonic of current disease. (Traylor, Farrall et al. 2012, Paynter, Ridker et al. 2016) Hence, at the current time, genetic approaches are not generally used for the assessment of the presence or absence of current CVD in general medical practice.

Alternatively, others have proposed that epigenetic techniques might be useful in assessing CVD. (Sharma, Kumar et al. 2008, Gluckman, Hanson et al. 2009, Breitling, Salzmann et al. 2012) Since replicated peripheral white blood cell DNA methylation signatures for the presence of type 2 diabetes, smoking and drinking have been developed, (Monick, Beach et al. 2012, Toperoff, Aran et al. 2012, Zeilinger, Kühnel et al. 2013, Philibert, Penaluna et al. 2014) this suggestion has strong face validity. Notably, using this approach, Brenner and colleagues have proposed that DNA methylation at cg03636183, a CpG residue found in Coagulation factor II (thrombin) receptor-like 3 (F2RL3), predicts risk for cardiac disease. (Breitling, Salzmann et al. 2012, Zhang, Yang et al. 2014) Although this is an extremely biologically plausible finding, their subsequent studies have demonstrated that the CVD related signal at cg03636183 completely co-segregates with smoking status as indicated by DNA methylation at cg05575921, (Zhang, Schöttker et al. 2015) a CpG residue found in the aryl hydrocarbon receptor repressor (AHRR) whose strong predictive power with respect to smoking status has been demonstrated in dozens of studies. (Andersen, Dogan et al. 2015)

However, the failure of the initially intriguing cg03636183 findings to independently identify additional risk outside of that conferred by smoking alone does not mean that methylation approaches for assessing the presence of CVD or other forms of CVD are destined to fail. Instead, they suggest that successful approaches need to be more nuanced and that reconsideration of our conceptualization of relationship of methylation status to CVD is in order. For example, the findings by Brenner's group strongly suggest that methylation algorithms for the prediction of current CVD should include an indicator of smoking status. Given the fact that smoking is the largest preventable risk factor for CVD (Center for Disease Control 2005), this is eminently logical. However, in addition, they may need to take into consideration that the long-term effects of exposure to environmental risk factors such as smoking or other cardiac risk factors such as hyperlipidemia may be obscured by gene-environment interactions.

The role of gene-environment interactions (GxE) effects in moderating vulnerability to illness is perhaps better appreciated in the behavioral sciences. The basic premise of GxE effects is that the influence of the environment during a developmentally sensitive period of time changes the biological properties of a system in a genetically contextual manner so that in the future-even in the absence of the environmental factor-enhanced vulnerability to illness is present. (Yang and Khoury 1997) Critically, because of confounding by the genetic variable, the direct effects of the environmental variable are generally not detectable. Rather, only when considered in the context of genetic variation can these be detected. Though the strength of some GxE findings are controversial, many investigators continue to stress the importance of these GxE effects in the pathogenesis of a variety of behavioral disorders such as depression, post-traumatic stress disorder and antisocial behavior. (Caspi, McClay et al. 2002, Caspi, Sugden et al. 2003, Kolassa, Ertl et al. 2010)

The physical basis for these GxE effects is thought to vary. For example, at the anatomical level, the GxE effects for behavioral disorders can be manifested by changes in synaptic structure. (McEwen 2007) However, at the molecular level, the physical manifestation of GxE effects is less certain. But a number of investigators have suggested that changes in DNA methylation may be one potential mechanism through which the physical effects of GxE effects are conveyed. (Klengel, Pape et al. 2014)

Interestingly, the fact that behaviorally relevant changes in the environment can alter DNA methylation and that the degree of those changes is influenced by genetic variation has been known for many years. In our early candidate gene studies, we showed that smoking altered DNA methylation in the promoter region of monoamine oxidase A (MAOA), a key regulator of monoaminergic neurotransmission, and that genotype at the well-characterized promoter associated variable nucleotide repeat (VNTR) altered the percent methylation at the status in both the presence and absence of smoking. (Philibert, Gunter et al. 2008, Philibert, Beach et al. 2010) Subsequently, methylation changes at those loci were shown to be functional by Volkow and colleagues. (Shumay, Logan et al. 2012)

In current terminology, those effects of the VNTR on smoking or basal DNA methylation are now referred to genotype-methylation interaction effects. These MAOA interaction effects had consequence on our ability to detect their relationship to smoking when we conducted our first genome wide studies. Despite the magnitude of the smoking induced change in DNA methylation in response to smoking, the probes surrounding the MAOA VNTR are not among the more highly ranked probes even in studies of DNA from subjects of only one gender. Other observations from those initial studies are equally instructive. First, the local methylation response to smoking was not homogenous. Factor analysis of the methylation status of the 88 CpG residues in the promoter associated islands showed that increases in methylation at one area of the island could be associated with demethylation at others. (Beach, Brody et al. 2010) Finally, the effects of smoking on DNA methylation were not static. After time, the signature tended to decay. (Philibert, Beach et al. 2010) Hence, from those early studies, it was clear that at MAOA promoter, genetic variation could alter the effects of environmental factor on the local DNA methylation signature in a complex manner.

Subsequent studies suggest that many of these same complexities in response to smoking are evident at the genome wide level. For example, it is clear that at the genome wide level, genetic variation affects the magnitude of the methylation response, and that when attempting to replicate signatures from those of differing ancestries, those interaction effects may impair the ability to replicate findings at a given locus in a subject pool of a different ancestry. (Tsaprouni, Yang et al. 2014, Dogan, Xiang et al. 2015) Second, and equally importantly, the reversion of the methylation signatures can be complex. (Tsaprouni, Yang et al. 2014, Guida, Sandanger et al. 2015) Guida and colleagues specifically examined the epigenomic response to smoking cessation in DNA from a collection of 745 subjects and found two classes of CpG sites, those whose methylation signature reverted with time and those that did not; and concluded that at the genome wide level the "dynamics of methylation changes following smoking cessation are driven by a differential and site specific magnitude of the smoking induced changes that is irrespective of the intensity and duration of smoking." (Guida, Sandanger et al. 2015) In summary, a substantial body of evidence suggests that the genome wide signature to smoking is only partially reversible and that a large chunk of the non-reversible changes may be complexly masked in interaction effects.

Since smoking is a major risk factor for CVD in general, and in particular stroke and CVD, this also suggests that a portion of the smoking induced risk present in the epigenome that moderates the risk for CVD may be somewhat non-reversible and masked in interaction effects. In addition, since smoking is only one of a number of factors can alter risk for CVD and these other factors also may have complex epigenetic signatures, it may well be that interrogation of peripheral WBC DNA methylation may reveal interaction effects that moderate risk for CVD and are relatively stable.

So in summary, the use of either genetic or epigenetic information for the prediction of various forms of CVD does not work well. However, it is possible the combinations of these measurements, in particular those that take into effect interactive effects, could perform superiorly.

In this communication, we used regression analytical approaches and the epigenetic and genetic resources from 324 subjects who participated in the Framingham Heart Study to test whether combinations of environmental (methylation) and genetic information (SNPs) together, or with their interactive effects, can make a better contribution to algorithms to predict CVD.

Methods

Framingham Heart Study. The data used in this study is derived from participants in the Framingham Heart Study (FHS). (Dawber, Kannel et al. 1963) FHS is a longitudinal study aimed at understanding the risks of cardiovascular disease (CVD) and consists of several cohorts including the Original Cohort, Offspring Cohort, Omni Cohort, Third Generation Cohort, New Offspring Spouse Cohort and Second Generation Omni Cohort. Specifically, the Offspring Cohort, initiated in 1971, consisting of the offspring of the Original Cohort and their spouses was used in this study. This cohort consists of 2,483 males and 2,641 females (total of 5,124). (Mahmood, Levy et al. 2014) The specific analyses described in this communication were approved by the University of Iowa Institutional Review Board.

Genome-wide DNA Methylation. Of the 5,124 individuals in the Offspring Cohort, only 2,567 individuals (duplicates removed) with DNA methylation data were considered. These individuals were included in the DNA methylation study because they attended the Framingham Offspring 8$^{th}$ exam, provided consent for genetic research, had a buffy coat sample, and had sufficient DNA quantity and quality for methylation profiling. Exam 8 took place between 2005 and 2008. Genomic DNA extracted from their white blood cells was bisulfite converted, then genome-wide DNA methylation was profiled using the Illumina HumanMethylation450 BeadChip (San Diego, Calif.) at either the University of Minnesota or Johns Hopkins University. The intensity data (IDAT) files of the samples alongside their slide and array information were used to perform the DASEN normalization using the MethyLumi, WateRmelon and IlluminaHumanMethylation450k.db R packages. (Pidsley, Y Wong et al. 2013) The DASEN normalization performs probe filtering, background correction and adjustment for probe types. Samples were removed if they contained >1% of CpG sites with a detection p-value >0.05. CpG sites were removed if they had a bead count of <3 and/or >1% of samples had a detection p-value >0.05. After DASEN normalization, there were 2,560 samples and 484, 241 sites remaining (484,125 CpG sites). CpG sites were grouped by chromosome. Of those CpG sites, 472,822 mapped to autosomes. Methylation beta values were converted to M values using the beta2m R function in the Lumi package and subsequently converted to z-scores using an R script. (Du, Kibbe et al. 2008)

Genome-wide Genotype. Of the 2,560 remaining individuals after DNA methylation quality control, 2,406 (1,100 males and 1,306 females) had genome-wide genotype data from the Affymetrix GeneChip HumanMapping 500K Array Set (Santa Clara, Calif.). This array is capable of profiling 500,568 SNPs in the genome. Quality control was performed at both the sample and SNP probe levels in PLINK. The initial quality control step involved identifying individuals with discordant sex information. None were identified. Next, individuals with a heterozygosity rate of greater or smaller than the mean±2SD and with a proportion of missing SNPs >0.03 were excluded. Related individuals were also excluded if the identity by descent value was >0.185 (halfway between second and third degree relatives). After performing these sample level quality control steps, 1,599 individuals remained (722 males and 877 females). On the probe level, SNPs with a minor allele frequency >1%, Hardy-Weinberg equilibrium p-value $>10^{-5}$ and SNP missing rate of <5% were retained. A total of 403,192 SNPs remained after these quality control steps. Using the recode option in PLINK, (Purcell, Neale et al. 2007) genotypes were coded as 0, 1 or 2 per minor allele frequency.

Phenotypes. For individuals in this study, their stroke and congestive heart failure (CHF) status were extracted. Since biomaterial for DNA methylation was collected during the eighth examination cycle of the Offspring cohort, only those with a stroke or CHF incidence date prior to this eighth examination were included. Based on this criterion, a total of 1,540 and 1,562 individuals remained for CHF and stroke analyses, respectively.

Among the 1,540 subjects available for CHF analyses, 40 were classified as having CHF. Major criteria of CHF according to the Framingham Study includes paroxysmal nocturnal dyspnea or orthopnea, distended neck veins, rales, increasing heart size by x-ray, acute pulmonary edema on chest x-ray, ventricular S(3) gallop, increased venous pressure >16 cm $H_2O$, hepatojugular reflux, pulmonary edema, visceral congestion, cardiomegaly shown on autopsy or weight loss on CHF Rx: 10 lbs./5 days. Minor criteria include bilateral ankle edema, night cough, dyspnea on ordinary exertion, hepatomegaly, pleural effusion by x-ray, decrease in vital capacity by one-third from maximum record, tachycardia (120 beats per minute or more) or pulmonary vascular engorgement on chest x-ray. To be classified as having CHF, an individual is required to have a minimum of two major or one major and two minor criteria present concurrently. The demographics of these 1,540 individuals are summarized in Table 17.

TABLE 17

Demographics of the 1,540 individuals in the CHF dataset

| | CHF present | CHF absent |
|---|---|---|
| n | | |
| Male | 22 | 664 |
| Female | 18 | 836 |
| Age | | |
| Male | 72.6 ± 7.2 | 66.7 ± 8.4 |
| Female | 75.5 ± 10.6 | 66.5 ± 8.4 |

Among the 1,562 subjects available for stroke analyses, 38 were classified as having had stroke. Stroke encompasses hemorrhagic stroke (subarachnoid hemorrhage or intracerebral hemorrhage), ischemic stroke (cerebral embolism or antherothrombotic brain infarction), transient ischemic stroke or death from stroke. The demographics of these 1,562 subjects are summarized in Table 18.

TABLE 18

Demographics of the 1,562 individuals in the stroke dataset

| | Stroke present | Stroke absent |
|---|---|---|
| n | | |
| Male | 15 | 685 |
| Female | 23 | 839 |
| Age | | |
| Male | 73.2 ± 9.2 | 70.0 ± 8.4 |
| Female | 73.1 ± 9.2 | 66.7 ± 8.6 |

Variable Reduction. The total number of genetic (SNP) and epigenetic (DNA methylation) probes remaining after quality control measures were 403,192 and 472,822, respectively. Due to the large number of variables (876,014 total, excluding possible interaction between SNPs and DNA methylation sites), and to avoid collinearity, variable reduction was performed.

Linkage disequilibrium based SNP pruning was performed in PLINK (Purcell, Neale et al. 2007) with a window size of 50 SNPs, window shift of 5 SNPs and a pairwise SNP-SNP LD threshold of 0.5. This reduced the number of SNPs from 403,192 to 161,474. To further reduce the number of SNPs, the chi-squared p-value was calculated between the remaining 161,474 SNPs and CHF and stroke status. Those with a chi-squared p-value <0.1 were retained for classification analyses, resulting in 15,132 SNPs for CHF and 14,819 SNPs for stroke.

To reduce the number of DNA methylation loci, first, the point bi-serial correlation was calculated between the 472, 822 CpG sites and CHF and stroke status. CpG sites were retained if the point bi-serial correlation was at least 0.1. A total of 19,112 and 22,837 CpG sites remained for CHF and stroke, respectively. Subsequently, Pearson correlations between sites were calculated independently for each illness. If the Pearson correlation between two loci were at least 0.8, the loci with a smaller point bi-serial correlation was discarded. In the end, 10,707 and 9,406 DNA methylation loci remained for the classification analyses of CHF and stroke, respectively.

Receiver Operating Characteristic Curve. A receiver operating characteristic (ROC) curve provides a graphical representation of binary classification performance with varying discrimination thresholds. Therefore, to assess the capability of DNA methylation and SNPs in classifying CHF and stroke, an R script was written to perform logistic regression of the models shown below and subsequently calculate the area under the curve (AUC) of the ROC curve (Beck and Shultz 1986) using the pROC package in R. This was performed systematically using DNA methylation sites that were ordered in descending order of point bi-serial with respect to the illness and SNPs that were order in ascending order of chi-squared p-value with respect to the illness. In the models listed below, SNP*meth term represents the gene-environment interaction.

$$CHF \sim SNP_j + meth_i + SNP_j * meth_i$$

$$Stroke \sim SNP_j + meth_i + SNP_j * meth_i$$

Results

Figure 10:
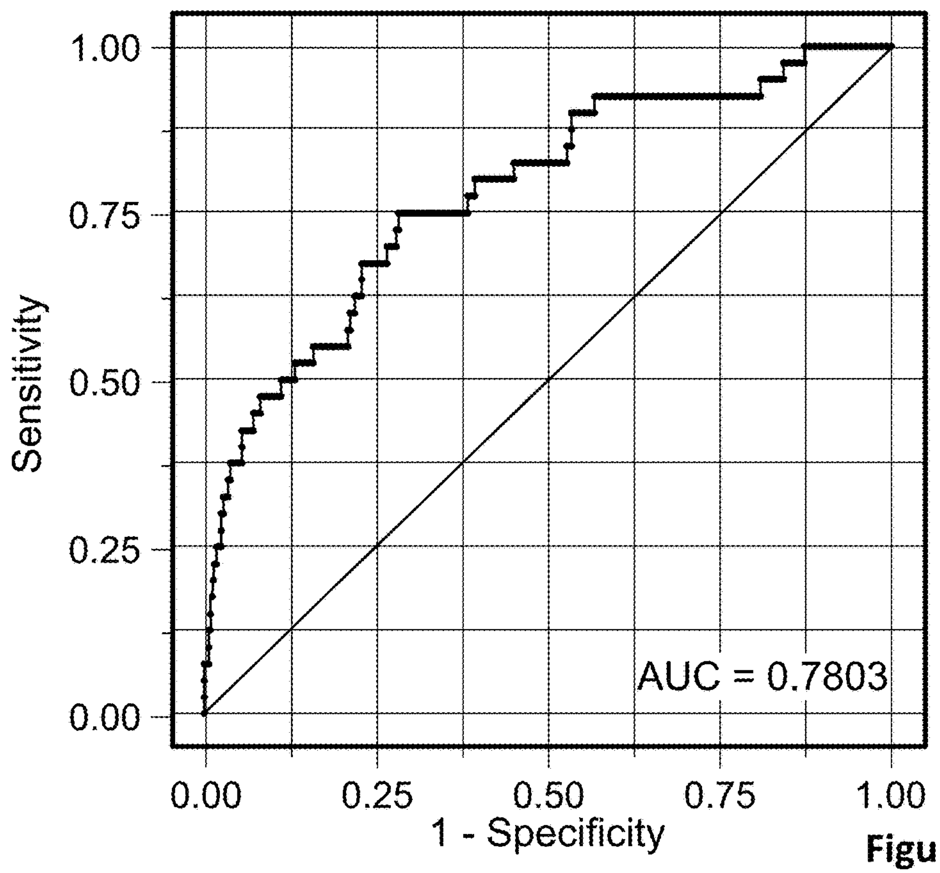
FIG. 10. ROC curve of main effects CHF classification model.

ROC of CHF Classification. Using the top three DNA methylation sites (cg09099697, cg19679281, cg25840850) and SNPs (rs10833199, rs11728055, rs16901105), a model incorporating only main effects were fitted for CHF. The ROC AUC was 0.78 and is shown in FIG. 10. The model parameters are summarized in Table 19.

TABLE 19

| Parameters of the main effects CHF model | | | | |
|---|---|---|---|---|
| Variable | Estimate | Std. Error | z value | Pr(>\|z\|) |
| cg09099697 | 0.3856 | 0.2201 | 1.752 | 0.0798 |
| cg19679281 | 0.3343 | 0.1942 | 1.721 | 0.0852 |
| cg25840850 | 0.2930 | 0.2238 | 1.310 | 0.1904 |
| rs10833199 | 0.6222 | 0.3522 | 1.767 | 0.0773 |
| rs11728055 | 0.3424 | 0.4367 | 0.784 | 0.4331 |
| rs16901105 | 0.6254 | 0.4466 | 1.401 | 0.1614 |

Figure 11:
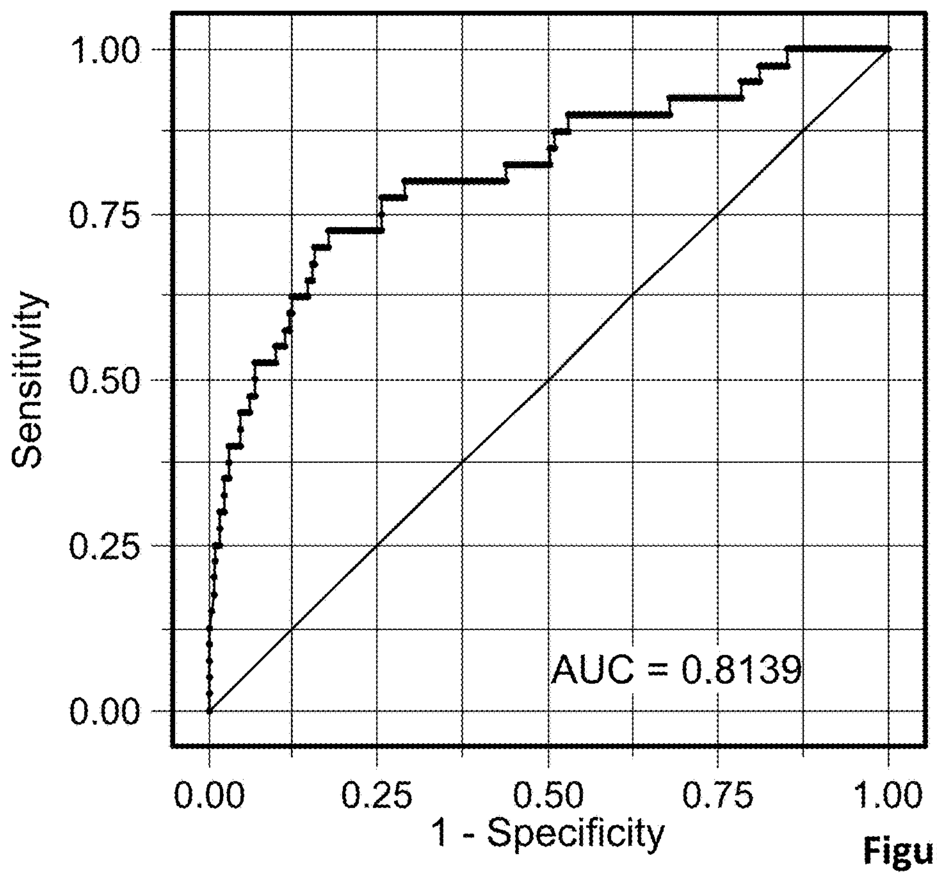
FIG. 11. ROC curve of interaction effects CHF classification model.

To further demonstrate the importance of incorporating both DNA methylation and SNPs in better predicting CHF, interaction terms as depicted in the methods section were included in the CHF model. The ROC AUC for this model increased from the previous model to 0.81 and is shown in FIG. 11. The model parameters are summarized in Table 20.

TABLE 20

| Parameters of the interaction effects CHF model | | | | |
|---|---|---|---|---|
| Variable | Estimate | Std. Error | z value | Pr(>\|z\|) |
| cg09099697 | 0.4972 | 0.2797 | 1.778 | 0.0754 |
| cg19679281 | 0.3602 | 0.2420 | 1.489 | 0.1366 |
| cg25840850 | 0.3280 | 0.2915 | 1.125 | 0.2605 |
| rs10833199 | 0.5076 | 0.5581 | 0.910 | 0.3631 |
| rs11728055 | 0.5905 | 0.5520 | 1.070 | 0.2847 |
| rs16901105 | 0.3865 | 0.7489 | 0.516 | 0.6058 |
| cg09099697:rs10833199 | −1.2780 | 0.5722 | −2.234 | 0.0255 |
| cg09099697:rs11728055 | 0.9940 | 0.7409 | 1.342 | 0.1797 |
| cg09099697:rs16901105 | 0.1493 | 0.8923 | 0.167 | 0.8671 |
| rs10833199:cg19679281 | 0.7185 | 0.5258 | 1.367 | 0.1718 |
| rs11728055:cg19679281 | −0.9245 | 0.5396 | −1.713 | 0.0867 |
| rs16901105:cg19679281 | −0.3603 | 0.7844 | −0.459 | 0.6460 |
| rs10833199:cg25840850 | 0.4609 | 0.4895 | 0.942 | 0.3464 |
| rs11728055:cg25840850 | −1.2994 | 0.6516 | −1.994 | 0.0461 |
| rs16901105:cg25840850 | 0.4543 | 0.8308 | 0.547 | 0.5845 |

These two models for CHF clearly demonstrate the importance of accounting for both genetic and epigenetic effects. As shown in Table 19, even though only three variables (two CpGs and one SNP) are marginally significant at the 0.05 level with respect to CHF, incorporating gene-environment interactions in the form of SNP-meth interactions strengthens prediction. This is shown in Table 20 where two interaction terms are significant at the 0.05 level in conjunction with one other interaction being marginally significant.

Figure 12:
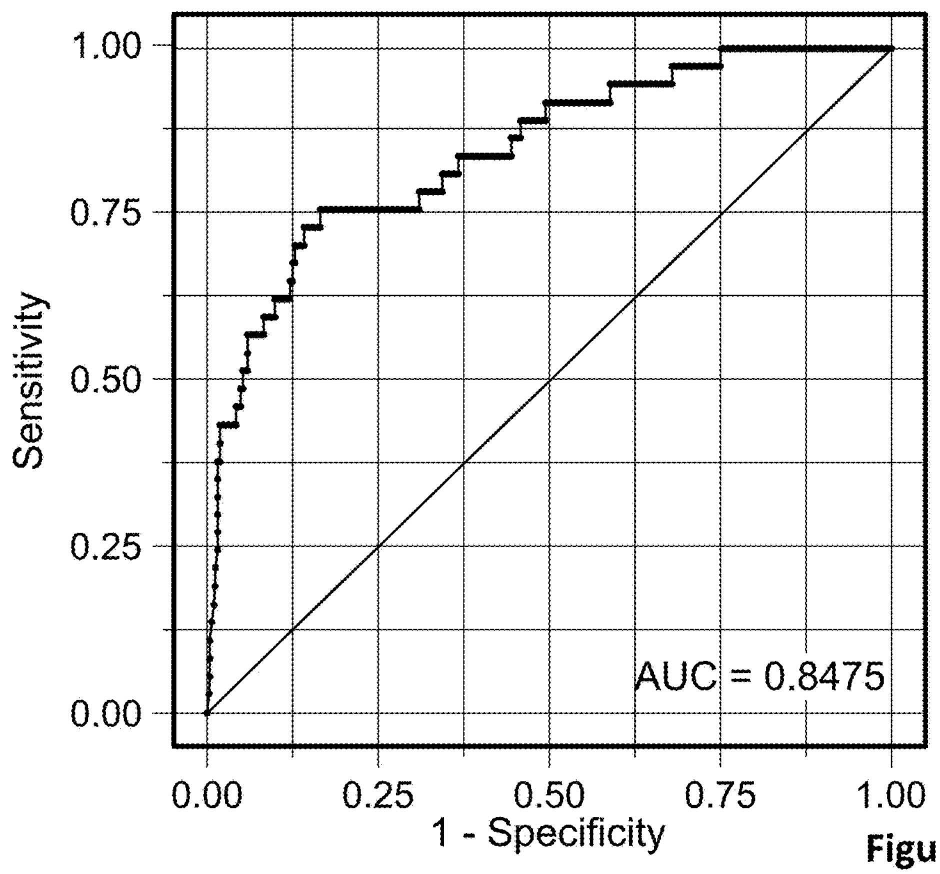
FIG. 12. ROC curve of main effects stroke classification model.

ROC of Stroke Classification. Using the top five DNA methylation sites (cg27209395, cg27551078, cg03130180, cg10319399, cg25861340) and top four SNPs (rs11007270, rs17073262, rs7190657, rs2411130), a main effects model was fitted for stroke. The ROC AUC was 0.85 and is shown in FIG. 12. The model parameters are summarized in Table 21.

TABLE 21

| Parameters of the main effects stroke model | | | | |
|---|---|---|---|---|
| Variable | Estimate | Std. Error | z value | Pr(>\|z\|) |
| cg27209395 | 0.2577 | 0.2225 | 1.158 | 0.246728 |
| cg27551078 | 0.2215 | 0.1064 | 2.082 | 0.037338 |
| cg03130180 | −0.0240 | 0.3378 | −0.071 | 0.943359 |
| cg10319399 | −0.4710 | 0.2880 | −1.636 | 0.101934 |
| cg25861340 | −0.4080 | 0.2716 | −1.502 | 0.133051 |
| rs11007270 | 1.3498 | 0.4006 | 3.369 | 0.000753 |
| rs17073262 | 0.8066 | 0.7543 | 1.069 | 0.284923 |
| rs7190657 | 1.1362 | 0.3993 | 2.845 | 0.004439 |
| rs2411130 | 1.3714 | 0.5702 | 2.405 | 0.016159 |

Figure 13:
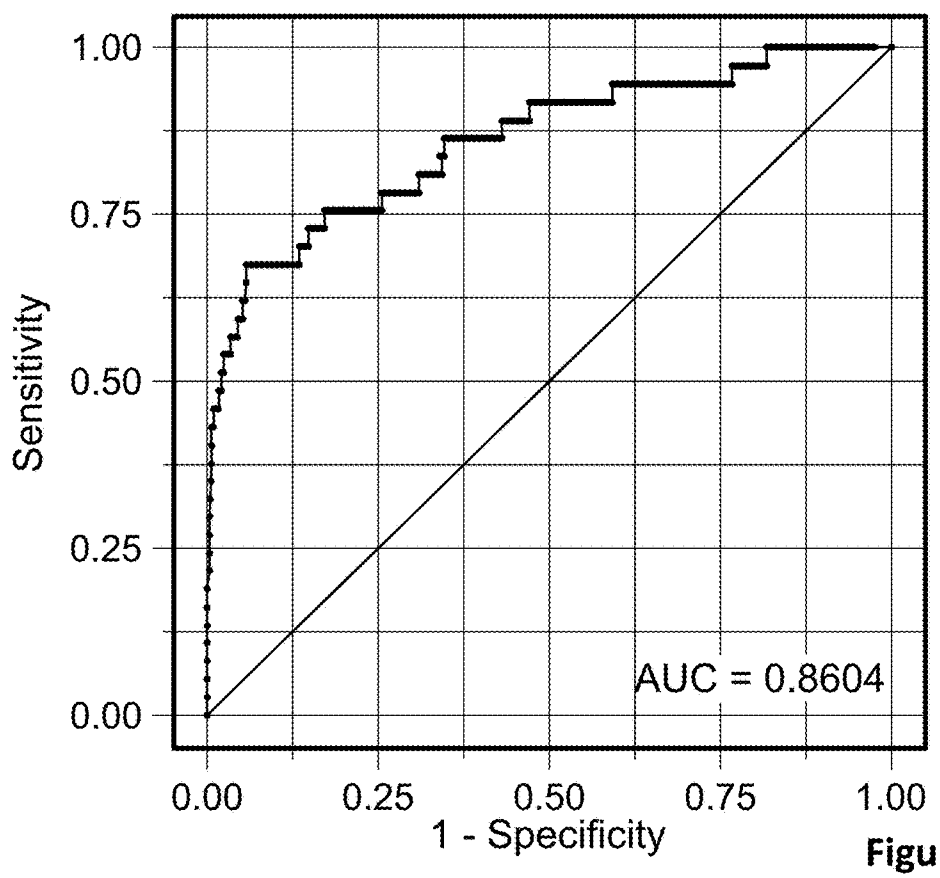
FIG. 13. ROC curve of interaction effects stroke classification model.

To again demonstrate the importance of DNA methylation sites and SNPs concurrently, an interaction effects model was fitted. The ROC AUC for this model was 0.86 and is shown in FIG. 13. The model parameters are summarized in Table 22.

TABLE 22

| Parameters of the interaction effects stroke model | | | | |
|---|---|---|---|---|
| Variable | Estimate | Std. Error | z value | Pr(>\|z\|) |
| cg27209395 | −2.213e−01 | 2.866e−01 | −0.772 | 0.4400 |
| cg27551078 | 2.525e−01 | 1.131e−01 | 2.231 | 0.0257 |
| cg03130180 | −7.973e−01 | 4.729e−01 | −1.686 | 0.0918 |
| cg10319399 | −2.266e−01 | 3.932e−01 | −0.576 | 0.5644 |
| cg25861340 | −4.281e−01 | 3.369e−01 | −1.271 | 0.2037 |
| rs11007270 | 1.329e+00 | 6.715e−01 | 1.980 | 0.0477 |
| rs17073262 | −2.989e+02 | 1.913e+04 | −0.016 | 0.9875 |
| rs7190657 | 1.114e−01 | 9.201e−01 | 0.121 | 0.9036 |
| rs2411130 | 1.235e−02 | 1.827e+00 | 0.007 | 0.9946 |
| cg27209395:rs11007270 | 1.30E+00 | 6.68E−01 | 1.952 | 0.0509 |
| cg27209395:rs17073262 | −2.20E+02 | 1.40E+04 | −0.016 | 0.9875 |
| cg27209395:rs7190657 | 2.19E+00 | 9.00E−01 | 2.434 | 0.0149 |
| rs11007270:cg27551078 | −2.05E−01 | 4.76E−01 | −0.431 | 0.6668 |
| rs17073262:cg27551078 | 1.89E+01 | 3.32E+03 | 0.006 | 0.9955 |
| rs7190657:cg27551078 | −6.56E−01 | 6.82E−01 | −0.962 | 0.3358 |
| rs11007270:cg03130180 | 8.84E−01 | 8.43E−01 | 1.049 | 0.294 |
| rs17073262:cg03130180 | 1.18E+01 | 4.34E+03 | 0.003 | 0.9978 |
| rs7190657:cg03130180 | 2.43E+00 | 1.18E+00 | 2.056 | 0.0398 |
| rs11007270:cg10319399 | −3.15E−01 | 8.41E−01 | −0.374 | 0.7081 |
| rs17073262:cg10319399 | −3.18E+01 | 2.65E+03 | −0.012 | 0.9904 |
| rs7190657:cg10319399 | −1.02E+00 | 8.99E−01 | −1.135 | 0.2565 |
| cg27209395:rs2411130 | 9.62E−01 | 1.47E+00 | 0.654 | 0.5134 |
| cg27551078:rs2411130 | 4.32E−01 | 1.02E+00 | 0.422 | 0.673 |
| cg03130180:rs2411130 | 3.64E+00 | 2.76E+00 | 1.319 | 0.1872 |
| cg10319399:rs2411130 | −9.70E−01 | 1.60E+00 | −0.605 | 0.5453 |
| rs11007270:cg25861340 | 9.13E−01 | 7.43E−01 | 1.229 | 0.2191 |
| rs17073262:cg25861340 | −3.72E+02 | 2.37E+04 | −0.016 | 0.9875 |
| rs7190657:cg25861340 | 2.51E−01 | 5.99E−01 | 0.418 | 0.6759 |
| rs2411130:cg25861340 | −2.42E+00 | 2.76E+00 | −0.877 | 0.3804 |

Once again, these two stroke models demonstrate the importance of genetic and environment in stroke. Both DNA methylation sites and SNPs are highly significant for classifying stroke. Furthermore, the classification performance is likely to increase in additional studies with diverse ethnic backgrounds and larger sample size.

Discussion

The results demonstrate that the presence of stroke or CHF can be inferred through the use of algorithms that take advantage of combination of SNPs, methylation values and or their interaction terms. However, before the results can be discussed, it is important to note several limitations to the current study. First, the Framingham cohort is exclusively White and most subjects are in their mid to late sixties and seventies. Therefore, the current findings may not apply to those of other ethnicities or different age range. Second, outside of cg05575921, the validity of the M (or B-values) for the other probes has not been confirmed by an independent technique such as pyrosequencing. Third, the Illumina array used in the studies is no longer available. Because of changes in design or availability of probes in the new generation of array, the ability to replicate and extend may be affected.

The current results underscore the value of resources such as the Framingham Heart Study furthering our understanding heart disease. In fact, without this resource, it is fair to say that this type of work would be difficult if not impossible to conduct. Still, even given the current results using this unique data set, a great deal of additional work will be necessary before a screening test such as that described in the current communication can be employed clinically. Most obviously, the current results will have to be replicated and refined in other data sets, then re-tested in research populations representative of their intended future clinical application. The latter point is particularly important because even well-designed cohort studies that were originally epidemiologically sound suffer from retention biases that enrich the remaining pool for less serious illness. This is particularly true with respect to illnesses associated with substance use, because probands with high levels of substance use are more often lost to longitudinal follow-up. (Wolke, Waylen et al. 2009) In addition, because SNP frequencies can vary between ethnicities, the effect size of a given interaction may also vary. Therefore, extensive testing and development in a variety of ethnically informative cohorts will be necessary.

There may be a hard ceiling for improvement of the AUC. Ironically, this has little to do with the quality or quantity of the epigenetic and genetic data. Rather, the limitation may be the uncertainty in the clinical characterizations. Sadly, even under the best conditions, clinically relevant forms of CVD can remain undetected. This is true even for the FHS cohort. As a result, the "gold standard" itself in the current study is somewhat inaccurate with respect to the actual clinical state. Since this inaccuracy increases the error of even a biomarker that is exactly targeted on the relevant biology, our ability to improve the AUC may be dependent on our ability to derive a more accurate clinical assessment. (Philibert, Gunter et al. 2014)

Another limitation to the use this approach is the constantly evolving epidemiology of CVD. Whereas the genetic contribution to CVD is relatively fixed, diets and other environmental exposures continue to vary from generation to generation. Perhaps the best illustration of this limitation can be by considering contribution of smoking to the predictive power of this test in prior generations. Since tobacco was introduced to Europe from the New World in the early 1500s, we can confidently state that the contribution of smoking to CVD in medieval Europe was limited and therefore, the impact of the cg05575921 on predictive power would have be nil. In contrast, because over 40% of US adults smoked in the 1960s, (Garrett, Dube et al. 2011) it is likely that the contribution of smoking behaviors, as captured by cg05575921, to the prediction of CVD would have been significantly greater in subjects from that era. However, smoking is not the only environmental factor that varies from generation to generation and from cohort to cohort. Over the past 20 years, there have been marked shifts in our understanding and public attitudes towards the amount of saturated and trans-fatty acids in a healthy diet. Since these environment factors also have strong influence on the likelihood of CVD, we would expect that the weighting of interaction effects loading on these dietary factors might vary with respect to age and ethnicity.

The improved predictive power of the smoking methylation biomarker cg05575921 as compared to self-reported smoking is not unexpected. In our initial studies, it has shown to be a potent indicator of current smoking status with an AUC of 0.99 in study that used well screened cases and controls. (Philibert, Hollenbeck et al. 2015) Unreliable self-report for smoking, particularly in high risk cohorts, is a well-established phenomenon. (Caraballo, Giovino et al. 2001, Webb, Boyd et al. 2003, Caraballo, Giovino et al. 2004, Shipton, Tappin et al. 2009) Furthermore, unlike cg05575921, categorical self-report does not capture the intensity of smoking. (Philibert, Hollenbeck et al. 2015) Finally, many subjects who may have participated in the study may have previously smoked, but did not smoke at the Wave 8 interview but still had residual demethylation of AHRR. In each of these instances, the use of the continuous metric may capture additional vulnerability to CVD that is not captured by a dichotomous smoking variable.

Since alcoholism is also a risk for CVD, (Mozaffarian, Benjamin et al. 2016) we were somewhat surprised that our previously established and validated biomarker approach for assessing alcohol intake did not have a greater predictive impact. (Philibert, Penaluna et al. 2014, Brückmann, Di Santo et al. 2016) In our initial models, the addition of methylation status at cg2313759 only improved AUC by 0.015. Although one reason for this failure to show the effect of alcohol use on risk for CVD may be that this marker is not as well validated as our smoking biomarker, there are other reasons as well. First and foremost, as opposed to methylation at cg05575921 which displays a tonic increasing risk for decreased life expectancies at all of levels of exposure, methylation at cg2313759 displays an inverted U-shaped distribution with respect to biological aging. Whether risk for CVD also follows a U shaped distribution with respect to alcohol intake is not known. But it does suggest that any successful algorithm incorporating the main effects of alcohol associated methylation cannot use a simple linear approach.

Our success in finding algorithms predictive of CVD in the absence of genome wide significant main effects may have significant implications for the searches for marker sets for other common complex disorders of adulthood. Of the top 10 leading causes of death in the United States, using main effects, reliable methylation signatures have been developed only for type 2 diabetes and chronic obstructive pulmonary disease (COPD). (Qiu, Baccarelli et al. 2012, Toperoff, Aran et al. 2012) Because the ability to find a good biomarker for illness is highly contingent on the reliability of the clinical diagnosis, the success in these two instances may be secondary to the excellent diagnostic reliability of the methods used to diagnose these two disorders, namely the hemoglobin A1C and spirometry. Additionally, it is important to note that the diagnostic signature for T2DM largely maps to pathways affected by excessive glucose levels while the signature associated with COPD largely overlaps with that of smoking which contributes to 95% of all cases of COPD. (Qiu, Baccarelli et al. 2012, Toperoff, Aran et al. 2012) Still, because many of the risk factors for other major causes of death, such as stroke, overlap with those for CVD (e.g. smoking), we are optimistic that similar profiles can be generated using this approach.

Unfortunately, the vast majority of adult onset common complex disorders do not have good existing biomarkers or large effect size etiological factors. In these cases, an approach that incorporates interaction effects may be beneficial—the real question is why?Although speculative, based on our experience with local and genome wide data indicates that chronic exposure to cellular stressors leads to a reorganization of the epigenome, which may be only partially reversible. If that disorganization of the genome, regardless of how long it lasts, is causally associated with illness, it can be used as a biomarker for illness. Understanding the reversion time of each of these effects may lead to additional insights. For example, pharmacological interventions may have effects at discrete subsets. By understanding the relationship between reversion at these loci and therapeutic outcomes, it may be possible to optimize existing medications or more adroitly tailor new combination regimens.

In summary, we report that an algorithm that incorporates information from interaction effects can predict the presence of stroke and CHF in the FCS. We suggest that further studies to replicate and expand the generalizability the approach in cohorts of other ethnicities are indicated. We furthermore suggest that similar approaches may lead to the generation of methylation profiles for other common complex disorders such as stroke.

EXAMPLE 5 REFERENCES

Andersen et al. (2015). "Current and Future Prospects for Epigenetic Biomarkers of Substance Use Disorders." Genes 6(4): 991-1022.

Auer et al. (2012). "Association of major and minor ecg abnormalities with coronary heart disease events." JAMA 307(14): 1497-1505.

Beach et al. (2010). "Child maltreatment moderates the association of MAOA with symptoms of depression and antisocial personality disorder." J Fam Psychol 24(1): 12-20.

Beck et al. (1986). "The use of relative operating characteristic (ROC) curves in test performance evaluation." Archives of pathology & laboratory medicine 110(1): 13-20.

Breitling et al. (2012). "Smoking, F2RL3 methylation, and prognosis in stable coronary heart disease." European Heart Journal.

Breitling et al. (2012). "Smoking, F2RL3 methylation, and prognosis in stable coronary heart disease." European heart journal 33(22): 2841-2848.

Brückmann et al. (2016). "Validation of differential GDAP1 DNA methylation in alcohol dependence and its potential function as a biomarker for disease severity and therapy outcome." Epigenetics (just-accepted): 00-00.

Buckley et al. (2009). "C-reactive protein as a risk factor for coronary heart disease: a systematic review and meta-analyses for the US Preventive Services Task Force." Annals of internal medicine 151(7): 483-495.

Caraballo et al. (2004). "Self-reported cigarette smoking vs. serum cotinine among U.S. adolescents." Nicotine & Tobacco Research 6(1): 19-25.

Caraballo et al. (2001). "Factors associated with discrepancies between self-reports on cigarette smoking and measured serum cotinine levels among persons aged 17 years or older: Third National Health and Nutrition Examination Survey, 1988-1994." Am J Epidemiol 153(8): 807-814.

Caspi et al. (2002). "Role of genotype in the cycle of violence in maltreated children." Science 297(5582): 851-854.

Caspi et al. (2003). "Influence of life stress on depression: moderation by a polymorphism in the 5-HTT gene." Science 301(5631): 386-389.

Center for Disease Control (2005). "Annual Smoking-Attributable Mortality, Years of Potential Life Lost, and Productivity Losses—United States, 1997-2001." MMWR 54(25): 625-628.

Centers for Disease Control and Prevention. "Heart Disease and Stroke Prevention, Addressing the Nation's Leading Killers: At A Glance 2011." Retrieved Feb. 2, 2012, from https://www.cdc.gov/dhdsp/docs/dhdsp_factsheet.pdf Dawber et al. (1963). "An approach to longitudinal studies in a community: the Framingham Study." Annals of the New York Academy of Sciences 107(2): 539-556.

Dogan et al. (2015). "Ethnicity and Smoking-Associated DNA Methylation Changes at HIV Co-Receptor GPR15." Frontiers in Psychiatry 6.

Du et al. (2008). "lumi: a pipeline for processing Illumina microarray." Bioinformatics 24(13): 1547-1548.

Garrett et al., C. f. D. Control and Prevention (2011). "Cigarette smoking-United States, 1965-2008." MMWR Surveill Summ 60(1): 109-113.

Gluckman et al. (2009). "Epigenetic mechanisms that underpin metabolic and cardiovascular diseases." Nat Rev Endocrinol 5(7): 401-408.

Guida et al. (2015). "Dynamics of Smoking-Induced Genome-Wide Methylation Changes with Time Since Smoking Cessation." Human Molecular Genetics.

Klengel et al. (2014). "The role of DNA methylation in stress-related psychiatric disorders." Neuropharmacology 80(0): 115-132.

Kolassa et al. (2010). "Association study of trauma load and SLC6A4 promoter polymorphism in posttraumatic stress disorder: evidence from survivors of the Rwandan genocide." J Clinical Psychiatry 71: 543-547.

Lao et al. (2011). "Epigenetics and colorectal cancer." Nat Rev Gastroenterol Hepatol 8(12): 686-700.

Mahmood et al. (2014). "The Framingham Heart Study and the epidemiology of cardiovascular disease: a historical perspective." The Lancet 383(9921): 999-1008.

McEwen (2007). "Physiology and Neurobiology of Stress and Adaptation: Central Role of the Brain." Physiological Reviews 87(3): 873-904.

Mega et al. "Genetic risk, coronary heart disease events, and the clinical benefit of statin therapy: an analysis of primary and secondary prevention trials." The Lancet 385 (9984): 2264-2271.

Monick et al. (2012). "Coordinated changes in AHRR methylation in lymphoblasts and pulmonary macrophages from smokers." Am. J. Med Genet. 159B(2): 141-151.

Mozaffarian et al. (2016). "Executive Summary: Heart Disease and Stroke Statistics-2016 Update: A Report From the American Heart Association." Circulation 133(4): 447-454.

Paynter et al. (2016). "Are Genetic Tests for Atherosclerosis Ready for Routine Clinical Use?" Circulation Research 118(4): 607-619.

Philibert et al. (2014). "The search for peripheral biomarkers for major depression: Benefiting from successes in the biology of smoking." American Journal of Medical Genetics Part B: Neuropsychiatric Genetics 165(3): 230-234.

Philibert et al. (2016). "Reversion of AHRR Demethylation Is a Quantitative Biomarker of Smoking Cessation." Frontiers in Psychiatry 7.

Philibert et al. (2015). "A Quantitative Epigenetic Approach for the Assessment of Cigarette Consumption." Frontiers in Psychology 6.

Philibert et al. (2014). "A pilot examination of the genome-wide DNA methylation signatures of subjects entering and exiting short-term alcohol dependence treatment programs." Epigenetics 9(9): 1-7.

Philibert et al. (2010). "The effect of smoking on MAOA promoter methylation in DNA prepared from lymphoblasts and whole blood." American Journal of Medical Genetics 153B(2): 619-628.

Philibert et al. (2008). "MAOA methylation is associated with nicotine and alcohol dependence in women." American Journal of Medical Genetics 147B(5): 565-570.

Pidsley et al. (2013). "A data-driven approach to preprocessing Illumina 450K methylation array data." BMC Genomics 14(1): 1-10.

Purcell et al. (2007). "PLINK: a tool set for whole-genome association and population-based linkage analyses." The American Journal of Human Genetics 81(3): 559-575.

Qiu et al. (2012). "Variable DNA Methylation Is Associated with Chronic Obstructive Pulmonary Disease and Lung Function." American Journal of Respiratory and Critical Care Medicine 185(4): 373-381.

Sharma et al. (2008). "Detection of altered global DNA methylation in coronary artery disease patients." DNA and cell biology 27(7): 357-365.

Shipton et al. (2009). "Reliability of self-reported smoking status by pregnant women for estimating smoking prevalence: a retrospective, cross sectional study." BMJ 339 (B4347).

Shumay et al. (2012). "Evidence that the methylation state of the monoamine oxidase A (MAOA) gene predicts brain activity of MAOA enzyme in healthy men." Epigenetics 7(10): 10-19.

Toperoff et al. (2012). "Genome-wide survey reveals predisposing diabetes type 2-related DNA methylation variations in human peripheral blood." Human Molecular Genetics 21(2): 371-383.

Traylor et al. (2012). "Genetic risk factors for ischaemic stroke and its subtypes (the METASTROKE Collaboration): a meta-analysis of genome-wide association studies." The Lancet Neurology 11(11): 951-962.

Tsaprouni et al. (2014). "Cigarette smoking reduces DNA methylation levels at multiple genomic loci but the effect is partially reversible upon cessation." Epigenetics 9(10): 1382-1396.

Webb et al. (2003). "The discrepancy between self-reported smoking status and urine continine levels among women enrolled in prenatal care at four publicly funded clinical sites." J Public Health Manag Pract 9(4): 322-325.

Wolke et al. (2009). "Selective drop-out in longitudinal studies and non-biased prediction of behaviour disorders." The British Journal of Psychiatry 195(3): 249-256.

Yang et al. (1997). "Evolving methods in genetic epidemiology. III. Gene-environment interaction in epidemiologic research." Epidemiol Rev 19(1): 33-43.

Zeilinger et al. (2013). "Tobacco smoking leads to extensive genome-wide changes in DNA methylation." PLoS ONE 8(5): e63812.

Zhang et al. (2015). "Smoking-Associated DNA Methylation Biomarkers and Their Predictive Value for All-Cause and Cardiovascular Mortality." Environmental health perspectives.

Zhang et al. (2014). "F2RL3 methylation in blood DNA is a strong predictor of mortality." International Journal of Epidemiology.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of determining the presence of a biomarker associated with coronary heart disease (CHD) in a patient sample, the method comprising:

(a) isolating a nucleic acid sample from the patient sample, (b) performing a genotyping assay on a first aliquot of the nucleic acid sample to detect the presence of at least one SNP to obtain genotype data, wherein the at least one SNP is rs11597065; and (c) bisulfite converting the nucleic acid in a second aliquot of the nucleic acid sample and performing methylation assessment on the second aliquot of the nucleic acid sample to detect methylation status of CpG site cg12586707 to obtain methylation data regarding whether the CpG residue is unmethylated; and (d) inputting genotype from step (b) and methylation data from step (c) into at least one algorithm that accounts for the contribution of at least one SNP main effect and at least one CpG main effect and, optionally, at least one interaction effect.

2. The method of claim 1, wherein the at least one interaction effect is selected from the group consisting of a gene-environment interaction (SNPxCpG) effect, a gene-gene interaction (SNPxSNP) effect, and an environment-environment interaction (CpGxCpG) effect.

3. The method of claim 1, wherein the at least one interaction effect comprises a gene-environment interaction (SNPxCpG) effect between CpG site cg12586707 and rs11597065.

4. The method of claim 1, wherein the at least one interaction effect comprises at least one environment-environment interaction (CpGxCpG) effect with CpG site cg12586707.

* * * * *